US007510854B2

(12) United States Patent
Pompejus et al.

(10) Patent No.: US 7,510,854 B2
(45) Date of Patent: Mar. 31, 2009

(54) CORYNEBACTERIUM GLUTAMICUM GENES ENCODING METABOLIC PATHWAY PROTEINS

(75) Inventors: Markus Pompejus, Freinsheim (DE); Burkhard Kröger, Limburgerhof (DE); Hartwig Schröder, Nußloch (DE); Oskar Zelder, Speyer (DE); Gregor Haberhauer, Limburgerhof (DE); Jun-Won Kim, Seoul (KR); Heung Shick-Lee, Seoul (KR); Byung-Joon Hwang, Seoul (KR)

(73) Assignee: Evonik Degussa GmbH (DE)

( * ) Notice: Subject to any disclaimer, the term of this patent is extended or adjusted under 35 U.S.C. 154(b) by 218 days.

(21) Appl. No.: 11/239,674

(22) Filed: Sep. 28, 2005

(65) Prior Publication Data

US 2006/0084152 A1 Apr. 20, 2006

Related U.S. Application Data

(63) Continuation of application No. 09/746,660, filed on Dec. 22, 2000, now abandoned, which is a continuation-in-part of application No. 09/606,740, filed on Jun. 23, 2000, now abandoned, and a continuation-in-part of application No. 09/603,124, filed on Jun. 23, 2000, now abandoned.

(60) Provisional application No. 60/187,970, filed on Mar. 9, 2000, provisional application No. 60/151,778, filed on Aug. 31, 1999, provisional application No. 60/148,613, filed on Aug. 12, 1999, provisional application No. 60/143,694, filed on Jul. 14, 1999, provisional application No. 60/142,101, filed on Jul. 2, 1999, provisional application No. 60/141,031, filed on Jun. 25, 1999.

(30) Foreign Application Priority Data

| Jul. 1, 1999 | (DE) | 199 30 476 |
| Jul. 8, 1999 | (DE) | 199 31 415 |
| Jul. 8, 1999 | (DE) | 199 31 418 |
| Jul. 8, 1999 | (DE) | 199 31 419 |
| Jul. 8, 1999 | (DE) | 199 31 420 |
| Jul. 8, 1999 | (DE) | 199 31 424 |
| Jul. 8, 1999 | (DE) | 199 31 428 |
| Jul. 8, 1999 | (DE) | 199 31 434 |
| Jul. 8, 1999 | (DE) | 199 31 435 |
| Jul. 8, 1999 | (DE) | 199 31 443 |
| Jul. 8, 1999 | (DE) | 199 31 453 |
| Jul. 8, 1999 | (DE) | 199 31 457 |
| Jul. 8, 1999 | (DE) | 199 31 465 |
| Jul. 8, 1999 | (DE) | 199 31 478 |
| Jul. 8, 1999 | (DE) | 199 31 510 |
| Jul. 8, 1999 | (DE) | 199 31 541 |
| Jul. 8, 1999 | (DE) | 199 31 573 |
| Jul. 8, 1999 | (DE) | 199 31 592 |
| Jul. 8, 1999 | (DE) | 199 31 632 |
| Jul. 8, 1999 | (DE) | 199 31 634 |
| Jul. 8, 1999 | (DE) | 199 31 636 |
| Jul. 8, 1999 | (DE) | 199 32 130 |
| Jul. 9, 1999 | (DE) | 199 32 124 |
| Jul. 9, 1999 | (DE) | 199 32 125 |
| Jul. 9, 1999 | (DE) | 199 32 126 |
| Jul. 9, 1999 | (DE) | 199 32 127 |
| Jul. 9, 1999 | (DE) | 199 32 133 |
| Jul. 9, 1999 | (DE) | 199 32 186 |
| Jul. 9, 1999 | (DE) | 199 32 206 |
| Jul. 9, 1999 | (DE) | 199 32 207 |
| Jul. 9, 1999 | (DE) | 199 32 208 |
| Jul. 9, 1999 | (DE) | 199 32 225 |
| Jul. 9, 1999 | (DE) | 199 32 227 |
| Jul. 9, 1999 | (DE) | 199 32 228 |
| Jul. 9, 1999 | (DE) | 199 32 229 |
| Jul. 9, 1999 | (DE) | 199 32 230 |
| Jul. 9, 1999 | (DE) | 199 32 914 |

(Continued)

(51) Int. Cl.
C12Q 1/68 (2006.01)
C12P 21/06 (2006.01)
C12N 15/74 (2006.01)
C07H 21/02 (2006.01)
C07H 21/04 (2006.01)

(52) U.S. Cl. .................. 435/69.1; 435/6; 435/29; 435/196; 435/471; 536/23.2; 536/23.7; 536/24.32; 536/24.5

(58) Field of Classification Search .................. 435/6, 435/91.1, 455, 375, 69.1, 70.1, 29, 91.31, 435/196, 471; 536/23.1, 23.2, 24.5, 23.7, 536/24.32
See application file for complete search history.

(56) References Cited

FOREIGN PATENT DOCUMENTS

EP 0857784 A2 12/1998
WO WO01/00843 A2 1/2001

OTHER PUBLICATIONS

Cole, S.T. et al., "Deciphering the biology of *Mycobacterium tuberculosis* from the complete genome sequence," *Nature*, vol. 393:537-544 (1998).

(Continued)

*Primary Examiner*—Jane Zara
(74) *Attorney, Agent, or Firm*—Lahive & Cockfield, LLP; Maria Laccotripe Zacharakis; Maneesh Gulati

(57) ABSTRACT

Isolated nucleic acid molecules, designated MP nucleic acid molecules, which encode novel MP proteins from *Corynebacterium glutamicum* are described. The invention also provides antisense nucleic acid molecules, recombinant expression vectors containing MP nucleic acid molecules, and host cells into which the expression vectors have been introduced. The invention still further provides isolated MP proteins, mutated MP proteins, fusion proteins, antigenic peptides and methods for the improvement of production of a desired compound from *C. glutamicum* based on genetic engineering of MP genes in this organism.

21 Claims, No Drawings

(30) Foreign Application Priority Data

| | | |
|---|---|---|
| Jul. 14, 1999 | (DE) | 199 32 922 |
| Jul. 14, 1999 | (DE) | 199 32 926 |
| Jul. 14, 1999 | (DE) | 199 32 928 |
| Jul. 14, 1999 | (DE) | 199 33 004 |
| Jul. 14, 1999 | (DE) | 199 33 005 |
| Jul. 14, 1999 | (DE) | 199 33 006 |
| Aug. 27, 1999 | (DE) | 199 40 764 |
| Aug. 27, 1999 | (DE) | 199 40 765 |
| Aug. 27, 1999 | (DE) | 199 40 766 |
| Aug. 27, 1999 | (DE) | 199 40 768 |
| Aug. 27, 1999 | (DE) | 199 40 831 |
| Aug. 27, 1999 | (DE) | 199 40 832 |
| Aug. 31, 1999 | (DE) | 199 41 378 |
| Aug. 31, 1999 | (DE) | 199 41 379 |
| Aug. 31, 1999 | (DE) | 199 41 380 |
| Aug. 31, 1999 | (DE) | 199 41 385 |
| Aug. 31, 1999 | (DE) | 199 41 394 |
| Aug. 31, 1999 | (DE) | 199 41 396 |
| Sep. 3, 1999 | (DE) | 199 42 076 |
| Sep. 3, 1999 | (DE) | 199 42 077 |
| Sep. 3, 1999 | (DE) | 199 42 079 |
| Sep. 3, 1999 | (DE) | 199 42 086 |
| Sep. 3, 1999 | (DE) | 199 42 087 |
| Sep. 3, 1999 | (DE) | 199 42 088 |
| Sep. 3, 1999 | (DE) | 199 42 095 |
| Sep. 3, 1999 | (DE) | 199 42 124 |
| Sep. 3, 1999 | (DE) | 199 42 129 |

OTHER PUBLICATIONS

Cremer, Josef et al., "Control of the Lysine Biosynthesis Sequence in *Corynebacterium glutamicum* as Analyzed by Overexpression of the Individual Corresponding Genes," *Applied and Environmental Microbiology*, vol. 57(6):1746-1752 (1991).

GenBank AC Al021841, Philipp, W.J. et al., "An independent map of the genome of the tubercle bacillus, *Mycobacterium tuberculosis* H37Rv, and comparison with *Mycobacterium leprae*," Proc. Natl. Acad. Sci. U.S.A., vol. 93(7):3132-3137 (1996) Feb. 13, 1998.

GenBank AC M89931, Rossol, I., et al., "The Corynebacterium glutamicum aecD gene encodes a C-S lyase with alpha, beta-elimination activity that degrades aminoethylcysteine," J. Bacteriol., vol. 174(9):2968-2977 (1992) Feb. 8, 2002.

Inamine, Julia M. et al., "Molecular and Genetic Characterization of Lactose-Metabolic Genes of *Streptococcus cremoris*," *Journal of Bacteriology*, vol. 167(3):855-862 (1986).

Park, Soo-Dong et al., "Isolation and Analysis of *metA*, a Methionine Biosynthetic Gene Encoding Homoserine Acetyltransferase in *Corynebacterium glutamicum*," *Mol. Cells*, vol. 8(3):286-294 (1998).

Peters-Wendisch, Petra G. et al., "Pyruvate carboxylase as an anaplerotic enzyme in *Corynebacterium glutamicum*," *Microbiology*, vol. 143:1095-1103 (1997).

Rossol, Ingrid et al., "The *Corynebacterium glutamicum aecD* Gene Encodes a C-S Lyase with α,β-Elimination Activity That Degrades Aminoethylcysteine," *Journal of Bacteriology*, vol. 174(9):2968-2977 (1992).

UniProtKB/TREMBL entry O06189, retrieved online at http://us.expasy.org/uniprot/O06189 (1997).

European Search Report for Application No. EP00987602, dated Jul. 23, 2004.

International Search Report for Application No. PCT/IB00/02035, dated Nov. 12, 2001.

US 7,510,854 B2

CORYNEBACTERIUM GLUTAMICUM GENES ENCODING METABOLIC PATHWAY PROTEINS

RELATED APPLICATIONS

The present application is an continuation in part of U.S. patent application Ser. No. 09/606,740, filed Jun. 23, 2000. This application is also a continuation in part of U.S. patent application Ser. No. 09/603,124, filed Jun. 23, 2000. The present application claims priority to prior filed U.S. Provisional Patent Application Ser. No. 60/141,031, filed Jun. 25, 1999, U.S. Provisional Patent Application Ser. No. 60/142,101, filed Jul. 2, 1999, U.S. Provisional Patent Application Ser. No. 60/148,613, filed Aug. 12, 1999, U.S. Provisional Patent Application Ser. No. 60/187,970, filed Mar. 9, 2000, and also to German Patent Application No. 19931420.9, filed Jul. 8, 1999. The entire contents of all of the aforementioned applications are hereby expressly incorporated herein by this reference.

BACKGROUND OF THE INVENTION

Certain products and by-products of naturally-occurring metabolic processes in cells have utility in a wide array of industries, including the food, feed, cosmetics, and pharmaceutical industries. These molecules, collectively termed 'fine chemicals', include organic acids, both proteinogenic and non-proteinogenic amino acids, nucleotides and nucleosides, lipids and fatty acids, diols, carbohydrates, aromatic compounds, vitamins and cofactors, and enzymes. Their production is most conveniently performed through large-scale culture of bacteria developed to produce and secrete large quantities of a particular desired molecule. One particularly useful organism for this purpose is *Corynebacterium glutamicum*, a gram positive, nonpathogenic bacterium. Through strain selection, a number of mutant strains have been developed which produce an array of desirable compounds. However, selection of strains improved for the production of a particular molecule is a time-consuming and difficult process.

SUMMARY OF THE INVENTION

The invention provides novel bacterial nucleic acid molecules which have a variety of uses. These uses include the identification of microorganisms which can be used to produce fine chemicals (e.g., amino acids, such as, for example, lysine and methionine), the modulation of fine chemical production in *C. glutamicum* or related bacteria, the typing or identification of *C. glutamicum* or related bacteria, as reference points for mapping the *C. glutamicum* genome, and as markers for transformation. These novel nucleic acid molecules encode proteins, referred to herein as metabolic pathway (MP) proteins.

*C. glutamicum* is a gram positive, aerobic bacterium which is commonly used in industry for the large-scale production of a variety of fine chemicals, and also for the degradation of hydrocarbons (such as in petroleum spills) and for the oxidation of terpenoids. The MP nucleic acid molecules of the invention, therefore, can be used to identify microorganisms which can be used to produce fine chemicals, e.g., by fermentation processes. Modulation of the expression of the MP nucleic acids of the invention, or modification of the sequence of the MP nucleic acid molecules of the invention, can be used to modulate the production of one or more fine chemicals from a microorganism (e.g., to improve the yield or production of one or more fine chemicals from a *Corynebacterium* or *Brevibacterium* species). In a preferred embodiment, the MP genes of the invention are combined with one or more genes involved in the same or different metabolic pathway to modulate the production of one or more fine chemicals from a microorganism.

The MP nucleic acids of the invention may also be used to identify an organism as being *Corynebacterium glutamicum* or a close relative thereof, or to identify the presence of *C. glutamicum* or a relative thereof in a mixed population of microorganisms. The invention provides the nucleic acid sequences of a number of *C. glutamicum* genes; by probing the extracted genomic DNA of a culture of a unique or mixed population of microorganisms under stringent conditions with a probe spanning a region of a *C. glutamicum* gene which is unique to this organism, one can ascertain whether this organism is present. Although *Corynebacterium glutamicum* itself is nonpathogenic, it is related to species pathogenic in humans, such as *Corynebacterium diphtheriae* (the causative agent of diphtheria); the detection of such organisms is of significant clinical relevance.

The MP nucleic acid molecules of the invention may also serve as reference points for mapping of the *C. glutamicum* genome, or of genomes of related organisms. Similarly, these molecules, or variants or portions thereof, may serve as markers for genetically engineered *Corynebacterium* or *Brevibacterium* species.

The MP proteins encoded by the novel nucleic acid molecules of the invention are capable of, for example, performing an enzymatic step involved in the metabolism of certain fine chemicals, including amino acids, e.g., lysine and methionine, vitamins, cofactors, nutraceuticals, nucleotides, nucleosides, and trehalose. Given the availability of cloning vectors for use in *Corynebacterium glutamicum*, such as those disclosed in Sinskey et al., U.S. Pat. No. 4,649,119, and techniques for genetic manipulation of *C. glutamicum* and the related *Brevibacterium* species (e.g., *lactofermentum*) (Yoshihama et al, *J. Bacteriol.* 162: 591-597 (1985); Katsumata et al., *J. Bacteriol.* 159: 306-311 (1984); and Santamaria et al., *J. Gen. Microbiol.* 130: 2237-2246 (1984)), the nucleic acid molecules of the invention may be utilized in the genetic engineering of this organism to make it a better or more efficient producer of one or more fine chemicals.

This improved production or efficiency of production of a fine chemical may be due to a direct effect of manipulation of a gene of the invention, or it may be due to an indirect effect of such manipulation. Specifically, alterations in *C. glutamicum* metabolic pathways for amino acids, e.g., lysine and methionine, vitamins, cofactors, nucleotides, and trehalose may have a direct impact on the overall production of one or more of these desired compounds from this organism. For example, optimizing the activity of a lysine or a methionine biosynthetic pathway protein or decreasing the activity of a lysine or methionine degradative pathway protein may result in an increase in the yield or efficiency of production of lysine or methionine from such an engineered organism. Alterations in the proteins involved in these metabolic pathways may also have an indirect impact on the production or efficiency of production of a desired fine chemical. For example, a reaction which is in competition for an intermediate necessary for the production of a desired molecule may be eliminated, or a pathway necessary for the production of a particular intermediate for a desired compound may be optimized. Further, modulations in the biosynthesis or degradation of, for example, an amino acid, e.g., lysine or methionine, a vitamin, or a nucleotide may increase the overall ability of the microorganism to rapidly grow and divide, thus increasing the number and/or production capacities of the microorganism in culture and thereby increasing the possible yield of the desired fine chemical.

The nucleic acid and protein molecules of the invention, alone or in combination with one or more nucleic acid and protein molecules of the same or different metabolic pathway, may be utilized to directly improve the production or efficiency of production of one or more desired fine chemicals from *Corynebacterium glutamicum* (e.g., methionine or lysine). Using recombinant genetic techniques well known in the art, one or more of the biosynthetic or degradative enzymes of the invention for amino acids, e.g., lysine and methionine, vitamins, cofactors, nutraceuticals, nucleotides, nucleosides, or trehalose may be manipulated such that its function is modulated. For example, a biosynthetic enzyme may be improved in efficiency, or its allosteric control region destroyed such that feedback inhibition of production of the compound is prevented. Similarly, a degradative enzyme may be deleted or modified by substitution, deletion, or addition such that its degradative activity is lessened for the desired compound without impairing the viability of the cell. In each case, the overall yield or rate of production of the desired fine chemical may be increased.

It is also possible that such alterations in the protein and nucleotide molecules of the invention may improve the production of other fine chemicals besides the amino acids, e.g., lysine and methionine, vitamins, cofactors, nutraceuticals, nucleotides, nucleosides, and trehalose through indirect mechanisms. Metabolism of any one compound is necessarily intertwined with other biosynthetic and degradative pathways within the cell, and necessary cofactors, intermediates, or substrates in one pathway are likely supplied or limited by another such pathway. Therefore, by modulating the activity of one or more of the proteins of the invention, the production or efficiency of activity of another fine chemical biosynthetic or degradative pathway may be impacted. For example, amino acids serve as the structural units of all proteins, yet may be present intracellularly in levels which are limiting for protein synthesis; therefore, by increasing the efficiency of production or the yields of one or more amino acids within the cell, proteins, such as biosynthetic or degradative proteins, may be more readily synthesized. Likewise, an alteration in a metabolic pathway enzyme such that a particular side reaction becomes more or less favored may result in the over- or under-production of one or more compounds which are utilized as intermediates or substrates for the production of a desired fine chemical.

This invention provides novel nucleic acid molecules which encode proteins, referred to herein as metabolic pathway ("MP") proteins, which are capable of, for example, performing an enzymatic step involved in the metabolism of molecules important for the normal functioning of cells, such as amino acids, e.g., lysine and methionine, vitamins, cofactors, nucleotides and nucleosides, or trehalose. Nucleic acid molecules encoding an MP protein are referred to herein as MP nucleic acid molecules. In a preferred embodiment, an MP protein, alone or in combination with one or more proteins of the same or different metabolic pathway, performs an enzymatic step related to the metabolism of one or more of the following: amino acids, e.g., lysine and methionine, vitamins, cofactors, nutraceuticals, nucleotides, nucleosides, and trehalose. Examples of such proteins include those encoded by the genes set forth in Table 1.

Accordingly, one aspect of the invention pertains to isolated nucleic acid molecules (e.g., cDNAs, DNAs, or RNAs) comprising a nucleotide sequence encoding an MP protein or biologically active portions thereof, as well as nucleic acid fragments suitable as primers or hybridization probes for the detection or amplification of MP-encoding nucleic acid (e.g., DNA or mRNA). In particularly preferred embodiments, the isolated nucleic acid molecule comprises one of the nucleotide sequences set forth as the odd-numbered SEQ ID NO in the Sequence Listing (e.g., SEQ ID NO:1, SEQ ID NO:3, or SEQ ID NO:5), or the coding region or a complement thereof of one of these nucleotide sequences. In other particularly preferred embodiments, the isolated nucleic acid molecule of the invention comprises a nucleotide sequence which hybridizes to or is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to a nucleotide sequence set forth as an odd-numbered SEQ ID NO in the Sequence Listing (e.g., SEQ ID NO:1, SEQ ID NO:3, or SEQ ID NO:5), or a portion thereof. In other preferred embodiments, the isolated nucleic acid molecule encodes one of the amino acid sequences set forth as an even-numbered SEQ ID NO in the Sequence Listing (e.g., SEQ ID NO:2, SEQ ID NO:4, or SEQ ID NO:6). The preferred MP proteins of the present invention also preferably possess at least one of the MP activities described herein.

In another embodiment, the isolated nucleic acid molecule encodes a protein or portion thereof wherein the protein or portion thereof includes an amino acid sequence which is sufficiently homologous to an amino acid sequence of the invention (e.g., a sequence having an even-numbered SEQ ID NO in the Sequence Listing, such as SEQ ID NO:2, SEQ ID NO:4, or SEQ ID NO:6), e.g., sufficiently homologous to an amino acid sequence of the invention such that the protein or portion thereof maintains an MP activity. Preferably, the protein or portion thereof encoded by the nucleic acid molecule maintains the ability to perform an enzymatic reaction in a amino acid, e.g., lysine or methionine, vitamin, cofactor, nutraceutical, nucleotide, nucleoside, or trehalose metabolic pathway. In one embodiment, the protein encoded by the nucleic acid molecule is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to an amino acid sequence of the invention (e.g., an entire amino acid sequence selected from those having an even-numbered SEQ ID NO in the Sequence Listing, such as SEQ ID NO:2, SEQ ID NO:4, or SEQ ID NO:6). In another preferred embodiment, the protein is a full length *C. glutamicum* protein which is substantially homologous to an entire amino acid sequence of the invention (encoded by an open reading frame shown in the corresponding odd-numbered SEQ ID NO in the Sequence Listing (e.g., SEQ ID NO:1, SEQ ID NO:3, or SEQ ID NO:5).

In another preferred embodiment, the isolated nucleic acid molecule is derived from *C. glutamicum* and encodes a protein (e.g., an MP fusion protein) which includes a biologically active domain which is at least about 50% or more homologous to one of the amino acid sequences of the invention (e.g., a sequence of one of the even-numbered SEQ ID NOs in the Sequence Listing, such as SEQ ID NO:2, SEQ ID NO:4, or SEQ ID NO:6) and is able to catalyze a reaction in a metabolic pathway for an amino acid, e.g., lysine or methionine, vitamin, cofactor, nutraceutical, nucleotide, nucleoside, or trehalose, or one or more of the activities set forth in Table 1, and which also includes heterologous nucleic acid sequences encoding a heterologous polypeptide or regulatory regions.

In another embodiment, the isolated nucleic acid molecule is at least 15 nucleotides in length and hybridizes under stringent conditions to a nucleic acid molecule comprising a nucleotide sequence of the invention (e.g., a sequence of an odd-numbered SEQ ID NO in the Sequence Listing, such as SEQ ID NO:1, SEQ ID NO:3, or SEQ ID NO:5). Preferably, the isolated nucleic acid molecule corresponds to a naturally-occurring nucleic acid molecule. More preferably, the isolated nucleic acid encodes a naturally-occurring *C. glutamicum* MP protein, or a biologically active portion thereof.

Another aspect of the invention pertains to vectors, e.g., recombinant expression vectors, containing the nucleic acid molecules of the invention, alone or in combination with one or more nucleic acid molecules involved in the same or different pathway, and host cells into which such vectors have been introduced. In one embodiment, such a host cell is used to produce an MP protein by culturing the host cell in a suitable medium. The MP protein can be then isolated from the medium or the host cell.

Yet another aspect of the invention pertains to a genetically altered microorganism in which one or more MP genes, alone or in combination with one or more genes involved in the same or different metabolic pathway, have been introduced or altered. In one embodiment, the genome of the microorganism has been altered by introduction of a nucleic acid molecule of the invention encoding one or more wild-type or mutated MP sequences as transgenes alone or in combination with one or more nucleic acid molecules involved in the same or different metabolic pathway. In another embodiment, one or more endogenous MP genes within the genome of the microorganism have been altered, e.g., functionally disrupted, by homologous recombination with one or more altered MP genes. In another embodiment, one or more endogenous or introduced MP genes, alone or in combination with one or more genes of the same or different metabolic pathway in a microorganism have been altered by one or more point mutations, deletions, or inversions, but still encode functional MP proteins. In still another embodiment, one or more of the regulatory regions (e.g., a promoter, repressor, or inducer) of one or more MP genes in a microorganism, alone or in combination with one or more MP genes or in combination with one or more genes of the same or different metabolic pathway, has been altered (e.g., by deletion, truncation, inversion, or point mutation) such that the expression of one or more MP genes is modulated. In a preferred embodiment, the microorganism belongs to the genus *Corynebacterium* or *Brevibacterium*, with *Corynebacterium glutamicum* being particularly preferred. In a preferred embodiment, the microorganism is also utilized for the production of a desired compound, such as an amino acid, with lysine and methionine being particularly preferred. In a particularly preferred embodiment, the MP gene is the metZ gene (SEQ ID NO:1), metC gene (SEQ ID NO:3), or the RXA00657 gene (SEQ ID NO:5), alone or in combination with one or more MP genes of the invention or in combination with one or more genes involved in methionine and/or lysine metabolism.

In another aspect, the invention provides a method of identifying the presence or activity of *Corynebacterium diphtheriae* in a subject. This method includes detection of one or more of the nucleic acid or amino acid sequences of the invention (e.g., the sequences set forth in Table 1 and in the Sequence Listing as SEQ ID NOs 1 through 122) in a subject, thereby detecting the presence or activity of *Corynebacterium diphtheriae* in the subject.

Still another aspect of the invention pertains to an isolated MP protein or portion, e.g., biologically active portion, thereof. In a preferred embodiment, the isolated MP protein or portion thereof, alone or in combination with one or more MP proteins of the invention or in combination with one or more proteins of the same or different metabolic pathway, can catalyze an enzymatic reaction involved in one or more pathways for the metabolism of an amino acid, e.g., lysine or methionine, a vitamin, a cofactor, a nutraceutical, a nucleotide, a nucleoside, or trehalose. In another preferred embodiment, the isolated MP protein or portion thereof, is sufficiently homologous to an amino acid sequence of the invention (e.g., a sequence of an even-numbered SEQ ID NO: in the Sequence Listing, such as SEQ ID NO:2, SEQ ID NO:4, or SEQ ID NO:6) such that the protein or portion thereof maintains the ability to catalyze an enzymatic reaction involved in one or more pathways for the metabolism of an amino acid, a vitamin, a cofactor, a nutraceutical, a nucleotide, a nucleoside, or trehalose.

The invention also provides an isolated preparation of an MP protein. In preferred embodiments, the MP protein comprises an amino acid sequence of the invention (e.g., a sequence of an even-numbered SEQ ID NO: of the Sequence Listing such as SEQ ID NO:2, SEQ ID NO:4, or SEQ ID NO:6). In another preferred embodiment, the invention pertains to an isolated full length protein which is substantially homologous to an entire amino acid sequence of the invention (e.g., a sequence of an even-numbered SEQ ID NO of the Sequence Listing such as SEQ ID NO:2, SEQ ID NO:4, or SEQ ID NO:6) (encoded by an open reading frame set forth in a corresponding odd-numbered SEQ ID NO: of the Sequence Listing such as SEQ ID NO:1, SEQ ID NO:3, or SEQ ID NO:5). In yet another embodiment, the protein is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to an entire amino acid sequence of the invention (e.g., a sequence of an even-numbered SEQ ID NO: of the Sequence Listing such as SEQ ID NO:2, SEQ ID NO:4, or SEQ ID NO:6). In other embodiments, the isolated MP protein comprises an amino acid sequence which is at least about 50% or more homologous to one of the amino acid sequences of the invention (e.g., a sequence of an even-numbered SEQ ID NO: of the Sequence Listing such as SEQ ID NO:2, SEQ ID NO:4, or SEQ ID NO:6) and is able to catalyze an enzymatic reaction in an amino acid, vitamin, cofactor, nutraceutical, nucleotide, nucleoside, or trehalose metabolic pathway either alone or in combination one or more MP proteins of the invention or any protein of the same or different metabolic pathway, or has one or more of the activities set forth in Table 1.

Alternatively, the isolated MP protein can comprise an amino acid sequence which is encoded by a nucleotide sequence which hybridizes, e.g., hybridizes under stringent conditions, or is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to a nucleotide sequence of one of the even-numbered SEQ ID NOs set forth in the Sequence Listing. It is also preferred that the preferred forms of MP proteins also have one or more of the MP bioactivities described herein.

The MP polypeptide, or a biologically active portion thereof, can be operatively linked to a non-MP polypeptide to form a fusion protein. In preferred embodiments, this fusion protein has an activity which differs from that of the MP protein alone. In other preferred embodiments, this fusion protein, when introduced into a *C. glutamicum* pathway for the metabolism of an amino acid, vitamin, cofactor, nutraceutical, results in increased yields and/or efficiency of production of a desired fine chemical from *C. glutamicum*. In particularly preferred embodiments, integration of this fusion protein into an amino acid, vitamin, cofactor, nutraceutical, nucleotide, nucleoside, or trehalose metabolic pathway of a host cell modulates production of a desired compound from the cell.

In another aspect, the invention provides methods for screening molecules which modulate the activity of an MP protein, either by interacting with the protein itself or a substrate or binding partner of the MP protein, or by modulating the transcription or translation of an MP nucleic acid molecule of the invention.

Another aspect of the invention pertains to a method for producing a fine chemical. This method involves the culturing of a cell containing one or more vectors directing the expression of one or more MP nucleic acid molecules of the either alone or in combination one or more MP nucleic acid molecules of the invention or any nucleic acid molecule of the same or different metabolic pathway, such that a fine chemical is produced. In a preferred embodiment, this method further includes the step of obtaining a cell containing such a vector, in which &cell is transfected with a vector directing the expression of an MP nucleic acid. In another preferred embodiment, this method further includes the step of recovering the fine chemical from the culture. In a particularly preferred embodiment, the cell is from the genus *Corynebacterium* or *Brevibacterium*, or is selected from those strains set forth in Table 3. In another preferred embodiment, the MP genes is the metZ gene (SEQ ID NO:1), metC gene (SEQ ID NO:3), or the gene designated as RXA00657 (SEQ ID NO:5) (see Table 1), alone or in combination with one or more MP nucleic acid molecules of the invention or with one or more genes involved in methionine and/or lysine metabolism. In yet another preferred embodiment, the fine chemical is an amino acid, e.g., L-lysine and L-methionine.

Another aspect of the invention pertains to methods for modulating production of a molecule from a microorganism. Such methods include contacting the cell with an agent which modulates MP protein activity or MP nucleic acid expression such that a cell associated activity is altered relative to this same activity in the absence of the agent. In a preferred embodiment, the cell is modulated for one or more *C. glutamicum* amino acid, vitamin, cofactor, nutraceutical, nucleotide, nucleoside, or trehalose metabolic pathways, such that the yields or rate of production of a desired fine chemical by this microorganism is improved. The agent which modulates MP protein activity can be an agent which stimulates MP protein activity or MP nucleic acid expression. Examples of agents which stimulate MP protein activity or MP nucleic acid expression include small molecules, active MP proteins, and nucleic acids encoding MP proteins that have been introduced into the cell. Examples of agents which inhibit MP activity or expression include small molecules and antisense MP nucleic acid molecules.

Another aspect of the invention pertains to methods for modulating yields of a desired compound from a cell, involving the introduction of a wild-type or mutant MP gene into a cell, either alone or in combination one or more MP nucleic acid molecules of the invention or any nucleic acid molecule of the same or different metabolic pathway, either maintained on a separate plasmid or integrated into the genome of the host cell. If integrated into the genome, such integration can be random, or it can take place by homologous recombination such that the native gene is replaced by the introduced copy, causing the production of the desired compound from the cell to be modulated. In a preferred embodiment, said yields are increased. In another preferred embodiment, said chemical is a fine chemical. In a particularly preferred embodiment, said fine chemical is an amino acid. In especially preferred embodiments, said amino acid are L-lysine and L-methionine. In another preferred embodiment, said gene is the metZ gene (SEQ ID NO:1), metC gene (SEQ ID NO:3), or the RXA00657 gene (SEQ ID NO:5), alone or in combination with one or more MP nucleic acid molecules of the invention or with one or more genes involved in methionine and/or lysine metabolism.

DETAILED DESCRIPTION OF THE INVENTION

The present invention provides MP nucleic acid and protein molecules which are involved in the metabolism of certain fine chemicals in *Corynebacterium glutamicum*, including amino acids, e.g., lysine and methionine, vitamins, cofactors, nutraceuticals, nucleotides, nucleosides, and trehalose. The molecules of the invention may be utilized in the modulation of production of fine chemicals from microorganisms, such as *C. glutamicum*, either directly (e.g., where modulation of the activity of a lysine or methionine biosynthesis protein has a direct impact on the production or efficiency of production of lysine or methionine from that organism), or may have an indirect impact which nonetheless results in an increase of yield or efficiency of production of the desired compound (e.g., where modulation of the activity of a nucleotide biosynthesis protein has an impact on the production of an organic acid or a fatty acid from the bacterium, perhaps due to improved growth or an increased supply of necessary co-factors, energy compounds, or precursor molecules). The MP molecules may be utilized alone or in combination with other MP molecules of the invention, or in combination with other molecules involved in the same or a different metabolic pathway (e.g., lysine or methione metabolism). In a preferred embodiment, the MP molecules are the metZ (SEQ ID NO:1), metC (SEQ ID NO:3), or RXA00657 (SEQ ID NO:5) nucleic acid molecules and the proteins encoded by these nucleic acid molecules (SEQ ID NO:2, SEQ ID NO.:4 and SEQ ID NO.:6, respectively). Aspects of the invention are further explicated below.

I. Fine Chemicals

The term 'fine chemical' is art-recognized and includes molecules produced by an organism which have applications in various industries, such as, but not limited to, the pharmaceutical, agriculture, and cosmetics industries. Such compounds include organic acids, such as tartaric acid, itaconic acid, and diaminopimelic acid, both proteinogenic and non-proteinogenic amino acids, purine and pyrimidine bases, nucleosides, and nucleotides (as described e.g. in Kuninaka, A. (1996) Nucleotides and related compounds, p. 561-612, in Biotechnology vol. 6, Rehm et al., eds. VCH: Weinheim, and references contained therein), lipids, both saturated and unsaturated fatty acids (e.g., arachidonic acid), diols (e.g., propane diol, and butane diol), carbohydrates (e.g., hyaluronic acid and trehalose), aromatic compounds (e.g., aromatic amines, vanillin, and indigo), vitamins and cofactors (as described in Ullmann's Encyclopedia of Industrial Chemistry, vol. A27, "Vitamins", p. 443-613 (1996) VCH: Weinheim and references therein; and Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press, (1995)), enzymes, polyketides (Cane et al. (1998) *Science* 282: 63-68), and all other chemicals described in Gutcho (1983) Chemicals by Fermentation, Noyes Data Corporation, ISBN: 0818805086 and references therein. The metabolism and uses of certain of these fine chemicals are further explicated below.

A. Amino Acid Metabolism and Uses

Amino acids comprise the basic structural units of all proteins, and as such are essential for normal cellular functioning in all organisms. The term "amino acid" is art-recognized. The proteinogenic amino acids, of which there are 20 species, serve as structural units for proteins, in which they are linked by peptide bonds, while the nonproteinogenic amino acids (hundreds of which are known) are not normally found in proteins (see Ulmann's Encyclopedia of Industrial Chemistry, vol. A2, p. 57-97 VCH: Weinheim (1985)). Amino acids may be in the D- or L-optical configuration, though L-amino acids are generally the only type found in naturally-occurring proteins. Biosynthetic and degradative pathways of each of the 20 proteinogenic amino acids have been well characterized in both prokaryotic and eukaryotic cells (see, for example, Stryer, L. Biochemistry, $3^{rd}$ edition, pages 578-590 (1988)). The 'essential' amino acids (histidine, isoleucine, leucine, lysine, methionine, phenylalanine, threonine, tryptophan, and valine), so named because they are generally a nutritional requirement due to the complexity of their biosyntheses, are readily converted by simple biosynthetic pathways to the remaining 11 'nonessential' amino acids (alanine, arginine, asparagine, aspartate, cysteine, glutamate, glutamine, glycine, proline, serine, and tyrosine). Higher animals do retain the ability to synthesize some of these amino acids, but the essential amino acids must be supplied from the diet in order for normal protein synthesis to occur.

Aside from their function in protein biosynthesis, these amino acids are interesting chemicals in their own right, and many have been found to have various applications in the food, feed, chemical, cosmetics, agriculture, and pharmaceutical industries. Lysine is an important amino acid in the nutrition not only of humans, but also of monogastric animals such as poultry and swine. Glutamate is most commonly used as a flavor additive (mono-sodium glutamate, MSG) and is widely used throughout the food industry, as are aspartate, phenylalanine, glycine, and cysteine. Glycine, L-methionine and tryptophan are all utilized in the pharmaceutical industry. Glutamine, valine, leucine, isoleucine, histidine, arginine, proline, serine and alanine are of use in both the pharmaceutical and cosmetics industries. Threonine, tryptophan, and D/L-methionine are common feed additives. (Leuchtenberger, W. (1996) Amino aids—technical production and use, p. 466-502 in Rehm et al. (eds.) Biotechnology vol. 6, chapter 14a, VCH: Weinheim). Additionally, these amino acids have been found to be useful as precursors for the synthesis of synthetic amino acids and proteins, such as N-acetylcysteine, S-carboxymethyl-L-cysteine, (S)-5-hydroxytryptophan, and others described in Ulmann's Encyclopedia of Industrial Chemistry, vol. A2, p. 57-97, VCH: Weinheim, 1985.

The biosynthesis of these natural amino acids in organisms capable of producing them, such as bacteria, has been well characterized (for review of bacterial amino acid biosynthesis and regulation thereof, see Umbarger, H. E. (1978) *Ann. Rev. Biochem.* 47: 533-606). Glutamate is synthesized by the reductive amination of α-ketoglutarate, an intermediate in the citric acid cycle. Glutamine, proline, and arginine are each subsequently produced from glutamate. The biosynthesis of serine is a three-step process beginning with 3-phosphoglycerate (an intermediate in glycolysis), and resulting in this amino acid after oxidation, transamination, and hydrolysis steps. Both cysteine and glycine are produced from serine; the former by the condensation of homocysteine with serine, and the latter by the transferal of the side-chain β-carbon atom to tetrahydrofolate, in a reaction catalyzed by serine transhydroxymethylase. Phenylalanine and tyrosine are synthesized from the glycolytic and pentose phosphate pathway precursors erythrose 4-phosphate and phosphoenolpyruvate in a 9-step biosynthetic pathway that differ only at the final two steps after synthesis of prephenate. Tryptophan is also produced from these two initial molecules, but its synthesis is an 11-step pathway. Tyrosine may also be synthesized from phenylalanine, in a reaction catalyzed by phenylalanine hydroxylase. Alanine, valine, and leucine are all biosynthetic products of pyruvate, the final product of glycolysis. Aspartate is formed from oxaloacetate, an intermediate of the citric acid cycle. Asparagine, methionine, threonine, and lysine are each produced by the conversion of aspartate. Isoleucine is formed from threonine.

The biosynthetic pathways leading to methionine have been studied in diverse organisms. The first step, acylation of homoserine, is common to all of the organisms, even though the source of the transferred acyl groups is different. *Escherichia coli* and the related species use succinyl-CoA (Michaeli, S. and Ron, E. Z. (1981) *Mol. Gen. Genet.* 182, 349-354), while *Saccharomyces cerevisiae* (Langin, T., et al. (1986) *Gene* 49, 283-293), *Brevibacterium flavum* (Miyajima, R. and Shiio, I. (1973) *J. Biochem.* 73, 1061-1068; Ozaki, H. and Shiio, I. (1982) *J. Biochem.* 91, 1163-1171), *C. glutamicum* (Park, S.-D., et al. (1998) *Mol. Cells* 8, 286-294), and *Leptospira meyeri* (Belfaiza, J. et al. (1998) 180, 250-255; Bourhy, P., et al. (1997) *J. Bacteriol.* 179, 4396-4398) use acetyl-CoA as the acyl donor; Formation of homocysteine from acylhomoserine can occur in two different ways. *E. coli* uses the transsulfuration pathway which is catalyzed by cystathionine γ-synthase (the product of metB) and cystathionine β-lyase (the product of metC). *S. cerevisiae* (Cherest, H. and Surdin-Kerjan, Y. (1992) *Genetics* 130, 51-58), *B. flavum* (Ozaki, H. and Shiio, I. (1982) *J. Biochem.* 91, 1163-1171), *Pseudomonas aeruginosa* (Foglino, M., et al. (1995) *Microbiology* 141, 431-439), and *L. meyeri* (Belfaiza, J., et al. (1998) *J. Bacteriol.* 180, 250-255) utilize the direct sulfhydrylation pathway which is catalyzed by acylhomoserine sulfhydrylase. Unlike closely related *B. flavum* which uses only the direct sulfhydrylation pathway, enzyme activities of the transsulfuration pathway have been detected in the extracts of the *C. glutamicum* cells and the pathway has been proposed to be the route for methionine biosynthesis in the organism (Hwang, B.-J., et al. (1999) *Mol. Cells* 9, 300-308; Kase, H. and Nakayama, K. (1974) *Agr. Biol. Chem.* 38, 2021-2030; Park, S.-D., et al. 1998) *Mol. Cells* 8, 286-294).

Although some genes involved in methionine biosynthesis in *C. glutamicum* have been isolated, information on the biosynthesis of methionine in *C. glutamicum* is still very limited. No genes other than metA and metB have been isolated from the organism. To understand the biosynthetic pathways leading to methionine in *C. glutamicum*, we have isolated and characterized the metC gene (SEQ ID NO:3) and the metZ (also called metY) gene (SEQ ID NO:1) of *C. glutamicum* (see Table 1).

Amino acids in excess of the protein synthesis needs of the cell cannot be stored, and are instead degraded to provide intermediates for the major metabolic pathways of the cell (for review see Stryer, L. Biochemistry $3^{rd}$ ed. Ch. 21 "Amino Acid Degradation and the Urea Cycle" p. 495-516 (1988)). Although the cell is able to convert unwanted amino acids into useful metabolic intermediates, amino acid production is costly in terms of energy, precursor molecules, and the enzymes necessary to synthesize them. Thus it is not surprising that amino acid biosynthesis is regulated by feedback inhibition, in which the presence of a particular amino acid serves to slow or entirely stop its own production (for overview of feedback mechanisms in amino acid biosynthetic pathways, see Stryer, L. Biochemistry, $3^{rd}$ ed. Ch. 24: "Biosynthesis of Amino Acids and Heme" p. 575-600 (1988)). Thus, the output of any particular amino acid is limited by the amount of that amino acid present in the cell.

B. Vitamin, Cofactor, and Nutraceutical Metabolism and Uses

Vitamins, cofactors, and nutraceuticals comprise another group of molecules which the higher animals have lost the ability to synthesize and so must ingest, although they are readily synthesized by other organisms, such as bacteria. These molecules are either bioactive substances themselves, or are precursors of biologically active substances which may serve as electron carriers or intermediates in a variety of metabolic pathways. Aside from their nutritive value, these compounds also have significant industrial value as coloring agents, antioxidants, and catalysts or other processing aids. (For an overview of the structure, activity, and industrial applications of these compounds, see, for example, Ullman's Encyclopedia of Industrial Chemistry, "Vitamins" vol. A27, p. 443-613, VCH: Weinheim, 1996.) The term "vitamin" is art-recognized, and includes nutrients which are required by an organism for normal functioning, but which that organism cannot synthesize by itself. The group of vitamins may encompass cofactors and nutraceutical compounds. The language "cofactor" includes nonproteinaceous compounds required for a normal enzymatic activity to occur. Such compounds may be organic or inorganic; the cofactor molecules of the invention are preferably organic. The term "nutraceutical" includes dietary supplements having health benefits in plants and animals, particularly humans. Examples of such molecules are vitamins, antioxidants, and also certain lipids (e.g., polyunsaturated fatty acids).

The biosynthesis of these molecules in organisms capable of producing them, such as bacteria, has been largely characterized (Ullman's Encyclopedia of Industrial Chemistry, "Vitamins" vol. A27, p. 443-613, VCH: Weinheim, 1996; Michal, G. (1999) Biochemical Pathways: An Atlas of Biochemistry and Molecular Biology, John Wiley & Sons; Ong, A. S., Niki, E. & Packer, L. (1995) "Nutrition, Lipids, Health, and Disease" Proceedings of the UNESCO/Confederation of Scientific and Technological Associations in Malaysia, and the Society for Free Radical Research—Asia, held Sep. 1-3, 1994 at Penang, Malaysia, AOCS Press: Champaign, Ill. X, 374 S).

Thiamin (vitamin $B_1$) is produced by the chemical coupling of pyrimidine and thiazole moieties. Riboflavin (vitamin $B_2$) is synthesized from guanosine-5'-triphosphate (GTP) and ribose-5'-phosphate. Riboflavin, in turn, is utilized for the synthesis of flavin mononucleotide (FMN) and flavin adenine dinucleotide (FAD). The family of compounds collectively termed 'vitamin $B_6$' (e.g., pyridoxine, pyridoxamine, pyridoxa-5'-phosphate, and the commercially used pyridoxin hydrochloride) are all derivatives of the common structural unit, 5-hydroxy-6-methylpyridine. Pantothenate (pantothenic acid, (R)-(+)-N-(2,4-dihydroxy-3,3-dimethyl-1-oxobutyl)-β-alanine) can be produced either by chemical synthesis or by fermentation. The final steps in pantothenate biosynthesis consist of the ATP-driven condensation of β-alanine and pantoic acid. The enzymes responsible for the biosynthesis steps for the conversion to pantoic acid, to β-alanine and for the condensation to panthotenic acid are known. The metabolically active form of pantothenate is Coenzyme A, for which the biosynthesis proceeds in 5 enzymatic steps. Pantothenate, pyridoxal-5'-phosphate, cysteine and ATP are the precursors of Coenzyme A. These enzymes not only catalyze the formation of panthothante, but also the production of (R)-pantoic acid, (R)-pantolacton, (R)-panthenol (provitamin $B_5$), panteheine (and its derivatives) and coenzyme A.

Biotin biosynthesis from the precursor molecule pimeloyl-CoA in microorganisms has been studied in detail and several of the genes involved have been identified. Many of the corresponding proteins have been found to also be involved in Fe-cluster synthesis and are members of the nifS class of proteins. Lipoic acid is derived from octanoic acid, and serves as a coenzyme in energy metabolism, where it becomes part of the pyruvate dehydrogenase complex and the α-ketoglutarate dehydrogenase complex. The folates are a group of substances which are all derivatives of folic acid, which is turn is derived from L-glutamic acid, p-amino-benzoic acid and 6-methylpterin. The biosynthesis of folic acid and its derivatives, starting from the metabolism intermediates guanosine-5'-triphosphate (GTP), L-glutamic acid and p-aminobenzoic acid has been studied in detail in certain microorganisms.

Corrinoids (such as the cobalamines and particularly vitamin $B_{12}$) and porphyrines belong to a group of chemicals characterized by a tetrapyrole ring system. The biosynthesis of vitamin $B_{12}$ is sufficiently complex that it has not yet been completely characterized, but many of the enzymes and substrates involved are now known. Nicotinic acid (nicotinate), and nicotinamide are pyridine derivatives which are also termed 'niacin'. Niacin is the precursor of the important coenzymes NAD (nicotinamide adenine dinucleotide) and NADP (nicotinamide adenine dinucleotide phosphate) and their reduced forms.

The large-scale production of these compounds has largely relied on cell-free chemical syntheses, though some of these chemicals have also been produced by large-scale culture of microorganisms, such as riboflavin, Vitamin $B_6$, pantothenate, and biotin. Only Vitamin $B_{12}$ is produced solely by fermentation, due to the complexity of its synthesis. In vitro methodologies require significant inputs of materials and time, often at great cost.

C. Purine, Pyrimidine, Nucleoside and Nucleotide Metabolism and Uses

Purine and pyrimidine metabolism genes and their corresponding proteins are important targets for the therapy of tumor diseases and viral infections. The language "purine" or "pyrimidine" includes the nitrogenous bases which are constituents of nucleic acids, co-enzymes, and nucleotides. The term "nucleotide" includes the basic structural units of nucleic acid molecules, which are comprised of a nitrogenous base, a pentose sugar (in the case of RNA, the sugar is ribose; in the case of DNA, the sugar is D-deoxyribose), and phosphoric acid. The language "nucleoside" includes molecules which serve as precursors to nucleotides, but which are lacking the phosphoric acid moiety that nucleotides possess. By inhibiting the biosynthesis of these molecules, or their mobilization to form nucleic acid molecules, it is possible to inhibit RNA and DNA synthesis; by inhibiting this activity in a fashion targeted to cancerous cells, the ability of tumor cells to divide and replicate may be inhibited. Additionally, there are nucleotides which do not form nucleic acid molecules, but rather serve as energy stores (i.e., AMP) or as coenzymes (i.e., FAD and NAD).

Several publications have described the use of these chemicals for these medical indications, by influencing purine and/or pyrimidine metabolism (e.g. Christopherson, R. I. and Lyons, S. D. (1990) "Potent inhibitors of de novo pyrimidine and purine biosynthesis as chemotherapeutic agents." Med. Res. Reviews 10: 505-548). Studies of enzymes involved in purine and pyrimidine metabolism have been focused on the development of new drugs which can be used, for example, as immunosuppressants or anti-proliferants (Smith, J. L., (1995) "Enzymes in nucleotide synthesis." Curr. Opin. Struct. Biol. 5: 752-757; (1995) Biochem Soc. Transact. 23: 877-902). However, purine and pyrimidine bases, nucleosides and nucleotides have other utilities: as intermediates in the biosynthesis of several fine chemicals (e.g., thiamine, S-adenosyl-methionine, folates, or riboflavin), as energy carriers for the cell (e.g., ATP or GTP), and for chemicals themselves, commonly used as flavor enhancers (e.g., IMP or GMP) or for several medicinal applications (see, for example, Kuninaka, A. (1996) Nucleotides and Related Compounds in Biotechnology vol. 6, Rehm et al., eds. VCH: Weinheim, p. 561-612). Also, enzymes involved in purine, pyrimidine, nucleoside, or nucleotide metabolism are increasingly serving as targets against which chemicals for crop protection, including fungicides, herbicides and insecticides, are developed.

The metabolism of these compounds in bacteria has been characterized (for reviews see, for example, Zalkin, H. and Dixon, J. E. (1992) "de novo purine nucleotide biosynthesis", in: Progress in Nucleic Acid Research and Molecular Biology, vol. 42, Academic Press:, p. 259-287; and Michal, G. (1999) "Nucleotides and Nucleosides", Chapter 8 in: Biochemical Pathways: An Atlas of Biochemistry and Molecular Biology, Wiley: New York). Purine metabolism has been the subject of intensive research, and is essential to the normal functioning of the cell. Impaired purine metabolism in higher animals can cause severe disease, such as gout. Purine nucleotides are synthesized from ribose-5-phosphate, in a series of steps through the intermediate compound inosine-5'-phosphate (IMP), resulting in the production of guanosine-5'-monophosphate (GMP) or adenosine-5'-monophosphate (AMP), from which the triphosphate forms utilized as nucleotides are readily formed. These compounds are also utilized as energy stores, so their degradation provides energy for many different biochemical processes in the cell. Pyrimidine biosynthesis proceeds by the formation of uridine-5'-monophosphate (UMP) from ribose-5-phosphate. UMP, in turn, is converted to cytidine-5'-triphosphate (CTP). The deoxy-forms of all of these nucleotides are produced in a one step reduction reaction from the diphosphate ribose form of the nucleotide to the diphosphate deoxyribose form of the nucleotide. Upon phosphorylation, these molecules are able to participate in DNA synthesis.

D. Trehalose Metabolism and Uses

Trehalose consists of two glucose molecules, bound in α, α-1,1 linkage. It is commonly used in the food industry as a sweetener, an additive for dried or frozen foods, and in beverages. However, it also has applications in the pharmaceutical, cosmetics and biotechnology industries (see, for example, Nishimoto et al., (1998) U.S. Pat. No. 5,759,610; Singer, M. A. and Lindquist, S. (1998) Trends Biotech. 16: 460-467; Paiva, C. L. A. and Panek, A. D. (1996) Biotech. Ann. Rev. 2: 293-314; and Shiosaka, M. (1997) J. Japan 172: 97-102). Trehalose is produced by enzymes from many microorganisms and is naturally released into the surrounding medium, from which it can be collected using methods known in the art.

II. Elements and Methods of the Invention

The present invention is based, at least in part, on the discovery of novel molecules, referred to herein as MP nucleic acid and protein molecules (see Table 1), which play a role in or function in one or more cellular metabolic pathways. In one embodiment, the MP molecules catalyze an enzymatic reaction involving one or more amino acid, e.g., lysine or methionine, vitamin, cofactor, nutraceutical, nucleotide, nucleoside, or trehalose metabolic pathways. In a preferred embodiment, the activity of one or more MP molecules of the present invention, alone or in combination with molecules involved in the same or different metabolic pathway (e.g., methionine or lysine metabolism), in one or more C. glutamicum metabolic pathways for amino acids, vitamins, cofactors, nutraceuticals, nucleotides, nucleosides or trehalose has an impact on the production of a desired fine chemical by this organism. In a particularly preferred embodiment, the MP molecules of the invention are modulated in activity, such that the C. glutamicum metabolic pathways in which the MP proteins of the invention are involved are modulated in efficiency or output, which either directly or indirectly modulates the production or efficiency of production of a desired fine chemical by C. glutamicum. In a preferred embodiment, the fine chemical is an amino acid, e.g., lysine or methionine. In another preferred embodiment, the MP molecules are metZ, metY, and/or RXA00657 (see Table 1).

The language, "MP protein" or "MP polypeptide" includes proteins which play a role in, e.g., catalyze an enzymatic reaction, in one or more amino acid, vitamin, cofactor, nutraceutical, nucleotide, nucleoside or trehalose metabolic pathways. Examples of MP proteins include those encoded by the MP genes set forth in Table 1 and by the odd-numbered SEQ ID NOs. The terms "MP gene" or "MP nucleic acid sequence" include nucleic acid sequences encoding an MP protein, which consist of a coding region and also corresponding untranslated 5' and 3' sequence regions. Examples of MP genes include those set forth in Table 1. The terms "production" or "productivity" are art-recognized and include the concentration of the fermentation product (for example, the desired fine chemical) formed within a given time and a given fermentation volume (e.g., kg product per hour per liter). The term "efficiency of production" includes the time required for a particular level of production to be achieved (for example, how long it takes for the cell to attain a particular rate of output of a fine chemical). The term "yield" or "product/carbon yield" is art-recognized and includes the efficiency of the conversion of the carbon source into the product (i.e., fine chemical). This is generally written as, for example, kg product per kg carbon source. By increasing the yield or production of the compound, the quantity of recovered molecules, or of useful recovered molecules of that compound in a given amount of culture over a given amount of time is increased. The terms "biosynthesis" or a "biosynthetic pathway" are art-recognized and include the synthesis of a compound, preferably an organic compound, by a cell from intermediate compounds in what may be a multistep and highly regulated process. The terms "degradation" or a "degradation pathway" are art-recognized and include the breakdown of a compound, preferably an organic compound, by a cell to degradation products (generally speaking, smaller or less complex molecules) in what may be a multistep and highly regulated process. The language "metabolism" is art-recognized and includes the totality of the biochemical reactions that take place in an organism. The metabolism of a particular compound, then, (e.g., the metabolism of an amino acid such as glycine) comprises the overall biosynthetic, modification, and degradation pathways in the cell related to this compound.

The MP molecules of the present invention may be combined with one or more MP molecules of the invention or one or more molecules of the same or different metabolic pathway to increase the yield of a desired fine chemical. In a preferred embodiment, the fine chemical is an amino acid, e.g., lysine or methionine. Alternatively, or in addition, a byproduct which is not desired may be reduced by combination or disruption of MP molecules or other metabolic molecules (e.g., molecules involved in lysine or methionine metabolism). MP molecules combined with other molecules of the same or a different metabolic pathway may be altered in their nucleotide sequence and in the corresponding amino acid sequence to alter their activity under physiological conditions, which leads to an increase in productivity and/or yield of a desired fine chemical. In a further embodiment, an MP molecule in its original or in its above-described altered form may be combined with other molecules of the same or a different metabolic pathway which are altered in their nucleotide sequence in such a way that their activity is altered under physiological conditions which leads to an increase in productivity and/or yield of a desired fine chemical, e.g., an amino acid such as methionine or lysine.

In another embodiment, the MP molecules of the invention, alone or in combination with one or more molecules of the same or different metabolic pathway, are capable of modulating the production of a desired molecule, such as a fine chemical, in a microorganism such as C. glutamicum. Using recombinant genetic techniques, one or more of the biosynthetic or degradative enzymes of the invention for amino acids, e.g., lysine or methionine, vitamins, cofactors, nutraceuticals, nucleotides, nucleosides, or trehalose may be manipulated such that its function is modulated. For example, a biosynthetic enzyme may be improved in efficiency, or its allosteric control region destroyed such that feedback inhibition of production of the compound is prevented. Similarly, a degradative enzyme may be deleted or modified by substitution, deletion, or addition such that its degradative activity is lessened for the desired compound without impairing the viability of the cell. In each case, the overall yield or rate of production of one of these desired fine chemicals may be increased.

It is also possible that such alterations in the protein and nucleotide molecules of the invention may improve the production of other fine chemicals besides the amino acids, vitamins, cofactors, nutraceuticals, nucleotides, nucleosides, and trehalose. Metabolism of any one compound is necessarily intertwined with other biosynthetic and degradative pathways within the cell, and necessary cofactors, intermediates, or substrates in one pathway are likely supplied or limited by another such pathway. Therefore, by modulating the activity of one or more of the proteins of the invention, the production or efficiency of activity of another fine chemical biosynthetic or degradative pathway may be impacted. For example, amino acids serve as the structural units of all proteins, yet may be present intracellularly in levels which are limiting for protein synthesis; therefore, by increasing the efficiency of production or the yields of one or more amino acids within the cell, proteins, such as biosynthetic or degradative proteins, may be more readily synthesized. Likewise, an alteration in a metabolic pathway enzyme such that a particular side reaction becomes more or less favored may result in the over- or under-production of one or more compounds which are utilized as intermediates or substrates for the production of a desired fine chemical.

The isolated nucleic acid sequences of the invention are contained within the genome of a Corynebacterium glutamicum strain available through the American Type Culture Collection, given designation ATCC 13032. The nucleotide sequence of the isolated C. glutamicum MP DNAs and the predicted amino acid sequences of the C. glutamicum MP proteins are shown in the Sequence Listing as odd-numbered SEQ ID NOs and even-numbered SEQ ID NOs, respectively. Computational analyses were performed which classified and/or identified these nucleotide sequences as sequences which encode metabolic pathway proteins, e.g., proteins involved in the methionine or lysine metabolic pathways.

The present invention also pertains to proteins which have an amino acid sequence which is substantially homologous to an amino acid sequence of the invention (e.g., the sequence of an even-numbered SEQ ID NO of the Sequence Listing). As used herein, a protein which has an amino acid sequence which is substantially homologous to a selected amino acid sequence is least about 50% homologous to the selected amino acid sequence, e.g., the entire selected amino acid sequence. A protein which has an amino acid sequence which is substantially homologous to a selected amino acid sequence can also be least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to the selected amino acid sequence.

An MP protein of the invention, or a biologically active portion or fragment thereof, alone or in combination with one or more proteins of the same or different metabolic pathway, can catalyze an enzymatic reaction in one or more amino acid, vitamin, cofactor, nutraceutical, nucleotide, nucleoside, or trehalose metabolic pathways, or have one or more of the activities set forth in Table 1 (e.g., metabolism of methionine or lysine biosynthesis).

Various aspects of the invention are described in further detail in the following subsections:

A. Isolated Nucleic Acid Molecules

One aspect of the invention pertains to isolated nucleic acid molecules that encode MP polypeptides or biologically active portions thereof, as well as nucleic acid fragments sufficient for use as hybridization probes or primers for the identification or amplification of MP-encoding nucleic acid (e.g., MP DNA). As used herein, the term "nucleic acid molecule" is intended to include DNA molecules (e.g., cDNA or genomic DNA) and RNA molecules (e.g., mRNA) and analogs of the DNA or RNA generated using nucleotide analogs. This term also encompasses untranslated sequence located at both the 3' and 5' ends of the coding region of the gene: at least about 100 nucleotides of sequence upstream from the 5' end of the coding region and at least about 20 nucleotides of sequence downstream from the 3' end of the coding region of the gene.

The nucleic acid molecule can be single-stranded or double-stranded, but preferably is double-stranded DNA. An "isolated" nucleic acid molecule is one which is separated from other nucleic acid molecules which are present in the natural source of the nucleic acid. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated MP nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived (e.g., a C. glutamicum cell). Moreover, an "isolated" nucleic acid molecule, such as a DNA molecule, can be substantially free of other cellular material, or culture medium when produced by recombinant techniques, or chemical precursors or other chemicals when chemically synthesized.

A nucleic acid molecule of the present invention, e.g., a nucleic acid molecule having a nucleotide sequence of an odd-numbered SEQ ID NO of the Sequence Listing, or a portion thereof, can be isolated using standard molecular biology techniques and the sequence information provided herein. For example, a C. glutamicum MP DNA can be isolated from a C. glutamicum library using all or portion of one of the odd-numbered SEQ ID NO sequences of the Sequence Listing as a hybridization probe and standard hybridization techniques (e.g., as described in Sambrook, J., Fritsh, E. F., and Maniatis, T. *Molecular Cloning. A Laboratory Manual. 2nd, ed., Cold Spring Harbor Laboratory*, Cold Spring Harbor Laboratory Press, Cold Spring Harbor, N.Y., 1989). Moreover, a nucleic acid molecule encompassing all or a portion of one of the nucleic acid sequences of the invention (e.g., an odd-numbered SEQ ID NO:) can be isolated by the polymerase chain reaction using oligonucleotide primers designed based upon this sequence (e.g., a nucleic acid molecule encompassing all or a portion of one of the nucleic acid sequences of the invention (e.g., an odd-numbered SEQ ID NO of the Sequence Listing) can be isolated by the polymerase chain reaction using oligonucleotide primers designed based upon this same sequence). For example, mRNA can be isolated from normal endothelial cells (e.g., by the guanidinium-thiocyanate extraction procedure of Chirgwin et al. (1979) *Biochemistry* 18: 5294-5299) and DNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon one of the nucleotide sequences shown in the Sequence Listing. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to an MP nucleotide sequence can be prepared by standard synthetic techniques, e.g., using an automated DNA synthesizer.

In a preferred embodiment, an isolated nucleic acid molecule of the invention comprises one of the nucleotide sequences shown in the Sequence Listing. The nucleic acid sequences of the invention, as set forth in the Sequence Listing, correspond to the *Corynebacterium glutamicum* MP DNAs of the invention. This DNA comprises sequences encoding MP proteins (i.e., the "coding region", indicated in each odd-numbered SEQ ID NO: sequence in the Sequence Listing), as well as 5' untranslated sequences and 3' untranslated sequences, also indicated in each odd-numbered SEQ ID NO: in the Sequence Listing. Alternatively, the nucleic acid molecule can comprise only the coding region of any of the nucleic acid sequences of the Sequence Listing.

For the purposes of this application, it will be understood that some of the MP nucleic acid and amino acid sequences set forth in the Sequence Listing have an identifying RXA, RXN, RXS, or RXC number having the designation "RXA", "RXN", "RXS", or "RXC" followed by 5 digits (i.e., RXA, RXN, RXS, or RXC). Each of the nucleic acid sequences comprises up to three parts: a 5' upstream region, a coding region, and a downstream region. Each of these three regions is identified by the same RXA, RXN, RXS, or RXC designation to eliminate confusion. The recitation "one of the odd-numbered sequences of the Sequence Listing", then, refers to any of the nucleic acid sequences in the Sequence Listing, which may also be distinguished by their differing RXA, RXN, RXS, or RXC designations. The coding region of each of these sequences is translated into a corresponding amino acid sequence, which is also set forth in the Sequence Listing, as an even-numbered SEQ ID NO: immediately following the corresponding nucleic acid sequence. For example, the coding region for RXA00115 is set forth in SEQ ID NO:69, while the amino acid sequence which it encodes is set forth as SEQ ID NO:70. The sequences of the nucleic acid molecules of the invention are identified by the same RXA, RXN, RXS, or RXC designations as the amino acid molecules which they encode, such that they can be readily correlated. For example, the amino acid sequences designated RXA00115, RXN00403, and RXS03158 are translations of the coding regions of the nucleotide sequences of nucleic acid molecules RXA00115, RXN00403, and RXS03158, respectively. The correspondence between the RXA, RXN, RXS, and RXC nucleotide and amino acid sequences of the invention and their assigned SEQ ID NOs is set forth in Table 1.

Several of the genes of the invention are "F-designated genes". An F-designated gene includes those genes set forth in Table 1 which have an 'F' in front of the RXA, RXN, RXS, or RXC designation. For example, SEQ ID NO:77, designated, as indicated on Table 1, as "F RXA00254", is an F-designated gene.

Also listed on Table 1 are the metZ (or metY) and metC genes (designated as SEQ ID NO:1 and SEQ ID NO:3, respectively. The corresponding amino acid sequence encoded by the metZ and metC genes are designated as SEQ ID NO:2 and SEQ ID NO:5, respectively.

In one embodiment, the nucleic acid molecules of the present invention are not intended to include those compiled in Table 2.

In another preferred embodiment, an isolated nucleic acid molecule of the invention comprises a nucleic acid molecule which is a complement of one of the nucleotide sequences of the invention (e.g., a sequence of an odd-numbered SEQ ID NO: of the Sequence Listing), or a portion thereof. A nucleic acid molecule which is complementary to one of the nucleotide sequences of the invention is one which is sufficiently complementary to one of the nucleotide sequences shown in the Sequence Listing (e.g., the sequence of an odd-numbered SEQ ID NO:) such that it can hybridize to one of the nucleotide sequences of the invention, thereby forming a stable duplex.

In still another preferred embodiment, an isolated nucleic acid molecule of the invention comprises a nucleotide sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to a nucleotide sequence of the invention (e.g., a sequence of an odd-numbered SEQ ID NO: of the Sequence Listing), or a portion thereof. Ranges and identity values intermediate to the above-recited ranges, (e.g., 70-90% identical or 80-95% identical) are also intended to be encompassed by the present invention. For example, ranges of identity values using a combination of any of the above values recited as upper and/or lower limits are intended to be included. In an additional preferred embodiment, an isolated nucleic acid molecule of the invention comprises a nucleotide sequence which hybridizes, e.g., hybridizes under stringent conditions, to one of the nucleotide sequences of the invention, or a portion thereof.

Moreover, the nucleic acid molecule of the invention can comprise only a portion of the coding region of the sequence of one of the odd-numbered SEQ ID NOs of the Sequence Listing, for example a fragment which can be used as a probe or primer or a fragment encoding a biologically active portion of an MP protein. The nucleotide sequences determined from the cloning of the MP genes from *C. glutamicum* allows for the generation of probes and primers designed for use in identifying and/or cloning MP homologues in other cell types and organisms, as well as MP homologues from other *Corynebacteria* or related species. The probe/primer typically comprises substantially purified oligonucleotide. The oligonucleotide typically comprises a region of nucleotide sequence that hybridizes under stringent conditions to at least about 12, preferably about 25, more preferably about 40, 50 or 75 consecutive nucleotides of a sense strand of one of the nucleotide sequences of the invention (e.g., a sequence of one of the odd-numbered SEQ ID NOs of the Sequence Listing), an anti-sense sequence of one of these sequences, or naturally occurring mutants thereof. Primers based on a nucleotide sequence of the invention can be used in PCR reactions to clone MP homologues. Probes based on the MP nucleotide sequences can be used to detect transcripts or genomic sequences encoding the same or homologous proteins. In preferred embodiments, the probe further comprises a label group attached thereto, e.g. the label group can be a radioisotope, a fluorescent compound, an enzyme, or an enzyme co-factor. Such probes can be used as a part of a diagnostic test kit for identifying cells which misexpress an MP protein, such as by measuring a level of an MP-encoding nucleic acid in a sample of cells from a subject e.g., detecting MP mRNA levels or determining whether a genomic MP gene has been mutated or deleted.

In one embodiment, the nucleic acid molecule of the invention encodes a protein or portion thereof which includes an amino acid sequence which is sufficiently homologous to an amino acid sequence of the invention (e.g., a sequence of an even-numbered SEQ ID NO of the Sequence Listing) such that the protein or portion thereof maintains the ability to catalyze an enzymatic reaction in an amino acid, vitamin, cofactor, nutraceutical, nucleotide, nucleoside, or trehalose metabolic pathway. As used herein, the language "sufficiently homologous" refers to proteins or portions thereof which have amino acid sequences which include a minimum number of identical or equivalent (e.g., an amino acid residue which has a similar side chain as an amino acid residue in a sequence of one of the even-numbered SEQ ID NOs of the Sequence Listing) amino acid residues to an amino acid sequence of the invention such that the protein or portion thereof is able to catalyze an enzymatic reaction in a *C. glutamicum* amino acid, vitamin, cofactor, nutraceutical, nucleotide, nucleoside or trehalose metabolic pathway. Protein members of such metabolic pathways, as described herein, function to catalyze the biosynthesis or degradation of one or more of: amino acids, vitamins, cofactors, nutraceuticals, nucleotides, nucleosides, or trehalose. Examples of such activities are also described herein. Thus, "the function of an MP protein" contributes to the overall functioning of one or more such metabolic pathway and contributes, either directly or indirectly, to the yield, production, and/or efficiency of production of one or more fine chemicals. Examples of MP protein activities are set forth in Table 1.

In another embodiment, the protein is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to an entire amino acid sequence of the invention (e.g., a sequence of an even-numbered SEQ ID NO: of the Sequence Listing).

Portions of proteins encoded by the MP nucleic acid molecules of the invention are preferably biologically active portions of one of the MP proteins. As used herein, the term "biologically active portion of an MP protein" is intended to include a portion, e.g., a domain/motif, of an MP protein that catalyzes an enzymatic reaction in one or more *C. glutamicum* amino acid, vitamin, cofactor, nutraceutical, nucleotide, nucleoside, or trehalose metabolic pathways, or has an activity as set forth in Table 1. To determine whether an MP protein or a biologically active portion thereof can catalyze an enzymatic reaction in an amino acid, vitamin, cofactor, nutraceutical, nucleotide, nucleoside, or trehalose metabolic pathway, an assay of enzymatic activity may be performed. Such assay methods are well known to those of ordinary skill in the art, as detailed in Example 8 of the Exemplification.

Additional nucleic acid fragments encoding biologically active portions of an MP protein can be prepared by isolating a portion of one of the amino acid sequences of the invention (e.g., a sequence of an even-numbered SEQ ID NO: of the Sequence Listing), expressing the encoded portion of the MP protein or peptide (e.g., by recombinant expression in vitro) and assessing the activity of the encoded portion of the MP protein or peptide.

The invention further encompasses nucleic acid molecules that differ from one of the nucleotide sequences of the invention (e.g., a sequence of an odd-numbered SEQ ID NO: of the Sequence Listing) (and portions thereof) due to degeneracy of the genetic code and thus encode the same MP protein as that encoded by the nucleotide sequences of the invention. In another embodiment, an isolated nucleic acid molecule of the invention has a nucleotide sequence encoding a protein having an amino acid sequence shown in the Sequence Listing (e.g., an even-numbered SEQ ID NO:). In a still further embodiment, the nucleic acid molecule of the invention encodes a full length *C. glutamicum* protein which is substantially homologous to an amino acid sequence of the invention (encoded by an open reading frame shown in an odd-numbered SEQ ID NO: of the Sequence Listing).

It will be understood by one of ordinary skill in the art that in one embodiment the sequences of the invention are not meant to include the sequences of the prior art, such as those Genbank sequences set forth in Table 2, which was available prior to the present invention. In one embodiment, the invention includes nucleotide and amino acid sequences having a percent identity to a nucleotide or amino acid sequence of the invention which is greater than that of a sequence of the prior art (e.g., a Genbank sequence (or the protein encoded by such a sequence) set forth in Table 2). For example, the invention includes a nucleotide sequence which is greater than and/or at least 45% identical to the nucleotide sequence designated RXA00657 SEQ ID NO:5 One of ordinary skill in the art would be able to calculate the lower threshold of percent identity for any given sequence of the invention by examining the GAP-calculated percent identity scores set forth in Table 4 for each of the three top hits for the given sequence, and by subtracting the highest GAP-calculated percent identity from 100 percent. One of ordinary skill in the art will also appreciate that nucleic acid and amino acid sequences having percent identities greater than the lower threshold so calculated (e.g., at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%; 93%, 94%, and even more preferably at least about 95%, 96%, 97%, 98%, 99%, 99.7% or more identical) are also encompassed by the invention.

In addition to the *C. glutamicum* MP nucleotide sequences set forth in the Sequence Listing as odd-numbered SEQ ID NOs, it will be appreciated by one of ordinary skill in the art that DNA sequence polymorphisms that lead to changes in the amino acid sequences of MP proteins may exist within a population (e.g., the *C. glutamicum* population). Such genetic polymorphism in the MP gene may exist among individuals within a population due to natural variation. As used herein, the terms "gene" and "recombinant gene" refer to nucleic acid molecules comprising an open reading frame encoding an MP protein, preferably a *C. glutamicum* MP protein. Such natural variations can typically result in 1-5% variance in the nucleotide sequence of the MP gene. Any and all such nucleotide variations and resulting amino acid polymorphisms in MP that are the result of natural variation and that do not alter the functional activity of MP proteins are intended to be within the scope of the invention.

Nucleic acid molecules corresponding to natural variants and non-*C. glutamicum* homologues of the *C. glutamicum* MP DNA of the invention can be isolated based on their homology to the *C. glutamicum* MP nucleic acid disclosed herein using the *C. glutamicum* DNA, or a portion thereof, as a hybridization probe according to standard hybridization techniques under stringent hybridization conditions. Accordingly, in another embodiment, an isolated nucleic acid molecule of the invention is at least 15 nucleotides in length and hybridizes under stringent conditions to the nucleic acid molecule comprising a nucleotide sequence of an odd-numbered SEQ ID NO: of the Sequence Listing. In other embodiments, the nucleic acid is at least 30, 50, 100, 250 or more nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to one of ordinary skill in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. Preferably, an isolated nucleic acid molecule of the invention that hybridizes under stringent conditions to a nucleotide sequence of the invention corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein). In one embodiment, the nucleic acid encodes a natural *C. glutamicum* MP protein.

In addition to naturally-occurring variants of the MP sequence that may exist in the population, one of ordinary skill in the art will further appreciate that changes can be introduced by mutation into a nucleotide sequence of the invention, thereby leading to changes in the amino acid sequence of the encoded MP protein, without altering the functional ability of the MP protein. For example, nucleotide substitutions leading to amino acid substitutions at "non-essential" amino acid residues can be made in a nucleotide sequence of the invention. A "non-essential" amino acid residue is a residue that can be altered from the wild-type sequence of one of the MP proteins (e.g., an even-numbered SEQ ID NO: of the Sequence Listing) without altering the activity of said MP protein, whereas an "essential" amino-acid residue is required for MP protein activity. Other amino acid residues, however, (e.g., those that are not conserved or only semi-conserved in the domain having MP activity) may not be essential for activity and thus are likely to be amenable to alteration without altering MP activity.

Accordingly, another aspect of the invention pertains to nucleic acid molecules encoding MP proteins that contain changes in amino acid residues that are not essential for MP activity. Such MP proteins differ in amino acid sequence from a sequence of an even-numbered SEQ ID NO: of the Sequence Listing yet retain at least one of the MP activities described herein. In one embodiment, the isolated nucleic acid molecule comprises a nucleotide sequence encoding a protein, wherein the protein comprises an amino acid sequence at least about 50% homologous to an amino acid sequence of the invention and is capable of catalyzing an enzymatic reaction in an amino acid, vitamin, cofactor, nutraceutical, nucleotide, nucleoside, or trehalose metabolic pathway, or has one or more activities set forth in Table 1. Preferably, the protein encoded by the nucleic acid molecule is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% homologous to one of the amino acid sequences of the invention.

To determine the percent homology of two amino acid sequences (e.g., one of the amino acid sequences of the invention and a mutant form thereof) or of two nucleic acids, the sequences are aligned for optimal comparison purposes (e.g., gaps can be introduced in the sequence of one protein or nucleic acid for optimal alignment with the other protein or nucleic acid). The amino acid residues or nucleotides at corresponding amino acid positions or nucleotide positions are then compared. When a position in one sequence (e.g., one of the amino acid sequences of the invention) is occupied by the same amino acid residue or nucleotide as the corresponding position in the other sequence (e.g., a mutant form of the amino acid sequence), then the molecules are homologous at that position (i.e., as used herein amino acid or nucleic acid "homology" is equivalent to amino acid or nucleic acid "identity"). The percent homology between the two sequences is a function of the number of identical positions shared by the sequences (i.e., % homology=# of identical positions/total # of positions×100).

An isolated nucleic acid molecule encoding an MP protein homologous to a protein sequence of the invention (e.g., a sequence of an even-numbered SEQ ID NO: of the Sequence Listing) can be created by introducing one or more nucleotide substitutions, additions or deletions into a nucleotide sequence of the invention such that one or more amino acid substitutions, additions or deletions are introduced into the encoded protein. Mutations can be introduced into one of the nucleotide sequences of the invention by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in an MP protein is preferably replaced with another amino acid residue from the same side chain family. Alternatively, in another embodiment, mutations can be introduced randomly along all or part of an MP coding sequence, such as by saturation mutagenesis, and the resultant mutants can be screened for an MP activity described herein to identify mutants that retain MP activity. Following mutagenesis of the nucleotide sequence of one of the odd-numbered SEQ ID NOs of the Sequence Listing, the encoded protein can be expressed recombinantly and the activity of the protein can be determined using, for example, assays described herein (see Example 8 of the Exemplification).

In addition to the nucleic acid molecules encoding MP proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded DNA molecule or complementary to an mRNA sequence. Accordingly, an antisense nucleic acid can hydrogen bond to a sense nucleic acid. The antisense nucleic acid can be complementary to an entire MP coding strand, or to only a portion thereof. In one embodiment, an antisense nucleic acid molecule is antisense to a "coding region" of the coding strand of a nucleotide sequence encoding an MP protein. The term "coding region" refers to the region of the nucleotide sequence comprising codons which are translated into amino acid residues (e.g., the entire coding region of SEQ ID NO.:1 (metZ) comprises nucleotides 363 to 1673). In another embodiment, the antisense nucleic acid molecule is antisense to a "noncoding region" of the coding strand of a nucleotide sequence encoding MP. The term "noncoding region" refers to 5' and 3' sequences which flank the coding region that are not translated into amino acids (i.e., also referred to as 5' and 3' untranslated regions).

Given the coding strand sequences encoding MP disclosed herein (e.g., the sequences set forth as odd-numbered SEQ ID NOs in the Sequence Listing), antisense nucleic acids of the invention can be designed according to the rules of Watson and Crick base pairing. The antisense nucleic acid molecule can be complementary to the entire coding region of MP mRNA, but more preferably is an oligonucleotide which is antisense to only a portion of the coding or noncoding region of MP mRNA. For example, the antisense oligonucleotide can be complementary to the region surrounding the translation start site of MP mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a cell or generated in situ such that they hybridize with or bind to cellular mRNA and/or genomic DNA encoding an MP protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. The antisense molecule can be modified such that it specifically binds to a receptor or an antigen expressed on a selected cell surface, e.g., by linking the antisense nucleic acid molecule to a peptide or an antibody which binds to a cell surface receptor or antigen. The antisense nucleic acid molecule can also be delivered to cells using the vectors described herein. To achieve sufficient intracellular concentrations of the antisense molecules, vector constructs in which the antisense nucleic acid molecule is placed under the control of a strong prokaryotic, viral, or eukaryotic promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave MP mRNA transcripts to thereby inhibit translation of MP mRNA. A ribozyme having specificity for an MP-encoding nucleic acid can be designed based upon the nucleotide sequence of an MP DNA disclosed herein (i.e., SEQ ID NO:1 (metZ). For example, a derivative of a *Tetrahymena* L-19 IVS RNA can be constructed in which the nucleotide sequence of the active site is complementary to the nucleotide sequence to be cleaved in an MP-encoding mRNA. See, e.g., Cech et al. U.S. Pat. No. 4,987,071 and Cech et al. U.S. Pat. No. 5,116,742. Alternatively, MP mRNA can be used to select a catalytic RNA having a specific ribonuclease activity from a pool of RNA molecules. See, e.g., Bartel, D. and Szostak, J. W. (1993) *Science* 261:1411-1418.

Alternatively, MP gene expression can be inhibited by targeting nucleotide sequences complementary to the regulatory region of an MP nucleotide sequence (e.g., an MP promoter and/or enhancers) to form triple helical structures that prevent transcription of an MP gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

Another aspect of the invention pertains to combinations of genes involved in methionine and/or lysine metabolism and the use of to combinations of genes involved in methionine and/or lysine metabolism in the methods of the invention. Preferred combinations are the combination of metZ with metC, metB (encoding Cystathionine-Synthase), metA (encoding homoserine-O-acetyltransferase), metE (encoding Methionine Synthase), metH (encoding Methionine Synthase), hom (encoding homoserine dehydrogenase), asd (encoding aspartatesemialdehyd dehydrogenase), lysC/ask (encoding aspartokinase) and rxa00657 (herein designated as SEQ ID NO.:5), dapA, (gene encoding DIHYDRODIPICOLINATE SYNTHASE), dapB (gene encoding DIHYDRODIPICOLINATE REDUCTASE), dapC (gene encoding 2,3,4,5-tetrahydropyridine-2-carboxylate N-succinyltransferase), dapD/argD (gene encoding acetylornithine transaminase), dapE (gene encoding succinyldiaminopimelate desuccinylase), dapF (gene encoding diaminopimelate epimerase), lysA (gene encoding diaminopimelate decarboxylase), ddh (gene encoding diaminopimelate dehydrogenase), lysE (gene encoding for the lysine exporter), lysG (gene encoding for the exporter regulator), hsk (gene encoding homoserine kinase) as well as genes involved in anaplerotic reaction such as ppc (gene encoding phosphoenolpyruvate carboxylase), ppcK (gene encoding phosphoenolpyruvate carboxykinase), pycA (gene encoding pyruvate carboxylase), accD, accA, accB, accC (genes encoding for subunits of acetyl-CoA-carboxylase), as well as genes of the pentose-phosphate pathway, gpdh genes encoding glucose-6-phophate-dehydrogenase, opcA, pgdh (gene encoding 6-phosphogluconate-dehydrogenase), ta (gene encoding transaldolase), tk (gene encoding gene encoding transketolase), pgl (gene encoding 6-PHOSPHOGLUCONO-LACTONASE), ripe (gene encoding RIBULOSE-PHOSPHATE 3-EPIMERASE) rpe (gene encoding RIBOSE 5-PHOSPHATE EPIMERASE) or combinations of the above-mentioned genes of the pentose-phosphate-pathways, or other MP genes of the invention.

The genes may be altered in their nucleotide sequence and in the corresponding amino acid sequence resulting in derivatives in such a way that their activity is altered under physiological conditions which leads to an increase in productivity and/or yield of a desired fine chemical, e.g., an amino acid such as methionine or lysine. One class of such alterations or derivatives is well known for the nucleotide sequence of the ask gene encoding aspartokinase. These alterations lead to removal of feed back inhibition by the amino acids lysine and threonine and subsequently to lysine overproduction. In a preferred embodiment the metZ gene or altered forms of the metZ gene are used in a *Corynebacterium* strain in combination with ask, hom, metA and metH or derivatives of these genes. In another preferred embodiment metZ or altered forms of the metZ gene are used in a *Corynebacterium* strain in combination with ask, hom, metA and metE or derivatives of these genes. In a more preferred embodiment, the gene combinations metZ or altered forms of the metZ gene are combined with ask, hom, metA and metH or derivatives of these genes, or metZ is combined with ask hom, metA and metE or derivatives of these genes in a *Corynebacterium* strain and sulfur sources such as sulfates, thiosulfates, sulfites and also more reduced sulfur sources such as $H_2S$ and sulfides and derivatives are used in the growth medium. Also, sulfur sources such as methyl mercaptan, methanesulfonic acid, thioglycolates, thiocyanates, thiourea, sulfur containing amino acids such as cysteine and other sulfur containing compounds can be used. Another aspect of the invention pertains to the use of the above mentioned gene combinations in a *Corynebacterium* strain which is, before or after introduction of the genes, mutagenized by radiation or by mutagenic chemicals well-known to one of ordinary skill in the art and selected for resistance against high concentrations of the fine chemical of interest, e.g. lysine or methionine or analogues of the desired fine chemical such as the methionine analogues ethionine, methyl methionine, or others. In another embodiment, the gene combinations mentioned above can be expressed in a *Corynebacterium* strain having particular gene disruptions. Preferred are gene disruptions that encode proteins that favor carbon flux to undesired metabolites. Where methionine is the desired fine chemical the formation of lysine may be unfavorable. In such a case the combination of the above mentioned genes should proceed in a *Corynebacterium* strain bearing a gene disruption of the lysA gene (encoding diaminopimelate decarboxylase) or the ddh gene (encoding the meso-diaminopimelate dehydrogenase catalysing the conversion of tetrahydropicolinate to meso-diaominopimelate). In a preferred embodiment, a favorable combination of the above-mentioned genes are all altered in such a way that their gene products are not feed back inhibited by end products or metabolites of the biosynthetic pathway leading to the desired fine chemical. In the case that the desired fine chemical is methionine, the gene combinations may be expressed in a strain previously treated with mutagenic agents or radiation and selected for the above-mentioned resistance. Additionally, the strain should be grown in a growth medium containing one or more of the above mentioned sulfur sources.

In another embodiment of the invention, a gene was identified from the genome of *Corynebacterium glutamicum* as a gene coding for a hypothetical transcriptional regulatory protein. This gene is described as RXA00657. The nucleotide sequence of RXA00657 corresponds to SEQ ID NO:5. The amino acid sequence of RXA00657 corresponds to SEQ ID NO:6. It was found that when the RXA00657 gene, as well as upstream and downstream regulatory regions described in the examples, was cloned into a vector capable of replicating in *Corynebacterium glutamicum* and transformed and expressed in a lysine producing strain such as ATCC13286, that this strain produced more lysine compared to the strain transformed with the same plasmid lacking the aforementioned nucleotide fragment RXA00657. In addition to the observation that the lysine titer was increased in the mentioned strain, the selectivity determined by the molar amount of lysine produced compared to the molar amount of sucrose consumed was increased (see Example 14). Overexpression of RXA00657 in combination with the overexpression of other genes either directly involved in the lysine specific pathway such as lysC, dapA, dapB, dapC, dapD, dapF, ddh, lysE, lysG, and lysR results in an increase in the production of lysine compared to RXA00657 alone.

B. Recombinant Expression Vectors and Host Cells

Another aspect of the invention pertains to vectors, preferably expression vectors, containing a nucleic acid encoding an MP protein (or a portion thereof) or combinations of genes wherein at least one gene encodes for an MP protein. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, repressor binding sites, activator binding sites, enhancers and other expression control elements (e.g., terminators, polyadenylation signals, or other elements of mRNA secondary structure). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells. Preferred regulatory sequences are, for example, promoters such as cos-, tac-, trp-, tet-, trp-tet-, lpp-, lac-, lpp-lac-, lacI$_q$, T7-, T5-, T3-, gal-, trc-, ara-, SP6-, arny, SPO2, $\lambda$-P$_R$- or $\lambda$ P$_L$, which are used preferably in bacteria. Additional regulatory sequences are, for example, promoters from yeasts and fungi, such as ADC1, MF$\alpha$, AC, P-60, CYC1, GAPDH, TEF, rp28, ADH, promoters from plants such as CaMV/$^{35}$S, SSU, OCS, lib4, usp, STLS1, B33, nos or ubiquitin- or phaseolin-promoters. It is also possible to use artificial promoters. It will be appreciated by one of ordinary skill in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., MP proteins, mutant forms of MP proteins, fusion proteins, etc.).

The recombinant expression vectors of the invention can be designed for expression of MP proteins in prokaryotic or eukaryotic cells. For example, MP genes can be expressed in bacterial cells such as *C. glutamicum*, insect cells (using baculovirus expression vectors), yeast and other fungal cells (see Romanos, M. A. et al. (1992) "Foreign gene expression in yeast: a review", Yeast 8: 423-488; van den Hondel, C. A. M. J. J. et al. (1991) "Heterologous gene expression in filamentous fungi" in: More Gene Manipulations in Fungi, J. W. Bennet & L. L. Lasure, eds., p. 396-428: Academic Press: San Diego; and van den Hondel, C. A. M. J. J. & Punt, P. J. (1991) "Gene transfer systems and vector development for filamentous fungi, in: Applied Molecular Genetics of Fungi, Peberdy, J. F. et al., eds., p. 1-28, Cambridge University Press: Cambridge), algae and multicellular plant cells-(see Schmidt, R. and Willmitzer, L. (1988) High efficiency *Agrobacterium tumefaciens*-mediated transformation of *Arabidopsis thaliana* leaf and cotyledon explants" *Plant Cell Rep.*: 583-586), or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out with vectors containing constitutive or inducible promoters directing the expression of either fusion or non-fusion proteins. Fusion vectors add a number of amino acids to a protein encoded therein, usually to the amino terminus of the recombinant protein but also to the C-terminus or fused within suitable regions in the proteins. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase.

Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. In one embodiment, the coding sequence of the MP protein is cloned into a pGEX expression vector to create a vector encoding a fusion protein comprising, from the N-terminus to the C-terminus, GST-thrombin cleavage site-X protein. The fusion protein can be purified by affinity chromatography using glutathione-agarose resin. Recombinant MP protein unfused to GST can be recovered by cleavage of the fusion protein with thrombin.

Examples of suitable inducible non-fusion *E. coli* expression vectors include pTrc (Amann et al., (1988) *Gene* 69:301-315) pLG338, pACYC184, pBR322, pUC18, pUC19, pKC30, pRep4, pHS1, pHS2, pPLc236, pMBL24, pLG200, pUR290, pIN-III113-B1, λgt11, pBdCl, and pET 11d (Studier et al., *Gene Expression Technology: Methods in Enzymology* 185, Academic Press, San Diego, Calif. (1990) 60-89; and Pouwels et al., eds. (1985) Cloning Vectors. Elsevier: New York IBSN 0 444 904018). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter. For transformation of other varieties of bacteria, appropriate vectors may be selected. For example, the plasmids pIJ101, pIJ364, pIJ702 and pIJ361 are known to be useful in transforming *Streptomyces*, while plasmids pUB110, pC194, or pBD214 are suited for transformation of *Bacillus* species. Several plasmids of use in the transfer of genetic information into *Corynebacterium* include pHM1519, pBL1, pSA77, or pAJ667 (Pouwels et al., eds. (1985) Cloning Vectors. Elsevier: New York IBSN 0 444 904018).

One strategy to maximize recombinant protein expression is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in the bacterium chosen for expression, such as *C. glutamicum* (Wada et al. (1992) *Nucleic Acids Res.* 20:2111-2118). Such alteration of nucleic acid sequences of the invention can be carried out by standard DNA synthesis techniques.

In another embodiment, the MP protein expression vector is a yeast expression vector. Examples of vectors for expression in yeast *S. cerevisiae* include pYepSec1 (Baldari, et al., (1987) *Embo J.* 6:229-234), 2µ, pAG-1, Yep6, Yep13, pEMBLYe23, pMFa (Kurjan and Herskowitz, (1982) *Cell* 30:933-943), pJRY88 (Schultz et al., (1987) *Gene* 54:113-123), and pYES2 (Invitrogen Corporation, San Diego, Calif.). Vectors and methods for the construction of vectors appropriate for use in other fungi, such as the filamentous fungi, include those detailed in: van den Hondel, C. A. M. J. J. & Punt, P. J. (1991) "Gene transfer systems and vector development for filamentous fungi, in: Applied Molecular Genetics of Fungi, J. F. Peberdy, et al., eds., p. 1-28, Cambridge University Press: Cambridge, and Pouwels et al., eds. (1985) Cloning Vectors. Elsevier: New York (IBSN 0 444 904018):

Alternatively, the MP proteins of the invention can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In another embodiment, the MP proteins of the invention may be expressed in unicellular plant cells (such as algae) or in plant cells from higher plants (e.g., the spermatophytes, such as crop plants). Examples of plant expression vectors include those detailed in: Becker, D., Kemper, E., Schell, J. and Masterson, R. (1992) "New plant binary vectors with selectable markers located proximal to the left border", *Plant Mol. Biol.* 20: 1195-1197; and Bevan, M. W. (1984) "Binary *Agrobacterium* vectors for plant transformation", *Nucl. Acid. Res.* 12: 8711-8721, and include pLGV23, pGHlac+, pBIN19, pAK2004, and pDH51 (Pouwels et al., eds. (1985) Cloning Vectors. Elsevier: New York IBSN 0 444 904018).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning: A Laboratory Manual. 2nd, ed,* Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *PNAS* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to MP mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a recombinant expression vector of the invention has been introduced. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, an MP protein can be expressed in bacterial cells such as *C. glutamicum*, insect cells, yeast or mammalian cells (such as Chinese hamster ovary cells (CHO) or COS cells). Other suitable host cells are known to those of ordinary skill in the art. Microorganisms related to *Corynebacterium glutamicum* which may be conveniently used as host cells for the nucleic acid and protein molecules of the invention are set forth in Table 3.

Vector DNA can be introduced into prokaryotic or eukaryotic cells via conventional transformation or transfection techniques. As used herein, the terms "transformation" and "transfection", "conjugation" and "transduction" are intended to refer to a variety of art-recognized techniques for introducing foreign nucleic acid (e.g., linear DNA or RNA (e.g., a linearized vector or a gene construct alone without a vector) or nucleic acid in the form of a vector (e.g., a plasmid, phage, phasmid, phagemid, transposon or other DNA) into a host cell, including calcium phosphate or calcium chloride co-precipitation, DEAE-dextran-mediated transfection, lipofection, natural competence, chemical-mediated transfer, or electroporation. Suitable methods for transforming or transfecting host cells can be found in Sambrook, et al. (*Molecular Cloning: A Laboratory Manual. 2nd, ed., Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding an MP protein or can be introduced on a separate vector. Cells stably transfected with the introduced nucleic acid can be identified by drug selection (e.g., cells that have incorporated the selectable marker gene will survive, while the other cells die).

To create a homologous recombinant microorganism, a vector is prepared which contains at least a portion of an MP gene into which a deletion, addition or substitution has been introduced to thereby alter, e.g., functionally disrupt, the MP gene. Preferably, this MP gene is a *Corynebacterium glutamicum* MP gene, but it can be a homologue from a related bacterium or even from a mammalian, yeast, or insect source. In a preferred embodiment, the vector is designed such that, upon homologous recombination, the endogenous MP gene is functionally disrupted (i.e., no longer encodes a functional protein; also referred to as a "knock out" vector). Alternatively, the vector can be designed such that, upon homologous recombination, the endogenous MP gene is mutated or otherwise altered but still encodes functional protein (e.g., the upstream regulatory region can be altered to thereby alter the expression of the endogenous MP protein). In the homologous recombination vector, the altered portion of the MP gene is flanked at its 5' and 3' ends by additional nucleic acid of the MP gene to allow for homologous recombination to occur between the exogenous MP gene carried by the vector and an endogenous MP gene in a microorganism. The additional flanking MP nucleic acid is of sufficient length for successful homologous recombination with the endogenous gene. Typically, several kilobases of flanking DNA (both at the 5' and 3' ends) are included in the vector (see e.g., Thomas, K. R., and Capecchi, M. R. (1987) Cell 51: 503 for a description of homologous recombination vectors). The vector is introduced into a microorganism (e.g., by electroporation) and cells in which the introduced MP gene has homologously recombined with the endogenous MP gene are selected, using art-known techniques.

In another embodiment, recombinant microorganisms can be produced which contain selected systems which allow for regulated expression of the introduced gene. For example, inclusion of an MP gene on a vector placing it under control of the lac operon permits expression of the MP gene only in the presence of IPTG. Such regulatory systems are well known in the art.

In another embodiment, an endogenous MP gene in a host cell is disrupted (e.g., by homologous recombination or other genetic means known in the art) such that expression of its protein product does not occur. In another embodiment, an endogenous or introduced MP gene in a host cell has been altered by one or more point mutations, deletions, or inversions, but still encodes a functional MP protein. In still another embodiment, one or more of the regulatory regions (e.g., a promoter, repressor, or inducer) of an MP gene in a microorganism has been altered (e.g., by deletion, truncation, inversion, or point mutation) such that the expression of the MP gene is modulated. One of ordinary skill in the art will appreciate that host cells containing more than one of the described MP gene and protein modifications may be readily produced using the methods of the invention, and are meant to be included in the present invention.

A host cell of the invention, such as a prokaryotic or eukaryotic host cell in culture, can be used to produce (i.e., express) an MP protein. Accordingly, the invention further provides methods for producing MP proteins using the host cells of the invention. In one embodiment, the method comprises culturing the host cell of invention (into which a recombinant expression vector encoding an MP protein has been introduced, or into which genome has been introduced a gene encoding a wild-type or altered MP protein) in a suitable medium until MP protein is produced. In another embodiment, the method further comprises isolating MP proteins from the medium or the host cell.

C. Isolated MP Proteins

Another aspect of the invention pertains to isolated MP proteins, and biologically active portions thereof. An "isolated" or "purified" protein or biologically active portion thereof is substantially free of cellular material when produced by recombinant DNA techniques, or chemical precursors or other chemicals when chemically synthesized. The language "substantially free of cellular material" includes preparations of MP protein in which the protein is separated from cellular components of the cells in which it is naturally or recombinantly produced. In one embodiment, the language "substantially free of cellular material" includes preparations of MP protein having less than about 30% (by dry weight) of non-MP protein (also referred to herein as a "contaminating protein"), more preferably less than about 20% of non-MP protein, still more preferably less than about 10% of non-MP protein, and most preferably less than about 5% non-MP protein. When the MP protein or biologically active portion thereof is recombinantly produced, it is also preferably substantially free of culture medium, i.e., culture medium represents less than about 20%, more preferably less than about 10%, and most preferably less than about 5% of the volume of the protein preparation. The language "substantially free of chemical precursors or other chemicals" includes preparations of MN protein in which the protein is separated from chemical precursors or other chemicals which are involved in the synthesis of the protein. In one embodiment, the language "substantially free of chemical precursors or other chemicals" includes preparations of MP protein having less than about 30% (by dry weight) of chemical precursors or non-MP chemicals, more preferably less than about 20% chemical precursors or non-MP chemicals, still more preferably less than about 10% chemical precursors or non-MP chemicals, and most preferably less than about 5% chemical precursors or non-MP chemicals. In preferred embodiments, isolated proteins or biologically active portions thereof lack contaminating proteins from the same organism from which the MP protein is derived. Typically, such proteins are produced by recombinant expression of, for example, a *C. glutamicum* MP protein in a microorganism such as *C. glutamicum*.

An isolated MP protein or a portion thereof of the invention can catalyze an enzymatic reaction in an amino acid, vitamin, cofactor, nutraceutical, nucleotide, nucleoside, or trehalose metabolic pathway, or has one or more of the activities set forth in Table 1. In preferred embodiments, the protein or portion thereof comprises an amino acid sequence which is sufficiently homologous to an amino acid sequence of the invention (e.g., a sequence of an even-numbered SEQ ID NO: of the Sequence Listing) such that the protein or portion thereof maintains the ability to catalyze an enzymatic reaction in an amino acid, vitamin, cofactor, nutraceutical, nucleotide, nucleoside, or trehalose metabolic pathway. The portion of the protein is preferably a biologically active portion as described herein. In another preferred embodiment, an MP protein of the invention has an amino acid sequence set forth as an even-numbered SEQ ID NO: of the Sequence Listing. In yet another preferred embodiment, the MP protein has an amino acid sequence which is encoded by a nucleotide sequence which hybridizes, e.g., hybridizes under stringent conditions, to a nucleotide sequence of the invention (e.g., a sequence of an odd-numbered SEQ ID NO: of the Sequence Listing). In still another preferred embodiment, the MP protein has an amino acid sequence which is encoded by a nucleotide sequence that is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to one of the nucleic acid sequences of the invention, or a portion thereof. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. The preferred MP proteins of the present invention also preferably possess at least one of the MP activities described herein. For example, a preferred MP protein of the present invention includes an amino acid sequence encoded by a nucleotide sequence which hybridizes, e.g., hybridizes under stringent conditions, to a nucleotide sequence of the invention, and which can catalyze an enzymatic reaction in an amino acid, vitamin, cofactor, nutraceutical, nucleotide, nucleoside, or trehalose metabolic pathway, or which has one or more of the activities set forth in Table 1.

In other embodiments, the MP protein is substantially homologous to an amino acid sequence of the invention (e.g., a sequence of an even-numbered SEQ ID NO: of the Sequence Listing) and retains the functional activity of the protein of one of the amino acid sequences of the invention yet differs in amino acid sequence due to natural variation or mutagenesis, as described in detail in subsection I above. Accordingly, in another embodiment, the MP protein is a protein which comprises an amino acid sequence which is at least about 50%, 51%, 52%, 53%, 54%, 55%, 56%, 57%, 58%, 59%, or 60%, preferably at least about 61%, 62%, 63%, 64%, 65%, 66%, 67%, 68%, 69%, or 70%, more preferably at least about 71%, 72%, 73%, 74%, 75%, 76%, 77%, 78%, 79%, or 80%, 81%, 82%, 83%, 84%, 85%, 86%, 87%, 88%, 89%, or 90%, or 91%, 92%, 93%, 94%, and even more preferably at least about 95%, 96%, 97%, 98%, 99%, 99.7% or more homologous to an entire amino acid sequence of the invention and which has at least one of the MP activities described herein. Ranges and identity values intermediate to the above-recited values, (e.g., 70-90% identical or 80-95% identical) are also intended to be encompassed by the present invention. For example, ranges of identity values using a combination of any of the above values recited as upper and/or lower limits are intended to be included. In another embodiment, the invention pertains to a full length *C. glutamicum* protein which is substantially homologous to an entire amino acid sequence of the invention.

Biologically active portions of an MP protein include peptides comprising amino acid sequences derived from the amino acid sequence of an MP protein, e.g., an amino acid sequence of an even-numbered SEQ ID NO: of the Sequence Listing or the amino acid sequence of a protein homologous to an MP protein, which include fewer amino acids than a full length MP protein or the full length protein which is homologous to an MP protein, and exhibit at least one activity of an MP protein. Typically, biologically active portions (peptides, e.g., peptides which are, for example, 5, 10, 15, 20, 30, 35, 36, 37, 38, 39, 40, 50, 100 or more amino acids in length) comprise a domain or motif with at least one activity of an MP protein. Moreover, other biologically active portions, in which other regions of the protein are deleted, can be prepared by recombinant techniques and evaluated for one or more of the activities described herein. Preferably, the biologically active portions of an MP protein include one or more selected domains/motifs or portions thereof having biological activity.

MP proteins are preferably produced by recombinant DNA techniques. For example, a nucleic acid molecule encoding the protein is cloned into an expression vector (as described above), the expression vector is introduced into a host cell (as described above) and the MP protein is expressed in the host cell. The MP protein can then be isolated from the cells by an appropriate purification scheme using standard protein purification techniques. Alternative to recombinant expression, an MP protein, polypeptide, or peptide can be synthesized chemically using standard peptide synthesis techniques. Moreover, native MP protein can be isolated from cells (e.g., endothelial cells), for example using an anti-MP antibody, which can be produced by standard techniques utilizing an MP protein or fragment thereof of this invention.

The invention also provides MP chimeric or fusion proteins. As used herein, an MP "chimeric protein" or "fusion protein" comprises an MP polypeptide operatively linked to a non-MP polypeptide. An "MP polypeptide" refers to a polypeptide having an amino acid sequence corresponding to MP, whereas a "non-MP polypeptide" refers to a polypeptide having an amino acid sequence corresponding to a protein which is not substantially homologous to the MP protein, e.g., a protein which is different from the MP protein and which is derived from the same or a different organism. Within the fusion protein, the term "operatively linked" is intended to indicate that the MP polypeptide and the non-MP polypeptide are fused in-frame to each other. The non-MP polypeptide can be fused to the N-terminus or C-terminus of the MP polypeptide. For example, in one embodiment the fusion protein is a GST-MP fusion protein in which the MP sequences are fused to the C-terminus of the GST sequences. Such fusion proteins can facilitate the purification of recombinant MP proteins. In another embodiment, the fusion protein is an MP protein containing a heterologous signal sequence at its N-terminus. In certain host cells (e.g., mammalian host cells), expression and/or secretion of an MP protein can be increased through use of a heterologous signal sequence.

Preferably, an MP chimeric or fusion protein of the invention is produced by standard recombinant DNA techniques; For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An MP-encoding nucleic acid can be cloned into such an expression vector such that the fusion moiety is linked in-frame to the MP protein.

Homologues of the MP protein can be generated by mutagenesis, e.g., discrete point mutation or truncation of the MP protein. As used herein, the term "homologue" refers to a variant form of the MP protein which acts as an agonist or antagonist of the activity of the MP protein. An agonist of the MP protein can retain substantially the same, or a subset, of the biological activities of the MP protein. An antagonist of the MP protein can inhibit one or more of the activities of the naturally occurring form of the MP protein, by, for example, competitively binding to a downstream or upstream member of the MP cascade which includes the MP protein. Thus, the *C. glutamicum* MP protein and homologues thereof of the present invention may modulate the activity of one or more metabolic pathways in which MP proteins play a role in this microorganism.

In an alternative embodiment, homologues of the MP protein can be identified by screening combinatorial libraries of mutants, e.g., truncation mutants, of the MP protein for MP protein agonist or antagonist activity. In one embodiment, a variegated library of MP variants is generated by combinatorial mutagenesis at the nucleic acid level and is encoded by a variegated gene library. A variegated library of MP variants can be produced by, for example, enzymatically ligating a mixture of synthetic oligonucleotides into gene sequences such that a degenerate set of potential MP sequences is expressible as individual polypeptides, or alternatively, as a set of larger fusion proteins (e.g., for phage display) containing the set of MP sequences therein. There are a variety of methods which can be used to produce libraries of potential MP homologues from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential MP sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of the MP protein coding can be used to generate a variegated population of MP fragments for screening and subsequent selection of homologues of an MP protein. In one embodiment, a library of coding sequence fragments can be generated by treating a double stranded PCR fragment of an MP coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with S1 nuclease, and ligating the resulting fragment library into an expression vector. By this method, an expression library can be derived which encodes N-terminal, C-terminal and internal fragments of various sizes of the MP protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of MP homologues. The most widely used techniques, which are amenable to high through-put analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recursive ensemble mutagenesis (REM), a new technique which enhances the frequency of functional mutants in the libraries, can be used in combination with the screening assays to identify MP homologues (Arkin and Yourvan (1992) *PNAS* 89:7811-7815; Delgrave et al. (1993) *Protein Engineering* 6(3):327-331).

In another embodiment, cell based assays can be exploited to analyze a variegated MP library, using methods well known in the art.

D. Uses and Methods of the Invention

The nucleic acid molecules, proteins, protein homologues, fusion proteins, primers, vectors, and host cells described herein can be used in one or more of the following methods: identification of *C. glutamicum* and related organisms; mapping of genomes of organisms related to *C. glutamicum*; identification and localization of *C. glutamicum* sequences of interest; evolutionary studies; determination of MP protein regions required for function; modulation of an MP protein activity; modulation of the activity of an MP pathway; and modulation of cellular production of a desired compound, such as a fine chemical.

The MP nucleic acid molecules of the invention have a variety of uses. First, they may be used to identify an organism as being *Corynebacterium glutamicum* or a close relative thereof. Also, they may be used to identify the presence of *C. glutamicum* or a relative thereof in a mixed population of microorganisms. The invention provides the nucleic acid sequences of a number of *C. glutamicum* genes; by probing the extracted genomic DNA of a culture of a unique or mixed population of microorganisms under stringent conditions with a probe spanning a region of a *C. glutamicum* gene which is unique to this organism, one can ascertain whether this organism is present. Although *Corynebacterium glutamicum* itself is not pathogenic to humans, it is related to species which are human pathogens, such as *Corynebacterium diphtheriae*. *Corynebacterium diphtheriae* is the causative agent of diphtheria, a rapidly developing, acute, febrile infection which involves both local and systemic pathology. In this disease, a local lesion develops in the upper respiratory tract and involves necrotic injury to epithelial cells; the bacilli secrete toxin which is disseminated through this lesion to distal susceptible tissues of the body. Degenerative changes brought about by the inhibition of protein synthesis in these tissues, which include heart, muscle, peripheral nerves, adrenals, kidneys, liver and spleen, result in the systemic pathology of the disease. Diphtheria continues to have high incidence in many parts of the world, including Africa, Asia, Eastern Europe and the independent states of the former Soviet Union. An ongoing epidemic of diphtheria in the latter two regions has resulted in at least 5,000 deaths since 1990.

In one embodiment, the invention provides a method of identifying the presence or activity of *Cornyebacterium diphtheriae* in a subject. This method includes detection of one or more of the nucleic acid or amino acid sequences of the invention (e.g., the sequences set forth as odd-numbered or even-numbered SEQ ID NOs, respectively, in the Sequence Listing) in a subject, thereby detecting the presence or activity of *Corynebacterium diphtheriae* in the subject. *C. glutamicum* and *C. diphtheriae* are related bacteria, and many of the nucleic acid and protein molecules in *C. glutamicum* are homologous to *C. diphtheriae* nucleic acid and protein molecules, and can therefore be used to detect *C. diphtheriae* in a subject.

The nucleic acid and protein molecules of the invention may also serve as markers for specific regions of the genome. This has utility not only in the mapping of the genome, but also for functional studies of *C. glutamicum* proteins. For example, to identify the region of the genome to which a particular *C. glutamicum* DNA-binding protein binds, the *C. glutamicum* genome could be digested, and the fragments incubated with the DNA-binding protein. Those which bind the protein may be additionally probed with the nucleic acid molecules of the invention, preferably with readily detectable labels; binding of such a nucleic acid molecule to the genome fragment enables the localization of the fragment to the genome map of *C. glutamicum*, and, when performed multiple times with different enzymes, facilitates a rapid determination of the nucleic acid sequence to which the protein binds. Further, the nucleic acid molecules of the invention may be sufficiently homologous to the sequences of related species such that these nucleic acid molecules may serve as markers for the construction of a genomic map in related bacteria, such as *Brevibacterium lactofermentum*.

The MP nucleic acid molecules of the invention are also useful for evolutionary and protein structural studies. The metabolic processes in which the molecules of the invention participate are utilized by a wide variety of prokaryotic and eukaryotic cells; by comparing the sequences of the nucleic acid molecules of the present invention to those encoding similar enzymes from other organisms, the evolutionary relatedness of the organisms can be assessed. Similarly, such a comparison permits an assessment of which regions of the sequence are conserved and which are not, which may aid in determining those regions of the protein which are essential for the functioning of the enzyme. This type of determination is of value for protein engineering studies and may give an indication of what the protein can tolerate in terms of mutagenesis without losing function.

Manipulation of the MP nucleic acid molecules of the invention may result in the production of MP proteins having functional differences from the wild-type MP proteins. These proteins may be improved in efficiency or activity, may be present in greater numbers in the cell than is usual, or may be decreased in efficiency or activity.

The invention also provides methods for screening molecules which modulate the activity of an MP protein, either by interacting with the protein itself or a substrate or binding partner of the MP protein, or by modulating the transcription or translation of an MP nucleic acid molecule of the invention. In such methods, a microorganism expressing one or more MP proteins of the invention is contacted with one or more test compounds, and the effect of each test compound on the activity or level of expression of the MP protein is assessed.

When the desired fine chemical to be isolated from large-scale fermentative culture of *C. glutamicum* is an amino acid, a vitamin, a cofactor, a nutraceutical, a nucleotide, a nucleoside, or trehalose, modulation of the activity or efficiency of activity of one or more of the proteins of the invention by recombinant genetic mechanisms may directly impact the production of one of these fine chemicals. For example, in the case of an enzyme in a biosynthetic pathway for a desired amino acid, improvement in efficiency or activity of the enzyme (including the presence of multiple copies of the gene) should lead to an increased production or efficiency of production of that desired amino acid. In the case of an enzyme in a biosynthetic pathway for an amino acid whose synthesis is in competition with the synthesis of a desired amino acid, any decrease in the efficiency or activity of this enzyme (including deletion of the gene) should result in an increase in production or efficiency of production of the desired amino acid, due to decreased competition for intermediate compounds and/or energy. In the case of an enzyme in a degradation pathway for a desired amino acid, any decrease in efficiency or activity of the enzyme should result in a greater yield or efficiency of production of the desired product due to a decrease in its degradation. Lastly, mutagenesis of an enzyme involved in the biosynthesis of a desired amino acid such that this enzyme is no longer is capable of feedback inhibition should result in increased yields or efficiency of production of the desired amino acid. The same should apply to the biosynthetic and degradative enzymes of the invention involved in the metabolism of vitamins, cofactors, nutraceuticals, nucleotides, nucleosides and trehalose.

Similarly, when the desired fine chemical is not one of the aforementioned compounds, the modulation of activity of one of the proteins of the invention may still impact the yield and/or efficiency of production of the compound from large-scale culture of C. glutamicum. The metabolic pathways of any organism are closely interconnected; the intermediate used by one pathway is often supplied by a different pathway. Enzyme expression and function may be regulated based on the cellular levels of a compound from a different metabolic process, and the cellular levels of molecules necessary for basic growth, such as amino acids and nucleotides, may critically affect the viability of the microorganism in large-scale culture. Thus, modulation of an amino acid biosynthesis enzyme, for example, such that it is no longer responsive to feedback inhibition or such that it is improved in efficiency or turnover may result in increased cellular levels of one or more amino acids. In turn, this increased pool of amino acids provides not only an increased supply of molecules necessary for protein synthesis, but also of molecules which are utilized as intermediates and precursors in a number of other biosynthetic pathways. If a particular amino acid had been limiting in the cell, its increased production might increase the ability of the cell to perform numerous other metabolic reactions, as well as enabling the cell to more efficiently produce proteins of all kinds, possibly increasing the overall growth rate or survival ability of the cell in large scale culture. Increased viability improves the number of cells capable of producing the desired fine chemical in fermentative culture, thereby increasing the yield of this compound. Similar processes are possible by the modulation of activity of a degradative enzyme of the invention such that the enzyme no longer catalyzes, or catalyzes less efficiently, the degradation of a cellular compound which is important for the biosynthesis of a desired compound, or which will enable the cell to grow and reproduce more efficiently in large-scale culture. It should be emphasized that optimizing the degradative activity or decreasing the biosynthetic activity of certain molecules of the invention may also have a beneficial effect on the production of certain fine chemicals from C. glutamicum. For example, by decreasing the efficiency of activity of a biosynthetic enzyme in a pathway which competes with the biosynthetic pathway of a desired compound for one or more intermediates, more of those intermediates should be available for conversion to the desired product. A similar situation may call for the improvement of degradative ability or efficiency of one or more proteins of the invention.

This aforementioned list of mutagenesis strategies for MP proteins to result in increased yields of a desired compound is not meant to be limiting; variations on these mutagenesis strategies will be readily apparent to one of ordinary skill in the art. By these mechanisms, the nucleic acid and protein molecules of the invention may be utilized to generate C. glutamicum or related strains of bacteria expressing mutated MP nucleic acid and protein molecules such that the yield, production, and/or efficiency of production of a desired compound is improved. This desired compound may be any natural product of C. glutamicum, which includes the final products of biosynthesis pathways and intermediates of naturally-occurring metabolic pathways, as well as molecules which do not naturally occur in the metabolism of C. glutamicum, but which are produced by a C. glutamicum strain of the invention. Preferred compounds to be produced by Corynebacterium glutamicum strains are the amino acids L-lysine and L-methionine.

In one embodiment, the metC gene encoding cystathionine β-lyase, the third enzyme in the methionine biosynthetic pathway, was isolated from Corynebacterium glutamicum. The translational product of the gene showed no significant homology with that of metC gene from other organisms. Introduction of the plasmid containing the metC gene into C. glutamicum resulted in a 5-fold increase in the activity of cystathionine β-lyase. The protein product, now designated MetC (corresponding to SEQ ID NO:4), which encodes a protein product of 35,574 Daltons and consists of 325 amino acids, is identical to the previously reported aecD gene (Rossol, I. and Puhler, A. (1992) J. Bacteriology 174, 2968-2977) except the existence of two different amino acids. Like aecD gene, when present in multiple copies, metC gene conferred resistance to S-(β-aminoethyl)-cysteine which is a toxic lysine analog. However, genetic and biochemical evidences suggest that the natural activity of metC gene product is to mediate methionine biosynthesis in C. glutamicum. Mutant strains of metC were constructed and the strains showed methionine prototrophy. The mutant strains completely lost their ability to show resistance to S-(γ-aminoethyl)-cysteine. These results show that, in addition to the transsulfuration, which is another biosynthetic pathway, the direct sulfhydrylation pathway is functional in C. glutamicum as a parallel biosynthetic route for methionine.

In yet another embodiment, it is also shown that the additional sulfhydrylation pathway is catalyzed by O-acetylhomoserine sulfhydrylase. The presence of the pathway is demonstrated by the isolation of the corresponding metZ (or metY) gene and enzyme (corresponding to SEQ ID NO:1 and SEQ ID NO:2, respectively). Among the eukaryotes, fungi and yeast species have been reported to have both the transsulfuration and direct sulfhydrylation pathway. Thus far, no prokaryotic organism which possesses both pathways has been found. Unlike E. coli which only possesses single biosynthetic route for lysine, C. glutamicum possesses two parallel biosynthetic pathways for the amino acid. The biosynthetic pathway for methionine in C. glutamicum is analogous to that of lysine in that aspect.

The gene metZ is located in the upstream region of metA, which is the gene encoding the enzyme catalysing the first step of methionine biosynthesis (Park, S.-D., et al. (1998) Mol. Cells 8, 286-294). Regions upstream and downstream of metA were sequenced to identify other met genes. It appears that metZ and metA form an operon. Expression of the genes encoding MetA and MetZ leads to overproduction of the corresponding polypeptides.

Surprisingly, metZ clones can complement methionine auxotrophic Escherichia coli metB mutant strains. This shows that the protein product of metZ catalyzes a step that can bypass the step catalyzed by the protein product of metB. MetZ was also disrupted and the mutant strain showed methionine prototrophy. Corynebacterium glutamicum metB and metZ double mutants were also constructed. The double mutant is auxotrophic for methionine. Thus, metZ encodes a protein catalysing the reaction from O-Acetyl-Homoserine to Homocysteine, which is one step in the sulfhydrylation pathway of methionine biosynthesis. Corynebacterium glutamicum contains both the transsulfuration and the sulfhydrylation pathway of methionine biosynthesis.

Introduction of metZ into C. glutamicum resulted in the expression of a 47,000 Dalton protein. Combined introduction of metZ and metA in C. glutamicum resulted in the appearance of metA and metZ proteins as shown by gel electrophoresis. If the *Corynebacterium* strain is a lysine overproducer, introduction of a plasmid containing metZ and metA resulted in a lower lysine titer but accumulation of homocysteine and methionine is detected.

In another embodiment metZ and metA were introduced into *Corynebacterium glutamicum* strains together with the hom gene, encoding the homoserine dehydrogenase, catalysing the conversion from aspartate semialdehyde to homoserine. Different hom genes from different organisms were chosen for this experiment. The *Corynebacterium glutamicum* hom gene can be used as well as hom genes from other procaryotes like *Escherichia coli* or *Bacillus subtilis* or the hom gene of eukaryotes such as *Saccharomyces cerevisiae, Shizosaccharomyces pombe, Ashbya gossypii* or algae, higher plants or animals. It may be that the hom gene is insensitive against feed back inhibition mediated by any metabolites that occur in the biosynthetic routes of the amino acids of the aspartate family, like aspatrate, lysine, threonine or methionine. Such metabolites are for example aspartate, lysine, methionine, threonine, aspartyl-phosphate, aspartate semialdehyd, homoserine, cystathionine, homocysteine or any other metabolite that occurs in this biosynthetic routes. In addition to the metabolites, the homoserine dehydrogenase may be insensitive against inhibition by analogues of all those metabolites or even against other compounds involved in this metabolism as there are other amino acids like cysteine or cofactors like vitamin B12 and all of its derivatives and S-adenosylmethionine and its metabolites and derivatives and analogues. The insensitivity of the homoserine dehydrogenase against all these, a part of these or only one of these compounds may either be its natural attitude or it may be the result from one or more mutations that resulted from classical mutation and selection using chemicals or irradiation or other mutagens. The mutations could also be introduced into the hom gene using gene technology, for example the introduction of site specific point mutations or by any method aforementioned for the MP or MP encoding DNA-sequences.

When a hom gene was combined with the metZ and metA genes and introduced into a *Corynebacterium glutamicum* strain that is a lysine overproducer, lysine accumulation was reduced and homocysteine and methionine accumulation was enhanced. A further enhancement of homocysteine and methionine concentrations can be achieved, if a lysine overproducing *Corynebacterium glutamicum* strain is used and a disruption of the ddh gene or the lysA gene was introduced prior to the transformation with DNA containing a hom gene and metZ and metA in combination. The overproduction of homocysteine and methionine was possible using different sulfur sources. Sulfates, thiosulfates, sulfites and also more reduced sulfur sources like $H_2S$ and sulfides and derivatives could be used. Also, organic sulfur sources like methyl mercaptan, thioglycolates, thiocyanates, thiourea, sulfur containing amino acids like cysteine and other sulfur containing compounds can be used to achieve homocysteine and methionine overproduction.

In another embodiment, the metC gene was introduced into a *Corynebacterium glutamicum* strain using aforementioned methods. The metC gene can be transformed into the strain in combination with other genes like metB, metA and metA. The hom gene can also be added. When the hom gene, the met C, metA and metB genes were combined on a vector and introduced into a *Corynebacterium glutamicum* strain, homocysteine and methionine overproduction was achieved. The overproduction of homocysteine and methionine was possible using different sulfur sources. Sulfates, thiosulfates, sulfites and also more reduced sulfur sources like $H_2S$ and sulfides and derivatives could be used. Also, organic sulfur sources like methyl mercaptan, thioglycolates, thiocyanates, thiourea, sulfur containing amino acids like cysteine and other sulfur containing compounds can be used to achieve homocysteine and methionine overproduction.

This invention is further illustrated by the following examples which should not be construed as limiting. The contents of all references, patent applications, patents, published patent applications, Tables, and the sequence listing cited throughout this application are hereby incorporated by reference.

EXEMPLIFICATION

Example 1

Preparation of Total Genomic DNA of
*Corynebacterium glutamicum* ATCC13032

A culture of *Corynebacterium glutamicum* (ATCC 13032) was grown overnight at 30° C. with vigorous shaking in BHI medium (Difco). The cells were harvested by centrifugation, the supernatant was discarded and the cells were resuspended in 5 ml buffer-I (5% of the original volume of the culture—all indicated volumes have been calculated for 100 ml of culture volume). Composition of buffer-I: 140.34 g/l sucrose, 2.46 g/l $MgSO_4 \times 7\ H_2O$, 10 ml/l $KH_2PO_4$ solution (100 g/l, adjusted to pH 6.7 with KOH), 50 ml/l M12 concentrate (10 g/l $(NH_4)_2SO_4$, 1 g/l NaCl, 2 g/l $MgSO_4 \times 7\ H_2O$, 0.2 g/l $CaCl_2$, 0.5 g/l yeast extract (Difco), 10 ml/l trace-elements-mix (200 mg/l $FeSO_4 \times H_2O$, 10 mg/l $ZnSO_4 \times 7\ H_2O$, 3 mg/l $MnCl_2 \times 4\ H_2O$, 30 mg/l $H_3BO_3$ 20 mg/l $CoCl_2 \times 6\ H_2O$, 1 mg/l $NiCl_2 \times 6\ H_2O$, 3 mg/l $Na_2MoO_4 \times 2\ H_2O$, 500 mg/l complexing agent (EDTA or critic acid), 100 ml/l vitamins-mix (0.2 mg/l biotin, 0.2 mg/l folic acid, 20 mg/l p-amino benzoic acid, 20 mg/l riboflavin, 40 mg/l ca-panthothenate, 140 mg/l nicotinic acid, 40 mg/l pyridoxole hydrochloride, 200 mg/l myo-inositol). Lysozyme was added to the suspension to a final concentration of 2.5 mg/ml. After an approximately 4 h incubation at 37° C., the cell wall was degraded and the resulting protoplasts are harvested by centrifugation. The pellet was washed once with 5 ml buffer-I and once with 5 ml TE-buffer (10 mM Tris-HCl, 1 mM EDTA, pH 8). The pellet was resuspended in 4 ml TE-buffer and 0.5 ml SDS solution (10%) and 0.5 ml NaCl solution (5 M) are added. After adding of proteinase K to a final concentration of 200 μg/ml, the suspension is incubated for ca. 18 h at 37° C. The DNA was purified by extraction with phenol, phenol-chloroform-isoamylalcohol and chloroform-isoamylalcohol using standard procedures. Then, the DNA was precipitated by adding 1/50 volume of 3 M sodium acetate and 2 volumes of ethanol, followed by a 30 min incubation at −20° C. and a 30 min centrifugation at 12,000 rpm in a high speed centrifuge using a SS34 rotor (Sorvall). The DNA was dissolved in 1 ml TE-buffer containing 20 μg/ml RNaseA and dialysed at 4° C. against 1000 ml TE-buffer for at least 3 hours. During this time, the buffer was exchanged 3 times. To aliquots of 0.4 ml of the dialysed DNA solution, 0.4 ml of 2 M LiCl and 0.8 ml of ethanol are added. After a 30 min incubation at −20° C., the DNA was collected by centrifugation (13,000 rpm, Biofuge Fresco, Heraeus, Hanau, Germany). The DNA pellet was dissolved in TE-buffer. DNA prepared by this procedure could be used for all purposes, including southern blotting or construction of genomic libraries.

Example 2

Construction of Genomic Libraries in *Escherichia coli* of *Corynebacterium glutamicum* ATCC13032

Using DNA prepared as described in Example 1, cosmid and plasmid libraries were constructed according to known and well established methods (see e.g., Sambrook, J. et al. (1989) "Molecular Cloning: A Laboratory Manual", Cold Spring Harbor Laboratory Press, or Ausubel, F. M. et al. (1994) "Current Protocols in Molecular Biology", John Wiley & Sons.)

Any plasmid or cosmid could be used. Of particular use were the plasmids pBR322 (Sutcliffe, J. G. (1979) *Proc. Natl. Acad. Sci. USA,* 75:3737-3741); pACYC177 (Change & Cohen (1978) *J. Bacteriol* 134:1141-1156), plasmids of the pBS series (pBSSK+, pBSSK– and others; Stratagene, LaJolla, USA), or cosmids as SuperCos1 (Stratagene, LaJolla, USA) or Lorist6 (Gibson, T. J., Rosenthal A. and Waterson, R. H. (1987) *Gene* 53:283-286. Gene libraries specifically for use in *C. glutamicum* may be constructed using plasmid pSL109 (Lee, H.-S. and A. J. Sinskey (1994) *J. Microbiol. Biotechnol.* 4: 256-263).

For the isolation of metC clones, *E. coli* JE6839 cells were transformed with the library DNA and plated onto the M9 minimal medium containing ampicillin and appropriate supplements. The plates were incubated at 37° C. for 5 days. Colonies were isolated and screened for the plasmid content. The complete nucleotide sequence of the isolated metC gene was determined by methods well-known to one of ordinary skill in the art.

Example 3

DNA Sequencing and Computational Functional Analysis

Genomic libraries as described in Example 2 were used for DNA sequencing according to standard methods, in particular by the chain termination method using ABI377 sequencing machines (see e.g., Fleischman, R. D. et al. (1995) "Whole-genome Random Sequencing and Assembly of *Haemophilus Influenzae* Rd., *Science,* 269:496-512). Sequencing primers with the following nucleotide sequences were used: 5'-GGAAACAGTATGACCATG-3' (SEQ ID NO:123) or 5'-GTAAAACGACGGCCAGT-3'(SEQ ID NO.:124).

Example 4

In vivo Mutagenesis

In vivo mutagenesis of *Corynebacterium glutamicum* can be performed by passage of plasmid (or other vector) DNA through *E. coli* or other microorganisms (e.g. *Bacillus* spp. or yeasts such as *Saccharomyces cerevisiae*) which are impaired in their capabilities to maintain the integrity of their genetic information. Typical mutator strains have mutations in the genes for the DNA repair system (e.g., mutHLS, mutD, mutT, etc.; for reference, see Rupp, W. D. (1996) DNA repair mechanisms, in: *Escherichia coli* and *Salmonella,* p. 2277-2294, ASM: Washington.) Such strains are well known to those of ordinary skill in the art. The use of such strains is illustrated, for example, in Greener, A. and Callahan, M. (1994) *Strategies* 7: 32-34.

Example 5

DNA Transfer Between *Escherichia coli* and *Corynebacterium glutamicum*

Several *Corynebacterium* and *Brevibacterium* species contain endogenous plasmids (as e.g., pHM1519 or pBL1) which replicate autonomously (for review see, e.g., Martin, J. F. et al. (1987) *Biotechnology,* 5:137-146). Shuttle vectors for *Escherichia coli* and *Corynebacterium glutamicum* can be readily constructed by using standard vectors for *E. coli* (Sambrook, J. et al. (1989), "Molecular Cloning: A Laboratory Manual", Cold Spring Harbor Laboratory Press or Ausubel, F. M. et al. (1994) "Current Protocols in Molecular Biology", John Wiley & Sons) to which a origin or replication for and a suitable marker from *Corynebacterium glutamicum* is added. Such origins of replication are preferably taken from endogenous plasmids isolated from *Corynebacterium* and *Brevibacterium* species. Of particular use as transformation markers for these species are genes for kanamycin resistance (such as those derived from the Tn5 or Tn903 transposons) or chloramphenicol (Winnacker, E. L. (1987) "From Genes to Clones—Introduction to Gene Technology, VCH, Weinheim). There are numerous examples in the literature of the construction of a wide variety of shuttle vectors which replicate in both *E. coli* and *C. glutamicum*, and which can be used for several purposes, including gene over-expression (for reference, see e.g., Yoshihama, M. et al. (1985) *J. Bacteriol.* 162:591-597, Martin J. F. et al. (1987) *Biotechnology,* 5:137-146 and Eikmanns, B. J. et al. (1991) *Gene,* 102:93-98).

Using standard methods, it is possible to clone a gene of interest into one of the shuttle vectors described above and to introduce such a hybrid vectors into strains of *Corynebacterium glutamicum*. Transformation of *C. glutamicum* can be achieved by protoplast transformation (Kastsumata, R. et al. (1984) *J. Bacteriol.* 159306-311), electroporation (Liebl, E. et al. (1989) *FEMS Microbiol. Letters,* 53:399-303) and in cases where special vectors are used, also by conjugation (as described e.g. in Schäfer, A et al. (1990) *J. Bacteriol.* 172: 1663-1666). It is also possible to transfer the shuttle vectors for *C. glutamicum* to *E. coli* by preparing plasmid DNA from *C. glutamicum* (using standard methods well-known in the art) and transforming it into *E. coli*. This transformation step can be performed using standard methods, but it is advantageous to use an Mcr-deficient *E. coli* strain, such as NM522 (Gough & Murray (1983) *J. Mol. Biol.* 166:1-19).

Genes may be overexpressed in *C. glutamicum* strains using plasmids which comprise pCG1 (U.S. Pat. No. 4,617, 267) or fragments thereof, and optionally the gene for kanamycin resistance from TN903 (Grindley, N. D. and Joyce, C. M. (1980) *Proc. Natl. Acad. Sci. USA* 77(12): 7176-7180). In addition, genes may be overexpressed in *C. glutamicum* strains using plasmid pSL109 (Lee, H.-S. and A. J. Sinskey (1994) *J. Microbiol. Biotechnol.* 4: 256-263).

Aside from the use of replicative plasmids, gene overexpression can also be achieved by integration into the genome. Genomic integration in *C. glutamicum* or other *Corynebacterium* or *Brevibacterium* species may be accomplished by well-known methods, such as homologous recombination with genomic region(s), restriction endonuclease mediated integration (REMI) (see, e.g., DE Patent 19823834), or through the use of transposons. It is also possible to modulate the activity of a gene of interest by modifying the regulatory regions (e.g., a promoter, a repressor, and/or an enhancer) by sequence modification, insertion, or deletion using site-directed methods (such as homologous recombination) or methods based on random events (such as transposon mutagenesis or REMI). Nucleic acid sequences which function as transcriptional terminators may also be inserted 3' to the coding region of one or more genes of the invention; such terminators are well-known in the art and are described, for example, in Winnacker, E. L. (1987) From Genes to Clones—Introduction to Gene Technology. VCH: Weinheim.

Example 6

Assessment of the Expression of the Mutant Protein

Observations of the activity of a mutated protein in a transformed host cell rely on the fact that the mutant protein is expressed in a similar fashion and in a similar quantity to that of the wild-type protein. A useful method to ascertain the level of transcription of the mutant gene (an indicator of the amount of mRNA available for translation to the gene product) is to perform a Northern blot (for reference see, for example, Ausubel et al. (1988) Current Protocols in Molecular Biology, Wiley: New York), in which a primer designed to bind to the gene of interest is labeled with a detectable tag (usually radioactive or chemiluminescent), such that when the total RNA of a culture of the organism is extracted, run on gel, transferred to a stable matrix and incubated with this probe, the binding and quantity of binding of the probe indicates the presence and also the quantity of mRNA for this gene. This information is evidence of the degree of transcription of the mutant gene. Total cellular RNA can be prepared from Corynebacterium glutamicum by several methods, all well-known in the art, such as that described in Bormann, E. R. et al. (1992) Mol. Microbiol. 6: 317-326.

To assess the presence or relative quantity of protein translated from this mRNA, standard techniques, such as SDS-acrylamide gel electrophoresis, were employed. The overproduction of metC and metZ in combination with metA in Corynebacterium glutamicum was demonstrated by this method. Western blot may also be employed (see, for example, Ausubel et al. (1988) Current Protocols in Molecular Biology, Wiley: New York). In this process, total cellular proteins are extracted, separated by gel electrophoresis, transferred to a matrix such as nitrocellulose, and incubated with a probe, such as an antibody, which specifically binds to the desired protein. This probe is generally tagged with a chemiluminescent or colorimetric label which may be readily detected. The presence and quantity of label observed indicates the presence and quantity of the desired mutant protein present in the cell.

Example 7

Growth of Escherichia coli and Genetically Modified Corynebacterium glutamicum—Media and Culture Conditions E. coli strains are routinely grown in MB and LB broth, respectively (Follettie, M. T., et al. (1993) J. Bacteriol. 175, 4096-4103). Minimal media for E. coli is M9 and modified MCGC (Yoshihama, M., et al. (1985) J. Bacteriol. 162, 591-507). Glucose was added to a final concentration of 1%. Antibiotics were added in the following amounts (micrograms per milliliter): ampicillin, 50; kanamycin, 25; nalidixic acid, 25. Amino acids, vitamins, and other supplements were added in the following amounts: methionine, 9.3 mM; arginine, 9.3 mM; histidine, 9.3 mM; thiamine, 0.05 mM. E. coli cells were routinely grown at 37° C., respectively.

Genetically modified Corynebacteria are cultured in synthetic or natural growth media. A number of different growth media for Corynebacteria are both well-known and readily available (Lieb et al. (1989) Appl. Microbiol. Biotechnol., 32:205-210; von der Osten et al. (1998) Biotechnology Letters, 11:11-16; Patent DE 4,120,867; Liebl (1992) "The Genus Corynebacterium, in: The Procaryotes, Volume II, Balows, A. et al., eds. Springer-Verlag). These media consist of one or more carbon sources, nitrogen sources, inorganic salts, vitamins and trace elements. Preferred carbon sources are sugars, such as mono-, di-, or polysaccharides. For example, glucose, fructose, mannose, galactose, ribose, sorbose, ribulose, lactose, maltose, sucrose, raffinose, starch or cellulose serve as very good carbon sources. It is also possible to supply sugar to the media via complex compounds such as molasses or other by-products from sugar refinement. It can also be advantageous to supply mixtures of different carbon sources. Other possible carbon sources are alcohols and organic acids, such as methanol, ethanol, acetic acid or lactic acid. Nitrogen sources are usually organic or inorganic nitrogen compounds, or materials which contain these compounds. Exemplary nitrogen sources include ammonia gas or ammonia salts, such as $NH_4Cl$ or $(NH_4)_2SO_4$, $NH_4OH$, nitrates, urea, amino acids or complex nitrogen sources like corn steep liquor, soy bean flour, soy bean protein, yeast extract, meat extract and others.

The overproduction of sulfur containing amino acids like homocysteine and methionine was made possible using different sulfur sources. Sulfates, thiosulfates, sulfites and also more reduced sulfur sources like $H_2S$ and sulfides and derivatives can be used. Also, organic sulfur sources like methyl mercaptan, thioglycolates, thiocyanates, thiourea, sulfur containing amino acids like cysteine and other sulfur containing compounds can be used to achieve homocysteine and methionine overproduction Inorganic salt compounds which may be included in the media include the chloride-, phosphorous- or sulfate-salts of calcium, magnesium, sodium, cobalt, molybdenum, potassium, manganese, zinc, copper and iron. Chelating compounds can be added to the medium to keep the metal ions in solution. Particularly useful chelating compounds include dihydroxyphenols, like catechol or protocatechuate, or organic acids, such as citric acid. It is typical for the media to also contain other growth factors, such as vitamins or growth promoters, examples of which include biotin, riboflavin, thiamin, folic acid, nicotinic acid, pantothenate and pyridoxin. Growth factors and salts frequently originate from complex media components such as yeast extract, molasses, corn steep liquor and others. The exact composition of the media compounds depends strongly on the immediate experiment and is individually decided for each specific case. Information about media optimization is available in the textbook "Applied Microbiol. Physiology, A Practical Approach (eds. P. M. Rhodes, P. F. Stanbury, IRL Press (1997) pp. 53-73, ISBN 0 19 963577 3). It is also possible to select growth media from commercial suppliers, like standard 1 (Merck) or BHI (grain heart infusion, DIFCO) or others.

All medium components are sterilized, either by heat (20 minutes at 1.5 bar and 121° C.) or by sterile filtration. The components can either be sterilized together or, if necessary, separately. All media components can be present at the beginning of growth, or they can optionally be added continuously or batchwise.

Culture conditions are defined separately for each experiment. The temperature should be in a range between 15° C. and 45° C. The temperature can be kept constant or can be altered during the experiment. The pH of the medium should be in the range of 5 to 8.5, preferably around 7.0, and can be maintained by the addition of buffers to the media. An exemplary buffer for this purpose is a potassium phosphate buffer.

Synthetic buffers such as MOPS, HEPES, ACES and others can alternatively or simultaneously be used. It is also possible to maintain a constant culture pH through the addition of NaOH or $NH_4OH$ during growth. If complex medium components such as yeast extract are utilized, the necessity for additional buffers may be reduced, due to the fact that many complex compounds have high buffer capacities. If a fermentor is utilized for culturing the micro-organisms, the pH can also be controlled using gaseous ammonia.

The incubation time is usually in a range from several hours to several days. This time is selected in order to permit the maximal amount of product to accumulate in the broth. The disclosed growth experiments can be carried out in a variety of vessels, such as microtiter plates, glass tubes, glass flasks or glass or metal fermentors of different sizes. For screening a large number of clones, the microorganisms should be cultured in microtiter plates, glass tubes or shake flasks, either with or without baffles. Preferably 100 ml shake flasks are used, filled with 10% (by volume) of the required growth medium. The flasks should be shaken on a rotary shaker (amplitude 25 mm) using a speed-range of 100-300 rpm. Evaporation losses can be diminished by the maintenance of a humid atmosphere; alternatively, a mathematical correction for evaporation losses should be performed.

If genetically modified clones are tested, an unmodified control clone or a control clone containing the basic plasmid without any insert should also be tested. The medium is inoculated to an $OD_{600}$ of O.5-1.5 using cells grown on agar plates, such as CM plates (10 g/l glucose, 2.5 g/l NaCl, 2 g/l urea, 10 g/l polypeptone, 5 g/l yeast extract, 5 g/l meat extract, 22 g/l NaCl, 2 g/l urea, 10 g/l polypeptone, 5 g/l yeast extract, 5 g/l meat extract, 22 g/l agar, pH 6.8 with 2M NaOH) that had been incubated at 30° C. Inoculation of the media is accomplished by either introduction of a saline suspension of *C. glutamicum* cells from CM plates or addition of a liquid preculture of this bacterium.

Example 8

In Vitro Analysis of the Function of Mutant Proteins

The determination of activities and kinetic parameters of enzymes is well established in the art. Experiments to determine the activity of any given altered enzyme must be tailored to the specific activity of the wild-type enzyme, which is well within the ability of one of ordinary skill in the art. Overviews about enzymes in general, as well as specific details concerning structure, kinetics, principles, methods, applications and examples for the determination of many enzyme activities may be found, for example, in the following references: Dixon, M., and Webb, E. C., (1979) Enzymes. Longmans: London; Fersht, (1985) Enzyme Structure and Mechanism. Freeman: New York; Walsh, (1979) Enzymatic Reaction Mechanisms. Freeman: San Francisco; Price, N. C., Stevens, L. (1982) Fundamentals of Enzymology. Oxford Univ. Press: Oxford; Boyer, P. D., ed. (1983) The Enzymes, $3^{rd}$ ed. Academic Press: New York; Bisswanger, H., (1994) Enzymkinetik, $2^{nd}$ ed. VCH: Weinheim (ISBN 3527300325); Bergmeyer, H. U., Bergmeyer, J., Graβl, M., eds. (1983-1986) Methods of Enzymatic Analysis, $3^{rd}$ ed., vol. I-XII, Verlag Chemie: Weinheim; and Ullmann's Encyclopedia of Industrial Chemistry (1987) vol. A9, "Enzymes". VCH: Weinheim, p. 352-363.

Cell extracts from *Corynebacterium glutamicum* were prepared as described previously (Park, S.-D., et al. (1998) *Mol. Cells* 8, 286-294). Cystathionine β-lyase was assayed as follows. The assay mixture contained 100 mM Tris-HCl (pH8.5), 0.1 mM NADH, 1 mM L-cystathionine, 5 units of L-lactate dehydrogenase, and appropriate amounts of crude extract. Optical changes were monitored at 340 nm. Assay for S-(□-aminoethyl)-cysteine (AEC) resistance was carried out as described in Rossol, I. and Pühler, A. (1992) *J. Bacteriol.* 174, 2968-77. The results of cystathionin β-lyase assays from extracts of different *Corynebacterium glutamicum* strains as well as results of AEC resistance assays of the same strain are summarized in Table 5, below.

TABLE 5

Expression of cystathionine β-lyase[a]

| Strains | Properties | Activity (nmol $min^{-1} mg^{-1}$) | Growth on $MM^b$ | Resistance to $AEC^c$ |
|---|---|---|---|---|
| C. glutamicum ASO19E12 | — | 146 | + | + |
| C. glutamicum ASO19E12/pMT1 | Empty vector | 145 | + | + |
| C. glutamicum ASO19E12/pSL173 | metC clone | 797 | + | ++ |
| C. glutamicum HL457 | metC mutant[d] | 19 | + | − |
| C. glutamicum HL459 | metC mutant[d] | 23 | + | − |
| E. coli JE6839 | metC mutant | 21 | − | $ND^e$ |

[a]The enzyme was induced by growth to the stationary phase on the minimal medium containing 1% glucose. Cells were harvested, disrupted, and assayed for the activity as described in the Materials and Methods.
[b]MCGC minimal media was used. Growth was monitored on plates.
[c]Cells were grown on plates containing 40 mM S-(β-aminoethyl)-cysteine (AEC) for 5 days.
[d]The mutants were generated in this study.
[e]Not determined.

The ability of the metC clones to express cystathionine β-lyase was tested by enzymatic assay. Crude extracts prepared from the *C. glutamicum* ASO19E12 cells harboring plasmid pSL173 were assayed. Cells harboring the plasmid showed approximately a 5-fold increase in the activity of cystathionine β-lyase compared to those harboring the empty vector pMT1 (Table 5), apparently due to the gene-dose effect. SDS-PAGE analysis of crude extracts revealed a putative cystathionine β-lyase band with approximate $M_r$ of 41,000. Intensity of each putative cystathionine β-lyase band agreed with the complementation and enzymatic assay data (Table 5). As described above, a region of metC appeared to be nearly identical to the previously reported aecD. Since the aecD gene was isolated on the basis of its ability to confer resistance to S-(β-aminoethyl)-cysteine (AEC), a toxic lysine analogue, we tested the protein product of metC for the presence of the activity. As shown in Table 5, cells overexpressing cystathionine β-lyase showed increased resistance to AEC. The strain carrying a mutation in metC gene (see below) completely lost its ability to show a resistant phenotype to AEC.

Assay for O-acetylhmoserine sulphydrylase was performed as follows (Belfaiza, J., et al. (1998) *J. Bacteriol.* 180, 250-255; Ravanel, S., M. Droux, and R. Douce (1995) *Arch. Biochem. Biophys.* 316, 572-584; Foglino, M. (1995) *Microbiology* 141, 431-439). Assay mixture of 0.1 ml contained 20 mM MOPS-NaOH (pH7.5), 10 mM O-acetylhomoserine, 2 mM $Na_2S$ in 50 mM NaOH, and an appropriate amount of enzyme. Immediately after the addition of $Na_2S$ which was added last, the reaction mixture was overlayed with 50 ul of mineral oil. After 30 minute incubation at 30° C., the reaction was stopped by boiling the mixture for 3 minutes. Homocysteine produced in the reaction was quantified as previously described (Yamagata, S. (1987) *Method Enzymol.* 143, 478-483.). Reaction mixture of 0.1 ml was taken and mixed with 0.1 ml of $H_2O$, 0.6 ml of saturated NaCl, 0.1 ml of 1.5 M $Na_2CO_3$ containing 67 mM KCN, and 0.1 ml of 2% nitroprusside. After 1 minute incubation at room temperature, optical density was measured at 520 nm. *Corynebacterium* cells harboring additional copies of the metZ gene, e.g., a plasmid containing the metZ gene, exhibited significantly higher metZ enzyme activities than the same type of *Corynebacterium* cells without additional copies of the metZ gene.

The activity of proteins which bind to DNA can be measured by several well-established methods, such as DNA band-shift assays (also called gel retardation assays). The effect of such proteins on the expression of other molecules can be measured using reporter gene assays (such as that described in Kolmar, H. et al. (1995) *EMBO J.* 14: 3895-3904 and references cited therein). Reporter gene test systems are well known and established for applications in both pro- and eukaryotic cells, using enzymes such as beta-galactosidase, green fluorescent protein, and several others.

The determination of activity of membrane-transport proteins can be performed according to techniques such as those described in Gennis, R. B. (1989) "Pores, Channels and Transporters", in Biomembranes, Molecular Structure and Function, Springer: Heidelberg, p. 85-137; 199-234; and 270-322.

Example 9

Analysis of Impact of Mutant Protein on the Production of the Desired Product

The effect of the genetic modification in *C. glutamicum* on production of a desired compound (such as an amino acid) can be assessed by growing the modified microorganism under suitable conditions (such as those described above) and analyzing the medium and/or the cellular component for increased production of the desired product (i.e., an amino acid). Such analysis techniques are well known to one of ordinary skill in the art, and include spectroscopy, thin layer chromatography, staining methods of various kinds, enzymatic and microbiological methods, and analytical chromatography such as high performance liquid chromatography (see, for example, Ullman, Encyclopedia of Industrial Chemistry, vol. A2, p. 89-90 and p. 443-613, VCH: Weinheim (1985); Fallon, A. et al., (1987) "Applications of HPLC in Biochemistry" in: Laboratory Techniques in Biochemistry and Molecular Biology, vol. 17; Rehm et al. (1993) Biotechnology, vol. 3, Chapter III: "Product recovery and purification", page 469-714, VCH: Weinheim; Belter, P. A. et al. (1988) Bioseparations: downstream processing for biotechnology, John Wiley and Sons; Kennedy, J. F. and Cabral, J. M. S. (1992) Recovery processes for biological materials, John Wiley and Sons; Shaeiwitz, J. A. and Henry, J. D. (1988) Biochemical separations, in: Ulmann's Encyclopedia of Industrial Chemistry, vol. B3, Chapter 11, page 1-27, VCH: Weinheim; and Dechow, F. J. (1989) Separation and purification techniques in biotechnology, Noyes Publications.)

In addition to the measurement of the final product of fermentation, it is also possible to analyze other components of the metabolic pathways utilized for the production of the desired compound, such as intermediates and side-products, to determine the overall efficiency of production of the compound. Analysis methods include measurements of nutrient levels in the medium (e.g., sugars, hydrocarbons, nitrogen sources, phosphate, and other ions), measurements of biomass composition and growth, analysis of the production of common metabolites of biosynthetic pathways, and measurement of gasses produced during fermentation. Standard methods for these measurements are outlined in Applied Microbial Physiology, A Practical Approach, P. M. Rhodes and P. F. Stanbury, eds., IRL Press, p. 103-129; 131-163; and 165-192 (ISBN: 0199635773) and references cited therein.

Example 10

Purification of the Desired Product from *C. glutamicum* Culture

Recovery of the desired product from the *C. glutamicum* cells or supernatant of the above-described culture can be performed by various methods well known in the art. If the desired product is not secreted from the cells, the cells can be harvested from the culture by low-speed centrifugation, the cells can be lysed by standard techniques, such as mechanical force or sonication. The cellular debris is removed by centrifugation, and the supernatant fraction containing the soluble proteins is retained for further purification of the desired compound. If the product is secreted from the *C. glutamicum* cells, then the cells are removed from the culture by low-speed centrifugation, and the supernate fraction is retained for further purification.

The supernatant fraction from either purification method is subjected to chromatography with a suitable resin, in which the desired molecule is either retained on a chromatography resin while many of the impurities in the sample are not, or where the impurities are retained by the resin while the sample is not. Such chromatography steps may be repeated as necessary, using the same or different chromatography resins. One of ordinary skill in the art would be well-versed in the selection of appropriate chromatography resins and in their most efficacious application for a particular molecule to be purified. The purified product may be concentrated by filtration or ultrafiltration, and stored at a temperature at which the stability of the product is maximized.

There are a wide array of purification methods known to the art and the preceding method of purification is not meant to be limiting. Such purification techniques are described, for example, in Bailey, J. E. & Ollis, D. F. Biochemical Engineering Fundamentals, McGraw-Hill: New York (1986).

The identity and purity of the isolated compounds may be assessed by techniques standard in the art. These include high-performance liquid chromatography (HPLC), spectroscopic methods, staining methods, thin layer chromatography, NIRS, enzymatic assay, or microbiologically. Such analysis methods are reviewed in: Patek et al. (1994) *Appl. Environ. Microbiol.* 60: 133-140; Malakhova et al. (1996) *Biotekhnologiya* 11: 27-32; and Schmidt et al. (1998) *Bioprocess Engineer.* 19: 67-70. Ulmann's Encyclopedia of Industrial Chemistry, (1996) vol. A27, VCH: Weinheim, p. 89-90, p. 521-540, p. 540-547, p. 559-566, 575-581 and p. 581-587; Michal, G. (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, vol. 17.

Example 11

Analysis of the Gene Sequences of the Invention

The comparison of sequences and determination of percent homology between two sequences are art-known techniques, and can be accomplished using a mathematical algorithm, such as the algorithm of Karlin and Altschul (1990) *Proc. Natl. Acad. Sci. USA* 87:2264-68, modified as in Karlin and Altschul (1993) *Proc. Natl. Acad. Sci. USA* 90:5873-77. Such an algorithm is incorporated into the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to MP nucleic acid molecules of the invention. BLAST protein searches can be performed with the XBLAST program, score=50, wordlength=3 to obtain amino acid sequences homologous to MP protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, one of ordinary skill in the art will know how to optimize the parameters of the program (e.g., XBLAST and NBLAST) for the specific sequence being analyzed.

Another example of a mathematical algorithm utilized for the comparison of sequences is the algorithm of Meyers and Miller ((1988) *Comput. Appl. Biosci.* 4: 11-17). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art, and include ADVANCE and ADAM. described in Torelli and Robotti (1994) *Comput. Appl. Biosci* 10:3-5; and FASTA, described in Pearson and Lipman (1988) *P.N.A.S.* 85:2444-8.

The percent homology between two amino acid sequences can also be accomplished using the GAP program in the GCG software package (available at http://www.gcg.com), using either a Blosum 62 matrix or a PAM250 matrix, and a gap weight of 12, 10, 8, 6, or 4 and a length weight of 2, 3, or 4. The percent homology between two nucleic acid sequences can be accomplished using the GAP program in the GCG software package, using standard parameters, such as a gap weight of 50 and a length weight of 3.

A comparative analysis of the gene sequences of the invention with those present in Genbank has been performed using techniques known in the art (see, e.g., Bexevanis and Ouellette, eds. (1998) Bioinformatics: A Practical Guide to the Analysis of Genes and Proteins. John Wiley and Sons: New York). The gene sequences of the invention were compared to genes present in Genbank in a three-step process. In a first step, a BLASTN analysis (e.g., a local alignment analysis) was performed for each of the sequences of the invention against the nucleotide sequences present in Genbank, and the top 500 hits were retained for further analysis. A subsequent FASTA search (e.g., a combined local and global alignment analysis, in which limited regions of the sequences are aligned) was performed on these 500 hits. Each gene sequence of the invention was subsequently globally aligned to each of the top three FASTA hits, using the GAP program in the GCG software package (using standard parameters). In order to obtain correct results, the length of the sequences extracted from Genbank were adjusted to the length of the query sequences by methods well-known in the art. The results of this analysis are set forth in Table 4. The resulting data is identical to that which would have been obtained had a GAP (global) analysis alone been performed on each of the genes of the invention in comparison with each of the references in Genbank, but required significantly reduced computational time as compared to such a database-wide GAP (global) analysis. Sequences of the invention for which no alignments above the cutoff values were obtained are indicated on Table 4 by the absence of alignment information. It will further be understood by one of ordinary skill in the art that the GAP alignment homology percentages set forth in Table 4 under the heading "% homology (GAP)" are listed in the European numerical format, wherein a ',' represents a decimal point. For example, a value of "40,345" in this column represents "40.345%".

Example 12

Construction and Operation of DNA Microarrays

The sequences of the invention may additionally be used in the construction and application of DNA microarrays (the design, methodology, and uses of DNA arrays are well known in the art, and are described, for example, in Schena, M. et al. (1995) *Science* 270: 467470; Wodicka, L. et al. (1997) *Nature Biotechnology* 15: 1359-1367; DeSaizieu, A. et al. (1998) *Nature Biotechnology* 16: 45-48; and DeRisi, J. L. et al. (1997) *Science* 278: 680-686).

DNA microarrays are solid or flexible supports consisting of nitrocellulose, nylon, glass, silicone, or other materials. Nucleic acid molecules may be attached to the surface in an ordered manner. After appropriate labeling, other nucleic acids or nucleic acid mixtures can be hybridized to the immobilized nucleic acid molecules, and the label may be used to monitor and measure the individual signal intensities of the hybridized molecules at defined regions. This methodology allows the simultaneous quantification of the relative or absolute amount of all or selected nucleic acids in the applied nucleic acid sample or mixture. DNA microarrays, therefore, permit an analysis of the expression of multiple (as many as 6800 or more) nucleic acids in parallel (see, e.g., Schena, M. (1996) *BioEssays* 18(5): 427-431).

The sequences of the invention may be used to design oligonucleotide primers which are able to amplify defined regions of one or more *C. glutamicum* genes by a nucleic acid amplification reaction such as the polymerase chain reaction. The choice and design of the 5' or 3' oligonucleotide primers or of appropriate linkers allows the covalent attachment of the resulting PCR products to the surface of a support medium described above (and also described, for example, Schena, M. et al. (1995) *Science* 270: 467-470).

Nucleic acid microarrays may also be constructed by in situ oligonucleotide synthesis as described by Wodicka, L. et al. (1997) *Nature Biotechnology* 15: 1359-1367. By photolithographic methods, precisely defined regions of the matrix are exposed to light. Protective groups which are photolabile are thereby activated and undergo nucleotide addition, whereas regions that are masked from light do not undergo any modification. Subsequent cycles of protection and light activation permit the synthesis of different oligonucleotides at defined positions. Small, defined regions of the genes of the invention may be synthesized on microarrays by solid phase oligonucleotide synthesis.

The nucleic acid molecules of the invention present in a sample or mixture of nucleotides may be hybridized to the microarrays. These nucleic acid molecules can be labeled according to standard methods. In brief, nucleic acid molecules (e.g., mRNA molecules or DNA molecules) are labeled by the incorporation of isotopically or fluorescently labeled nucleotides, e.g., during reverse transcription or DNA synthesis. Hybridization of labeled nucleic acids to microarrays is described (e.g., in Schena, M. et al. (1995) supra; Wodicka, L. et al. (1997), supra; and DeSaizieu A. et al. (1998), supra). The detection and quantification of the hybridized molecule are tailored to the specific incorporated label.

Radioactive labels can be detected, for example, as described in Schena, M. et al. (1995) supra) and fluorescent labels may be detected, for example, by the method of Shalon et al. (1996) *Genome Research* 6: 639-645).

The application of the sequences of the invention to DNA microarray technology, as described above, permits comparative analyses of different strains of *C. glutamicum* or other *Corynebacteria*. For example, studies of inter-strain variations based on individual transcript profiles and the identification of genes that are important for specific and/or desired strain properties such as pathogenicity, productivity and stress tolerance are facilitated by nucleic acid array methodologies. Also, comparisons of the profile of expression of genes of the invention during the course of a fermentation reaction are possible using nucleic acid array technology.

Example 13

Analysis of the Dynamics of Cellular Protein Populations (Proteomics)

The genes, compositions, and methods of the invention may be applied to study the interactions and dynamics of populations of proteins, termed 'proteomics'. Protein populations of interest include, but are not limited to, the total protein population of *C. glutamicum* (e.g., in comparison with the protein populations of other organisms), those proteins which are active under specific environmental or metabolic conditions (e.g., during fermentation, at high or low temperature, or at high or low pH), or those proteins which are active during specific phases of growth and development.

Protein populations can be analyzed by various well-known techniques, such as gel electrophoresis. Cellular proteins may be obtained, for example, by lysis or extraction, and may be separated from one another using a variety of electrophoretic techniques. Sodium dodecyl sulfate polyacrylamide gel electrophoresis (SDS-PAGE) separates proteins largely on the basis of their molecular weight. Isoelectric focusing polyacrylamide gel electrophoresis (IEF-PAGE) separates proteins by their isoelectric point (which reflects not only the amino acid sequence but also posttranslational modifications of the protein). Another, more preferred method of protein analysis is the consecutive combination of both IEF-PAGE and SDS-PAGE, known as 2-D-gel electrophoresis (described, for example, in Hermann et al. (1998) *Electrophoresis* 19: 3217-3221; Fountoulakis et al. (1998) *Electrophoresis* 19: 1193-1202; Langen et al. (1997) *Electrophoresis* 18: 1184-1192; Antelmann et al. (1997) *Electrophoresis* 18: 1451-1463). Other separation techniques may also be utilized for protein separation, such as capillary gel electrophoresis; such techniques are well known in the art.

Proteins separated by these methodologies can be visualized by standard techniques, such as by staining or labeling. Suitable stains are known in the art, and include Coomassie Brilliant Blue, silver stain, or fluorescent dyes such as Sypro Ruby (Molecular Probes). The inclusion of radioactively labeled amino acids or other protein precursors (e.g., $^{35}$S-methionine, $^{35}$S-cysteine, $^{14}$C-labelled amino acids, $^{15}$N-amino acids, $^{15}$NO$_3$ or $^{15}$NH$_4^+$ or $^{13}$C-labelled amino acids) in the medium of *C. glutamicum* permits the labeling of proteins from these cells prior to their separation. Similarly, fluorescent labels may be employed. These labeled proteins can be extracted, isolated and separated according to the previously described techniques.

Proteins visualized by these techniques can be further analyzed by measuring the amount of dye or label used. The amount of a given protein can be determined quantitatively using, for example, optical methods and can be compared to the amount of other proteins in the same gel or in other gels. Comparisons of proteins on gels can be made, for example, by optical comparison, by spectroscopy, by image scanning and analysis of gels, or through the use of photographic films and screens. Such techniques are well-known in the art.

To determine the identity of any given protein, direct sequencing or other standard techniques may be employed. For example, N- and/or C-terminal amino acid sequencing (such as Edman degradation) may be used, as may mass spectrometry (in particular MALDI or ESI techniques (see, e.g., Langen et al. (1997) *Electrophoresis* 18: 1184-1192)). The protein sequences provided herein can be used for the identification of *C. glutamicum* proteins by these techniques.

The information obtained by these methods can be used to compare patterns of protein presence, activity, or modification between different samples from various biological conditions (e.g., different organisms, time points of fermentation, media conditions, or different biotopes, among others). Data obtained from such experiments alone, or in combination with other techniques, can be used for various applications, such as to compare the behavior of various organisms in a given (e.g., metabolic) situation, to increase the productivity of strains which produce fine chemicals or to increase the efficiency of the production of fine chemicals.

Example 14

Cloning of Genes by Application of the Polymerase Chain Reaction (PCR)

Genes can be amplified using specific oligonucleotides comprising either nucleotide sequences homologous to sequences of *Corynebacterium glutamicum* or other strains as well as recognition sites of restriction enzymes well known in the art (e.g., as described in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989). Theses oligonucleotides can be used to amplify specific DNA-fragments containing parts of the chromosome of mentioned strains using DNA-polymerases such as *T. aquaticus* DNA-polymerase, *P. furiosus* DNA-polymerase, or *P. woesei* DNA-polymerase and dNTPs nucleotides in an appropriate buffer solution as described by the manufacturer.

Gene fragments such as coding sequences from RXA00657 including appropriate upstream and downstream regions not contained in the coding region of the mentioned gene can be amplified using the aforementioned technologies. Furthermore, these fragments can be purified from unincorporated oligonucleotides and nucleotides. DNA restriction enzymes can be used to produce protruding ends that can be used to ligate DNA fragments to vectors digested with complementary enzymes or compatible enzymes producing ends that can be used to ligate the DNA into the vectors mentioned in Sinskey et al., U.S. Pat. No. 4,649,119, and techniques for genetic manipulation of *C. glutamicum* and the related *Brevibacterium* species (e.g., *lactofermentum*) (Yoshihama et al, *J. Bacteriol.* 162: 591-597 (1985); Katsumata et al., *J. Bacteriol.* 159: 306-311 (1984); and Santamaria et al., *J. Gen. Microbiol.* 130: 2237-2246 (1984). Oligonucleotides used as primers for the amplification of upstream DNA sequence, the coding region sequence and the downstream region of RXA00657 were as follows:

```
TCGGGTATCCGCGCTACACTTAGA;      (SEQ ID NO: 121)

GGAAACCGGGGCATCGAAACTTA.       (SEQ ID NO: 122)
```

*Corynebacterium glutamicum* chromosomal DNA with an amount of 200 ng was used as a template in a 100 µl reaction volume containing 2.5 U Pfu Turbo-Polymerase™ (Stratagene™), and 200 µM dNTP-nucleotides The PCR was performed on a PCR-Cycler™ (Perkin Elmer 2400™) using the following temperature/time protocol:

1 cycle: 94° C.: 2 min.;

20 cycle: 94° C.: 1 min.;

52° C.: 1 min, 72° C.: 1.5 min., 1 cycle: 72° C.: 5 min.

Primers were removed from the resulting amplified DNA fragment and the resulting fragment was cloned into the blunt EcoRV site of pBS KS (Stratagene™). The fragment was excised by digestion with the restriction enzymes BamHI/XhoI and ligated into a BamHI SalI digested vector pB (SEQ ID NO.:125). The resulting vector is called pB RXA00657.

Resulting recombinant vectors can be analyzed using standard techniques described in e.g., Sambrook, J., Fritsh, E. F., and Maniatis, T. *Molecular Cloning: A Laboratory Manual 2nd, ed, Cold Spring Harbor Laboratory*, Cold Spring Harbor Laboratory Press, Cold Spring Harbor, N.Y., 1989), and can be transferred into *C. glutamicum* using aforementioned techniques.

A *Corynebacterium* strain (ATCC 13286) was treated for a transformation as described. Transformation of *C. glutamicum* can be achieved by protoplast transformation (Kastsumata, R. et al. (1984) *J. Bacteriol.* 159306-311), electroporation (Liebl, E. et al. (1989) *FEMS Microbiol. Letters*, 53:399-303) and in cases where special vectors are used, also by conjugation (as described, e.g., in Schäfer, A. et al. (1990) *J. Bacteriol.* 172:1663-1666). It is also possible to transfer the shuttle vectors for *C. glutamicum* to *E. coli* by preparing plasmid DNA from *C. glutamicum* (using standard methods well-known in the art) and transforming it into *E. coli*. This transformation step can be performed using standard methods, but it is advantageous to use an Mcr-deficient *E. coli* strain, such as NM522 (Gough & Murray (1983) *J. Mol. Biol.* 166:1-19).

Transformation of a bacterial strain such as *Corynebacterium glutamicum* strain (ATCC 13286) was performed with a plasmid pB containing the aforementioned DNA regions of RXA00657 (SEQ ID NO.:6) and in another case with the vector pB (SEQ ID NO.: ) carrying no additional insertion of nucleic acids.

The resulting strains were plated on and isolated from CM-Medium (10 g/l Glucose 2.5 g/l NaCl, 2.0 g/l Urea, 10 g/l Bacto Peptone (Difco/Becton Dicinson/Sparks USA™), 5 g/l yeast extract (Difco/Becton Dicinson/Sparks USA™), 5 g/l meat extract (Difco/Becton Dicinson/Sparks USA™), 22 g/l Agar (Difco/Becton Dickinson/Sparks USA™) and 15 µg/ml kanamycin sulfate (Serva, Germany) with a adjusted with NaOH to pH of 6.8.

Strains isolated from the aforementioned agar medium were inoculated in 10 ml in a 100 ml shake flask containing no baffles in liquid medium containing 100 g/l sucrose 50 g/l $(NH_4)_2SO_4$, 2.5 g/l NaCl, 2.0 g/l Urea, 10 g/l Bacto Peptone (Difco/Becton Dickinson/Sparks USA), 5 g/l yeast extract (Difco/Becton Dickinson/Sparks USA), 5 g/l meat extract (Difco/Becton Dickinson/Sparks USA), and 25 g/l CaCO3 (Riedel de Haen, Germany). Medium was a adjusted with NaOH to pH of 6.8.

Strains were incubated at 30° C. for 48 h. Supernatants of incubations were prepared by centrifugation 20' at 12,000 rpm in an Eppendorf™ microcentrifuge. Liquid supernatants were diluted and subjected to amino acid analysis (Standard methods for these measurements are outlined in Applied Microbial Physiology, A Practical Approach, P. M. Rhodes and P. F. Stanbury, eds., IRL Press, p. 103-129; 131-163; and 165-192 (ISBN: 0199635773) and references cited therein).

The results are shown in Table 6, below.

TABLE 6

| | Results: | | |
|---|---|---|---|
| Strain ATCC 13286 | Plasmid contained | pB | pB RXA00657 |
| lysin produced (g/l) | | 13.5 | 14.93 |
| Selectivity (mol lysine/mol consumed Saccharose) | | 0.235 | 0.25 |

Equivalents

Those of ordinary skill in the art will recognize, or will be able to ascertain using no more than routine experimentation, many equivalents to the specific embodiments of the invention described herein. Such equivalents are intended to be encompassed by the following claims.

TABLE 1

| | | | | Included Genes | | |
|---|---|---|---|---|---|---|
| Nucleic Acid SEQ ID NO | Amino Acid SEQ ID NO | Identification Code | Contig. | NT Start | NT Stop | Function |
| | | | | Lysine biosynthesis | | |
| 5 | 6 | RXA00657 | | | | AMINOACID BIOSYNTHESIS REGULATOR |
| 7 | 8 | RXA02229 | GR00653 | 2793 | 3617 | DIAMINOPIMELATE EPIMERASE (EC 5.1.1.7) |
| 9 | 10 | RXS02970 | | | | ACETYLORNITHINE AMINOTRANSFERASE (EC 2.6.1.11) |
| 11 | 12 | F RXA01009 | GR00287 | 4714 | 5943 | ACETYLORNITHINE AMINOTRANSFERASE (EC 2.6.1.11) |
| 13 | 14 | RXC02390 | | | | MEMBRANE SPANNING PROTEIN INVOLVED IN LYSINE METABOLISM |
| 15 | 16 | RXC01796 | | | | MEMBRANE ASSOCIATED PROTEIN INVOLVED IN LYSINE METABOLISM |
| 17 | 18 | RXC01207 | | | | CYTOSOLIC PROTEIN INVOLVED IN METABOLISM OF LYSINE AND THREONINE |

TABLE 1-continued

Included Genes

| Nucleic Acid SEQ ID NO | Amino Acid SEQ ID NO | Identification Code | Contig. | NT Start | NT Stop | Function |
|---|---|---|---|---|---|---|
| 19 | 20 | RXC00657 | | | | TRANSCRIPTIONAL REGULATOR INVOLVED IN LYSINE METABOLISM |
| 21 | 22 | RXC00552 | | | | CYTOSOLIC PROTEIN INVOLVED IN LYSINE METABOLISM |
| 23 | 24 | RXA00534 | GR00137 | 4758 | 3496 | ASPARTOKINASE ALPHA AND BETA SUBUNITS (EC 2.7.2.4) |
| 25 | 26 | RXA00533 | GR00137 | 3469 | 2438 | ASPARTATE-SEMIALDEHYDE DEHYDROGENASE (EC 1.2.1.11) |
| 27 | 28 | RXA02843 | GR00842 | 543 | 4 | 2,3,4,5-TETRAHYDROPYRIDINE-2-CARBOXYLATE N-SUCCINYLTRANSFERASE (EC 2.3.1.117) |
| 29 | 30 | RXA02022 | GR00613 | 2063 | 3169 | SUCCINYL-DIAMINOPIMELATE DESUCCINYLASE (EC 3.5.1.18) |
| 31 | 32 | RXA00044 | GR00007 | 3458 | 4393 | DIHYDRODIPICOLINATE SYNTHASE (EC 4.2.1.52) |
| 33 | 34 | RXA00863 | GR00236 | 896 | 1639 | DIHYDRODIPICOLINATE REDUCTASE (EC 1.3.1.26) |
| 35 | 36 | RXA00864 | GR00236 | 1694 | 2443 | probable 2,3-dihydrodipicolinate N-C6-lyase (cyclizing) (EC 4.3.3.-) - Corynebacterium glutamicum |
| 37 | 38 | RXA02843 | GR00842 | 543 | 4 | 2,3,4,5-TETRAHYDROPYRIDINE-2-CARBOXYLATE N-SUCCINYLTRANSFERASE (EC 2.3.1.117) |
| 39 | 40 | RXN00355 | VV0135 | 31980 | 30961 | MESO-DIAMINOPIMELATE D-DEHYDROGENASE |
| 41 | 42 | F RXA00352 | GR00068 | 861 | 4 | MESO-DIAMINOPIMELATE D-DEHYDROGENASE (EC 1.4.1.16) |
| 43 | 44 | RXA00972 | GR00274 | 3 | 1379 | DIAMINOPIMELATE DECARBOXYLASE (EC 4.1.1.20) |
| 45 | 46 | RXA02653 | GR00752 | 5237 | 7234 | DIAMINOPIMELATE DECARBOXYLASE (EC 4.1.1.20) |
| 47 | 48 | RXA01393 | GR00408 | 4249 | 3380 | LYSINE EXPORT REGULATOR PROTEIN |
| 49 | 50 | RXA00241 | GR00036 | 5443 | 6945 | L-LYSINE TRANSPORT PROTEIN |
| 51 | 52 | RXA01394 | GR00408 | 4320 | 5018 | LYSINE EXPORTER PROTEIN |
| 53 | 54 | RXA00865 | GR00236 | 2647 | 3549 | DIHYDRODIPICOLINATE SYNTHASE (EC 4.2.1.52) |
| 55 | 56 | RXS02021 | | | | 2,3,4,5-TRAHYDROPYRIDINE-2-CARBOXYLATE N-SUCCINYLTRANSFERASE (EC 2.3.1.117) |
| 57 | 58 | RXS02157 | | | | ACETYLORNITHINE AMINOTRANSFERASE (EC 2.6.1.11) |
| 59 | 60 | RXC00733 | | | | ABC TRANSPORTER ATP-BINDING PROTEIN INVOLVED IN LYSINE METABOLISM |
| 61 | 62 | RXC00861 | | | | PROTEIN INVOLVED IN LYSINE METABOLISM |
| 63 | 64 | RXC00866 | | | | ZN-DEPENDENT HYDROLASE INVOLVED IN LYSINE METABOLISM |
| 65 | 66 | RXC02095 | | | | ABC TRANSPORTER ATP-BINDING PROTEIN INVOLVED IN LYSINE METABOLISM |
| 67 | 68 | RXC03185 | | | | PROTEIN INVOLVED IN LYSINE METABOLISM |
| Metabolism of methionine and S-adenosyl methionine ||||||||
| 1 | 2 | metZ or met | | | | O-ACETYLHOMOSERINE SULFHYDRYLASE (EC 4.2.99.10) |
| 3 | 4 | metC | | | | Cystathionine-γ-lyase |
| 69 | 70 | RXA00115 | GR00017 | 5359 | 4313 | HOMOSERINE O-ACETYLTRANSFERASE (EC 2.3.1.31) |
| 71 | 72 | RXN00403 | VV0086 | 70041 | 68911 | HOMOSERINE O-ACETYLTRANSFERASE |
| 73 | 74 | F RXA00403 | GR00088 | 723 | 1832 | HOMOSERINE O-ACETYLTRANSFERASE (EC 2.3.1.11) |
| 75 | 76 | RXS03158 | | | | CYSTATHIONINE GAMMA-SYNTHASE (EC 4.2.99.9) |
| 77 | 78 | F RXA00254 | GR00038 | 2404 | 1811 | CYSTATHIONINE GAMMA-SYNTHASE (EC 4.2.99.9) |
| 79 | 80 | RXA02532 | GR00726 | 3085 | 2039 | CYSTATHIONINE GAMMA-SYNTHASE (EC 4.2.99.9) |
| 81 | 82 | RXS03159 | | | | CYSTATHIONINE GAMMA-SYNTHASE (EC 4.2.99.9) |
| 83 | 84 | F RXA02768 | GR00770 | 1919 | 2521 | CYSTATHIONINE GAMMA-SYNTHASE (EC 4.2.99.9) |
| 85 | 86 | RXA00216 | GR00032 | 16286 | 15297 | 5-methyltetrahydrofolate-homocysteine methyltransferase (methionine synthetase) |
| 87 | 94 | RXN02197 | GR00645 | 4552 | 4025 | 5-METHYLTETRAHYDROFOLATE-HOMOCYSTEINE METHYLTRANSFERASE (EC 2.1.1.13) |
| 89 | 90 | RXN02198 | VV0302 | 9228 | 11726 | 5-METHYLTETRAHYDROFOLATE-HOMOCYSTEINE METHYLTRANSFERASE (EC 2.1.1.13) |
| 91 | 91 | F RXA02198 | GR00646 | 2483 | 6 | 5-METHYLTETRAHYDROFOLATE-HOMOCYSTEINE METHYLTRANSFERASE (EC 2.1.1.13) |
| 93 | 94 | RXN03074 | VV0042 | 2238 | 1741 | S-ADENOSYLMETHIONINE:2-DEMETHYLMENAQUINONE METHYLTRANSFERASE (EC 2.1.-.-) |
| 95 | 96 | F RXA02906 | GR10044 | 1142 | 645 | S-ADENOSYLMETHIONINE:2-DEMETHYLMENAQUINONE METHYLTRANSFERASE (EC 2.1.-.-) |
| 97 | 98 | RXN00132 | VV0124 | 3612 | 5045 | ADENOSYLHOMOCYSTEINASE (EC 3.3.1.1) |
| 99 | 100 | F RXA00132 | GR00020 | 7728 | 7624 | ADENOSYLHOMOCYSTEINASE (EC 3.3.1.1) |
| 101 | 102 | F RXA01371 | GR00398 | 2339 | 3634 | ADENOSYLHOMOCYSTEINASE (EC 3.3.1.1) |
| 103 | 104 | RXN02085 | | | | 5-METHYLTETRAHYDROPTEROYLTRIGLUTAMATE--HOMOCYSTEINE METHYLTRANSFERASE (EC 2.1.1.14) |
| 105 | 106 | F RXA02085 | GR00629 | 3496 | 5295 | 5-METHYLTETRAHYDROPTEROYLTRIGLUTAMATE--HOMOCYSTEINE METHYLTRANSFERASE (EC 2.1.1.14) |
| 107 | 108 | F RXA02086 | GR00629 | 5252 | 5731 | 5-METHYLTETRAHYDROPTEROYLTRIGLUTAMATE--HOMOCYSTEINE METHYLTRANSFERASE (EC 2.1.1.14) |
| 109 | 110 | RXN02648 | | | | 5-METHYLTETRAHYDROPTEROYLTRIGLUTAMATE--HOMOCYSTEINE METHYLTRANSFERASE (EC 2.1.1.14) |
| 111 | 112 | F RXA02648 | GR00751 | 5254 | 4730 | 5-METHYLTETRAHYDROPTEROYLTRIGLUTAMATE--HOMOCYSTEINE METHYLTRANSFERASE (EC 2.1.1.14) |
| 113 | 114 | F RXA02658 | GR00752 | 14764 | 15447 | 5-METHYLTETRAHYDROPTEROYLTRIGLUTAMATE--HOMOCYSTEINE METHYLTRANSFERASE (EC 2.1.1.14) |
| 115 | 116 | RXC02238 | | | | PROTEIN INVOLVED IN METABOLISM OF S-ADENOSYLMETHIONINE, PURINES AND PANTOTHENATE |

TABLE 1-continued

| | | Included Genes | | | | |
|---|---|---|---|---|---|---|
| Nucleic Acid SEQ ID NO | Amino Acid SEQ ID NO | Identification Code | Contig. | NT Start | NT Stop | Function |
| 117 | 118 | RXC00128 | | | | EXPORTED PROTEIN INVOLVED IN METABOLISM OF PYRIDIMES AND ADENOSYLHOMOCYSTEINE |
| | | | S-2adenosyl methionine (SAM) Biosynthesis | | | |
| 119 | 120 | RXA02240 | GR00654 | 7160 | 8380 | S-ADENOSYLMETHIONINE SYNTHETASE (EC 2.5.1.6) |

TABLE 2

GENES IDENTIFIED FROM GENBANK

| GenBank™ Accession No. | Gene Name | Gene Function | Reference |
|---|---|---|---|
| A09073 | ppg | Phosphoenol pyruvate carboxylase | Bachmann, B. et al. "DNA fragment coding for phosphoenolpyruvat corboxylase, recombinant DNA carrying said fragment, strains carrying the recombinant DNA and method for producing L-aminino acids using said strains," Patent: EP 0358940-A 3 Mar. 21, 1990 |
| A45579, A45581, A45583, A45585 A45587 | | Threonine dehydratase | Moeckel, B. et al. "Production of L-isoleucine by means of recombinant micro-organisms with deregulated threonine dehydratase," Patent: WO 9519442-A 5 Jul. 20, 1995 |
| AB003132 | murC; ftsQ; ftsZ | | Kobayashi, M. et al. "Cloning, sequencing, and characterization of the ftsZ gene from coryneform bacteria," Biochem. Biophys. Res. Commun., 236(2): 383-388 (1997) |
| AB015023 | murC; ftsQ | | Wachi, M. et al. "A murC gene from Coryneform bacteria," Appl. Microbiol. Biotechnol., 51(2): 223-228 (1999) |
| AB018530 | dtsR | | Kimura, E. et al. "Molecular cloning of a novel gene, dtsR, which rescues the detergent sensitivity of a mutant derived from *Brevibacterium lactofermentum*," Biosci. Biotechnol. Biochem., 60(10): 1565-1570 (1996) |
| AB018531 | dtsR1; dtsR2 | | |
| AB020624 | murI | D-glutamate racemase | |
| AB023377 | tkt | transketolase | |
| AB024708 | gltB; gltD | Glutamine 2-oxoglutarate aminotransferase large and small subunits | |
| AB025424 | acn | aconitase | |
| AB027714 | rep | Replication protein | |
| AB027715 | rep; aad | Replication protein; aminoglycoside adenyltransferase | |
| AF005242 | argC | N-acetylglutamate-5-semialdehyde dehydrogenase | |
| AF005635 | glnA | Glutamine synthetase | |
| AF030405 | hisF | cyclase | |
| AF030520 | argG | Argininosuccinate synthetase | |
| AF031518 | argF | Ornithine carbamolytransferase | |
| AF036932 | aroD | 3-dehydroquinate dehydratase | |
| AF038548 | pyc | Pyruvate carboxylase | |
| AF038651 | dciAE; apt; rel | Dipeptide-binding protein; adenine phosphoribosyltransferase; GTP pyrophosphokinase | Wehmeier, L. et al. "The role of the *Corynebacterium glutamicum* rel gene in (p)ppGpp metabolism," Microbiology, 144: 1853-1862 (1998) |
| AF041436 | argR | Arginine repressor | |
| AF045998 | impA | Inositol monophosphate phosphatase | |
| AF048764 | argH | Argininosuccinate lyase | |
| AF049897 | argC; argJ; argB; argD; argF; argR; argG; argH | N-acetylglutamylphosphate reductase; ornithine acetyltransferase; N-acetylglutamate kinase; acetylornithine transminase; ornithine carbamoyltransferase; arginine repressor; argininosuccinate synthase; argininosuccinate lyase | |
| AF050109 | inhA | Enoyl-acyl carrier protein reductase | |
| AF050166 | hisG | ATP phosphoribosyltransferase | |
| AF051846 | hisA | Phosphoribosylformimino-5-amino-1-phosphoribosyl-4-imidazolecarboxamide isomerase | |

TABLE 2-continued

GENES IDENTIFIED FROM GENBANK

| GenBank™ Accession No. | Gene Name | Gene Function | Reference |
|---|---|---|---|
| AF052652 | metA | Homoserine O-acetyltransferase | Park, S. et al. "Isolation and analysis of metA, a methionine biosynthetic gene encoding homoserine acetyltransferase in *Corynebacterium glutamicum*," Mol. Cells., 8(3): 286-294 (1998) |
| AF053071 | aroB | Dehydroquinate synthetase | |
| AF060558 | hisH | Glutamine amidotransferase | |
| AF086704 | hisE | Phosphoribosyl-ATP-pyrophosphohydrolase | |
| AF114233 | aroA | 5-enolpyruvylshikimate 3-phosphate synthase | |
| AF116184 | panD | L-aspartate-alpha-decarboxylase precursor | Dusch, N. et al. "Expression of the *Corynebacterium glutamicum* panD gene encoding L-aspartate-alpha-decarboxylase leads to pantothenate overproduction in *Escherichia coli*," Appl. Environ. Microbiol., 65(4)1530-1539 (1999) |
| AF124518 | aroD; aroE | 3-dehydroquinase; shikimate dehydrogenase | |
| AF124600 | aroC; aroK; aroB; pepQ | Chorismate synthase; shikimate kinase; 3-dehydroquinate synthase; putative cytoplasmic peptidase | |
| AF145897 | inhA | | |
| AF145898 | inhA | | |
| AJ001436 | ectP | Transport of ectoine, glycine betaine, proline | Peter, H. et al. "*Corynebacterium glutamicum* is equipped with four secondary carriers for compatible solutes: Identification, sequencing, and characterization of the proline/ectoine uptake system, ProP, and the ectoine/proline/glycine betaine carrier, EctP," J. Bacteriol., 180(22): 6005-6012 (1998) |
| AJ004934 | dapD | Tetrahydrodipicolinate succinylase (incomplete$^f$) | Wehrmann, A. et al. "Different modes of diaminopimelate synthesis and their role in cell wall integrity: A study with *Corynebacterium glutamicum*," J. Bacteriol., 180(12): 3159-3165 (1998) |
| AJ007732 | ppc; secG; amt; ocd; soxA | Phosphoenolpyruvate-carboxylase; ?; high affinity ammonium uptake protein; putative ornithine-cyclodecarboxylase; sarcosine oxidase | |
| AJ010319 | ftsY, glnB, glnD; srp; amtP | Involved in cell division; PII protein; uridylyltransferase (uridylyl-removing enzmye); signal recognition particle; low affinity ammonium uptake protein | Jakoby, M. et al. "Nitrogen regulation in *Corynebacterium glutamicum*; Isolation of genes involved in biochemical characterization of corresponding proteins," FEMS Microbiol., 173(2): 303-310 (1999) |
| AJ132968 | cat | Chloramphenicol acetyl transferase | |
| AJ224946 | mqo | L-malate: quinone oxidoreductase | Molenaar, D. et al. "Biochemical and genetic characterization of the membrane-associated malate dehydrogenase (acceptor) from *Corynebacterium glutamicum*," Eur. J. Biochem., 254(2): 395-403 (1998) |
| AJ238250 | ndh | NADH dehydrogenase | |
| AJ238703 | porA | Porin | Lichtinger, T. et al. "Biochemical and biophysical characterization of the cell wall porin of *Corynebacterium glutamicum*: The channel is formed by a low molecular mass polypeptide," Biochemistry, 37(43): 15024-15032 (1998) |
| D17429 | | Transposable element IS31831 | Vertes et al. "Isolation and characterization of IS31831, a transposable element from *Corynebacterium glutamicum*," Mol. Microbiol., 11(4): 739-746 (1994) |
| D84102 | odhA | 2-oxoglutarate dehydrogenase | Usuda, Y. et al. "Molecular cloning of the *Corynebacterium glutamicum* (*Brevibacterium lactofermentum* AJ12036) odhA gene encoding a novel type of 2-oxoglutarate dehydrogenase," Microbiology, 142: 3347-3354 (1996) |
| E01358 | hdh; hk | Homoserine dehydrogenase; homoserine kinase | Katsumata, R. et al. "Production of L-thereonine and L-isoleucine," Patent: JP 1987232392-A 1 Oct. 12, 1987 |
| E01359 | | Upstream of the start codon of homoserine kinase gene | Katsumata, R. et al. "Production of L-thereonine and L-isoleucine," Patent: JP 1987232392-A 2 Oct. 12, 1987 |
| E01375 | | Tryptophan operon | |
| E01376 | trpL; trpE | Leader peptide; anthranilate synthase | Matsui, K. et al. "Tryptophan operon, peptide and protein coded thereby, utilization of tryptophan operon gene expression and production of tryptophan," Patent: JP 1987244382-A 1 Oct. 24, 1987 |
| E01377 | | Promoter and operator regions of tryptophan operon | Matsui, K. et al. "Tryptophan operon, peptide and protein coded thereby, utilization of tryptophan operon gene expression and production of tryptophan," Patent: JP 1987244382-A 1 Oct. 24, 1987 |
| E03937 | | Biotin-synthase | Hatakeyama, K. et al. "DNA fragment containing gene capable of coding biotin synthetase and its utilization," Patent: JP 1992278088-A 1 Oct. 02, 1992 |
| E04040 | | Diamino pelargonic acid aminotransferase | Kohama, K. et al. "Gene coding diaminopelargonic acid aminotransferase and desthiobiotin synthetase and its utilization," Patent: JP 1992330284-A 1 Nov. 18, 1992 |
| E04041 | | Desthiobiotinsynthetase | Kohama, K. et al. "Gene coding diaminopelargonic acid aminotransferase and desthiobiotin synthetase and its utilization," Patent: JP 1992330284-A 1 Nov. 18, 1992 |
| E04307 | | Flavum aspartase | Kurusu, Y. et al. "Gene DNA coding aspartase and utilization thereof," Patent: JP 1993030977-A 1 Feb. 09, 1993 |
| E04376 | | Isocitric acid lyase | Katsumata, R. et al. "Gene manifestation controlling DNA," Patent: JP 1993056782-A 3 Mar. 09, 1993 |

TABLE 2-continued

GENES IDENTIFIED FROM GENBANK

| GenBank™ Accession No. | Gene Name | Gene Function | Reference |
|---|---|---|---|
| E04377 | | Isocitric acid lyase N-terminal fragment | Katsumata, R. et al. "Gene manifestation controlling DNA," Patent: JP 1993056782-A 3 Mar. 09, 1993 |
| E04484 | | Prephenate dehydratase | Sotouchi, N. et al. "Production of L-phenylalanine by fermentation," Patent: JP 1993076352-A 2 Mar. 30, 1993 |
| E05108 | | Aspartokinase | Fugono, N. et al. "Gene DNA coding Aspartokinase and its use," Patent: JP 1993184366-A 1 Jul. 27, 1993 |
| E05112 | | Dihydro-dipichorinate synthetase | Hatakeyama, K. et al. "Gene DNA coding dihydrodipicolinic acid synthetase and its use," Patent: JP 1993184371-A 1 Jul. 27, 1993 |
| E05776 | | Diaminopimelic acid dehydrogenase | Kobayashi, M. et al. "Gene DNA coding Diaminopimelic acid dehydrogenase and its use," Patent: JP 1993284970-A 1 Nov. 02, 1993 |
| E05779 | | Threonine synthase | Kohama, K. et al. "Gene DNA coding threonine synthase and its use," Patent: JP 1993284972-A 1 Nov. 02, 1993 |
| E06110 | | Prephenate dehydratase | Kikuchi, T. et al. "Production of L-phenylalanine by fermentation method," Patent: JP 1993344881-A 1 Dec. 27, 1993 |
| E06111 | | Mutated Prephenate dehydratase | Kikuchi, T. et al. "Production of L-phenylalanine by fermentation method," Patent: JP 1993344881-A 1 Dec. 27, 1993 |
| E06146 | | Acetohydroxy acid synthetase | Inui, M. et al. "Gene capable of coding Acetohydroxy acid synthetase and its use," Patent: JP 1993344893-A 1 Dec. 27, 1993 |
| E06825 | | Aspartokinase | Sugimoto, M. et al. "Mutant aspartokinase gene," patent: JP 1994062866-A 1 Mar. 08, 1994 |
| E06826 | | Mutated aspartokinase alpha subunit | Sugimoto, M. et al. "Mutant aspartokinase gene," patent: JP 1994062866-A 1 Mar. 08, 1994 |
| E06827 | | Mutated aspartokinase alpha subunit | Sugimoto, M. et al. "Mutant aspartokinase gene," patent: JP 1994062866-A 1 Mar. 08, 1994 |
| E07701 | secY | | Honno, N. et al. "Gene DNA participating in integration of membraneous protein to membrane," Patent: JP 1994169780-A 1 Jun. 21, 1994 |
| E08177 | | Aspartokinase | Sato, Y. et al. "Genetic DNA capable of coding Aspartokinase released from feedback inhibition and its utilization," Patent: JP 1994261766-A 1 Sep. 20, 1994 |
| E08178, E08179, E08180, E08181, E08182 | | Feedback inhibition-released Aspartokinase | Sato, Y. et al. "Genetic DNA capable of coding Aspartokinase released from feedback inhibition and its utilization," Patent: JP 1994261766-A 1 Sep. 20, 1994 |
| E08232 | | Acetohydroxy-acid isomeroreductase | Inui, M. et al. "Gene DNA coding acetohydroxy acid isomeroreductase," Patent: JP 1994277067-A 1 Oct. 04, 1994 |
| E08234 | secE | | Asai, Y. et al. "Gene DNA coding for translocation machinery of protein," Patent: JP 1994277073-A 1 Oct. 04, 1994 |
| E08643 | | FT aminotransferase and desthiobiotin synthetase promoter region | Hatakeyama, K. et al. "DNA fragment having promoter function in coryneform bacterium," Patent: JP 1995031476-A 1 Feb. 03, 1995 |
| E08646 | | Biotin synthetase | Hatakeyama, K. et al. "DNA fragment having promoter function in coryneform bacterium," Patent: JP 1995031476-A 1 Feb. 03, 1995 |
| E08649 | | Aspartase | Kohama, K. et al "DNA fragment having promoter function in coryneform bacterium," Patent: JP 1995031478-A 1 Feb. 03, 1995 |
| E08900 | | Dihydrodipicolinate reductase | Madori, M. et al. "DNA fragment containing gene coding Dihydrodipicolinate acid reductase and utilization thereof," Patent: JP 1995075578-A 1 Mar. 20, 1995 |
| E08901 | | Diaminopimelic acid decarboxylase | Madori, M. et al. "DNA fragment containing gene coding Diaminopimelic acid decarboxylase and utilization thereof," Patent: JP 1995075579-A 1 Mar. 20, 1995 |
| E12594 | | Serine hydroxymethyltransferase | Hatakeyama, K. et al. "Production of L-trypophan," Patent: JP 1997028391-A 1 Feb. 04, 1997 |
| E12760, E12759, E12758 | | transposase | Moriya, M. et al. "Amplification of gene using artificial transposon," Patent: JP 1997070291-A Mar. 18, 1997 |
| E12764 | | Arginyl-tRNA synthetase; diaminopimelic acid decarboxylase | Moriya, M. et al. "Amplification of gene using artificial transposon," Patent: JP 1997070291-A Mar. 18, 1997 |
| E12767 | | Dihydrodipicolinic acid synthetase | Moriya, M. et al. "Amplification of gene using artificial transposon," Patent: JP 1997070291-A Mar. 18, 1997 |
| E12770 | | aspartokinase | Moriya, M. et al. "Amplification of gene using artificial transposon," Patent: JP 1997070291-A Mar. 18, 1997 |
| E12773 | | Dihydrodipicolinic acid reductase | Moriya, M. et al. "Amplification of gene using artificial transposon," Patent: JP 1997070291-A Mar. 18, 1997 |
| E13655 | | Glucose-6-phosphate dehydrogenase | Hatakeyama, K. et al. "Glucose-6-phosphate dehydrogenase and DNA capable of coding the same," Patent: JP 1997224661-A 1 Sep. 02, 1997 |
| L01508 | IlvA | Threonine dehydratase | Moeckel, B. et al. "Functional and structural analysis of the threonine dehydratase of *Corynebacterium glutamicum*," J. Bacteriol., 174: 8065-8072 (1992) |
| L07603 | EC 4.2.1.15 | 3-deoxy-D-arabinoheptulosonate-7-phosphate synthase | Chen, C. et al. "The cloning and nucleotide sequence of *Corynebacterium glutamicum* 3-deoxy-D-arabinoheptulosonate-7-phosphate synthase gene," FEMS Microbiol. Lett., 107: 223-230 (1993) |
| L09232 | IlvB; ilvN; ilvC | Acetohydroxy acid synthase large subunit; Acetohydroxy acid synthase small subunit; Acetohydroxy acid isomeroreductase | Keilhauer, C. et al. "Isoleucine synthesis in *Corynebacterium glutamicum*: molecular analysis of the ilvB-ilvN-ilvC operon," J. Bacteriol., 175(17): 5595-5603 (1993) |

TABLE 2-continued

GENES IDENTIFIED FROM GENBANK

| GenBank™ Accession No. | Gene Name | Gene Function | Reference |
|---|---|---|---|
| L18874 | PtsM | Phosphoenolpyruvate sugar phosphotransferase | Fouet, A et al. "*Bacillus subtilis* sucrose-specific enzyme II of the phosphotransferase system: expression in *Escherichia coli* and homology to enzymes II from enteric bacteria," PNAS USA, 84(24): 8773-8777 (1987); Lee, J. K. et al. "Nucleotide sequence of the gene encoding the *Corynebacterium glutamicum* mannose enzyme II and analyses of the deduced protein sequence," FEMS Microbiol. Lett., 119(1-2): 137-145 (1994) |
| L27123 | aceB | Malate synthase | Lee, H-S. et al. "Molecular characterization of aceB, a gene encoding malate synthase in *Corynebacterium glutamicum*," J. Microbiol. Biotechnol., 4(4): 256-263 (1994) |
| L27126 | | Pyruvate kinase | Jetten, M. S. et al. "Structural and functional analysis of pyruvate kinase from *Corynebacterium glutamicum*," Appl. Environ. Microbiol., 60(7): 2501-2507 (1994) |
| L28760 | aceA | Isocitrate lyase | |
| L35906 | dtxr | Diphtheria toxin repressor | Oguiza, J. A. et al. "Molecular cloning, DNA sequence analysis, and characterization of the *Corynebacterium diphtheriae* dtxR from *Brevibacterium lactofermentum*," J. Bacteriol., 177(2): 465-467 (1995) |
| M13774 | | Prephenate dehydratase | Follettie, M. T. et al. "Molecular cloning and nucleotide sequence of the *Corynebacterium glutamicum* pheA gene," J. Bacteriol., 167: 695-702 (1986) |
| M16175 | 5S rRNA | | Park, Y-H. et al. "Phylogenetic analysis of the coryneform bacteria by 5S rRNA sequences," J. Bacteriol., 169: 1801-1806 (1987) |
| M16663 | trpE | Anthranilate synthase, 5' end | Sano, K. et al. "Structure and function of the trp operon control regions of *Brevibacterium lactofermentum*, a glutamic-acid-producing bacterium," Gene, 52: 191-200 (1987) |
| M16664 | trpA | Tryptophan synthase, 3'end | Sano, K. et al. "Structure and function of the trp operon control regions of *Brevibacterium lactofermentum*, a glutamic-acid-producing bacterium," Gene, 52: 191-200 (1987) |
| M25819 | | Phosphoenolpyruvate carboxylase | O'Regan, M. et al. "Cloning and nucleotide sequence of the Phosphoenolpyruvate carboxylase-coding gene of *Corynebacterium glutamicum* ATCC13032," Gene, 77(2): 237-251 (1989) |
| M85106 | | 23S rRNA gene insertion sequence | Roller, C. et al. "Gram-positive bacteria with a high DNA G + C content are characterized by a common insertion within their 23S rRNA genes," J. Gen. Microbiol., 138: 1167-1175 (1992) |
| M85107, M85108 | | 23S rRNA gene insertion sequence | Roller, C. et al. "Gram-positive bacteria with a high DNA G + C content are characterized by a common insertion within their 23S rRNA genes," J. Gen. Microbiol., 138: 1167-1175 (1992) |
| M89931 | aecD; brnQ; yhbw | Beta C-S lyase; branched-chain amino acid uptake carrier; hypothetical protein yhbw | Rossol, I. et al. "The *Corynebacterium glutamicum* aecD gene encodes a C-S lyase with alpha, beta-elimination activity that degrades aminoethylcysteine," J. Bacteriol., 174(9): 2968-2977 (1992); Tauch, A. et al. "Isoleucine uptake in *Corynebacterium glutamicum* ATCC 13032 is directed by the brnQ gene product," Arch. Microbiol., 169(4): 303-312 (1998) |
| S59299 | trp | Leader gene (promoter) | Herry, D. M. et al. "Cloning of the trp gene cluster from a tryptophan-hyperproducing strain of *Corynebacterium glutamicum*: identification of a mutation in the trp leader sequence," Appl. Environ. Microbiol., 59(3): 791-799 (1993) |
| U11545 | trpD | Anthranilate phosphoribosyltransferase | O'Gara, J. P. and Dunican, L. K. (1994) Complete nucleotide sequence of the *Corynebacterium glutamicum* ATCC 21850 tpD gene." Thesis, Microbiology Department, University College Galway, Ireland. |
| U13922 | cglIM; cglIR; clgIIR | Putative type II 5-cytosoine methyltransferase; putative type II restriction endonuclease; putative type I or type III restriction endonuclease | Schafer, A. et al. "Cloning and characterization of a DNA region encoding a stress-sensitive restriction system from *Corynebacterium glutamicum* ATCC 13032 and analysis of its role in intergeneric conjugation with *Escherichia coli*," J. Bacteriol., 176(23): 7309-7319 (1994); Schafer, A. et al. "The *Corynebacterium glutamicum* cglIM gene encoding a 5-cytosine in an McrBC-deficient *Escherichia coli* strain," Gene, 203(2): 95-101 (1997) |
| U14965 | recA | | |
| U31224 | ppx | | Ankri, S. et al. "Mutations in the *Corynebacterium glutamicum* proline biosynthetic pathway: A natural bypass of the proA step," J. Bacteriol., 178(15): 4412-4419 (1996) |
| U31225 | proC | L-proline: NADP+ 5-oxidoreductase | Ankri, S. et al. "Mutations in the *Corynebacterium glutamicum* proline biosynthetic pathway: A natural bypass of the proA step," J. Bacteriol., 178(15): 4412-4419 (1996) |
| U31230 | obg; proB; unkdh | ?; gamma glutamyl kinase; similar to D-isomer specific 2-hydroxyacid dehydrogenases | Ankri, S. et al. "Mutations in the *Corynebacterium glutamicum* proline biosynthetic pathway: A natural bypass of the proA step," J. Bacteriol., 178(15): 4412-4419 (1996) |
| U31281 | bioB | Biotin synthase | Serebriiskii, I. G., "Two new members of the bio B superfamily: Cloning, sequencing and expression of bio B genes of *Methylobacillus flagellatum* and *Corynebacterium glutamicum*," Gene, 175: 15-22 (1996) |
| U35023 | thtR; accBC | Thiosulfate sulfurtransferase; acyl CoA carboxylase | Jager, W. et al. "A *Corynebacterium glutamicum* gene encoding a two-domain protein similar to biotin carboxylases and biotin-carboxyl-carrier proteins," Arch. Microbiol., 166(2); 76-82 (1996) |
| U43535 | cmr | Multidrug resistance protein | Jager, W. et al. "A *Corynebacterium glutamicum* gene conferring multidrug resistance in the heterologous host *Escherichia coli*," J. Bacteriol., 179(7): 2449-2451 (1997) |

TABLE 2-continued

GENES IDENTIFIED FROM GENBANK

| GenBank ™ Accession No. | Gene Name | Gene Function | Reference |
|---|---|---|---|
| U43536 | clpB | Heat shock ATP-binding protein | |
| U53587 | aphA-3 | 3'5''-aminoglycoside phosphotransferase | |
| U89648 | | *Corynebacterium glutamicum* unidentified sequence involved in histidine biosynthesis, partial sequence | |
| X04960 | trpA; trpB; trpC; trpD; trpE; trpG; trpL | Tryptophan operon | Matsui, K. et al. "Complete nucleotide and deduced amino acid sequences of the *Brevibacterium lactofermentum* tryptophan operon," Nucleic Acids Res., 14(24): 10113-10114 (1986) |
| X07563 | lysA | DAP decarboxylase (meso-diaminopimelate decarboxylase, EC 4.1.1.20) | Yeh, P. et al. "Nucleic sequence of the lysA gene of *Corynebacterium glutamicum* and possible mechanisms for modulation of its expression," Mol. Gen. Genet., 212(1): 112-119 (1988) |
| X14234 | EC 4.1.1.31 | Phosphoenolpyruvate carboxylase | Eikmanns, B. J. et al. "The Phosphoenolpyruvate carboxylase gene of *Corynebacterium glutamicum*: Molecular cloning, nucleotide sequence, and expression," Mol. Gen. Genet., 218(2): 330-339 (1989); Lepiniec, L. et al. "Sorghum Phosphoenolpyruvate carboxylase gene family: structure, function and molecular evolution," Plant. Mol. Biol., 21 (3): 487-502 (1993) |
| X17313 | fda | Fructose-bisphosphate aldolase | Von der Osten, C. H. et al. "Molecular cloning, nucleotide sequence and fine-structural analysis of the *Corynebacterium glutamicum* fda gene: structural comparison of *C. glutamicum* fructose-1,6-biphosphate aldolase to class I and class II aldolases," Mol. Microbiol., |
| X53993 | dapA | L-2,3-dihydrodipicolinate synthetase (EC 4.2.1.52) | Bonnassie, S. et al. "Nucleic sequence of the dapA gene from *Corynebacterium glutamicum*," Nucleic Acids Res., 18(21): 6421 (1990) |
| X54223 | | AttB-related site | Cianciotto, N. et al. "DNA sequence homology between att B-related sites of *Corynebacterium diphtheriae, Corynebacterium ulcerans, Corynebacterium glutamicum*, and the attP site of lambdacorynephage," FEMS. Microbiol, Lett., 66: 299-302 (1990) |
| X54740 | argS; lysA | Arginyl-tRNA synthetase; Diaminopimelate decarboxylase | Marcel, T. et al. "Nucleotide sequence and organization of the upstream region of the *Corynebacterium glutamicum* lysA gene," Mol. Microbiol., 4(11): 1819-1830 (1990) |
| X55994 | trpL; trpE | Putative leader peptide; anthranilate synthase component 1 | Heery, D. M. et al. "Nucleotide sequence of the *Corynebacterium glutamicum* trpE gene," Nucleic Acids Res., 18(23): 7138 (1990) |
| X56037 | thrC | Threonine synthase | Han, K. S. et al. "The molecular structure of the *Corynebacterium glutamicum* threonine synthase gene," Mol. Microbiol., 4(10): 1693-1702 (1990) |
| X56075 | attB-related site | Attachment site | Cianciotto, N. et al. "DNA sequence homology between att B-related sites of *Corynebacterium diphtheriae, Corynebacterium ulcerans, Corynebacterium glutamicum*, and the attP site of lambdacorynephage," FEMS. Microbiol, Lett., 66: 299-302 (1990) |
| X57226 | lysC-alpha; lysC-beta; asd | Aspartokinase-alpha subunit; Aspartokinase-beta subunit; aspartate beta semialdehyde dehydrogenase | Kalinowski, J. et al. "Genetic and biochemical analysis of the Aspartokinase from *Corynebacterium glutamicum*," Mol. Microbiol., 5(5): 1197-1204 (1991); Kalinowski, J. et al. "Aspartokinase genes lysC alpha and lysC beta overlap and are adjacent to the aspertate beta-semialdehyde dehydrogenase gene asd in *Corynebacterium glutamicum*," Mol. Gen. Genet., 224(3): 317-324 (1990) |
| X59403 | gap; pgk; tpi | Glyceraldehyde-3-phosphate; phosphoglycerate kinase; triosephosphate isomerase | Eikmanns, B. J. "Identification, sequence analysis, and expression of a *Corynebacterium glutamicum* gene cluster encoding the three glycolytic enzymes glyceraldehyde-3-phosphate dehydrogenase, 3-phosphoglycerate kinase, and triosephosphate isomeras," J. Bacteriol., 174(19): 6076-6086 (1992) |
| X59404 | gdh | Glutamate dehydrogenase | Bormann, E. R. et al. "Molecular analysis of the *Corynebacterium glutamicum* gdh gene encoding glutamate dehydrogenase," Mol. Microbiol., 6(3): 317-326 (1992) |
| X60312 | lysI | L-lysine permease | Seep-Feldhaus, A. H. et al. "Molecular analysis of the *Corynebacterium glutamicum* lysI gene involved in lysine uptake," Mol. Microbiol., 5(12): 2995-3005 (1991) |
| X66078 | cop1 | Ps1 protein | Joliff, G. et al. "Cloning and nucleotide sequence of the csp1 gene encoding PS1, one of the two major secreted proteins of *Corynebacterium glutamicum*: The deduced N-terminal region of PS1 is similar to the Mycobacterium antigen 85 complex," Mol. Microbiol., 6(16): 2349-2362 (1992) |
| X66112 | glt | Citrate synthase | Eikmanns, B. J. et al. "Cloning sequence, expression and transcriptional analysis of the *Corynebacterium glutamicum* gltA gene encoding citrate synthase," Microbiol., 140: 1817-1828 (1994) |
| X67737 | dapB | Dihydrodipicolinate reductase | |
| X69103 | csp2 | Surface layer protein PS2 | Peyret, J. L. et al. "Characterization of the cspB gene encoding PS2, an ordered surface-layer protein in *Corynebacterium glutamicum*," Mol. Microbiol., 9(1): 97-109 (1993) |
| X69104 | | IS3 related insertion element | Bonamy, C. et al. "Identification of IS1206, a *Corynebacterium glutamicum* IS3-related insertion sequence and phylogenetic analysis," Mol. Microbiol., 14(3): 571-581 (1994) |

TABLE 2-continued

GENES IDENTIFIED FROM GENBANK

| GenBank ™ Accession No. | Gene Name | Gene Function | Reference |
|---|---|---|---|
| X70959 | leuA | Isopropylmalate synthase | Patek, M. et al. "Leucine synthesis in *Corynebacterium glutamicum*: enzyme activities, structure of leuA, and effect of leuA inactivation on lysine synthesis," Appl. Environ. Microbiol., 60(1): 133-140 (1994) |
| X71489 | icd | Isocitrate dehydrogenase (NADP+) | Eikmanns, B. J. et al. "Cloning sequence analysis, expression, and inactivation of the *Corynebacterium glutamicum* icd gene encoding isocitrate dehydrogenase and biochemical characterization of the enzyme," J. Bacteriol., 177(3): 774-782 (1995) |
| X72855 | GDHA | Glutamate dehydrogenase (NADP+) | |
| X75083, X70584 | mtrA | 5-methyltryptophan resistance | Heery, D. M. et al. "A sequence from a tryptophan-hyperproducing strain of *Corynebacterium glutamicum* encoding resistance to 5-methyltryptophan," Biochem. Biophys. Res. Commun., 201(3): 1255-1262 (1994) |
| X75085 | recA | | Fitzpatrick, R. et al. "Construction and characterization of recA mutant strains of *Corynebacterium glutamicum* and *Brevibacterium lactofermentum*," Appl. Microbiol. Biotechnol., 42(4): 575-580 (1994) |
| X75504 | aceA; thiX | Partial Isocitrate lyase; ? | Reinscheid, D. J. et al. "Characterization of the isocitrate lyase gene from *Corynebacterium glutamicum* and biochemical analysis of the enzyme," J. Bacteriol., 176(12): 3474-3483 (1994) |
| X76875 | | ATPase beta-subunit | Ludwig, W. et al. "Phylogenetic relationships of bacteria based on comparative sequence analysis, of elongation factor Tu and ATP-synthase beta-subunit genes," Antonie Van Leeuwenhoek, 64: 285-305 (1993) |
| X77034 | tuf | Elongation factor Tu | Ludwig, W. et al. "Phylogenetic relationships of bacteria based on comparative sequence analysis of elongation factor Tu and ATP-synthase beta-subunit genes," Antonie Van Leeuwenhoek, 64: 285-305 (1993) |
| X77384 | recA | | Billman-Jacobe, H. "Nucleotide sequence of a recA gene from *Corynebacterium glutamicum*," DNA Seq., 4(6): 403-404 (1994) |
| X78491 | aceB | Malate synthase | Reinscheid, D. J. et al. "Malate synthase from *Corynebacterium glutamicum* pta-ack operon encoding phosphotransacetylase: sequence analysis," Microbiology, 140: 3099-3108 (1994) |
| X80629 | 16S rDNA | 16S ribosomal RNA | Rainey, F. A. et al. "Phylogenetic analysis of the genera *Rhodococcus* and *Norcardia* and evidence for the evolutionary origin of the genus *Norcardia* from within the radiation of *Rhodococcus* species," Microbiol., 141: 523-528 (1995) |
| X81191 | gluA; gluB; gluC; gluD | Glutamate uptake system | Kronemeyer, W. et al. "Structure of the gluABCD cluster encoding the glutamate uptake system of *Corynebacterium glutamicum*," J. Bacteriol., 177(5): 1152-1158 (1995) |
| X81379 | dapE | Succinyldiaminopimelate desuccinylase | Wehrmann, A. et al. "Analysis of different DNA fragments of *Corynebacterium glutamicum* complementing dapE of *Escherichia coli*," Microbiology, 40: 3349-56 (1994) |
| X82061 | 16S rDNA | 16S ribosomal RNA | Ruimy, R. et al. "Phylogeny of the genus *Corynebacterium* deduced from analyses of small-subunit ribosomal DNA sequences," Int. J. Syst. Bacteriol., 45(4): 740-746 (1995) |
| X82928 | asd; lysC | Aspartate-semialdehyde dehydrogenase; ? | Serebrijski, I. et al. "Multicopy suppression by asd gene and osmotic stress-dependent complementation by heterologous proA in proA mutants," J. Bacteriol., 177(24): 7255-7260 (1995) |
| X82929 | proA | Gamma-glutamyl phosphate reductase | Serebrijski, I. et al. "Multicopy suppression by asd gene and osmotic stress-dependent complementation by heterologous proA in proA mutants," J. Bacteriol., 177(24): 7255-7260 (1995) |
| X84257 | 16S rDNA | 16S ribosomal RNA | Pascual, C. et al. "Phylogenetic analysis of the genus *Corynebacterium* based on 16S rRNA gene sequences," Int. J. Syst. Bacteriol., 45(4): 724-728 (1995) |
| X85965 | aroP; dapE | Aromatic amino acid permease; ? | Wehrmann et al. "Functional analysis of sequences adjacent to dapE of C. glutamicum proline reveals the presence of aroP, which encodes the aromatic amino acid transporter," J. Bacteriol., 177(20): 5991-5993 (1995) |
| X86157 | argB; argC; argD; argF; argJ | Acetylglutamate kinase; N-acetyl-gamma-glutamyl-phosphate reductase; acetylornithine aminotransferase; ornithine carbamoyltransferase; glutamate N-acetyltransferase | Sakanyan, V. et al. "Genes and enzymes of the acetyl cycle of arginine biosynthesis in *Corynebacterium glutamicum*: enzyme evolution in the early steps of the arginine pathway," Microbiology, 142: 99-108 (1996) |
| X89084 | pta; ackA | Phosphate acetyltransferase; acetate kinase | Reinscheid, D. J. et al. "Cloning, sequence analysis, expression and inactivation of the *Corynebacterium glutamicum* pta-ack operon encoding phosphotransacetylase and acetate kinase," Microbiology, 145: 503-513 (1999) |
| X89850 | attB | Attachment site | Le Marrec, C. et al. "Genetic characterization of site-specific integration functions of phi AAU2 infecting "Arthrobacter aureus C70," J. Bacteriol., 178(7): 1996-2004 (1996) |
| X90356 | | Promoter fragment F1 | Patek, M. et al. "Promoters from *Corynebacterium glutamicum*: cloning, molecular analysis and search for a consensus motif," Microbiology, 142: 1297-1309 (1996) |
| X90357 | | Promoter fragment F2 | Patek, M. et al. "Promoters from *Corynebacterium glutamicum*: cloning, molecular analysis and search for a consensus motif," Microbiology, 142: 1297-1309 (1996) |
| X90358 | | Promoter fragment F10 | Patek, M. et al. "Promoters from *Corynebacterium glutamicum*: cloning, molecular analysis and search for a consensus motif," Microbiology, 142: 1297-1309 (1996) |

TABLE 2-continued

GENES IDENTIFIED FROM GENBANK

| GenBank ™ Accession No. | Gene Name | Gene Function | Reference |
|---|---|---|---|
| X90359 | | Promoter fragment F13 | Patek, M. et al. "Promoters from *Corynebacterium glutamicum*: cloning, molecular analysis and search for a consensus motif," Microbiology, 142: 1297-1309 (1996) |
| X90360 | | Promoter fragment F22 | Patek, M. et al. "Promoters from *Corynebacterium glutamicum*: cloning, molecular analysis and search for a consensus motif," Microbiology, 142: 1297-1309 (1996) |
| X90361 | | Promoter fragment F34 | Patek, M. et al. "Promoters from *Corynebacterium glutamicum*: cloning, molecular analysis and search for a consensus motif," Microbiology, 142: 1297-1309 (1996) |
| X90362 | | Promoter fragment F37 | Patek, M. et al. "Promoters from *C. glutamicum*: cloning, molecular analysis and search for a consensus motif," Microbiology, 142: 1297-1309 (1996) |
| X90363 | | Promoter fragment F45 | Patek, M. et al. "Promoters from *Corynebacterium glutamicum*: cloning, molecular analysis and search for a consensus motif," Microbiology, 142: 1297-1309 (1996) |
| X90364 | | Promoter fragment F64 | Patek, M. et al. "Promoters from *Corynebacterium glutamicum*: cloning, molecular analysis and search for a consensus motif," Microbiology, 142: 1297-1309 (1996) |
| X90365 | | Promoter fragment F75 | Patek, M. et al. "Promoters from *Corynebacterium glutamicum*: cloning, molecular analysis and search for a consensus motif," Microbiology, 142: 1297-1309 (1996) |
| X90366 | | Promoter fragment PF101 | Patek, M. et al. "Promoters from *Corynebacterium glutamicum*: cloning, molecular analysis and search for a consensus motif," Microbiology, 142: 1297-1309 (1996) |
| X90367 | | Promoter fragment PF104 | Patek, M. et al. "Promoters from *Corynebacterium glutamicum*: cloning, molecular analysis and search for a consensus motif," Microbiology, 142: 1297-1309 (1996) |
| X90368 | | Promoter fragment PF109 | Patek, M. et al. "Promoters from *Corynebacterium glutamicum*: cloning, molecular analysis and search for a consensus motif," Microbiology, 142: 1297-1309 (1996) |
| X93513 | amt | Ammonium transport system | Siewe, R. M. et al. "Functional and genetic characterization of the (methyl) ammonium uptake carrier of *Corynebacterium glutamicum*," J. Biol. Chem., 271(10): 5398-5403 (1996) |
| X93514 | betP | Glycine betaine transport system | Peter, H. et al. "Isolation, characterization, and expression of the *Corynebacterium glutamicum* betP gene, encoding the transport system for the compatible solute glycine betaine," J. Bacteriol., 178(17): 5229-5234 (1996) |
| X95649 | orf4 | | Patek, M. et al. "Identification and transcriptional analysis of the dapB-ORF2-dapA-ORF4 operon of *Corynebacterium glutamicum*, encoding two enzymes involved in L-lysine synthesis," Biotechnol. Lett., 19: 1113-1117 (1997) |
| X96471 | lysE; lysG | Lysine exporter protein; Lysine export regulator protein | Vrljic, M. et al. "A new type of transporter with a new type of cellular function: L-lysine export from *Corynebacterium glutamicum*," Mol. Microbiol., 22(5): 815-826 (1996) |
| X96580 | panB; panC; xylB | 3-methyl-2-oxobutanoate hydroxymethyltransferase; pantoate-beta-alanine ligase; xylulokinase | Sahm, H. et al. "D-pantothenate synthesis in *Corynebacterium glutamicum* and use of panBC and genes encoding L-valine synthesis for D-pantothenate overproduction," Appl. Environ. Microbiol., 65(5): 1973-1979 (1999) |
| X96962 | | Insertion sequence IS1207 and transposase | |
| X99289 | | Elongation factor P | Ramos, A. et al. "Cloning, sequencing and expression of the gene encoding elongation factor P in the amino-acid producer *Brevibacterium lactofermentum* (*Corynebacterium glutamicum* ATCC 13869)," Gene, 198: 217-222 (1997) |
| Y00140 | thrB | Homoserine kinase | Mateos, L. M. et al. "Nucleotide sequence of the homoserine kinase (thrB) gene of the *Brevibacterium lactofermentum*," Nucleic Acids Res., 15(9): 3922 (1987) |
| Y00151 | ddh | Meso-diaminopimelate D-dehydrogenase (EC 1.4.1.16) | Ishino, S. et al. "Nucleotide sequence of the meso-diaminopimelate D-dehydrogenase gene from *Corynebacterium glutamicum*," Nucleic Acids Res., 15(9): 3917 (1987) |
| Y00476 | thrA | Homoserine dehydrogenase | Mateos, L. M. et al. "Nucleotide sequence of the homoserine dehydrogenase (thrA) gene of the *Brevibacterium lactofermentum*," Nucleic Acids Res., 15(24): 10598 (1987) |
| Y00546 | hom; thrB | Homoserine dehydrogenase; homoserine kinase | Peoples, O. P. et al. "Nucleotide sequence and fine structural analysis of the *Corynebacterium glutamicum* hom-thrB operon," Mol. Microbiol., 2(1): 63-72 (1988) |
| Y08964 | murC; ftsQ/divD; ftsZ | UPD-N-acetylmuramate-alanine ligase; division initiation protein or cell division protein; cell division protein | Honrubia, M. P. et al. "Identification, characterization, and chromosomal organization of the ftsZ gene from *Brevibacterium lactofermentum*," Mol. Gen. Genet., 259(1): 97-104 (1998) |
| Y09163 | putP | High affinity proline transport system | Peter, H. et al. "Isolation of the putP gene of *Corynebacterium glutamicumproline* and characterization of a low-affinity uptake system for compatible solutes," Arch. Microbiol., 168(2): 143-151 (1997) |
| Y09548 | pyc | Pyruvate carboxylase | Peters-Wendisch, P. G. et al. "Pyruvate carboxylase from *Corynebacterium glutamicum*: characterization, expression and inactivation of the pyc gene," Microbiology, 144: 915-927 (1998) |
| Y09578 | leuB | 3-isopropylmalate dehydrogenase | Patek, M. et al. "Analysis of the leuB gene from *Corynebacterium glutamicum*," Appl. Microbiol. Biotechnol., 50(1): 42-47 (1998) |
| Y12472 | | Attachment site bacteriophage Phi-16 | Moreau, S. et al. "Site-specific integration of corynephage Phi-16: The construction of an integration vector," Microbiol., 145: 539-548 (1999) |

TABLE 2-continued

GENES IDENTIFIED FROM GENBANK

| GenBank™ Accession No. | Gene Name | Gene Function | Reference |
|---|---|---|---|
| Y12537 | proP | Proline/ectoine uptake system protein | Peter, H. et al. "*Corynebacterium glutamicum* is equipped with four secondary carriers for compatible solutes: Identification, sequencing, and characterization of the proline/ectoine uptake system, ProP, and the ectoine/proline/glycine betaine carrier, EctP," J. Bacteriol., 180(22): 6005-6012 (1998) |
| Y13221 | glnA | Glutamine synthetase I | Jakoby, M. et al. "Isolation of *Corynebacterium glutamicum* glnA gene encoding glutamine synthetase I," FEMS Microbiol. Lett., 154(1): 81-88 (1997) |
| Y16642 | lpd | Dihydrolipoamide dehydrogenase | |
| Y18059 | | Attachment site Corynephage 304L | Moreau, S. et al. "Analysis of the integration functions of φ 304L: An integrase module among corynephages," Virology, 255(1): 150-159 (1999) |
| Z21501 | argS; lysA | Arginyl-tRNA synthetase; diaminopimelate decarboxylase (partial) | Oguiza, J. A. et al. "A gene encoding arginyl-tRNA synthetase is located in the upstream region of the lysA gene in *Brevibacterium lactofermentum*: Regulation of argS-lysA cluster expression by arginine," J. Bacteriol., 175(22): 7356-7362 (1993) |
| Z21502 | dapA; dapB | Dihydrodipicolinate synthase; dihydrodipicolinate reductase | Pisabarro, A. et al. "A cluster of three genes (dapA, orf2, and dapB) of *Brevibacterium lactofermentum* encodes dihydrodipicolinate reductase, and a third polypeptide of unknown function," J. Bacteriol., 175(9): 2743-2749 (1993) |
| Z29563 | thrC | Threonine synthase | Malumbres, M. et al. "Analysis and expression of the thrC gene of the encoded threonine synthase," Appl. Environ. Microbiol., 60(7)2209-2219 (1994) |
| Z46753 | 16S rDNA | Gene for 16S ribosomal RNA | |
| Z49822 | sigA | SigA sigma factor | Oguiza, J. A. et al "Multiple sigma factor genes in *Brevibacterium lactofermentum*: Characterization of sigA and sigB," J. Bacteriol., 178(2): 550-553 (1996) |
| Z49823 | galE; dtxR | Catalytic activity UDP-galactose 4-epimerase; diphtheria toxin regulatory protein | Oguiza, J. A. et al "The galE gene encoding the UDP-galactose 4-epimerase of *Brevibacterium lactofermentum* is coupled transcriptionally to the dmdR gene," Gene, 177: 103-107 (1996) |
| Z49824 | orf1; sigB | ?; SigB sigma factor | Oguiza, J. A. et al "Multiple sigma factor genes in *Brevibacterium lactofermentum*: Characterization of sigA and sigB," J. Bacteriol., 178(2): 550-553 (1996) |
| Z66534 | | Transposase | Correia, A. et al. "Cloning and characterization of an IS-like element present in the genome of *Brevibacterium lactofermentum* ATCC 13869," Gene, 170(1): 91-94 (1996) |

[1] A sequence for this gene was published in the indicated reference. However, the sequence obtained by the inventors of the present application is significantly longer than the published version. It is believed that the published version relied on an incorrect start codon, and thus represents only a fragment of the actual coding region.

TABLE 3

*Corynebacterium* and *Brevibacterium* Strains Which May be Used in the Practice of the Invention

| Genus | species | ATCC | FERM | NRRI | CECT | NCIMB | CBS | NCTC | DSMZ | Other origin |
|---|---|---|---|---|---|---|---|---|---|---|
| *Brevibacterium* | *ammoniagenes* | 21054 | | | | | | | | |
| *Brevibacterium* | *ammoniagenes* | 19350 | | | | | | | | |
| *Brevibacterium* | *ammoniagenes* | 19351 | | | | | | | | |
| *Brevibacterium* | *ammoniagenes* | 19352 | | | | | | | | |
| *Brevibacterium* | *ammoniagenes* | 19353 | | | | | | | | |
| *Brevibacterium* | *ammoniagenes* | 19354 | | | | | | | | |
| *Brevibacterium* | *ammoniagenes* | 19355 | | | | | | | | |
| *Brevibacterium* | *ammoniagenes* | 19356 | | | | | | | | |
| *Brevibacterium* | *ammoniagenes* | 21055 | | | | | | | | |
| *Brevibacterium* | *ammoniagenes* | 21077 | | | | | | | | |
| *Brevibacterium* | *ammoniagenes* | 21553 | | | | | | | | |
| *Brevibacterium* | *ammoniagenes* | 21580 | | | | | | | | |
| *Brevibacterium* | *ammoniagenes* | 39101 | | | | | | | | |
| *Brevibacterium* | *butanicum* | 21196 | | | | | | | | |
| *Brevibacterium* | *divaricatum* | 21792 | P928 | | | | | | | |
| *Brevibacterium* | *flavum* | 21474 | | | | | | | | |
| *Brevibacterium* | *flavum* | 21129 | | | | | | | | |
| *Brevibacterium* | *flavum* | 21518 | | | | | | | | |
| *Brevibacterium* | *flavum* | | | B11474 | | | | | | |
| *Brevibacterium* | *flavum* | | | B11472 | | | | | | |
| *Brevibacterium* | *flavum* | 21127 | | | | | | | | |
| *Brevibacterium* | *flavum* | 21128 | | | | | | | | |
| *Brevibacterium* | *flavum* | 21427 | | | | | | | | |
| *Brevibacterium* | *flavum* | 21475 | | | | | | | | |
| *Brevibacterium* | *flavum* | 21517 | | | | | | | | |
| *Brevibacterium* | *flavum* | 21528 | | | | | | | | |
| *Brevibacterium* | *flavum* | 21529 | | | | | | | | |
| *Brevibacterium* | *flavum* | | | B11477 | | | | | | |

TABLE 3-continued

Corynebacterium and Brevibacterium Strains Which May be Used in the Practice of the Invention

| Genus | species | ATCC | FERM | NRRI | CECT | NCIMB | CBS | NCTC | DSMZ | Other origin |
|---|---|---|---|---|---|---|---|---|---|---|
| Brevibacterium | flavum | | | B11478 | | | | | | |
| Brevibacterium | flavum | 21127 | | | | | | | | |
| Brevibacterium | flavum | | | B11474 | | | | | | |
| Brevibacterium | healii | 15527 | | | | | | | | |
| Brevibacterium | ketoglutamicum | 21004 | | | | | | | | |
| Brevibacterium | ketoglutamicum | 21089 | | | | | | | | |
| Brevibacterium | ketosoreductum | 21914 | | | | | | | | |
| Brevibacterium | lactofermentum | | | | 70 | | | | | |
| Brevibacterium | lactofermentum | | | | 74 | | | | | |
| Brevibacterium | lactofermentum | | | | 77 | | | | | |
| Brevibacterium | lactofermentum | 21798 | | | | | | | | |
| Brevibacterium | lactofermentum | 21799 | | | | | | | | |
| Brevibacterium | lactofermentum | 21800 | | | | | | | | |
| Brevibacterium | lactofermentum | 21801 | | | | | | | | |
| Brevibacterium | lactofermentum | | | B11470 | | | | | | |
| Brevibacterium | lactofermentum | | | B11471 | | | | | | |
| Brevibacterium | lactofermentum | 21086 | | | | | | | | |
| Brevibacterium | lactofermentum | 21420 | | | | | | | | |
| Brevibacterium | lactofermentum | 21086 | | | | | | | | |
| Brevibacterium | lactofermentum | 31269 | | | | | | | | |
| Brevibacterium | linens | 9174 | | | | | | | | |
| Brevibacterium | linens | 19391 | | | | | | | | |
| Brevibacterium | linens | 8377 | | | | | | | | |
| Brevibacterium | paraffinolyticum | | | | | 11160 | | | | |
| Brevibacterium | spec. | | | | | | 717.73 | | | |
| Brevibacterium | spec. | | | | | | 717.73 | | | |
| Brevibacterium | spec. | 14604 | | | | | | | | |
| Brevibacterium | spec. | 21860 | | | | | | | | |
| Brevibacterium | spec. | 21864 | | | | | | | | |
| Brevibacterium | spec. | 21865 | | | | | | | | |
| Brevibacterium | spec. | 21866 | | | | | | | | |
| Brevibacterium | spec. | 19240 | | | | | | | | |
| Corynebacterium | acetoacidophilum | 21476 | | | | | | | | |
| Corynebacterium | acetoacidophilum | 13870 | | | | | | | | |
| Corynebacterium | acetoglutamicum | | | B11473 | | | | | | |
| Corynebacterium | acetoglutamicum | | | B11475 | | | | | | |
| Corynebacterium | acetoglutamicum | 15806 | | | | | | | | |
| Corynebacterium | acetoglutamicum | 21491 | | | | | | | | |
| Corynebacterium | acetoglutamicum | 31270 | | | | | | | | |
| Corynebacterium | acetophilum | | | B3671 | | | | | | |
| Corynebacterium | ammoniagenes | 6872 | | | | | | | 2399 | |
| Corynebacterium | ammoniagenes | 15511 | | | | | | | | |
| Corynebacterium | fujiokense | 21496 | | | | | | | | |
| Corynebacterium | glutamicum | 14067 | | | | | | | | |
| Corynebacterium | glutamicum | 39137 | | | | | | | | |
| Corynebacterium | glutamicum | 21254 | | | | | | | | |
| Corynebacterium | glutamicum | 21255 | | | | | | | | |
| Corynebacterium | glutamicum | 31830 | | | | | | | | |
| Corynebacterium | glutamicum | 13032 | | | | | | | | |
| Corynebacterium | glutamicum | 14305 | | | | | | | | |
| Corynebacterium | glutamicum | 15455 | | | | | | | | |
| Corynebacterium | glutamicum | 13058 | | | | | | | | |
| Corynebacterium | glutamicum | 13059 | | | | | | | | |
| Corynebacterium | glutamicum | 13060 | | | | | | | | |
| Corynebacterium | glutamicum | 21492 | | | | | | | | |
| Corynebacterium | glutamicum | 21513 | | | | | | | | |
| Corynebacterium | glutamicum | 21526 | | | | | | | | |
| Corynebacterium | glutamicum | 21543 | | | | | | | | |
| Corynebacterium | glutamicum | 13287 | | | | | | | | |
| Corynebacterium | glutamicum | 21851 | | | | | | | | |
| Corynebacterium | glutamicum | 21253 | | | | | | | | |
| Corynebacterium | glutamicum | 21514 | | | | | | | | |
| Corynebacterium | glutamicum | 21516 | | | | | | | | |
| Corynebacterium | glutamicum | 21299 | | | | | | | | |
| Corynebacterium | glutamicum | 21300 | | | | | | | | |
| Corynebacterium | glutamicum | 39684 | | | | | | | | |
| Corynebacterium | glutamicum | 21488 | | | | | | | | |
| Corynebacterium | glutamicum | 21649 | | | | | | | | |
| Corynebacterium | glutamicum | 21650 | | | | | | | | |
| Corynebacterium | glutamicum | 19223 | | | | | | | | |
| Corynebacterium | glutamicum | 13869 | | | | | | | | |
| Corynebacterium | glutamicum | 21157 | | | | | | | | |
| Corynebacterium | glutamicum | 21158 | | | | | | | | |
| Corynebacterium | glutamicum | 21159 | | | | | | | | |

TABLE 3-continued

Corynebacterium and Brevibacterium Strains Which May be Used in the Practice of the Invention

| Genus | species | ATCC | FERM | NRRI | CECT | NCIMB | CBS | NCTC | DSMZ | Other origin |
|---|---|---|---|---|---|---|---|---|---|---|
| Corynebacterium | glutamicum | 21355 | | | | | | | | |
| Corynebacterium | glutamicum | 31808 | | | | | | | | |
| Corynebacterium | glutamicum | 21674 | | | | | | | | |
| Corynebacterium | glutamicum | 21562 | | | | | | | | |
| Corynebacterium | glutamicum | 21563 | | | | | | | | |
| Corynebacterium | glutamicum | 21564 | | | | | | | | |
| Corynebacterium | glutamicum | 21565 | | | | | | | | |
| Corynebacterium | glutamicum | 21566 | | | | | | | | |
| Corynebacterium | glutamicum | 21567 | | | | | | | | |
| Corynebacterium | glutamicum | 21568 | | | | | | | | |
| Corynebacterium | glutamicum | 21569 | | | | | | | | |
| Corynebacterium | glutamicum | 21570 | | | | | | | | |
| Corynebacterium | glutamicum | 21571 | | | | | | | | |
| Corynebacterium | glutamicum | 21572 | | | | | | | | |
| Corynebacterium | glutamicum | 21573 | | | | | | | | |
| Corynebacterium | glutamicum | 21579 | | | | | | | | |
| Corynebacterium | glutamicum | 19049 | | | | | | | | |
| Corynebacterium | glutamicum | 19050 | | | | | | | | |
| Corynebacterium | glutamicum | 19051 | | | | | | | | |
| Corynebacterium | glutamicum | 19052 | | | | | | | | |
| Corynebacterium | glutamicum | 19053 | | | | | | | | |
| Corynebacterium | glutamicum | 19054 | | | | | | | | |
| Corynebacterium | glutamicum | 19055 | | | | | | | | |
| Corynebacterium | glutamicum | 19056 | | | | | | | | |
| Corynebacterium | glutamicum | 19057 | | | | | | | | |
| Corynebacterium | glutamicum | 19058 | | | | | | | | |
| Corynebacterium | glutamicum | 19059 | | | | | | | | |
| Corynebacterium | glutamicum | 19060 | | | | | | | | |
| Corynebacterium | glutamicum | 19185 | | | | | | | | |
| Corynebacterium | glutamicum | 13286 | | | | | | | | |
| Corynebacterium | glutamicum | 21515 | | | | | | | | |
| Corynebacterium | glutamicum | 21527 | | | | | | | | |
| Corynebacterium | glutamicum | 21544 | | | | | | | | |
| Corynebacterium | glutamicum | 21492 | | | | | | | | |
| Corynebacterium | glutamicum | | | B8183 | | | | | | |
| Corynebacterium | glutamicum | | | B8182 | | | | | | |
| Corynebacterium | glutamicum | | | B12416 | | | | | | |
| Corynebacterium | glutamicum | | | B12417 | | | | | | |
| Corynebacterium | glutamicum | | | B12418 | | | | | | |
| Corynebacterium | glutamicum | | | B11476 | | | | | | |
| Corynebacterium | glutamicum | 21608 | | | | | | | | |
| Corynebacterium | lilium | | P973 | | | | | | | |
| Corynebacterium | nitrilophilus | 21419 | | | | 11594 | | | | |
| Corynebacterium | spec. | | P4445 | | | | | | | |
| Corynebacterium | spec. | | P4446 | | | | | | | |
| Corynebacterium | spec. | 31088 | | | | | | | | |
| Corynebacterium | spec. | 31089 | | | | | | | | |
| Corynebacterium | spec. | 31090 | | | | | | | | |
| Corynebacterium | spec. | 31090 | | | | | | | | |
| Corynebacterium | spec. | 31090 | | | | | | | | |
| Corynebacterium | spec. | 15954 | | | | | | | 20145 | |
| Corynebacterium | spec. | 21857 | | | | | | | | |
| Corynebacterium | spec. | 21862 | | | | | | | | |
| Corynebacterium | spec. | 21863 | | | | | | | | |
| Corynebacterium | Glutamicum* | | | | | | | | | ASO19 |
| Corynebacterium | Glutamicum** | | | | | | | | | ASO19 E12 |
| Corynebacterium | Glutamicum*** | | | | | | | | | HL457 |
| Corynebacterium | Glutamicum**** | | | | | | | | | HL459 |

ATCC: American Type Culture Collection, Rockville, MD, USA
FERM: Fermentation Research Institute, Chiba, Japan
NRRL: ARS Culture Collection, Northern Regional Research Laboratory, Peoria, IL, USA
CECT: Coleccion Espanola de Cultivos Tipo, Valencia, Spain
NCIMB: National Collection of Industrial and Marine Bacteria Ltd., Aberdeen, UK
CBS: Centraalbureau voor Schimmelcultures, Baam, NL
NCTC: National Collection of Type Cultures, London, UK
DSMZ: Deutsche Sammlung von Mikroorganismen und Zellkulturen, Braunschweig, Germany
For reference see Sugawara, H. et al. (1993) World directory of collections of cultures of microorganisms: Bacteria, fungi and yeasts (4$^{th}$ edn), World federation for culture collections world data center on microorganisms, Saimata, Japen.
*Spontaneous rifampin-resistant mutant of C. glutamicum ATCC13059$^d$ Yoshihama et al., 1985
**Restriction-deficient variant of ASO19 Follettie et al., 1993
***metC-disrupted mutant of ASO19E12 This study
****metC-disrupted mutant of ASO19E12 This study

TABLE 4

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00657 | 906 | GB_BA1:AF064700 | 3481 | AF064700 | *Rhodococous* sp. NO1-1 CprS and CprR genes, complete cds. | *Rhodococcus* sp | 40,265 | 15-Jul.-98 |
| metz | 1314 | GB_BA2:MTV016 | 53662 | AL021841 | *Mycobacterium tuberculosis* H37Rv complete genome; segment 143/162. | *Mycobacterium tuberculosis* | 61,278 | 23-Jun.-1999 |
| metc | 978 | GB_BA2:CORCSLYS | 2821 | M89931 | *Corynebacterium glutamicum* beta C-S lyase (aecD) and branched-chain amino acid upta | *Corynebacterium glutamicum* | 99,591 | 04-Jun.-1998 |
| rxa00023 | 3579 | GB_EST33:A1776129 | 483 | A1776129 | EST257217 tomato resistant, Cornell *Lycopersicon esculentum* cDNA clone cLER17D3, mRNA sequence. | *Lycopersicon esculentum* | 40,956 | 29-Jun.-1999 |
| | | GB_EST33:A1776129 | 483 | A1776129 | EST257217 tomato resistant, Cornell *Lycopersicon esculentum* cDNA clone cLER17D3, mRNA sequence. | *Lycopersicon esculentum* | 40,956 | 29-Jun.-1999 |
| rxa00044 | 1059 | EM_PAT:E11760 | 6911 | E11760 | Base sequence of sucrase gene. | *Corynebacterium glutamicum* | 42,979 | 08-Oct.-1997 (Rel. 52, Created) |
| | | GB_PAT:I26124 | 6911 | I26124 | Sequence 4 from patent US 5556776. | Unknown. | 42,979 | 07-Oct.-1996 |
| | | GB_BA2:ECOUW89 | 176195 | U00006 | *E. coli* chromosomal region from 89.2 to 92.8 minutes. | *Escherichia coli* | 39,097 | 17-Dec.-1993 |
| rxa00064 | 1401 | GB_PAT:E16763 | 2517 | E16763 | gDNA encoding aspartate transferase (AAT). | *Corynebacterium glutamicum* | 95,429 | 28-Jul.-1999 |
| | | GB_HTG2:AC007892 | 134257 | AC007892 | *Drosophila melanogaster* chromosome 3 clone BACR02O03 (D797) RPCI-98 02.O.3 map 99B-99B strain y; cn bw sp, *** SEQUENCING IN PROGRESS ***, 113 unordered pieces. | *Drosophila melanogaster* | 31,111 | 2-Aug.-1999 |
| rxa00072 | | GB_HTG2:AC007892 | 134257 | AC007892 | *Drosophila melanogaster* chromosome 3 clone BACR02O03 (D797) RPCI-98 02.O.3 map 99B-99B strain y; cn bw sp, *** SEQUENCING IN PROGRESS ***, 113 unordered pieces. | *Drosophila melanogaster* | 31,111 | 2-Aug.-1999 |
| rxa00105 | 798 | GB_BA1:MTV002 | 56414 | AL008967 | *Mycobacterium tuberculosis* H37Rv complete genome; segment 122/162. | *Mycobacterium tuberculosis* | 37,753 | 17-Jun.-1998 |
| | | GB_BA1:ECU29581 | 71128 | U29581 | *Escherichia coli* K-12 genome; approximately 63 to 64 minutes. | *Escherichia coli* | 35,669 | 14-Jan.-1997 |
| | | GB_BA2:AE000366 | 10405 | AE000366 | *Escherichia coil* K-12 MG1655 section 256 of 400 of the complete genome. | *Escherichia coli* | 35,669 | 12-Nov.-1998 |
| rxa00106 | 579 | GB_EST15:AA494237 | 367 | AA494237 | ng83f04.s1 NCL_CGAP_Pr6 *Homo sapiens* cDNA clone IMAGE:941407 similar to SW:DYR_LACCA P00381 DIHYDROFOLATE REDUCTASE;, mRNA sequence. | *Homo sapiens* | 42,896 | 20-Aug.-1997 |
| | | GB_BA2:AF161327 | 2021 | AF161327 | *Corynebacterium diphtheriae* histidine kinase ChrS (chrS) and response regulator ChrA (chrA) genes, complete cds. | *Corynebacterium diphtheriae* | 40,210 | 9-Sep.-1999 |
| | | GB_PAT:AR041189 | 654 | AR041189 | Sequence 4 from patent U.S. 5811286. | Unknown. | 41,176 | 29-Sep.-1999 |
| rxa00115 | 1170 | GB_PR4:AC007110 | 148336 | AC007110 | *Homo sapiens* chromosome 17, clone hRPK.472_J_18, complete sequence. | *Homo sapiens* | 36,783 | 30-Mar.-1999 |
| | | GB_HTG3:AC008537 | 170030 | AC008537 | *Homo sapiens* chromosome 19 clone CIT-HSPC_490E21, *** SEQUENCING IN PROGRESS ***, 93 unordered pieces. | *Homo sapiens* | 40,296 | 2-Sep.-1999 |
| | | GB_HTG3:AC008537 | 170030 | AC008537 | *Homo sapiens* chromosome 19 clone CIT-HSPC_490E21, *** SEQUENCING IN PROGRESS ***, 93 unordered pieces. | *Homo sapiens* | 40,296 | 2-Sep.-1999 |
| rxa00116 | 1284 | GB_BA2:AF062345 | 16458 | AF062345 | *Caulobacter crescentus* Sst1 (sst1), S-layer protein subunit (rsaA), ABC transporter (rsaD), membrane forming unit (rsaE), putative GDP-mannose-4,6-dehydratase (lpaA), putative acetyltransferase (lpsB), putative perosamine synthetase (lpsC), putative mannosyltransferase (lpsE), putative mannosyltransferase (lpsE), outer membrane protein (rsaF), and putative perosamine transferase (lpsE) genes, complete cds. | *Caulobacter crescentus* | 36,235 | 19-Oct.-1999 |
| | | GB_PAT:I18647 | 3300 | I18647 | Sequence 6 from patent U.S. 5500353. | Unknown. | 36,821 | 07-Oct.-1996 |
| | | GB_GSS13:AQ446197 | 751 | AQ446197 | nbxb0062D16r CUGI Rice BAC Library *Oryza sativa* genomic clone nbxb0062D16r, genomic survey sequence. | *Oryza sativa* | 38,124 | 8-Apr.-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00131 | 732 | GB_BA1:MTY20B11 | 36330 | Z95121 | Mycobacterium tuberculosis H37Rv complete genome; segment 139/162. | Mycobacterium tuberculosis | 43,571 | 17-Jun.-1998 |
| | | GB_BA1:SAR7932 | 15176 | AJ007932 | Streptomyces argillaceus mithramycin biosynthetic genes. | Streptomyces argillaceus | 41,116 | 15-Jun.-1999 |
| | | GB_BA1:MTY20B11 | 36330 | Z95121 | Mycobacterium tuberculosis H37Rv complete genome; segment 139/162. | Mycobacterium tuberculosis | 39,726 | 17-Jun.-1998 |
| | | GB_BA1:MTY20B11 | 36330 | Z95121 | Mycobacterium tuberculosis H37Rv complete genome; segment 139/162. | Mycobacterium tuberculosis | 36,788 | 17-Jun.-1998 |
| rxa00132 | 1557 | GB_IN2:TVU40872 | 1882 | U40872 | Trichomonas vaginalis S-adenosyl-L-homocysteine hydrolase gene, complete cds. | Trichomonas vaginalis | 61,914 | 31-Oct-1996 |
| | | GB_HTG6:AC010706 | 169265 | AC010706 | Drosophila melanogaster chromosome X clone BACR36D15 (D887) RPCI-98 36.D.15 map 13C-13F strain y; cn bw sp, *** SEQUENCING IN PROGRESS ***, 74 unordered pieces. | Drosophila melanogaster | 51,325 | 22-Nov-1999 |
| rxa00145 | 1059 | GB_BA1:MTCY2B12 | 20431 | Z81011 | Mycobacterium tuberculosis H37Rv complete genome; segment 61/162. | Mycobacterium tuberculosis | 63,365 | 18-Jun.-1998 |
| | | GB_BA1:PSEPYRBX | 2273 | L19649 | Pseudomonas aeruginosa aspartate transcarbamoylase (pyrB) and dihydroorotase-like (pyrX) genes, complete cds's. | Pseudomonas aeruginosa | 56,080 | 26-Jul.-1993 |
| | | GB_BA1:LLPYRBDNA | 1468 | X84262 | L.leichmannii pyrB gene. | Lactobacillus leichmannii | 47,514 | 29-Apr.-1997 |
| rxa00146 | 1464 | GB_BA1:MTCY2B12 | 20431 | Z81011 | Mycobacterium tuberculosis H37Rv complete genome; segment 61/162. | Mycobacterium tuberculosis | 60,714 | 18-Jun.-1998 |
| | | GB_BA1:MTCY154 | 13935 | Z98209 | Mycobacterium tuberculosis H37Rv complete genome; segment 121/162. | Mycobacterium tuberculosis | 39,229 | 17-Jun.-1998 |
| | | GB_BA1:MSGY154 | 40221 | AD000002 | Mycobacterium tuberculosis sequence from clone y154. | Mycobacterium tuberculosis | 36,618 | 03-Dec.-1996 |
| rxa00147 | 1302 | GB_BA1:MTCY2B12 | 20431 | Z81011 | Mycobacterium tuberculosis H37Rv complete genome; segment 61/162. | Mycobacterium tuberculosis | 61,527 | 18-Jun.-1998 |
| | | GB_BA1:MSGB937CS | 38914 | L78820 | Mycobacterium leprae cosmid B937 DNA sequence. | Mycobacterium leprae | 59,538 | 15-Jun.-1996 |
| | | GB_BA1:PAU81259 | 7285 | U81259 | Pseudomonas aeruginosa dihydrodipicolinate reductase (dapB) gene, partial cds, carbamoylphosphate synthetase small subunit (carA) and carbamoylphosphate synthetase large subunit (carB) genes, complete cds, and FtsJ homolog (ftsJ) gene, partial cds. | Pseudomonas aeruginosa | 55,396 | 23-Dec.-1996 |
| rxa00156 | 1233 | GB_BA1:SC9B10 | 33320 | AL009204 | Streptomyces coelicolor cosmid 9B10. | Streptomyces coelicolor | 52,666 | 10-Feb.-1999 |
| | | GB_BA2:AF002133 | 15437 | AF002133 | Mycobacterium avium strain GIR10 transcriptional regulator (mav81) gene, partial cds, aconitase (acn), invasin 1 (inv1), invasin 2 (inv2), transcriptional regulator (moxR), ketoacyl-reductase (fabG), enoyl-reductase (inhA) and ferrochelatase (mav272) genes, complete cds. | Mycobacterium avium | 54,191 | 26-Mar.-1998 |
| | | GB_BA1:D85417 | 7984 | D85417 | Propionibacterium freudenreichii hemY, hemH, hemB, hemX, hemR and hemL genes, complete cds. | Propionibacterium freudenreichii | 46,667 | 6-Feb.-1999 |
| rxa00166 | 783 | GB_HTG3:AC008167 | 174223 | AC008167 | Homo sapiens clone NH0172O13, *** SEQUENCING IN PROGRESS ***, 7 unordered pieces. | Homo sapiens | 37,451 | 21-Aug.-1999 |
| | | GB_HTG3:AC008167 | 174223 | AC008167 | Homo sapiens clone NH0172O13, *** SEQUENCING IN PROGRESS ***, 7 unordered pieces. | Homo sapiens | 37,451 | 21-Aug.-1999 |
| | | GB_HTG4:AC010118 | 80605 | AC01118 | Drosophila melanogaster chromosome 3L/62B1 clone RPC198-10D15, *** SEQUENCING IN PROGRESS ***, 51 unordered pieces. | Drosophila melanogaster | 38,627 | 16-Oct-1999 |
| rxa00198 | 672 | GB_BA1:AB024708 | 8734 | AB024708 | Corynebacterium glutamicum gltB and gltD genes for glutamine 2-oxoglutarate aminotransferase large and small subunits, complete cds. | Corynebacterium glutamicum | 92,113 | 13-Mar.-1999 |
| | | GB_BA1:AB024708 | 8734 | AB024708 | Corynebacterium glutamicum gltB and gltD genes for glutamine 2-oxoglutarate aminotransferase large and small subunits, complete cds. | Corynebacterium glutamicum | 93,702 | 13-Mar.-1999 |
| | | GB_EST24:AI232702 | 528 | AI232702 | EST229390 Normalized rat kidney, Bento Soares Rattus sp. cDNA clone RKICF35 3' end, mRNA sequence. | Rattus sp. | 34,221 | 31-Jan.-1999 |
| rxa00216 | 1113 | GB_HTG2:HSDJ850E9 | 117353 | AL121758 | Homo sapiens chromosome 20 clone RP5-850E9, *** SEQUENCING IN PROGRESS ***, in unordered pieces. | Homo sapiens | 37,965 | 03-Dec.-1999 |
| | | GB_HTG2:HSDJ850E9 | 117353 | AL121758 | Homo sapiens chromosome 20 clone RP5-850E9, *** SEQUENCING IN PROGRESS ***, in unordered pieces. | Homo sapiens | 37,965 | 03-Dec.-1999 |
| | | GB_PR2:CNS01DSA | 159400 | AL121766 | Human chromosome 14 DNA sequence *** IN PROGRESS *** BAC R-412H8 | Homo sapiens | 38,796 | 11-Nov-1999 |

TABLE 4-continued

ALIGNMENT RESULTS

| ID # | length (NT) | Genbank Hit | Accession | Name of Genbank Hit | Source of Genbank Hit | % homology (GAP) | Date of Deposit |
|---|---|---|---|---|---|---|---|
| rxa00219 | 1065 | GB_HTG2:AC005079_0 | 110000 AC005079 | of RPCI-11 library from chromosome 14 of *Homo sapiens* (Human), complete sequence. | *Homo sapiens* | 38,227 | 22-Nov-1998 |
| | | GB_HTG2:AC005079_1 | 110000 AC005079 | *Homo sapiens* clone RG252P22, *** SEQUENCING IN PROGRESS ***, 3 unordered pieces. | *Homo sapiens* | 38,227 | 22-Nov-1998 |
| | | GB_HTG2:AC005079_1 | 110000 AC005079 | *Homo sapiens* clone RG252P22, *** SEQUENCING IN PROGRESS ***, 3 unordered pieces. | *Homo sapiens* | 38,227 | 22-Nov-1998 |
| | | GB_HTG2:AC005079_1 | 110000 AC005079 | *Homo sapiens* clone RG252P22, *** SEQUENCING IN PROGRESS ***, 3 unordered pieces. | *Homo sapiens* | 38,227 | 22-Nov-1998 |
| rxa00223 | 1212 | GB_BA1:PPEA3NIF | 19771 X99694 | Plasmid pEA3 nitrogen fixation genes. | *Enterobacter agglomerans* | 48,826 | 2-Aug-1996 |
| | | GB_BA2:AF128444 | 2477 AF128444 | *Rhodobacter capsulatus* molybdenum cofactor biosynthetic gene cluster, partial sequence. | *Rhodobacter capsulatus* | 40,135 | 22-Mar-1999 |
| | | GB_HTG4:AC010111 | 138938 AC010111 | *Drosophila melanogaster* chromosome 3L/70C1 clone RPCI98-9B18, *** SEQUENCING IN PROGRESS ***, 64 unordered pieces. | *Drosophila melanogaster* | 39,527 | 16-Oct-1999 |
| rxa00229 | 803 | GB_BA2:AF124518 | 1758 AF124518 | *Corynebacterium glutamicum* 3-dehydroquinase (aroD) and shikimate dehydrogenase (aroE) genes, complete cds. | *Corynebacterium glutamicum* | 98,237 | 18-May-1999 |
| | | GB_PR3:AC004593 | 150221 AC004593 | *Homo sapiens* PAC clone DJ0964C11 from 7p14-p15, complete sequence. | *Homo sapiens* | 36,616 | 18-Apr-1998 |
| | | GB_HTG2:AC006907 | 188972 AC006907 | *Caenorhabditis elegans* clone Y76B12, *** SEQUENCING IN PROGRESS ***, 25 unordered pieces. | *Caenorhabditis elegans* | 37,095 | 26-Feb-1999 |
| rxa00241 | 1626 | GB_BA1:CGLYSI | 4232 X60312 | *C. glutamicum* lysI gene for L-lysine permease. | *Corynebacterium glutamicum* | 100,000 | 30-Jan-1992 |
| | | GB_HTG1:PFMAL13P1 | 192581 AL049180 | *Plasmodium falciparum* chromosome 13 strain 3D7, *** SEQUENCING IN PROGRESS ***, in unordered pieces. | *Plasmodium falciparum* | 34,947 | 11-Aug-1999 |
| | | GB_HTG1:PFMAL13P1 | 192581 AL049180 | *Plasmodium falciparum* chromosome 13 strain 3D7, *** SEQUENCING IN PROGRESS ***, in unordered pieces. | *Plasmodium falciparum* | 34,947 | 11-Aug-1999 |
| rxa00262 | 1197 | GB_IN2:EHU89655 | 3219 U89655 | *Entamoeba histolytica* unconventional myosin IB mRNA, complete cds. | *Entamoeba histolytica* | 36,496 | 23-May-1997 |
| | | GB_IN2:EHU89655 | 3219 U89655 | *Entamoeba histolytica* unconventional myosin IB mRNA, complete cds. | *Entamoeba histolytica* | 37,544 | 23-May-1997 |
| rxa00266 | 531 | GB_RO:AF016190 | 2939 AF016190 | *Mus musculus* connexin-36 (Cx36) gene, complete cds. | *Mus musculus* | 41,856 | 9-Feb-1999 |
| | | EM_PAT:E09719 | 3505 E09719 | DNA encoding precursor protein of alkaline cellulase. | *Bacillus* sp. | 34,741 | 08-Oct-1997 (Rel. 52, Created) |
| rxa00278 | 1155 | GB_PAT:E02133 | 3494 E02133 | gDNA encoding alkaline cellulase. | *Bacillus* sp. | 34,741 | 29-Sep-1997 |
| | | GB_IN1:CELK05F6 | 36912 AF040653 | *Caenorhabditis elegans* cosmid K05F6. | *Caenorhabditis elegans* | 36,943 | 6-Jan-1998 |
| | | GB_BA1:CGU43535 | 2531 U43535 | *Corynebacterium glutamicum* multidrug resistance protein (cmr) gene, complete cds. | *Corynebacterium glutamicum* | 36,658 | 9-Apr-1997 |
| rxa00295 | 1125 | GB_RO:RNU30789 | 3510 U30789 | *Rattus norvegicus* clone N27 mRNA. | *Rattus norvegicus* | 38,190 | 20-Aug-1996 |
| | | GB_BA2:CGU31281 | 1614 U31281 | *Corynebacterium glutamicum* biotin synthase (bioB) gene, complete cds. | *Corynebacterium glutamicum* | 99,111 | 21-Nov-1996 |
| | | GB_BA1:BRLBIOBA | 1647 D14084 | *Brevibacterium flavum* gene for biotin synthetase, complete cds. | *Corynebacterium glutamicum* | 98,489 | 3-Feb-1999 |
| | | GB_PAT:E03937 | 1005 E03937 | DNA sequence encoding *Brevibacterium flavum* biotin-synthase. | *Corynebacterium glutamicum* | 98,207 | 29-Sep-1997 |
| rxa00323 | 1461 | GB_BA1:MTCY427 | 38110 Z70692 | *Mycobacterium tuberculosis* H37Rv complete genome; segment 99/162. | *Mycobacterium tuberculosis* | 35,615 | 24-Jun-1999 |
| | | GB_BA1:MSGB32CS | 36404 L78818 | *Mycobacterium leprae* cosmid B32 DNA sequence. | *Mycobacterium leprae* | 60,917 | 15-Jun-1996 |
| | | GB_BA1:MTCY427 | 38110 Z70692 | *Mycobacterium tuberculosis* H37Rv complete genome; segment 99/162. | *Mycobacterium tuberculosis* | 44,606 | 24-Jun-1999 |
| rxa00324 | 3258 | GB_BA1:MSGB32CS | 36404 L78818 | *Mycobacterium leprae* cosmid B32 DNA sequence. | *Mycobacterium leprae* | 52,516 | 15-Jun-1996 |
| | | GB_BA1:MTCY427 | 38110 Z70692 | *Mycobacterium tuberculosis* H37Rv complete genome; segment 99/162. | *Mycobacterium tuberculosis* | 38,079 | 24-Jun-1999 |
| | | GB_OM:BOVELA | 3242 J02717 | Bovine elastin a mRNA, complete cds. | *Bos taurus* | 39,351 | 27-Apr-1993 |
| rxa00330 | 1566 | GB_BA1:CGTHRC | 3120 X56037 | *Corynebacterium glutamicum* thrC gene for threonine synthase (EC 4.2.99.2). | *Corynebacterium glutamicum* | 99,808 | 17-Jun-1997 |
| | | GB_PAT:I09078 | 3146 I09078 | Sequence 4 from Patent WO 8809819. | Unknown. | 99,617 | 02-Dec-1994 |
| | | GB_BA1:BLTHRESYN | 1892 Z29563 | *Brevibacterium lactofermentum*; ATCC 13869;; DNA (genomic). | *Corynebacterium glutamicum* | 99,170 | 20-Sep-1995 |
| rxa00335 | 1554 | GB_BA1:CGGLNA | 3686 Y13221 | *Corynebacterium glutamicum* glnA gene. | *Corynebacterium glutamicum* | 100,000 | 28-Aug-1997 |

TABLE 4-continued

ALIGNMENT RESULTS

| ID # | length (NT) | Genbank Hit | Accession | Name of Genbank Hit | Source of Genbank Hit | % homology (GAP) | Date of Deposit |
|---|---|---|---|---|---|---|---|
| rxa00347 |  | GB_BA2:AF005635 | AF005635 | *Corynebacterium glutamicum* glutamine synthetase (glnA) gene, complete cds. | *Corynebacterium glutamicum* | 98.906 | 14-Jun.-1999 |
|  |  | GB_BA1:MSGB27CS | L78817 | *Mycobacterium leprae* cosmid B27 DNA sequence. | *Mycobacterium leprae* | 66.345 | 15-Jun.-1996 |
|  | 891 | GB_EST27:AI455217 | AI455217 | LD21828.3prime LD *Drosophila melanogaster* embryo pOT2 *Drosophila melanogaster* cDNA clone LD21828 3prime, mRNA sequence. | *Drosophila melanogaster* | 34.510 | 09-Mar.-1999 |
|  |  | GB_BA2:SSU30252 | U30252 | *Synechococcus* PCC7942 nucleoside diphosphate kinase and ORF2 protein genes, complete cds, ORF1 protein gene, partial cds, and neutral site I for vector use. | *Synechococcus* PCC7942 | 37.084 | 29-Oct.-1999 |
|  |  | GB_EST21:AA911262 | AA911262 | oe75a02.s1 NCI_CGAP_Lu5 *Homo sapiens* cDNA clone IMAGE:1417418 3' similar to gb:AI8757 UROKINASE PLASMINOGEN ACTIVATOR SURFACE RECEPTOR, GPI-ANCHORED (HUMAN); mRNA sequence. | *Homo sapiens* | 37.500 | 21-Apr.-1998 |
| rxa00351 | 1578 | GB_BA1:MLU15187 | U15187 | *Mycobacterium leprae* cosmid L296. | *Mycobacterium leprae* | 52.972 | 09-Mar.-1995 |
|  |  | GB_IN2:AC004373 | AC004373 | *Drosophila melanogaster* DNA sequence (P1 DS05273 (D80)) complete sequence. | *Drosophila melanogaster* | 46.341 | 17-Jul.-1998 |
|  |  | GB_IN2:AF145653 | AF145653 | *Drosophila melanogaster* clone GH08860 BcDNA.GH08860 (BcDNA.GH08a6O) mRNA, complete cds. | *Drosophila melanogaster* | 49.471 | 14-Jun.-1999 |
| rxa00365 | 727 | GB_BA1:AB024708 | AB024708 | *Corynebacterium glutamicum* gltB and gltD genes for glutamine 2-oxoglutarate aminotransferase large and small subunits, complete cds. | *Corynebacterium glutamicum* | 96.556 | 13-Mar.-1999 |
|  |  | GB_BA1:MTCY1A6 | Z83864 | *Mycobacterium tuberculosis* H37Rv complete genome; segment 159/162. | *Mycobacterium tuberculosis* | 39.496 | 17-Jun.-1998 |
|  |  | GB_BA1:SC3A3 | AL109849 | *Streptomyces coelicolor* cosmid 3A3. | *Streptomyces coelicolor* A3(2) | 37.946 | 16-Aug.-1999 |
| rxa00366 | 480 | GB_BA1:AB024708 | AB024708 | *Corynebacterium glutamicum* gltB and gltD genes for glutamine 2-oxoglutarate aminotransferase large and small subunits, complete cds. | *Corynebacterium glutamicum* | 99.374 | 13-Mar.-1999 |
| rxa00367 | 4653 | GB_BA1:MTCY1A6 | Z83864 | *Mycobacterium tuberculosis* H37Rv complete genome; segment 159/162. | *Mycobacterium tuberculosis* | 41.333 | 17-Jun.-1998 |
|  |  | GB_BA1:SC3A3 | AL109849 | *Streptomyces coelicolor* cosmid 3A3. | *Streptomyces coelicolor* A3(2) | 37.554 | 16-Aug.-1999 |
|  |  | GB_BA1:AB024708 | AB024708 | *Corynebacterium glutamicum* gltB and gltD genes for glutamine 2-oxoglutarate aminotransferase large and small subunits, complete cds. | *Corynebacterium glutamicum* | 99.312 | 13-Mar.-1999 |
| rxa00371 | 1917 | GB_BA1:MTCY1A6 | Z83864 | *Mycobacterium tuberculosis* H37Rv complete genome; segment 159/162. | *Mycobacterium tuberculosis* | 36.971 | 17-Jun.-1998 |
|  |  | GB_BA1:SC3A3 | AL109849 | *Streptomyces coelicolor* cosmid 3A3. | *Streptomyces coelicolor* A3(2) | 37.905 | 16-Aug.-1999 |
|  |  | GB_VI:SBVORFS | M89923 | Sugarcane bacilliform virus ORF 1, 2, and 3 DNA, complete cds. | Sugarcane bacilliform virus | 35.843 | 12-Jun.-1993 |
|  |  | GB_EST37:AI967505 | AI967505 | Ljimpest03.215-c10 Ljimp Lambda HybriZap two-hybrid library *Lotus japonicus* cDNA clone LP215-03-c10 5' similar to 60S ribosomal protein L39, mRNA sequence. | *Lotus japonicus* | 42.593 | 24-Aug.-1999 |
| rxa00377 |  | GB_IN1:CELK09H9 | AF043700 | *Caenorhabditis elegans* cosmid K09H9. | *Caenorhabditis elegans* | 34.295 | 22-Jan.-1998 |
|  | 1245 | GB_BA1:CCU13664 | U13664 | *Caulobacter crescentus* uroporphyrinogen decarboxylase homolog (hemE) gene, partial cds. | *Caulobacter crescentus* | 36.832 | 24-Mar.-1995 |
|  |  | GB_PL1:ANSDGENE | Y08866 | *A.nidulans* sD gene. | *Emericella nidulans* | 39.603 | 17-Oct.-1996 |
|  |  | GB_GSS4:AQ730303 | AQ730303 | HS_5505_B1_C04_T7A RPCI-11 Human Male BAC Library *Homo sapiens* genomic clone Plate=1081 Col=7 Row=F, genomic survey sequence. | *Homo sapiens* | 36.728 | 15-Jul.-1999 |
| rxa00382 | 1425 | GB_BA1:PAHEML | X82072 | P.aeruginosa hemL gene. | *Pseudomonas aeruginosa* | 54.175 | 18-Dec.-1995 |
|  |  | GB_BA1:MTY25D10 | Z95558 | *Mycobacterium tuberculosis* H37Rv complete genome; segment 28/162. | *Mycobacterium tuberculosis* | 61.143 | 17-Jun.-1998 |
|  |  | GB_BA1:MSGy224 | AD000004 | *Mycobacterium tuberculosis* sequence from clone y224. | *Mycobacterium tuberculosis* | 61.143 | 03-Dec.-1996 |
| rxa00383 | 1467 | GB_BA1:MLCB1222 | AL049491 | *Mycobacterium leprae* cosmid B1222. | *Mycobacterium leprae* | 43.981 | 27-Aug.-1999 |
|  |  | GB_HTG2:AC006269 | AC006269 | *Homo sapiens* chromosome 17 clone hRPK.515_E_23 map 17, *** SEQUENCING IN PROGRESS ***, 2 ordered pieces. | *Homo sapiens* | 35.444 | 10-Jun.-1999 |
|  |  | GB_HTG2:AC007638 | AC007638 | *Homo sapiens* chromosome 17 clone hRPK.515_O_17 map 17, *** SEQUENCING IN PROGRESS ***, 8 unordered pieces. | *Homo sapiens* | 34.821 | 22-May-1999 |
| rxa00391 | 843 | GB_EST38:AW017053 | AW017053 | EST272398 *Schistosoma mansoni* male, Phil LoVerde/Joe Merrick *Schistosoma mansoni* cDNA clone SMMAS14 5' end, mRNA sequence. | *Schistosoma mansoni* | 40.472 | 10-Sep.-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| | | GB_PAT:AR065852 | 32207 | AR065852 | Sequence 20 from patent U.S. 5849564. | Unknown. | 38,586 | 29-Sep-1999 |
| | | GB_VI:AF148805 | 28559 | AF148805 | Kaposi's sarcoma-associated herpesvirus ORF 68 gene, partial cds; and ORF 69, kaposin, v-FLIP, v-cyclin, latent nuclear antigen, ORF K14, v-GPCR, putative phosphoribosylformylglycinamidine synthase, and LAMP (LAMP) genes, complete cds. | Kaposi's sarcoma-associated herpesvirus | 38,509 | 2-Aug-1999 |
| rxa00393 | 1017 | GB_BA1:MTY25D10 | 40838 | Z95558 | Mycobacterium tuberculosis H37Rv complete genome; segment 28/162. | Mycobacterium tuberculosis | 36,308 | 17-Jun-1998 |
| | | GB_BA1:MSGY224 | 40051 | AD000004 | Mycobacterium tuberculosis sequence from clone y224. | Mycobacterium tuberculosis | 39,282 | 03-Dec-1996 |
| | | GB_BA1:MLB1306 | 7762 | Y13603 | Mycobacterium leprae cosmid B1306 DNA. | Mycobacterium leprae | 39,228 | 24-Jun-1997 |
| rxa00402 | 623 | GB_BA2:AF052652 | 2096 | AF052652 | Corynebacterium glutamicum homoserine O-acetyltransferase (metA) gene, complete cds. | Corynebacterium glutamicum | 99,672 | 19-Mar-1998 |
| | | GB_BA2:AF109162 | 4514 | AF109162 | Corynebacterium diphtheriae heme uptake locus, complete sequence. | Corynebacterium diphtheriae | 40,830 | 8-Jun-1999 |
| | | GB_BA2:AF092918 | 20758 | AF092918 | Pseudomonas alcaligenes outer membrane Xcp-secretion system gene cluster. | Pseudomonas alcaligenes | 50,161 | 06-Dec-1998 |
| rxa00403 | 1254 | GB_BA2:AF052652 | 2096 | AF052652 | Corynebacterium glutamicum homoserine O-acetyltransferase (metA) gene, complete cds. | Corynebacterium glutamicum | 99,920 | 19-Mar-1998 |
| | | GB_BA1:MTV016 | 53662 | AL021841 | Mycobacterium tuberculosis H37Rv complete genome; segment 143/162. | Mycobacterium tuberculosis | 52,898 | 23-Jun-1999 |
| | | GB_EST23:AI111288 | 750 | AI111288 | SWOvAMCAQO2AOSSK Onchocerca volvulus adult male cDNA (SAW98MLW-OvAM) Onchocerca volvulus cDNA clone SWOvAMCAQO2A05 5', mRNA sequence. | Onchocerca volvulus | 37,565 | 31-Aug-1998 |
| rxa00405 | 813 | GB_BA1:MTV016 | 53662 | AL021841 | Mycobacterium tuberculosis H37Rv complete genome; segment 143/162. | Mycobacterium tuberculosis | 57,259 | 23-Jun-1999 |
| | | GB_AC:AC005145 | 143678 | AC005145 | Homo sapiens Xp22-166-169 GSHB-523A23 (Genome Systems Human BAC library) complete sequence. | Homo sapiens | 34,179 | 08-Dec-1998 |
| rxa00420 | 1587 | GB_BA1:MTV016 | 53662 | AL021841 | Mycobacterium tuberculosis H37Rv complete genome; segment 143/162. | Mycobacterium tuberculosis | 40,169 | 23-Jun-1999 |
| | | GB_BA1:MTY13D12 | 37085 | Z80343 | Mycobacterium tuberculosis H37Rv complete genome; segment 156/162. | Mycobacterium tuberculosis | 62,031 | 17-Jun-1998 |
| | | GB_BA1:MSGY126 | 37164 | AD000012 | Mycobacterium tuberculosis sequence from clone y126. | Mycobacterium tuberculosis | 61,902 | 10-Dec-1996 |
| | | GB_BA1:MSGB971CS | 37566 | L78821 | Mycobacterium leprae cosmid B971 DNA sequence. | Mycobacterium leprae | 39,651 | 15-Jun-1996 |
| rxa00435 | 1296 | GB_BA1:AFACBBTZ | 2760 | M68904 | Alcaligenes eutrophus chromosomal transketolase (cbbTc) and phosphoglycolate phosphatase (cbbZc) genes, complete cds. | Ralstonia eutropha | 38,677 | 27-Jul-1994 |
| | | GB_HTG4:AC009541 | 169583 | AC009541 | Homo sapiens chromosome 7, *** SEQUENCING IN PROGRESS ***, 25 unordered pieces. | Homo sapiens | 36,335 | 12-Oct-1999 |
| | | GB_HTG4:AC009541 | 169583 | AC009541 | Homo sapiens chromosome 7, *** SEQUENCING IN PROGRESS ***, 25 unordered pieces. | Homo sapiens | 36,335 | 12-Oct-1999 |
| rxa00437 | 579 | GB_PR4:AC005951 | 155450 | AC005951 | Homo sapiens chromosome 17, clone hRPK.372_K_20, complete sequence. | Homo sapiens | 31,738 | 18-Nov-1998 |
| | | GB_BA1:SC2A11 | 22789 | AL031184 | Streptomyces coelicolor cosmid 2A11. | Streptomyces coelicolor | 43,262 | 5-Aug-1998 |
| | | GB_PR4:AC005951 | 155450 | AC005951 | Homo sapiens chromosome 17, done hRPK.372_K_20, complete sequence. | Homo sapiens | 37,647 | 18-Nov-1998 |
| rxa00439 | 591 | GB_BA1:MTV016 | 53662 | AL021841 | Mycobacterium tuberculosis H37Rv complete genome; segment 143/162. | Mycobacterium tuberculosis | 37,088 | 23-Jun-1999 |
| | | GB_PL2:AF167358 | 1022 | AF167358 | Rumex acetosa expansin (EXP3) gene, partial cds. | Rumex acetosa | 46,538 | 17-Aug-1999 |
| | | GB_HTG3:AC009120 | 269445 | AC009120 | Homo sapiens chromosome 16 clone RPCI-11_484E3, *** SEQUENCING IN PROGRESS ***, 34 unordered pieces. | Homo sapiens | 43,276 | 3-Aug-1999 |
| rxa00440 | 582 | GB_BA2:SKZ86111 | 7860 | Z86111 | Streptomyces lividans rpsP, trmD, rplS, sipW, sipX, sipY, sipZ, mutT genes and 4 open reading frames. | Streptomyces lividans | 43,080 | 27-Oct-1999 |
| | | GB_BA1:SC2E1 | 38962 | AL023797 | Streptomyces coelicolor cosmid 2E1. | Streptomyces coelicolor | 42,931 | 4-Jun-1998 |
| | | GB_BA1:SC2E1 | 38962 | AL023797 | Streptomyces coelicolor cosmid 2E1. | Streptomyces coelicolor | 36,702 | 4-Jun-1998 |
| nca00441 | 1287 | GB_PR2:HS173D1 | 117338 | AL031984 | Human DNA sequence from clone 173D1 on chromosome 1p36.21-36.33.Contains ESTs, STSs and GSSs, complete sequence. | Homo sapiens | 38,027 | 23-Nov-1999 |
| | | GB_HTG2:HSDJ719K3 | 267114 | AL109931 | Homo sapiens chromosome X clone RP4-719K3 map q21.1-21.31, *** | Homo sapiens | 34,521 | 03-Dec-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00446 | | GB_HTG2:H5DJ719K3 | 267114 | AL109931 | SEQUENCING IN PROGRESS ***, in unordered pieces. | Homo sapiens | 34,521 | 03-Dec.-1999 |
| | 987 | GB_BA1:SCD78 | 36224 | AL034355 | Homo sapiens chromosome X clone RP4-719K3 map q21.1-21.31, *** SEQUENCING IN PROGRESS ***, in unordered pieces. | Streptomyces coelicolor | 56,410 | 26-Nov.-1998 |
| | | GB_HTG4:AC009367 | 226055 | AC009367 | Streptomyces coelicolor cosmid D78. | Drosophila melanogaster | 34,959 | 16-Oct.-1999 |
| | | GB_HTG4:AC009367 | 226055 | AC009367 | Drosophila melanogaster chromosome 3L/76A2 clone RPC198-48B15, *** SEQUENCING IN PROGRESS ***, 44 unordered pieces. | Drosophila melanogaster | 34,959 | 16-Oct.-1999 |
| rxa00448 | 1143 | GB_PR3:AC003670 | 88945 | AC003670 | Drosophila melanogaster chromosome 3L/76A2 clone RPC198-48B15, *** SEQUENCING IN PROGRESS ***, 44 unordered pieces. | Homo sapiens | 35,682 | 9-Jun.-1998 |
| | | GB_HTG2:AF029367 | 148676 | AF029367 | Homo sapiens 12q13.1 PAC RPCI1-130F5 (Roswell Park Cancer Institute Human PAC library) complete sequence. | Homo sapiens | 31,373 | 18-Oct.-1997 |
| | | GB_HTG2:AF029367 | 148676 | AF029367 | Homo sapiens chromosome 12 clone RPCI-1 130F5 map 12q13.1, *** SEQUENCING IN PROGRESS ***, 156 unordered pieces. | Homo sapiens | 31,373 | 18-Oct.-1997 |
| rxa00450 | | GB_HTG2:AC007824 | 133361 | AC007824 | Homo sapiens chromosome 12 clone RPCI-1 1 30F5 map 12q13.1, *** SEQUENCING IN PROGRESS ***, 156 unordered pieces. | Drosophila melanogaster | 40,000 | 2-Aug.-1999 |
| | 424 | GB_HTG2:AC007824 | 133361 | AC007824 | Drosophila melanogaster chromosome 3 clone BACR02L16 (D715) RPCI-1998 02.L16 map 89E-90A strain y; cn bw sp, SEQUENCING IN PROGRESS ***, 91 unordered pieces. | Drosophila melanogaster | 40,000 | 2-Aug.-1999 |
| | | GB_EST35:AI816057 | 412 | AI818057 | Drosophila melanogaster chromosome 3 clone BACR02L16 (D715) RPCI-1998 02.L16 map 89E-90A strain y; cn bw sp, SEQUENCING IN PROGRESS ***, 91 unordered pieces. | Homo sapiens | 35,714 | 24-Aug.-1999 |
| rxa00461 | 975 | GB_BA1:MLCB1779 | 43254 | Z98271 | wk14a08.x1 NCI_CGAP_Lym12 Homo sapiens cDNA clone IMAGE:2412278 3' similar to gb:Y00764 UBIQUINOL-CYTOCHROME C REDUCTASE 11 KD PROTEIN (HUMAN); mRNA sequence. | Mycobacterium leprae | 39,308 | 8-Aug.-1997 |
| | | GB_IN1:DMC86E4 | 29352 | AL021086 | Mycobacterium leprae cosmid B1779. | Drosophila melanogaster | 37,487 | 27-Apr.-1999 |
| | | GB_GSS15:AQ640325 | 467 | AQ640325 | Drosophila melanogaster cosmid clone 86E4. | Trypanosoma brucei | 38,116 | 8-Jul.-1999 |
| rxa00465 | | | | | 927P1-2H3.TP 927P1 Trypanosoma brucei genomic clone 927P1-2H3, genomic survey sequence. | | | |
| rxa00487 | 1692 | GB_BA1:BAGUAA | 3866 | Y10499 | B.ammoniagenes guaA gene. | Corynebacterium ammoniagenes | 74,259 | 8-Jan.-1998 |
| rxa00488 | | GB_BA2:U00015 | 42325 | U00015 | Mycobacterium leprae cosmid B1620. | Mycobacterium leprae | 37,248 | 01-Mar.-1994 |
| | | GB_BA1:MTCY78 | 33818 | Z77165 | Mycobacterium tuberculosis H37Rv complete genome; segment 145/162. | Mycobacterium tuberculosis | 39,725 | 17-Jun.-1998 |
| | 1641 | GB_BA1:MTCY78 | 33818 | Z77165 | Mycobacterium tuberculosis H37Rv complete genome; segment 145/162. | Mycobacterium tuberculosis | 39,451 | 17-Jun.-1998 |
| | | GB_BA2:U00015 | 42325 | U00015 | Mycobacterium leprae cosmid B1620. | Mycobacterium leprae | 39,178 | 01-Mar.-1994 |
| | | GB_BA1:SCAJI0601 | 4692 | AJO10601 | Streptomyces coelicolor A3(2) DNA for whiD and whiK loci. | Streptomyces coelicolor | 60,835 | 17-Sep.-1998 |
| rxa00489 | 1245 | GB_BA2:U00015 | 42325 | U00015 | Mycobacterium leprae cosmid B1620. | Mycobacterium leprae | 38,041 | 01-Mar.-1994 |
| | | GB_HTG2:HS225E12 | 126464 | AL031772 | Homo sapiens chromosome 6 clone RP1-225E12 map q24, *** SEQUENCING IN PROGRESS ***, in unordered pieces. | Homo sapiens | 36,756 | 03-Dec.-1999 |
| | | GB_HTG2:HS225E12 | 126464 | AL031772 | Homo sapiens chromosome 6 clone RPi-225E12 map q24, *** SEQUENCING IN PROGRESS ***, in unordered pieces. | Homo sapiens | 36,756 | 03-Dec.-1999 |
| rxa00533 | 1155 | GB_BA1:CGLYS | 2803 | X57226 | C.glutamicum lysC-alpha, lysC-beta and asd genes for aspartokinase-alpha and -beta subunits, and aspartate beta semialdehyde dehydrogenase, respectively (EC 2.7.2.4; EC 1.2.1.11). | Corynebacterium glutamicum | 99,913 | 17-Feb.-1997 |
| | | GB_BA1:CGCYSCASD | 1591 | X82928 | C.glutamicum aspartate-semialdehyde dehydrogenase gene. | Corynebacterium glutamicum | 99,221 | 17-Feb.-1997 |
| | | GB_PAT:A07546 | 2112 | A07546 | Recombinant DNA fragment (PstI-XhoI). | synthetic construct | 99,391 | 30-Jul.-1993 |
| rxa00534 | 1386 | GB_BA1:CGLYS | 2803 | X57226 | C. glutamicum lysC-alpha, lysC-beta and asd genes for aspartokinase-alpha | Corynebacterium glutamicum | 99,856 | 17-Feb.-1997 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| | | GB_BA1:CORASKD | 2957 | L16848 | and -beta subunits, and aspartate beta semialdehyde dehydrogenase, respectively (EC 2.7.2.4; EC 1.2.1.11). Corynebacterium flavum aspartokinase (ask), and aspartate-semialdehyde dehydrogenase (asd) genes, complete cds. | Corynebacterium flavescens | 98,701 | 11-Jun.-1993 |
| | | GB_PAT:E14514 | 1643 | E14514 | DNA encoding Brevibacterium aspartokinase. | Corynebacterium glutamicum | 98,773 | 28-Jul.-1999 |
| rxa00536 | 1494 | GB_BA1:CGLEUA | 3492 | X70959 | C.glutamicum gene leuA for isopropylmalate synthase. | Corynebacterium glutamicum | 100,000 | 10-Feb.-1999 |
| | | GB_BA1:MTV025 | 121125 | AL022121 | Mycobacterium tuberculosis H37Rv complete genome; segment 155/162. | Mycobacterium tuberculosis | 68,003 | 24-Jun.-1999 |
| | | GB_BA1:MTU88526 | 2412 | U88526 | Mycobacterium tuberculosis putative alpha-isopropyl malate synthase (leuA) gene, complete cds. | Mycobacterium tuberculosis | 68,185 | 26-Feb.-1997 |
| rxa00537 | 2409 | GB_BA2:SCD2S | 41622 | AL118514 | Streptomyces coelicolor cosmid D25. | Streptomyces coelicolor A3(2) | 63,187 | 21-Sep.-1999 |
| | | GB_BA1:MTCY7H7A | 10451 | Z95618 | Mycobacterium tuberculosis H37Rv complete genome: segment 39/162. | Mycobacterium tuberculosis | 62,401 | 17-Jun.-1998 |
| | | GB_BA1:MTU34956 | 2462 | U34956 | Mycobacterium tuberculosis phosphoribosylformylglycinamgdine synthase (purL) gene, complete cds. | Mycobacterium tuberculosis | 62,205 | 28-Jan.-1997 |
| rxa00541 | 792 | GB_PAT:I92052 | 2115 | I92052 | Sequence 19 from patent U.S. Pat. No. 5726299. | Unknown. | 98,359 | 01-Dec.-1998 |
| | | GB_BA1:MLCBS | 38109 | Z95151 | Mycobacterium leprae cosmid B5. | Mycobacterium leprae | 62,468 | 24-Jun.-1997 |
| | | GB_BA1:MTCY369 | 36850 | Z80226 | Mycobacterium tuberculosis H37Rv complete genome; segment 36/162. | Mycobacterium tuberculosis | 60,814 | 17-Jun.-1998 |
| rxa00558 | 1470 | GB_BA1:BAPURF | 1885 | X91252 | B.ammoniagenes purF gene. | Corynebacterium ammoniagenes | 66,095 | 5-Jun.-1997 |
| rxa00579 | 1983 | GB_BA1:MLU15182 | 40123 | U15182 | Mycobacterium leprae cosmid B2266. | Mycobacterium leprae | 64,315 | 09-Mar.-1995 |
| | | GB_BA1:MTCY7H7A | 10451 | Z95618 | Mycobacterium tuberculosis H37Rv complete genome; segment 39/162. | Mycobacterium tuberculosis | 64,863 | 17-Jun.-1998 |
| | | GB_PAT:AR016483 | 2104 | AR016483 | Sequence 1 from patent U.S. Pat. No. 5776740. | Unknown. | 98,810 | 05-Dec.-1998 |
| | | EM_PAT:E11273 | 2104 | E11273 | DNA encoding serine hydroxymethyl transferase. | Corynebacterium glutamicum | 98,810 | 08-Oct.-1997 (Rel. 52. Created) |
| rxa00580 | 1425 | GB_PAT:E12594 | 2104 | E12594 | DNA encoding serine hydroxymethyltransferase from Brevibacterium flavum. | Corynebacterium glutamicum | 98,810 | 24-Jun.-1998 |
| | | GB_PAT:E12594 | 2104 | E12594 | DNA encoding serine hydroxymethyltransferase from Brevibacterium flavum. | Corynebacterium glutamicum | 99,368 | 24-Jun.-1998 |
| | | GB_PAT:AR016483 | 2104 | AR016483 | Sequence 1 from patent U.S. 5776740. | Unknown. | 99,368 | 05-Dec.-1998 |
| | | EM_PAT:E11273 | 2104 | E11273 | DNA encoding serine hydroxymethyl transferase. | Corynebacterium glutamicum | 99,368 | 08-Oct.-1997 (Rel. 52, Created) |
| rxa00581 | 1092 | GB_PAT:E12594 | 2104 | E12594 | DNA encoding serine hydroxymethyltransferase from Brevibacterium flavum. | Corynebacterium glutamicum | 98,810 | 24-Jun.-1998 |
| | | EM_PAT:E11273 | 2104 | E11273 | DNA encoding serine hydroxymethyl transferase. | Corynebacterium glutamicum | 37,071 | 08-Oct.-1997 (Rel. 52. Created) |
| rxa00584 | 1248 | GB_PAT:AR018483 | 2104 | AR018483 | Sequence 1 from patent U.S. 5776740. | Unknown. | 37,071 | 05-Dec.-1998 |
| | | GB_BA1:CORAHPS | 2570 | L07603 | Corynebacterium glutamicum 3-deoxy-D-arabinoheptulosonate-7-phosphate synthase gene, complete cds. | Corynebacterium glutamicum | 98,236 | 26-Apr.-1993 |
| rxa00618 | 1230 | GB_BA1:AOPCZA361 | 37941 | AJ223998 | Amycolatopsis orientalis cosmid PCZA361. | Amycolatopsis orientalis | 54,553 | 29-Mar.-1999 |
| | | GB_BA1:D90714 | 14358 | D90714 | Escherichia coli genomic DNA. (16.8-17.1 min). | Escherichia coli | 53,312 | 7-Feb.-1999 |
| | | GB_EST19:AA802737 | 280 | AA802737 | GM06236.5prime GM Drosophila melanogaster ovary BlueScript Drosophila melanogaster cDNA clone GM06236 5prime, mRNA sequence. | Drosophila melanogaster | 39,928 | 25-Nov.-1998 |
| | | GB_EST28:AI534381 | 581 | AI534381 | SD07186.5prime SD Drosophila melanogaster Schneider L2 cell culture pOT2 Drosophila melanogaster cDNA clone SD07186 5prime similar to X89858:Ani FBgn0011558 PID:g927407 SPTREMBL:Q24240, mRNA sequence. | Drosophila melanogaster | 41,136 | 18-Mar.-1999 |
| | | GB_IN1:DMANILLIN | 4029 | X89858 | D.melanogaster mRNA for anillin protein. | Drosophila melanogaster | 34,398 | 8-Nov.-1995 |
| rxa00619 | 1551 | GB_BA1:MTCY369 | 36850 | Z80226 | Mycobacterium tuberculosis H37Rv complete genome; segment 36/162. | Mycobacterium tuberculosis | 62,776 | 17-Jun.-1998 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00620 | 1014 | GB_BA1:MLCB5 | 38109 | Z95151 | Mycobacterium leprae cosmid B5. | Mycobacterium leprae | 61,831 | 24-Jun.-1997 |
|  |  | GB_PAT:A60305 | 1845 | A60305 | Sequences 5 from Patent WO9708323. | unidentified | 61,785 | 06-Mar.-1998 |
|  |  | GB_PL2:AF063247 | 1450 | AF063247 | Pneumocystis carinii f. sp. ratti enolase mRNA, complete cds. | Pneumocystis carinii f. sp. ratti | 41,060 | 5-Jan.-1999 |
|  |  | GB_BA1:STMAPP | 2069 | M91546 | Streptomyces lividans aminopeptidase P (PepP) gene, complete cds. | Streptomyces lividans | 37,126 | 12-Jun.-1993 |
|  |  | GB_HTG3:AC008783 | 214575 | AC008783 | Homo sapiens chromosome 19 clone CITB-E1_3214H19, *** SEQUENCING IN PROGRESS ***, 21 unordered pieces. | Homo sapiens | 40,020 | 3-Aug.-1999 |
| rxa00624 | 810 | GB_IN1:CEY4IE3 | 150841 | Z95559 | Caenorhabditis elegans cosmid Y41E3, complete sequence. | Caenorhabditis elegans | 36,986 | 2-Sep.-1999 |
|  |  | GB_EST13:AA362167 | 372 | AA362167 | E5T71561 Macrophage I Homo sapiens cDNA 5' end, mRNA sequence. | Homo sapiens | 38,378 | 21-Apr.-1997 |
|  |  | GB_IN1:CEY4IE3 | 150641 | Z95559 | Caenorhabditis elegans cosmid Y41E3, complete sequence. | Caenorhabditis elegans | 37,694 | 2-Sep.-1999 |
| rxa00826 | 1386 | GB_BA1:MTCY369 | 36850 | Z80226 | Mycobacterium tuberculosis H37Rv complete genome; segment 36/162. | Mycobacterium tuberculosis | 57,971 | 17-Jun.-1998 |
|  |  | GB_BA1:MLCB5 | 38109 | Z95151 | Mycobacterium leprae cosmid B5. | Mycobacterium leprae | 58,806 | 24-Jun.-1997 |
|  |  | GB_BA1:MLU15187 | 36138 | U15187 | Mycobacterium leprae cosmid L296. | Mycobacterium leprae | 38,007 | 09-Mar.-1995 |
| rxa00632 | 795 | GB_BA1:BRLBIOAD | 2272 | D14083 | Brevibacterium flavum genes for 7,8-diaminopelargonic acid aminotransferase and dethiobiotin synthetase, complete cds. | Corynebacterium glutamicum | 97,358 | 3-Feb.-1999 |
|  |  | GB_PAT:E04041 | 675 | E04041 | DNA sequence coding for desthiobiotinsynthetase. | Corynebacterium glutamicum | 98,074 | 29-Sep.-1997 |
|  |  | GB_PAT:E04040 | 1272 | E04040 | DNA sequence coding for diamino pelargonic acid aminotransferase. | Corynebacterium glutamicum | 93,814 | 29-Sep.-1997 |
| rxa00633 | 1392 | GB_BA1:BRLBIOAD | 2272 | D14083 | Brevibacterium flavum genes for 7,8-diaminopelargonic acid aminotransferase and dethiobiotin synthetase, complete cds. | Corynebacterium glutamicum | 95,690 | 3-Feb.-1999 |
|  |  | GB_PAT:E04040 | 1272 | E04040 | DNA sequence coding for diamino pelargonic acid aminotransferase. | Corynebacterium glutamicum | 95,755 | 29-Sep.-1997 |
|  |  | GB_BA2:EHU38519 | 1290 | U38519 | Erwinia herbicola adenosylmethionine-8-amino-7-oxononanoate transaminase (bioA) gene, complete cds. | Erwinia herbicola | 55,564 | 4-Nov.-1996 |
| rxa00688 | 666 | GB_BA1:MTV041 | 28826 | AL021958 | Mycobacterium tuberculosis H37Rv complete genome; segment 35/162. | Mycobacterium tuberculosis | 60,030 | 17-Jun.-1998 |
|  |  | GB_BA1:BRLSECY | 1516 | D14162 | Brevibacterium flavum gene for SecY protein (complete cds) and gene or adenylate kinase (partial cds). | Corynebacterium glutamicum | 99,563 | 3-Feb.-1999 |
|  |  | GB_BA2:MBU77912 | 7163 | U77912 | Mycobacterium bovis MBE5Oa gene, partial cds; and MBE50b, MBE50c, preprotein translocase SecY subunit (secY), adenylate kinase (adk), methionine aminopeptidase (map), RNA polymerase ECF sigma factor (sigE50), MBE50d, and MBE50e genes, complete cds. | Mycobacterium bovis | 60,030 | 27-Jan.-1999 |
| rxa00708 | 930 | GB_BA2:AF157493 | 25454 | AF157493 | Zymomonas mobilis ZM4 fosmid clone 42D7, complete sequence. | Zymomonas mobilis | 39,116 | 5-Jul.-1999 |
|  |  | GB_PAT:I00836 | 1853 | I00836 | Sequence 1 from Patent U.S. 4758514. | Unknown. | 47,419 | 21-May-1993 |
|  |  | GB_PAT:E00311 | 1853 | E0031 | DNA coding of 2,5-diketogluconic acid reductase. | unidentified | 47,419 | 29-Sep.-1997 |
| rxa00717 | 1083 | GB_PAT:I78753 | 1187 | I78753 | Sequence 9 from patent U.S. 5693781. | Unknown. | 37,814 | 3-Apr.-1998 |
|  |  | GB_PAT:I92042 | 1187 | I92042 | Sequence 9 from patent U.S. 5726299. | Unknown. | 37,814 | 01-Dec.-1998 |
|  |  | GB_BA1:MTCI125 | 37432 | Z98268 | Mycobacterium tuberculosis H37Rv complete genome; segment 76/162. | Mycobacterium tuberculosis | 50,647 | 17-Jun.-1998 |
| rxa00718 | 831 | GB_BA1:MTCI125 | 37432 | Z98268 | Mycobacterium tuberculosis H37Rv complete genome; segment 76/162. | Mycobacterium tuberculosis | 55,228 | 17-Jun.-1998 |
|  |  | GB_BA1:MTCI125 | 37432 | Z98268 | Mycobacterium tuberculosis H37Rv complete genome; segment 76/162. | Mycobacterium tuberculosis | 40,300 | 17-Jun.-1998 |
|  |  | GB_GSS12:AQ420755 | 671 | AQ420755 | RPCI-11-168G18.TJ RPCI-11 Homo sapiens genomic clone RPCI-11-168G18, genomic survey sequence. | Homo sapiens | 35,750 | 23-Mar.-1999 |
| rxa00727 | 1035 | GB_HTG3:AC008332 | 118545 | AC008332 | Drosophila melanogaster chromosome 2 clone BACR48D10 (D867) RPCI-98 48.D.10 map 34A-34A strain y; cn bw sp, *** SEQUENCING IN PROGRESS ***, 78 unordered pieces. | Drosophila melanogaster | 40,634 | 6-Aug.-1999 |
|  |  | GB_HTG3:AC008332 | 118545 | AC008332 | Drosophila melanogaster chromosome 2 clone BACR48D10 (D867) RPCI-98 48.D.10 map 34A-34A strain y; cn bw sp, *** SEQUENCING IN PROGRESS***, 78 unordered pieces. | Drosophila melanogaster | 40,634 | 6-Aug.-1999 |
|  |  | GB_HTG3:AC008332 | 118545 | AC008332 | Drosophila melanogaster chromosome 2 clone BACR48D10 (D867) RPCI-98 48.D.10 map 34A-34A strain y; cn bw sp, *** SEQUENCING IN PROGRESS***, 78 unordered pieces. | Drosophila melanogaster | 33,888 | 6-Aug.-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00766 | 966 | GB_HTG2:AC006789 | 83823 | AC006789 | Caenorhabditis elegans clone Y49F6, *** SEQUENCING IN PROGRESS ***, 2 unordered pieces. | Caenorhabditis elegans | 36,737 | 25-Feb.-1999 |
| | | GB_HTG2:AC006789 | 83823 | AC006789 | Ceenorhabditis elegans clone Y49F6, *** SEQUENCING IN PROGRESS ***, 2 unordered pieces. | Caenorhabditis elegans | 36,737 | 25-Feb.-1999 |
| rxa00770 | 1293 | GB_BA1:D90810 | 20476 | D90810 | E.coli genomic DNA, Kohara clone #319(37.4-37.8min.). | Escherichia coli | 36,526 | 29-May-1997 |
| | | GB_BA1:MT1V043 | 68848 | AL022004 | Mycobacterium tuberculosis H37Rv complete genome; segment 40/162. | Mycobacterium tuberculosis | 66,193 | 24-Jun.-1999 |
| | | GB_BA1:MLU15182 | 40123 | U15182 | Mycobacterium leprae cosmid N2266. | Mycobacterium leprae | 61,443 | 09-Mar.-1995 |
| | | GB_BA2:SCD25 | 41622 | AL118514 | Streptomyces coelicolor cosmid D25. | Streptomyces coelicolor A3(2) | 59,938 | 21-Sep.-1999 |
| rxa00779 | 1056 | GB_HTG1:CER08A5 | 51920 | Z82281 | Caenorhabditis elegans chromosome V clone R08A5, *** SEQUENCING IN PROGRESS ***, in unordered pieces. | Caenorhabditis elegans | 64,896 | 14-Oct.-1998 |
| | | GB_HTG1:CER08A5 | 51920 | Z82281 | Ceenorhabditis elegans chromosome V clone R08A5, SEQUENCING IN PROGRESS ***, in unordered pieces. | Caenorhabditis elegans | 64,896 | 14-Oct.-1998 |
| | | GB_PL2:AF078693 | 1492 | AF078693 | Chlamydomonas reinhardtii putative O-acetylserine(thiol)lyase precursor (Croys-1A) mRNA, nuclear gene encoding organellar protein, complete cds. | Chlamydomonas reinhardtii | 57,970 | 3-Nov.-1999 |
| rxa00780 | 669 | GB_BA1:MTCY98 | 31225 | Z83880 | Mycobacterium tuberculosis H37Rv complete genome; segment 103/162. | Mycobacterium tuberculosis | 54,410 | 17-Jun.-1998 |
| | | GB_BA1:AVINIFREG | 7099 | M60090 | Azotobacter chroococcum nifU, nifS, nifV, nifP, nifW, nifZ and nifM genes, complete cds. | Azotobacter chroococcum | 51,729 | 26-Apr.-1993 |
| rxa00838 | 1023 | GB_BA2:AF001780 | 6701 | AF001780 | Cyanothece PCC 8801 NifP (nifP), nitrogenase (nifB), FdxN (fdxN), NifS (nifS) and NifU (nifU) genes, complete cds, and NifH (nifH) gene, partial cds. | Cyanothece PCC8801 | 36,309 | 08-Mar.-1999 |
| | | GB_EST1:Z30506 | 329 | Z30506 | ATTS2430 AC16H Arabidopsis thaliana cDNA clone TAI306 3'; mRNA sequence. | Arabidopsis thaliana | 44,308 | 11-Mar.-1994 |
| | | GB_PL2:AC006258 | 110469 | AC006258 | Arabidopsis thaliana BAC F18G18 from chromosome V near 60.5 cM, complete sequence. | Arabidopsis thaliana | 35,571 | 28-Dec.-1998 |
| | | GB_EST37:AI998439 | 455 | AI998439 | 701545695 A. thaliana, Columbia Col-0, rosette-2 Arabidopsis thaliana cDNA clone 701545695, mRNA sequence. | Arabidopsis thaliana | 36,044 | 8-Sep.-1999 |
| rxa00863 | 867 | GB_BA1:BLDAPAB | 3572 | Z21502 | B.lactofermentum dapA and dapB genes for dihydrodipicolinate synthase and dihydrodipicolinate reductase. | Corynebacterium glutamicum | 99,539 | 16-Aug.-1993 |
| | | GB_PAT:E16749 | 2001 | E16749 | gDNA encoding dihydrodipicolinate synthase (DDPS). | Corynebacterium glutamicum | 99,539 | 28-Jul.-1999 |
| | | GB_PAT:E14520 | 2001 | E14520 | DNA encoding Brevibacterium dihydrodipicolinic acid synthase. | Corynebacterium glutamicum | 99,539 | 28-Jul.-1999 |
| rxa00864 | 873 | GB_BA1:BLDAPAB | 3572 | Z21502 | B.lactofermentum dapA and dapB genes far dihydrodipicolinate synthase and dihydrodipicolinate reductase. | Corynebacterium glutamicum | 99,885 | 16-Aug.-1993 |
| rxa00865 | 1026 | GB_BA1:CGDAPB | 1902 | X67737 | C.glutamicum dapB gene for dihydrodipicolinate reductase. | Corynebacterium glutamicum | 100,000 | 1-Apr.-1993 |
| | | GB_PAT:E14520 | 2001 | E14520 | DNA encoding Brevibacterium dihydrodipicolinic acid synthase. | Corynebacterium glutamicum | 100,000 | 28-Jul.-1999 |
| | | GB_BA1:BLDAPAB | 3572 | Z21502 | B.lactofermentum dapA and dapB genes for dihydrodipicolinate synthase and dihydrodipicolinate reductase. | Corynebacterium glutamicum | 100,000 | 16-Aug.-1993 |
| rxa00867 | 650 | GB_PAT:E16752 | 1411 | E16752 | gDNA encoding dihydrodipicolinate reductase (DDPR). | Corynebacterium glutamicum | 99,805 | 28-Jul.-1999 |
| | | GB_PAT:AR038113 | 1411 | AR038113 | Sequence 18 from patent U.S. Pat. No. 5804414. | Unknown. | 99,805 | 29-Sep.-1999 |
| | | GB_BA1:MTV002 | 56414 | AL008967 | Mycobacterium tuberculosis H37Rv complete genome; segment 122/162. | Mycobacterium tuberculosis | 39,179 | 17-Jun.-1998 |
| | | GB_BA1:MLCB22 | 40281 | Z98741 | Mycobacterium leprae cosmid B22. | Mycobacterium leprae | 39,482 | 22-Aug.-1997 |
| | | GB_BA1:SAU19858 | 2838 | U19858 | Streptomyces antibioticus guanosine pentaphosphate synthetase (gpsI) gene, complete cds. | Streptomyces antibioticus | 69,706 | 25-Oct.-1996 |
| rxa00873 | 779 | GB_BA1:SCO001206 | 9184 | AJ001206 | Streptomyces coelicolor A3(2), glycogen metabolism cluster II. | Streptomyces coelicolor | 63,415 | 29-Mar.-1999 |
| | | GB_BA1:SCO001205 | 9589 | AJ001205 | Streptomyces coelicolor A3(2) glycogen metabolism clusterI. | Streptomyces coelicolor | 61,617 | 29-Mar.-1999 |
| | | GB_BA1:D78198 | 2304 | D78198 | Pimelobacter sp. DNA for trehalose synthase, complete cds. | Pimelobacter sp. | 60,594 | 5-Feb.-1999 |
| rxa00884 | 1263 | GB_BA1:MTCY253 | 41230 | Z81368 | Mycobacterium tuberculosis H37Rv complete genome; segment 106/162. | Mycobacterium tuberculosis | 37,785 | 17-Jun.-1998 |
| | | GB_BA1:MSGY222 | 41156 | AD000010 | Mycobacterium tuberculosis sequence from clone y222. | Mycobacterium tuberculosis | 38,006 | 03-Dec.-1996 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00891 | 1102 | GB_GSS15:AQ654600 | 468 | AQ654600 | Sheared DNA-1O14.TF Sheared DNA *Trypanosoma brucei* genomic clone Sheared DNA-1O14, genomic survey sequence. | *Trypanosoma brucei* | 33,974 | 22-Jun-1999 |
| | | GB_BA1:MTCI418B | 11700 | Z96071 | *Mycobacterium tuberculosis* H37Rv complete genome; segment 7/162. | *Mycobacterium tuberculosis* | 63,297 | 18-Jun-1998 |
| | | GB_BA1:SC0001206 | 9184 | AJ001206 | *Streptomyces coelicolor*A3(2), glycogen metabolism cluster II. | *Streptomyces coelicolor* | 61,965 | 29-Mar-1999 |
| | | GB_BA1:SC0001205 | 9589 | AJ001205 | *Streptomyces coelicolor* A3(2) glycogen metabolism clusterI. | *Streptomyces coelicolor* | 61,727 | 29-Mar-1999 |
| rxa00952 | 963E | EM_PAT:E10963 | 3118 | E10963 | gDNA encoding tryptophan synthase. | *Corynebacterium glutamicum* | 99,6888 | 08-Oct-1997 (Rel. 52, Created) |
| | | GB_BA1:BLTRP | 7726 | X04960 | *Brevibacterium lactofermentum* tryptophan operon. | *Corynebacterium glutamicum* | 98,847 | 10-Feb-1999 |
| | | GB_PAT:E01688 | 7725 | E01688 | Genomic DNA of trp operon of *prepibacterium latophelmentann*. | unidentified | 98,428 | 29-Sep-1997 |
| rxa00954 | 644 | GB_PAT:E01375 | 7725 | E01375 | DNA sequence of tryptophan operon. | *Corynebacterium glutamicum* | 98,758 | 29-Sep-1997 |
| | | GB_PAT:E01688 | 7725 | E01688 | Genomic DNA of trp operon of *prepibacterium latophelmentann*. | unidentified | 98,758 | 29-Sep-1997 |
| | | GB_BA1:BLTRP | 7725 | X04960 | *Brevibacterium lactofermentum* tryptophan operon. | *Corynebacterium glutamicum* | 98,758 | 10-Feb-1999 |
| rxa00955 | 1545 | GB_PAT:E01375 | 7726 | E01375 | DNA sequence of tryptophan operon. | *Corynebacterium glutamicum* | 98,372 | 29-Sep-1997 |
| | | GB_BA1:BLTRP | 7726 | X04960 | *Brevibacterium lactofermentum* tryptophan operon. | *Corynebacterium glutamicum* | 98,372 | 10-Feb-1999 |
| | | GB_PAT:E01688 | 7725 | E01688 | Genomic DNA of trp operon of *prepibacterium latophelmentann*. | unidentified | 98,242 | 29-Sep-1997 |
| rxa00958 | 1237 | EM_PAT:E10963 | 3118 | E10963 | gDNA encoding tryptophan synthase. | *Corynebacterium glutamicum* | 98,949 | 08-Oct-1997 (Rel. 52, Created) |
| | | GB_BA1:BLTRP | 7726 | X04960 | *Brevibacterium lactofermentum* tryptophan operon. | *Corynebacterium glutamicum* | 99,107 | 10-Feb-1999 |
| | | GB_PAT:E01375 | 7726 | E01375 | DNA sequence of tryptophan operon. | *Corynebacterium glutamicum* | 98,945 | 29-Sep-1997 |
| rxa00957 | 1677 | GB_BA1:BLTRP | 7725 | X04960 | *Brevibacterium lactofermentum* tryptophan operon. | *Corynebacterium glutamicum* | 99,165 | 10-Feb-1999 |
| | | GB_PAT:E01375 | 7726 | E01375 | DNA sequence of tryptophan operon. | *Corynebacterium glutamicum* | 98,927 | 29-Sep-1997 |
| | | GB_PAT:E01688 | 7725 | E01688 | Genomic DNA of trp operon of *prepibacterium latophelmentann*. | unidentified | 98,867 | 29-Sep-1997 |
| rxa00958 | 747 | GB_BA1:BLTRP | 7726 | X04960 | *Brevibacterium lactofermentum* tryptophan operon. | *Corynebacterium glutamicum* | 98,792 | 10-Feb-1999 |
| | | GB_PAT:E01375 | 7726 | E01375 | DNA sequence of tryptophan operon. | *Corynebacterium glutamicum* | 98,792 | 29-Sep-1997 |
| | | GB_PAT:E01688 | 7725 | E01688 | Genomic DNA of trp operon of *prepibacterium latophelmentann*. | unidentified | 98,658 | 29-Sep-1997 |
| rxa00970 | 1050 | GB_BA1:CGHOMTHR | 3885 | Y00546 | *Corynebacterium glutamicum* hom-thrB genes for homoserine dehydrogenase and homoserine kinase. | *Corynebacterium glutamicum* | 99,905 | 12-Sep-1993 |
| | | GB_PAT:109077 | 3685 | I09077 | Sequence 1 from Patent WO 8809819. | Unknown. | 99,810 | 02-Dec-1994 |
| | | GB_PAT:E01358 | 2615 | E01358 | DNA encoding for homoserine dehydrogenase(HDH)and homoserine kinase(HK). | *Corynebacterium glutamicum* | 97,524 | 29-Sep-1997 |
| rxa00972 | 1458 | GB_PAT:E16755 | 3579 | E16755 | gDNA encoding diaminopimelate decarboxylase (DDC) and arginyl-tRNA synthase. | *Corynebacterium glutamicum* | 99,931 | 28-Jul-1999 |
| | | GB_PAT:AR038110 | 3579 | AR038110 | Sequence 15 from patent U.S. 5804414. | Unknown. | 99,931 | 29-Sep-1999 |
| | | GB_PAT:E14508 | 3579 | E14508 | DNA encoding *Brevibacterium diaminopimelic pk acid decarboxylase and arginyl-tRNA synthase*. | *Corynebacterium glutamicum* | 99,931 | 28-Jul-1999 |
| rxa00981 | 753 | GB_OV:GGA245684 | 512 | AJ245664 | *Gallus gallus* partial mRNA for ATP-citrate lyase (ACL gene). | *Gallus gallus* | 37,538 | 28-Sep-1999 |
| | | GB_PL2:AC007887 | 159434 | AC007887 | Genomic sequence for *Arabidopsis thaliana* pk BAC F1504 from chromosome I, complete sequence. | *Arabidopsis thaliana* | 37,600 | 04-Oct-1999 |
| | | GB_GSS1:CNS00RNW | 542 | AL087338 | *Arabidopsis thaliana* genome survey sequence T7 end of SAC F14D7 of IGF library from strain Columbia of *Arabidopsis thaliana*, genomic survey sequence. | *Arabidopsis thaliana* | 41,264 | 28-Jun-1999 |
| rxa00989 | 1644 | GB_BA1:MTV008 | 63033 | AL021246 | *Mycobacterium tuberculosis* H37Rv complete genome; segment 108/162. | *Mycobacterium tuberculosis* | 40,773 | 17-Jun-1998 |
| | | GB_BA1:SCVALSFP | 3619 | Y13070 | *S.coelicolor* valS, fpgs, ndk genes. | *Streptomyces coelicolor* | 58,119 | 03-Mar-1998 |
| | | GB_BA1:MTV008 | 63033 | AL021246 | *Mycobacterium tuberculosis* H37Rv complete genome; segment 108/162. | *Mycobacterium tuberculosis* | 38,167 | 17-Jun-1998 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa00997 | 705 | GB_BA2:CGU31225 | 1817 | U31225 | Corynebacterium glutamicum L-proline:NADP+5-oxidoreductase (proC) gene, complete cds. | Corynebacterium glutamicum | 40,841 | 2-Aug.-1996 |
|  |  | GB_HTG1:CEY39C12 | 282838 | AL009026 | Caenorhabditis elegans chromosome IV clone Y39C12, *** SEQUENCING IN PROGRESS ***, In unordered pieces. | Caenorhabditis elegans | 36,416 | 26-OCT-1999 |
| rxa01019 | 1110 | GB_IN1:CEB0001 | 39416 | Z69634 | Caenorhabditis elegans cosmid B0001, complete sequence. | Caenorhabditis elegans | 36,416 | 2-Sep.-1999 |
|  |  | GB_HTG2:AC005052 | 144734 | AC005052 | Homo sapiens clone RG038K21, *** SEQUENCING IN PROGRESS ***, 3 unordered pieces. | Homo sapiens | 39,172 | 12-Jun.-1998 |
|  |  | GB_HTG2:AC005052 | 144734 | AC005052 | Homo sapiens clone RG038K21, *** IN PROGRESS ***, 3 unordered pieces. | Homo sapiens | 39,172 | 12-Jun.-1998 |
|  |  | GB_GSS9:AQ171808 | 512 | AQ171808 | HS_3179_A1_G03_T7 CIT Approved Human Genomic Sperm Library D Homo sapiens genomic clone Plate = 3179 Col = 5 Row = M, genomic survey sequence. | Homo sapiens | 34,661 | 17-Oct.-1998 |
| rxa01026 | 1782 | GB_BA1:SCIC2 | 42210 | AL031124 | Streptomyces coelicolor cosmid 1C2. | Streptomyces coelicolor | 68,275 | 15-Jan.-1999 |
|  |  | GB_BA1:ATLEUCD | 2982 | X84647 | A.teichomyceticus leuC and leuD genes. | Actinoplanes teichomyceticus | 65,935 | 04-Oct.-1995 |
|  |  | GB_BA1:MTV012 | 70287 | AL021287 | Mycobacterium tuberculosis H37Rv complete genome; segment 132/162. | Mycobacterium tuberculosis | 40,454 | 23-Jun.-1999 |
| rxa01027 | 1131 | GB_BA1:MLCB637 | 44882 | Z99263 | Mycobacterium leprae cosmid B637. | Mycobacterium leprae | 38,636 | 17-Sep.-1997 |
|  |  | GB_BA1:MTCY349 | 43523 | Z83018 | Mycobacterium tuberculosis H37Rv complete genome; segment 131/162. | Mycobacterium tuberculosis | 51,989 | 17-Jun.-1998 |
|  |  | GB_BA1:SPUNGMUTX | 1172 | Z21702 | S.pneumoniae ung gene and mutX genes encoding uracil-DNA glycosylase and 8-oxoGTP nucleoside triphosphatase. | Streptococcus pneumoniae | 38,088 | 15-Jun.-1994 |
| rxa01073 | 954 | GB_BA1:BACOUTB | 1004 | M15811 | Bacillus subtilis outB gene encoding a sporulation protein, complete cds. | Bacillus subtilis | 53,723 | 26-Apr.-1993 |
|  |  | GB_PR4:AC007938 | 167237 | AC007938 | Homo sapiens clone UWGC:djs201 from 7q31, complete sequence. | Homo sapiens | 34,322 | 1-Jul.-1999 |
|  |  | GB_PL2:ATAC006282 | 92577 | AC006282 | Arabidopsis thaliana chromosome II BAC F13K3 genomic sequence, complete sequence. | Arabidopsis thaliana | 36,181 | 13-Mar.-1999 |
| rxa01079 | 2226 | GB_BA2:AF112535 | 4363 | AF112535 | Corynebacterium glutamicum putative glutaredoxin NrdH (nrdH), and ribonucleotide reductase alpha-chain (nrdE) genes, complete cds. | Corynebacterium glutamicum | 99,820 | 5-Aug.-1999 |
|  |  | GB_BA1:CANRDFGEN | 6054 | Y09572 | Corynebacterium ammoniagenes nrdH, nrdI, nrdE, nrdF genes. | Corynebacterium | 75,966 | 18-Apr.-1998 |
| rxa01080 | 567 | GB_BA1:MTV012 | 70287 | AL021287 | Mycobacterium tuberculosis H37Rv complete genome; segment 132/162. | Mycobacterium tuberculosis | 38,296 | 23-Jun.-1999 |
|  |  | GB_BA2:AF112535 | 4363 | AF112535 | Corynebacterium glutamicum putative glutaredoxin NrdH (nrdH), NrdI (nrdI), and ribonucleotide reductase alpha-chain (nrdE) genes, complete cds. | Corynebacterium glutamicum | 100,000 | 5-Aug.-1999 |
|  |  | GB_BA1:CANRDFGEN | 6054 | Y09572 | Corynebacterium ammoniagenes nrdH, nrdI, nrdE, nrdF genes. | Corynebacterium ammoniagenes | 65,511 | 18-Apr.-1998 |
| rxa01087 | 999 | GB_BA1:STNRD | 4894 | X73226 | S.typhimurium nrdEF operon. | Salmonella typhimurium | 52,477 | 03-Mar.-1997 |
|  |  | GB_IN2:AF083412 | 1093 | AF083412 | Limnadia lenticulans elongation factor 1-alpha mRNA, partial cds. | Limnadia lenticulans | 43,750 | 29-Mar.-1999 |
|  |  | GB_PR3:HS24M15 | 134539 | Z94055 | Human DNA sequence from PAC 24M15 on chromosome 1. Contains tenascin-R (restnctin), EST. | Homo sapiens | 37,475 | 23-Nov.-1999 |
| rxa01095 | 857 | GB_IN2:ARU85702 | 1240 | U85702 | Anathix ralla elongation factor-1 alpha (EF-1a) gene, partial cds. | Anathix ralla | 37,319 | 16-Jul.-1997 |
|  |  | GB_BA1:MTCY01B2 | 35938 | Z95554 | Mycobacterium tuberculosis H37Rv complete genome; segment 72/162. | Mycobacterium tuberculosis | 43,243 | 17-Jun.-1998 |
|  |  | GB_HTG5:AC011632 | 175917 | AC011632 | Homo sapiens clone RP11-3N13, WORKING DRAFT SEQUENCE, 9 unordered pieces. | Homo sapiens | 36,471 | 19-Nov.-1999 |
|  |  | GB_HTG5:AC011632 | 175917 | AC011632 | Homo sapiens clone RP11-3N13, WORKING DRAFT SEQUENCE, 9 unordered pieces. | Homo sapiens | 36,836 | 19-Nov.99 |
| rxa01097 | 477 | GB_BA2:AF030405 | 774 | AF030405 | Corynebacterium glutamicum cyclase (hisF) gene, complete cds. | Corynebacterium glutamicum | 100,000 | 13-Nov.-1997 |
|  |  | GB_BA2:AF030405 | 774 | AF030405 | Corynebacterium glutamicum cyclase (hisF) gene, complete cds. | Corynebacterium glutamicum | 41,206 | 13-Nov.-1997 |
| rxa01098 | 897 | GB_BA2:AF030405 | 774 | AF030405 | Corynebacterium glutamicum cyclase (hisF) gene, complete cds. | Corynebacterium glutamicum | 97,933 | 13-Nov.-1997 |
|  |  | GB_BA1:MSGY223 | 42061 | AD000019 | Mycobacterium tuberculosis sequence from clone y223. | Mycobacterium tuberculosis | 40,972 | 10-Dec.-1996 |
|  |  | GB_BA1:MLCB1610 | 40055 | AL049913 | Mycobacterium leprae cosmid B1610. | Mycobacterium leprae | 61,366 | 27-Aug.-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa01100 | 861 | GB_BA2:AF051846 | 738 | AF051846 | *Corynebacterium glutamicum* phosphoribosylformimino-5-amino-1 phosphoribosyl-4-imidazolecarboxamide isomerase (hisA) gene, complete cds. | *Corynebacterium glutamicum* | 97,154 | 12-Mar-1998 |
|  |  | GB_BA2:AF060558 | 636 | AF060558 | *Corynebacterium glutamicum* glutamine amidotransferase (hisH) gene, complete cds. | *Corynebacterium glutamicum* | 95,455 | 29-Apr-1998 |
|  |  | GB_HTG1:HSDJ140A9 | 221755 | AL109917 | *Homo sapiens* chromosome 1 clone RP1-140A9, *** SEQUENCING IN PROGRESS ***, in unordered pieces. | *Homo sapiens* | 30,523 | 23-Nov-1999 |
| rxa01101 | 756 | GB_BA2:AF060558 | 636 | AF060558 | *Corynebacterium glutamicum* glutamine amidotransferase (hisH) gene, complete cds. | *Corynebacterium glutamicum* | 94,462 | 29-Apr-1998 |
|  |  | GB_BA1:SC4G6 | 36917 | AL096884 | *Streptomyces coelicolor* cosmid 4G6. | *Streptomyces coelicolor* A3(2) | 38,378 | 23-Jul-1999 |
|  |  | GB_BA1:STMHISOPA | 3981 | M31628 | S.coelicolor histidine biosynthesis operon encoding hisD, partial cds., and hisC, hisB, hisH, and hisA genes, complete cds. | *Streptomyces coelicolor* | 60,053 | 26-Apr-1993 |
| rxa01104 | 729 | GB_BA1:STMHISOPA | 3981 | M31628 | S.coelicolor histidine biosynthesis operon encoding hisD, partial cds., and hisO, hisB, hisH, and hisA genes, complete cds. | *Streptomyces coelicolor* | 58,333 | 26-Apr-1993 |
|  |  | GB_BA1:SC4G6 | 36917 | AL096884 | *Streptomyces coelicolor* cosmid 4G6. | *Streptomyces coelicolor* A3(2) | 39,045 | 23-Jul-1999 |
| rxa01105 | 1221 | GB_BA1:MTCY336 | 32437 | Z95586 | Mycobacterium tuberculosis H37Rv complete genome; segment 70/162. | *Mycobacterium tuberculosis* | 60,364 | 24-Jun-1999 |
|  |  | GB_BA1:MTCY336 | 32437 | Z95586 | Mycobacterium tuberculosis H37Rv complete genome; segment 70/162. | *Mycobacterium tuberculosis* | 60,931 | 24-Jun-1999 |
|  |  | GB_BA1:M5GY223 | 42061 | AD000019 | Mycobacterium tuberculosis sequence from clone y223. | *Mycobacterium tuberculosis* | 36,851 | 10-Dec-1996 |
|  |  | GB_BA1:MLCB1610 | 40055 | AL049913 | *Mycobacterium leprae* cosmid B1610. | *Mycobacterium leprae* | 60,902 | 27-Aug-1999 |
| rxa01106 | 1449 | GB_BA1:M5GY223 | 42061 | AD000019 | Mycobacterium tuberculosis sequence from clone y223. | *Mycobacterium tuberculosis* | 37,233 | 10-Dec-1996 |
|  |  | GB_BA1:MSHISCD | 2298 | X65542 | M.smegmatis genes hisD and hisC for histidinol dehydrogenase and histidinol-phosphate aminotransferase, respectively. | *Mycobacterium smegmatis* | 60,111 | 30-Jun-1993 |
| rxa01145 | 1137 | GB_BA1:MTCY336 | 32437 | Z95586 | Mycobacterium tuberculosis H37Rv complete genome; segment 70/162. | *Mycobacterium tuberculosis* | 58,420 | 24-Jun-1999 |
|  |  | GB_BA1:CORAIA | 4705 | L09232 | *Corynebacterium glutamicum* acetohydroxy acid synthase (ilvB) and (ilvN) genes, and acetohydroxy acid isomeroreductase (ilvC) gene, complete cds. | *Corynebacterium glutamicum* | 100,000 | 23-Feb-1995 |
|  |  | GB_BA1:BRLILVCA | 1364 | D14551 | *Brevibacterium flavum* ilvC gene for acetohydroxy acid isomeroreductase, complete ods. | *Corynebacterium glutamicum* | 99,560 | 3-Feb-1999 |
| rxa01162 | 1449 | GB_PAT:E08232 | 1017 | E08232 | DNA encoding acetohydroxy-acid isomeroreductase. | *Corynebacterium glutamicum* | 99,803 | 29-Sep-1997 |
|  |  | GB_PAT:A60299 | 2869 | A60299 | Sequence 18 from Patent WO9706261. | *Aspergillus niger* | 38,675 | 06-Mar-1998 |
|  |  | GB_PR3:H524E5 | 35506 | Z82185 | Human DNA sequence from Fosmid 24E5 on chromosome 22q11.2-qter contains parvalbumin, ESTs, STS. | *Homo sapiens* | 36,204 | 23-Nov-1999 |
| rxa01208 | 848 | GB_PR3:AC005265 | 43900 | AC005265 | *Homo sapiens* chromosome 19, cosmid F19750, complete sequence. | *Homo sapiens* | 38,363 | 6-Jul-1998 |
|  |  | GB_HTG2:AC004965 | 323792 | AC004965 | *Homo sapiens* clone DJ1 106H14, *** SEQUENCING IN PROGRESS ***, 42 unordered pieces. | *Homo sapiens* | 36,058 | 12-Jun-1998 |
|  |  | GB_HTG2:AC004965 | 323792 | AC004965 | *Homo sapiens* clone DJ1106H14, *** SEQUENCING IN PROGRESS ***, 42 unordered pieces. | *Homo sapiens* | 36,058 | 12-Jun-1998 |
| rxa01209 | 1528 | GB_PL2:TAU55859 | 2397 | U55859 | *Triticum aestivum* heat shock protein 80 mRNA, complete cds. | *Triticum aestivum* | 37,269 | 1-Feb-1999 |
|  |  | GB_HTG3:AC011469 | 113436 | AC011469 | *Homo sapiens* chromosome 19 clone CIT-HSPC 475D23, *** SEQUENCING IN PROGRESS ***, 31 unordered pieces. | *Homo sapiens* | 40000 | 07-Oct-1999 |
|  |  | GB_HTG3:AC011469 | 113436 | AC011469 | *Homo sapiens* chromosome 19 clone CIT-HSPC_475D23, *** SEQUENCING IN PROGRESS ***, 31 unordered pieces. | *Homo sapiens* | 40,000 | 07-Oct-1999 |
|  |  | GB_PL1:AB010077 | 77380 | AB010077 | *Arabidopsis thaliana* genomic DNA, chromosome 5, P1 clone: MYH19, complete sequence. | *Arabidopsis thaliana* | 36,803 | 20-Nov-1999 |
| rxa01215 | 1098 | GB_BA1:MTCY10G2 | 38970 | Z92539 | Mycobacterium tuberculosis H37Rv complete genome; segment 47/162. | *Mycobacterium tuberculosis* | 37,047 | 17-Jun-1998 |
|  |  | GB_IN1:LEIPRPP | 1887 | M76553 | Leishmania donovani phosphoribosylpyrophosphate synthetase gene, complete cds. | *Leishmania donovani* | 50,738 | 7-Jun-1993 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa01239 | 2558 | GB_HTG2:HSJ799D16 | 130149 | AL050344 | *Homo sapiens* chromosome 1 clone RP4-799D16 map p34.3-36.1, *** SEQUENCING IN PROGRESS ***, In unordered pieces. | *Homo sapiens* | 38,135 | 29-Nov-1999 |
|  |  | GB_BA1:MTCY48 | 35377 | Z74020 | Mycobacterium tuberculosis H37Rv complete genome; segment 69/162. | Mycobacterium tuberculosis | 38,139 | 17-Jun-1998 |
|  |  | GB_PR2:AB029032 | 8377 | AB029032 | *Homo sapiens* mRNA for KIAA1 109 protein, partial cds. | *Homo sapiens* | 39,394 | 4-Aug-1999 |
|  |  | GB_GSS9:AQ107201 | 355 | AQ107201 | HS_3098_A1_C03_T7 CIT Approved Human Genomic Sperm Library D *Homo sapiens* genomic clone Plate = 3098 Col = 5 Row = E, genomic survey sequence. | *Homo sapiens* | 41,408 | 28-Aug-1998 |
| rxa01253 | 873 | GB_PL2:F508 | 99923 | AC005990 | *Arabidopsis thaliana* chromosome 1 BAC P508 sequence, complete sequence. | *Arabidopsis thaliana* | 36,118 | 23-Dec-1998 |
|  |  | GB_PL2:F508 | 99923 | AC005990 | *Arabidopsis thaliana* chromosome 1 BAC F508 sequence, complete | *Arabidopsis thaliana* | 35,574 | 23-Dec-1998 |
| rxa01321 | 1044 | GB_IN1:CELCO6G1 | 31205 | U41014 | *Caenorhabditis elegans* cosmid CO6G1. | *Caenorhabditis elegans* | 38,560 | 30-Nov-1995 |
|  |  | GB_GSS14:AQ518843 | 441 | AQ518843 | HS_5106_A1_D10_SP6E RPCI-11 Human Male BAC Library *Home sapiens* genomic clone Plate = 682 Col = 19 Row = G, genomic survey sequence. | *Homo sapiens* | 41,121 | 05-May-1999 |
|  |  | GB_HTG2:AC007473 | 194859 | AC007473 | *Drosophila melanogaster* chromosome 2 clone BACR38D12 (D590) RPCI-98 38.D.12 map 48A-48B strain y; cn bw sp, **** SEQUENCING IN PROGRESS ****, 60 unordered pieces. | *Drosophila melanogaster* | 40,634 | 2-Aug-1999 |
|  |  | GB_HTG4:AC011696 | 115847 | AC011696 | *Drosophila melanogaster* chromosome 2 clone BACR35F01 (D1156) RPCI-98 35.F.1 map 48A-48C strain y; cn bw sp, SEQUENCING IN PROGRESS ***, 108 unordered pieces. | *Drosophila melanogaster* | 38,290 | 26-Oct-1999 |
| rxa01352 | 706 | GB_PL2:ATAC005167 | 83260 | AC005187 | *Arabidopsis thaliana* chromosome II BAC F12A24 genomic sequence, complete sequence. | *Arabidopsis thaliana* | 34,311 | 15-Oct-1998 |
|  |  | GB_PL2:ATAC005825 | 97380 | AC005825 | *Arabidopsis thaliana* chromosome II BAC T24121 genomic sequence. complete sequence. | *Arabidopsis thaliana* | 34,311 | 12-Apr-1999 |
| rxa01360 | 259 | GB_HTG3:AC011150 | 127222 | AC011150 | *Homo sapiens* clone 4_K_17, LOW-PASS SEQUENCE SAMPLING. | *Homo sapiens* | 37,722 | 01-Oct-1999 |
|  |  | GB_EST32:A1725583 | 728 | A1725583 | BNLGHI12371 Six-day Cotton fiber *Gossypium hirsutum* cDNA 5' similar to (U86081) root hair defective 3 [*Arabidopsis thaliana*], mRNA sequence. | *Gossypium hirsutum* | 38,492 | 11-Jun-1999 |
|  |  | GB_PR2:HS227P17 | 82951 | Z81007 | Human DNA sequence from PAC 227P17, between markers DX56791 andDXS8038 on chromosome X contains CpG island, EST. | *Homo sapiens* | 39,738 | 23-Nov-1999 |
|  |  | GB_EST34:AV171099 | 173 | AV171099 | AV171099 *Mus musculus* head C576L16J 14, 17 day embryo *Mus musculus* cDNA clone 3200002M11, mRNA sequence. | *Mus musculus* | 46,237 | 6-Jul-1999 |
| rxa01361 | 629 | GB_RO:AB008915S1 | 530 | AB008915 | *Mus musculus* mGpi1 gene, exon 1. | *Mus musculus* | 45,574 | 28-Sep-1999 |
|  |  | GB_EST22:AI050532 | 293 | AI050532 | uc83d10.y1 Sugano mouse kidney mkia *Mus musculus* cDNA clone IMAGE:1432243 5' similar to TR:O35120 O35120 MGPI1P.;, mRNA sequence. | *Mus musculus* | 44,097 | 9-Jul-1998 |
| rxa01381 | 3062 | GB_RO:AB008895 | 3062 | AB008895 | *Mus musculus* mRNA for mGpi1p, complete cds. | *Mus musculus* | 41,316 | 23-Nov-1997 |
|  | 944 | GB_PL1:AB005237 | 87835 | AB005237 | *Arabidopsis thaliana* genomic DNA, chromosome 5, P1 clone: MJJ3,complete sequence. | *Arabidopsis thaliana* | 36,606 | 20-Nov-1999 |
|  |  | GB_GSS5:AQ766840 | 491 | AQ766840 | HS_2026_A2_C09_T7C CIT Approved Human Genomic Sperm Library D *Homo sapiens* genomic clone Plate = 2026 Col = 18 Row = E, genomic survey sequence. | *Homo sapiens* | 37,916 | 28-Jul-1999 |
| rxa01393 | 68848 | GB_BA1:MTV043 | 68848 | AL022004 | Mycobacterium tuberculosis H37Rv complete genome; segment 40/162. | Mycobacterium tuberculosis | 37,419 | 24-Jun-1999 |
|  | 993 | GB_BA1:CGLYSEG | 2374 | X96471 | *C. glutamicum* lysE and lysG genes. | *Corynebacterium glutamicum* | 34,831 | 24-Feb-1997 |
|  |  | GB_BA1:SC5A7 | 40337 | AL031107 | *Streptomyces coelicolor* cosmid 5A7. | *Streptomyces coelicolor* | 35,138 | 27-Jul-1998 |
|  |  | GB_PR3:AC004054 | 112184 | AC004054 | *Homo sapiens* chromosome 4 clone B220G8 map 4q21, complete sequence. | *Homo sapiens* | 37,277 | 9-Jul-1998 |
| rxa01394 | 822 | GB_BA1:CGLYSEG | 2374 | X96471 | *C. glutamicum* lysE and lysG genes. | *Corynebacterium glutamicum* | 100,000 | 24-Feb-1997 |
|  |  | GB_GSS5:AQ769223 | 500 | AQ769223 | HS_3155_B2_G10_T7C CIT Approved Human Genomic Sperm Library D | *Homo sapiens* | 38,400 | 28-Jul-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| | | | | | Homo sapiens genomic clone Plate=3155 Col=20 Row=N, genomic survey sequence. | | | |
| rxa01416 | 630 | GB_BA1:CGLYSEG | 2374 | X96471 | C.glutamicum lysE and lysG genes. | Corynebacterium glutamicum | 33,665 | 24-Feb.-1997 |
| | | GB_BA1:SC3C3 | 31382 | AL031231 | Streptomyces coelicolor cosmid 3C3. | Streptomyces coelicolor | 62,726 | 10-Aug.-1998 |
| | | GB_BA1:MLCB22 | 40281 | Z98741 | Mycobacterium leprae cosmid B22. | Mycobacterium leprae | 39,159 | 22-Aug.-1997 |
| | | GB_BA1:MTV002 | 56414 | AL008967 | Mycobacterium tuberculosis H37Rv complete genome; segment 122/162. | Mycobacterium tuberculosis | 37,340 | 17-Jun.-1998 |
| rxa01442 | 1347 | GB_BA1:D90827 | 18886 | D90827 | E.coli genomic DNA, Kohara clone #336(41.2-41.6 min.). | Escherichia coli | 58,517 | 21-Mar.-1997 |
| | | GB_BA1:D90828 | 14590 | D90828 | E.coli genomic DNA, Kohara clone #336gap(41.6-41.9 min.). | Escherichia coli | 56,151 | 21-Mar.-1997 |
| | | GB_BA2:AE000279 | 10855 | AE000279 | Escherichia coli K-12 MG1655 section 169 of 400 of the complete genome. | Escherichia coli | 56,021 | 12-Nov.-1998 |
| rxa01446 | 1413 | GB_BA1:SCH10 | 39524 | AL049754 | Streptomyces coelicolor cosmid H10. | Streptomyces coelicolor | 39,037 | 04-May-1999 |
| | | GB_BA1:MTY13E10 | 35019 | Z95324 | Mycobacterium tuberculosis H37Rv complete genome: segment 18/162. | Mycobacterium tuberculosis | 40,130 | 17-Jun.-1998 |
| | | GB_BA1:MLCB4 | 36310 | AL023514 | Mycobacterium leprae cosmid B4. | Mycobacterium leprae | 37,752 | 27-Aug.-1999 |
| rxa01483 | 1395 | GB_BA1:MTCY98 | 31225 | Z83860 | Mycobacterium tuberculosis H37Rv complete genome; segment 103/162. | Mycobacterium tuberculosis | 39,057 | 17-Jun.-1998 |
| | | GB_BA1:MSGB_1229CS | 30670 | L78812 | Mycobacterium leprae cosmid B1229 DNA sequence. | Mycobacterium leprae | 54,382 | 15-Jun.-1996 |
| | | GB_BA2:AF027507 | 5168 | AF027507 | Mycobacterium smegmatis dGTPase (dgt), and pnuase (dnaG) genes, complete cds; tRNA-Asn gene, complete sequence. | Mycobacterium smegmatis | 52,941 | 16-Jan.-1998 |
| rxa01486 | 757 | GB_BA1:MTV002 | 58414 | AL008967 | Mycobacterium tuberculosis H37Rv complete genome; segment 122/162. | Mycobacterium tuberculosis | 40,941 | 17-Jun.-1998 |
| | | GB_BA1:MLCB22 | 40281 | Z98741 | Mycobacterium leprae cosmid B22. | Mycobacterium leprae | 38,451 | 22-Aug.-1997 |
| | | GB_BA1:SC3C3 | 31382 | AL031231 | Streptomyces coelicolor cosmid 3C3. | Streptomyces coelicolor | 61194 | 10-Aug.-1998 |
| rxa01489 | 1146 | GB_BA1:CORFADS | 1547 | D37967 | Corynebacterium ammoniagenes gene for FAD synthetase, complete cds. | Corynebacterium ammoniagenes | 58,021 | 8-Feb.-1999 |
| | | GB_BA1:MLCB22 | 40281 | Z98741 | Mycobacterium leprae cosmid 822. | Mycobacterium leprae | 38,414 | 22-Aug.-1997 |
| | | GB_BA1:SC10A7 | 39739 | AL078618 | Streptomyces coelicolor cosmid 10A7. | Streptomyces coelicolor | 36,930 | 9-Jun.-1999 |
| rxa01491 | 774 | GB_BA1:MTV002 | 56414 | AL008967 | Mycobacterium tuberculosis H37Rv complete genome; segment 122/162. | Mycobacterium tuberculosis | 37,062 | 17-Jun.-1998 |
| | | GB_EST13:AA356956 | 255 | AA356956 | EST65614 Jurkat T-cells III Homo sapiens cDNA 5 end, mRNA sequence. | Homo sapiens | 37,647 | 21-Apr.-1997 |
| | | GB_OV:OMDNAPROI | 7327 | X92380 | O.mossambicus prolactin I gene. | Tilapia mossambica | 38,289 | 19-Oct.-1995 |
| rxa01508 | 1662 | GB_IN1:CEF28C12 | 14653 | Z93380 | Caenorhabditis elegans cosmid F28C12, complete sequence. | Caenorhabditis elegans | 37,984 | 23-Nov.-1998 |
| | | GB_IN1:CEF28C12 | 14653 | Z93380 | Caenorhabditis elegans cosmid F28C12, complete sequence. | Caenorhabditis elegans | 38,469 | 23-Nov.-1998 |
| rxa01512 | 723 | GB_BA1:SCE9 | 37730 | AL049841 | Streptomyces coelicolor cosmid E9. | Streptomyces coelicolor | 39,021 | 19-May-1999 |
| | | GB_BA1:MAU88875 | 840 | U88875 | Mycobacterium avium hypoxanthine-guanine phosphoribosyl transferase gene, complete cds. | Mycobacterium avium | 57,521 | 05-Mar.-1997 |
| rxa01514 | 711 | GB_BA1:MTY15C10 | 33050 | Z95436 | Mycobacterium tuberculosis H37Rv complete genome; segment 154/162. | Mycobacterium tuberculosis | 40,086 | 17-Jun.-1998 |
| | | GB_BA1:MTCY7H7B | 24244 | Z95557 | Mycobacterium tuberculosis H37Rv complete genome; segment 153/162. | Mycobacterium tuberculosis | 43,343 | 18-Jun.-1998 |
| | | GB_BA1:MLCB2548 | 38916 | AL023093 | Mycobacterium leprae cosmid 82548. | Mycobacterium leprae | 38,177 | 27-Aug.-1999 |
| | | GB_PL1:EGGTPCHI | 242 | Z49757 | E.gracills mRNA for GTP cyclohydrolase I (core region). | Euglena gracilis | 64,876 | 20-Oct.-1995 |
| rxa01515 | 975 | GB_BA1:ECOUW93 | 338534 | U14003 | Escherichia coli K-12 chromosomal region from 92.8 to 00.1 minutes. | Escherichia coli | 38,943 | 17-Apr.-1996 |
| | | GB_BA1:ECOUW93 | 338534 | U14003 | Escherichia coli K-12 chromosomal region from 92.8 to 00.1 minutes. | Escherichia coli | 37,500 | 17-Apr.-1996 |
| | | GB_BA1:MTCY49 | 39430 | Z73966 | Mycobacterium tuberculosis H37Rv complete genome; segment 93/162. | Mycobacterium tuberculosis | 38,010 | 24-Jun.-1999 |
| rxa01516 | 513 | GB_IN1:DME238847 | 5419 | AJ238847 | Drosophila melanogaster mRNA for drosophila dodeca-satellite protein 1 (DDP-1). | Drosophila melanogaster | 36,346 | 13-Aug.-1999 |
| | | GB_HTG3:AC009210 | 103814 | AC009210 | Drosophila melanogaster chromosome 2 clone BACR01106 (D1054) RPCI-98 01.1.6 map 55D-55D strain y; cn bw sp, *** SEQUENCING IN PROGRESS ***, 86 unordered pieces. | Drosophila melanogaster | 37,897 | 20-Aug.-1999 |
| rxa01517 | 600 | GB_IN2:AF132179 | 4842 | AF132179 | Drosophila melanogaster clone LD21677 unknown mRNA. | Drosophila melanogaster | 36,149 | 3-Jun.-1999 |
| | | GB_PL2:F6H8 | 82596 | AF178045 | Arabidopsis thaliana SAC F6H8. | Arabidopsis thaliana | 35,846 | 19-Aug.-1999 |
| | | GB_PL2:AF038831 | 647 | AF038831 | Sorosporium saponariae internal transcribed spacer 1, 5.8 S ribosomal RNA gene, and internal transcribed spacer 2, complete sequence. | Sorosporium saponariae | 40,566 | 13-Apr.-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa01521 | | GB_PL2:ATAC005957 | 108355 | AC005957 | *Arabidopsis thaliana* chromosome II BAC T15I14 genomic sequence, complete sequence. | *Arabidopsis thaliana* | 38,095 | 7-Jan.-1999 |
| | 921 | GB_BA1:ANANIFBH | 5936 | J05111 | *Anabaena* sp. (clone AnH20.1) nitrogen fixation operon nifB, fdxN, nifS, nifU, and nifH genes, complete cds. | *Anabaena* sp. | 38,206 | 26-Apr.-1993 |
| | | GB_PR2:AC002461 | 197273 | AC002461 | Human BAC clone RG204|16 from 7q31, complete sequence. | *Homo sapiens* | 36,623 | 20-Aug.-1997 |
| | | GB_PR2:AC002461 | 197273 | AC002461 | Human BAC clone RG204|16 from 7q31, complete sequence. | *Homo sapiens* | 34,719 | 20-Aug.-1997 |
| rxa01528 | 651 | GB_RO:MM437P9 | 165901 | AL049866 | *Mus musculus* chromosome X, clone 437P9. | *Mus musculus* | 37,500 | 29-Jun.-1999 |
| | | GB_PR3:AC005740 | 186780 | AC005740 | *Homo sapiens* chromosome 5p, BAC clone 50g21 (LBNL H154) complete sequence. | *Homo sapiens* | 37,031 | 01-Oct.-1998 |
| | | GB_PR3:AC005740 | 186780 | AC005740 | *Homo sapiens* chromosome 5p, BAC clone 50g21 (LBNL H154), complete sequence. | *Homo sapiens* | 38,035 | 01-Oct.-1998 |
| rxa01551 | 1998 | GB_BA1:MTCY22G10 | 35420 | Z84724 | *Mycobacterium tuberculosis* H37Rv complete genome; segment 21/162. | *Mycobacterium tuberculosis* | 38,371 | 17-Jun.-1998 |
| | | GB_BA2:ECOUW89 | 176195 | U00006 | *E. coli* chromosomal region from 89.2 to 92.8 minutes. | *Escherichia coli* | 38,064 | 17-Dec.-1993 |
| | | GB_BA1:SCQ11 | 15441 | AL096823 | *Streptomyces coelicolor* cosmid Q11. | *Streptomyces coelicolor* | 60,775 | 8-Jul.-1999 |
| rxa01561 | 1053 | GB_IN1:CEY62H9A | 47396 | AL032630 | *Caenorhabditis elegans* cosmid Y62H9A, complete sequence. | *Caenorhabditis elegans* | 38,514 | 2-Sep.-1999 |
| | | GB_PR4:HSU51003 | 3202 | U51003 | *Homo sapiens* DLX-2 (DLX-2) gene, complete cds. | *Homo sapiens* | 37,730 | 07-Dec.-1999 |
| | | GB_OM:PIGDAO1 | 395 | M18444 | Pig D-amino acid oxidase (DAO) gene, exon 1. | *Sus scrofa* | 39,340 | 27-Apr.-1993 |
| rxa01599 | 1785 | GB_BA1:MTCI125 | 37432 | Z98268 | *Mycobacterium tuberculosis* H37Rv complete genome; segment 76/162. | *Mycobacterium tuberculosis* | 63,300 | 17-Jun.-1998 |
| | | GB_BA1:U00021 | 39193 | U00021 | *Mycobacterium leprae* cosmid L247. | *Mycobacterium leprae* | 36,756 | 29-Sep.-1994 |
| | | GB_BA1:MLCB1351 | 38936 | Z95117 | *Mycobacterium leprae* cosmid B1351. | *Mycobacterium leprae* | 36,756 | 24-Jun.-1997 |
| rxa01617 | 795 | GB_PR2:HSMTM0 | 217657 | AL034384 | Human chromosome Xq28, cosmid clones 7H3, 14D7, C1230, 11E7, F1096, A12197, 12G8, A09100; complete sequence bases 1..217657. | *Homo sapiens* | 40,811 | 5-Jul.-1999 |
| | | GB_PR2:HS13D10 | 153147 | AL021407 | *Homo sapiens* DNA sequence from PAC 13D10 on chromosome 6p22.3-23. Contains CpG island. | *Homo sapiens* | 38,768 | 23-Nov.-1999 |
| | | GB_PR2:HSMTM0 | 217657 | AL034384 | Human chromosome Xq28, cosmid clones 7H3, 14D7, C1230, 11E7, F1096, A12197, 12G8, A09100; complete sequence bases 1..217657. | *Homo sapiens* | 39,018 | 5-Jul.-1999 |
| rxa01657 | 723 | GB_BA1:MTCY1A10 | 25949 | Z95387 | *Mycobacterium tuberculosis* H37Rv complete genome; segment 117/162. | *Mycobacterium tuberculosis* | 40,656 | 17-Jun.-1998 |
| | | GB_EST6:D79278 | 392 | D79278 | HUM213DO6B Human aorta polyA+ (TFujiwara) *Homo sapiens* cDNA clone GEN-213D06 5', mRNA sequence. | *Homo sapiens* | 44,262 | 9-Feb.-1996 |
| rxa01660 | | GB_BA2:AF129925 | 10243 | AF129925 | *Thiobacillus ferrooxidans* carboxysome operon, complete cds. | *Thiobacillus ferrooxidans* | 40,709 | 17-May-1999 |
| | 675 | GB_BA1:MTV013 | 11364 | AL021309 | *Mycobacterium tuberculosis* H37Rv complete genome; segment 134/162. | *Mycobacterium tuberculosis* | 40,986 | 17-Jun.-1998 |
| | | GB_RO:MMFVI | 6480 | X97719 | *M.musculus* retrovirus restriction gene Fv1. | *Mus musculus* | 35,364 | 29-Aug.-1996 |
| | | GB_PAT:A67508 | 6480 | A67508 | Sequence 1 from Patent W09743410. | *Mus musculus* | 35,364 | 05-May-1999 |
| rxa01678 | 651 | GB_VI:TVU95309 | 600 | U95309 | Tula virus O64 nucleocapsid protein gene, partial cds. | Tula virus | 41,894 | 28-Oct.-1997 |
| | | GB_VI:TVU95303 | 600 | U95303 | Tula virus O52 nucleocapsid protein gene, partial cds. | Tula virus | 41,712 | 28-Oct.-1997 |
| | | GB_VI:TVU95302 | 600 | U95302 | Tula virus O24 nucleocapsid protein gene, partial cds. | Tula virus | 39,576 | 26-Oct.-1997 |
| rxa01679 | 1359 | GB_EST5:H91843 | 362 | H91843 | ys81e01.s1 Soares retina N2b4HR *Homo sapiens* cDNA clone IMAGE:221208 3' similar to gb:X63749_mal GUANINE NUCLEOTIDE-BINDING PROTEIN G(T), ALPHA-1 (HUMAN); mRNA sequence. | *Homo sapiens* | 39,157 | 29-Nov.-1995 |
| | | GB_STS:G26925 | 362 | G26925 | human STS SHGC-30023, sequence tagged site. | *Homo sapiens* | 39,157 | 14-Jun.-1996 |
| | | GB_PL2:AF139451 | 1202 | AF139451 | *Gossypium robinsonii* CelA2 pseudogene, partial sequence. | *Gossypium robinsonii* | 38,910 | 1-Jun.-1999 |
| rxa01690 | 1224 | GB_BA1:SC1C2 | 42210 | AL031124 | *Streptomyces coelicolor* cosmid 1C2. | *Streptomyces coelicolor* | 60,644 | 15-Jan.-1999 |
| | | GB_EST22:A1064232 | 493 | A1064232 | GH04563.5prime GH *Drosophila melanogaster* head pOT2 *Drosophila melanogaster* cDNA clone GH04563 5prime, mRNA sequence. | *Drosophila melanogaster* | 38,037 | 24-Nov.-1998 |
| rxa01692 | 1020 | GB_IN2:AF117896 | 1020 | AF117896 | *Drosophila melanogaster* neuropeptide F (npf) gene, complete cds. | *Drosophila melanogaster* | 36,122 | 2-Jul.-1999 |
| | | GB_BA2:AF067123 | 1034 | AF067123 | *Lactobacillus reuteri* cobalamin biosynthesis protein J (cbiJ) gene, partial cds; and uroporphyrin-III C-methyltransferase (sumT) gene, complete cds. | *Lactobacillus reuteri* | 48,079 | 3-Jun.-1998 |

TABLE 4-continued

ALIGNMENT RESULTS

| ID # | length (NT) | Genbank Hit | Accession | Name of Genbank Hit | Source of Genbank Hit | % homology (GAP) | Date of Deposit |
|---|---|---|---|---|---|---|---|
| rxa01698 | 1353 | GB_RO:RATNFHPEP | M37227 | Rat heavy neurofilament (NF-H) polypeptide, partial cds. | Rattus norvegicus | 37,093 | 27-Apr-1993 |
| | | GB_RO:RSNFH | X13804 | Rat mRNA for heavy neurofilament polypeptide NF-H C-terminus. | Rattus sp. | 37,093 | 14-Jul-1995 |
| | | GB_8A2:AF124600 | AF124600 | Corynebacterium glutamicum chorismate synthase (aroC), shikimate kinase (aroK), and 3-dehydroquinate synthase (aroB) genes, complete cds; and putative cytoplasmic peptidase (pepQ) gene, partial cds. | Corynebacterium glutamicum | 100,000 | 04-May-1999 |
| rxa01699 | 693 | GB_BA1:MTCY159 | Z83863 | Mycobacterium tuberculosis H37Rv complete genome; segment 111/162. | Mycobacterium tuberculosis | 36,323 | 17-Jun-1998 |
| | | GB_BA1:MSGB937CS | L78820 | Mycobacterium leprae cosmid B937 DNA sequence. | Mycobacterium leprae | 62,780 | 15-Jun-1996 |
| | | GB_BA2:AF124600 | AF124600 | Corynebacterium glutamicum chorismate synthase (aroC), shikimate kinase (aroK), and 3-dehydroquinate synthase (aroB) genes, complete cds; and putative cytoplasmic peptidase (pepQ) gene, partial cds. | Corynebacterium glutamicum | 100,000 | 04-May-1999 |
| | | GB_BA2:AF016585 | AF016585 | Streptomyces caelestis cytochrome P-450 hydroxylase homolog (nidi) gene, partial cds; polyketide synthase modules 1 through 7 (nidA) genes, complete cds; and N-methyltransferase homolog gene, partial cds. | Streptomyces caelestis | 40,260 | 07-Dec-1997 |
| | | GB_EST9:C19712 | C19712 | Rice panicle at ripening stage Oryza sativa cDNA clone E10821_1A, mRNA sequence. | Oryza sativa | 45,425 | 24-Oct-1996 |
| rxa01712 | 805 | GB_EST21:M952466 | AA952466 | TENS1404 T. cruzi epimastigote normalized cDNA Library Trypanosoma cruzi cDNA clone 1404 5', mRNA sequence. | Trypanosoma cruzi | 40,876 | 29-Oct-1998 |
| | | GB_EST21:M952466 | AA952466 | TENS1404 T. cruzi epimastigote normalized cDNA Library Trypanosoma cruzi cDNA clone 1404 5', mRNA sequence. | Trypanosoma cruzi | 41,367 | 29-Oct-1998 |
| rxa01719 | 684 | GB_HTG1:HSDJ534K7 | AL109925 | Homo sapiens chromosome 1 clone RP4-534K7, *** SEQUENCING IN PROGRESS ***, in unordered pieces. | Homo sapiens | 35,651 | 23-Nov-1999 |
| | | GB_HTG1:HSDJ534K7 | AL109925 | Homo sapiens chromosome 1 clone RP4-534K7, *** SEQUENCING IN PROGRESS ***, in unordered pieces. | Homo sapiens | 35651 | 23-Nov-1999 |
| | | GB_EST27:AI447108 | AI447108 | mq91e08.x1 Stratagene mouse heart (#937316) Mus musculus cDNA clone IMAGE:586118 3', mRNA sequence. | Mus musculus | 39,671 | 09-Mar-1999 |
| rxa01720 | 1332 | GB_PR4:AC006322 | AC006322 | Homo sapiens PAC clone DJ1060B11 from 7q11.23-q21.1, complete sequence. | Homo sapiens | 35,817 | 18-Mar-1999 |
| | | GB_PL2:TM018A10 | AF013294 | Arabidopsis thaliana BAC TM018A10. | Arabidopsis thaliana | 35,698 | 12-Jul-1997 |
| | | GB_PR4:AC006322 | AC006322 | Homo sapiens PAC clone DJ106OB11 from 7q11.23-q21.1, complete sequence. | Homo sapiens | 37,243 | 18-Mar-1999 |
| rxa01746 | 876 | GB_EST3:R46227 | R46227 | yg52a03.s1 Soares infant brain 1NIB Homo sapiens cDNA clone IMAGE:36000 3', mRNA sequence. | Homo sapiens | 42,812 | 22-May-1995 |
| | | GB_EST3:R46227 | R46227 | yg52a03.s1 Soares infant brain 1NIB Homo sapiens cDNA clone IMAGE:36000 3', mRNA sequence. | Homo sapiens | 42,655 | 22-May-1995 |
| rxa01747 | 1167 | GB_BA1:MTCY190 | Z70283 | Mycobacterium tuberculosis H37Rv complete genome; segment 98/162. | Mycobacterium tuberculosis | 59,294 | 17-Jun-1998 |
| | | GB_BA1:MLCB22 | Z98741 | Mycobacterium leprae cosmid B22. | Mycobacterium leprae | 57,584 | 22-Aug-1997 |
| | | GB_BA1:SC5F7 | AL096872 | Streptomyces coelicolor cosmid 5F7. | Streptomyces coelicolor A3(2) | 61,810 | 22-Jul-1999 |
| rxa01757 | 924 | GB_EST21:AA918454 | AA918454 | om38c02.s1 Soares NFL_T_GBC_S1 Homo sapiens cDNA clone IMAGE1543298 3'similar to WP:F28F8.3 CE09757 SMALL NUCLEAR RIBONUCLEOPROTEIN E:, mRNA sequence. | Homo sapiens | 39,655 | 23-Jun-1998 |
| | | GB_EST4:H34042 | H34042 | EST110563 Rat PC-12 cells, NGF-treated (9 days) Rattus sp. cDNA clone RPNB181 5' end, mRNA sequence. | Rattus sp. | 35,942 | 2-Apr-1998 |
| | | GB_EST20:M899038 | AA899038 | NCP6G8T7 Perithecial Neurospora crassa cDNA clone NP6G8 3' end, mRNA sequence. | Neurospora crassa | 40,000 | 12-Apr-1998 |
| rxa01807 | 915 | GB_BA1:AP000063 | AP000063 | Aeropyrum pernix genomic DNA, section 6/7. | Aeropyrum pernix | 40,067 | 22-Jun-1999 |
| | | GB_HTG4:AC010694 | AC010694 | Drosophila melanogaster clone RPCI98-6H2, *** SEQUENCING IN PROGRESS ***, 75 unordered pieces. | Drosophila melanogaster | 35,450 | 16-Oct-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa01821 | | GB_HTG4:AC010694 | 115857 | AC010694 | *Drosophila melanogaster* clone RPCI98-6H2, *** SEQUENCING IN PROGRESS ***, 75 unordered pieces. | *Drosophila melanogaster* | 35,450 | 16-Oct-1999 |
| | 401 | GB_BA1:CGL007732 | 4460 | AJ007732 | *Corynebacterium glutamicum* 3' ppc gene, secG gene, amt gene, ocd gene and 5' soxA gene. | *Corynebacterium glutamicum* | 100,000 | 7-Jan-1999 |
| | | GB_RO:RATATLGL | 7601 | M24108 | *Rattus norvegicus* (clone A2U42) alpha2u globulin gene, exons 1-7. | *Rattus norvegicus* | 38,692 | 15-Dec-1994 |
| | | GB_OV:APIGY2 | 1381 | X78272 | *Anas platyrhynchos* (Super M) IgY upsilon heavy chain gene, exon 2. | *Anas platyrhynchos* | 36,962 | 15-Feb-1999 |
| rxa01835 | 654 | GB_EST30:A1629479 | 353 | A1629479 | 486101D10.x1 486- leaf pilmordia cDNA library from Hake lab *Zea mays* cDNA, mRNA sequence. | *Zea mays* | 38,109 | 26-Apr-1999 |
| | | GB_STS:G48245 | 515 | G48245 | SHGC-6915 Human *Homo sapiens* STS genomic, sequence tagged site. | *Homo sapiens* | 37,021 | 26-Mar-1999 |
| | | GB_GSS3:B49052 | 515 | B49052 | RPCI11-4I12.TV RPCI-11 *Homo sapiens* genomic clone RPCI-11-4I12, genomic survey sequence. | *Homo sapiens* | 37,021 | 8-Apr-1999 |
| rxa01850 | 1470 | GB_BA2:ECOUW67_0 | 110000 | U18997 | *Escherichia coli* K-12 chromosomal region from 67.4 to 76.0 minutes. | *Escherichia coli* | 37,196 | U18997 |
| | | GB_BA2:AF000392 | 10345 | AE000392 | *Escherichia coli* K-12 MG1655 section 282 of 400 of the complete genome. | *Escherichia coli* | 38,021 | 12-Nov-1998 |
| | | GB_BA2:U32715 | 13136 | U32715 | *Haemophilus influenzae* Rd section 30 of 163 of the complete genome. | *Haemophilus influenzae* Rd | 39,860 | 29-May-1998 |
| rxa01878 | 1002 | GB_HTG1:CEY64F11 | 177748 | Z99776 | *Caenorhabditis elegans* chromosome IV clone Y64F11, *** SEQUENCING IN PROGRESS ***, in unordered pieces. | *Caenorhabditis elegans* | 37,564 | 14-Oct-1998 |
| | | GB_HTG1:CEYB4F11 | 177748 | Z99776 | *Caenorhabditis elegans* chromosome IV clone Y64F11, *** SEQUENCING IN PROGRESS ***, in unordered pieces. | *Caenorhabditis elegans* | 37,564 | 14-Oct-1998 |
| | | GB_HTG1:CEY64F11 | 177748 | Z99776 | *Caenorhabditis elegans* chromosome IV clone Y64F11, *** SEQUENCING IN PROGRESS ***, in unordered pieces. | *Caenorhabditis elegans* | 37,576 | 14-Oct-1998 |
| rxa01892 | 852 | GB_BA1:MTCY274 | 39991 | Z74024 | *Mycobacterium tuberculosis* H37Rv complete genome; segment 126/162. | *Mycobacterium tuberculosis* | 35,910 | 19-Jun-1998 |
| | | GB_BA1:MLCB250 | 40603 | Z97369 | *Mycobacterium leprae* cosmid B250. | *Mycobacterium leprae* | 64,260 | 27-Aug-1999 |
| | | GB_BA1:MSGB1529CS | 36985 | L78824 | *Mycobacterium leprae* cosmid Bi 529 DNA sequence. | *Mycobacterium leprae* | 64,260 | 15-Jun-1996 |
| rxa01894 | 978 | GB_BA1:MTCY274 | 39991 | Z74024 | *Mycobacterium tuberculosis* H37Rv complete genome; segment 126/162. | *Mycobacterium tuberculosis* | 37,229 | 19-Jun-1998 |
| | | GB_IN1:CELF46H5 | 38886 | U41543 | *Caenorhabditis elegans* cosmid F46H5. | *Caenorhabditis elegans* | 38,525 | 29-Nov-1996 |
| | | GB_HTG3:AC009204 | 115633 | AC009204 | *Drosophila melanogaster* chromosome 2 clone BACRO3E19 (D1033) RPCI-98 03.E.19 map 36E-37C strain y; cn bw sp, *** SEQUENCING IN PROGRESS ***, 94 unordered pieces. | *Drosophila melanogaster* | 31,579 | 18-Aug-1999 |
| rxa01920 | 1125 | GB_BA2:AF112536 | 1798 | AF112536 | *Corynebacterium glutamicum* ribonucleotide reductase beta-chain (nrdF) gene, complete cds. | *Corynebacterium glutamicum* | 99,733 | 5-Aug-1999 |
| | | GB_BA1:CANRDFGEN | 6054 | Y09572 | *Corynebacterium ammoniagenes* nrdH, nrdI, nrdE, nrdF genes. | *Corynebacterium ammoniagenes* | 70,321 | 18-Apr-1998 |
| | | GB_BA2:AF050168 | 1228 | AF050168 | *Corynebacterium ammoniagenes* ribonucleoside diphosphate reductase small subunit (nrdF) gene, complete cds. | *Corynebacterium ammoniagenes* | 72,082 | 23-Apr-1998 |
| rxa01928 | 960 | GB_BA1:CGPAN | 2164 | X96580 | *C.glutamicum* panD, panC &xyIB genes. | *Corynebacterium glutamicum* | 100,000 | 11-May-1999 |
| | | GB_PL1:AP000423 | 154478 | AP000423 | *Arabidopsis thaliana* chloroplast genomic DNA, complete sequence, strain:Columbia. | Chloroplast *Arabidopsis thaliana* | 35,917 | 15-Sep-1999 |
| | | GB_PL1:AP000423 | 154478 | AP000423 | *Arabidopsis thaliana* chloroplast genomic DNA, complete sequence, strain:Columbia. | Chloroplast *Arabidopsis thaliana* | 33,925 | 15-Sep-1999 |
| rxa01929 | 938 | GB_BA1:CGPAN | 2164 | X96580 | *C.glutamicum* panB, panC &xyIB genes. | *Corynebacterium glutamicum* | 100,0001 | 1-May-1999 |
| | | GB_BA1:XCU33548 | 8429 | U33548 | *Xanthomonas campestris* hrpB pathogenicity locus proteins HrpBI, HrpB2, HrpB3, HrpB4, HrpB5, HrpB6, HrpB7, HrpB8, HpAI, and ORF62 genes, complete cds. | *Xanthomonas campestris* pv. vesicatona | 38,749 | 19-Sep-1996 |
| rxa01940 | 1059 | GB_BA1:XANHRPB6A | 1329 | M99174 | *Xanthomonas campestris* hrpB6 gene, complete cds. | *Xanthomonas campestris* | 39,305 | 14-Sep-1993 |
| | | GB_IN2:CFU43371 | 1060 | U43371 | *Crithidia fasciculata* inosine-undine preferring nucleoside hydrolase (IUNH) gene, complete cds. | *Crithidia fasciculata* | 61,417 | 18-Jun-1996 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa02022 | | GB_BA2:AE001467 | 11601 | AE001467 | Helicobacter pylori, strain J99 section 28 of 132 of the complete genome. | Helicobacter pylori J99 | 38,560 | 20-Jan.-1999 |
| | | GB_RO:AF175967 | 3492 | AF175967 | Homo sapiens Leman coiled-coil protein (LCCP) mRNA, complete cds. | Mus musculus | 40,275 | 26-Sep.-1999 |
| | 1230 | GB_BA1:CGDAPE | 1966 | X81379 | C.glutamicum dapE gene and orf2. | Corynebacterium glutamicum | 100,000 | 8-Aug.-1995 |
| | | GB_BA1:CGDNMROP | 2612 | X85965 | C.glutamicum ORF3 and aroP gene. | Corynebacterium glutamicum | 38,889 | 30-Nov.-1997 |
| | | GB_BA1:APU47055 | 6469 | U47055 | Anabaena PCC7120 nitrogen fixation proteins (nifE, nifN, nifX, nifW) genes, complete cds, and nitrogenase (nifK) and hesA genes, partial cds. | Anabaena PCC7120 | 36,647 | 17-Feb.-1996 |
| rxa02024 | 859 | GB_BA1:MTCI364 | 29540 | Z93777 | Mycobacterium tuberculosis H37Rv complete genome; segment 52/162. | Mycobacterium tuberculosis | 59,415 | 17-Jun.-1998 |
| | | GB_BA1:MSGB_1912CS | 38503 | L01536 | M. leprae genomic dna sequence, cosmid b1912. | Mycobacterium leprae | 57,093 | 14-Jun.-1996 |
| rxa02027 nca02031 | | GB_BA1:MLU15180 | 38675 | U15180 | Mycobacterium leprae cosmid B1756. | Mycobacterium leprae | 57,210 | 09-Mar.-1995 |
| rxa02072 | 1464 | GB_BA1:CGGDHA | 2037 | X72855 | C. glutamicum GDHA gene. | Corynebacterium glutamicum | 99,317 | 24-May-1993 |
| | | GB_BA1:CGGDH | 2037 | X59404 | Corynebacterium glutamicum , gdh gen for glutamate dehydrogenase. | Corynebacterium glutamicum | 94,387 | 30-Jul.-1999 |
| | | GB_BA1:PAE18494 | 1628 | Y18494 | Pseudomonas aeruginosa gdhA gene, strain PAC1. | Pseudomonas aeruginosa | 62,247 | 6-Feb.-1999 |
| rxa02085 | 2358 | GB_BA1:MTCY22G8 | 22550 | Z95585 | Mycobacterium tuberculosis H37Rv complete genome: segment 49/162. | Mycobacterium tuberculosis | 38,442 | 17-Jun.-1998 |
| | | GB_BA1:MLCB33 | 42224 | Z94723 | Mycobacterium leprae cosmid B33. | Mycobacterium leprae | 56,486 | 24-Jun.-1997 |
| | | GB_BA1:ECOUW85 | 91414 | M87049 | E. coli genomic sequence of the region from 84.5 to 86.5 minutes. | Escherichia coli | 52,127 | 29-May-1995 |
| rxa02093 | 927 | GB_EST14:M448146 | 452 | AA448146 | zw82h01.r1 Soares_testis_NHT Homo sapiens cDNA clone IMAGE:782737 5′, mRNA sequence. | Homo sapiens | 34,163 | 4-Jun.-1997 |
| | | GB_EST17:M641937 | 444 | AA641937 | ns18b10.r1 NCI_CGAPG_CB1 Homo sapiens cDNA clone IMAGE:1 183963 5′, mRNA sequence. | Homo sapiens | 35,586 | 27-Oct.1997 |
| rxa02106 | 1179 | GB_PR3:AC003074 | 143029 | AC003074 | Human PAC clone DJ0596009 from 7p15, complete sequence. | Homo sapiens | 31,917 | 6-Nov.-1997 |
| | | GB_BA1:SC1A6 | 37620 | AL023496 | Streptomyces coelicolor cosmid 1A6. | Streptomyces coelicolor | 35,818 | 13-Jan.-1999 |
| | | GB_PR4:AC005553 | 179651 | AC005553 | Homo sapiens chromosome 17, clone hRPK.112_J_9, complete sequence. | Homo sapiens | 34,274 | 31-Dec.-1998 |
| | | GB_EST3:R49746 | 397 | R49746 | yg71g10.r1 Soares infant brain 1NIB Homo sapiens cDNA clone IMAGE:38768 5′ similar to gb:V00567 BETA-2-MICROGLOBULIN PRECURSOR (HUMAN); mRNA sequence. | Homo sapiens | 41,162 | 18-May-1995 |
| rxa02111 | 1407 | GB_BA1:SC6G10 | 36734 | AL049497 | Streptomyces coelicolor cosmid 6G10. | Streptomyces coelicolor | 50,791 | 24-Mar.-1999 |
| | | GB_BA1:U00010 | 41171 | U00010 | Mycobacterium leprae cosmid B1170. | Mycobacterium leprae | 37,563 | 01-Mar.-1994 |
| | | GB_BA1:MTCY336 | 32437 | Z95586 | Mycobacterium tuberculosis H37Rv complete genome; segment 70/162. | Mycobacterium tuberculosis | 39,504 | 24-Jun.-1996 |
| rxa02112 | 960 | GB_HTG3:AC010579 | 157658 | AC010579 | Drosophila melanogaster chromosome 3 clone BACR09D08 (D1101) RPCI-98 09.D.8 map 96F-96F strain y; cn bw sp, *** SEQUENCING IN PROGRESS ***, 121 unordered pieces. | Drosophila melanogaster | 37,909 | 24-Sep.-1999 |
| | | GB_GSS3:B09839 | 1191 | B09839 | T12A12-Sp6 TAMU Arabidopsis thaliana genomic clone T12A12, genomic survey sequence. | Arabidopsis thaliana | 37,843 | 14-May-1997 |
| | | GB_HTG3:AC010579 | 157658 | AC010579 | Drosophila melanogaster chromosome 3 clone BACR09D08 (D1101) RPCI-98 09.D.8 map 96F-1996F strain y; cn bw sp, *** SEQUENCING IN PROGRESS ***, 121 unordered pieces. | Drosophila melanogaster | 37,909 | 24-Sep.-1999 |
| rxa02134 | 1044 | GB_BA1:SCSECYDNA | 6154 | X83011 | S.coelicolor secY locus DNA. | Streptomyces coelicolor | 36,533 | 02-Mar.-1998 |
| | | GB_EST32:AI731596 | 568 | AI731596 | BNLGH10185 Six-day Cotton fiber Gossypium hirsutum cDNA 5′ similar to (AC004005) putative ribosomal protein L7 [Arabidopsis thaliana], mRNA sequence. | Gossypium hirsutum | 33,451 | 11-Jun.-1999 |
| rxa02135 | 1197 | GB_BA1:SCSECYDNA | 6154 | X83011 | S.coelicolor secY locus DNA. | Streptomyces coelicolor | 36,756 | 02-Mar.-1998 |
| | | GB_PR3:HS525L6 | 168111 | AL023807 | Human DNA sequence from clone RP3-525L6 on chromosome 6p22.3-23 Contains CA repeat, STSs, GSSs and a CpG Island, complete sequence. | Homo sapiens | 34,365 | 23-Nov.-1999 |
| | | GB_PL2:ATF21P8 | 85785 | AL022347 | Arabidopsis thaliana DNA chromosome 4, BAC clone F21P8 (ESSA project). | Arabidopsis thaliana | 34,325 | 9-Jun.-1999 |
| | | GB_PL2:U89959 | 106973 | U89959 | Arabidopsis thaliana BAC T7123, complete sequence. | Arabidopsis thaliana | 33,874 | 26-Jun.-1998 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa02136 | 645 | GB_PL2:ATAC005819 | 57752 | AC005819 | *Arabidopsis thaliana* chromosome II BAC T3A4 genomic sequence, complete sequence. | *Arabidopsis thaliana* | 34,123 | 3-Nov.-1998 |
|  |  | GB_PL2:F15K9 | 71097 | AC005278 | *Arabidopsis thaliana* chromosome 1 BAC F15K9 sequence, complete sequence. | *Arabidopsis thaliana* | 31,260 | 7-Nov.-1998 |
| rxa02139 | 1962 | GB_PL2:U89959 | 106973 | U89959 | *Arabidopsis thaliana* BAC T7123, complete sequence. | *Arabidopsis thaliana* | 34,281 | 26-Jun.-1998 |
|  |  | GB_BA1:MTCY190 | 34150 | Z70283 | *Mycobacterium tuberculosis* H37Rv complete genome; segment 98/162. | *Mycobacterium tuberculosis* | 62,904 | 17-Jun.-1998 |
|  |  | GBBA1:MSGB_1554CS | 36648 | L78814 | *Mycobacterium leprae* cosmid 51554 DNA sequence. | *Mycobacterium leprae* | 36,648 | 15-Jun.-1996 |
|  |  | GBBA1:MSGB_1551CS | 36648 | L78813 | *Mycobacterium leprae* cosmid B1551 DNA sequence. | *Mycobacterium leprae* | 36,648 | 15-Jun.-1996 |
| rxa02153 | 903 | GB_BA2:AF049897 | 9196 | AF049897 | *Corynebacterium glutamicum* N-acetylglutamylphosphate reductase (argC), ornithine acetyltransferase (argJ), N-acetylglutamate kinase (argB), acetylornithine transaminase (argD), ornithine carbamoyltransferase (argF), arginine repressor (argR), argininosuccinate synthase (argG), and argininosuccinate lyase (argH) genes, complete cds. | *Corynebacterium glutamicum* | 99,104 | 1-Jul.-1998 |
| rxa02154 | 1044 | GB_BA1:AF005242 | 1044 | AF005242 | *Corynebacterium glutamicum* N-acetylglutamate-5-semialdehyde dehydrogenase (argC) gene, complete cds. | *Corynebacterium glutamicum* | 99,224 | 2-Jul.-1997 |
|  | 414 | GB_BA1:CGARGCJBD | 4355 | X86157 | C.glutamicum argC, argJ, argB, argD, and argF genes. | *Corynebacterium glutamicum* | 100,000 | 25-Jul.-1996 |
|  |  | GB_BA2:AF049897 | 9196 | AF049897 | *Corynebacterium glutamicum* N-acetylglutamylphosphate reductase (argC), ornithine acetyltransferase (argJ), N-acetylglutamate kinase (argB), acetylornithine transaminase (argD), ornithine carbamoyltransferase (argF), arginine repressor (argR), argininosuccinate synthase (argG), and argininosuccinate lyase (argH) genes, complete cds. | *Corynebacterium glutamicum* | 98,551 | 1-Jul.-1998 |
| rxa02155 | 1287 | GB_BA1:AF005242 | 1044 | AF005242 | *Corynebacterium glutamicum* N-acetylglutamate-5-semialdehyde dehydrogenase (argC) gene, complete cds. | *Corynebacterium glutamicum* | 98,477 | 2-Jul.-1997 |
|  |  | GB_BA1:CGARGCJBD | 4355 | X86157 | C.glutamicum argC, argJ, argB, argD, and argF genes. | *Corynebacterium glutamicum* | 100,000 | 25-Jul.-1996 |
|  |  | GB_BA1:CGARGCJBD | 4355 | X86157 | C.glutamicum argC, argJ, argB, argD, and argF genes. | *Corynebacterium glutamicum* | 99,767 | 25-Jul.-1996 |
|  |  | GB_BA2:AF049897 | 9196 | AF049897 | *Corynebacterium glutamicum* N-acetylglutamylphosphate reductase (argC), ornithine acetyltransferase (argJ), N-acetylglutamate kinase (argS), acetylornithine transaminase (argD), ornithine carbamoyltransferase (argF), arginine repressor (argR), argininosuccinate synthase (argG), and argininosuccinate lyase (argH) genes, complete cds. | *Corynebacterium glutamicum* | 99,378 | 1-Jul.-1998 |
| rxa02156 | 1074 | GB_BA1:MSGB1133CS | 42106 | L78811 | *Mycobacterium leprae* cosmid Bi 133 DNA sequence. | *Mycobacterium leprae* | 55,504 | 15-Jun.-1996 |
|  |  | GB_BA2:AF049897 | 9196 | AF049897 | *Corynebacterium glutamicum* N-acetylglutamylphosphate reductase (argC), ornithine acetyltransferase (argJ), N-acetylglutamate kinase (argB), acetylornithine transaminase (argD), ornithine carbamoyltransferase (argF), arginine repressor (argR), argininosuccinate synthase (argG), and argininosuccinate lyase (argH) genes, complete cds. | *Corynebacterium glutamicum* | 100,000 | 1-Jul.-1998 |
| rxa02157 | 1296 | GB_BA1:CGARGCJBD | 4355 | X86157 | C.glutamicum argC, argJ, argB, argD, and argF genes. | *Corynebacterium glutamicum* | 100,000 | 25-Jul.-1996 |
|  |  | GB_BA2:AE001818 | 10007 | AE001816 | *Thermotoga maritima* section 128 of 136 of the complete genome. | *Thermotoga maritima* | 50,238 | 2-Jun.-1999 |
|  |  | GB_BA2:AF049897 | 9196 | AF049897 | *Corynebacterium glutamicum* N-acetylglutamylphosphate reductase (argC), ornithine acetyltransferase (argJ), N-acetylglutamate kinase (argB), acetylornithine transaminase (argD), ornithine carbamoyltransferase (argF), arginine repressor (argR), argininosuccinate synthase (argG), and argininosuccinate lyase (argH) genes, complete cds. | *Corynebacterium glutamicum* | 99,612 | 1-Jul.-1998 |
| rxa02158 | 1080 | GB_BA1:CGARGCJBD | 4355 | X86157 | C.glutamicum argC, argJ, argB, argD, and argF genes. | *Corynebacterium glutamicum* | 99,612 | 25-Jul.-1996 |
|  |  | GB_BA1:MTCY06H11 | 38000 | Z85982 | *Mycobacterium tuberculosis* H37Rv complete genome; segment 73/162. | *Mycobacterium tuberculosis* | 57,278 | 17-Jun.-1998 |
|  |  | GB_BA2:AF049897 | 9196 | AF049897 | *Corynebacterium glutamicum* N-acetylglutamylphosphate reductase (argC), ornithine acetyltransferase (argJ), N-acetylglutamate kinase (argB), | *Corynebacterium glutamicum* | 100,000 | 1-Jul.-1998 |

TABLE 4-continued

ALIGNMENT RESULTS

| ID # | length (NT) | Genbank Hit | Accession | Name of Genbank Hit | Source of Genbank Hit | % homology (GAP) | Date of Deposit |
|---|---|---|---|---|---|---|---|
| | | | | acetylornithine transaminase (argD), ornithine carbamoyltransferase (argF), arginine repressor (argR), argininosuccinate synthase (argG), and argininosuccinate lyase (argH) genes, complete cds. | | | |
| rxa02159 | | GB_BA2:AF031518 | 2045 AF031518 | Corynebacterium glutamicum ornithine carbamoyltransferase (argF) gene, complete cds. | Corynebacterium glutamicum | 99,898 | 5-Jan.-1999 |
| | | GB_BA1:CGARGCJBD | 4355 X86157 | C.glutamicum argC, argJ, argB, argO, and argF genes. | Corynebacterium glutamicum | 100,000 | 25-Jul.-1996 |
| | 636 | GB_BA2:AF049897 | 9196 AF049897 | Corynebacterium glutamicum N-acetylglutamylphosphate reductase (argC), ornithine acetyltransferase (argJ), N-acetylglutamate kinase (argB), acetylornithine transaminase (argD), ornithine carbamoyltransferase (argF), arginine repressor (argR), argininosuccinate synthase (argG), and argininosuccinate lyase (argH) genes, complete cds. | Corynebacterium glutamicum | 99,843 | 1-Jul.-1998 |
| rxa02160 | | GB_BA2:AF031518 | 2045 AF031518 | Corynebacterium glutamicum ornithine carbamoyltransferase (argF) gene, complete cds. | Corynebacterium glutamicum | 88,679 | 5-Jan.-1999 |
| | | GB_BA1:AF041436 | 516 AF041436 | Corynebacterium glutamicum arginine repressor (argR) gene, complete cds. | Corynebacterium glutamicum | 100,000 | 5-Jan.-1999 |
| | 1326 | GB_BA2:AF049897 | 9196 AF049897 | Corynebacterium glutamicum N-acetylglutamylphosphate reductase (argC), ornithine acetyltransferase (argJ), N-acetylglutamate kinase (argB), acetylornithine transaminase (argD), ornithine carbamoyltransferase (argF), arginine repressor (argR), argininosuccinate synthase (argG), and argininosucanate lyase (argH) genes, complete cds. | Corynebacterium glutamicum | 99,774 | 1-Jul.-1998 |
| rxa02162 | | GB_BA2:AF030520 | 1206 AF030520 | Corynebacterium glutamicum argininosuccinate synthetase (argG) gene, complete cds. | Corynebacterium glutamicum | 99,834 | 19-Nov.-1997 |
| | | GB_BA1:SCARGGH | 1909 Z49111 | S.clavuligerus argG gene and argH gene (partial). | Streptomyces clavuligerus | 65,913 | 22-Apr.-1996 |
| | 1554 | GB_BA2:AF049897 | 9196 AF049897 | Corynebacterium glutamicum N-acetylglutamylphosphate reductase (argC), ornithine acetyltransferase (argJ), N-acetylglutamate kinase (argB), acetylornithine transaminase (argD), ornithine carbamoyltransferase (argF), arginine repressor (argR), argininosuccinate synthase (argG), and arginlnosuccinate lyase (argH) genes, complete cds. | Corynebacterium glutamicum | 88,524 | 01-Jul.-1998 |
| | | GB_BA2:AF048764 | 1437 AF048764 | Corynebacterium glutamicum argininosuccinate lyase (argH) gene, complete cds. | Corynebacterium glutamicum | 87,561 | 1-Jul.-1998 |
| rxa02176 | 1251 | GB_BA1:MTCY06H11 | 38000 Z85982 | Mycobacterium tuberculosis H37Rv complete genome; segment 73/162. | Mycobacterium tuberculosis | 64,732 | 17-Jun.-1998 |
| | | GB_BA1:MTCY31 | 37630 Z73101 | Mycobacterium tuberculosis H37Rv complete genome; segment 41/162. | Mycobacterium tuberculosis | 36,998 | 17-Jun.-1998 |
| | | GB_BA1:CGGLTG | 3013 X66112 | C. glutamicum glt gene for citrate synthase and ORF. | Corynebacterium glutamicum | 39,910 | 17-Feb.-1995 |
| | | GB_PL2:PGU65399 | 2700 U65399 | Basidiomycete CECT 20197 phenoloxidase (pox1) gene, complete cds. | basidiomycete CECT 20197 | 38,474 | 19-Jul.-1997 |
| rxa02189 | 861 | GB_PR3:AC002468 | 115888 AC002468 | Human Chromosome 15q26.1 PAC clone pDJ417d7, complete sequence. | Homo sapiens | 35,941 | 16-Sep.-1998 |
| | | GB_BA1:MSGB1970CS | 39399 L78815 | Mycobacterium leprae cosmid B1970 DNA sequence. | Mycobacterium leprae | 40,286 | 15-Jun.-1996 |
| | | GB_PR3:AC002468 | 115888 AC002468 | Human Chromosome 15q26.1 PAC clone pDJ417d7, complete sequence. | Homo sapiens | 33,689 | 16-Sep.-1998 |
| rxa02193 | 1701 | GB_BA1:BRLASPA | 1987 D25316 | Brevibacterium flavum aspA gene for aspartase, complete cds. | Corynebacterium glutamicum | 99,353 | 6-Feb.-1999 |
| | | GB_PAT:E04307 | 1581 E04307 | DNA encoding Brevibacterium flavum aspartase. | Corynebacterium glutamicum | 99,367 | 29-Sep.-1997 |
| | | GB_BA1:ECOUW93 | 338534 U14003 | Escherichia coli K-12 chromosomal region from 92.8 to 00.1 minutes. | Escherichia coli | 37,651 | 17-Apr.-1996 |
| rxa02194 | 968 | GB_BA2:AF050166 | 840 AF050166 | Corynebacterium glutamicum ATP phosphoribosyltransferase (hisG) gene, complete cds. | Corynebacterium glutamicum | 98,214 | 5-Jan.-1999 |
| | | GB_BA1:BRLASPA | 1987 D25316 | Brevibacterium flavum aspA gene for aspartase, complete cds. | Corynebacterium glutamicum | 93,805 | 6-Feb.-1999 |
| | | GB_PAT:E08649 | 188 E08649 | DNA encoding part of aspartase from coryneform bacteria. | Corynebacterium glutamicum | 100,000 | 29-Sep.-1997 |
| rxa02195 | 393 | GB_BA2:AF086704 | 284 AF086704 | Corynebacterium glutamicum phosphoribosyl-ATP-pyrophoshohydrolase (hisE) gene, complete cds. | Corynebacterium glutamicum | 100,000 | 8-Feb.-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| | | GB_BA1:EAY17145 | 6019 | Y17145 | Eubacterium acidaminophilum grdR, grdI, grdH genes and partial ldc, grdT genes. | Eubacterium acidaminophilum | 39075 | 5-Aug.-1998 |
| rxa02197 | 551 | GB_STS:G01195 | 332 | G01195 | fruit fly STS Dm1930 clone DS06959 T7. | Drosophila melanogaster | 35,542 | 28-Feb.-1995 |
| | | GB_BA1:MTCY261 | 27322 | Z97559 | Mycobacterium tuberculosis H37Rv complete genome; segment 95/162. | Mycobacterium tuberculosis | 33,938 | 17-Jun.-1998 |
| | | GB_BA1:MLOB2533 | 40245 | AL035310 | Mycobacterium leprae cosmid B2533. | Mycobacterium leprae | 65,517 | 27-Aug.-1999 |
| | | GB_BA1:U00017 | 42157 | U00017 | Mycobacterium leprae cosmid B2126. | Mycobacterium leprae | 36,770 | 01-Mar.-1994 |
| rxa02198 | 2599 | GB_BA1:U00017 | 42157 | U00017 | Mycobacterium leprae cosmid B2126. | Mycobacterium leprae | 38,674 | 01-Mar.-1994 |
| | | GB_BA1:MLCB2533 | 40245 | AL035310 | Mycobacterium leprae cosmid B2533. | Mycobacterium leprae | 65,465 | 27-Aug.-1999 |
| | | GB_BA1:MTCY261 | 27322 | Z97559 | Mycobacterium tuberculosis H37Rv complete genome; segment 95/162. | Mycobacterium tuberculosis | 37,577 | 17-Jun.-1998 |
| rxa02208 | 1025 | GB_BA1:U00017 | 42157 | U00017 | Mycobacterium leprae cosmid B2126. | Mycobacterium leprae | 59,823 | 01-Mar.-1994 |
| | | GB_BA1:AP000063 | 185300 | AP000063 | Aeropyrum pernix genomic DNA, section 6/7. | Aeropyrum pernix | 39,442 | 22-Jun.-1999 |
| | | GB_YR4:AC006236 | 127593 | AC006236 | Homo sapiens chromosome 17, clone hCIT.162_E_12, complete sequence. | Homo sapiens | 37,191 | 29-Dec.-1998 |
| rxa02229 | 948 | GB_BA1:MSGY154 | 40221 | AD000002 | Mycobacterium tuberculosis sequence from clone y154. | Mycobacterium tuberculosis | 53,541 | 03-Dec.-1996 |
| | | GB_BA1:MTCY154 | 13935 | Z98209 | Mycobacterium tuberculosis H37Rv complete genome; segment 121/162. | Mycobacterium tuberculosis | 40,407 | 17-Jun.-1998 |
| | | GB_BA1:U00019 | 36033 | U00019 | Mycobacterium leprae cosmid B2235. | Mycobacterium leprae | 40,541 | 01-Mar.-1994 |
| nca02234 | 3462 | GB_BA1:MSGB937CS | 38914 | L78820 | Mycobacterium leprae cosmid B937 DNA sequence. | Mycobacterium leprae | 66,027 | 15-Jun.-1996 |
| | | GB_BA1:MTCY2B12 | 20431 | Z81011 | Mycobacterium tuberculosis H37Rv complete genome; segment 61/162. | Mycobacterium tuberculosis | 71,723 | 18-Jun.-1998 |
| | | GB_BA2:U01072 | 4393 | U01072 | Mycobacterium bovis BOG orotidine-5-monophosphate decarboxylase (uraA) gene. | Mycobacterium bovis | 67,101 | 22-Dec.-1993 |
| rxa02235 | 727 | GB_BA1:M5U91572 | 960 | U91572 | Mycobacterium smegmatis carbamoyl phosphate synthetase (pyrAB) gene, partial cds and orotidine 5-monophosphate decarboxylase (pyrF) gene, complete cds. | Mycobacterium smegmatis | 60,870 | 22-Mar.-1997 |
| | | GB_HTG3:AC009364 | 192791 | AC009364 | Homo sapiens chromosome 7, ***SEQUENCING IN PROGRESS ***, 57 unordered pieces. | Homo sapiens | 37,994 | 1-Sep.-1999 |
| | | GB_HTG3:AC009364 | 192791 | AC009364 | Homo sapiens chromosome 7, *** SEQUENCING IN PROGRESS ***, 57 unordered pieces. | Homo sapiens | 37,994 | 1-Sep.-1999 |
| rxa02237 | 693 | GB_BA1:MTCY21B4 | 39150 | Z80108 | Mycobacterium tuberculosis H37Rv complete genome; segment 62/162. | Mycobacterium tuberculosis | 55,844 | 23-Jun.-1998 |
| | | GB_BA2:AF077324 | 5228 | AF077324 | Rhodococcus equi strain 103 plasmid RE-VP1 fragment f. | Rhodococcus equi | 41,185 | 5-Nov.-1998 |
| | | GB_EST22:AU017763 | 586 | AU017763 | AU017763 Mouse two-cell stage embryo cDNA Mus musculus cDNA clone J0744A04 3', mRNA sequence. | Mus musculus | 38,616 | 19-Oct.-1998 |
| rxa02239 | 1389 | GB_BA1:MTCY21B4 | 39150 | Z80108 | Mycobacterium tuberculosis H37Rv complete genome: segment 62/162. | Mycobacterium tuberculosis | 56,282 | 23-Jun.-1998 |
| | | GB_HTG3:AC010745 | 193862 | AC010745 | Homo sapiens clone NH0549D18, *** SEQUENCING IN PROGRESS ***, 30 unordered pieces. | Home sapiens | 36,772 | 21-Sep.-1999 |
| | | GB_HTG3:AC010745 | 193862 | AC010745 | Homo sapiens clone NH0549D18, *** SEQUENCING IN PROGRESS ***, 30 unordered pieces. | Homo sapiens | 36,772 | 21-Sep.-1999 |
| rxa02240 | 1344 | EM_PAT:E09855 | 1239 | E09855 | gDNA encoding 5-adenosylmethionine synthetase. | Corynebacterium glutamicum | 99,515 | 07-Oct.-1997 (Rel. 52, Created) |
| | | GB_PAT:A37831 | 5392 | A37831 | Sequence 1 from Patent W09408014. | Streptomyces pristinaespiralis | 63,568 | 05-Mar.-1997 |
| | | GB_BA2:AF117274 | 2303 | AF117274 | Streptomyces spectabilis flavoprotein homolog Dfp (dfp) gene, partial cds; and S-adenosylmethionine synthetase (metK) gene, complete cds. | Streptomyces spectabilis | 65,000 | 31-Mar.-1999 |
| rxa02246 | 1107 | EM_BA1:AB003693 | 5589 | AB003693 | Corynebacterium ammoniagenes DNA for rib operon, complete cds. | Corynebacterium ammoniagenes | 52,909 | 03-Oct.-1997 (Rel. 52, Created) |
| | | GB_PAT:E07957 | 5589 | E07957 | gDNA encoding at least guanosine triphosphate cyclohydrolase and riboflavin synthase. | Corynebacterium ammoniagenes | 52,909 | 29-Sep.-1997 |
| | | GB_PAT:I32742 | 5589 | I32742 | Sequence 1 from patent U.S. Pat. No. 5589355. | Unknown. | 52,909 | 6-Feb.-1997 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa02247 | 756 | GB_PAT:I32743 | 2689 | I32743 | Sequence 2 from patent U.S. Pat. No. 5589355. | Unknown. | 57,937 | 6-Feb.-1997 |
| | | EM_BA1:AB003693 | 5589 | AB003693 | Corynebacterium ammoniagenes DNA for rib operon, complete cds. | Corynebacterium ammoniagenes | 57,937 | 03-Oct.-1997 (Rel. 52, Created) |
| rxa02248 | 1389 | GB_PAT:I32742 | 5589 | I32742 | Sequence 1 from patent U.S. Pat. No. 5589355. | Unknown. | 57,937 | 6-Feb.-1997 |
| | | GB_PAT:I32742 | 5589 | I32742 | Sequence 1 from patent U.S. Pat. No. 5589355. | Unknown. | 61,843 | 6-Feb.-1997 |
| | | EM_BA1:AB003693 | 5589 | AB003693 | Corynebacterium ammoniagenes DNA for rib operon, complete cds. | Corynebacterium ammoniagenes | 61,843 | 03-Oct.-1997 (Rel. 52, Created) |
| rxa02249 | 600 | GB_PAT:E07957 | 5589 | E07957 | gDNA encoding at least guanosine triphosphate cyclohydrolase and riboflavin synthase. | Corynebacterium ammoniagenes | 61,843 | 29-Sep.-1997 |
| | | GB_PAT:E07957 | 5589 | E07957 | gDNA encoding at least guanosine triphosphate cyclohydrolase and riboflavin synthase. | Corynebacterium ammoniagenes | 64,346 | 29-Sep.-1997 |
| | | GB_PAT:I32742 | 5589 | I32742 | Sequence 1 from patent U.S. Pat. No. 5589355. | Unknown. | 64,346 | 6-Feb.-1997 |
| | | GB_PAT:I32743 | 2689 | I32743 | Sequence 2 from patent U.S. Pat. No. 5589355. | Unknown. | 64,346 | 6-Feb.-1997 |
| nca02250 | 643 | GB_PAT:E07957 | 5589 | E07957 | gDNA encoding at least guanosine triphosphate cyclohydrolase and riboflavin synthase. | Corynebacterium ammoniagenes | 56,318 | 29-Sep.-1997 |
| | | GB_PAT:I32742 | 5589 | I32742 | Sequence 1 from patent U.S. Pat. No. 5589355. | Unknown. | 56,318 | 6-Feb.-1997 |
| | | EM_BA1:AB003693 | 5589 | AB003693 | Corynebacterium ammoniagenes DNA for rib operon, complete cds. | Carynebacterium ammoniagenes | 56,318 | 03-Oct.-1997 (Rel. 52, Created) |
| rxa02262 | 1269 | GB_BA1:CGL007732 | 4460 | AJ007732 | Corynebacterium glutamicum 3'ppc gene, secG gene, amt gene, ocd gene and 5' soxA gene. | Corynebacterium glutamicum | 100,000 | 7-Jan.-1999 |
| | | GB_BA1:CGAMTGENE | 2028 | X93513 | C. glutamicum amt gene. | Corynebacterium glutamicum | 100,000 | 29-May-1996 |
| | | GB_VI:HEHCMVCG | 229354 | X17403 | Human cytomegalovirus strain AD169 complete genome. | human herpesvirus 5 | 38,651 | 10-Feb.-1999 |
| rxa02263 | 488 | GB_BA1:CGL007732 | 4460 | AJ007732 | Corynebacterium glutamicum 3'ppc gene, secG gene, amt gene, ocd gene and 5' soxA gene. | Corynebacterium glutamicum | 100,000 | 7-Jan.-1999 |
| rxa02272 | 1368 | EM_PAT:E09373 | 1591 | E09373 | Creatinine deiminase gene. | Corynebacterium glutamicum | 37,526 | 7-Jan.-1999 |
| | | GB_BA1:D38505 | 1591 | D38505 | Bacillus sp. gene for creatinine deaminase, complete cds. | Bacillus sp. | 96,928 | 08-Oct.-1997 (Rel. 52, Created) |
| rxa02281 | 1545 | GB_HTG2:AC008595 | 146070 | AC008595 | Homo sapiens, *** SEQUENCING IN PROGRESS ***, 4 unordered pieces. | Bacillus sp. | 96,781 | 7-Aug.-1998 |
| | | GB_GSS12:AQ411010 | 551 | AQ411010 | HS_2257_B1_H02_MR CIT Approved Human Genomic Sperm Library D Homo sapiens genomic clone Plate = 2257 Col = 3 Row = P, genomic survey sequence. | Homo sapiens | 36,264 | 20-Feb.-1999 |
| | | GB_EST23:AI128623 | 363 | AI128623 | qa62-01.si Scares_fetal_heart_NbHH19W Homo sapiens cDNA clone IMAGE:1691328 3', mRNA sequence. | Homo sapiens | 36,197 | 17-Mar.-1999 |
| | | GB_PL2:ATAC007019 | 102335 | AC007019 | Arabidopsis thaliana chromosome II BAC F7D8 genomic sequence, complete sequence. | Homo sapiens | 37,017 | 05-Oct.-1998 |
| rxa02299 | 531 | GB_BA2:AF116184 | 540 | AF116184 | Corynebacterium glutamicum L-aspartate-alpha-decarboxylase precursor (panD) gene, complete cds. | Arabidopsis thaliana | 33,988 | 16-Mar.-1999 |
| | | GB_GSS9:AQ164310 | 507 | AQ164310 | HS_2171_A2E01MR CIT Approved Human Genomic Sperm Library D Homo sapiens genomic clone Plate = 2171 Col = 2 Row = 1, genomic survey sequence. | Corynebacterium glutamicum | 100,000 | 02-May-1999 |
| | | GB_VI:MH68TKH | 4557 | X93468 | Murine herpesvirus type 68 thymidine kinase and glycoprotein H genes. | Homo sapiens | 37,278 | 16-Oct.-1998 |
| | | | | | | murine herpesvirus 68 | 40,288 | 3-Sep.-1996 |

TABLE 4-continued

ALIGNMENT RESULTS

| ID # | length (NT) | Genbank Hit | Accession | Name of Genbank Hit | Source of Genbank Hit | % homology (GAP) | Date of Deposit |
|---|---|---|---|---|---|---|---|
| rxa02311 | 813 | GB_HTG4:AC006091 | 176878 AC006091 | *Drosophila melanogaster* chromosome 3 clone BACR48G05 (D475) RPCI-98 48.G.5 map 91F1-91F13 strain y; cn bwsp, *** SEQUENCING IN PROGRESS ***, 4 unordered pieces. | *Drosophila melanogaster* | 36,454 | 27-Oct.-1999 |
| | | GB_HTG4:AC006091 | 176878 AC006091 | *Drosophila melanogaster* chromosome 3 clone BACR48G05 (D475) RPCI-98 48.G.5 map 91F1-91F13 strain y; cn bw sp, *** SEQUENCING IN PROGRESS ***, 4 unordered pieces. | *Drosophila melanogaster* | 36,454 | 27-Oct.-1999 |
| | | GB_BA2:RRU65510 | 16259 U65510 | *Rhodospirillum rubrum* CO-induced hydrogenase operon (cooM, cooK, cooL, cooX, cooLJ, cooH) genes, iron sulfur protein (cooF) gene, carbon monoxide dehydrogenase (cooS) gene, carbon monoxide dehydrogenase accessory proteins (cooC, cooT, cooJ) genes, putative transcriptional activator (cooA) gene, nicotinate-nucleotide pyrophosphorylase (nadC) gene, complete cds, L-aspartate oxidase (nadB) gene, and alkyl hydroperoxide reductase (ahpC) gene, partial cds. | *Rhodospirillum rubrum* | 37,828 | 9-Apr.-1997 |
| rxa02315 | 1752 | GB_BA1:MSGY224 | 40051 AD000004 | *Mycobacterium tuberculosis* sequence from clone y224. | *Mycobacterium tuberculosis* | 49,418 | 03-Dec.-1996 |
| | | GB_BA1:MTY25D10 | 40838 Z95558 | *Mycobacterium tuberculosis* H37Rv complete genome; segment 28/162. | *Mycobacterium tuberculosis* | 49,360 | 17-Jun.-1998 |
| | | GB_BA1:MSGY224 | 40051 AD000004 | *Mycobacterium tuberculosis* sequence from clone y224. | *Mycobacterium tuberculosis* | 38,150 | 03-Dec.-1996 |
| rxa02318 | 402 | GB_HTG3:AC011348 | 111083 AC011348 | *Homo sapiens* chromosome 5 clone CIT-HSPC_303E13, *** SEQUENCING IN PROGRESS ***, 3 ordered pieces. | *Homo sapiens* | 35,821 | 06-Oct.-1999 |
| | | GB_HTG3:AC011348 | 111083 AC011348 | *Homo sapiens* chromosomes 5 clone CIT-HSPC_303E13, *** SEQUENCING IN PROGRESS ***, 3 ordered pieces. | *Homo sapiens* | 35,821 | 06-Oct.-1999 |
| | | GB_HTG3:AC011412 | 89234 AC011412 | *Homo sapiens* chromosome 5 clone CIT978SKB_81K21, *** SEQUENCING IN PROGRESS ***, 3 ordered pieces. | *Homo sapiens* | 36,181 | 06-Oct.-1999 |
| rxa02319 | 1080 | GB_BA1:MSGY224 | 40051 AD000004 | *Mycobacterium tuberculosis* sequence from clone y224. | *Mycobacterium tuberculosis* | 37,792 | 03-Dec.-1996 |
| | | GB_BA1:MTY25D10 | 40838 Z95558 | *Mycobacterium tuberculosis* H37Rv complete genome; segment 28/162. | *Mycobacterium tuberculosis* | 37,792 | 17-Jun.-1998 |
| | | GB_EST23:AI117213 | 476 AI117213 | ub83h02.r1 Soares 2NbMT *Mus musculus* cDNA clone IMAGE:1395123 5', mRNA sequence. | *Mus musculus* | 35,084 | 2-Sep.-1998 |
| rxa02345 | 1320 | GB_BA1:BAPURKE | 2582 X91189 | *B. ammoniagenes* purK and purE genes. | *Corynebacterium ammoniagenes* | 61,731 | 14-Jan.-1997 |
| rxa02350 | 618 | GB_BA1:MTCY71 | 42729 Z92771 | *Mycobacterium tuberculosis* H37Rv complete genome; segment 141/162. | *Mycobacterium tuberculosis* | 39,624 | 10-Feb.-1999 |
| | | GB_BA1:MTCY71 | 42729 Z92771 | *Mycobacterium tuberculosis* H37Rv complete genome; segment 141/162. | *Mycobacterium tuberculosis* | 39,847 | 10-Feb.-1999 |
| | | GB_BA1:BAPURKE | 2582 X91189 | *B. ammoniagenes* purK and purE genes. | *Corynebacterium ammoniagenes* | 64,286 | 14-Jan.-1997 |
| rxa02373 | 1038 | GB_PL1:SC130KBXV | 129528 X94335 | *S. cerevisiae* 130 kb DNA fragment from chromosome XV. | *Saccharomyces cerevisiae* | 36,617 | 15-Jul.-1997 |
| | | GB_PL1:SCXVORFS | 50984 X90518 | *S. cerevisiae* DNA of 51 Kb from chromosome XV right arm. | *Saccharomyces cerevisiae* | 36,617 | 1-Nov.-1995 |
| | | GB_PAT:E00311 | 1853 E00311 | DNA coding of 2,5-diketogluconic acid reductase. | unidentified | 56,123 | 29-Sep.-1997 |
| | | GB_PAT:I06030 | 1853 I06030 | Sequence 4 from Patent EP 0305608. | Unknown. | 56,220 | 02-Dec.-1994 |
| | | GB_PAT:I00836 | 1853 I00836 | Sequence 1 from Patent U.S. Pat. No. 4758514. | Unknown. | 56,220 | 21-May-1993 |
| rxa02375 | 1350 | GB_BA2:CGU31230 | 3005 U31230 | *Corynebacterium glutamicum* Obg protein homolog gene, partial cds, gamma glutamyl kinase (proB) gene, complete cds, and (unkdh) gene, complete cds. | *Corynebacterium glutamicum* | 99,332 | 2-Aug.-1996 |
| | | GB_HTG3:AC009946 | 169072 AC009946 | *Homo sapiens* clone NH0012C17, *** SEQUENCING IN PROGRESS ***, 1 unordered pieces. | *Homo sapiens* | 36,115 | 8-Sep.-1999 |
| | | GB_HTG3:AC009946 | 169072 AC009946 | *Homo sapiens* clone NH0012C17, tmSEQUENCING IN PROGRESS ***, 1 unordered pieces. | *Homo sapiens* | 36,115 | 8-Sep.-1999 |
| rxa02380 | 777 | GB_BA1:MTCY253 | 41230 Z81368 | *Mycobacterium tuberculosis* H37Rv complete genome; segment 106/162. | *Mycobacterium tuberculosis* | 38,088 | 17-Jun.-1998 |
| | | GB_HTG4:AC010658 | 120754 AC010858 | *Drosophila melanogaster* chromosome 3L175C1 clone RPCI98-3B20, *** SEQUENCING IN PROGRESS ***, 78 unordered pieces. | *Drosophila melanogaster* | 35,817 | 16-Oct.-1999 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa02382 | | GB_HTG4:AC010658 | 120754 | AC010658 | *Drosophila melanogaster* chromosome 3L175C1 clone RPCI98-3B20, *** SEQUENCING IN PROGRESS ***, 78 unordered pieces. | *Drosophila melanogaster* | 35,817 | 16-Oct-1999 |
| | 1419 | GB_BA1:CGPROAGEN | 1783 | X82929 | *C. glutamicum* proA gene. | *Corynebacterium glutamicum* | 98,802 | 23-Jan.97 |
| | | GB_BA1:MTCY428 | 26914 | Z81451 | *Mycobacterium tuberculosis* H37Rv complete genome; segment 107/162. | *Mycobacterium tuberculosis* | 38,054 | 17-Jun.-1998 |
| | | GB_BA2:CGU31230 | 3005 | U31230 | *Corynebacterium glutamicum* Obg protein homolog gene, partial cds, gamma glutamyl kinase (proB) gene, complete cds, and (unkdl) gene, complete cds. | *Corynebacterium glutamicum* | 98,529 | 2-Aug.-1996 |
| rxa02400 | 693 | GB_BA1:CGACEA | 2427 | X75504 | *C. glutamicum* aceA gene and thiX genes (partial). | *Corynebacterium glutamicum* | 100,000 | 9-Sep.-1994 |
| | | GB_PAT:I86191 | 2135 | I86191 | Sequence 3 from patent U.S. Pat. No. 5700661. | Unknown. | 100,000 | 10-Jun.-1998 |
| | | GB_PAT:I13693 | 2135 | I13693 | Sequence 3 from patent U.S. Pat. No. 5439822. | Unknown. | 100,000 | 26-Sep.-1995 |
| rxa02432 | 1098 | GB_GSS15:AQ606842 | 574 | AQ606842 | HS_5404_B2_E07_T7A RPCI-11 Human Male BAC Library *Homo sapiens* genomic clone Plate = 980 Col = 14 Row = J, genomic survey sequence. | *Homo sapiens* | 39,716 | 10-Jun.-1999 |
| | | GB_EST1:T05804 | 406 | T05804 | EST03693 Fetal brain, Stratagene (cat#936206) *Homo sapiens* cDNA clone HFBDG63 similar to EST containing Alu repeat, mRNA sequence. | *Homo sapiens* | 37,915 | 30-Jun.-1993 |
| | | GB_PL1:AB006699 | 77363 | AB006699 | *Arabidopsis thaliana* genomic DNA, chromosome 5, P1 clone: MDJ22, complete sequence. | *Arabidopsis thaliana* | 35,526 | 20-Nov.-1999 |
| rxa02458 | 1413 | GB_BA2:AF114233 | 1852 | AF114233 | *Corynebacterium glutamicum* 5-enolpyruvylshikimate 3-phosphate synthase (aroA) gene, complete cds. | *Corynebacterium glutamicum* | 100,000 | 7-Feb.-1999 |
| | | GB_EST37:AW013061 | 578 | AW013061 | ODT-0033 Winter flounder ovary *Pleuronectes americanus* cDNA clone ODT-0033 5'similar to FRUCTOSE-BISPHOSPHATE ALDOLASE B (LIVER), mRNA sequence. | *Pleuronectes americanus* | 39,175 | 10-Sep.-1999 |
| rxa02469 | | GB_GSS15:AQ650027 | 728 | AQ650027 | Sheared DNA-5L2.TF Sheared DNA *Trypanosoma brucei* genomic clone Sheared DNA-5L2, genomic survey sequence. | *Trypanosoma brucei* | 39,281 | 22-Jun.-1999 |
| | 1554 | GB_BA1:MTCY359 | 36021 | Z83859 | *Mycobacterium tuberculosis* H37Rv complete genome; segment 84/162. | *Mycobacterium tuberculosis* | 39,634 | 17-Jun.-1998 |
| | | GB_BA1:MLCB1788 | 39228 | AL008609 | *Mycobacterium leprae* cosmid B1788. | *Mycobacterium leprae* | 59,343 | 27-Aug.-1999 |
| | | GB_BA1:SCAJ10601 | 4692 | AJ010601 | *Streptomyces coelicolor* A3(2)-DNA for whiD and whiK loci. | *Streptomyces coelicolor* | 48,899 | 17-Sep.-1998 |
| rxa02497 | 1050 | GB_BA2:CGU31224 | 422 | U31224 | *Corynebacterium glutamicum* (ppx) gene, partial cds. | *Corynebacterium glutamicum* | 96,445 | 2-Aug.-1996 |
| | | GB_BA1:MTCY20G9 | 37218 | Z77162 | *Mycobacterium tuberculosis* H37Rv complete genome; segment 25/162. | *Mycobacterium tuberculosis* | 59,429 | 17-Jun.-1998 |
| rxa02499 | | GB_BA1:SCE7 | 16911 | AL049819 | *Streptomyces coelicolor* cosmid E7. | *Streptomyces coelicolor* | 39,510 | 10-May-1999 |
| | 933 | GB_BA2:CGU31225 | 1817 | U31225 | *Corynebacterium glutamicum* L-proline:NADP+5-oxidoreductase (proC) gene, complete cds. | *Corynebacterium glutamicum* | 97,749 | 2-Aug.-1996 |
| rxa02501 | | GB_BA1:NG17PILA | 1920 | X13965 | *Neisseria gonorrhoeae* pilA gene. | *Neisseria gonorrhoeae* | 43,249 | 30-Sep.-1993 |
| | 1188 | GB_HTG2:AC007984 | 129715 | AC007984 | *Drosophila melanogaster* chromosome 3 clone BACRO5C10 (D781) RPCI-98 05.C.10 map 97D-1997E strain y; cn bw sp, *** SEQUENCING IN PROGRESS ***, 87 unordered pieces. | *Drosophila melanogaster* | 33,406 | 2-Aug.-1999 |
| rxa02503 | | GB_BA1:MTCY2OG9 | 37218 | Z77162 | *Mycobacterium tuberculosis* H37Rv complete genome; segment 25/162. | *Mycobacterium tuberculosis* | 39,357 | 17-Jun.-1998 |
| | 522 | GB_BA1:U00018 | 42991 | U00018 | *Mycobacterium leprae* cosmid B2168. | *Mycobacterium leprae* | 51,768 | 01-Mar-1994 |
| | | GB_VI:HEICG | 152261 | X14112 | Herpes simplex virus (HSV) type 1 complete genome. | human herpesvirus 1 | 39,378 | 17-Apr-1997 |
| | | GB_PR3:AC005328 | 35414 | AC005328 | *Homo sapiens* chromosome 19, cosmid R26660, complete sequence. | *Homo sapiens* | 39,922 | 28-Jul.-1998 |
| | | GB_PR3:AC005545 | 43514 | AC005545 | *Homo sapiens* chromosome 19, cosmid R26634, complete sequence. | *Homo sapiens* | 39,922 | 3-Sep.-1998 |
| rxa02504 | 681 | GB_PR3:AC005328 | 35414 | AC005328 | *Homo sapiens* chromosome 19, cosmid R26660, complete sequence. | *Homo sapiens* | 34,911 | 28-Jul.-1998 |
| | | GB_BA1:MTCY20G9 | 37218 | Z77162 | *Mycobacterium tuberculosis* H37Rv complete genome; segment 25/162. | *Mycobacterium tuberculosis* | 54,940 | 17-Jun.-1998 |
| | | GB_PR3:AC005328 | 35414 | AC005328 | *Homo sapiens* chromosome 19, cosmid R26660, complete sequence. | *Homo sapiens* | 41,265 | 28-Jul.-1998 |
| | | GB_PR3:AC005545 | 43514 | AC005545 | *Homo sapiens* chromosome 19, cosmid R26634, complete sequence. | *Homo sapiens* | 41,265 | 3-Sep.-1998 |
| rxa02516 | 1386 | GB_BA1:MLCL536 | 36224 | Z99125 | *Mycobacterium leprae* cosmid L536. | *Mycobacterium leprae* | 37,723 | 04-Dec-1998 |
| | | GB_BA1:U00013 | 35881 | U00013 | *Mycobacterium leprae* cosmid B1496. | *Mycobacterium leprae* | 37,723 | 01-Mar-1994 |
| | | GB_BA1:MTV007 | 32806 | AL021184 | *Mycobacterium tuberculosis* H37Rv complete genome; segment 64/162. | *Mycobacterium tuberculosis* | 61,335 | 17-Jun.98 |
| rxa02517 | 570 | GB_BA1:MLCL536 | 36224 | Z99125 | *Mycobacterium leprae* cosmid L536. | *Mycobacterium leprae* | 37,018 | 4-Dec-1998 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
| rxa02532 | 1170 | GB_BA1:U00013 | 35881 | U00013 | *Mycobacterium leprae* cosmid B1496. | *Mycobacterium leprae* | 37,018 | 01-Mar-1994 |
| | | GB_BA1:SCC22 | 22115 | AL096839 | *Streptomyces coelicolor* cosmid C22. | *Streptomyces coelicolor* | 37,071 | 12-Jul.-1999 |
| | | GB_OV:AF137219 | 831 | AF137219 | *Amia calva* mixed lineage leukemia-like protein (MII) gene, partial cds. | *Amia calva* | 36,853 | 7-Sep.-1999 |
| | | GB_EST30:AI645057 | 301 | AI645057 | vs52a10.y1 Stratagene mouse Tcell 937311 *Mus musculus* cDNA clone IMAGE:1149882 5', mRNA sequence. | *Mus musculus* | 41860 | 29-Apr.-1999 |
| rxa02536 | | GB_EST20:AA822595 | 429 | AA822595 | vs52a10.r1 Stratagene mouse Tcell 937311 *Mus musculus* cDNA clone IMAGE:1149882 5', mRNA sequence. | *Mus musculus* | 42,353 | 17-Feb.-1998 |
| | 879 | GB_HTG2:AF130866 | 118874 | AF130866 | *Homo sapiens* chromosome 8 clone PAC 172N13 map 8q24, *** SEQUENCING IN PROGRESS ***, in unordered pieces. | *Homo sapiens* | 40,754 | 21-Mar.-1999 |
| | | GB_HTG2:AF130866 | 118874 | AF130866 | *Homo sapiens* chromosome 8 clone PAC 172N13 map 8q24, *** SEQUENCING IN PROGRESS ***, in unordered pieces. | *Homo sapiens* | 40,754 | 21-Mar.-1999 |
| rxa02550 | | GB_PL1:ATT12J5 | 84499 | AL035522 | *Arabidopsis thaliana* DNA chromosome 4, BAC clone T12I5 (ESSAII project). | *Arabidopsis thaliana* | 35,063 | 24-Feb.-1999 |
| | 1434 | GB_BA1:MTCY279 | 9150 | Z97991 | *Mycobacterium tuberculosis* H37Rv complete genome; segment 17/162. | *Mycobacterium tuberculosis* | 37,773 | 17-Jun.-1998 |
| | | GB_BA1:MSGB1970CS | 39399 | L78815 | *Mycobacterium leprae* cosmid B1970 DNA sequence. | *Mycobacterium leprae* | 39,024 | 15-Jun.-1996 |
| | | GB_BA2:SC2H4 | 25970 | AL031514 | *Streptomyces coelicolor* cosmid 2H4. | *Streptomyces coelicolor* A3(2) | 37,906 | 19-Oct.-1999 |
| rxa02559 | 1026 | GB_BA1:MTV004 | 69350 | AL009198 | *Mycobacterium tuberculosis* H37Rv complete genome; segment 144/162. | *Mycobacterium tuberculosis* | 47,358 | 18-Jun.-1998 |
| | | GB_PAT:I28684 | 5100 | I28684 | Sequence 1 from patent U.S. Pat. No. 5573915. | Unknown. | 39,138 | 6-Feb.-1997 |
| | | GB_BA1:MTU27357 | 5100 | U27357 | *Mycobacterium tuberculosis* cyclopropane mycolic acid synthase (cma1) gene, complete cds. | *Mycobacterium tuberculosis* | 39,138 | 26-Sep.-1995 |
| rxa02622 | 1683 | GB_BA2:AE001780 | 11997 | AE001780 | *Thermotoga maritima* section 92 of 136 of the complete genome. | *Thermotoga maritima* | 44,914 | 2-Jun.-1999 |
| | | GB_OV:AF064564 | 49254 | AF064564 | *Fugu rubripes* neurofibromatosis type 1 (NF1), A-kinase anchor protein (AKAP84), BAW protein (BAW), and WSB1 protein WSB1) genes, complete cds. | *Fugu rubripes* | 39,732 | 17-Aug.-1999 |
| | | GB_OV:AF064564 | 49254 | AF064564 | *Fugu rubripes* neurofibromatosis type 1 (NF1), A-kinase anchor protein (AKAP84), BAW protein (BAW), and WSB1 protein (WSB1) genes, complete cds. | *Fugu rubripes* | 36,703 | 17-Aug.-1999 |
| rxa02623 | 714 | GB_GSS5:AQ818728 | 444 | AQ818728 | HS_5268_A1_G09_SP6E RPCI-11 Human Male BAC Library *Homo sapiens* genomic clone Plate = 844 Col = 17 Row = M, genomic survey sequence. | *Homo sapiens* | 38,801 | 26-Aug.-1999 |
| | | GB_HTG2:AC011083 | 198586 | AC011083 | *Homo sapiens* chromosome 9 clone RP11-111M7 map 9, WORKING DRAFT SEQUENCE, 51 unordered pieces. | *Homo sapiens* | 35,714 | 19-Nov.-1999 |
| | | GB_GSS6:AQ826948 | 544 | AQ826948 | HS_5014_A2_C12_T7A RPCI-11 Human Male BAC Library *Homo sapiens* genomic clone Plate = 590 Col = 24 Row = E, genomic survey sequence. | *Homo sapiens* | 39,146 | 27-Aug.-1999 |
| rxa02629 | 708 | GB_VI:BRSMGP | 462 | M86652 | Bovine respiratory syncytial virus membrane glycoprotein mRNA, complete cds. | Bovine respiratory syncytial virus | 37,013 | 28-Apr.-1993 |
| | | GB_VI:BRSMGP | 462 | M86652 | Bovine respiratory syncytial virus membrane glycoprotein mRNA, complete cds. | Bovine respiratory syncytial virus | 37,0132 | 8-Apr.-1993 |
| rxa02645 | 1953 | GB_PAT:A45577 | 1925 | A45577 | Sequence 1 from Patent WO9519442. | *Corynebacterium glutamicum* | 39,130 | 07-Mar.-1997 |
| | | GB_PAT:A45581 | 1925 | A45581 | Sequence 5 from Patent WO9519442. | *Corynebacterium glutamicum* | 39,130 | 07-Mar.-1997 |
| | | GB_BA1:CORILVA | 1925 | L01508 | *Corynebacterium glutamicum* threonine dehydratase (ilvA) gene, complete cds. | *Corynebacterium glutamicum* | 39,130 | 26-Apr.-1993 |
| rxa02646 | 1392 | GB_BA1:CORILVA | 1925 | L01508 | *Corynebacterium glutamicum* threonine dehydratase (ilvA) gene, complete cds. | *Corynebacterium glutamicum* | 99,138 | 26-Apr.-1993 |
| | | GB_PAT:A45585 | 1925 | A45585 | Sequence 9 from Patent WO9519442. | *Corynebacterium glutamicum* | 99,066 | 07-Mar.-1997 |
| | | GB_PAT:A45583 | 1925 | A45583 | Sequence 7 from Patent WO9519442. | *Corynebacterium glutamicum* | 99,066 | 07-Mar.-1997 |
| rca02648 | 1326 | GB_OV:ICTCNC | 2049 | M83111 | *Ictalurus punctatus* cyclic nucleotide-gated channel RNA sequence. | *Ictalurus punctatus* | 38,402 | 24-May-1993 |
| | | GB_EST11:AA265464 | 345 | AA265464 | mx91cd06.r1 Soares mouse NML *Mus musculus* cDNA clone IMAGE:693706 5', mRNA sequence. | *Mus musculus* | 38,655 | 20-Mar.-1997 |

TABLE 4-continued

ALIGNMENT RESULTS

| ID # | Genbank Hit | length (NT) | Accession | Name of Genbank Hit | Source of Genbank Hit | % homology (GAP) | Date of Deposit |
|---|---|---|---|---|---|---|---|
| rxa02653 | GB_GSS8:AQ006950 | 480 | AQ006950 | CIT-HSP-2294E14.TR CIT-HSP Homo sapiens genomic clone 2294E14, genomic survey sequence. | Homo sapiens | 36,074 | 27-Jun-1998 |
| rxa02687 | GB_BA1:CORPHEA | 1068 | M13774 | C.glutamicum pheA gene encoding prephenate dehydratase, complete cds. | Corynebacterium glutamicum | 99,715 | 26-Apr-1993 |
| | GB_PAT:E04483 | 948 | E04483 | DNA encoding prephenate dehydratase. | Corynebacterium glutamicum | 98,523 | 29-Sep-1997 |
| | GB_PAT:E06110 | 948 | E06110 | DNA encoding prephenate dehydratase. | Corynebacterium glutamicum | 98,523 | 29-Sep-1997 |
| rxa02717 | GB_PL1:HVCH4H | 59748 | Y14573 | Hordeum vulgare DNA for chromosome 4H. | Hordeum vulgare | 36,593 | 25-Mar-1999 |
| | GB_PR2:HS310H5 | 29718 | Z69705 | Human DNA sequence from cosmid 310H5 from a contig from the tip of the short arm of chromosome 16, spanning 2Mb of 16p13.3. Contains EST and CpG island. | Homo sapiens | 36,089 | 22-Nov-1999 |
| | GB_PR3:AC004754 | 39188 | AC004754 | Homo sapiens chromosome 16, cosmid clone RT286 (LANL), complete sequence. | Homo sapiens | 36,089 | 28-May-1998 |
| rxa02754 | GB_HTG2:AC008223 | 130212 | AC008223 | Drosophila melanogaster chromosome 3 clone BACR16I18 (D815) RPCI-98 16.I.18 map 95A-1995A strain y; cn bw sp, *** SEQUENCING IN PROGRESS****; 101 unordered pieces. | Drosophila melanogaster | 32,757 | 2-Aug.-1999 |
| | GB_HTG2:AC008223 | 130212 | AC008223 | Drosophila melanogaster chromosome 3 clone BACR16I18 (D815) RPCI-98 16.I.18 map 95A-95A strain y; cn bw sp. *** SEQUENCING IN PROGRESS ***, 101 unordered pieces. | Drosophila melanogaster | 32,757 | 2-Aug.-1999 |
| rxa02758 | GB_BA1:MTCY71 | 42729 | Z92771 | Mycobacterium tuberculosis H37Rv complete genome: segment 141/162. | Mycobacterium tuberculosis | 37,838 | 10-Feb-1999 |
| | GB_HTG5:AC011678 | 171967 | AC011678 | Homo sapiens clone 14_B_7, *** SEQUENCING IN PROGRESS ***, 20 unordered pieces. | Homo sapiens | 35,331 | 5-Nov-1999 |
| | GB_HTG5:AC011678 | 171967 | AC011678 | Homo sapiens clone 14_B_7, *** SEQUENCING IN PROGRESS ***, 20 unordered pieces. | Homo sapiens | 33,807 | 5-Nov-1999 |
| | GB_BA2:AF064070 | 23183 | AF084070 | Burkholderia pseudomallei putative dihydroorotase (pyrC) gene, partial cds; putative 1-acyl-sn-glycerol-3-phosphate acyltransferase (plsC), putative diadenosine tetraphosphatase (apaH), complete cds; type II O-antigen biosynthesis gene cluster, complete sequence; putative undecaprenyl phosphate N-acetylglucosaminyltransferase, and putative UDP-glucose 4-epimerase genes, complete cds; and putative galactosyl transferase gene, partial cds. | Burkholderia pseudomallei | 36,929 | 20-Jan-1999 |
| rxa02771 | GB_BA2:AF038651 | 4077 | AF038651 | Corynebacterium glutamicum dipeptide-binding protein (dciAE) gene, partial cds; adenine phosphonbosyltransferase (apt) and GTP pyrophosphokinase (rel) genes, complete cds; and unknown gene. | Corynebacterium glutamicum | 99,852 | 14-Sep-1998 |
| | GB_IN1:CELT19B4 | 37121 | U80438 | Caenorhabditis elegans cosmid T19B4. | Caenorhabditis elegans | 43,836 | 04-Dec-1996 |
| | GB_EST3G:AV193572 | 360 | AV193572 | AV193572 Yuji Kohara unpublished cDNA:Strain N2 hermaphrodite embryo Caenorhabditis elegans cDNA clone yk618h8 5'. mRNA sequence. | Caenorhabditis elegans | 48,588 | 22-Jul-1999 |
| rxa02772 | GB_BA2:AF038651 | 1158 | AF038651 | Corynebacterium glutamicum dipeptide-binding protein (dciAE) gene, partial cds; adenine phosphonbosyltransferase (apt) and GTP pyrophosphokinase (rel) genes, complete cds; and unknown gene. | Corynebacterium glutamicum | 99,914 | 14-Sep-1998 |
| | GB_BA1:MTCY227 | 35946 | Z77724 | Mycobacterium tuberculosis H37Rv complete genome: segment 114/162. | Mycobacterium tuberculosis | 38,339 | 17-Jun-1998 |
| | GB_BA1:U00011 | 40429 | U00011 | Mycobacterium leprae cosmid B1177. | Mycobacterium leprae | 38,996 | 01-Mar-1994 |
| rxa02790 | GB_BA1:MTCY159 | 33818 | Z83863 | Mycobacterium tuberculosis H37Rv complete genome; segment 111/162. | Mycobacterium tuberculosis | 37,640 | 17-Jun-1998 |

TABLE 4-continued

ALIGNMENT RESULTS

| ID # | length (NT) | Genbank Hit | Length | Accession | Name of Genbank Hit | Source of Genbank Hit | % homology (GAP) | Date of Deposit |
|---|---|---|---|---|---|---|---|---|
|  |  | GB_PR4:AC006581 | 172931 | AC006581 | Homo sapiens 12p21 BAC RPCI11-259O18 (Roswell Park Cancer Institute Human BAC Library) complete sequence. | Homo sapiens | 37,906 | 3-Jun-1999 |
|  |  | GB_PR4:AC006581 | 172931 | AC006581 | Homo sapiens 12p21 BAC RPCI11-259O18 (Roswell Park Cancer Institute Human BAC Library) complete sequence. | Homo sapiens | 35,280 | 3-Jun-1999 |
| rxa02791 | 951 | GB_BA1:MTCY159 | 33818 | Z83863 | Mycobacterium tuberculosis H37Rv complete genome; segment 111/162. | Mycobacterium tuberculosis | 39,765 | 17-Jun-1998 |
|  |  | GB_OV:CHKCEK2 | 3694 | M35195 | Chicken tyrosine kinase (cek2) mRNA, complete cds. | Gallus gallus | 38,937 | 28-Apr-1993 |
|  |  | GB_BA1:MSASDASK | 5037 | Z17372 | M.smegmatis asd, ask-alpha, and ask-beta genes. | Mycobacterium smegmatis | 38,495 | 9-Aug-1994 |
| rxa02802 | 1194 | GB_EST24:AI223401 | 169 | AI223401 | qg48g01.x1 Soares_testis_NHT Homo sapiens cDNA clone IMAGE:1838448 3' similar to WP:C25D7.8 CE08394;; mRNA sequence. | Homo sapiens | 40,828 | 27-Oct-1998 |
|  |  | GB_EST24:AI223401 | 169 | AI223401 | qg48g01.x1 Soares_testis_NHT Homo sapiens cDNA clone IMAGE:1838448 3' similar to WP:C25D7.8 CE08394;; mRNA sequence. | Homo sapiens | 40,828 | 27-Oct-1998 |
| rxa02814 | 494 | GB_BA1:MTCY7D11 | 22070 | Z95120 | Mycobacterium tuberculosis H37Rv complete genome; segment 138/162. | Mycobacterium tuberculosis | 58,418 | 17-Jun-1998 |
|  |  | GB_BA1:MTCY7D11 | 22070 | Z95120 | Mycobacterium tuberculosis H37Rv complete genome; segment 138/162. | Mycobacterium tuberculosis | 40,496 | 17-Jun-1998 |
|  |  | GB_PR1:HSAJ2962 | 778 | AJ002962 | Homo sapiens mRNA for hB-FABP. | Homo sapiens | 39,826 | 8-Jan-1998 |
| rxa02843 | 608 | GB_BA1:CGAJ4934 | 1160 | AJ004934 | Corynebacterium glutamicum dapD gene, complete CDS. | Corynebacterium glutamicum | 100,000 | 17-Jun-1998 |
|  |  | GB_BA1:MTCI364 | 29540 | Z93777 | Mycobacterium tuberculosis H37Rv complete genome; segment 52/162. | Mycobacterium tuberculosis | 37,710 | 17-Jun-1998 |
|  |  | GB_BA1:MLU15180 | 38675 | U15180 | Mycobacterium leprae cosmid B1756. | Mycobacterium leprae | 39,626 | 09-Mar-1995 |
| rxs03205 | 963 | GB_BA1:BLSIGBGN | 2906 | Z49824 | B. lactofermentum orf1 gene and sigB gene. | Corynebacterium glutamicum | 98,854 | 25-Apr-1996 |
|  |  | GB_EST21:AA980237 | 377 | M980237 | ua3a12.r1 Soares_mammary_gland_NbMMG Mus musculus cDNA clone IMAGE:1348414 5' similar to TR:Q61025 061025 HYPOTHETICAL 15.2 KD PROTEIN.;; mRNA sequence. | Mus musculus | 41,489 | 27-May-1998 |
|  |  | GB_EST23:AI158316 | 371 | AI158316 | ud27c05.r1 Soares_thymus_2NbMT Mus musculus cDNA clone IMAGE:1447112 5', mRNA sequence. | Mus musculus | 38,005 | 30-Sep-1998 |
| rxs03223 | 1237 | GB_IN1:LMFL2743 | 38368 | AL031910 | Leishmania major Friedlin chromosome 4 cosmid L2743. | Leishmania major | 39,869 | 15-Dec-1999 |
|  |  | GB_PR3:HSDJ61B2 | 119666 | AL096710 | Human DNA sequence from clone RP1-61B2 on chromosome 6p11.2-12.3 Contains isoforms 1 and 3 of BPAG1 (bullous pemphigoid antigen 1 (230/240 kD), an exon of a gene similar to murine MACF cytoskeletal protein, STSs and GSSs, complete sequence. | Homo sapiens | 34,930 | 17-Dec-1999 |
|  |  | GB_PR3:HSDJ61B2 | 119666 | AL096710 | Human DNA sequence from clone RP1-61B2 on chromosome 6p11.2-12.3 Contains isoforms 1 and 3 of BPAG1 (bullous pemphigoid antigen 1 (230/240 kD), an exon of a gene similar to murine MACF cytoskeletal protein, STSs and GSSs, complete sequence. | Homo sapiens | 34,634 | 17-Dec-1999 |

What is claimed:

1. An isolated nucleic acid molecule comprising the nucleotide sequence of SEQ ID NO: 1, or a full complement thereof.

2. An isolated nucleic acid molecule which encodes a polypeptide comprising the amino acid sequence of SEQ ID NO:2, or a full complement thereof.

3. An isolated nucleic acid molecule comprising a nucleotide sequence which is at least 90% identical to the entire nucleotide sequence of SEQ ID NO:1, wherein the nucleic acid molecule encodes a polypeptide having an O-acetylhomoserine sulfhydrylase activity, or a full complement thereof.

4. An isolated nucleic acid molecule consisting of a fragment of at least 25 contiguous nucleotides of the nucleotide sequence of SEQ ID NO:1, or a full complement thereof.

5. An isolated nucleic acid molecule comprising a fragment of at least 25 contiguous nucleotides of the nucleotide sequence of SEQ ID NO:1, wherein the nucleotide sequence of SEQ ID NO:1 encodes a polypeptide having an O-acetyl-homoserine sulfhydrylase activity, or a full complement thereof.

6. An isolated nucleic acid molecule which encodes a polypeptide comprising an amino acid sequence which is at least 90% identical to the entire amino acid sequence of SEQ ID NO:2, wherein the polypeptide has an O-acetylhomoserine sulfhydrylase activity, or a full complement thereof.

7. An isolated nucleic acid molecule which hybridizes to the complement of the nucleotide sequence of SEQ ID NO:1 in 6× sodium chloride/sodium citrate (SSG) at 45° C., followed by one or more washes in 0.2×SSC, 0.1% SDS at 50-65° C., wherein said nucleic acid molecule encodes a polypeptide having an O-acetylhomoserine sulfhydrylase activity, or a full complement thereof.

8. An isolated nucleic acid molecule comprising the nucleic acid molecule of any one of claims 1, 2, 3, 4, 5, 6, and 7 and a nucleotide sequence encoding a heterologous polypeptide.

9. A vector comprising the nucleic acid molecule of any one of claims 1, 2, 3, 4, 5, 6, and 7.

10. The vector of claim 9, which is an expression vector.

11. An isolated host cell transfected with the expression vector of claim 10.

12. The host cell of claim 11, wherein said cell is a microorganism.

13. The host cell of claim 12, wherein said cell belongs to the genus *Corynebacterium* or *Brevibacterium*.

14. A method of producing a polypeptide comprising culturing the host cell of claim 11 in an appropriate culture medium to, thereby, produce the polypeptide.

15. A method for producing an amino acid, comprising culturing the host cell of claim 11, such that the amino acid is produced.

16. The method of claim 15, wherein said cell is cultured in the presence of a sulfur source.

17. The method of claim 15, wherein said method further comprises the step of recovering the amino acid.

18. The method of claim 15, wherein said amino acid is methionine or lysine.

19. The method of claim 15, wherein said cell belongs to the genus *Corynebacterium* or *Brevibacterium*.

20. The method of claim 15, wherein said cell is selected from the group consisting of: *Corynebacterium glutamicum, Corynebacterium herculis, Corynebacterium lilium, Corynebacterium acetoacidophilum, Corynebacterium acetoglutamicum, Corynebacterium acetophilum, Corynebacte-* rium ammoniagenes, Corynebacterium fujiokense, Corynebacterium nitrilophilus, Brevibacterium ammoniagenes, Brevibacterium butanicum, Brevibacterium divaricatum, Brevibacterium flavum, Brevibacterium healii, Brevibacterium ketoglutamicum, Brevibacterium ketosoreductum, Brevibacterium lactofermentum, Brevibacterium linens, Brevibacterium paraffinolyticum.

21. A method for producing an amino acid, comprising culturing a cell whose genomic DNA has been altered by the inclusion of the nucleic acid molecule of any one of claims 1, 2, 3, 4, 5, 6 and 7.

* * * * *

SEQUENCE LISTING

<160> NUMBER OF SEQ ID NOS: 125

<210> SEQ ID NO 1
<211> LENGTH: 1840
<212> TYPE: DNA
<213> ORGANISM: Corynebacterium glutamicum
<220> FEATURE:
<221> NAME/KEY: CDS
<222> LOCATION: (363)..(1676)

<400> SEQUENCE: 1

```
cagaaactgt gtgcagaaat gcatgcagaa aaaggaaagt tcgggccaag atgggtgttt      60
ctgtatgccg atgatcggat ctttgacagc tgggtatgcg acaaatcacc gagagttgtt     120
aattcttaac aatggaaaag taacattgag agatgattta taccatcctg caccatttag     180
agtggggcta gtcataccc cataacccta gctgtacgca atcgatttca atcagttgg       240 aaaaagtcaa gaaaattacc cgagaattaa tttataccac acagtctatt gcaatagacc     300
aagctgttca gtagggtgca tgggagaaga atttcctaat aaaaactctt aaggacctcc     360 aa atg cca aag tac gac aat tcc aat gct gac cag tgg ggc ttt gaa        407
   Met Pro Lys Tyr Asp Asn Ser Asn Ala Asp Gln Trp Gly Phe Glu
    1               5                  10                  15 acc cgc tcc att cac gca ggc cag tca gta gac gca cag acc agc gca       455
Thr Arg Ser Ile His Ala Gly Gln Ser Val Asp Ala Gln Thr Ser Ala
                 20                  25                  30 cga aac ctt ccg atc tac caa tcc acc gct ttc gtg ttc gac tcc gct       503
Arg Asn Leu Pro Ile Tyr Gln Ser Thr Ala Phe Val Phe Asp Ser Ala
             35                  40                  45 gag cac gcc aag cag cgt ttc gca ctt gag gat cta ggc cct gtt tac       551
Glu His Ala Lys Gln Arg Phe Ala Leu Glu Asp Leu Gly Pro Val Tyr
         50                  55                  60 tcc cgc ctc acc aac cca acc gtt gag gct ttg gaa aac cgc atc gct       599
Ser Arg Leu Thr Asn Pro Thr Val Glu Ala Leu Glu Asn Arg Ile Ala
 65                  70                  75 tcc ctc gaa ggt ggc gtc cac gct gta gcg ttc tcc tcc gga cag gcc       647
Ser Leu Glu Gly Gly Val His Ala Val Ala Phe Ser Ser Gly Gln Ala
 80                  85                  90                  95 gca acc acc aac gcc att ttg aac ctg gca gga gcg ggc gac cac atc       695
Ala Thr Thr Asn Ala Ile Leu Asn Leu Ala Gly Ala Gly Asp His Ile
                100                 105                 110 gtc acc tcc cca cgc ctc tac ggt ggc acc gag act cta ttc ctt atc       743
Val Thr Ser Pro Arg Leu Tyr Gly Gly Thr Glu Thr Leu Phe Leu Ile
            115                 120                 125 act ctt aac cgc ctg ggt atc gat gtt tcc ttc gtg gaa aac ccc gac       791
Thr Leu Asn Arg Leu Gly Ile Asp Val Ser Phe Val Glu Asn Pro Asp
        130                 135                 140 gac cct gag tcc tgg cag gca gcc gtt cag cca aac acc aaa gca ttc       839
Asp Pro Glu Ser Trp Gln Ala Ala Val Gln Pro Asn Thr Lys Ala Phe
    145                 150                 155 ttc ggc gag act ttc gcc aac cca cag gca gac gtc ctg gat att cct       887
Phe Gly Glu Thr Phe Ala Asn Pro Gln Ala Asp Val Leu Asp Ile Pro
160                 165                 170                 175 gcg gtg gct gaa gtt gcg cac cgc aac agc gtt cca ctg atc atc gac       935
Ala Val Ala Glu Val Ala His Arg Asn Ser Val Pro Leu Ile Ile Asp
                180                 185                 190 aac acc atc gct acc gca gcg ctc gtg cgc ccg ctc gag ctc ggc gca       983
Asn Thr Ile Ala Thr Ala Ala Leu Val Arg Pro Leu Glu Leu Gly Ala
            195                 200                 205
```

```
gac gtt gtc gtc gct tcc ctc acc aag ttc tac acc ggc aac ggc tcc     1031
Asp Val Val Val Ala Ser Leu Thr Lys Phe Tyr Thr Gly Asn Gly Ser
        210                 215                 220 gga ctg ggc ggc gtg ctt atc gac ggc gga aag ttc gat tgg act gtc     1079
Gly Leu Gly Gly Val Leu Ile Asp Gly Gly Lys Phe Asp Trp Thr Val
    225                 230                 235 gaa aag gat gga aag cca gta ttc ccc tac ttc gtc act cca gat gct     1127
Glu Lys Asp Gly Lys Pro Val Phe Pro Tyr Phe Val Thr Pro Asp Ala
240                 245                 250                 255 gct tac cac gga ttg aag tac gca gac ctt ggt gca cca gcc ttc ggc     1175
Ala Tyr His Gly Leu Lys Tyr Ala Asp Leu Gly Ala Pro Ala Phe Gly
                260                 265                 270 ctc aag gtt cgc gtt ggc ctt cta cgc gac acc ggc tcc acc ctc tcc     1223
Leu Lys Val Arg Val Gly Leu Leu Arg Asp Thr Gly Ser Thr Leu Ser
            275                 280                 285 gca ttc aac gca tgg gct gca gtc cag ggc atc gac acc ctt tcc ctg     1271
Ala Phe Asn Ala Trp Ala Ala Val Gln Gly Ile Asp Thr Leu Ser Leu
        290                 295                 300 cgc ctg gag cgc cac aac gaa aac gcc atc aag gtt gca gaa ttc ctc     1319
Arg Leu Glu Arg His Asn Glu Asn Ala Ile Lys Val Ala Glu Phe Leu
    305                 310                 315 aac aac cac gag aag gtg gaa aag gtt aac ttc gca ggc ctg aag gat     1367
Asn Asn His Glu Lys Val Glu Lys Val Asn Phe Ala Gly Leu Lys Asp
320                 325                 330                 335 tcc cct tgg tac gca acc aag gaa aag ctt ggc ctg aag tac acc ggc     1415
Ser Pro Trp Tyr Ala Thr Lys Glu Lys Leu Gly Leu Lys Tyr Thr Gly
                340                 345                 350 tcc gtt ctc acc ttc gag atc aag ggc ggc aag gat gag gct tgg gca     1463
Ser Val Leu Thr Phe Glu Ile Lys Gly Gly Lys Asp Glu Ala Trp Ala
            355                 360                 365 ttt atc gac gcc ctg aag cta cac tcc aac ctt gca aac atc ggc gat     1511
Phe Ile Asp Ala Leu Lys Leu His Ser Asn Leu Ala Asn Ile Gly Asp
        370                 375                 380 gtt cgc tcc ctc gtt gtt cac cca gca acc acc acc cat tca cag tcc     1559
Val Arg Ser Leu Val Val His Pro Ala Thr Thr Thr His Ser Gln Ser
    385                 390                 395 gac gaa gct ggc ctg gca cgc gcg ggc gtt acc cag tcc acc gtc cgc     1607
Asp Glu Ala Gly Leu Ala Arg Ala Gly Val Thr Gln Ser Thr Val Arg
400                 405                 410                 415 ctg tcc gtt ggc atc gag acc att gat gat atc atc gct gac ctc gaa     1655
Leu Ser Val Gly Ile Glu Thr Ile Asp Asp Ile Ile Ala Asp Leu Glu
                420                 425                 430 ggc ggc ttt gct gca atc tag ctttaaatag actcacccca gtgcttaaag        1706
Gly Gly Phe Ala Ala Ile
            435 cgctgggttt ttcttttca gactcgtgag aatgcaaact agactagaca gagctgtcca    1766 tatacactgg acgaagtttt agtcttgtcc acccagaaca ggcggttatt ttcatgccca   1826 ccctcgcgcc ttca                                                    1840

<210> SEQ ID NO 2
<211> LENGTH: 437
<212> TYPE: PRT
<213> ORGANISM: Corynebacterium glutamicum

<400> SEQUENCE: 2

Met Pro Lys Tyr Asp Asn Ser Asn Ala Asp Gln Trp Gly Phe Glu Thr
 1               5                  10                  15

Arg Ser Ile His Ala Gly Gln Ser Val Asp Ala Gln Thr Ser Ala Arg
            20                  25                  30
```

```
Asn Leu Pro Ile Tyr Gln Ser Thr Ala Phe Val Phe Asp Ser Ala Glu
             35                  40                  45

His Ala Lys Gln Arg Phe Ala Leu Glu Asp Leu Gly Pro Val Tyr Ser
     50                  55                  60

Arg Leu Thr Asn Pro Thr Val Glu Ala Leu Glu Asn Arg Ile Ala Ser
 65                  70                  75                  80

Leu Glu Gly Gly Val His Ala Val Ala Phe Ser Ser Gly Gln Ala Ala
                 85                  90                  95

Thr Thr Asn Ala Ile Leu Asn Leu Ala Gly Ala Gly Asp His Ile Val
                100                 105                 110

Thr Ser Pro Arg Leu Tyr Gly Gly Thr Glu Thr Leu Phe Leu Ile Thr
            115                 120                 125

Leu Asn Arg Leu Gly Ile Asp Val Ser Phe Val Glu Asn Pro Asp Asp
        130                 135                 140

Pro Glu Ser Trp Gln Ala Ala Val Gln Pro Asn Thr Lys Ala Phe Phe
145                 150                 155                 160

Gly Glu Thr Phe Ala Asn Pro Gln Ala Asp Val Leu Asp Ile Pro Ala
                165                 170                 175

Val Ala Glu Val Ala His Arg Asn Ser Val Pro Leu Ile Ile Asp Asn
                180                 185                 190

Thr Ile Ala Thr Ala Ala Leu Val Arg Pro Leu Glu Leu Gly Ala Asp
        195                 200                 205

Val Val Val Ala Ser Leu Thr Lys Phe Tyr Thr Gly Asn Gly Ser Gly
    210                 215                 220

Leu Gly Gly Val Leu Ile Asp Gly Gly Lys Phe Asp Trp Thr Val Glu
225                 230                 235                 240

Lys Asp Gly Lys Pro Val Phe Pro Tyr Phe Val Thr Pro Asp Ala Ala
                245                 250                 255

Tyr His Gly Leu Lys Tyr Ala Asp Leu Gly Ala Pro Ala Phe Gly Leu
                260                 265                 270

Lys Val Arg Val Gly Leu Leu Arg Asp Thr Gly Ser Thr Leu Ser Ala
        275                 280                 285

Phe Asn Ala Trp Ala Ala Val Gln Gly Ile Asp Thr Leu Ser Leu Arg
    290                 295                 300

Leu Glu Arg His Asn Glu Asn Ala Ile Lys Val Ala Glu Phe Leu Asn
305                 310                 315                 320

Asn His Glu Lys Val Glu Lys Val Asn Phe Ala Gly Leu Lys Asp Ser
                325                 330                 335

Pro Trp Tyr Ala Thr Lys Glu Lys Leu Gly Leu Lys Tyr Thr Gly Ser
                340                 345                 350

Val Leu Thr Phe Glu Ile Lys Gly Gly Lys Asp Glu Ala Trp Ala Phe
        355                 360                 365

Ile Asp Ala Leu Lys Leu His Ser Asn Leu Ala Asn Ile Gly Asp Val
    370                 375                 380

Arg Ser Leu Val Val His Pro Ala Thr Thr Thr His Ser Gln Ser Asp
385                 390                 395                 400

Glu Ala Gly Leu Ala Arg Ala Gly Val Thr Gln Ser Thr Val Arg Leu
                405                 410                 415

Ser Val Gly Ile Glu Thr Ile Asp Asp Ile Ile Ala Asp Leu Glu Gly
                420                 425                 430

Gly Phe Ala Ala Ile
            435
```

-continued

```
<210> SEQ ID NO 3
<211> LENGTH: 1495
<212> TYPE: DNA
<213> ORGANISM: Corynebacterium glutamicum
<220> FEATURE:
<221> NAME/KEY: CDS
<222> LOCATION: (287)..(1264)

<400> SEQUENCE: 3
ccatggtttc tcagcggaa acggcttggc tatcagcact ttcacccgaa cagcctgcaa      60
gaagtgcgac ggctaacagg gctgggattg tcctcaactt cacttcgggc tccttcttag    120
taataggttc gtagaaaagt ttactagcct agagagtatg cgatttcctg aactcgaaga    180
attgaagaat cgccggacct tgaaatggac ccggtttcca gaagacgtgc ttcctttgtg    240
ggttgcggaa agtgattttg gcacctgccc gcagttgaag gaagct atg gca gat       295
                                                   Met Ala Asp
                                                     1 gcc gtt gag cgc gag gtc ttc gga tac cca cca gat gct act ggg ttg      343
Ala Val Glu Arg Glu Val Phe Gly Tyr Pro Pro Asp Ala Thr Gly Leu
      5                  10                  15 aat gat gcg ttg act gga ttc tac gag cgt cgc tat ggg ttt ggc cca      391
Asn Asp Ala Leu Thr Gly Phe Tyr Glu Arg Arg Tyr Gly Phe Gly Pro
 20                  25                  30                  35 aat ccg gaa agt gtt ttc gcc att ccg gat gtg gtt cgt ggc ctg aag      439
Asn Pro Glu Ser Val Phe Ala Ile Pro Asp Val Val Arg Gly Leu Lys
                 40                  45                  50 ctt gcc att gag cat ttc act aag cct ggt tcg gcg atc att gtg ccg      487
Leu Ala Ile Glu His Phe Thr Lys Pro Gly Ser Ala Ile Ile Val Pro
             55                  60                  65 ttg cct gca tac cct cct ttc att gag ttg cct aag gtg act ggt cgt      535
Leu Pro Ala Tyr Pro Pro Phe Ile Glu Leu Pro Lys Val Thr Gly Arg
         70                  75                  80 cag gcg atc tac att gat gcg cat gag tac gat ttg aag gaa att gag      583
Gln Ala Ile Tyr Ile Asp Ala His Glu Tyr Asp Leu Lys Glu Ile Glu
     85                  90                  95 aag gcc ttc gct gac ggt gcg gga tca ctg ttg ttc tgc aat cca cac      631
Lys Ala Phe Ala Asp Gly Ala Gly Ser Leu Leu Phe Cys Asn Pro His
100                 105                 110                 115 aac cca ctg ggc acg gtc ttt tct gaa gag tac atc cgc gag ctc acc      679
Asn Pro Leu Gly Thr Val Phe Ser Glu Glu Tyr Ile Arg Glu Leu Thr
                120                 125                 130 gat att gcg gcg aag tac gat gcc cgc atc atc gtc gat gag atc cac      727
Asp Ile Ala Ala Lys Tyr Asp Ala Arg Ile Ile Val Asp Glu Ile His
            135                 140                 145 gcg cca ctg gtt tat gaa ggc acc cat gtg gtt gct gct ggt gtt tct      775
Ala Pro Leu Val Tyr Glu Gly Thr His Val Val Ala Ala Gly Val Ser
        150                 155                 160 gag aac gct gca aac act tgc atc acc atc acc gca act tct aag gcg      823
Glu Asn Ala Ala Asn Thr Cys Ile Thr Ile Thr Ala Thr Ser Lys Ala
    165                 170                 175 tgg aac act gct ggt ttg aag tgt gct cag atc ttc ttc agt aat gaa      871
Trp Asn Thr Ala Gly Leu Lys Cys Ala Gln Ile Phe Phe Ser Asn Glu
180                 185                 190                 195 gcc gat gtg aag gcc tgg aag aat ttg tcg gat att acc cgt gac ggt      919
Ala Asp Val Lys Ala Trp Lys Asn Leu Ser Asp Ile Thr Arg Asp Gly
                200                 205                 210 gtg tcc atc ctt gga ttg atc gct gcg gag aca gtg tac aac gag ggc      967
Val Ser Ile Leu Gly Leu Ile Ala Ala Glu Thr Val Tyr Asn Glu Gly
            215                 220                 225
```

```
gaa gaa ttc ctt gat gag tca att cag att ctc aag gac aac cgt gac       1015
Glu Glu Phe Leu Asp Glu Ser Ile Gln Ile Leu Lys Asp Asn Arg Asp
        230                 235                 240 ttt gcg gct gct gaa ctg gaa aag ctt ggc gtg aag gtc tac gca ccg       1063
Phe Ala Ala Ala Glu Leu Glu Lys Leu Gly Val Lys Val Tyr Ala Pro
245                 250                 255 gac tcc act tat ttg atg tgg ttg gac ttc gct ggc acc aag atc gaa       1111
Asp Ser Thr Tyr Leu Met Trp Leu Asp Phe Ala Gly Thr Lys Ile Glu
260                 265                 270                 275 gag gcg cct tct aaa att ctt cgt gag gag ggt aag gtc atg ctg aat       1159
Glu Ala Pro Ser Lys Ile Leu Arg Glu Glu Gly Lys Val Met Leu Asn
            280                 285                 290 gat ggc gca gct ttt ggt ggt ttc acc acc tgc gct cgt ctt aat ttt       1207
Asp Gly Ala Ala Phe Gly Gly Phe Thr Thr Cys Ala Arg Leu Asn Phe
        295                 300                 305 gcg tgt tcc aga gag acc ctt gag gag ggg ctg cgc cgt atc gcc agc       1255
Ala Cys Ser Arg Glu Thr Leu Glu Glu Gly Leu Arg Arg Ile Ala Ser
    310                 315                 320 gtg ttg taa ataatgagta aaaagtctgt cctgattact tctttgatgc               1304
Val Leu
    325 tgttttccat gttcttcgga gctggaaacc tcatcttccc gccgatgctt ggattgtcgg     1364 caggaaccaa ctatctacca gctatcttag gatttctagc aacgagtgtt ctgctcccgg     1424 tgctggcgat tatcgcggtg gtgttgtcgg gagaaaatgt caaggacatg gcttctcgtg     1484 gcggtaagat c                                                          1495

<210> SEQ ID NO 4
<211> LENGTH: 325
<212> TYPE: PRT
<213> ORGANISM: Corynebacterium glutamicum

<400> SEQUENCE: 4

Met Ala Asp Ala Val Glu Arg Glu Val Phe Gly Tyr Pro Pro Asp Ala
1               5                   10                  15

Thr Gly Leu Asn Asp Ala Leu Thr Gly Phe Tyr Glu Arg Arg Tyr Gly
            20                  25                  30

Phe Gly Pro Asn Pro Glu Ser Val Phe Ala Ile Pro Asp Val Val Arg
        35                  40                  45

Gly Leu Lys Leu Ala Ile Glu His Phe Thr Lys Pro Gly Ser Ala Ile
    50                  55                  60

Ile Val Pro Leu Pro Ala Tyr Pro Pro Ile Glu Leu Pro Lys Val
65                  70                  75                  80

Thr Gly Arg Gln Ala Ile Tyr Ile Asp Ala His Glu Tyr Asp Leu Lys
                85                  90                  95

Glu Ile Glu Lys Ala Phe Ala Asp Gly Ala Gly Ser Leu Leu Phe Cys
            100                 105                 110

Asn Pro His Asn Pro Leu Gly Thr Val Phe Ser Glu Glu Tyr Ile Arg
        115                 120                 125

Glu Leu Thr Asp Ile Ala Ala Lys Tyr Asp Ala Arg Ile Ile Val Asp
    130                 135                 140

Glu Ile His Ala Pro Leu Val Tyr Glu Gly Thr His Val Val Ala Ala
145                 150                 155                 160

Gly Val Ser Glu Asn Ala Ala Asn Thr Cys Ile Thr Ile Thr Ala Thr
                165                 170                 175

Ser Lys Ala Trp Asn Thr Ala Gly Leu Lys Cys Ala Gln Ile Phe Phe
            180                 185                 190
```

```
Ser Asn Glu Ala Asp Val Lys Ala Trp Lys Asn Leu Ser Asp Ile Thr
        195                 200                 205

Arg Asp Gly Val Ser Ile Leu Gly Leu Ile Ala Ala Glu Thr Val Tyr
    210                 215                 220

Asn Glu Gly Glu Glu Phe Leu Asp Glu Ser Ile Gln Ile Leu Lys Asp
225                 230                 235                 240

Asn Arg Asp Phe Ala Ala Ala Glu Leu Glu Lys Leu Gly Val Lys Val
                245                 250                 255

Tyr Ala Pro Asp Ser Thr Tyr Leu Met Trp Leu Asp Phe Ala Gly Thr
                260                 265                 270

Lys Ile Glu Glu Ala Pro Ser Lys Ile Leu Arg Glu Glu Gly Lys Val
        275                 280                 285

Met Leu Asn Asp Gly Ala Ala Phe Gly Gly Phe Thr Thr Cys Ala Arg
    290                 295                 300

Leu Asn Phe Ala Cys Ser Arg Glu Thr Leu Glu Glu Gly Leu Arg Arg
305                 310                 315                 320

Ile Ala Ser Val Leu
                325

<210> SEQ ID NO 5
<211> LENGTH: 1033
<212> TYPE: DNA
<213> ORGANISM: Corynebacterium glutamicum
<220> FEATURE:
<221> NAME/KEY: CDS
<222> LOCATION: (101)..(1006)

<400> SEQUENCE: 5
gtgcggatcg ggtatccgcg ctacacttag aggtgttaga gatcatgagt ttccacgaac      60
tgtaacgcag gattcaccaa tcaatgaaag gtcgaccgac atg agc act gaa gac     115
                                            Met Ser Thr Glu Asp
                                              1               5 att gtc gtc gta gca gta gat ggc tcg gac gcc tca aaa caa gct gtt     163
Ile Val Val Val Ala Val Asp Gly Ser Asp Ala Ser Lys Gln Ala Val
            10                  15                  20 cgg tgg gct gca aat acc gcc aac aaa cgt ggc att cca ctt cgc ttg     211
Arg Trp Ala Ala Asn Thr Ala Asn Lys Arg Gly Ile Pro Leu Arg Leu
        25                  30                  35 gct tcc agc tac acc atg cct cag ttc ctc tac gca gag gga atg gtt     259
Ala Ser Ser Tyr Thr Met Pro Gln Phe Leu Tyr Ala Glu Gly Met Val
    40                  45                  50 cca cca caa gag ctt ttc gat gac ctc cag gcc gaa gcc ctg gaa aag     307
Pro Pro Gln Glu Leu Phe Asp Asp Leu Gln Ala Glu Ala Leu Glu Lys
55                  60                  65 att aac gaa gcc cgt gac atc gcc cat gag gta gcg cca gaa atc aag     355
Ile Asn Glu Ala Arg Asp Ile Ala His Glu Val Ala Pro Glu Ile Lys
70                  75                  80                  85 atc ggg cac acc atc gct gaa ggc agt ccc atc gac atg ctg ttg gaa     403
Ile Gly His Thr Ile Ala Glu Gly Ser Pro Ile Asp Met Leu Leu Glu
            90                  95                 100 atg tct ccc gat gcc aca atg atc gtc atg ggt tcc cgc gga ctc ggc     451
Met Ser Pro Asp Ala Thr Met Ile Val Met Gly Ser Arg Gly Leu Gly
        105                 110                 115 gga ctc tcc gga atg gtc atg ggc tcc gtc tcc ggt gca gtg gtc agc     499
Gly Leu Ser Gly Met Val Met Gly Ser Val Ser Gly Ala Val Val Ser
    120                 125                 130 cac gca aag tgt cca gtc gtt gtt gtc cgt gaa gac agc gca gtc aac     547
His Ala Lys Cys Pro Val Val Val Val Arg Glu Asp Ser Ala Val Asn
```

```
                            135                 140                 145
gaa gac agc aag tac ggc cca gtc gtc gtc ggt gtg gat ggc tcc gaa         595
Glu Asp Ser Lys Tyr Gly Pro Val Val Val Gly Val Asp Gly Ser Glu
150                 155                 160                 165 gtc tcc caa cag gca acc gaa tac gca ttt gcg gaa gct gaa gct cgt         643
Val Ser Gln Gln Ala Thr Glu Tyr Ala Phe Ala Glu Ala Glu Ala Arg
                170                 175                 180 ggc gcc gaa ctc gtt gca gtt cac acc tgg atg gac atg cag gta cag         691
Gly Ala Glu Leu Val Ala Val His Thr Trp Met Asp Met Gln Val Gln
            185                 190                 195 gca tca ctt gca ggt ctt gca gct gct caa cag cag tgg gat gaa gtg         739
Ala Ser Leu Ala Gly Leu Ala Ala Ala Gln Gln Gln Trp Asp Glu Val
        200                 205                 210 gaa cgt cag caa acc gac atg ctg atc gaa cgc ctc gca cca ctg gtg         787
Glu Arg Gln Gln Thr Asp Met Leu Ile Glu Arg Leu Ala Pro Leu Val
    215                 220                 225 gaa aag tac cca agt gta acc gtc aag aag atc atc acc cgt gac cgc         835
Glu Lys Tyr Pro Ser Val Thr Val Lys Lys Ile Ile Thr Arg Asp Arg
230                 235                 240                 245 cca gtt cgc gca ctt gca gaa gca tct gaa aac gcg cag ctc cta gtc         883
Pro Val Arg Ala Leu Ala Glu Ala Ser Glu Asn Ala Gln Leu Leu Val
                250                 255                 260 gtt ggt tcc cat ggt cgt ggc gga ttt aag ggc atg ctc ctt ggc tcc         931
Val Gly Ser His Gly Arg Gly Gly Phe Lys Gly Met Leu Leu Gly Ser
            265                 270                 275 acc tcc cgc gca ctg ctg caa tcc gca ccg tgc cca atg atg gtg gtt         979
Thr Ser Arg Ala Leu Leu Gln Ser Ala Pro Cys Pro Met Met Val Val
        280                 285                 290 cgc cca cct gag aag att aag aag tag tttcttttaa gtttcgatgc cccggtt      1033
Arg Pro Pro Glu Lys Ile Lys Lys
    295                 300

<210> SEQ ID NO 6
<211> LENGTH: 301
<212> TYPE: PRT
<213> ORGANISM: Corynebacterium glutamicum

<400> SEQUENCE: 6

Met Ser Thr Glu Asp Ile Val Val Ala Val Asp Gly Ser Asp Ala
1               5                   10                  15

Ser Lys Gln Ala Val Arg Trp Ala Ala Asn Thr Ala Asn Lys Arg Gly
                20                  25                  30

Ile Pro Leu Arg Leu Ala Ser Ser Tyr Thr Met Pro Gln Phe Leu Tyr
            35                  40                  45

Ala Glu Gly Met Val Pro Pro Gln Glu Leu Phe Asp Asp Leu Gln Ala
        50                  55                  60

Glu Ala Leu Glu Lys Ile Asn Glu Ala Arg Asp Ile Ala His Glu Val
65                  70                  75                  80

Ala Pro Glu Ile Lys Ile Gly His Thr Ile Ala Glu Gly Ser Pro Ile
                85                  90                  95

Asp Met Leu Leu Glu Met Ser Pro Asp Ala Thr Met Ile Val Met Gly
            100                 105                 110

Ser Arg Gly Leu Gly Gly Leu Ser Gly Met Val Met Gly Ser Val Ser
        115                 120                 125

Gly Ala Val Val Ser His Ala Lys Cys Pro Val Val Val Arg Glu
    130                 135                 140

Asp Ser Ala Val Asn Glu Asp Ser Lys Tyr Gly Pro Val Val Val Gly
145                 150                 155                 160
```

```
Val Asp Gly Ser Glu Val Ser Gln Gln Ala Thr Glu Tyr Ala Phe Ala
            165                 170                 175

Glu Ala Glu Ala Arg Gly Ala Glu Leu Val Ala Val His Thr Trp Met
            180                 185                 190

Asp Met Gln Val Gln Ala Ser Leu Ala Gly Leu Ala Ala Ala Gln Gln
            195                 200                 205

Gln Trp Asp Glu Val Glu Arg Gln Thr Asp Met Leu Ile Glu Arg
            210                 215                 220

Leu Ala Pro Leu Val Glu Lys Tyr Pro Ser Val Thr Val Lys Lys Ile
225                 230                 235                 240

Ile Thr Arg Asp Arg Pro Val Arg Ala Leu Ala Glu Ala Ser Glu Asn
            245                 250                 255

Ala Gln Leu Leu Val Val Gly Ser His Gly Arg Gly Phe Lys Gly
            260                 265                 270

Met Leu Leu Gly Ser Thr Ser Arg Ala Leu Leu Gln Ser Ala Pro Cys
            275                 280                 285

Pro Met Met Val Val Arg Pro Pro Glu Lys Ile Lys Lys
            290                 295                 300

<210> SEQ ID NO 7
<211> LENGTH: 948
<212> TYPE: DNA
<213> ORGANISM: Corynebacterium glutamicum
<220> FEATURE:
<221> NAME/KEY: CDS
<222> LOCATION: (101)..(925)
<223> OTHER INFORMATION: RXA02229

<400> SEQUENCE: 7
gctggttcaa cagagaccac cgcgtgtcct gggtcgacgc ctctggcgat cccaccgcac      60
aagccttgga gattttgggt ctacaatagc gagggtgaat ttg acc atc ccc ttt      115
                                              Leu Thr Ile Pro Phe
                                                1               5 gcc aaa ggc cac gcc acc gaa aac gac ttc atc atc atc ccc gat gag      163
Ala Lys Gly His Ala Thr Glu Asn Asp Phe Ile Ile Ile Pro Asp Glu
                10                  15                  20 gat gcg cgc cta gat tta act cca gaa atg gtg gtc acg ctg tgt gac      211
Asp Ala Arg Leu Asp Leu Thr Pro Glu Met Val Val Thr Leu Cys Asp
            25                  30                  35 cgc cgc gcc ggg atc ggt gct gat ggt atc ctc cgc gtg gtt aaa gct      259
Arg Arg Ala Gly Ile Gly Ala Asp Gly Ile Leu Arg Val Val Lys Ala
        40                  45                  50 gca gac gta gaa ggc tcc acg gtc gac cca tcg ctg tgg ttc atg gat      307
Ala Asp Val Glu Gly Ser Thr Val Asp Pro Ser Leu Trp Phe Met Asp
    55                  60                  65 tac cgc aac gcc gat gga tct ttg gct gaa atg tgc ggc aat ggt gtg      355
Tyr Arg Asn Ala Asp Gly Ser Leu Ala Glu Met Cys Gly Asn Gly Val
70                  75                  80                  85 cgc ctg ttc gcg cac tgg ctg tac tcc cgc ggt ctt gtt gat aat acg      403
Arg Leu Phe Ala His Trp Leu Tyr Ser Arg Gly Leu Val Asp Asn Thr
                90                  95                 100 agc ttt gat atc ggt acc cgc gcc ggt gtc cgc cac gtt gat att ttg      451
Ser Phe Asp Ile Gly Thr Arg Ala Gly Val Arg His Val Asp Ile Leu
            105                 110                 115 cag gca gat caa cat tct gcg cag gtc cgc gtt gat atg ggc atc cct      499
Gln Ala Asp Gln His Ser Ala Gln Val Arg Val Asp Met Gly Ile Pro
        120                 125                 130 gac gtc acg gga tta tcc acc tgc gac atc aac ggc caa gta ttc gct      547
```

```
Asp Val Thr Gly Leu Ser Thr Cys Asp Ile Asn Gly Gln Val Phe Ala
            135                 140                 145 ggc ctt ggc gtt gat atg ggt aac cca cac cta gcg tgc gtt gtg ccg        595
Gly Leu Gly Val Asp Met Gly Asn Pro His Leu Ala Cys Val Val Pro
150                 155                 160                 165 ggc tta agt gcg tcg gct ctt gcc gat atg gaa ctg cgc gca cct acg        643
Gly Leu Ser Ala Ser Ala Leu Ala Asp Met Glu Leu Arg Ala Pro Thr
                170                 175                 180 ttt gat cag gaa ttc ttc ccc cac ggt gtg aac gta gaa atc gtc aca        691
Phe Asp Gln Glu Phe Phe Pro His Gly Val Asn Val Glu Ile Val Thr
            185                 190                 195 gaa tta gaa gat gac gca gta tcg atg cgc gtg tgg gaa cgc gga gtg        739
Glu Leu Glu Asp Asp Ala Val Ser Met Arg Val Trp Glu Arg Gly Val
        200                 205                 210 ggc gaa acc cgc tcc tgt ggc acg gga acc gtt gct gca gcg tgt gct        787
Gly Glu Thr Arg Ser Cys Gly Thr Gly Thr Val Ala Ala Cys Ala
    215                 220                 225 gct tta gct gat gct gga ttg gga gaa ggc aca gct aaa gtg tgc gtt        835
Ala Leu Ala Asp Ala Gly Leu Gly Glu Gly Thr Ala Lys Val Cys Val
230                 235                 240                 245 cca cgt ggg gaa gta gaa gtc cag atc ttt gac gac ggc tcc aca ctc        883
Pro Arg Gly Glu Val Glu Val Gln Ile Phe Asp Asp Gly Ser Thr Leu
                250                 255                 260 acc ggc cca agc gcc atc atc gca ctc ggt gag gtg cag atc                925
Thr Gly Pro Ser Ala Ile Ile Ala Leu Gly Glu Val Gln Ile
            265                 270                 275 taagattcgc gattgtagtt cgg                                              948

<210> SEQ ID NO 8
<211> LENGTH: 275
<212> TYPE: PRT
<213> ORGANISM: Corynebacterium glutamicum

<400> SEQUENCE: 8

Leu Thr Ile Pro Phe Ala Lys Gly His Ala Thr Glu Asn Asp Phe Ile
 1               5                  10                  15

Ile Ile Pro Asp Glu Asp Ala Arg Leu Asp Leu Thr Pro Glu Met Val
            20                  25                  30

Val Thr Leu Cys Asp Arg Arg Ala Gly Ile Gly Ala Asp Gly Ile Leu
        35                  40                  45

Arg Val Val Lys Ala Ala Asp Val Glu Gly Ser Thr Val Asp Pro Ser
    50                  55                  60

Leu Trp Phe Met Asp Tyr Arg Asn Ala Asp Gly Ser Leu Ala Glu Met
65                  70                  75                  80

Cys Gly Asn Gly Val Arg Leu Phe Ala His Trp Leu Tyr Ser Arg Gly
                85                  90                  95

Leu Val Asp Asn Thr Ser Phe Asp Ile Gly Thr Arg Ala Gly Val Arg
            100                 105                 110

His Val Asp Ile Leu Gln Ala Asp Gln His Ser Ala Gln Val Arg Val
        115                 120                 125

Asp Met Gly Ile Pro Asp Val Thr Gly Leu Ser Thr Cys Asp Ile Asn
    130                 135                 140

Gly Gln Val Phe Ala Gly Leu Gly Val Asp Met Gly Asn Pro His Leu
145                 150                 155                 160

Ala Cys Val Val Pro Gly Leu Ser Ala Ser Ala Leu Ala Asp Met Glu
                165                 170                 175

Leu Arg Ala Pro Thr Phe Asp Gln Glu Phe Phe Pro His Gly Val Asn
```

-continued

```
                    180                 185                 190
Val Glu Ile Val Thr Glu Leu Glu Asp Asp Ala Val Ser Met Arg Val
        195                 200                 205

Trp Glu Arg Gly Val Gly Glu Thr Arg Ser Cys Gly Thr Gly Thr Val
        210                 215                 220

Ala Ala Ala Cys Ala Ala Leu Ala Asp Ala Gly Leu Gly Glu Gly Thr
225                 230                 235                 240

Ala Lys Val Cys Val Pro Arg Gly Glu Val Glu Val Gln Ile Phe Asp
                    245                 250                 255

Asp Gly Ser Thr Leu Thr Gly Pro Ser Ala Ile Ala Leu Gly Glu
        260                 265                 270

Val Gln Ile
        275

<210> SEQ ID NO 9
<211> LENGTH: 1491
<212> TYPE: DNA
<213> ORGANISM: Corynebacterium glutamicum
<220> FEATURE:
<221> NAME/KEY: CDS
<222> LOCATION: (101)..(1468)
<223> OTHER INFORMATION: RXS02970

<400> SEQUENCE: 9
```

| | | |
|---|---|---|
| aaccgacaaa acagccgttc acgtgctaaa gcagctcggc ttgatctagg gtgaggtgag | | 60 |
| ttatttaaag acttcataat attttgggga gtgaactggt ttg gca ttg aag ggt<br>Leu Ala Leu Lys Gly<br>1                                 5 | | 115 |
| tac acc aac ttt gac ggt gaa ttc atc gaa ttc gga tct gtg caa gca<br>Tyr Thr Asn Phe Asp Gly Glu Phe Ile Glu Phe Gly Ser Val Gln Ala<br>          10                   15                   20 | | 163 |
| aaa gaa gag gaa aaa cgg gca ttc gac aac gat cgc gcg cac gtt ttc<br>Lys Glu Glu Glu Lys Arg Ala Phe Asp Asn Asp Arg Ala His Val Phe<br>           25                    30                  35 | | 211 |
| cac tcc tgg tcc gcg cag gac aaa atc agc ccc aaa gta tgg gca gct<br>His Ser Trp Ser Ala Gln Asp Lys Ile Ser Pro Lys Val Trp Ala Ala<br>      40                    45                  50 | | 259 |
| gcc gaa ggt tcc acg ctg tac gac ttc gac ggc aac gcc ttc atc gac<br>Ala Glu Gly Ser Thr Leu Tyr Asp Phe Asp Gly Asn Ala Phe Ile Asp<br>55                      60                      65 | | 307 |
| atg ggt tcc caa ctt gtc tcg gca aac tta ggc cac aac aac cct cga<br>Met Gly Ser Gln Leu Val Ser Ala Asn Leu Gly His Asn Asn Pro Arg<br>70                      75                      80                  85 | | 355 |
| tta gtt gag gcg atc cag cgc caa gca gcc cgg ttg acc aac atc aac<br>Leu Val Glu Ala Ile Gln Arg Gln Ala Ala Arg Leu Thr Asn Ile Asn<br>                90                    95                  100 | | 403 |
| ccg gcc ttc ggc aat gat gtg cgc tct gat gtt gct gca aag atc gtg<br>Pro Ala Phe Gly Asn Asp Val Arg Ser Asp Val Ala Ala Lys Ile Val<br>           105                    110                  115 | | 451 |
| tcg atg gcc cgt ggc gaa ttc tcc cac gtg ttt ttc acc aac ggc ggc<br>Ser Met Ala Arg Gly Glu Phe Ser His Val Phe Phe Thr Asn Gly Gly<br>      120                    125                  130 | | 499 |
| gcc gac gcc atc gag cac tcc atc cgc atg gct cgc ctg cac acc gga<br>Ala Asp Ala Ile Glu His Ser Ile Arg Met Ala Arg Leu His Thr Gly<br>135                      140                  145 | | 547 |
| cgc aac aaa att ctg tcc gca tac cgc agc tac cac ggc gca acc gga<br>Arg Asn Lys Ile Leu Ser Ala Tyr Arg Ser Tyr His Gly Ala Thr Gly<br>150                      155                  160                  165 | | 595 |
| tcc gcg atg atg ctc acc ggc gaa cac cgc cgc ctg ggc aac ccc acc | | 643 |

```
Ser Ala Met Met Leu Thr Gly Glu His Arg Arg Leu Gly Asn Pro Thr
                170                 175                 180 acc gac cca gat atc tac cac ttc tgg gca cca ttc ctg cac cac tcc          691
Thr Asp Pro Asp Ile Tyr His Phe Trp Ala Pro Phe Leu His His Ser
            185                 190                 195 tca ttc ttt gcc acc acc caa gaa gaa gaa tgc gaa cgc gca ctc aag          739
Ser Phe Phe Ala Thr Thr Gln Glu Glu Glu Cys Glu Arg Ala Leu Lys
        200                 205                 210 cac ttg gaa gat gtc atc gcg ttt gaa ggt gct ggc atg atc gca gcg          787
His Leu Glu Asp Val Ile Ala Phe Glu Gly Ala Gly Met Ile Ala Ala
    215                 220                 225 atc gtc ctg gag cca gtg gtg gga tca tca gga atc atc ctg cca cca          835
Ile Val Leu Glu Pro Val Val Gly Ser Ser Gly Ile Ile Leu Pro Pro
230                 235                 240                 245 gca ggt tac tta aat ggc gtg cgc gaa ctt tgc aac aag cac ggc atc          883
Ala Gly Tyr Leu Asn Gly Val Arg Glu Leu Cys Asn Lys His Gly Ile
                250                 255                 260 ctc ttc atc gcc gac gaa gtc atg gtc gga ttc gga cgc acc gga aaa          931
Leu Phe Ile Ala Asp Glu Val Met Val Gly Phe Gly Arg Thr Gly Lys
            265                 270                 275 ctg ttt gct tac gag cat gct ggc gac gat ttc cag cca gac atg atc          979
Leu Phe Ala Tyr Glu His Ala Gly Asp Asp Phe Gln Pro Asp Met Ile
        280                 285                 290 acc ttc gcc aag ggt gtt aac gca ggt tac gcc cca ctc ggt ggc atc         1027
Thr Phe Ala Lys Gly Val Asn Ala Gly Tyr Ala Pro Leu Gly Gly Ile
    295                 300                 305 gtg atg acc caa tca atc cgc gat acc ttc gga tca gag gca tac tcc         1075
Val Met Thr Gln Ser Ile Arg Asp Thr Phe Gly Ser Glu Ala Tyr Ser
310                 315                 320                 325 ggc gga ctc acc tac tcc gga cac cca ctt gca gta gca ccc gcc aag         1123
Gly Gly Leu Thr Tyr Ser Gly His Pro Leu Ala Val Ala Pro Ala Lys
                330                 335                 340 gca gcg ctg gag att tac gcg gaa gga gag atc att cca cgc gta gct         1171
Ala Ala Leu Glu Ile Tyr Ala Glu Gly Glu Ile Ile Pro Arg Val Ala
            345                 350                 355 cga ctt ggc gct gaa ctg atc gaa cct cgc ctt cgt gaa cta gcg gaa         1219
Arg Leu Gly Ala Glu Leu Ile Glu Pro Arg Leu Arg Glu Leu Ala Glu
        360                 365                 370 gaa aac gta gcg atc gct gac gtg cgg ggc atc gga ttc ttc tgg gca         1267
Glu Asn Val Ala Ile Ala Asp Val Arg Gly Ile Gly Phe Phe Trp Ala
    375                 380                 385 gtg gag ttc aat gca gac gcc act gcc atg gct gcc ggt gct gca gaa         1315
Val Glu Phe Asn Ala Asp Ala Thr Ala Met Ala Ala Gly Ala Ala Glu
390                 395                 400                 405 ttc aag gaa cgc ggc gtg tgg ccg atg atc tcc ggc aac cga ttc cac         1363
Phe Lys Glu Arg Gly Val Trp Pro Met Ile Ser Gly Asn Arg Phe His
                410                 415                 420 atc gcg ccg ccg ctg acc acc act gat gac gaa ttg gta gca ctg ctg         1411
Ile Ala Pro Pro Leu Thr Thr Thr Asp Asp Glu Leu Val Ala Leu Leu
            425                 430                 435 gac gcg gtg gaa gct gca gcc caa gct gtc gag ctg acc ttc gct ggg         1459
Asp Ala Val Glu Ala Ala Ala Gln Ala Val Glu Leu Thr Phe Ala Gly
        440                 445                 450 gcg ttg ttc taagttttct agataacaag gcc                                    1491
Ala Leu Phe
    455

<210> SEQ ID NO 10
<211> LENGTH: 456
<212> TYPE: PRT
```

<213> ORGANISM: Corynebacterium glutamicum

<400> SEQUENCE: 10

| | | | | | | | | | | | | | | |
|---|---|---|---|---|---|---|---|---|---|---|---|---|---|---|
| Leu | Ala | Leu | Lys | Gly | Tyr | Thr | Asn | Phe | Asp | Gly | Glu | Phe | Ile | Glu | Phe |
| 1 | | | | 5 | | | | | 10 | | | | | 15 | |
| Gly | Ser | Val | Gln | Ala | Lys | Glu | Glu | Lys | Arg | Ala | Phe | Asp | Asn | Asp | |
| | | | 20 | | | | | 25 | | | | | 30 | | |
| Arg | Ala | His | Val | Phe | His | Ser | Trp | Ser | Ala | Gln | Asp | Lys | Ile | Ser | Pro |
| | | 35 | | | | | 40 | | | | | 45 | | | |
| Lys | Val | Trp | Ala | Ala | Ala | Glu | Gly | Ser | Thr | Leu | Tyr | Asp | Phe | Asp | Gly |
| | 50 | | | | | 55 | | | | | 60 | | | | |
| Asn | Ala | Phe | Ile | Asp | Met | Gly | Ser | Gln | Leu | Val | Ser | Ala | Asn | Leu | Gly |
| 65 | | | | | 70 | | | | | 75 | | | | | 80 |
| His | Asn | Asn | Pro | Arg | Leu | Val | Glu | Ala | Ile | Gln | Arg | Gln | Ala | Ala | Arg |
| | | | | 85 | | | | | 90 | | | | | 95 | |
| Leu | Thr | Asn | Ile | Asn | Pro | Ala | Phe | Gly | Asn | Asp | Val | Arg | Ser | Asp | Val |
| | | | 100 | | | | | 105 | | | | | 110 | | |
| Ala | Ala | Lys | Ile | Val | Ser | Met | Ala | Arg | Gly | Glu | Phe | Ser | His | Val | Phe |
| | | 115 | | | | | 120 | | | | | 125 | | | |
| Phe | Thr | Asn | Gly | Gly | Ala | Asp | Ala | Ile | Glu | His | Ser | Ile | Arg | Met | Ala |
| | 130 | | | | | 135 | | | | | 140 | | | | |
| Arg | Leu | His | Thr | Gly | Arg | Asn | Lys | Ile | Leu | Ser | Ala | Tyr | Arg | Ser | Tyr |
| 145 | | | | | 150 | | | | | 155 | | | | | 160 |
| His | Gly | Ala | Thr | Gly | Ser | Ala | Met | Met | Leu | Thr | Gly | Glu | His | Arg | Arg |
| | | | | 165 | | | | | 170 | | | | | 175 | |
| Leu | Gly | Asn | Pro | Thr | Thr | Asp | Pro | Asp | Ile | Tyr | His | Phe | Trp | Ala | Pro |
| | | | 180 | | | | | 185 | | | | | 190 | | |
| Phe | Leu | His | His | Ser | Ser | Phe | Phe | Ala | Thr | Thr | Gln | Glu | Glu | Cys | |
| | | 195 | | | | | 200 | | | | | 205 | | | |
| Glu | Arg | Ala | Leu | Lys | His | Leu | Glu | Asp | Val | Ile | Ala | Phe | Glu | Gly | Ala |
| | 210 | | | | | 215 | | | | | 220 | | | | |
| Gly | Met | Ile | Ala | Ala | Ile | Val | Leu | Glu | Pro | Val | Val | Gly | Ser | Ser | Gly |
| 225 | | | | | 230 | | | | | 235 | | | | | 240 |
| Ile | Ile | Leu | Pro | Pro | Ala | Gly | Tyr | Leu | Asn | Gly | Val | Arg | Glu | Leu | Cys |
| | | | | 245 | | | | | 250 | | | | | 255 | |
| Asn | Lys | His | Gly | Ile | Leu | Phe | Ile | Ala | Asp | Glu | Val | Met | Val | Gly | Phe |
| | | | 260 | | | | | 265 | | | | | 270 | | |
| Gly | Arg | Thr | Gly | Lys | Leu | Phe | Ala | Tyr | Glu | His | Ala | Gly | Asp | Asp | Phe |
| | | 275 | | | | | 280 | | | | | 285 | | | |
| Gln | Pro | Asp | Met | Ile | Thr | Phe | Ala | Lys | Gly | Val | Asn | Ala | Gly | Tyr | Ala |
| | 290 | | | | | 295 | | | | | 300 | | | | |
| Pro | Leu | Gly | Gly | Ile | Val | Met | Thr | Gln | Ser | Ile | Arg | Asp | Thr | Phe | Gly |
| 305 | | | | | 310 | | | | | 315 | | | | | 320 |
| Ser | Glu | Ala | Tyr | Ser | Gly | Gly | Leu | Thr | Tyr | Ser | Gly | His | Pro | Leu | Ala |
| | | | | 325 | | | | | 330 | | | | | 335 | |
| Val | Ala | Pro | Ala | Lys | Ala | Ala | Leu | Glu | Ile | Tyr | Ala | Glu | Gly | Glu | Ile |
| | | | 340 | | | | | 345 | | | | | 350 | | |
| Ile | Pro | Arg | Val | Ala | Arg | Leu | Gly | Ala | Glu | Leu | Ile | Glu | Pro | Arg | Leu |
| | | 355 | | | | | 360 | | | | | 365 | | | |
| Arg | Glu | Leu | Ala | Glu | Glu | Asn | Val | Ala | Ile | Ala | Asp | Val | Arg | Gly | Ile |
| | 370 | | | | | 375 | | | | | 380 | | | | |
| Gly | Phe | Phe | Trp | Ala | Val | Glu | Phe | Asn | Ala | Asp | Ala | Thr | Ala | Met | Ala |
| 385 | | | | | 390 | | | | | 395 | | | | | 400 |

```
                Ala Gly Ala Ala Glu Phe Lys Glu Arg Gly Val Trp Pro Met Ile Ser
                                405                 410                 415

Gly Asn Arg Phe His Ile Ala Pro Pro Leu Thr Thr Asp Asp Glu
                            420                 425                 430

Leu Val Ala Leu Leu Asp Ala Val Glu Ala Ala Gln Ala Val Glu
                        435                 440                 445

Leu Thr Phe Ala Gly Ala Leu Phe
                    450                 455

<210> SEQ ID NO 11
<211> LENGTH: 1330
<212> TYPE: DNA
<213> ORGANISM: Corynebacterium glutamicum
<220> FEATURE:
<221> NAME/KEY: CDS
<222> LOCATION: (101)..(1330)
<223> OTHER INFORMATION: FRXA01009

<400> SEQUENCE: 11
aaccgacaaa acagccgttc acgtgctaaa gcagctcggc ttgatctagg gtgaggtgag       60
ttatttaaag acttcataat attttgggga gtgaactggt ttg gca ttg aag ggt      115
                                              Leu Ala Leu Lys Gly
                                                1               5 tac acc aac ttt gac ggt gaa ttc atc gaa ttc gga tct gtg caa gca      163
Tyr Thr Asn Phe Asp Gly Glu Phe Ile Glu Phe Gly Ser Val Gln Ala
                 10                  15                  20 aaa gaa gag gaa aaa cgg gca ttc gac aac gat cgc gcg cac gtt ttc      211
Lys Glu Glu Glu Lys Arg Ala Phe Asp Asn Asp Arg Ala His Val Phe
             25                  30                  35 cac tcc tgg tcc gcg cag gac aaa atc agc ccc aaa gta tgg gca gct      259
His Ser Trp Ser Ala Gln Asp Lys Ile Ser Pro Lys Val Trp Ala Ala
         40                  45                  50 gcc gaa ggt tcc acg ctg tac gac ttc gac ggc aac gcc ttc atc gac      307
Ala Glu Gly Ser Thr Leu Tyr Asp Phe Asp Gly Asn Ala Phe Ile Asp
     55                  60                  65 atg ggt tcc caa ctt gtc tcg gca aac tta ggc cac aac aac cct cga      355
Met Gly Ser Gln Leu Val Ser Ala Asn Leu Gly His Asn Asn Pro Arg
 70                  75                  80                  85 tta gtt gag gcg atc cag cgc caa gca gcc cgg ttg acc aac atc aac      403
Leu Val Glu Ala Ile Gln Arg Gln Ala Ala Arg Leu Thr Asn Ile Asn
                 90                  95                 100 ccg gcc ttc ggc aat gat gtg cgc tct gat gtt gct gca aag atc gtg      451
Pro Ala Phe Gly Asn Asp Val Arg Ser Asp Val Ala Ala Lys Ile Val
            105                 110                 115 tcg atg gcc cgt ggc gaa ttc tcc cac gtg ttt ttc acc aac ggc ggc      499
Ser Met Ala Arg Gly Glu Phe Ser His Val Phe Phe Thr Asn Gly Gly
        120                 125                 130 gcc gac gcc atc gag cac tcc atc cgc atg gct cgc ctg cac acc gga      547
Ala Asp Ala Ile Glu His Ser Ile Arg Met Ala Arg Leu His Thr Gly
    135                 140                 145 cgc aac aaa att ctg tcc gca tac cgc agc tac cac ggc gca acc gga      595
Arg Asn Lys Ile Leu Ser Ala Tyr Arg Ser Tyr His Gly Ala Thr Gly
150                 155                 160                 165 tcc gcg atg atg ctc acc ggc gaa cac cgc cgc ctg ggc aac ccc acc      643
Ser Ala Met Met Leu Thr Gly Glu His Arg Arg Leu Gly Asn Pro Thr
                170                 175                 180 acc gac cca gat atc tac cac ttc tgg gca cca ttc ctg cac cac tcc      691
Thr Asp Pro Asp Ile Tyr His Phe Trp Ala Pro Phe Leu His His Ser
            185                 190                 195 tca ttc ttt gcc acc acc caa gaa gaa gaa tgc gaa cgc gca ctc aag      739
```

```
Ser Phe Phe Ala Thr Thr Gln Glu Glu Cys Glu Arg Ala Leu Lys
        200                 205                 210 cac ttg gaa gat gtc atc gcg ttt gaa ggt gct ggc atg atc gca gcg     787
His Leu Glu Asp Val Ile Ala Phe Glu Gly Ala Gly Met Ile Ala Ala
        215                 220                 225 atc gtc ctg gag cca gtg gtg gga tca tca gga atc atc ctg cca cca     835
Ile Val Leu Glu Pro Val Val Gly Ser Ser Gly Ile Ile Leu Pro Pro
230                 235                 240                 245 gca ggt tac tta aat ggc gtg cgc gaa ctt tgc aac aag cac ggc atc     883
Ala Gly Tyr Leu Asn Gly Val Arg Glu Leu Cys Asn Lys His Gly Ile
            250                 255                 260 ctc ttc atc gcc gac gaa gtc atg gtc gga ttc gga cgc acc gga aaa     931
Leu Phe Ile Ala Asp Glu Val Met Val Gly Phe Gly Arg Thr Gly Lys
                265                 270                 275 ctg ttt gct tac gag cat gct ggc gac gat ttc cag cca gac atg atc     979
Leu Phe Ala Tyr Glu His Ala Gly Asp Asp Phe Gln Pro Asp Met Ile
        280                 285                 290 acc ttc gcc aag ggt gtt aac gca ggt tac gcc cca ctc ggt ggc atc    1027
Thr Phe Ala Lys Gly Val Asn Ala Gly Tyr Ala Pro Leu Gly Gly Ile
        295                 300                 305 gtg atg acc caa tca atc cgc gat acc ttc gga tca gag gca tac tcc    1075
Val Met Thr Gln Ser Ile Arg Asp Thr Phe Gly Ser Glu Ala Tyr Ser
310                 315                 320                 325 ggc gga ctc acc tac tcc gga cac cca ctt gca gta gca ccc gcc aag    1123
Gly Gly Leu Thr Tyr Ser Gly His Pro Leu Ala Val Ala Pro Ala Lys
                330                 335                 340 gca gcg ctg gag att tac gcg gaa gga gag atc att cca cgc gta gct    1171
Ala Ala Leu Glu Ile Tyr Ala Glu Gly Glu Ile Ile Pro Arg Val Ala
            345                 350                 355 cga ctt ggc gct gaa ctg atc gaa cct cgc ctt cgt gaa cta gcg gaa    1219
Arg Leu Gly Ala Glu Leu Ile Glu Pro Arg Leu Arg Glu Leu Ala Glu
        360                 365                 370 gaa aac gta gcg atc gct gac gtg cgg ggc atc gga ttc ttc tgg gca    1267
Glu Asn Val Ala Ile Ala Asp Val Arg Gly Ile Gly Phe Phe Trp Ala
        375                 380                 385 gtg gag ttc aat gca gac gcc act gcc atg gct gcc ggt gct gca gaa    1315
Val Glu Phe Asn Ala Asp Ala Thr Ala Met Ala Ala Gly Ala Ala Glu
390                 395                 400                 405 ttc aag gaa cgc ggc                                                 1330
Phe Lys Glu Arg Gly
            410

<210> SEQ ID NO 12
<211> LENGTH: 410
<212> TYPE: PRT
<213> ORGANISM: Corynebacterium glutamicum

<400> SEQUENCE: 12

Leu Ala Leu Lys Gly Tyr Thr Asn Phe Asp Gly Glu Phe Ile Glu Phe
1               5                   10                  15

Gly Ser Val Gln Ala Lys Glu Glu Lys Arg Ala Phe Asp Asn Asp
            20                  25                  30

Arg Ala His Val Phe His Ser Trp Ser Ala Gln Asp Lys Ile Ser Pro
        35                  40                  45

Lys Val Trp Ala Ala Ala Glu Gly Ser Thr Leu Tyr Asp Phe Asp Gly
    50                  55                  60

Asn Ala Phe Ile Asp Met Gly Ser Gln Leu Val Ser Ala Asn Leu Gly
65                  70                  75                  80

His Asn Asn Pro Arg Leu Val Glu Ala Ile Gln Arg Gln Ala Ala Arg
```

-continued

```
                85                  90                  95
Leu Thr Asn Ile Asn Pro Ala Phe Gly Asn Asp Val Arg Ser Asp Val
            100                 105                 110
Ala Ala Lys Ile Val Ser Met Ala Arg Gly Glu Phe Ser His Val Phe
        115                 120                 125
Phe Thr Asn Gly Gly Ala Asp Ala Ile Glu His Ser Ile Arg Met Ala
    130                 135                 140
Arg Leu His Thr Gly Arg Asn Lys Ile Leu Ser Ala Tyr Arg Ser Tyr
145                 150                 155                 160
His Gly Ala Thr Gly Ser Ala Met Met Leu Thr Gly Glu His Arg Arg
                165                 170                 175
Leu Gly Asn Pro Thr Thr Asp Pro Asp Ile Tyr His Phe Trp Ala Pro
            180                 185                 190
Phe Leu His His Ser Ser Phe Ala Thr Thr Gln Glu Glu Glu Cys
        195                 200                 205
Glu Arg Ala Leu Lys His Leu Glu Asp Val Ile Ala Phe Glu Gly Ala
    210                 215                 220
Gly Met Ile Ala Ala Ile Val Leu Glu Pro Val Val Gly Ser Ser Gly
225                 230                 235                 240
Ile Ile Leu Pro Pro Ala Gly Tyr Leu Asn Gly Val Arg Glu Leu Cys
                245                 250                 255
Asn Lys His Gly Ile Leu Phe Ile Ala Asp Glu Val Met Val Gly Phe
            260                 265                 270
Gly Arg Thr Gly Lys Leu Phe Ala Tyr Glu His Ala Gly Asp Asp Phe
        275                 280                 285
Gln Pro Asp Met Ile Thr Phe Ala Lys Gly Val Asn Ala Gly Tyr Ala
    290                 295                 300
Pro Leu Gly Gly Ile Val Met Thr Gln Ser Ile Arg Asp Thr Phe Gly
305                 310                 315                 320
Ser Glu Ala Tyr Ser Gly Gly Leu Thr Tyr Ser Gly His Pro Leu Ala
                325                 330                 335
Val Ala Pro Ala Lys Ala Ala Leu Glu Ile Tyr Ala Glu Gly Glu Ile
            340                 345                 350
Ile Pro Arg Val Ala Arg Leu Gly Ala Glu Leu Ile Glu Pro Arg Leu
        355                 360                 365
Arg Glu Leu Ala Glu Glu Asn Val Ala Ile Ala Asp Val Arg Gly Ile
    370                 375                 380
Gly Phe Phe Trp Ala Val Glu Phe Asn Ala Asp Ala Thr Ala Met Ala
385                 390                 395                 400
Ala Gly Ala Ala Glu Phe Lys Glu Arg Gly
                405                 410
```

<210> SEQ ID NO 13
<211> LENGTH: 792
<212> TYPE: DNA
<213> ORGANISM: Corynebacterium glutamicum
<220> FEATURE:
<221> NAME/KEY: CDS
<222> LOCATION: (101)..(769)
<223> OTHER INFORMATION: RXC02390

<400> SEQUENCE: 13

```
gctggtggtg ctgacccata cgctggaact ccaactgctg ttgataccgc caagatgttt    60
ggccgcgagg atctcgtagc tcgcttcgag tcataggccg gtg gag tgg acc gct   115
                                            Val Glu Trp Thr Ala
                                            1               5
```

```
ttt ggc acc ctg att ctg ctc aat ttg gtg ggc agt tta tcc ccg ggg      163
Phe Gly Thr Leu Ile Leu Leu Asn Leu Val Gly Ser Leu Ser Pro Gly
             10                  15                  20 cct gat acc ttt ttc ctc ctc cgc tta gcc acc cgc tcc aga gcg cac      211
Pro Asp Thr Phe Phe Leu Leu Arg Leu Ala Thr Arg Ser Arg Ala His
                 25                  30                  35 gcg atc gct ggc gtc gcc ggc atc gtc acc gga ctc acg gtg tgg gtg      259
Ala Ile Ala Gly Val Ala Gly Ile Val Thr Gly Leu Thr Val Trp Val
             40                  45                  50 acg ctg acg gtc gtg gga gca gcg gcg ctg ctc acc act tat ccg tcg      307
Thr Leu Thr Val Val Gly Ala Ala Ala Leu Leu Thr Thr Tyr Pro Ser
 55                  60                  65 att ctc gga atc atc cag ctc gtc ggc ggc acg tac cta agc ttc att      355
Ile Leu Gly Ile Ile Gln Leu Val Gly Gly Thr Tyr Leu Ser Phe Ile
 70                  75                  80                  85 ggg tac aag ttg ctg cgc tcg gcg tcg aga gag ctt atc gac gcc cgc      403
Gly Tyr Lys Leu Leu Arg Ser Ala Ser Arg Glu Leu Ile Asp Ala Arg
                 90                  95                 100 cag ttc cgt ttc aac gcc gat gcc cga cct atc ccg gat gcg gta gaa      451
Gln Phe Arg Phe Asn Ala Asp Ala Arg Pro Ile Pro Asp Ala Val Glu
            105                 110                 115 gca ctg gga acc cgc act cag gta tat cga caa ggt ttg gcc acc aac      499
Ala Leu Gly Thr Arg Thr Gln Val Tyr Arg Gln Gly Leu Ala Thr Asn
            120                 125                 130 ctg tca aac cct aaa gtt gtc atg tac ttc gcg gca att ctg gct ccg      547
Leu Ser Asn Pro Lys Val Val Met Tyr Phe Ala Ala Ile Leu Ala Pro
135                 140                 145 ttg atg cca gcg cac cca tca ccg gtg ctg gcg ttc tct atc atc gtg      595
Leu Met Pro Ala His Pro Ser Pro Val Leu Ala Phe Ser Ile Ile Val
150                 155                 160                 165 gcg att tta gtg cag acc ttt gtt acc ttc tct gct gtg tgc ctc att      643
Ala Ile Leu Val Gln Thr Phe Val Thr Phe Ser Ala Val Cys Leu Ile
                170                 175                 180 gtc tct acg gag cgt gtg cgc aaa gca atg ctg cgt gca ggt ccc tgg      691
Val Ser Thr Glu Arg Val Arg Lys Ala Met Leu Arg Ala Gly Pro Trp
            185                 190                 195 ttt gac ctg ctt gct ggc gtt gtc ttc ctc gtt gtg ggt gtg act ctg      739
Phe Asp Leu Leu Ala Gly Val Val Phe Leu Val Val Gly Val Thr Leu
            200                 205                 210 ctg tat gaa ggc ctg acc ggt tta ctc ggg taaaggcata aaaatggct         789
Leu Tyr Glu Gly Leu Thr Gly Leu Leu Gly
            215                 220 tcc                                                                   792

<210> SEQ ID NO 14
<211> LENGTH: 223
<212> TYPE: PRT
<213> ORGANISM: Corynebacterium glutamicum

<400> SEQUENCE: 14

Val Glu Trp Thr Ala Phe Gly Thr Leu Ile Leu Leu Asn Leu Val Gly
 1               5                  10                  15

Ser Leu Ser Pro Gly Pro Asp Thr Phe Phe Leu Leu Arg Leu Ala Thr
            20                  25                  30

Arg Ser Arg Ala His Ala Ile Ala Gly Val Ala Gly Ile Val Thr Gly
        35                  40                  45

Leu Thr Val Trp Val Thr Leu Thr Val Val Gly Ala Ala Ala Leu Leu
    50                  55                  60
```

```
Thr Thr Tyr Pro Ser Ile Leu Gly Ile Ile Gln Leu Val Gly Gly Thr
 65                  70                  75                  80

Tyr Leu Ser Phe Ile Gly Tyr Lys Leu Leu Arg Ser Ala Ser Arg Glu
                 85                  90                  95

Leu Ile Asp Ala Arg Gln Phe Arg Phe Asn Ala Asp Ala Arg Pro Ile
            100                 105                 110

Pro Asp Ala Val Glu Ala Leu Gly Thr Arg Thr Gln Val Tyr Arg Gln
        115                 120                 125

Gly Leu Ala Thr Asn Leu Ser Asn Pro Lys Val Val Met Tyr Phe Ala
    130                 135                 140

Ala Ile Leu Ala Pro Leu Met Pro Ala His Pro Ser Pro Val Leu Ala
145                 150                 155                 160

Phe Ser Ile Ile Val Ala Ile Leu Val Gln Thr Phe Val Thr Phe Ser
                165                 170                 175

Ala Val Cys Leu Ile Val Ser Thr Glu Arg Val Arg Lys Ala Met Leu
            180                 185                 190

Arg Ala Gly Pro Trp Phe Asp Leu Leu Ala Gly Val Val Phe Leu Val
        195                 200                 205

Val Gly Val Thr Leu Leu Tyr Glu Gly Leu Thr Gly Leu Leu Gly
    210                 215                 220

<210> SEQ ID NO 15
<211> LENGTH: 897
<212> TYPE: DNA
<213> ORGANISM: Corynebacterium glutamicum
<220> FEATURE:
<221> NAME/KEY: CDS
<222> LOCATION: (101)..(874)
<223> OTHER INFORMATION: RXC01796

<400> SEQUENCE: 15
atgtaactcg atcaggtgga aatgcccgca aaagtggcgg cggtggccga gggatggccg       60
ttggtgcggc atcggtggcc tgctactagt cgggctcttc ttg ctc ctt ggc ggt      115
                                              Leu Leu Leu Gly Gly
                                                1               5 aac cct gcc gag atc gac cag gtt tta ggt ggc gat caa acc cag atc      163
Asn Pro Ala Glu Ile Asp Gln Val Leu Gly Gly Asp Gln Thr Gln Ile
             10                  15                  20 gag tct gga gag tcc acc gga gcc ggc gac ttt gat cac tgc caa acc      211
Glu Ser Gly Glu Ser Thr Gly Ala Gly Asp Phe Asp His Cys Gln Thr
                 25                  30                  35 ggc gca gat gcc aac gcc agt gat gat tgt cgc ctt tac tac acc tca      259
Gly Ala Asp Ala Asn Ala Ser Asp Asp Cys Arg Leu Tyr Tyr Thr Ser
         40                  45                  50 ttc tcc gtc aat gaa atg tgg cag act ttg ctt cca gct cag gct ggt      307
Phe Ser Val Asn Glu Met Trp Gln Thr Leu Leu Pro Ala Gln Ala Gly
 55                  60                  65 atc gaa tac acc gag ccg aca ttg act ctt ttc aaa aac tcc acc caa      355
Ile Glu Tyr Thr Glu Pro Thr Leu Thr Leu Phe Lys Asn Ser Thr Gln
 70                  75                  80                  85 acc ggc tgc ggt ttc gct tct gcg tcc act ggg ccg ttt tac tgt ccg      403
Thr Gly Cys Gly Phe Ala Ser Ala Ser Thr Gly Pro Phe Tyr Cys Pro
                 90                  95                 100 tca gac caa gat gct tat ttt gac ttg act ttc ttc gat cag atg cgt      451
Ser Asp Gln Asp Ala Tyr Phe Asp Leu Thr Phe Phe Asp Gln Met Arg
                105                 110                 115 cag ttc ggt gca gaa aac gcc ccg ctt gcc cag atg tac atc gtg gcg      499
Gln Phe Gly Ala Glu Asn Ala Pro Leu Ala Gln Met Tyr Ile Val Ala
        120                 125                 130
```

```
cac gag tac ggc cac cac gtc caa aac ctc gag ggc aca ctc gga ctg      547
His Glu Tyr Gly His His Val Gln Asn Leu Glu Gly Thr Leu Gly Leu
        135                 140                 145 tcc aat tac aac gat ccg ggc gct gat tcc aac gcc gtc aag atc gag      595
Ser Asn Tyr Asn Asp Pro Gly Ala Asp Ser Asn Ala Val Lys Ile Glu
150                 155                 160                 165 ttg cag gcc gat tgc tac gca ggc att tgg gct aat cac tcc agc gaa      643
Leu Gln Ala Asp Cys Tyr Ala Gly Ile Trp Ala Asn His Ser Ser Glu
                170                 175                 180 ggc ccg gat ccg cta ctc caa ccc atc acc gaa tct gag cta gat tcc      691
Gly Pro Asp Pro Leu Leu Gln Pro Ile Thr Glu Ser Glu Leu Asp Ser
            185                 190                 195 gct ctc ctt gct gca agc gcc gtg ggc gac gac aat atc cag caa cga      739
Ala Leu Leu Ala Ala Ser Ala Val Gly Asp Asp Asn Ile Gln Gln Arg
        200                 205                 210 tcc ggt ggc gat gtc aat cct gaa agc tgg act cac ggc tca tcg cag      787
Ser Gly Gly Asp Val Asn Pro Glu Ser Trp Thr His Gly Ser Ser Gln
215                 220                 225 cag cgc aaa gac gcg ttc ctc gcc ggc tac aac acc ggc cag atg agc      835
Gln Arg Lys Asp Ala Phe Leu Ala Gly Tyr Asn Thr Gly Gln Met Ser
230                 235                 240                 245 gcc tgc gac ttc ctc ggc cgg ggc gtc tac aac gac gct taaagcattg       884
Ala Cys Asp Phe Leu Gly Arg Gly Val Tyr Asn Asp Ala
                250                 255 cttttcgacg tct                                                       897

<210> SEQ ID NO 16
<211> LENGTH: 258
<212> TYPE: PRT
<213> ORGANISM: Corynebacterium glutamicum

<400> SEQUENCE: 16

Leu Leu Leu Gly Gly Asn Pro Ala Glu Ile Asp Gln Val Leu Gly Gly
1               5                   10                  15

Asp Gln Thr Gln Ile Glu Ser Gly Glu Ser Thr Gly Ala Gly Asp Phe
            20                  25                  30

Asp His Cys Gln Thr Gly Ala Asp Ala Asn Ala Ser Asp Asp Cys Arg
        35                  40                  45

Leu Tyr Tyr Thr Ser Phe Ser Val Asn Glu Met Trp Gln Thr Leu Leu
    50                  55                  60

Pro Ala Gln Ala Gly Ile Glu Tyr Thr Glu Pro Thr Leu Thr Leu Phe
65                  70                  75                  80

Lys Asn Ser Thr Gln Thr Gly Cys Gly Phe Ala Ser Ala Ser Thr Gly
                85                  90                  95

Pro Phe Tyr Cys Pro Ser Asp Gln Asp Ala Tyr Phe Asp Leu Thr Phe
            100                 105                 110

Phe Asp Gln Met Arg Gln Phe Gly Ala Glu Asn Ala Pro Leu Ala Gln
        115                 120                 125

Met Tyr Ile Val Ala His Glu Tyr Gly His His Val Gln Asn Leu Glu
    130                 135                 140

Gly Thr Leu Gly Leu Ser Asn Tyr Asn Asp Pro Gly Ala Asp Ser Asn
145                 150                 155                 160

Ala Val Lys Ile Glu Leu Gln Ala Asp Cys Tyr Ala Gly Ile Trp Ala
                165                 170                 175

Asn His Ser Ser Glu Gly Pro Asp Pro Leu Leu Gln Pro Ile Thr Glu
            180                 185                 190
```

-continued

```
Ser Glu Leu Asp Ser Ala Leu Leu Ala Ala Ser Ala Val Gly Asp Asp
        195                 200                 205

Asn Ile Gln Gln Arg Ser Gly Gly Asp Val Asn Pro Glu Ser Trp Thr
210                 215                 220

His Gly Ser Ser Gln Gln Arg Lys Asp Ala Phe Leu Ala Gly Tyr Asn
225                 230                 235                 240

Thr Gly Gln Met Ser Ala Cys Asp Phe Leu Gly Arg Gly Val Tyr Asn
                245                 250                 255

Asp Ala

<210> SEQ ID NO 17
<211> LENGTH: 771
<212> TYPE: DNA
<213> ORGANISM: Corynebacterium glutamicum
<220> FEATURE:
<221> NAME/KEY: CDS
<222> LOCATION: (101)..(748)
<223> OTHER INFORMATION: RXC01207

<400> SEQUENCE: 17
cttcatgatc tcaccggcag agcgcgtttt gttacagcgc gtaaactgtg actttgaaaa      60 attttgaac aatccgtaca ccaacttcag gagaaaaaca gtg agc aga atc tat       115
                                            Val Ser Arg Ile Tyr
                                              1               5 gac tgt gcc gac caa gac tcc cgt gca gca ggc cta aag gcg gct gtc      163
Asp Cys Ala Asp Gln Asp Ser Arg Ala Ala Gly Leu Lys Ala Ala Val
             10                  15                  20 gat gca gtc aaa gcc ggt cag ctc gtt gtc ctt ccc acg gat acc ctt      211
Asp Ala Val Lys Ala Gly Gln Leu Val Val Leu Pro Thr Asp Thr Leu
         25                  30                  35 tat gga ctc ggc tgc gac gct ttc aac aac gag gca gta gcc aac ctt      259
Tyr Gly Leu Gly Cys Asp Ala Phe Asn Asn Glu Ala Val Ala Asn Leu
     40                  45                  50 ctg gcc acc aaa cac cgt ggc ccc gat atg ccc gtt cca gtg ctc gtc      307
Leu Ala Thr Lys His Arg Gly Pro Asp Met Pro Val Pro Val Leu Val
 55                  60                  65 ggc agc tgg gac acc att caa gga ctt gtg cac tcc tat tct gcg cag      355
Gly Ser Trp Asp Thr Ile Gln Gly Leu Val His Ser Tyr Ser Ala Gln
 70                  75                  80                  85 gca aaa gcg ctt gtg gag gcg ttc tgg cct ggt gga ctg tcc atc atc      403
Ala Lys Ala Leu Val Glu Ala Phe Trp Pro Gly Gly Leu Ser Ile Ile
                 90                  95                 100 gtt ccg cag gca cca agc ctt ccg tgg aac ctt ggc gat acc cgt ggc      451
Val Pro Gln Ala Pro Ser Leu Pro Trp Asn Leu Gly Asp Thr Arg Gly
            105                 110                 115 acc gta atg ctg cgc atg cca ctg cac cca gtt gcc att gaa ttg ctg      499
Thr Val Met Leu Arg Met Pro Leu His Pro Val Ala Ile Glu Leu Leu
        120                 125                 130 cgc caa acc gga cca atg gct gtc tcc tcc gcc aac atc tcc gga cat      547
Arg Gln Thr Gly Pro Met Ala Val Ser Ser Ala Asn Ile Ser Gly His
    135                 140                 145 act cct cca acc acc gtg ctg gag gct cgt cag cag ctc aac caa aat      595
Thr Pro Pro Thr Thr Val Leu Glu Ala Arg Gln Gln Leu Asn Gln Asn
150                 155                 160                 165 gtc gct gtc tac ctc gat ggt ggc gaa tgc gcg ctg gcc acc cct tca      643
Val Ala Val Tyr Leu Asp Gly Gly Glu Cys Ala Leu Ala Thr Pro Ser
                170                 175                 180 acc atc gtg gat att tca ggc ccc gca cca aag att ttg cgt gag ggt      691
Thr Ile Val Asp Ile Ser Gly Pro Ala Pro Lys Ile Leu Arg Glu Gly
            185                 190                 195
```

```
gcc atc agc gca gaa cgc gtt ggc gaa gta ctt gga gtg tcg gca gaa    739
Ala Ile Ser Ala Glu Arg Val Gly Glu Val Leu Gly Val Ser Ala Glu
        200                 205                 210 agc ctg cgc taaatgggag tcggtttcgc ggg                              771
Ser Leu Arg
    215

<210> SEQ ID NO 18
<211> LENGTH: 216
<212> TYPE: PRT
<213> ORGANISM: Corynebacterium glutamicum

<400> SEQUENCE: 18

Val Ser Arg Ile Tyr Asp Cys Ala Asp Gln Asp Ser Arg Ala Ala Gly
 1               5                  10                  15

Leu Lys Ala Ala Val Asp Ala Val Lys Ala Gly Gln Leu Val Val Leu
            20                  25                  30

Pro Thr Asp Thr Leu Tyr Gly Leu Gly Cys Asp Ala Phe Asn Asn Glu
        35                  40                  45

Ala Val Ala Asn Leu Leu Ala Thr Lys His Arg Gly Pro Asp Met Pro
    50                  55                  60

Val Pro Val Leu Val Gly Ser Trp Asp Thr Ile Gln Gly Leu Val His
 65                  70                  75                  80

Ser Tyr Ser Ala Gln Ala Lys Ala Leu Val Glu Ala Phe Trp Pro Gly
                85                  90                  95

Gly Leu Ser Ile Ile Val Pro Gln Ala Pro Ser Leu Pro Trp Asn Leu
            100                 105                 110

Gly Asp Thr Arg Gly Thr Val Met Leu Arg Met Pro Leu His Pro Val
        115                 120                 125

Ala Ile Glu Leu Leu Arg Gln Thr Gly Pro Met Ala Val Ser Ser Ala
    130                 135                 140

Asn Ile Ser Gly His Thr Pro Pro Thr Thr Val Leu Glu Ala Arg Gln
145                 150                 155                 160

Gln Leu Asn Gln Asn Val Ala Val Tyr Leu Asp Gly Gly Glu Cys Ala
                165                 170                 175

Leu Ala Thr Pro Ser Thr Ile Val Asp Ile Ser Gly Pro Ala Pro Lys
            180                 185                 190

Ile Leu Arg Glu Gly Ala Ile Ser Ala Glu Arg Val Gly Glu Val Leu
        195                 200                 205

Gly Val Ser Ala Glu Ser Leu Arg
    210                 215

<210> SEQ ID NO 19
<211> LENGTH: 1026
<212> TYPE: DNA
<213> ORGANISM: Corynebacterium glutamicum
<220> FEATURE:
<221> NAME/KEY: CDS
<222> LOCATION: (101)..(1003)
<223> OTHER INFORMATION: RXC00657

<400> SEQUENCE: 19
gtgcggatcg ggtatccgcg ctacacttag aggtgttaga gatcatgagt ttccacgaac    60
tgtaacgcag gattcaccaa tcaatgaaag gtcgaccgac atg agc act gaa gac   115
                                            Met Ser Thr Glu Asp
                                             1               5 att gtc gtc gta gca gta gat ggc tcg gac gcc tca aaa caa gct gtt   163
Ile Val Val Val Ala Val Asp Gly Ser Asp Ala Ser Lys Gln Ala Val
```

```
                    10                   15                   20
cgg tgg gct gca aat acc gcc aac aaa cgt ggc att cca ctt cgc ttg    211
Arg Trp Ala Ala Asn Thr Ala Asn Lys Arg Gly Ile Pro Leu Arg Leu
             25                   30                   35 gct tcc agc tac acc atg cct cag ttc ctc tac gca gag gga atg gtt    259
Ala Ser Ser Tyr Thr Met Pro Gln Phe Leu Tyr Ala Glu Gly Met Val
         40                   45                   50 cca cca caa gag ctt ttc gat gac ctc cag gcc gaa gcc ctg gaa aag    307
Pro Pro Gln Glu Leu Phe Asp Asp Leu Gln Ala Glu Ala Leu Glu Lys
     55                   60                   65 att aac gaa gcc cgt gac atc gcc cat gag gta gcg cca gaa atc aag    355
Ile Asn Glu Ala Arg Asp Ile Ala His Glu Val Ala Pro Glu Ile Lys
 70                   75                   80                   85 atc ggg cac acc atc gct gaa ggc agt ccc atc gac atg ctg ttg gaa    403
Ile Gly His Thr Ile Ala Glu Gly Ser Pro Ile Asp Met Leu Leu Glu
                 90                   95                  100 atg tct ccc gat gcc aca atg atc gtc atg ggt tcc cgc gga ctc ggc    451
Met Ser Pro Asp Ala Thr Met Ile Val Met Gly Ser Arg Gly Leu Gly
            105                  110                  115 gga ctc tcc gga atg gtc atg ggc tcc gtc tcc ggt gca gtg gtc agc    499
Gly Leu Ser Gly Met Val Met Gly Ser Val Ser Gly Ala Val Val Ser
        120                  125                  130 cac gca aag tgt cca gtc gtt gtt gtc cgt gaa gac agc gca gtc aac    547
His Ala Lys Cys Pro Val Val Val Val Arg Glu Asp Ser Ala Val Asn
    135                  140                  145 gaa gac agc aag tac ggc cca gtc gtc gtc ggt gtg gat ggc tcc gaa    595
Glu Asp Ser Lys Tyr Gly Pro Val Val Val Gly Val Asp Gly Ser Glu
150                  155                  160                  165 gtc tcc caa cag gca acc gaa tac gca ttt gcg gaa gct gaa gct cgt    643
Val Ser Gln Gln Ala Thr Glu Tyr Ala Phe Ala Glu Ala Glu Ala Arg
                 170                  175                  180 ggc gcc gaa ctc gtt gca gtt cac acc tgg atg gac atg cag gta cag    691
Gly Ala Glu Leu Val Ala Val His Thr Trp Met Asp Met Gln Val Gln
            185                  190                  195 gca tca ctt gca ggt ctt gca gct gct caa cag cag tgg gat gaa gtg    739
Ala Ser Leu Ala Gly Leu Ala Ala Ala Gln Gln Gln Trp Asp Glu Val
        200                  205                  210 gaa cgt cag caa acc gac atg ctg atc gaa cgc ctc gca cca ctg gtg    787
Glu Arg Gln Gln Thr Asp Met Leu Ile Glu Arg Leu Ala Pro Leu Val
    215                  220                  225 gaa aag tac cca agt gta acc gtc aag aag atc atc acc cgt gac cgc    835
Glu Lys Tyr Pro Ser Val Thr Val Lys Lys Ile Ile Thr Arg Asp Arg
230                  235                  240                  245 cca gtt cgc gca ctt gca gaa gca tct gaa aac gcg cag ctc cta gtc    883
Pro Val Arg Ala Leu Ala Glu Ala Ser Glu Asn Ala Gln Leu Leu Val
                 250                  255                  260 gtt ggt tcc cat ggt cgt ggc gga ttt aag ggc atg ctc ctt ggc tcc    931
Val Gly Ser His Gly Arg Gly Gly Phe Lys Gly Met Leu Leu Gly Ser
            265                  270                  275 acc tcc cgc gca ctg ctg caa tcc gca ccg tgc cca atg atg gtg gtt    979
Thr Ser Arg Ala Leu Leu Gln Ser Ala Pro Cys Pro Met Met Val Val
        280                  285                  290 cgc cca cct gag aag att aag aag tagtttcttt taagtttcga tgc         1026
Arg Pro Pro Glu Lys Ile Lys Lys
    295                  300

<210> SEQ ID NO 20
<211> LENGTH: 301
<212> TYPE: PRT
<213> ORGANISM: Corynebacterium glutamicum
```

<400> SEQUENCE: 20

| | | | | | | | | | | | | | | | |
|---|---|---|---|---|---|---|---|---|---|---|---|---|---|---|---|
|Met|Ser|Thr|Glu|Asp|Ile|Val|Val|Ala|Val|Asp|Gly|Ser|Asp|Ala|
|1| | | |5| | | | |10| | | | |15|
|Ser|Lys|Gln|Ala|Val|Arg|Trp|Ala|Ala|Asn|Thr|Ala|Asn|Lys|Arg|Gly|
| | | |20| | | | |25| | | | |30| | |
|Ile|Pro|Leu|Arg|Leu|Ala|Ser|Ser|Tyr|Thr|Met|Pro|Gln|Phe|Leu|Tyr|
| | |35| | | | |40| | | | |45| | | |
|Ala|Glu|Gly|Met|Val|Pro|Pro|Gln|Glu|Leu|Phe|Asp|Asp|Leu|Gln|Ala|
| |50| | | | |55| | | | |60| | | | |
|Glu|Ala|Leu|Glu|Lys|Ile|Asn|Glu|Ala|Arg|Asp|Ile|Ala|His|Glu|Val|
|65| | | |70| | | | |75| | | | |80| |
|Ala|Pro|Glu|Ile|Lys|Ile|Gly|His|Thr|Ile|Ala|Glu|Gly|Ser|Pro|Ile|
| | | | |85| | | | |90| | | | |95| |
|Asp|Met|Leu|Leu|Glu|Met|Ser|Pro|Asp|Ala|Thr|Met|Ile|Val|Met|Gly|
| | | |100| | | | |105| | | | |110| | |
|Ser|Arg|Gly|Leu|Gly|Gly|Leu|Ser|Gly|Met|Val|Met|Gly|Ser|Val|Ser|
| | |115| | | | |120| | | | |125| | | |
|Gly|Ala|Val|Val|Ser|His|Ala|Lys|Cys|Pro|Val|Val|Val|Arg|Glu|
| |130| | | | |135| | | | |140| | | | |
|Asp|Ser|Ala|Val|Asn|Glu|Asp|Ser|Lys|Tyr|Gly|Pro|Val|Val|Val|Gly|
|145| | | | |150| | | | |155| | | | |160|
|Val|Asp|Gly|Ser|Glu|Val|Ser|Gln|Gln|Ala|Thr|Glu|Tyr|Ala|Phe|Ala|
| | | | |165| | | | |170| | | | |175| |
|Glu|Ala|Glu|Ala|Arg|Gly|Ala|Glu|Leu|Val|Ala|Val|His|Thr|Trp|Met|
| | | |180| | | | |185| | | | |190| | |
|Asp|Met|Gln|Val|Gln|Ala|Ser|Leu|Ala|Gly|Leu|Ala|Ala|Ala|Gln|Gln|
| | |195| | | | |200| | | | |205| | | |
|Gln|Trp|Asp|Glu|Val|Glu|Arg|Gln|Gln|Thr|Asp|Met|Leu|Ile|Glu|Arg|
| |210| | | | |215| | | | |220| | | | |
|Leu|Ala|Pro|Leu|Val|Glu|Lys|Tyr|Pro|Ser|Val|Thr|Val|Lys|Lys|Ile|
|225| | | | |230| | | | |235| | | | |240|
|Ile|Thr|Arg|Asp|Arg|Pro|Val|Arg|Ala|Leu|Ala|Glu|Ala|Ser|Glu|Asn|
| | | | |245| | | | |250| | | | |255| |
|Ala|Gln|Leu|Leu|Val|Val|Gly|Ser|His|Gly|Arg|Gly|Gly|Phe|Lys|Gly|
| | | |260| | | | |265| | | | |270| | |
|Met|Leu|Leu|Gly|Ser|Thr|Ser|Arg|Ala|Leu|Leu|Gln|Ser|Ala|Pro|Cys|
| | |275| | | | |280| | | | |285| | | |
|Pro|Met|Met|Val|Val|Arg|Pro|Pro|Glu|Lys|Ile|Lys|Lys|
| |290| | | | |295| | | | |300| | | | |

<210> SEQ ID NO 21
<211> LENGTH: 1059
<212> TYPE: DNA
<213> ORGANISM: Corynebacterium glutamicum
<220> FEATURE:
<221> NAME/KEY: CDS
<222> LOCATION: (101)..(1036)
<223> OTHER INFORMATION: RXC00552

<400> SEQUENCE: 21
ccgccaacaa ggcagcaaag ctcgatccaa ttgacgcctt gcgttatgag taaaagcctc    60
gtttttaagg tagccacaca tcgcactaga ctgaagaact gtg gct acc tca aaa   115
                                              Val Ala Thr Ser Lys
                                              1               5 att ctt ctt tat tac gca ttc acc ccg ctc tct gac cct aaa gcg gtt   163

```
                Ile Leu Leu Tyr Tyr Ala Phe Thr Pro Leu Ser Asp Pro Lys Ala Val
                                 10                  15                  20 cag ctg tgg cag cgt gag ctc tgc gag tca ctg aat ctt cgt ggc cgc              211
Gln Leu Trp Gln Arg Glu Leu Cys Glu Ser Leu Asn Leu Arg Gly Arg
             25                  30                  35 atc ctg atc tcc act cac ggc atc aat gga acc gtg ggc gga gat att              259
Ile Leu Ile Ser Thr His Gly Ile Asn Gly Thr Val Gly Gly Asp Ile
         40                  45                  50 gat gat tgc aag gcg tac att aaa aag acc cgc gag tac cca ggt ttc              307
Asp Asp Cys Lys Ala Tyr Ile Lys Lys Thr Arg Glu Tyr Pro Gly Phe
     55                  60                  65 aac cgc atg cag ttt aag tgg tcc gag ggt ggc gct gag gat ttc cca              355
Asn Arg Met Gln Phe Lys Trp Ser Glu Gly Gly Ala Glu Asp Phe Pro
 70                  75                  80                      85 aag ctc agt gtc aaa gtc cgc gat gag atc gtt gcc ttc ggc gct cca              403
Lys Leu Ser Val Lys Val Arg Asp Glu Ile Val Ala Phe Gly Ala Pro
                 90                  95                 100 gat gag ctc aaa gtg gat gaa aac ggc gtc gtc ggt ggc ggc gtt cac              451
Asp Glu Leu Lys Val Asp Glu Asn Gly Val Val Gly Gly Gly Val His
             105                 110                 115 ctg aaa cca cag cag gtc aat gag ctt gtg gaa gcc cgt ggc gat gaa              499
Leu Lys Pro Gln Gln Val Asn Glu Leu Val Glu Ala Arg Gly Asp Glu
         120                 125                 130 gtt gtg ttc ttt gac ggc cgc aac gca atg gaa gcc cag atc ggc aag              547
Val Val Phe Phe Asp Gly Arg Asn Ala Met Glu Ala Gln Ile Gly Lys
     135                 140                 145 ttc aag gac gct gtt gtc cct gac gta gaa acc act cat gat ttc atc              595
Phe Lys Asp Ala Val Val Pro Asp Val Glu Thr Thr His Asp Phe Ile
150                 155                 160                     165 gca gaa att gag tct gga aaa tac gac gat ctc aaa gac aag cct gtg              643
Ala Glu Ile Glu Ser Gly Lys Tyr Asp Asp Leu Lys Asp Lys Pro Val
                 170                 175                 180 gtc acc tac tgc acc ggc gga att cgt tgt gag atc ctg agt tca ctc              691
Val Thr Tyr Cys Thr Gly Gly Ile Arg Cys Glu Ile Leu Ser Ser Leu
             185                 190                 195 atg atc aac cgt ggt ttc aaa gag gtc tac caa atc gat ggc ggc atc              739
Met Ile Asn Arg Gly Phe Lys Glu Val Tyr Gln Ile Asp Gly Gly Ile
         200                 205                 210 gtt cgc tac ggc gag cag ttt ggc aac aag ggc ctg tgg gaa ggc tcc              787
Val Arg Tyr Gly Glu Gln Phe Gly Asn Lys Gly Leu Trp Glu Gly Ser
     215                 220                 225 ctc tac gtt ttc gat aag cgc atg cat atg gaa ttc ggc gag gat tac              835
Leu Tyr Val Phe Asp Lys Arg Met His Met Glu Phe Gly Glu Asp Tyr
230                 235                 240                     245 aaa gag gtc gga cac tgc atc cat tgc gat act ccc acc aac aaa ttt              883
Lys Glu Val Gly His Cys Ile His Cys Asp Thr Pro Thr Asn Lys Phe
                 250                 255                 260 gag cac tgc ctc aac gaa gat gat tgc cgc gag ctc gtg ttg atg tgc              931
Glu His Cys Leu Asn Glu Asp Asp Cys Arg Glu Leu Val Leu Met Cys
             265                 270                 275 cct gat tgc ttc gcc aat gtt gag acc cgt cat tgc aag cgc gaa cgc              979
Pro Asp Cys Phe Ala Asn Val Glu Thr Arg His Cys Lys Arg Glu Arg
         280                 285                 290 tgt gca gca att gct gcg gat ttc gct gag caa gga att gat ccg ctc             1027
Cys Ala Ala Ile Ala Ala Asp Phe Ala Glu Gln Gly Ile Asp Pro Leu
     295                 300                 305 gtt act tct taaaagggt atggtggctg ggt                                        1059
Val Thr Ser
310
```

<210> SEQ ID NO 22
<211> LENGTH: 312
<212> TYPE: PRT
<213> ORGANISM: Corynebacterium glutamicum

<400> SEQUENCE: 22

```
Val Ala Thr Ser Lys Ile Leu Leu Tyr Tyr Ala Phe Thr Pro Leu Ser
 1               5                  10                  15

Asp Pro Lys Ala Val Gln Leu Trp Gln Arg Glu Leu Cys Glu Ser Leu
            20                  25                  30

Asn Leu Arg Gly Arg Ile Leu Ile Ser Thr His Gly Ile Asn Gly Thr
        35                  40                  45

Val Gly Gly Asp Ile Asp Asp Cys Lys Ala Tyr Ile Lys Lys Thr Arg
    50                  55                  60

Glu Tyr Pro Gly Phe Asn Arg Met Gln Phe Lys Trp Ser Glu Gly Gly
65                  70                  75                  80

Ala Glu Asp Phe Pro Lys Leu Ser Val Lys Val Arg Asp Glu Ile Val
                85                  90                  95

Ala Phe Gly Ala Pro Asp Glu Leu Lys Val Asp Glu Asn Gly Val Val
            100                 105                 110

Gly Gly Gly Val His Leu Lys Pro Gln Gln Val Asn Glu Leu Val Glu
        115                 120                 125

Ala Arg Gly Asp Glu Val Val Phe Phe Asp Gly Arg Asn Ala Met Glu
    130                 135                 140

Ala Gln Ile Gly Lys Phe Lys Asp Ala Val Val Pro Val Glu Thr
145                 150                 155                 160

Thr His Asp Phe Ile Ala Glu Ile Glu Ser Gly Lys Tyr Asp Asp Leu
                165                 170                 175

Lys Asp Lys Pro Val Val Thr Tyr Cys Thr Gly Gly Ile Arg Cys Glu
            180                 185                 190

Ile Leu Ser Ser Leu Met Ile Asn Arg Gly Phe Lys Glu Val Tyr Gln
        195                 200                 205

Ile Asp Gly Gly Ile Val Arg Tyr Gly Glu Gln Phe Gly Asn Lys Gly
    210                 215                 220

Leu Trp Glu Gly Ser Leu Tyr Val Phe Asp Lys Arg Met His Met Glu
225                 230                 235                 240

Phe Gly Glu Asp Tyr Lys Glu Val Gly His Cys Ile His Cys Asp Thr
                245                 250                 255

Pro Thr Asn Lys Phe Glu His Cys Leu Asn Glu Asp Asp Cys Arg Glu
            260                 265                 270

Leu Val Leu Met Cys Pro Asp Cys Phe Ala Asn Val Glu Thr Arg His
        275                 280                 285

Cys Lys Arg Glu Arg Cys Ala Ala Ile Ala Ala Asp Phe Ala Glu Gln
    290                 295                 300

Gly Ile Asp Pro Leu Val Thr Ser
305                 310
```

<210> SEQ ID NO 23
<211> LENGTH: 1386
<212> TYPE: DNA
<213> ORGANISM: Corynebacterium glutamicum
<220> FEATURE:
<221> NAME/KEY: CDS
<222> LOCATION: (101)..(1363)
<223> OTHER INFORMATION: RXA00534

<400> SEQUENCE: 23

```
ctgtgcagaa agaaaacact cctctggcta ggtagacaca gtttataaag gtagagttga        60
gcgggtaact gtcagcacgt agatcgaaag gtgcacaaag gtg gcc ctg gtc gta       115
                                            Val Ala Leu Val Val
                                             1               5 cag aaa tat ggc ggt tcc tcg ctt gag agt gcg gaa cgc att aga aac       163
Gln Lys Tyr Gly Gly Ser Ser Leu Glu Ser Ala Glu Arg Ile Arg Asn
                10                  15                  20 gtc gct gaa cgg atc gtt gcc acc aag aag gct gga aat gat gtc gtg       211
Val Ala Glu Arg Ile Val Ala Thr Lys Lys Ala Gly Asn Asp Val Val
            25                  30                  35 gtt gtc tgc tcc gca atg gga gac acc acg gat gaa ctt cta gaa ctt       259
Val Val Cys Ser Ala Met Gly Asp Thr Thr Asp Glu Leu Leu Glu Leu
        40                  45                  50 gca gcg gca gtg aat ccc gtt ccg cca gct cgt gaa atg gat atg ctc       307
Ala Ala Ala Val Asn Pro Val Pro Pro Ala Arg Glu Met Asp Met Leu
    55                  60                  65 ctg act gct ggt gag cgt att tct aac gct ctc gtc gcc atg gct att       355
Leu Thr Ala Gly Glu Arg Ile Ser Asn Ala Leu Val Ala Met Ala Ile
70                  75                  80                  85 gag tcc ctt ggc gca gaa gcc caa tct ttc acg ggc tct cag gct ggt       403
Glu Ser Leu Gly Ala Glu Ala Gln Ser Phe Thr Gly Ser Gln Ala Gly
                90                  95                 100 gtg ctc acc acc gag cgc cac gga aac gca cgc att gtt gat gtc act       451
Val Leu Thr Thr Glu Arg His Gly Asn Ala Arg Ile Val Asp Val Thr
               105                 110                 115 cca ggt cgt gtg cgt gaa gca ctc gat gag ggc aag atc tgc att gtt       499
Pro Gly Arg Val Arg Glu Ala Leu Asp Glu Gly Lys Ile Cys Ile Val
           120                 125                 130 gct ggt ttc cag ggt gtt aat aaa gaa acc cgc gat gtc acc acg ttg       547
Ala Gly Phe Gln Gly Val Asn Lys Glu Thr Arg Asp Val Thr Thr Leu
       135                 140                 145 ggt cgt ggt ggt tct gac acc act gca gtt gcg ttg gca gct gct ttg       595
Gly Arg Gly Gly Ser Asp Thr Thr Ala Val Ala Leu Ala Ala Ala Leu
150                 155                 160                 165 aac gct gat gtg tgt gag att tac tcg gac gtt gac ggt gtg tat acc       643
Asn Ala Asp Val Cys Glu Ile Tyr Ser Asp Val Asp Gly Val Tyr Thr
                170                 175                 180 gct gac ccg cgc atc gtt cct aat gca cag aag ctg gaa aag ctc agc       691
Ala Asp Pro Arg Ile Val Pro Asn Ala Gln Lys Leu Glu Lys Leu Ser
            185                 190                 195 ttc gaa gaa atg ctg gaa ctt gct gct gtt ggc tcc aag att ttg gtg       739
Phe Glu Glu Met Leu Glu Leu Ala Ala Val Gly Ser Lys Ile Leu Val
        200                 205                 210 ctg cgc agt gtt gaa tac gct cgt gca ttc aat gtg cca ctt cgc gta       787
Leu Arg Ser Val Glu Tyr Ala Arg Ala Phe Asn Val Pro Leu Arg Val
    215                 220                 225 cgc tcg tct tat agt aat gat ccc ggc act ttg att gcc ggc tct atg       835
Arg Ser Ser Tyr Ser Asn Asp Pro Gly Thr Leu Ile Ala Gly Ser Met
230                 235                 240                 245 gag gat att cct gtg gaa gaa gca gtc ctt acc ggt gtc gca acc gac       883
Glu Asp Ile Pro Val Glu Glu Ala Val Leu Thr Gly Val Ala Thr Asp
                250                 255                 260 aag tcc gaa gcc aaa gta acc gtt ctg ggt att tcc gat aag cca ggc       931
Lys Ser Glu Ala Lys Val Thr Val Leu Gly Ile Ser Asp Lys Pro Gly
            265                 270                 275 gag gct gcg aag gtt ttc cgt gcg ttg gct gat gca gaa atc aac att       979
Glu Ala Ala Lys Val Phe Arg Ala Leu Ala Asp Ala Glu Ile Asn Ile
        280                 285                 290
```

-continued

```
gac atg gtt ctg cag aac gtc tct tct gta gaa gac ggc acc acc gac      1027
Asp Met Val Leu Gln Asn Val Ser Ser Val Glu Asp Gly Thr Thr Asp
295                 300                 305 atc acc ttc acc tgc cct cgt tcc gac ggc cgc cgc gcg atg gag atc      1075
Ile Thr Phe Thr Cys Pro Arg Ser Asp Gly Arg Arg Ala Met Glu Ile
310                 315                 320                 325 ttg aag aag ctt cag gtt cag ggc aac tgg acc aat gtg ctt tac gac      1123
Leu Lys Lys Leu Gln Val Gln Gly Asn Trp Thr Asn Val Leu Tyr Asp
            330                 335                 340 gac cag gtc ggc aaa gtc tcc ctc gtg ggt gct ggc atg aag tct cac      1171
Asp Gln Val Gly Lys Val Ser Leu Val Gly Ala Gly Met Lys Ser His
        345                 350                 355 cca ggt gtt acc gca gag ttc atg gaa gct ctg cgc gat gtc aac gtg      1219
Pro Gly Val Thr Ala Glu Phe Met Glu Ala Leu Arg Asp Val Asn Val
    360                 365                 370 aac atc gaa ttg att tcc acc tct gag att cgt att tcc gtg ctg atc      1267
Asn Ile Glu Leu Ile Ser Thr Ser Glu Ile Arg Ile Ser Val Leu Ile
375                 380                 385 cgt gaa gat gat ctg gat gct gct gca cgt gca ttg cat gag cag ttc      1315
Arg Glu Asp Asp Leu Asp Ala Ala Ala Arg Ala Leu His Glu Gln Phe
390                 395                 400                 405 cag ctg ggc ggc gaa gac gaa gcc gtc gtt tat gca ggc acc gga cgc      1363
Gln Leu Gly Gly Glu Asp Glu Ala Val Val Tyr Ala Gly Thr Gly Arg
            410                 415                 420 taaagtttta aggagtagt ttt                                             1386

<210> SEQ ID NO 24
<211> LENGTH: 421
<212> TYPE: PRT
<213> ORGANISM: Corynebacterium glutamicum

<400> SEQUENCE: 24

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
```

```
                  195                 200                 205
Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Ala Val Leu Thr
                245                 250                 255

Gly Val Ala Thr Asp Lys Ser Glu Ala Lys Val Thr Val Leu Gly Ile
                260                 265                 270

Ser Asp Lys Pro Gly Glu Ala Ala Lys Val Phe Arg Ala Leu Ala Asp
            275                 280                 285

Ala Glu Ile Asn Ile Asp Met Val Leu Gln Asn Val Ser Ser Val Glu
    290                 295                 300

Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
                355                 360                 365

Arg Asp Val Asn Val Asn Ile Glu Leu Ile Ser Thr Ser Glu Ile Arg
    370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
            420

<210> SEQ ID NO 25
<211> LENGTH: 1155
<212> TYPE: DNA
<213> ORGANISM: Corynebacterium glutamicum
<220> FEATURE:
<221> NAME/KEY: CDS
<222> LOCATION: (101)..(1132)
<223> OTHER INFORMATION: RXA00533

<400> SEQUENCE: 25
ctgcacgtgc attgcatgag cagttccagc tgggcggcga agacgaagcc gtcgtttatg    60
caggcaccgg acgctaaagt tttaaggag tagttttaca atg acc acc atc gca      115
                                            Met Thr Thr Ile Ala
                                            1               5 gtt gtt ggt gca acc ggc cag gtc ggc cag gtt atg cgc acc ctt ttg      163
Val Val Gly Ala Thr Gly Gln Val Gly Gln Val Met Arg Thr Leu Leu
            10                  15                  20 gaa gag cgc aat ttc cca gct gac act gtt cgt ttc ttt gct tcc cca      211
Glu Glu Arg Asn Phe Pro Ala Asp Thr Val Arg Phe Phe Ala Ser Pro
        25                  30                  35 cgt tcc gca ggc cgt aag att gaa ttc cgt ggc acg gaa atc gag gta      259
Arg Ser Ala Gly Arg Lys Ile Glu Phe Arg Gly Thr Glu Ile Glu Val
    40                  45                  50 gaa gac att act cag gca acc gag gag tcc ctc aag gac atc gac gtt      307
Glu Asp Ile Thr Gln Ala Thr Glu Glu Ser Leu Lys Asp Ile Asp Val
55                  60                  65 gcg ttg ttc tcc gct gga ggc acc gct tcc aag cag tac gct cca ctg      355
```

```
                Ala Leu Phe Ser Ala Gly Gly Thr Ala Ser Lys Gln Tyr Ala Pro Leu
                 70                  75                  80                  85 ttc gct gct gca ggc gcg act gtt gtg gat aac tct tct gct tgg cgc          403
Phe Ala Ala Ala Gly Ala Thr Val Val Asp Asn Ser Ser Ala Trp Arg
                 90                  95                 100 aag gac gac gag gtt cca cta atc gtc tct gag gtg aac cct tcc gac          451
Lys Asp Asp Glu Val Pro Leu Ile Val Ser Glu Val Asn Pro Ser Asp
                105                 110                 115 aag gat tcc ctg gtc aag ggc att att gcg aac cct aac tgc acc acc          499
Lys Asp Ser Leu Val Lys Gly Ile Ile Ala Asn Pro Asn Cys Thr Thr
                120                 125                 130 atg gct gcg atg cca gtg ctg aag cca ctt cac gat gcc gct ggt ctt          547
Met Ala Ala Met Pro Val Leu Lys Pro Leu His Asp Ala Ala Gly Leu
135                 140                 145 gta aag ctt cac gtt tcc tct tac cag gct gtt tcc ggt tct ggt ctt          595
Val Lys Leu His Val Ser Ser Tyr Gln Ala Val Ser Gly Ser Gly Leu
150                 155                 160                 165 gca ggt gtg gaa acc ttg gca aag cag gtt gct gca gtt gga gac cac          643
Ala Gly Val Glu Thr Leu Ala Lys Gln Val Ala Ala Val Gly Asp His
                170                 175                 180 aac gtt gag ttc gtc cat gat gga cag gct gct gac gca ggc gat gtc          691
Asn Val Glu Phe Val His Asp Gly Gln Ala Ala Asp Ala Gly Asp Val
                185                 190                 195 gga cct tat gtt tca cca atc gct tac aac gtg ctg cca ttc gcc gga          739
Gly Pro Tyr Val Ser Pro Ile Ala Tyr Asn Val Leu Pro Phe Ala Gly
                200                 205                 210 aac ctc gtc gat gac ggc acc ttc gaa acc gat gaa gag cag aag ctg          787
Asn Leu Val Asp Asp Gly Thr Phe Glu Thr Asp Glu Glu Gln Lys Leu
215                 220                 225 cgc aac gaa tcc cgc aag att ctc ggt ctc cca gac ctc aag gtc tca          835
Arg Asn Glu Ser Arg Lys Ile Leu Gly Leu Pro Asp Leu Lys Val Ser
230                 235                 240                 245 ggc acc tgc gtc cgc gtg ccg gtt ttc acc ggc cac acg ctg acc att          883
Gly Thr Cys Val Arg Val Pro Val Phe Thr Gly His Thr Leu Thr Ile
                250                 255                 260 cac gcc gaa ttc gac aag gca atc acc gtg gac cag gcg cag gag atc          931
His Ala Glu Phe Asp Lys Ala Ile Thr Val Asp Gln Ala Gln Glu Ile
                265                 270                 275 ttg ggt gcc gct tca ggc gtc aag ctt gtc gac gtc cca acc cca ctt          979
Leu Gly Ala Ala Ser Gly Val Lys Leu Val Asp Val Pro Thr Pro Leu
                280                 285                 290 gca gct gcc ggc att gac gaa tcc ctc gtt gga cgc atc cgt cag gac         1027
Ala Ala Ala Gly Ile Asp Glu Ser Leu Val Gly Arg Ile Arg Gln Asp
                295                 300                 305 tcc act gtc gac gat aac cgc ggt ctg gtt ctc gtc gta tct ggc gac         1075
Ser Thr Val Asp Asp Asn Arg Gly Leu Val Leu Val Val Ser Gly Asp
310                 315                 320                 325 aac ctc cgc aag ggt gct gcg cta aac acc atc cag atc gct gag ctg         1123
Asn Leu Arg Lys Gly Ala Ala Leu Asn Thr Ile Gln Ile Ala Glu Leu
                330                 335                 340 ctg gtt aag taaaaacccg ccattaaaaa ctc                                   1155
Leu Val Lys
```

<210> SEQ ID NO 26
<211> LENGTH: 344
<212> TYPE: PRT
<213> ORGANISM: Corynebacterium glutamicum

<400> SEQUENCE: 26

Met Thr Thr Ile Ala Val Val Gly Ala Thr Gly Gln Val Gly Gln Val

```
            1               5              10              15
Met Arg Thr Leu Leu Glu Glu Arg Asn Phe Pro Ala Asp Thr Val Arg
             20                  25                  30

Phe Phe Ala Ser Pro Arg Ser Ala Gly Arg Lys Ile Glu Phe Arg Gly
             35                  40                  45

Thr Glu Ile Glu Val Glu Asp Ile Thr Gln Ala Thr Glu Glu Ser Leu
             50                  55                  60

Lys Asp Ile Asp Val Ala Leu Phe Ser Ala Gly Gly Thr Ala Ser Lys
 65                  70                  75                  80

Gln Tyr Ala Pro Leu Phe Ala Ala Gly Ala Thr Val Val Asp Asn
                 85                  90                  95

Ser Ser Ala Trp Arg Lys Asp Glu Val Pro Leu Ile Val Ser Glu
                100                 105                 110

Val Asn Pro Ser Asp Lys Asp Ser Leu Val Lys Gly Ile Ile Ala Asn
                115                 120                 125

Pro Asn Cys Thr Thr Met Ala Ala Met Pro Val Leu Lys Pro Leu His
130                 135                 140

Asp Ala Ala Gly Leu Val Lys Leu His Val Ser Ser Tyr Gln Ala Val
145                 150                 155                 160

Ser Gly Ser Gly Leu Ala Gly Val Glu Thr Leu Ala Lys Gln Val Ala
                165                 170                 175

Ala Val Gly Asp His Asn Val Glu Phe Val His Asp Gly Gln Ala Ala
                180                 185                 190

Asp Ala Gly Asp Val Gly Pro Tyr Val Ser Pro Ile Ala Tyr Asn Val
                195                 200                 205

Leu Pro Phe Ala Gly Asn Leu Val Asp Asp Gly Thr Phe Glu Thr Asp
                210                 215                 220

Glu Glu Gln Lys Leu Arg Asn Glu Ser Arg Lys Ile Leu Gly Leu Pro
225                 230                 235                 240

Asp Leu Lys Val Ser Gly Thr Cys Val Arg Val Pro Val Phe Thr Gly
                245                 250                 255

His Thr Leu Thr Ile His Ala Glu Phe Asp Lys Ala Ile Thr Val Asp
                260                 265                 270

Gln Ala Gln Glu Ile Leu Gly Ala Ala Ser Gly Val Lys Leu Val Asp
                275                 280                 285

Val Pro Thr Pro Leu Ala Ala Ala Gly Ile Asp Glu Ser Leu Val Gly
                290                 295                 300

Arg Ile Arg Gln Asp Ser Thr Val Asp Asp Asn Arg Gly Leu Val Leu
305                 310                 315                 320

Val Val Ser Gly Asp Asn Leu Arg Lys Gly Ala Ala Leu Asn Thr Ile
                325                 330                 335

Gln Ile Ala Glu Leu Leu Val Lys
                340
```

<210> SEQ ID NO 27
<211> LENGTH: 608
<212> TYPE: DNA
<213> ORGANISM: Corynebacterium glutamicum
<220> FEATURE:
<221> NAME/KEY: CDS
<222> LOCATION: (69)..(608)
<223> OTHER INFORMATION: RXA02843

<400> SEQUENCE: 27
cccattgcgc ggaggtcgca ccccttccga cttgaactga taggccgata gaaattattc    60

```
tggacgtc atg act act gct tcc gca acc gga att gca aca ctg acc tcc      110
         Met Thr Thr Ala Ser Ala Thr Gly Ile Ala Thr Leu Thr Ser
         1               5                   10 acc ggc gac gtc ctg gac gtg tgg tat cca gaa atc ggg tcc acc gac      158
Thr Gly Asp Val Leu Asp Val Trp Tyr Pro Glu Ile Gly Ser Thr Asp
 15              20                  25                  30 cag tcc gcg ctc aca cct cta gaa ggc gtc gat gaa gat cga aac gtc      206
Gln Ser Ala Leu Thr Pro Leu Glu Gly Val Asp Glu Asp Arg Asn Val
                 35                  40                  45 acc cgc aaa atc gtg acg aca act atc gac acc gac gca gcc ccc acc      254
Thr Arg Lys Ile Val Thr Thr Thr Ile Asp Thr Asp Ala Ala Pro Thr
             50                  55                  60 gac acc tac gat gca tgg ctg cgc ctt cac ctc ctc tcc cac cgc gtt      302
Asp Thr Tyr Asp Ala Trp Leu Arg Leu His Leu Leu Ser His Arg Val
         65                  70                  75 ttc cgc cct cac acc atc aac cta gac ggc att ttc ggc ctc ctc aac      350
Phe Arg Pro His Thr Ile Asn Leu Asp Gly Ile Phe Gly Leu Leu Asn
 80                  85                  90 aat gtc gtg tgg acc aac ttc gga ccg tgc gca gtt gac ggt ttc gca      398
Asn Val Val Trp Thr Asn Phe Gly Pro Cys Ala Val Asp Gly Phe Ala
 95              100                 105                 110 ctc acc cgc gcg cgc ctg tca cgc cga ggc caa gtt acg gtt tat agc      446
Leu Thr Arg Ala Arg Leu Ser Arg Arg Gly Gln Val Thr Val Tyr Ser
                 115                 120                 125 gtc gac aag ttc cca cgc atg gtc gac tat gtg gtt ccc tcg ggc gtg      494
Val Asp Lys Phe Pro Arg Met Val Asp Tyr Val Val Pro Ser Gly Val
             130                 135                 140 cgc atc ggt gac gcc gac cgc gtc cga ctt ggc gcg tac ctg gca gat      542
Arg Ile Gly Asp Ala Asp Arg Val Arg Leu Gly Ala Tyr Leu Ala Asp
         145                 150                 155 ggc acc acc gtg atg cat gag ggc ttc gtg aac ttc aac gct ggc acg      590
Gly Thr Thr Val Met His Glu Gly Phe Val Asn Phe Asn Ala Gly Thr
 160                 165                 170 ctc ggc gct tcc atg gtt                                              608
Leu Gly Ala Ser Met Val
175             180
```

<210> SEQ ID NO 28
<211> LENGTH: 180
<212> TYPE: PRT
<213> ORGANISM: Corynebacterium glutamicum

<400> SEQUENCE: 28

```
Met Thr Thr Ala Ser Ala Thr Gly Ile Ala Thr Leu Thr Ser Thr Gly
1               5                   10                  15

Asp Val Leu Asp Val Trp Tyr Pro Glu Ile Gly Ser Thr Asp Gln Ser
            20                  25                  30

Ala Leu Thr Pro Leu Glu Gly Val Asp Glu Asp Arg Asn Val Thr Arg
        35                  40                  45

Lys Ile Val Thr Thr Thr Ile Asp Thr Asp Ala Ala Pro Thr Asp Thr
    50                  55                  60

Tyr Asp Ala Trp Leu Arg Leu His Leu Leu Ser His Arg Val Phe Arg
65                  70                  75                  80

Pro His Thr Ile Asn Leu Asp Gly Ile Phe Gly Leu Leu Asn Val
                85                  90                  95

Val Trp Thr Asn Phe Gly Pro Cys Ala Val Asp Gly Phe Ala Leu Thr
            100                 105                 110

Arg Ala Arg Leu Ser Arg Arg Gly Gln Val Thr Val Tyr Ser Val Asp
        115                 120                 125
```

```
Lys Phe Pro Arg Met Val Asp Tyr Val Val Pro Ser Gly Val Arg Ile
    130                 135                 140

Gly Asp Ala Asp Arg Val Arg Leu Gly Ala Tyr Leu Ala Asp Gly Thr
145                 150                 155                 160

Thr Val Met His Glu Gly Phe Val Asn Phe Asn Ala Gly Thr Leu Gly
                165                 170                 175

Ala Ser Met Val
            180

<210> SEQ ID NO 29
<211> LENGTH: 1230
<212> TYPE: DNA
<213> ORGANISM: Corynebacterium glutamicum
<220> FEATURE:
<221> NAME/KEY: CDS
<222> LOCATION: (101)..(1207)
<223> OTHER INFORMATION: RXA02022

<400> SEQUENCE: 29
tatttgcgat tccaactgct tgggctccgc gaatgttttc actcattttt taatcgaccg      60
cttccatcat gttttaacta aggtttgtag cttaaacct gtg aac tct gaa ctc       115
                                            Val Asn Ser Glu Leu
                                              1               5 aaa cca gga tta gat ctc ctc ggc gac cca att gtc ctt act caa cgt      163
Lys Pro Gly Leu Asp Leu Leu Gly Asp Pro Ile Val Leu Thr Gln Arg
             10                  15                  20 ttg gta gat ata ccg agt ccg tcg ggt cag gaa aag cag att gct gat      211
Leu Val Asp Ile Pro Ser Pro Ser Gly Gln Glu Lys Gln Ile Ala Asp
         25                  30                  35 gaa att gaa gat gcc ctt cgg aac ctt aat cta cct ggt gta gag gtc      259
Glu Ile Glu Asp Ala Leu Arg Asn Leu Asn Leu Pro Gly Val Glu Val
     40                  45                  50 ttc cgc ttc aac aac aac gtt ctt gct cgc acg aac agg gga ttg gcc      307
Phe Arg Phe Asn Asn Asn Val Leu Ala Arg Thr Asn Arg Gly Leu Ala
 55                  60                  65 tcg agg gtc atg ctt gct ggt cat atc gat aca gtg ccg atc gcg gac      355
Ser Arg Val Met Leu Ala Gly His Ile Asp Thr Val Pro Ile Ala Asp
 70                  75                  80                  85 aat ctg cca agc cgt gtg gaa gac ggc atc atg tat ggc tgt ggc acc      403
Asn Leu Pro Ser Arg Val Glu Asp Gly Ile Met Tyr Gly Cys Gly Thr
                 90                  95                 100 gtc gat atg aaa tct ggg ttg gcg gtg tat ttg cat act ttt gcc acc      451
Val Asp Met Lys Ser Gly Leu Ala Val Tyr Leu His Thr Phe Ala Thr
             105                 110                 115 ttg gcc acg tcg act gag ctt aaa cat gat ctg acg ctg att gcg tat      499
Leu Ala Thr Ser Thr Glu Leu Lys His Asp Leu Thr Leu Ile Ala Tyr
         120                 125                 130 gag tgc gag gaa gtt gct gat cac ctc aat ggt ttg ggc cac att cgc      547
Glu Cys Glu Glu Val Ala Asp His Leu Asn Gly Leu Gly His Ile Arg
     135                 140                 145 gat gag cat ccg gag tgg ttg gcg gct gat ttg gcg ttg ttg ggt gag      595
Asp Glu His Pro Glu Trp Leu Ala Ala Asp Leu Ala Leu Leu Gly Glu
150                 155                 160                 165 cct act ggc ggc tgg att gag gcg ggc tgc cag ggc aat ctg cgc atc      643
Pro Thr Gly Gly Trp Ile Glu Ala Gly Cys Gln Gly Asn Leu Arg Ile
                170                 175                 180 aag gtg acg gcg cat ggt gtg cgt gcc cat tcg gcg aga agc tgg ttg      691
Lys Val Thr Ala His Gly Val Arg Ala His Ser Ala Arg Ser Trp Leu
            185                 190                 195
```

```
ggt gat aat gcg atg cat aag ttg tcg ccg atc att tcg aag gtt gct      739
Gly Asp Asn Ala Met His Lys Leu Ser Pro Ile Ile Ser Lys Val Ala
            200                 205                 210 gcg tat aag gcc gca gaa gtc aac att gat ggc ttg acc tac cgt gaa      787
Ala Tyr Lys Ala Ala Glu Val Asn Ile Asp Gly Leu Thr Tyr Arg Glu
        215                 220                 225 ggc ctc aac atc gtt ttc tgc gaa tcg ggc gtg gca aac aac gtc att      835
Gly Leu Asn Ile Val Phe Cys Glu Ser Gly Val Ala Asn Asn Val Ile
230                 235                 240                 245 cca gac ctc gcg tgg atg aac ctc aac ttc cgt ttc gcg ccg aat cgc      883
Pro Asp Leu Ala Trp Met Asn Leu Asn Phe Arg Phe Ala Pro Asn Arg
                250                 255                 260 gat ctc aac gag gcg atc gag cat gtc gtc gaa acg ctt gag ctt gac      931
Asp Leu Asn Glu Ala Ile Glu His Val Val Glu Thr Leu Glu Leu Asp
            265                 270                 275 ggt caa gac ggc atc gaa tgg gcc gta gaa gac ggg gca ggc ggt gcc      979
Gly Gln Asp Gly Ile Glu Trp Ala Val Glu Asp Gly Ala Gly Gly Ala
        280                 285                 290 ctt cca ggc ttg ggg cag cag gtg aca agc ggg ctt atc gac gcc gtc     1027
Leu Pro Gly Leu Gly Gln Gln Val Thr Ser Gly Leu Ile Asp Ala Val
295                 300                 305 ggc cgc gaa aaa atc cgc gca aaa ttc ggc tgg acc gat gtc tca cgt     1075
Gly Arg Glu Lys Ile Arg Ala Lys Phe Gly Trp Thr Asp Val Ser Arg
310                 315                 320                 325 ttt tca gcc atg gga att cca gcc cta aac ttt ggc gct ggt gat cca     1123
Phe Ser Ala Met Gly Ile Pro Ala Leu Asn Phe Gly Ala Gly Asp Pro
                330                 335                 340 agt ttc gcg cat aaa cgc gac gag cag tgc cca gtg gag caa atc acg     1171
Ser Phe Ala His Lys Arg Asp Glu Gln Cys Pro Val Glu Gln Ile Thr
            345                 350                 355 gat gtg gca gca att ttg aag cag tac ctg agc gag taaccgcatt          1217
Asp Val Ala Ala Ile Leu Lys Gln Tyr Leu Ser Glu
        360                 365 cggggttatc gtg                                                      1230
```

<210> SEQ ID NO 30
<211> LENGTH: 369
<212> TYPE: PRT
<213> ORGANISM: Corynebacterium glutamicum

<400> SEQUENCE: 30

```
Val Asn Ser Glu Leu Lys Pro Gly Leu Asp Leu Leu Gly Asp Pro Ile
 1               5                  10                  15

Val Leu Thr Gln Arg Leu Val Asp Ile Pro Ser Pro Ser Gly Gln Glu
            20                  25                  30

Lys Gln Ile Ala Asp Glu Ile Glu Asp Ala Leu Arg Asn Leu Asn Leu
        35                  40                  45

Pro Gly Val Glu Val Phe Arg Phe Asn Asn Asn Val Leu Ala Arg Thr
    50                  55                  60

Asn Arg Gly Leu Ala Ser Arg Val Met Leu Ala Gly His Ile Asp Thr
65                  70                  75                  80

Val Pro Ile Ala Asp Asn Leu Pro Ser Arg Val Glu Asp Gly Ile Met
                85                  90                  95

Tyr Gly Cys Gly Thr Val Asp Met Lys Ser Gly Leu Ala Val Tyr Leu
            100                 105                 110

His Thr Phe Ala Thr Leu Ala Thr Ser Thr Glu Leu Lys His Asp Leu
        115                 120                 125

Thr Leu Ile Ala Tyr Glu Cys Glu Glu Val Ala Asp His Leu Asn Gly
```

-continued

```
                130                 135                 140
Leu Gly His Ile Arg Asp Glu His Pro Glu Trp Leu Ala Ala Asp Leu
145                 150                 155                 160

Ala Leu Leu Gly Glu Pro Thr Gly Gly Trp Ile Glu Ala Gly Cys Gln
                165                 170                 175

Gly Asn Leu Arg Ile Lys Val Thr Ala His Gly Val Arg Ala His Ser
                180                 185                 190

Ala Arg Ser Trp Leu Gly Asp Asn Ala Met His Lys Leu Ser Pro Ile
                195                 200                 205

Ile Ser Lys Val Ala Ala Tyr Lys Ala Ala Glu Val Asn Ile Asp Gly
210                 215                 220

Leu Thr Tyr Arg Glu Gly Leu Asn Ile Val Phe Cys Glu Ser Gly Val
225                 230                 235                 240

Ala Asn Asn Val Ile Pro Asp Leu Ala Trp Met Asn Leu Asn Phe Arg
                245                 250                 255

Phe Ala Pro Asn Arg Asp Leu Asn Glu Ala Ile Glu His Val Val Glu
                260                 265                 270

Thr Leu Glu Leu Asp Gly Gln Asp Gly Ile Glu Trp Ala Val Glu Asp
                275                 280                 285

Gly Ala Gly Gly Ala Leu Pro Gly Leu Gly Gln Gln Val Thr Ser Gly
                290                 295                 300

Leu Ile Asp Ala Val Gly Arg Glu Lys Ile Arg Ala Lys Phe Gly Trp
305                 310                 315                 320

Thr Asp Val Ser Arg Phe Ser Ala Met Gly Ile Pro Ala Leu Asn Phe
                325                 330                 335

Gly Ala Gly Asp Pro Ser Phe His Lys Arg Asp Glu Gln Cys Pro
                340                 345                 350

Val Glu Gln Ile Thr Asp Val Ala Ala Ile Leu Lys Gln Tyr Leu Ser
                355                 360                 365

Glu
```

```
<210> SEQ ID NO 31
<211> LENGTH: 1059
<212> TYPE: DNA
<213> ORGANISM: Corynebacterium glutamicum
<220> FEATURE:
<221> NAME/KEY: CDS
<222> LOCATION: (101)..(1036)
<223> OTHER INFORMATION: RXA00044

<400> SEQUENCE: 31
attacctcag ccttccaagc tgatgatgca ttacttaaaa actgcagaca cttgaaaaac      60
ttctcacccg cactcgttcc ctcaacccac aaggagcacc atg gct tcc gca act     115
                                              Met Ala Ser Ala Thr
                                                1               5 ttc acc ggc gtg atc cca ccc gta atg acc cca ctc cac gcc gac ggc     163
Phe Thr Gly Val Ile Pro Pro Val Met Thr Pro Leu His Ala Asp Gly
                 10                  15                  20 agt gtg gat gta gaa agc ctc cgc aag ctc gtt gac cac ctc atc aat     211
Ser Val Asp Val Glu Ser Leu Arg Lys Leu Val Asp His Leu Ile Asn
             25                  30                  35 ggt ggc gtc gac gga ctt ttc gca ctg ggc tcc tca ggc gaa gcg gca     259
Gly Gly Val Asp Gly Leu Phe Ala Leu Gly Ser Ser Gly Glu Ala Ala
         40                  45                  50 ttc ctc acc cgc gcc cag cgc aaa ctc gca ctg acc acc atc atc gag     307
Phe Leu Thr Arg Ala Gln Arg Lys Leu Ala Leu Thr Thr Ile Ile Glu
     55                  60                  65
```

```
cac acc gca ggc cgc gtt ccc gta act gct ggt gtc att gaa acc acc    355
His Thr Ala Gly Arg Val Pro Val Thr Ala Gly Val Ile Glu Thr Thr
         70                  75                  80                  85 act gct cgc gtg att gag ctc gtg gaa gat gcc ctg gag gct ggt gcc    403
Thr Ala Arg Val Ile Glu Leu Val Glu Asp Ala Leu Glu Ala Gly Ala
                 90                  95                 100 gaa ggc ctc gtt gcc act gca cct ttc tac acc cgc acc cac gat gtg    451
Glu Gly Leu Val Ala Thr Ala Pro Phe Tyr Thr Arg Thr His Asp Val
                105                 110                 115 gaa att gaa gaa cac ttc cgc aag atc cac gcc gcc gct cca gag ctt    499
Glu Ile Glu Glu His Phe Arg Lys Ile His Ala Ala Ala Pro Glu Leu
        120                 125                 130 cca ctg ttt gcc tac aac atc cca gtg tcg gtg cac tcc aac ctc aac    547
Pro Leu Phe Ala Tyr Asn Ile Pro Val Ser Val His Ser Asn Leu Asn
            135                 140                 145 cca gtc atg ctt ttg acg ctg gcc aag gat ggc gtt ctt gca ggc acc    595
Pro Val Met Leu Leu Thr Leu Ala Lys Asp Gly Val Leu Ala Gly Thr
150                 155                 160                 165 aag gat tcc agt ggc aat gat ggc gca atc cgc tca ctg atc gaa gct    643
Lys Asp Ser Ser Gly Asn Asp Gly Ala Ile Arg Ser Leu Ile Glu Ala
                170                 175                 180 cgt gat gat gct gga ctc act gag cag ttc aag atc ctc acc ggc agc    691
Arg Asp Asp Ala Gly Leu Thr Glu Gln Phe Lys Ile Leu Thr Gly Ser
            185                 190                 195 gaa acc acc gtt gat ttc gcc tac ctt gcg ggt gcc gat gga gtt gtc    739
Glu Thr Thr Val Asp Phe Ala Tyr Leu Ala Gly Ala Asp Gly Val Val
        200                 205                 210 cca ggc ctg ggc aat gtt gat cct gca gca tac gca gct tta gca aaa    787
Pro Gly Leu Gly Asn Val Asp Pro Ala Ala Tyr Ala Ala Leu Ala Lys
215                 220                 225 ctc tgc ctc gat gga aag tgg gca gaa gct gct gct ttg cag aag cgc    835
Leu Cys Leu Asp Gly Lys Trp Ala Glu Ala Ala Ala Leu Gln Lys Arg
230                 235                 240                 245 atc aac cac ctc ttc cac atc gtc ttc gtg gga gac acc tcc cat atg    883
Ile Asn His Leu Phe His Ile Val Phe Val Gly Asp Thr Ser His Met
                250                 255                 260 tcc gga tcc agc gct ggt ttg ggc ggt ttc aag aca gca ctc gca cac    931
Ser Gly Ser Ser Ala Gly Leu Gly Gly Phe Lys Thr Ala Leu Ala His
            265                 270                 275 ctt ggc att att gaa tcc aat gcg atg gca gtt cct cac cag agc ctc    979
Leu Gly Ile Ile Glu Ser Asn Ala Met Ala Val Pro His Gln Ser Leu
        280                 285                 290 agc gac gaa gaa act gct cgc att cac gcc att gtt gat gaa ttc ctg   1027
Ser Asp Glu Glu Thr Ala Arg Ile His Ala Ile Val Asp Glu Phe Leu
295                 300                 305 tac acc gct taaggcccac acctcatgac tga                              1059
Tyr Thr Ala
310

<210> SEQ ID NO 32
<211> LENGTH: 312
<212> TYPE: PRT
<213> ORGANISM: Corynebacterium glutamicum

<400> SEQUENCE: 32

Met Ala Ser Ala Thr Phe Thr Gly Val Ile Pro Pro Val Met Thr Pro
 1               5                  10                  15

Leu His Ala Asp Gly Ser Val Asp Val Glu Ser Leu Arg Lys Leu Val
            20                  25                  30
```

```
Asp His Leu Ile Asn Gly Gly Val Asp Gly Leu Phe Ala Leu Gly Ser
    35                  40                  45

Ser Gly Glu Ala Ala Phe Leu Thr Arg Ala Gln Arg Lys Leu Ala Leu
    50                  55                  60

Thr Thr Ile Ile Glu His Thr Ala Gly Arg Val Pro Val Thr Ala Gly
65                  70                  75                  80

Val Ile Glu Thr Thr Thr Ala Arg Val Ile Glu Leu Val Glu Asp Ala
                85                  90                  95

Leu Glu Ala Gly Ala Glu Gly Leu Val Ala Thr Ala Pro Phe Tyr Thr
                100                 105                 110

Arg Thr His Asp Val Glu Ile Glu Glu His Phe Arg Lys Ile His Ala
            115                 120                 125

Ala Ala Pro Glu Leu Pro Leu Phe Ala Tyr Asn Ile Pro Val Ser Val
    130                 135                 140

His Ser Asn Leu Asn Pro Val Met Leu Leu Thr Leu Ala Lys Asp Gly
145                 150                 155                 160

Val Leu Ala Gly Thr Lys Asp Ser Ser Gly Asn Asp Gly Ala Ile Arg
                165                 170                 175

Ser Leu Ile Glu Ala Arg Asp Asp Ala Gly Leu Thr Glu Gln Phe Lys
                180                 185                 190

Ile Leu Thr Gly Ser Glu Thr Thr Val Asp Phe Ala Tyr Leu Ala Gly
            195                 200                 205

Ala Asp Gly Val Val Pro Gly Leu Gly Asn Val Asp Pro Ala Ala Tyr
    210                 215                 220

Ala Ala Leu Ala Lys Leu Cys Leu Asp Gly Lys Trp Ala Glu Ala Ala
225                 230                 235                 240

Ala Leu Gln Lys Arg Ile Asn His Leu Phe His Ile Val Phe Val Gly
                245                 250                 255

Asp Thr Ser His Met Ser Gly Ser Ala Gly Leu Gly Gly Phe Lys
                260                 265                 270

Thr Ala Leu Ala His Leu Gly Ile Ile Glu Ser Asn Ala Met Ala Val
            275                 280                 285

Pro His Gln Ser Leu Ser Asp Glu Glu Thr Ala Arg Ile His Ala Ile
    290                 295                 300

Val Asp Glu Phe Leu Tyr Thr Ala
305                 310

<210> SEQ ID NO 33
<211> LENGTH: 867
<212> TYPE: DNA
<213> ORGANISM: Corynebacterium glutamicum
<220> FEATURE:
<221> NAME/KEY: CDS
<222> LOCATION: (101)..(844)
<223> OTHER INFORMATION: RXA00863

<400> SEQUENCE: 33
aacggtcagt taggtatgga tatcagcacc ttctgaacgg gtacgtctag actggtgggc      60
gtttgaaaaa ctcttcgccc cacgaaaatg aaggagcata atg gga atc aag gtt     115
                                              Met Gly Ile Lys Val
                                                1               5 ggc gtt ctc gga gcc aaa ggc cgt gtt ggt caa act att gtg gca gca     163
Gly Val Leu Gly Ala Lys Gly Arg Val Gly Gln Thr Ile Val Ala Ala
                10                  15                  20 gtc aat gag tcc gac gat ctg gag ctt gtt gca gag atc ggc gtc gac     211
Val Asn Glu Ser Asp Asp Leu Glu Leu Val Ala Glu Ile Gly Val Asp
        25                  30                  35
```

```
gat gat ttg agc ctt ctg gta gac aac ggc gct gaa gtt gtc gtt gac      259
Asp Asp Leu Ser Leu Leu Val Asp Asn Gly Ala Glu Val Val Val Asp
         40                  45                  50 ttc acc act cct aac gct gtg atg ggc aac ctg gag ttc tgc atc aac      307
Phe Thr Thr Pro Asn Ala Val Met Gly Asn Leu Glu Phe Cys Ile Asn
 55                  60                  65 aac ggc att tct gcg gtt gtt gga acc acg ggc ttc gat gat gct cgt      355
Asn Gly Ile Ser Ala Val Val Gly Thr Thr Gly Phe Asp Asp Ala Arg
 70                  75                  80                  85 ttg gag cag gtt cgc gac tgg ctt gaa gga aaa gac aat gtc ggt gtt      403
Leu Glu Gln Val Arg Asp Trp Leu Glu Gly Lys Asp Asn Val Gly Val
                 90                  95                 100 ctg atc gca cct aac ttt gct atc tct gcg gtg ttg acc atg gtc ttt      451
Leu Ile Ala Pro Asn Phe Ala Ile Ser Ala Val Leu Thr Met Val Phe
                105                 110                 115 tcc aag cag gct gcc cgc ttc ttc gaa tca gct gaa gtt att gag ctg      499
Ser Lys Gln Ala Ala Arg Phe Phe Glu Ser Ala Glu Val Ile Glu Leu
            120                 125                 130 cac cac ccc aac aag ctg gat gca cct tca ggc acc gcg atc cac act      547
His His Pro Asn Lys Leu Asp Ala Pro Ser Gly Thr Ala Ile His Thr
 135                 140                 145 gct cag ggc att gct gcg gca cgc aaa gaa gca ggc atg gac gca cag      595
Ala Gln Gly Ile Ala Ala Ala Arg Lys Glu Ala Gly Met Asp Ala Gln
150                 155                 160                 165 cca gat gcg acc gag cag gca ctt gag ggt tcc cgt ggc gca agc gta      643
Pro Asp Ala Thr Glu Gln Ala Leu Glu Gly Ser Arg Gly Ala Ser Val
                170                 175                 180 gat gga atc ccg gtt cat gca gtc cgc atg tcc ggc atg gtt gct cac      691
Asp Gly Ile Pro Val His Ala Val Arg Met Ser Gly Met Val Ala His
            185                 190                 195 gag caa gtt atc ttt ggc acc cag ggt cag acc ttg acc atc aag cag      739
Glu Gln Val Ile Phe Gly Thr Gln Gly Gln Thr Leu Thr Ile Lys Gln
        200                 205                 210 gac tcc tat gat cgc aac tca ttt gca cca ggt gtc ttg gtg ggt gtg      787
Asp Ser Tyr Asp Arg Asn Ser Phe Ala Pro Gly Val Leu Val Gly Val
215                 220                 225 cgc aac att gca cag cac cca ggc cta gtc gta gga ctt gag cat tac      835
Arg Asn Ile Ala Gln His Pro Gly Leu Val Val Gly Leu Glu His Tyr
230                 235                 240                 245 cta ggc ctg taaaggctca tttcagcagc ggg                                 867
Leu Gly Leu <210> SEQ ID NO 34
<211> LENGTH: 248
<212> TYPE: PRT
<213> ORGANISM: Corynebacterium glutamicum

<400> SEQUENCE: 34

Met Gly Ile Lys Val Gly Val Leu Gly Ala Lys Gly Arg Val Gly Gln
 1               5                  10                  15

Thr Ile Val Ala Ala Val Asn Glu Ser Asp Asp Leu Glu Leu Val Ala
             20                  25                  30

Glu Ile Gly Val Asp Asp Leu Ser Leu Leu Val Asp Asn Gly Ala
         35                  40                  45

Glu Val Val Val Asp Phe Thr Thr Pro Asn Ala Val Met Gly Asn Leu
     50                  55                  60

Glu Phe Cys Ile Asn Asn Gly Ile Ser Ala Val Val Gly Thr Thr Gly
 65                  70                  75                  80
```

```
Phe Asp Asp Ala Arg Leu Glu Gln Val Arg Asp Trp Leu Glu Gly Lys
             85                  90                  95
Asp Asn Val Gly Val Leu Ile Ala Pro Asn Phe Ala Ile Ser Ala Val
            100                 105                 110
Leu Thr Met Val Phe Ser Lys Gln Ala Ala Arg Phe Phe Glu Ser Ala
            115                 120                 125
Glu Val Ile Glu Leu His His Pro Asn Lys Leu Asp Ala Pro Ser Gly
            130                 135                 140
Thr Ala Ile His Thr Ala Gln Gly Ile Ala Ala Arg Lys Glu Ala
145                 150                 155                 160
Gly Met Asp Ala Gln Pro Asp Ala Thr Glu Gln Ala Leu Glu Gly Ser
                165                 170                 175
Arg Gly Ala Ser Val Asp Gly Ile Pro Val His Ala Val Arg Met Ser
                180                 185                 190
Gly Met Val Ala His Glu Gln Val Ile Phe Gly Thr Gln Gly Gln Thr
            195                 200                 205
Leu Thr Ile Lys Gln Asp Ser Tyr Asp Arg Asn Ser Phe Ala Pro Gly
            210                 215                 220
Val Leu Val Gly Val Arg Asn Ile Ala Gln His Pro Gly Leu Val Val
225                 230                 235                 240
Gly Leu Glu His Tyr Leu Gly Leu
                245

<210> SEQ ID NO 35
<211> LENGTH: 873
<212> TYPE: DNA
<213> ORGANISM: Corynebacterium glutamicum
<220> FEATURE:
<221> NAME/KEY: CDS
<222> LOCATION: (101)..(850)
<223> OTHER INFORMATION: RXA00864

<400> SEQUENCE: 35
acagcaccca ggcctagtcg taggacttga gcattaccta ggcctgtaaa ggctcatttc      60
agcagcgggt ggaattttt aaaaggagcg tttaaaggct gtg gcc gaa caa gtt      115
                                              Val Ala Glu Gln Val
                                                1               5 aaa ttg agc gtg gag ttg ata gcg tgc agt tct ttt act cca ccc gct      163
Lys Leu Ser Val Glu Leu Ile Ala Cys Ser Ser Phe Thr Pro Pro Ala
         10                  15                  20 gat gtt gag tgg tca act gat gtt gag ggc gcg gaa gca ctc gtc gag      211
Asp Val Glu Trp Ser Thr Asp Val Glu Gly Ala Glu Ala Leu Val Glu
     25                  30                  35 ttt gcg ggt cgt gcc tgc tac gaa act ttt gat aag ccg aac cct cga      259
Phe Ala Gly Arg Ala Cys Tyr Glu Thr Phe Asp Lys Pro Asn Pro Arg
 40                  45                  50 act gct tcc aat gct gcg tat ctg cgc cac atc atg gaa gtg ggg cac      307
Thr Ala Ser Asn Ala Ala Tyr Leu Arg His Ile Met Glu Val Gly His
 55                  60                  65 act gct ttg ctt gag cat gcc aat gcc acg atg tat atc cga ggc att      355
Thr Ala Leu Leu Glu His Ala Asn Ala Thr Met Tyr Ile Arg Gly Ile
70                  75                  80                  85 tct cgg tcc gcg acc cat gaa ttg gtc cga cac cgc cat ttt tcc ttc      403
Ser Arg Ser Ala Thr His Glu Leu Val Arg His Arg His Phe Ser Phe
                 90                  95                 100 tct caa ctg tct cag cgt ttc gtg cac agc gga gaa tcg gaa gta gtg      451
Ser Gln Leu Ser Gln Arg Phe Val His Ser Gly Glu Ser Glu Val Val
            105                 110                 115
```

```
gtg ccc act ctc atc gat gaa gat ccg cag ttg cgt gaa ctt ttc atg      499
Val Pro Thr Leu Ile Asp Glu Asp Pro Gln Leu Arg Glu Leu Phe Met
            120                 125                 130 cac gcc atg gat gag tct cgg ttc gct ttc aat gag ctg ctt aat gcg      547
His Ala Met Asp Glu Ser Arg Phe Ala Phe Asn Glu Leu Leu Asn Ala
            135                 140                 145 ctg gaa gaa aaa ctt ggc gat gaa ccg aat gca ctt tta agg aaa aag      595
Leu Glu Glu Lys Leu Gly Asp Glu Pro Asn Ala Leu Leu Arg Lys Lys
150                 155                 160                 165 cag gct cgt caa gca gct cgc gct gtg ctg ccc aac gct aca gag tcc      643
Gln Ala Arg Gln Ala Ala Arg Ala Val Leu Pro Asn Ala Thr Glu Ser
                170                 175                 180 aga atc gtg gtg tct gga aac ttc cgc acc tgg agg cat ttc att ggc      691
Arg Ile Val Val Ser Gly Asn Phe Arg Thr Trp Arg His Phe Ile Gly
                    185                 190                 195 atg cga gcc agt gaa cat gca gac gtc gaa atc cgc gaa gta gcg gta      739
Met Arg Ala Ser Glu His Ala Asp Val Glu Ile Arg Glu Val Ala Val
                200                 205                 210 gaa tgt tta aga aag ctg cag gta gca gcg cca act gtt ttc ggt gat      787
Glu Cys Leu Arg Lys Leu Gln Val Ala Ala Pro Thr Val Phe Gly Asp
            215                 220                 225 ttt gag att gaa act ttg gca gac gga tcg caa atg gca aca agc ccg      835
Phe Glu Ile Glu Thr Leu Ala Asp Gly Ser Gln Met Ala Thr Ser Pro
230                 235                 240                 245 tat gtc atg gac ttt taacgcaaag ctcacaccca cga                        873
Tyr Val Met Asp Phe
                250

<210> SEQ ID NO 36
<211> LENGTH: 250
<212> TYPE: PRT
<213> ORGANISM: Corynebacterium glutamicum

<400> SEQUENCE: 36

Val Ala Glu Gln Val Lys Leu Ser Val Glu Leu Ile Ala Cys Ser Ser
 1               5                  10                  15

Phe Thr Pro Pro Ala Asp Val Glu Trp Ser Thr Asp Val Glu Gly Ala
                20                  25                  30

Glu Ala Leu Val Glu Phe Ala Gly Arg Ala Cys Tyr Glu Thr Phe Asp
            35                  40                  45

Lys Pro Asn Pro Arg Thr Ala Ser Asn Ala Ala Tyr Leu Arg His Ile
        50                  55                  60

Met Glu Val Gly His Thr Ala Leu Leu Glu His Ala Asn Ala Thr Met
 65                  70                  75                  80

Tyr Ile Arg Gly Ile Ser Arg Ser Ala Thr His Glu Leu Val Arg His
                85                  90                  95

Arg His Phe Ser Phe Ser Gln Leu Ser Gln Arg Phe Val His Ser Gly
            100                 105                 110

Glu Ser Glu Val Val Pro Thr Leu Ile Asp Glu Pro Gln Leu
        115                 120                 125

Arg Glu Leu Phe Met His Ala Met Asp Glu Ser Arg Phe Ala Phe Asn
130                 135                 140

Glu Leu Leu Asn Ala Leu Glu Glu Lys Leu Gly Asp Glu Pro Asn Ala
145                 150                 155                 160

Leu Leu Arg Lys Lys Gln Ala Arg Gln Ala Ala Arg Ala Val Leu Pro
                165                 170                 175

Asn Ala Thr Glu Ser Arg Ile Val Val Ser Gly Asn Phe Arg Thr Trp
            180                 185                 190
```

Arg His Phe Ile Gly Met Arg Ala Ser Glu His Ala Asp Val Glu Ile
            195                 200                 205

Arg Glu Val Ala Val Glu Cys Leu Arg Lys Leu Gln Val Ala Ala Pro
    210                 215                 220

Thr Val Phe Gly Asp Phe Glu Ile Glu Thr Leu Ala Asp Gly Ser Gln
225                 230                 235                 240

Met Ala Thr Ser Pro Tyr Val Met Asp Phe
                245                 250

<210> SEQ ID NO 37
<211> LENGTH: 608
<212> TYPE: DNA
<213> ORGANISM: Corynebacterium glutamicum
<220> FEATURE:
<221> NAME/KEY: CDS
<222> LOCATION: (69)..(608)
<223> OTHER INFORMATION: RXA02843

<400> SEQUENCE: 37
cccattgcgc ggaggtcgca ccccttccga cttgaactga taggccgata gaaattattc      60 tggacgtc atg act act gct tcc gca acc gga att gca aca ctg acc tcc     110
         Met Thr Thr Ala Ser Ala Thr Gly Ile Ala Thr Leu Thr Ser
           1               5                  10 acc ggc gac gtc ctg gac gtg tgg tat cca gaa atc ggg tcc acc gac     158
Thr Gly Asp Val Leu Asp Val Trp Tyr Pro Glu Ile Gly Ser Thr Asp
 15                  20                  25                  30 cag tcc gcg ctc aca cct cta gaa ggc gtc gat gaa gat cga aac gtc     206
Gln Ser Ala Leu Thr Pro Leu Glu Gly Val Asp Glu Asp Arg Asn Val
                 35                  40                  45 acc cgc aaa atc gtg acg aca act atc gac acc gac gca gcc ccc acc     254
Thr Arg Lys Ile Val Thr Thr Thr Ile Asp Thr Asp Ala Ala Pro Thr
             50                  55                  60 gac acc tac gat gca tgg ctg cgc ctt cac ctc ctc tcc cac cgc gtt     302
Asp Thr Tyr Asp Ala Trp Leu Arg Leu His Leu Leu Ser His Arg Val
         65                  70                  75 ttc cgc cct cac acc atc aac cta gac ggc att ttc ggc ctc ctc aac     350
Phe Arg Pro His Thr Ile Asn Leu Asp Gly Ile Phe Gly Leu Leu Asn
     80                  85                  90 aat gtc gtg tgg acc aac ttc gga ccg tgc gca gtt gac ggt ttc gca     398
Asn Val Val Trp Thr Asn Phe Gly Pro Cys Ala Val Asp Gly Phe Ala
 95                 100                 105                 110 ctc acc cgc gcg cgc ctg tca cgc cga ggc caa gtt acg gtt tat agc     446
Leu Thr Arg Ala Arg Leu Ser Arg Arg Gly Gln Val Thr Val Tyr Ser
                115                 120                 125 gtc gac aag ttc cca cgc atg gtc gac tat gtg gtt ccc tcg ggc gtg     494
Val Asp Lys Phe Pro Arg Met Val Asp Tyr Val Val Pro Ser Gly Val
            130                 135                 140 cgc atc ggt gac gcc gac cgc gtc cga ctt ggc gcg tac ctg gca gat     542
Arg Ile Gly Asp Ala Asp Arg Val Arg Leu Gly Ala Tyr Leu Ala Asp
        145                 150                 155 ggc acc acc gtg atg cat gag ggc ttc gtg aac ttc aac gct ggc acg     590
Gly Thr Thr Val Met His Glu Gly Phe Val Asn Phe Asn Ala Gly Thr
    160                 165                 170 ctc ggc gct tcc atg gtt                                              608
Leu Gly Ala Ser Met Val
175                 180

<210> SEQ ID NO 38
<211> LENGTH: 180
<212> TYPE: PRT

-continued

<213> ORGANISM: Corynebacterium glutamicum

<400> SEQUENCE: 38

```
Met Thr Thr Ala Ser Ala Thr Gly Ile Ala Thr Leu Thr Ser Thr Gly
1               5                   10                  15

Asp Val Leu Asp Val Trp Tyr Pro Glu Ile Gly Ser Thr Asp Gln Ser
            20                  25                  30

Ala Leu Thr Pro Leu Glu Gly Val Asp Glu Asp Arg Asn Val Thr Arg
        35                  40                  45

Lys Ile Val Thr Thr Thr Ile Asp Thr Asp Ala Ala Pro Thr Asp Thr
    50                  55                  60

Tyr Asp Ala Trp Leu Arg Leu His Leu Leu Ser His Arg Val Phe Arg
65                  70                  75                  80

Pro His Thr Ile Asn Leu Asp Gly Ile Phe Gly Leu Leu Asn Asn Val
                85                  90                  95

Val Trp Thr Asn Phe Gly Pro Cys Ala Val Asp Gly Phe Ala Leu Thr
            100                 105                 110

Arg Ala Arg Leu Ser Arg Arg Gly Gln Val Thr Val Tyr Ser Val Asp
        115                 120                 125

Lys Phe Pro Arg Met Val Asp Tyr Val Val Pro Ser Gly Val Arg Ile
    130                 135                 140

Gly Asp Ala Asp Arg Val Arg Leu Gly Ala Tyr Leu Ala Asp Gly Thr
145                 150                 155                 160

Thr Val Met His Glu Gly Phe Val Asn Phe Asn Ala Gly Thr Leu Gly
                165                 170                 175

Ala Ser Met Val
            180
```

<210> SEQ ID NO 39
<211> LENGTH: 1143
<212> TYPE: DNA
<213> ORGANISM: Corynebacterium glutamicum
<220> FEATURE:
<221> NAME/KEY: CDS
<222> LOCATION: (101)..(1120)
<223> OTHER INFORMATION: RXN00355

<400> SEQUENCE: 39

```
aatagatcag cgcatccgtg gtggaaccaa aaggctcaac aatacgaaac gttcgctttc       60
ggtcctgatg aaagagatgt ccctgaatca tcatctaagt atg cat ctc ggt aag      115
                                             Met His Leu Gly Lys
                                               1               5 ctc gac cag gac agt gcc acc aca att ttg gag gat tac aag aac atg     163
Leu Asp Gln Asp Ser Ala Thr Thr Ile Leu Glu Asp Tyr Lys Asn Met
                10                  15                  20 acc aac atc cgc gta gct atc gtg ggc tac gga aac ctg gga cgc agc     211
Thr Asn Ile Arg Val Ala Ile Val Gly Tyr Gly Asn Leu Gly Arg Ser
            25                  30                  35 gtc gaa aag ctt att gcc aag cag ccc gac atg gac ctt gta gga atc     259
Val Glu Lys Leu Ile Ala Lys Gln Pro Asp Met Asp Leu Val Gly Ile
        40                  45                  50 ttc tcg cgc cgg gcc acc ctc gac aca aag acg cca gtc ttt gat gtc     307
Phe Ser Arg Arg Ala Thr Leu Asp Thr Lys Thr Pro Val Phe Asp Val
    55                  60                  65 gcc gac gtg gac aag cac gcc gac gac gtg gac gtg ctg ttc ctg tgc     355
Ala Asp Val Asp Lys His Ala Asp Asp Val Asp Val Leu Phe Leu Cys
70                  75                  80                  85 atg ggc tcc gcc acc gac atc cct gag cag gca cca aag ttc gcg cag     403
```

```
                Met Gly Ser Ala Thr Asp Ile Pro Glu Gln Ala Pro Lys Phe Ala Gln
                             90                  95                 100 ttc gcc tgc acc gta gac acc tac gac aac cac cgc gac atc cca cgc                451
Phe Ala Cys Thr Val Asp Thr Tyr Asp Asn His Arg Asp Ile Pro Arg
            105                 110                 115 cac cgc cag gtc atg aac gaa gcc gcc acc gca gcc ggc aac gtt gca                499
His Arg Gln Val Met Asn Glu Ala Ala Thr Ala Ala Gly Asn Val Ala
        120                 125                 130 ctg gtc tct acc ggc tgg gat cca gga atg ttc tcc atc aac cgc gtc                547
Leu Val Ser Thr Gly Trp Asp Pro Gly Met Phe Ser Ile Asn Arg Val
    135                 140                 145 tac gca gcg gca gtc tta gcc gag cac cag cag cac acc ttc tgg ggc                595
Tyr Ala Ala Ala Val Leu Ala Glu His Gln Gln His Thr Phe Trp Gly
150                 155                 160                 165 cca ggt ttg tca cag ggc cac tcc gat gct ttg cga cgc atc cct ggc                643
Pro Gly Leu Ser Gln Gly His Ser Asp Ala Leu Arg Arg Ile Pro Gly
                170                 175                 180 gtt caa aag gca gtc cag tac acc ctc cca tcc gaa gac gcc ctg gaa                691
Val Gln Lys Ala Val Gln Tyr Thr Leu Pro Ser Glu Asp Ala Leu Glu
            185                 190                 195 aag gcc cgc cgc ggc gaa gcc ggc gac ctt acc gga aag caa acc cac                739
Lys Ala Arg Arg Gly Glu Ala Gly Asp Leu Thr Gly Lys Gln Thr His
        200                 205                 210 aag cgc caa tgc ttc gtg gtt gcc gac gcg gcc gat cac gag cgc atc                787
Lys Arg Gln Cys Phe Val Val Ala Asp Ala Ala Asp His Glu Arg Ile
    215                 220                 225 gaa aac gac atc cgc acc atg cct gat tac ttc gtt ggc tac gaa gtc                835
Glu Asn Asp Ile Arg Thr Met Pro Asp Tyr Phe Val Gly Tyr Glu Val
230                 235                 240                 245 gaa gtc aac ttc atc gac gaa gca acc ttc gac tcc gag cac acc ggc                883
Glu Val Asn Phe Ile Asp Glu Ala Thr Phe Asp Ser Glu His Thr Gly
                250                 255                 260 atg cca cac ggt ggc cac gtg att acc acc ggc gac acc ggt ggc ttc                931
Met Pro His Gly Gly His Val Ile Thr Thr Gly Asp Thr Gly Gly Phe
            265                 270                 275 aac cac acc gtg gaa tac atc ctc aag ctg gac cga aac cca gat ttc                979
Asn His Thr Val Glu Tyr Ile Leu Lys Leu Asp Arg Asn Pro Asp Phe
        280                 285                 290 acc gct tcc tca cag atc gct ttc ggt cgc gca gct cac cgc atg aag               1027
Thr Ala Ser Ser Gln Ile Ala Phe Gly Arg Ala Ala His Arg Met Lys
    295                 300                 305 cag cag ggc caa agc gga gct ttc acc gtc ctc gaa gtt gct cca tac               1075
Gln Gln Gly Gln Ser Gly Ala Phe Thr Val Leu Glu Val Ala Pro Tyr
310                 315                 320                 325 ctg ctc tcc cca gag aac ttg gac gat ctg atc gca cgc gac gtc                   1120
Leu Leu Ser Pro Glu Asn Leu Asp Asp Leu Ile Ala Arg Asp Val
                330                 335                 340 taatttagct cgaggggcaa gga                                                     1143

<210> SEQ ID NO 40
<211> LENGTH: 340
<212> TYPE: PRT
<213> ORGANISM: Corynebacterium glutamicum

<400> SEQUENCE: 40

Met His Leu Gly Lys Leu Asp Gln Asp Ser Ala Thr Thr Ile Leu Glu
 1               5                  10                  15

Asp Tyr Lys Asn Met Thr Asn Ile Arg Val Ala Ile Val Gly Tyr Gly
             20                  25                  30
```

-continued

```
Asn Leu Gly Arg Ser Val Glu Lys Leu Ile Ala Lys Gln Pro Asp Met
         35                  40                  45

Asp Leu Val Gly Ile Phe Ser Arg Arg Ala Thr Leu Asp Thr Lys Thr
 50                  55                  60

Pro Val Phe Asp Val Ala Asp Val Asp Lys His Ala Asp Asp Val Asp
 65                  70                  75                  80

Val Leu Phe Leu Cys Met Gly Ser Ala Thr Asp Ile Pro Glu Gln Ala
                 85                  90                  95

Pro Lys Phe Ala Gln Phe Ala Cys Thr Val Asp Thr Tyr Asp Asn His
                100                 105                 110

Arg Asp Ile Pro Arg His Arg Gln Val Met Asn Glu Ala Thr Ala
            115                 120                 125

Ala Gly Asn Val Ala Leu Val Ser Thr Gly Trp Asp Pro Gly Met Phe
    130                 135                 140

Ser Ile Asn Arg Val Tyr Ala Ala Val Leu Ala Glu His Gln Gln
145                 150                 155                 160

His Thr Phe Trp Gly Pro Gly Leu Ser Gln Gly His Ser Asp Ala Leu
                165                 170                 175

Arg Arg Ile Pro Gly Val Gln Lys Ala Val Gln Tyr Thr Leu Pro Ser
            180                 185                 190

Glu Asp Ala Leu Glu Lys Ala Arg Arg Gly Glu Ala Gly Asp Leu Thr
        195                 200                 205

Gly Lys Gln Thr His Lys Arg Gln Cys Phe Val Val Ala Asp Ala Ala
    210                 215                 220

Asp His Glu Arg Ile Glu Asn Asp Ile Arg Thr Met Pro Asp Tyr Phe
225                 230                 235                 240

Val Gly Tyr Glu Val Glu Val Asn Phe Ile Asp Glu Ala Thr Phe Asp
                245                 250                 255

Ser Glu His Thr Gly Met Pro His Gly Gly His Val Ile Thr Thr Gly
            260                 265                 270

Asp Thr Gly Gly Phe Asn His Thr Val Glu Tyr Ile Leu Lys Leu Asp
        275                 280                 285

Arg Asn Pro Asp Phe Thr Ala Ser Ser Gln Ile Ala Phe Gly Arg Ala
    290                 295                 300

Ala His Arg Met Lys Gln Gln Gly Gln Ser Gly Ala Phe Thr Val Leu
305                 310                 315                 320

Glu Val Ala Pro Tyr Leu Leu Ser Pro Glu Asn Leu Asp Asp Leu Ile
                325                 330                 335

Ala Arg Asp Val
            340

<210> SEQ ID NO 41
<211> LENGTH: 958
<212> TYPE: DNA
<213> ORGANISM: Corynebacterium glutamicum
<220> FEATURE:
<221> NAME/KEY: CDS
<222> LOCATION: (101)..(958)
<223> OTHER INFORMATION: FRXA00352

<400> SEQUENCE: 41
aatagatcag cgcatccgtg gtggaaccaa aaggctcaac aatacgaaac gttcgctttc      60
ggtcctgatg aaagagatgt ccctgaatca tcatctaagt atg cat ctc ggt aag     115
                                              Met His Leu Gly Lys
                                                1               5 ctc gac cag gac agt gcc acc aca att ttg gag gat tac aag aac atg     163
```

```
                Leu Asp Gln Asp Ser Ala Thr Thr Ile Leu Glu Asp Tyr Lys Asn Met
                         10                  15                  20 acc aac atc cgc gta gct atc gtg ggc tac gga aac ctg gga cgc agc                211
Thr Asn Ile Arg Val Ala Ile Val Gly Tyr Gly Asn Leu Gly Arg Ser
             25                  30                  35 gtc gaa aag ctt att gcc aag cag ccc gac atg gac ctt gta gga atc                259
Val Glu Lys Leu Ile Ala Lys Gln Pro Asp Met Asp Leu Val Gly Ile
         40                  45                  50 ttc tcg cgc cgg gcc acc ctc gac aca aag acg cca gtc ttt gat gtc                307
Phe Ser Arg Arg Ala Thr Leu Asp Thr Lys Thr Pro Val Phe Asp Val
     55                  60                  65 gcc gac gtg gac aag cac gcc gac gac gtg gac gtg ctg ttc ctg tgc                355
Ala Asp Val Asp Lys His Ala Asp Asp Val Asp Val Leu Phe Leu Cys
 70                  75                  80                  85 atg ggc tcc gcc acc gac atc cct gag cag gca cca aag ttc gcg cag                403
Met Gly Ser Ala Thr Asp Ile Pro Glu Gln Ala Pro Lys Phe Ala Gln
                 90                  95                 100 ttc gcc tgc acc gta gac acc tac gac aac cac cgc gac atc cca cgc                451
Phe Ala Cys Thr Val Asp Thr Tyr Asp Asn His Arg Asp Ile Pro Arg
            105                 110                 115 cac cgc cag gtc atg aac gaa gcc gcc acc gca gcc ggc aac gtt gca                499
His Arg Gln Val Met Asn Glu Ala Ala Thr Ala Ala Gly Asn Val Ala
        120                 125                 130 ctg gtc tct acc ggc tgg gat cca gga atg ttc tcc atc aac cgc gtc                547
Leu Val Ser Thr Gly Trp Asp Pro Gly Met Phe Ser Ile Asn Arg Val
    135                 140                 145 tac gca gcg gca gtc tta gcc gag cac cag cag cac acc ttc tgg ggc                595
Tyr Ala Ala Ala Val Leu Ala Glu His Gln Gln His Thr Phe Trp Gly
150                 155                 160                 165 cca ggt ttg tca cag ggc cac tcc gat gct ttg cga cgc atc cct ggc                643
Pro Gly Leu Ser Gln Gly His Ser Asp Ala Leu Arg Arg Ile Pro Gly
                170                 175                 180 gtt caa aag gca gtc cag tac acc ctc cca tcc gaa gac gcc ctg gaa                691
Val Gln Lys Ala Val Gln Tyr Thr Leu Pro Ser Glu Asp Ala Leu Glu
            185                 190                 195 aag gcc cgc cgc ggc gaa gcc ggc gac ctt acc gga aag caa acc cac                739
Lys Ala Arg Arg Gly Glu Ala Gly Asp Leu Thr Gly Lys Gln Thr His
        200                 205                 210 aag cgc caa tgc ttc gtg gtt gcc gac gcg gcc gat cac gag cgc atc                787
Lys Arg Gln Cys Phe Val Val Ala Asp Ala Ala Asp His Glu Arg Ile
    215                 220                 225 gaa aac gac atc cgc acc atg cct gat tac ttc gtt ggc tac gaa gtc                835
Glu Asn Asp Ile Arg Thr Met Pro Asp Tyr Phe Val Gly Tyr Glu Val
230                 235                 240                 245 gaa gtc aac ttc atc gac gaa gca acc ttc gac tcc gag cac acc ggc                883
Glu Val Asn Phe Ile Asp Glu Ala Thr Phe Asp Ser Glu His Thr Gly
                250                 255                 260 atg cca cac ggt ggc cac gtg att acc acc ggc gac acc ggt ggc ttc                931
Met Pro His Gly Gly His Val Ile Thr Thr Gly Asp Thr Gly Gly Phe
            265                 270                 275 aac cac acc gtg gaa tac atc ctc aag                                            958
Asn His Thr Val Glu Tyr Ile Leu Lys
        280                 285

<210> SEQ ID NO 42
<211> LENGTH: 286
<212> TYPE: PRT
<213> ORGANISM: Corynebacterium glutamicum

<400> SEQUENCE: 42
```

-continued

```
Met His Leu Gly Lys Leu Asp Gln Asp Ser Ala Thr Thr Ile Leu Glu
 1               5                  10                  15

Asp Tyr Lys Asn Met Thr Asn Ile Arg Val Ala Ile Val Gly Tyr Gly
             20                  25                  30

Asn Leu Gly Arg Ser Val Glu Lys Leu Ile Ala Lys Gln Pro Asp Met
         35                  40                  45

Asp Leu Val Gly Ile Phe Ser Arg Arg Ala Thr Leu Asp Thr Lys Thr
     50                  55                  60

Pro Val Phe Asp Val Ala Asp Val Asp Lys His Ala Asp Asp Val Asp
 65                  70                  75                  80

Val Leu Phe Leu Cys Met Gly Ser Ala Thr Asp Ile Pro Glu Gln Ala
                 85                  90                  95

Pro Lys Phe Ala Gln Phe Ala Cys Thr Val Asp Thr Tyr Asp Asn His
             100                 105                 110

Arg Asp Ile Pro Arg His Arg Gln Val Met Asn Glu Ala Ala Thr Ala
         115                 120                 125

Ala Gly Asn Val Ala Leu Val Ser Thr Gly Trp Asp Pro Gly Met Phe
     130                 135                 140

Ser Ile Asn Arg Val Tyr Ala Ala Ala Val Leu Ala Glu His Gln Gln
145                 150                 155                 160

His Thr Phe Trp Gly Pro Gly Leu Ser Gln Gly His Ser Asp Ala Leu
                 165                 170                 175

Arg Arg Ile Pro Gly Val Gln Lys Ala Val Gln Tyr Thr Leu Pro Ser
             180                 185                 190

Glu Asp Ala Leu Glu Lys Ala Arg Arg Gly Glu Ala Gly Asp Leu Thr
         195                 200                 205

Gly Lys Gln Thr His Lys Arg Gln Cys Phe Val Val Ala Asp Ala Ala
     210                 215                 220

Asp His Glu Arg Ile Glu Asn Asp Ile Arg Thr Met Pro Asp Tyr Phe
225                 230                 235                 240

Val Gly Tyr Glu Val Glu Val Asn Phe Ile Asp Glu Ala Thr Phe Asp
                 245                 250                 255

Ser Glu His Thr Gly Met Pro His Gly Gly His Val Ile Thr Thr Gly
             260                 265                 270

Asp Thr Gly Gly Phe Asn His Thr Val Glu Tyr Ile Leu Lys
         275                 280                 285
```

<210> SEQ ID NO 43
<211> LENGTH: 1400
<212> TYPE: DNA
<213> ORGANISM: Corynebacterium glutamicum
<220> FEATURE:
<221> NAME/KEY: CDS
<222> LOCATION: (1)..(1377)
<223> OTHER INFORMATION: RXA00972

<400> SEQUENCE: 43

```
cct gca cct ggt tgg cgt ttc cgc acc gga gaa gat gta aca atg gct      48
Pro Ala Pro Gly Trp Arg Phe Arg Thr Gly Glu Asp Val Thr Met Ala
 1               5                  10                  15 aca gtt gaa aat ttc aat gaa ctt ccc gca cac gta tgg cca cgc aat      96
Thr Val Glu Asn Phe Asn Glu Leu Pro Ala His Val Trp Pro Arg Asn
             20                  25                  30 gcc gtg cgc caa gaa gac ggc gtt gtc acc gtc gct ggt gtg cct ctg     144
Ala Val Arg Gln Glu Asp Gly Val Val Thr Val Ala Gly Val Pro Leu
         35                  40                  45 cct gac ctc gct gaa gaa tac gga acc cca ctg ttc gta gtc gac gag     192
```

```
                                                                -continued

Pro Asp Leu Ala Glu Glu Tyr Gly Thr Pro Leu Phe Val Val Asp Glu
                 50                  55                  60 gac gat ttc cgt tcc cgc tgt cgc gac atg gct acc gca ttc ggt gga       240
            Asp Asp Phe Arg Ser Arg Cys Arg Asp Met Ala Thr Ala Phe Gly Gly
             65                  70                  75                  80 cca ggc aat gtg cac tac gca tct aaa gcg ttc ctg acc aag acc att       288
            Pro Gly Asn Val His Tyr Ala Ser Lys Ala Phe Leu Thr Lys Thr Ile
                             85                  90                  95 gca cgt tgg gtt gat gaa gag ggg ctg gca ctg gac att gca tcc atc       336
            Ala Arg Trp Val Asp Glu Glu Gly Leu Ala Leu Asp Ile Ala Ser Ile
                        100                 105                 110 aac gaa ctg ggc att gcc ctg gcc gct ggt ttc ccc gcc agc cgt atc       384
            Asn Glu Leu Gly Ile Ala Leu Ala Ala Gly Phe Pro Ala Ser Arg Ile
                    115                 120                 125 acc gcg cac ggc aac aac aaa ggc gta gag ttc ctg cgc gcg ttg gtt       432
            Thr Ala His Gly Asn Asn Lys Gly Val Glu Phe Leu Arg Ala Leu Val
                130                 135                 140 caa aac ggt gtg gga cac gtg gtg ctg gac tcc gca cag gaa cta gaa       480
            Gln Asn Gly Val Gly His Val Val Leu Asp Ser Ala Gln Glu Leu Glu
            145                 150                 155                 160 ctg ttg gat tac gtt gcc gct ggt gaa ggc aag att cag gac gtg ttg       528
            Leu Leu Asp Tyr Val Ala Ala Gly Glu Gly Lys Ile Gln Asp Val Leu
                            165                 170                 175 atc cgc gta aag cca ggc atc gaa gca cac acc cac gag ttc atc gcc       576
            Ile Arg Val Lys Pro Gly Ile Glu Ala His Thr His Glu Phe Ile Ala
                        180                 185                 190 act agc cac gaa gac cag aag ttc gga ttc tcc ctg gca tcc ggt tcc       624
            Thr Ser His Glu Asp Gln Lys Phe Gly Phe Ser Leu Ala Ser Gly Ser
                    195                 200                 205 gca ttc gaa gca gca aaa gcc gcc aac aac gca gaa aac ctg aac ctg       672
            Ala Phe Glu Ala Ala Lys Ala Ala Asn Asn Ala Glu Asn Leu Asn Leu
                210                 215                 220 gtt ggc ctg cac tgc cac gtt ggt tcc cag gtg ttc gac gcc gaa ggc       720
            Val Gly Leu His Cys His Val Gly Ser Gln Val Phe Asp Ala Glu Gly
            225                 230                 235                 240 ttc aag ctg gca gca gaa cgc gtg ttg ggc ctg tac tca cag atc cac       768
            Phe Lys Leu Ala Ala Glu Arg Val Leu Gly Leu Tyr Ser Gln Ile His
                            245                 250                 255 agc gaa ctg ggc gtt gcc ctt cct gaa ctg gat ctc ggt ggc gga tac       816
            Ser Glu Leu Gly Val Ala Leu Pro Glu Leu Asp Leu Gly Gly Gly Tyr
                        260                 265                 270 ggc att gcc tat acc gca gct gaa gaa cca ctc aac gtc gca gaa gtt       864
            Gly Ile Ala Tyr Thr Ala Ala Glu Glu Pro Leu Asn Val Ala Glu Val
                    275                 280                 285 gcc tcc gac ctg ctc acc gca gtc gga aaa atg gca gcg gaa cta ggc       912
            Ala Ser Asp Leu Leu Thr Ala Val Gly Lys Met Ala Ala Glu Leu Gly
                290                 295                 300 atc gac gca cca acc gtg ctt gtt gag ccc ggc cgc gct atc gca ggc       960
            Ile Asp Ala Pro Thr Val Leu Val Glu Pro Gly Arg Ala Ile Ala Gly
            305                 310                 315                 320 ccc tcc acc gtg acc atc tac gaa gtc ggc acc acc aaa gac gtc cac      1008
            Pro Ser Thr Val Thr Ile Tyr Glu Val Gly Thr Thr Lys Asp Val His
                            325                 330                 335 gta gac gac gac aaa acc cgc cgt tac atc gcc gtg gac gga ggc atg      1056
            Val Asp Asp Asp Lys Thr Arg Arg Tyr Ile Ala Val Asp Gly Gly Met
                        340                 345                 350 tcc gac aac atc cgc cca gca ctc tac ggg tcc gaa tac gac gcc cgc      1104
            Ser Asp Asn Ile Arg Pro Ala Leu Tyr Gly Ser Glu Tyr Asp Ala Arg
                    355                 360                 365
```

```
gta gta tcc cgc ttc gcc gaa gga gac cca gta agc acc cgc atc gtg    1152
Val Val Ser Arg Phe Ala Glu Gly Asp Pro Val Ser Thr Arg Ile Val
    370                 375                 380 ggc tcc cac tgc gaa tcc ggc gat atc ctg atc aac gat gaa atc tac    1200
Gly Ser His Cys Glu Ser Gly Asp Ile Leu Ile Asn Asp Glu Ile Tyr
385                 390                 395                 400 cca tct gac atc acc agc ggc gac ttc ctt gca ctc gcc acc ggc        1248
Pro Ser Asp Ile Thr Ser Gly Asp Phe Leu Ala Leu Ala Ala Thr Gly
                405                 410                 415 gca tac tgc tac gcc atg agc tcc cgc tac aac gcc ttc aca cgg ccc    1296
Ala Tyr Cys Tyr Ala Met Ser Ser Arg Tyr Asn Ala Phe Thr Arg Pro
            420                 425                 430 gcc gtc gtg tcc gtc cgc gct ggc agc tcc cgc ctc atg ctg cgc cgc    1344
Ala Val Val Ser Val Arg Ala Gly Ser Ser Arg Leu Met Leu Arg Arg
        435                 440                 445 gaa acg ctc gac gac atc ctc tca cta gag gca taacgctttt cgacgcctga  1397
Glu Thr Leu Asp Asp Ile Leu Ser Leu Glu Ala
    450                 455 ccc                                                                1400

<210> SEQ ID NO 44
<211> LENGTH: 459
<212> TYPE: PRT
<213> ORGANISM: Corynebacterium glutamicum

<400> SEQUENCE: 44

Pro Ala Pro Gly Trp Arg Phe Arg Thr Gly Glu Asp Val Thr Met Ala
1               5                   10                  15

Thr Val Glu Asn Phe Asn Glu Leu Pro Ala His Val Trp Pro Arg Asn
            20                  25                  30

Ala Val Arg Gln Glu Asp Gly Val Thr Val Ala Gly Val Pro Leu
        35                  40                  45

Pro Asp Leu Ala Glu Glu Tyr Gly Thr Pro Leu Phe Val Val Asp Glu
    50                  55                  60

Asp Asp Phe Arg Ser Arg Cys Arg Asp Met Ala Thr Ala Phe Gly Gly
65                  70                  75                  80

Pro Gly Asn Val His Tyr Ala Ser Lys Ala Phe Leu Thr Lys Thr Ile
                85                  90                  95

Ala Arg Trp Val Asp Glu Glu Gly Leu Ala Leu Asp Ile Ala Ser Ile
            100                 105                 110

Asn Glu Leu Gly Ile Ala Leu Ala Ala Gly Phe Pro Ala Ser Arg Ile
        115                 120                 125

Thr Ala His Gly Asn Asn Lys Gly Val Glu Phe Leu Arg Ala Leu Val
    130                 135                 140

Gln Asn Gly Val Gly His Val Val Leu Asp Ser Ala Gln Glu Leu Glu
145                 150                 155                 160

Leu Leu Asp Tyr Val Ala Ala Gly Glu Gly Lys Ile Gln Asp Val Leu
                165                 170                 175

Ile Arg Val Lys Pro Gly Ile Glu Ala His Thr His Glu Phe Ile Ala
            180                 185                 190

Thr Ser His Glu Asp Gln Lys Phe Gly Phe Ser Leu Ala Ser Gly Ser
        195                 200                 205

Ala Phe Glu Ala Ala Lys Ala Ala Asn Asn Ala Glu Asn Leu Asn Leu
    210                 215                 220

Val Gly Leu His Cys His Val Gly Ser Gln Val Phe Asp Ala Glu Gly
225                 230                 235                 240
```

```
Phe Lys Leu Ala Ala Glu Arg Val Leu Gly Leu Tyr Ser Gln Ile His
                245                 250                 255
Ser Glu Leu Gly Val Ala Leu Pro Glu Leu Asp Leu Gly Gly Gly Tyr
            260                 265                 270
Gly Ile Ala Tyr Thr Ala Ala Glu Glu Pro Leu Asn Val Ala Glu Val
        275                 280                 285
Ala Ser Asp Leu Leu Thr Ala Val Gly Lys Met Ala Ala Glu Leu Gly
    290                 295                 300
Ile Asp Ala Pro Thr Val Leu Val Glu Pro Gly Arg Ala Ile Ala Gly
305                 310                 315                 320
Pro Ser Thr Val Thr Ile Tyr Glu Val Gly Thr Thr Lys Asp Val His
                325                 330                 335
Val Asp Asp Lys Thr Arg Arg Tyr Ile Ala Val Asp Gly Gly Met
            340                 345                 350
Ser Asp Asn Ile Arg Pro Ala Leu Tyr Gly Ser Glu Tyr Asp Ala Arg
        355                 360                 365
Val Val Ser Arg Phe Ala Glu Gly Asp Pro Val Ser Thr Arg Ile Val
    370                 375                 380
Gly Ser His Cys Glu Ser Gly Asp Ile Leu Ile Asn Asp Glu Ile Tyr
385                 390                 395                 400
Pro Ser Asp Ile Thr Ser Gly Asp Phe Leu Ala Leu Ala Ala Thr Gly
                405                 410                 415
Ala Tyr Cys Tyr Ala Met Ser Ser Arg Tyr Asn Ala Phe Thr Arg Pro
            420                 425                 430
Ala Val Val Ser Val Arg Ala Gly Ser Ser Arg Leu Met Leu Arg Arg
        435                 440                 445
Glu Thr Leu Asp Asp Ile Leu Ser Leu Glu Ala
    450                 455

<210> SEQ ID NO 45
<211> LENGTH: 2121
<212> TYPE: DNA
<213> ORGANISM: Corynebacterium glutamicum
<220> FEATURE:
<221> NAME/KEY: CDS
<222> LOCATION: (101)..(2098)
<223> OTHER INFORMATION: RXA02653

<400> SEQUENCE: 45
agacagagtg ttagtgcgtg gggcagctct cactttcatc gacatcactc gagtatgctc     60
accggccgta ttcattccaa taccccgcac agggaaacta atg ata ccg aag ccc     115
                                             Met Ile Pro Lys Pro
                                               1               5 gac gtg acc gac tta tat tta gag gac ctc tta aat gag ggt tcg gaa     163
Asp Val Thr Asp Leu Tyr Leu Glu Asp Leu Leu Asn Glu Gly Ser Glu
             10                  15                  20 aag att cgg tcc gcc aag gat ctt tcc gaa ctt agg aca gtt cta aaa     211
Lys Ile Arg Ser Ala Lys Asp Leu Ser Glu Leu Arg Thr Val Leu Lys
         25                  30                  35 gag gtt tcc tcc caa att cag gaa cga gct ggg aaa aaa gat gaa gaa     259
Glu Val Ser Ser Gln Ile Gln Glu Arg Ala Gly Lys Lys Asp Glu Glu
     40                  45                  50 tgg gga atg ggg gcc act tgg cgg gag ctg tac ccc agc atc gtg gaa     307
Trp Gly Met Gly Ala Thr Trp Arg Glu Leu Tyr Pro Ser Ile Val Glu
 55                  60                  65 cgc gct tcc tac gaa ggg cgt gac agc cta atc gga ttt gat cac tta     355
Arg Ala Ser Tyr Glu Gly Arg Asp Ser Leu Ile Gly Phe Asp His Leu
 70                  75                  80                  85
```

```
gcc cgg gaa atg gaa aga tta gcc ttc ggc cca cca tcc gaa agt ttt      403
Ala Arg Glu Met Glu Arg Leu Ala Phe Gly Pro Pro Ser Glu Ser Phe
             90                  95                 100 gaa tac ctc caa gaa ctc gta aaa tcc gga gtg gta gac atc act cac      451
Glu Tyr Leu Gln Glu Leu Val Lys Ser Gly Val Val Asp Ile Thr His
        105                 110                 115 ctg cat cgt ggc cgg gaa cca ctg aca gat tta gtt cgt gaa ctt gaa      499
Leu His Arg Gly Arg Glu Pro Leu Thr Asp Leu Val Arg Glu Leu Glu
    120                 125                 130 ata act gtg gtg ata gac gct gtt ctt ccc ccg ccg gga gta gtg cca      547
Ile Thr Val Val Ile Asp Ala Val Leu Pro Pro Pro Gly Val Val Pro
135                 140                 145 ggc aca ttg gtg cac aat ttg gta aaa gag gga tat gcc aga atg cgt      595
Gly Thr Leu Val His Asn Leu Val Lys Glu Gly Tyr Ala Arg Met Arg
150                 155                 160                 165 cct ggg act cgg ggg tta gat gta gcg gct gac ggc acc gtt caa ggg      643
Pro Gly Thr Arg Gly Leu Asp Val Ala Ala Asp Gly Thr Val Gln Gly
                170                 175                 180 caa cga cat ttg gct gca gtc gga cgg atg acg gaa gat gtg gtt ttg      691
Gln Arg His Leu Ala Ala Val Gly Arg Met Thr Glu Asp Val Val Leu
            185                 190                 195 ggt aat gac aca ttg tcg cga tca tta cat gac ata atc ccg aag tgg      739
Gly Asn Asp Thr Leu Ser Arg Ser Leu His Asp Ile Ile Pro Lys Trp
        200                 205                 210 gct cgt cga gtt atc cgc gac gcg agc acg tat ccc gat agg gta cat      787
Ala Arg Arg Val Ile Arg Asp Ala Ser Thr Tyr Pro Asp Arg Val His
    215                 220                 225 ggt act cca ccg ctt ccg gca cgg ttg gaa ccc tgg gcg gaa aag ctc      835
Gly Thr Pro Pro Leu Pro Ala Arg Leu Glu Pro Trp Ala Glu Lys Leu
230                 235                 240                 245 act tca gat ccg gcc aca tgc cgc cac ctg att gaa gaa ttc ggg agt      883
Thr Ser Asp Pro Ala Thr Cys Arg His Leu Ile Glu Glu Phe Gly Ser
                250                 255                 260 cct gtg aat gta ctc cat tca ggt tct atg cct cgt aat ata aat gag      931
Pro Val Asn Val Leu His Ser Gly Ser Met Pro Arg Asn Ile Asn Glu
            265                 270                 275 ttg gtt gac gcc ggc att cag atg ggg gtg gat act cga ata ttt ttt      979
Leu Val Asp Ala Gly Ile Gln Met Gly Val Asp Thr Arg Ile Phe Phe
        280                 285                 290 gcc cgc aaa gcg aat aag ggt ctt acc ttc gtt gat gcc gtt aaa gac     1027
Ala Arg Lys Ala Asn Lys Gly Leu Thr Phe Val Asp Ala Val Lys Asp
    295                 300                 305 acc ggt cat ggt gta gat gta gcc agt gaa cga gag tta tct cag gtg     1075
Thr Gly His Gly Val Asp Val Ala Ser Glu Arg Glu Leu Ser Gln Val
310                 315                 320                 325 ctt aat cgt gga gtc cca gga gag cgg atc att cta tcc gca gct atc     1123
Leu Asn Arg Gly Val Pro Gly Glu Arg Ile Ile Leu Ser Ala Ala Ile
                330                 335                 340 aaa ccg gac aga cta ttg gca tta gcg atc gaa aat ggc gtg atc atc     1171
Lys Pro Asp Arg Leu Leu Ala Leu Ala Ile Glu Asn Gly Val Ile Ile
            345                 350                 355 tct gtg gat tcg cgt gat gaa tta gat cgc att tcg gct ttg gtt ggt     1219
Ser Val Asp Ser Arg Asp Glu Leu Asp Arg Ile Ser Ala Leu Val Gly
        360                 365                 370 gac cgc gtt gca cga gtt gcg cct aga gta gct cca gat cct gca gtc     1267
Asp Arg Val Ala Arg Val Ala Pro Arg Val Ala Pro Asp Pro Ala Val
    375                 380                 385 tta cct cca act aga ttt ggt gag cgt gct gca gac tgg ggt aat cgg     1315
Leu Pro Pro Thr Arg Phe Gly Glu Arg Ala Ala Asp Trp Gly Asn Arg
```

-continued

| | | | | |
|---|---|---|---|---|
| ctt acc gag gtg ata ccc ggc gtg gat att gtg ggt ctt cac gtt cac<br>Leu Thr Glu Val Ile Pro Gly Val Asp Ile Val Gly Leu His Val His<br>390                        395                    400                    405<br>                            410                    415                    420 | 1363 |

```
ctt acc gag gtg ata ccc ggc gtg gat att gtg ggt ctt cac gtt cac    1363
Leu Thr Glu Val Ile Pro Gly Val Asp Ile Val Gly Leu His Val His
            410                 415                 420 ctc cat ggc tat gct gca aaa gac cgt gct ctg gct ctg cag gaa tgt    1411
Leu His Gly Tyr Ala Ala Lys Asp Arg Ala Leu Ala Leu Gln Glu Cys
                425                 430                 435 tgc caa ctc gtc gat tct ctc aga gaa tgc ggg cat tcc cca cag ttt    1459
Cys Gln Leu Val Asp Ser Leu Arg Glu Cys Gly His Ser Pro Gln Phe
        440                 445                 450 att gac ctt gga gga ggg gtg cct atg agc tac att gaa tct gag gaa    1507
Ile Asp Leu Gly Gly Gly Val Pro Met Ser Tyr Ile Glu Ser Glu Glu
    455                 460                 465 gat tgg atc cgt tat caa tcc gct aaa tct gcg act tca gcc ggg tat    1555
Asp Trp Ile Arg Tyr Gln Ser Ala Lys Ser Ala Thr Ser Ala Gly Tyr
470                 475                 480                 485 gcc gaa tcc ttt acg tgg aaa gac gat ccg tta tct aat acg tac ccg    1603
Ala Glu Ser Phe Thr Trp Lys Asp Asp Pro Leu Ser Asn Thr Tyr Pro
                490                 495                 500 ttc tat cag acc cca gtg cgc ggt aat tgg ttg aaa gac gtg ctt tct    1651
Phe Tyr Gln Thr Pro Val Arg Gly Asn Trp Leu Lys Asp Val Leu Ser
            505                 510                 515 aag ggg gta gct cag atg ctc att gac cgg gga ttg cgg tta cac ata    1699
Lys Gly Val Ala Gln Met Leu Ile Asp Arg Gly Leu Arg Leu His Ile
        520                 525                 530 gag cct ggt cga agt tta cta gat ggg tgt ggc gtc act ctt gcc gaa    1747
Glu Pro Gly Arg Ser Leu Leu Asp Gly Cys Gly Val Thr Leu Ala Glu
    535                 540                 545 gtt gct ttt gtg aaa acc cga agt gac ggg ttg cct cta gtg gga ctg    1795
Val Ala Phe Val Lys Thr Arg Ser Asp Gly Leu Pro Leu Val Gly Leu
550                 555                 560                 565 gct atg aac cga acg cag tgc cgg act aca tcc gat gat ttt ctc att    1843
Ala Met Asn Arg Thr Gln Cys Arg Thr Thr Ser Asp Asp Phe Leu Ile
                570                 575                 580 gat ccc ctg cat atc act gac ggt gat gta ggc gag gaa atc gaa gca    1891
Asp Pro Leu His Ile Thr Asp Gly Asp Val Gly Glu Glu Ile Glu Ala
            585                 590                 595 tat cta gtg ggt gcc tac tgc atc gaa gat gag ctg att tta cgc cgg    1939
Tyr Leu Val Gly Ala Tyr Cys Ile Glu Asp Glu Leu Ile Leu Arg Arg
        600                 605                 610 cga atc cgc ttc ccg aga gga gtc aaa cca gga gat atc atc gga att    1987
Arg Ile Arg Phe Pro Arg Gly Val Lys Pro Gly Asp Ile Ile Gly Ile
    615                 620                 625 cct aac acc gca gga tac ttc atg cat atc ttg gaa agt gca tcg cac    2035
Pro Asn Thr Ala Gly Tyr Phe Met His Ile Leu Glu Ser Ala Ser His
630                 635                 640                 645 caa atc ccg ttg gcg aaa aat gta gtg tgg ccg gag ggg cag tta gac    2083
Gln Ile Pro Leu Ala Lys Asn Val Val Trp Pro Glu Gly Gln Leu Asp
                650                 655                 660 gat atc gat gcg gat taagacataa ccattcgcta atc                      2121
Asp Ile Asp Ala Asp
            665

<210> SEQ ID NO 46
<211> LENGTH: 666
<212> TYPE: PRT
<213> ORGANISM: Corynebacterium glutamicum

<400> SEQUENCE: 46

Met Ile Pro Lys Pro Asp Val Thr Asp Leu Tyr Leu Glu Asp Leu Leu
```

-continued

```
  1               5                 10                15
Asn Glu Gly Ser Glu Lys Ile Arg Ser Ala Lys Asp Leu Ser Glu Leu
             20                  25                  30
Arg Thr Val Leu Lys Glu Val Ser Ser Gln Ile Gln Glu Arg Ala Gly
             35                  40                  45
Lys Lys Asp Glu Glu Trp Gly Met Gly Ala Thr Trp Arg Glu Leu Tyr
 50                  55                  60
Pro Ser Ile Val Glu Arg Ala Ser Tyr Glu Gly Arg Asp Ser Leu Ile
 65                  70                  75                  80
Gly Phe Asp His Leu Ala Arg Glu Met Glu Arg Leu Ala Phe Gly Pro
             85                  90                  95
Pro Ser Glu Ser Phe Glu Tyr Leu Gln Glu Leu Val Lys Ser Gly Val
            100                 105                 110
Val Asp Ile Thr His Leu His Arg Gly Arg Glu Pro Leu Thr Asp Leu
            115                 120                 125
Val Arg Glu Leu Glu Ile Thr Val Val Ile Asp Ala Val Leu Pro Pro
            130                 135                 140
Pro Gly Val Val Pro Gly Thr Leu Val His Asn Leu Val Lys Glu Gly
145                 150                 155                 160
Tyr Ala Arg Met Arg Pro Gly Thr Arg Gly Leu Asp Val Ala Ala Asp
            165                 170                 175
Gly Thr Val Gln Gly Gln Arg His Leu Ala Ala Val Gly Arg Met Thr
            180                 185                 190
Glu Asp Val Val Leu Gly Asn Asp Thr Leu Ser Arg Ser Leu His Asp
            195                 200                 205
Ile Ile Pro Lys Trp Ala Arg Arg Val Ile Arg Asp Ala Ser Thr Tyr
            210                 215                 220
Pro Asp Arg Val His Gly Thr Pro Pro Leu Pro Ala Arg Leu Glu Pro
225                 230                 235                 240
Trp Ala Glu Lys Leu Thr Ser Asp Pro Ala Thr Cys Arg His Leu Ile
            245                 250                 255
Glu Glu Phe Gly Ser Pro Val Asn Val Leu His Ser Gly Ser Met Pro
            260                 265                 270
Arg Asn Ile Asn Glu Leu Val Asp Ala Gly Ile Gln Met Gly Val Asp
            275                 280                 285
Thr Arg Ile Phe Phe Ala Arg Lys Ala Asn Lys Gly Leu Thr Phe Val
            290                 295                 300
Asp Ala Val Lys Asp Thr Gly His Gly Val Asp Val Ala Ser Glu Arg
305                 310                 315                 320
Glu Leu Ser Gln Val Leu Asn Arg Gly Val Pro Gly Glu Arg Ile Ile
            325                 330                 335
Leu Ser Ala Ala Ile Lys Pro Asp Arg Leu Leu Ala Leu Ala Ile Glu
            340                 345                 350
Asn Gly Val Ile Ile Ser Val Asp Ser Arg Asp Glu Leu Asp Arg Ile
            355                 360                 365
Ser Ala Leu Val Gly Asp Arg Val Ala Arg Val Ala Pro Arg Val Ala
            370                 375                 380
Pro Asp Pro Ala Val Leu Pro Pro Thr Arg Phe Gly Glu Arg Ala Ala
385                 390                 395                 400
Asp Trp Gly Asn Arg Leu Thr Glu Val Ile Pro Gly Val Asp Ile Val
            405                 410                 415
Gly Leu His Val His Leu His Gly Tyr Ala Ala Lys Asp Arg Ala Leu
            420                 425                 430
```

```
Ala Leu Gln Glu Cys Cys Gln Leu Val Asp Ser Leu Arg Glu Cys Gly
            435                 440                 445

His Ser Pro Gln Phe Ile Asp Leu Gly Gly Gly Val Pro Met Ser Tyr
        450                 455                 460

Ile Glu Ser Glu Glu Asp Trp Ile Arg Tyr Gln Ser Ala Lys Ser Ala
465                 470                 475                 480

Thr Ser Ala Gly Tyr Ala Glu Ser Phe Thr Trp Lys Asp Asp Pro Leu
                485                 490                 495

Ser Asn Thr Tyr Pro Phe Tyr Gln Thr Pro Val Arg Gly Asn Trp Leu
            500                 505                 510

Lys Asp Val Leu Ser Lys Gly Val Ala Gln Met Leu Ile Asp Arg Gly
        515                 520                 525

Leu Arg Leu His Ile Glu Pro Gly Arg Ser Leu Leu Asp Gly Cys Gly
    530                 535                 540

Val Thr Leu Ala Glu Val Ala Phe Val Lys Thr Arg Ser Asp Gly Leu
545                 550                 555                 560

Pro Leu Val Gly Leu Ala Met Asn Arg Thr Gln Cys Arg Thr Thr Ser
                565                 570                 575

Asp Asp Phe Leu Ile Asp Pro Leu His Ile Thr Asp Gly Asp Val Gly
            580                 585                 590

Glu Glu Ile Glu Ala Tyr Leu Val Gly Ala Tyr Cys Ile Glu Asp Glu
        595                 600                 605

Leu Ile Leu Arg Arg Arg Ile Arg Phe Pro Arg Gly Val Lys Pro Gly
    610                 615                 620

Asp Ile Ile Gly Ile Pro Asn Thr Ala Gly Tyr Phe Met His Ile Leu
625                 630                 635                 640

Glu Ser Ala Ser His Gln Ile Pro Leu Ala Lys Asn Val Val Trp Pro
                645                 650                 655

Glu Gly Gln Leu Asp Asp Ile Asp Ala Asp
            660                 665

<210> SEQ ID NO 47
<211> LENGTH: 993
<212> TYPE: DNA
<213> ORGANISM: Corynebacterium glutamicum
<220> FEATURE:
<221> NAME/KEY: CDS
<222> LOCATION: (101)..(970)
<223> OTHER INFORMATION: RXA01393

<400> SEQUENCE: 47
caaaagcaga cctgtaatga agatttccat gatcaccatc gtgacctatg gaagtactta      60
agtaaaatga ttggttctta acatggttta atatagcttc atg aac ccc att caa     115
                                              Met Asn Pro Ile Gln
                                                1               5 ctg gac act ttg ctc tca atc att gat gaa ggc agc ttc gaa ggc gcc     163
Leu Asp Thr Leu Leu Ser Ile Ile Asp Glu Gly Ser Phe Glu Gly Ala
             10                  15                  20 tcc tta gcc ctt tcc att tcc ccc tcg gcg gtg agt cag cgc gtt aaa     211
Ser Leu Ala Leu Ser Ile Ser Pro Ser Ala Val Ser Gln Arg Val Lys
         25                  30                  35 gct ctc gag cat cac gtg ggt cga gtg ttg gta tcg cgc acc caa ccg     259
Ala Leu Glu His His Val Gly Arg Val Leu Val Ser Arg Thr Gln Pro
     40                  45                  50 gcc aaa gca acc gaa gcg ggt gaa gtc ctt gtg caa gca gcg cgg aaa     307
Ala Lys Ala Thr Glu Ala Gly Glu Val Leu Val Gln Ala Ala Arg Lys
 55                  60                  65
```

```
atg gtg ttg ctg caa gca gaa act aaa gcg caa cta tct gga cgc ctt      355
Met Val Leu Leu Gln Ala Glu Thr Lys Ala Gln Leu Ser Gly Arg Leu
 70              75                  80                  85 gct gaa atc ccg tta acc atc gcc atc aac gca gat tcg cta tcc aca      403
Ala Glu Ile Pro Leu Thr Ile Ala Ile Asn Ala Asp Ser Leu Ser Thr
                 90                  95                 100 tgg ttt cct ccc gtg ttc aac gag gta gct tct tgg ggt gga gca acg      451
Trp Phe Pro Pro Val Phe Asn Glu Val Ala Ser Trp Gly Gly Ala Thr
            105                 110                 115 ctc acg ctg cgc ttg gaa gat gaa gcg cac aca tta tcc ttg ctg cgg      499
Leu Thr Leu Arg Leu Glu Asp Glu Ala His Thr Leu Ser Leu Leu Arg
        120                 125                 130 cgt gga gat gtt tta gga gcg gta acc cgt gaa gct aat ccc gtg gcg      547
Arg Gly Asp Val Leu Gly Ala Val Thr Arg Glu Ala Asn Pro Val Ala
    135                 140                 145 gga tgt gaa gta gta gaa ctt gga acc atg cgc cac ttg gcc att gca      595
Gly Cys Glu Val Val Glu Leu Gly Thr Met Arg His Leu Ala Ile Ala
150                 155                 160                 165 acc ccc tca ttg cgg gat gcc tac atg gtt gat ggg aaa cta gat tgg      643
Thr Pro Ser Leu Arg Asp Ala Tyr Met Val Asp Gly Lys Leu Asp Trp
                170                 175                 180 gct gcg atg ccc gtc tta cgc ttc ggt ccc aaa gat gtg ctt caa gac      691
Ala Ala Met Pro Val Leu Arg Phe Gly Pro Lys Asp Val Leu Gln Asp
            185                 190                 195 cgt gac ctg gac ggg cgc gtc gat ggt cct gtg ggg cgc agg cgc gta      739
Arg Asp Leu Asp Gly Arg Val Asp Gly Pro Val Gly Arg Arg Arg Val
        200                 205                 210 tcc att gtc ccg tcg gcg gaa ggt ttt ggt gag gca att cgc cga ggc      787
Ser Ile Val Pro Ser Ala Glu Gly Phe Gly Glu Ala Ile Arg Arg Gly
    215                 220                 225 ctt ggt tgg gga ctt ctt ccc gaa acc caa gct gct ccc atg cta aaa      835
Leu Gly Trp Gly Leu Leu Pro Glu Thr Gln Ala Ala Pro Met Leu Lys
230                 235                 240                 245 gca gga gaa gtg atc ctc ctc gat gag ata ccc att gac aca ccg atg      883
Ala Gly Glu Val Ile Leu Leu Asp Glu Ile Pro Ile Asp Thr Pro Met
                250                 255                 260 tat tgg caa cga tgg cgc ctg gaa tct aga tct cta gct aga ctc aca      931
Tyr Trp Gln Arg Trp Arg Leu Glu Ser Arg Ser Leu Ala Arg Leu Thr
            265                 270                 275 gac gcc gtc gtt gat gca gca atc gag gga ttg cgg cct tagttacttc      980
Asp Ala Val Val Asp Ala Ala Ile Glu Gly Leu Arg Pro
        280                 285                 290 tgaaaaggtt cag                                                       993

<210> SEQ ID NO 48
<211> LENGTH: 290
<212> TYPE: PRT
<213> ORGANISM: Corynebacterium glutamicum

<400> SEQUENCE: 48

Met Asn Pro Ile Gln Leu Asp Thr Leu Leu Ser Ile Ile Asp Glu Gly
 1               5                  10                  15

Ser Phe Glu Gly Ala Ser Leu Ala Leu Ser Ile Ser Pro Ser Ala Val
            20                  25                  30

Ser Gln Arg Val Lys Ala Leu Glu His His Val Gly Arg Val Leu Val
        35                  40                  45

Ser Arg Thr Gln Pro Ala Lys Ala Thr Glu Ala Gly Glu Val Leu Val
    50                  55                  60
```

```
Gln Ala Ala Arg Lys Met Val Leu Leu Gln Ala Glu Thr Lys Ala Gln
 65                  70                  75                  80

Leu Ser Gly Arg Leu Ala Glu Ile Pro Leu Thr Ile Ala Ile Asn Ala
             85                  90                  95

Asp Ser Leu Ser Thr Trp Phe Pro Val Phe Asn Glu Val Ala Ser
            100                 105                 110

Trp Gly Gly Ala Thr Leu Thr Leu Arg Leu Glu Asp Glu Ala His Thr
        115                 120                 125

Leu Ser Leu Leu Arg Arg Gly Asp Val Leu Gly Ala Val Thr Arg Glu
    130                 135                 140

Ala Asn Pro Val Ala Gly Cys Glu Val Val Glu Leu Gly Thr Met Arg
145                 150                 155                 160

His Leu Ala Ile Ala Thr Pro Ser Leu Arg Asp Ala Tyr Met Val Asp
                165                 170                 175

Gly Lys Leu Asp Trp Ala Ala Met Pro Val Leu Arg Phe Gly Pro Lys
            180                 185                 190

Asp Val Leu Gln Asp Arg Asp Leu Asp Gly Arg Val Asp Gly Pro Val
        195                 200                 205

Gly Arg Arg Arg Val Ser Ile Val Pro Ser Ala Glu Gly Phe Gly Glu
    210                 215                 220

Ala Ile Arg Arg Gly Leu Gly Trp Gly Leu Leu Pro Glu Thr Gln Ala
225                 230                 235                 240

Ala Pro Met Leu Lys Ala Gly Glu Val Ile Leu Leu Asp Glu Ile Pro
                245                 250                 255

Ile Asp Thr Pro Met Tyr Trp Gln Arg Trp Arg Leu Glu Ser Arg Ser
            260                 265                 270

Leu Ala Arg Leu Thr Asp Ala Val Val Asp Ala Ala Ile Glu Gly Leu
        275                 280                 285

Arg Pro
    290

<210> SEQ ID NO 49
<211> LENGTH: 1626
<212> TYPE: DNA
<213> ORGANISM: Corynebacterium glutamicum
<220> FEATURE:
<221> NAME/KEY: CDS
<222> LOCATION: (101)..(1603)
<223> OTHER INFORMATION: RXA00241

<400> SEQUENCE: 49
ggtctccagc ctttctaaac aattcatctg cacttgatta attggcccca agattacgcg      60
aagtttagcg acttcgccgt acgtcaacta cgttaaatga gtg aat act caa tca      115
                                              Val Asn Thr Gln Ser
                                                1               5 gat tct gcg ggg tct caa ggt gca gcg gcc aca agt cgt act gta tct      163
Asp Ser Ala Gly Ser Gln Gly Ala Ala Ala Thr Ser Arg Thr Val Ser
             10                  15                  20 att aga acc ctc atc gcg ctg atc atc gga tcg acc gtc ggc gcg gga      211
Ile Arg Thr Leu Ile Ala Leu Ile Ile Gly Ser Thr Val Gly Ala Gly
         25                  30                  35 att ttc tcc atc cct caa aac atc ggc tca gtc gca ggt ccc ggc gcg      259
Ile Phe Ser Ile Pro Gln Asn Ile Gly Ser Val Ala Gly Pro Gly Ala
     40                  45                  50 atg ctc atc ggc tgg ctg atc gcc ggt gtg ggc atg ttg tcc gta gcg      307
Met Leu Ile Gly Trp Leu Ile Ala Gly Val Gly Met Leu Ser Val Ala
 55                  60                  65
```

|  |  |
|---|---|
| ttc gtg ttc cat gtt ctt gcc cgc cgt aaa cct cac ctc gat tct ggc<br>Phe Val Phe His Val Leu Ala Arg Arg Lys Pro His Leu Asp Ser Gly<br>70                       75                    80                  85 | 355 |
| gtc tac gca tat gcg cgt gtt gga ttg ggc gat tat gta ggt ttc tcc<br>Val Tyr Ala Tyr Ala Arg Val Gly Leu Gly Asp Tyr Val Gly Phe Ser<br>                    90                    95                   100 | 403 |
| tcc gct tgg ggt tat tgg ctg ggt tca gtc atc gcc caa gtt ggc tac<br>Ser Ala Trp Gly Tyr Trp Leu Gly Ser Val Ile Ala Gln Val Gly Tyr<br>            105                   110                   115 | 451 |
| gca acg tta ttt ttc tcc acg ttg ggc cac tac gta ccg ctg ttt tcc<br>Ala Thr Leu Phe Phe Ser Thr Leu Gly His Tyr Val Pro Leu Phe Ser<br>        120                   125                   130 | 499 |
| caa gat cat cca ttt gtg tca gcg ttg gca gtt agc gct ttg acc tgg<br>Gln Asp His Pro Phe Val Ser Ala Leu Ala Val Ser Ala Leu Thr Trp<br>135                      140                   145 | 547 |
| ctg gtg ttt gga gtt gtt tcc cga gga att agc caa gct gct ttc ttg<br>Leu Val Phe Gly Val Val Ser Arg Gly Ile Ser Gln Ala Ala Phe Leu<br>150                     155                   160                   165 | 595 |
| aca acg gtc acc acc gtg gcc aaa att ctg cct ctg ttg tgc ttc atc<br>Thr Thr Val Thr Thr Val Ala Lys Ile Leu Pro Leu Leu Cys Phe Ile<br>                    170                   175                   180 | 643 |
| atc ctt gtt gca ttc ttg ggc ttt agc tgg gag aag ttc act gtt gat<br>Ile Leu Val Ala Phe Leu Gly Phe Ser Trp Glu Lys Phe Thr Val Asp<br>                185                   190                   195 | 691 |
| tta tgg gcg cgt gat ggt ggc gtg ggc agc att ttt gat cag gtg cgc<br>Leu Trp Ala Arg Asp Gly Gly Val Gly Ser Ile Phe Asp Gln Val Arg<br>             200                   205                   210 | 739 |
| ggc atc atg gtg tac acc gtg tgg gtg ttc atc ggt atc gaa ggt gca<br>Gly Ile Met Val Tyr Thr Val Trp Val Phe Ile Gly Ile Glu Gly Ala<br>215                      220                   225 | 787 |
| tcg gta tat tcc cgc cag gca cgc tca cgc agt gat gtc agc cga gct<br>Ser Val Tyr Ser Arg Gln Ala Arg Ser Arg Ser Asp Val Ser Arg Ala<br>230                      235                   240                   245 | 835 |
| acc gtg att ggt ttt gtg gct gtt ctc ctt ttg ctg gtg tcg att tct<br>Thr Val Ile Gly Phe Val Ala Val Leu Leu Leu Leu Val Ser Ile Ser<br>                    250                   255                   260 | 883 |
| tcg ctg agc ttc ggt gta ctg acc caa caa gag ctc gct gcg tta cca<br>Ser Leu Ser Phe Gly Val Leu Thr Gln Gln Glu Leu Ala Ala Leu Pro<br>             265                   270                   275 | 931 |
| gat aat tcc atg gcg tcg gtg ctc gaa gct gtt gtt ggt cca tgg ggt<br>Asp Asn Ser Met Ala Ser Val Leu Glu Ala Val Val Gly Pro Trp Gly<br>280                      285                   290 | 979 |
| gcc gca ttg att tcg ttg ggt ctg tgt ctt tcg gtt ctt ggg gcc tat<br>Ala Ala Leu Ile Ser Leu Gly Leu Cys Leu Ser Val Leu Gly Ala Tyr<br>295                      300                   305 | 1027 |
| gtg tcc tgg cag atg ctc tgc gca gaa cca ctg gcg ttg atg gca atg<br>Val Ser Trp Gln Met Leu Cys Ala Glu Pro Leu Ala Leu Met Ala Met<br>310                      315                   320                   325 | 1075 |
| gat ggc ctc att cca agc aaa atc ggg gcc atc aac agc cgc ggt gct<br>Asp Gly Leu Ile Pro Ser Lys Ile Gly Ala Ile Asn Ser Arg Gly Ala<br>                    330                   335                   340 | 1123 |
| gcc tgg atg gct cag ctg atc tcc acc atc gtg att cag att ttc atc<br>Ala Trp Met Ala Gln Leu Ile Ser Thr Ile Val Ile Gln Ile Phe Ile<br>                345                   350                   355 | 1171 |
| atc att ttc ttc ctc aac gag acc acc tac gtc tcc atg gtg caa ttg<br>Ile Ile Phe Phe Leu Asn Glu Thr Thr Tyr Val Ser Met Val Gln Leu<br>             360                   365                   370 | 1219 |
| gct acc aac cta tac ttg gtg cct tac ctg ttc tct gcc ttt tat ctg<br>Ala Thr Asn Leu Tyr Leu Val Pro Tyr Leu Phe Ser Ala Phe Tyr Leu<br>375                      380                   385 | 1267 |

```
gtc atg ctg gca aca cgt gga aaa gga atc acc cac cca cat gcc ggc      1315
Val Met Leu Ala Thr Arg Gly Lys Gly Ile Thr His Pro His Ala Gly
390                 395                 400                 405 aca cgt ttt gat gat tcc ggt cca gag ata tcc cgc cga gaa aac cgc      1363
Thr Arg Phe Asp Asp Ser Gly Pro Glu Ile Ser Arg Arg Glu Asn Arg
            410                 415                 420 aaa cac ctc atc gtc ggt tta gta gca acg gtg tat tca gtg tgg ctg      1411
Lys His Leu Ile Val Gly Leu Val Ala Thr Val Tyr Ser Val Trp Leu
                425                 430                 435 ttt tac gct gca gaa ccg cag ttt gtc ctc ttc gga gcc atg gcg atg      1459
Phe Tyr Ala Ala Glu Pro Gln Phe Val Leu Phe Gly Ala Met Ala Met
            440                 445                 450 ctt ccc ggc tta atc ccc tat gtg tgg aca agg att tat cgt ggc gaa      1507
Leu Pro Gly Leu Ile Pro Tyr Val Trp Thr Arg Ile Tyr Arg Gly Glu
455                 460                 465 cag gtg ttt aac cgc ttt gaa atc ggc gtg gtt gtt gtc ctg gtc gtt      1555
Gln Val Phe Asn Arg Phe Glu Ile Gly Val Val Val Val Leu Val Val
470                 475                 480                 485 gct gcc agc gcg ggc gtt att ggt ttg gtc aac gga tca cta tcg ctt      1603
Ala Ala Ser Ala Gly Val Ile Gly Leu Val Asn Gly Ser Leu Ser Leu
                490                 495                 500 taaacaccga aaccttcctg cta                                            1626

<210> SEQ ID NO 50
<211> LENGTH: 501
<212> TYPE: PRT
<213> ORGANISM: Corynebacterium glutamicum

<400> SEQUENCE: 50

Val Asn Thr Gln Ser Asp Ser Ala Gly Ser Gln Gly Ala Ala Ala Thr
1               5                   10                  15

Ser Arg Thr Val Ser Ile Arg Thr Leu Ile Ala Leu Ile Ile Gly Ser
                20                  25                  30

Thr Val Gly Ala Gly Ile Phe Ser Ile Pro Gln Asn Ile Gly Ser Val
            35                  40                  45

Ala Gly Pro Gly Ala Met Leu Ile Gly Trp Leu Ile Ala Gly Val Gly
        50                  55                  60

Met Leu Ser Val Ala Phe Val Phe His Val Leu Ala Arg Arg Lys Pro
65                  70                  75                  80

His Leu Asp Ser Gly Val Tyr Ala Tyr Ala Arg Val Gly Leu Gly Asp
                85                  90                  95

Tyr Val Gly Phe Ser Ser Ala Trp Gly Tyr Trp Leu Gly Ser Val Ile
                100                 105                 110

Ala Gln Val Gly Tyr Ala Thr Leu Phe Phe Ser Thr Leu Gly His Tyr
            115                 120                 125

Val Pro Leu Phe Ser Gln Asp His Pro Phe Val Ser Ala Leu Ala Val
        130                 135                 140

Ser Ala Leu Thr Trp Leu Val Phe Gly Val Val Ser Arg Gly Ile Ser
145                 150                 155                 160

Gln Ala Ala Phe Leu Thr Thr Val Thr Val Ala Lys Ile Leu Pro
                165                 170                 175

Leu Leu Cys Phe Ile Ile Leu Val Ala Phe Leu Gly Phe Ser Trp Glu
            180                 185                 190

Lys Phe Thr Val Asp Leu Trp Ala Arg Asp Gly Gly Val Gly Ser Ile
        195                 200                 205

Phe Asp Gln Val Arg Gly Ile Met Val Tyr Thr Val Trp Val Phe Ile
```

```
                    210                 215                 220
Gly Ile Glu Gly Ala Ser Val Tyr Ser Arg Gln Ala Arg Ser Arg Ser
225                 230                 235                 240

Asp Val Ser Arg Ala Thr Val Ile Gly Phe Val Ala Val Leu Leu Leu
                245                 250                 255

Leu Val Ser Ile Ser Ser Leu Ser Phe Gly Val Leu Thr Gln Gln Glu
                260                 265                 270

Leu Ala Ala Leu Pro Asp Asn Ser Met Ala Ser Val Leu Glu Ala Val
            275                 280                 285

Val Gly Pro Trp Gly Ala Ala Leu Ile Ser Leu Gly Leu Cys Leu Ser
290                 295                 300

Val Leu Gly Ala Tyr Val Ser Trp Gln Met Leu Cys Ala Glu Pro Leu
305                 310                 315                 320

Ala Leu Met Ala Met Asp Gly Leu Ile Pro Ser Lys Ile Gly Ala Ile
                325                 330                 335

Asn Ser Arg Gly Ala Ala Trp Met Ala Gln Leu Ile Ser Thr Ile Val
                340                 345                 350

Ile Gln Ile Phe Ile Ile Ile Phe Phe Leu Asn Glu Thr Thr Tyr Val
            355                 360                 365

Ser Met Val Gln Leu Ala Thr Asn Leu Tyr Leu Val Pro Tyr Leu Phe
370                 375                 380

Ser Ala Phe Tyr Leu Val Met Leu Ala Thr Arg Gly Lys Gly Ile Thr
385                 390                 395                 400

His Pro His Ala Gly Thr Arg Phe Asp Asp Ser Gly Pro Glu Ile Ser
                405                 410                 415

Arg Arg Glu Asn Arg Lys His Leu Ile Val Gly Leu Val Ala Thr Val
            420                 425                 430

Tyr Ser Val Trp Leu Phe Tyr Ala Ala Glu Pro Gln Phe Val Leu Phe
            435                 440                 445

Gly Ala Met Ala Met Leu Pro Gly Leu Ile Pro Tyr Val Trp Thr Arg
450                 455                 460

Ile Tyr Arg Gly Glu Gln Val Phe Asn Arg Phe Glu Ile Gly Val Val
465                 470                 475                 480

Val Val Leu Val Val Ala Ala Ser Ala Gly Val Ile Gly Leu Val Asn
                485                 490                 495

Gly Ser Leu Ser Leu
            500

<210> SEQ ID NO 51
<211> LENGTH: 822
<212> TYPE: DNA
<213> ORGANISM: Corynebacterium glutamicum
<220> FEATURE:
<221> NAME/KEY: CDS
<222> LOCATION: (101)..(799)
<223> OTHER INFORMATION: RXA01394

<400> SEQUENCE: 51
gagcaaagtg tccagttgaa tggggttcat gaagctatat taaaccatgt taagaaccaa      60
tcattttact taagtacttc cataggtcac gatggtgatc atg gaa atc ttc att     115
                                              Met Glu Ile Phe Ile
                                                1               5 aca ggt ctg ctt ttg ggg gcc agt ctt tta ctg tcc atc gga ccg cag     163
Thr Gly Leu Leu Leu Gly Ala Ser Leu Leu Leu Ser Ile Gly Pro Gln
             10                  15                  20 aat gta ctg gtg att aaa caa gga att aag cgc gaa gga ctc att gcg     211
```

```
                                                                             -continued Asn Val Leu Val Ile Lys Gln Gly Ile Lys Arg Glu Gly Leu Ile Ala
            25                  30                  35 gtt ctt ctc gtg tgt tta att tct gac gtc ttt ttg ttc atc gcc ggc        259
Val Leu Leu Val Cys Leu Ile Ser Asp Val Phe Leu Phe Ile Ala Gly
        40                  45                  50 acc ttg ggc gtt gat ctt ttg tcc aat gcc gcg ccg atc gtg ctc gat        307
Thr Leu Gly Val Asp Leu Leu Ser Asn Ala Ala Pro Ile Val Leu Asp
    55                  60                  65 att atg cgc tgg ggt ggc atc gct tac ctg tta tgg ttt gcc gtc atg        355
Ile Met Arg Trp Gly Gly Ile Ala Tyr Leu Leu Trp Phe Ala Val Met
70                  75                  80                  85 gca gcg aaa gac gcc atg aca aac aag gtg gaa gcg cca cag atc att        403
Ala Ala Lys Asp Ala Met Thr Asn Lys Val Glu Ala Pro Gln Ile Ile
                90                  95                  100 gaa gaa aca gaa cca acc gtg ccc gat gac acg cct ttg ggc ggt tcg        451
Glu Glu Thr Glu Pro Thr Val Pro Asp Asp Thr Pro Leu Gly Gly Ser
            105                 110                 115 gcg gtg gcc act gac acg cgc aac cgg gtg cgg gtg gag gtg agc gtc        499
Ala Val Ala Thr Asp Thr Arg Asn Arg Val Arg Val Glu Val Ser Val
        120                 125                 130 gat aag cag cgg gtt tgg gta aag ccc atg ttg atg gca atc gtg ctg        547
Asp Lys Gln Arg Val Trp Val Lys Pro Met Leu Met Ala Ile Val Leu
    135                 140                 145 acc tgg ttg aac ccg aat gcg tat ttg gac gcg ttt gtg ttt atc ggc        595
Thr Trp Leu Asn Pro Asn Ala Tyr Leu Asp Ala Phe Val Phe Ile Gly
150                 155                 160                 165 ggc gtc ggc gcg caa tac ggc gac acc gga cgg tgg att ttc gcc gct        643
Gly Val Gly Ala Gln Tyr Gly Asp Thr Gly Arg Trp Ile Phe Ala Ala
                170                 175                 180 ggc gcg ttc gcg gca agc ctg atc tgg ttc ccg ctg gtg ggt ttc ggc        691
Gly Ala Phe Ala Ala Ser Leu Ile Trp Phe Pro Leu Val Gly Phe Gly
            185                 190                 195 gca gca gca ttg tca cgc ccg ctg tcc agc ccc aag gtg tgg cgc tgg        739
Ala Ala Ala Leu Ser Arg Pro Leu Ser Ser Pro Lys Val Trp Arg Trp
        200                 205                 210 atc aac gtc gtc gtg gca gtt gtg atg acc gca ttg gcc atc aaa ctg        787
Ile Asn Val Val Val Ala Val Val Met Thr Ala Leu Ala Ile Lys Leu
    215                 220                 225 atg ttg atg ggt tagttttcgc gggttttgga atc                              822
Met Leu Met Gly
230

<210> SEQ ID NO 52
<211> LENGTH: 233
<212> TYPE: PRT
<213> ORGANISM: Corynebacterium glutamicum

<400> SEQUENCE: 52

Met Glu Ile Phe Ile Thr Gly Leu Leu Leu Gly Ala Ser Leu Leu Leu
1               5                   10                  15

Ser Ile Gly Pro Gln Asn Val Leu Val Ile Lys Gln Gly Ile Lys Arg
            20                  25                  30

Glu Gly Leu Ile Ala Val Leu Leu Val Cys Leu Ile Ser Asp Val Phe
        35                  40                  45

Leu Phe Ile Ala Gly Thr Leu Gly Val Asp Leu Leu Ser Asn Ala Ala
    50                  55                  60

Pro Ile Val Leu Asp Ile Met Arg Trp Gly Gly Ile Ala Tyr Leu Leu
65                  70                  75                  80

Trp Phe Ala Val Met Ala Ala Lys Asp Ala Met Thr Asn Lys Val Glu
```

```
                    85                  90                  95
Ala Pro Gln Ile Ile Glu Glu Thr Glu Pro Thr Val Pro Asp Asp Thr
                100                 105                 110
Pro Leu Gly Gly Ser Ala Val Ala Thr Asp Thr Arg Asn Arg Val Arg
            115                 120                 125
Val Glu Val Ser Val Asp Lys Gln Arg Val Trp Val Lys Pro Met Leu
        130                 135                 140
Met Ala Ile Val Leu Thr Trp Leu Asn Pro Asn Ala Tyr Leu Asp Ala
145                 150                 155                 160
Phe Val Phe Ile Gly Gly Val Gly Ala Gln Tyr Gly Asp Thr Gly Arg
                165                 170                 175
Trp Ile Phe Ala Ala Gly Ala Phe Ala Ala Ser Leu Ile Trp Phe Pro
                180                 185                 190
Leu Val Gly Phe Gly Ala Ala Ala Leu Ser Arg Pro Leu Ser Ser Pro
            195                 200                 205
Lys Val Trp Arg Trp Ile Asn Val Val Ala Val Val Met Thr Ala
        210                 215                 220
Leu Ala Ile Lys Leu Met Leu Met Gly
225                 230
```

<210> SEQ ID NO 53
<211> LENGTH: 1026
<212> TYPE: DNA
<213> ORGANISM: Corynebacterium glutamicum
<220> FEATURE:
<221> NAME/KEY: CDS
<222> LOCATION: (101)..(1003)
<223> OTHER INFORMATION: RXA00865

<400> SEQUENCE: 53

```
ttatcggaat gtggcttggg cgattgttat gcaaaagttg ttaggttttt tgcggggttg       60
tttaaccccc aaatgaggga agaaggtaac cttgaactct atg agc aca ggt tta      115
                                            Met Ser Thr Gly Leu
                                              1               5 aca gct aag acc gga gta gag cac ttc ggc acc gtt gga gta gca atg     163
Thr Ala Lys Thr Gly Val Glu His Phe Gly Thr Val Gly Val Ala Met
             10                  15                  20 gtt act cca ttc acg gaa tcc gga gac atc gat atc gct gct ggc cgc     211
Val Thr Pro Phe Thr Glu Ser Gly Asp Ile Asp Ile Ala Ala Gly Arg
         25                  30                  35 gaa gtc gcg gct tat ttg gtt gat aag ggc ttg gat tct ttg gtt ctc     259
Glu Val Ala Ala Tyr Leu Val Asp Lys Gly Leu Asp Ser Leu Val Leu
     40                  45                  50 gcg ggc acc act ggt gaa tcc cca acg aca acc gcc gct gaa aaa cta     307
Ala Gly Thr Thr Gly Glu Ser Pro Thr Thr Thr Ala Ala Glu Lys Leu
 55                  60                  65 gaa ctg ctc aag gcc gtt cgt gag gaa gtt ggg gat cgg gcg aag ctc     355
Glu Leu Leu Lys Ala Val Arg Glu Glu Val Gly Asp Arg Ala Lys Leu
 70                  75                  80                  85 atc gcc ggt gtc gga acc aac aac acg cgg aca tct gtg gaa ctt gcg     403
Ile Ala Gly Val Gly Thr Asn Asn Thr Arg Thr Ser Val Glu Leu Ala
             90                  95                 100 gaa gct gct gct tct gct ggc gca gac ggc ctt tta gtt gta act cct     451
Glu Ala Ala Ala Ser Ala Gly Ala Asp Gly Leu Leu Val Val Thr Pro
        105                 110                 115 tat tac tcc aag ccg agc caa gag gga ttg ctg gcg cac ttc ggt gca     499
Tyr Tyr Ser Lys Pro Ser Gln Glu Gly Leu Leu Ala His Phe Gly Ala
    120                 125                 130
```

```
att gct gca gca aca gag gtt cca att tgt ctc tat gac att cct ggt      547
Ile Ala Ala Ala Thr Glu Val Pro Ile Cys Leu Tyr Asp Ile Pro Gly
    135                 140                 145 cgg tca ggt att cca att gag tct gat acc atg aga cgc ctg agt gaa      595
Arg Ser Gly Ile Pro Ile Glu Ser Asp Thr Met Arg Arg Leu Ser Glu
150                 155                 160                 165 tta cct acg att ttg gcg gtc aag gac gcc aag ggt gac ctc gtt gca      643
Leu Pro Thr Ile Leu Ala Val Lys Asp Ala Lys Gly Asp Leu Val Ala
            170                 175                 180 gcc acg tca ttg atc aaa gaa acg gga ctt gcc tgg tat tca ggc gat      691
Ala Thr Ser Leu Ile Lys Glu Thr Gly Leu Ala Trp Tyr Ser Gly Asp
                185                 190                 195 gac cca cta aac ctt gtt tgg ctt gct ttg ggc gga tca ggt ttc att      739
Asp Pro Leu Asn Leu Val Trp Leu Ala Leu Gly Gly Ser Gly Phe Ile
    200                 205                 210 tcc gta att gga cat gca gcc ccc aca gca tta cgt gag ttg tac aca      787
Ser Val Ile Gly His Ala Ala Pro Thr Ala Leu Arg Glu Leu Tyr Thr
215                 220                 225 agc ttc gag gaa ggc gac ctc gtc cgt gcg cgg gaa atc aac gcc aaa      835
Ser Phe Glu Glu Gly Asp Leu Val Arg Ala Arg Glu Ile Asn Ala Lys
230                 235                 240                 245 cta tca ccg ctg gta gct gcc caa ggt cgc ttg ggt gga gtc agc ttg      883
Leu Ser Pro Leu Val Ala Ala Gln Gly Arg Leu Gly Gly Val Ser Leu
            250                 255                 260 gca aaa gct gct ctg cgt ctg cag ggc atc aac gta gga gat cct cga      931
Ala Lys Ala Ala Leu Arg Leu Gln Gly Ile Asn Val Gly Asp Pro Arg
                265                 270                 275 ctt cca att atg gct cca aat gag cag gaa ctt gag gct ctc cga gaa      979
Leu Pro Ile Met Ala Pro Asn Glu Gln Glu Leu Glu Ala Leu Arg Glu
    280                 285                 290 gac atg aaa aaa gct gga gtt cta taaatatgaa tgattcccga aat           1026
Asp Met Lys Lys Ala Gly Val Leu
295                 300
```

<210> SEQ ID NO 54
<211> LENGTH: 301
<212> TYPE: PRT
<213> ORGANISM: Corynebacterium glutamicum

<400> SEQUENCE: 54

```
Met Ser Thr Gly Leu Thr Ala Lys Thr Gly Val Glu His Phe Gly Thr
1               5                   10                  15

Val Gly Val Ala Met Val Thr Pro Phe Thr Glu Ser Gly Asp Ile Asp
            20                  25                  30

Ile Ala Ala Gly Arg Glu Val Ala Ala Tyr Leu Val Asp Lys Gly Leu
        35                  40                  45

Asp Ser Leu Val Leu Ala Gly Thr Thr Gly Glu Ser Pro Thr Thr Thr
    50                  55                  60

Ala Ala Glu Lys Leu Glu Leu Leu Lys Ala Val Arg Glu Glu Val Gly
65                  70                  75                  80

Asp Arg Ala Lys Leu Ile Ala Gly Val Gly Thr Asn Asn Thr Arg Thr
                85                  90                  95

Ser Val Glu Leu Ala Glu Ala Ala Ala Ser Ala Gly Ala Asp Gly Leu
            100                 105                 110

Leu Val Val Thr Pro Tyr Tyr Ser Lys Pro Ser Gln Glu Gly Leu Leu
        115                 120                 125

Ala His Phe Gly Ala Ile Ala Ala Ala Thr Glu Val Pro Ile Cys Leu
    130                 135                 140
```

-continued

```
Tyr Asp Ile Pro Gly Arg Ser Gly Ile Pro Ile Glu Ser Asp Thr Met
145                 150                 155                 160

Arg Arg Leu Ser Glu Leu Pro Thr Ile Leu Ala Val Lys Asp Ala Lys
            165                 170                 175

Gly Asp Leu Val Ala Ala Thr Ser Leu Ile Lys Glu Thr Gly Leu Ala
        180                 185                 190

Trp Tyr Ser Gly Asp Asp Pro Leu Asn Leu Val Trp Leu Ala Leu Gly
    195                 200                 205

Gly Ser Gly Phe Ile Ser Val Ile Gly His Ala Ala Pro Thr Ala Leu
210                 215                 220

Arg Glu Leu Tyr Thr Ser Phe Glu Glu Gly Asp Leu Val Arg Ala Arg
225                 230                 235                 240

Glu Ile Asn Ala Lys Leu Ser Pro Leu Val Ala Ala Gln Gly Arg Leu
                245                 250                 255

Gly Gly Val Ser Leu Ala Lys Ala Ala Leu Arg Leu Gln Gly Ile Asn
            260                 265                 270

Val Gly Asp Pro Arg Leu Pro Ile Met Ala Pro Asn Glu Gln Glu Leu
        275                 280                 285

Glu Ala Leu Arg Glu Asp Met Lys Lys Ala Gly Val Leu
    290                 295                 300

<210> SEQ ID NO 55
<211> LENGTH: 1071
<212> TYPE: DNA
<213> ORGANISM: Corynebacterium glutamicum
<220> FEATURE:
<221> NAME/KEY: CDS
<222> LOCATION: (101)..(1048)
<223> OTHER INFORMATION: RXS02021

<400> SEQUENCE: 55
ttgggtcgcc gaggagatct aatcctggtt tgagttcaga gttcacaggt ttaagcctac      60
aaaccttagt taaacatga tggaagcggt cgattaaaaa atg agt gaa aac att       115
                                          Met Ser Glu Asn Ile
                                            1               5 cgc gga gcc caa gca gtt gga atc gca aat atc gcc atg gac ggg acc      163
Arg Gly Ala Gln Ala Val Gly Ile Ala Asn Ile Ala Met Asp Gly Thr
         10                  15                  20 atc ctg gac acg tgg tac cca gaa ccc caa att ttc aac ccg gat cag      211
Ile Leu Asp Thr Trp Tyr Pro Glu Pro Gln Ile Phe Asn Pro Asp Gln
             25                  30                  35 tgg gct gaa cgc tac cca ttg gaa gtg ggc acc aca cgc ctc gga gca      259
Trp Ala Glu Arg Tyr Pro Leu Glu Val Gly Thr Thr Arg Leu Gly Ala
        40                  45                  50 aac gaa ctc acc cca cgg atg ctg cag ttg gta aaa ctg gac caa gat      307
Asn Glu Leu Thr Pro Arg Met Leu Gln Leu Val Lys Leu Asp Gln Asp
 55                  60                  65 cgc ctc gtc gaa cag gta gca gtc cgc acc gtt atc ccc gat ctg tct      355
Arg Leu Val Glu Gln Val Ala Val Arg Thr Val Ile Pro Asp Leu Ser
 70                  75                  80                  85 caa cct cca gta gac gcg cac gat gtt tac ctg cgc ctc cac ctg ctt      403
Gln Pro Pro Val Asp Ala His Asp Val Tyr Leu Arg Leu His Leu Leu
                 90                  95                 100 tcc cac cgg ctg gtc cgc ccc cac gaa atg cac atg caa aac acc ttg      451
Ser His Arg Leu Val Arg Pro His Glu Met His Met Gln Asn Thr Leu
            105                 110                 115 gag ctg ctg tcc gac gtg gtg tgg aca aac aag ggc cct tgc ctt cct      499
Glu Leu Leu Ser Asp Val Val Trp Thr Asn Lys Gly Pro Cys Leu Pro
        120                 125                 130
```

```
gaa aac ttt gag tgg gtg cgt ggt gct ctg cgg tcc cgc gga ctc atc      547
Glu Asn Phe Glu Trp Val Arg Gly Ala Leu Arg Ser Arg Gly Leu Ile
    135                 140                 145 cac gtc tac tgt gtg gac cgt ctt ccc cgc atg gtc gac tat gtg gtt      595
His Val Tyr Cys Val Asp Arg Leu Pro Arg Met Val Asp Tyr Val Val
150                 155                 160                 165 ccc cct gga gtc cgc atc tcc gaa gca gaa cgc gtg cgc cta ggt gca      643
Pro Pro Gly Val Arg Ile Ser Glu Ala Glu Arg Val Arg Leu Gly Ala
                170                 175                 180 tac ctt gct ccg ggt acc tct gtg ctg cgt gaa ggt ttc gtg tct ttc      691
Tyr Leu Ala Pro Gly Thr Ser Val Leu Arg Glu Gly Phe Val Ser Phe
            185                 190                 195 aac tcc ggc acc ttg ggt gcc gca aag gtg gaa ggc cgc ctg agt tcc      739
Asn Ser Gly Thr Leu Gly Ala Ala Lys Val Glu Gly Arg Leu Ser Ser
        200                 205                 210 ggt gtg gtc atc ggt gaa ggt tcc gag att gga ctg tct tct act att      787
Gly Val Val Ile Gly Glu Gly Ser Glu Ile Gly Leu Ser Ser Thr Ile
    215                 220                 225 cag tcc ccg aga gat gaa cag cgc cgc gtt ttg ccg ttg agc atc ggc      835
Gln Ser Pro Arg Asp Glu Gln Arg Arg Val Leu Pro Leu Ser Ile Gly
230                 235                 240                 245 caa aac tgc aac ttt ggt gtc agc tcc gga atc atc gga gtc agt ctg      883
Gln Asn Cys Asn Phe Gly Val Ser Ser Gly Ile Ile Gly Val Ser Leu
                250                 255                 260 gga gac aat tgc gac atc gga aat aac att gtc ttg gat gga gat acc      931
Gly Asp Asn Cys Asp Ile Gly Asn Asn Ile Val Leu Asp Gly Asp Thr
            265                 270                 275 ccc att tgg ttc gca gcc gat gag gag tta cgc act atc gac tcc atc      979
Pro Ile Trp Phe Ala Ala Asp Glu Glu Leu Arg Thr Ile Asp Ser Ile
        280                 285                 290 gaa ggc caa gca aat tgg tca atc aag cgt gaa tcc ggc ttc cat gag     1027
Glu Gly Gln Ala Asn Trp Ser Ile Lys Arg Glu Ser Gly Phe His Glu
    295                 300                 305 cca gtt gcc cgc ctc aaa gct tgacccattt tcataaccag tgc                1071
Pro Val Ala Arg Leu Lys Ala
310                 315

<210> SEQ ID NO 56
<211> LENGTH: 316
<212> TYPE: PRT
<213> ORGANISM: Corynebacterium glutamicum

<400> SEQUENCE: 56

Met Ser Glu Asn Ile Arg Gly Ala Gln Ala Val Gly Ile Ala Asn Ile
1               5                   10                  15

Ala Met Asp Gly Thr Ile Leu Asp Thr Trp Tyr Pro Glu Pro Gln Ile
            20                  25                  30

Phe Asn Pro Asp Gln Trp Ala Glu Arg Tyr Pro Leu Glu Val Gly Thr
        35                  40                  45

Thr Arg Leu Gly Ala Asn Glu Leu Thr Pro Arg Met Leu Gln Leu Val
    50                  55                  60

Lys Leu Asp Gln Asp Arg Leu Val Glu Gln Ala Val Arg Thr Val
65                  70                  75                  80

Ile Pro Asp Leu Ser Gln Pro Val Asp Ala His Asp Val Tyr Leu
            85                  90                  95

Arg Leu His Leu Leu Ser His Arg Leu Val Arg Pro His Glu Met His
            100                 105                 110

Met Gln Asn Thr Leu Glu Leu Leu Ser Asp Val Val Trp Thr Asn Lys
```

```
                115                 120                 125
Gly Pro Cys Leu Pro Glu Asn Phe Glu Trp Val Arg Gly Ala Leu Arg
    130                 135                 140

Ser Arg Gly Leu Ile His Val Tyr Cys Val Asp Arg Leu Pro Arg Met
145                 150                 155                 160

Val Asp Tyr Val Val Pro Pro Gly Val Arg Ile Ser Glu Ala Glu Arg
                165                 170                 175

Val Arg Leu Gly Ala Tyr Leu Ala Pro Gly Thr Ser Val Leu Arg Glu
            180                 185                 190

Gly Phe Val Ser Phe Asn Ser Gly Thr Leu Gly Ala Ala Lys Val Glu
        195                 200                 205

Gly Arg Leu Ser Ser Gly Val Val Ile Gly Glu Gly Ser Glu Ile Gly
    210                 215                 220

Leu Ser Ser Thr Ile Gln Ser Pro Arg Asp Glu Gln Arg Arg Arg Leu
225                 230                 235                 240

Pro Leu Ser Ile Gly Gln Asn Cys Asn Phe Gly Val Ser Ser Gly Ile
                245                 250                 255

Ile Gly Val Ser Leu Gly Asp Asn Cys Asp Ile Gly Asn Asn Ile Val
            260                 265                 270

Leu Asp Gly Asp Thr Pro Ile Trp Phe Ala Ala Asp Glu Glu Leu Arg
        275                 280                 285

Thr Ile Asp Ser Ile Glu Gly Gln Ala Asn Trp Ser Ile Lys Arg Glu
    290                 295                 300

Ser Gly Phe His Glu Pro Val Ala Arg Leu Lys Ala
305                 310                 315

<210> SEQ ID NO 57
<211> LENGTH: 1296
<212> TYPE: DNA
<213> ORGANISM: Corynebacterium glutamicum
<220> FEATURE:
<221> NAME/KEY: CDS
<222> LOCATION: (101)..(1273)
<223> OTHER INFORMATION: RXS02157

<400> SEQUENCE: 57
gggtggaatt ggcacgatgg tgctgccgga tgttttgat cgggagaatt atcctgaagg      60
caccgttttt agaaaagacg acaaggatgg ggaactgtaa atg agc acg ctg gaa     115
                                             Met Ser Thr Leu Glu
                                               1               5 act tgg cca cag gtc att att aat acg tac ggc acc cca cca gtt gag    163
Thr Trp Pro Gln Val Ile Ile Asn Thr Tyr Gly Thr Pro Pro Val Glu
         10                  15                  20 ctg gtg tcc ggc aag ggc gca acc gtc act gat gac cag ggc aat gtc    211
Leu Val Ser Gly Lys Gly Ala Thr Val Thr Asp Asp Gln Gly Asn Val
     25                  30                  35 tac atc gac ttg ctc gcg ggc atc gca gtc aac gcg ttg ggc cac gcc    259
Tyr Ile Asp Leu Leu Ala Gly Ile Ala Val Asn Ala Leu Gly His Ala
 40                  45                  50 cac ccg gcg atc atc gag gcg gtc acc aac cag atc ggc caa ctt ggt    307
His Pro Ala Ile Ile Glu Ala Val Thr Asn Gln Ile Gly Gln Leu Gly
             55                  60                  65 cac gtc tca aac ttg ttc gca tcc agg ccc gtc gtc gag gtc gcc gag    355
His Val Ser Asn Leu Phe Ala Ser Arg Pro Val Val Glu Val Ala Glu
         70                  75                  80                  85 gag ctc atc aag cgt ttt tcg ctt gac gac gcc acc ctc gcc gcg caa    403
Glu Leu Ile Lys Arg Phe Ser Leu Asp Asp Ala Thr Leu Ala Ala Gln
                 90                  95                 100
```

```
acc cgg gtt ttc ttc tgc aac tcg ggc gcc gaa gca aac gag gct gct       451
Thr Arg Val Phe Phe Cys Asn Ser Gly Ala Glu Ala Asn Glu Ala Ala
        105                 110                 115 ttc aag att gca cgc ttg act ggt cgt tcc cgg att ctg gct gca gtt       499
Phe Lys Ile Ala Arg Leu Thr Gly Arg Ser Arg Ile Leu Ala Ala Val
    120                 125                 130 cat ggt ttc cac ggc cgc acc atg ggt tcc ctc gcg ctg act ggc cag       547
His Gly Phe His Gly Arg Thr Met Gly Ser Leu Ala Leu Thr Gly Gln
135                 140                 145 cca gac aag cgt gaa gcg ttc ctg cca atg cca agc ggt gtg gag ttc       595
Pro Asp Lys Arg Glu Ala Phe Leu Pro Met Pro Ser Gly Val Glu Phe
150                 155                 160                 165 tac cct tac ggc gac acc gat tac ttg cgc aaa atg gta gaa acc aac       643
Tyr Pro Tyr Gly Asp Thr Asp Tyr Leu Arg Lys Met Val Glu Thr Asn
                170                 175                 180 cca acg gat gtg gct gct atc ttc ctc gag cca atc cag ggt gaa acg       691
Pro Thr Asp Val Ala Ala Ile Phe Leu Glu Pro Ile Gln Gly Glu Thr
            185                 190                 195 ggc gtt gtt cca gca cct gaa gga ttc ctc aag gca gtg cgc gag ctg       739
Gly Val Val Pro Ala Pro Glu Gly Phe Leu Lys Ala Val Arg Glu Leu
        200                 205                 210 tgc gat gag tac ggc atc ttg atg atc acc gat gaa gtc cag act ggc       787
Cys Asp Glu Tyr Gly Ile Leu Met Ile Thr Asp Glu Val Gln Thr Gly
    215                 220                 225 gtt ggc cgt acc ggc gat ttc ttt gca cat cag cac gat ggc gtt gtt       835
Val Gly Arg Thr Gly Asp Phe Phe Ala His Gln His Asp Gly Val Val
230                 235                 240                 245 ccc gat gtg gtg acc atg gcc aag gga ctt ggc ggc ggt ctt ccc atc       883
Pro Asp Val Val Thr Met Ala Lys Gly Leu Gly Gly Gly Leu Pro Ile
                250                 255                 260 ggt gct tgt ttg gcc act ggc cgt gca gct gaa ttg atg acc cca ggc       931
Gly Ala Cys Leu Ala Thr Gly Arg Ala Ala Glu Leu Met Thr Pro Gly
            265                 270                 275 aag cac ggc acc act ttc ggt ggc aac cca gtt gct tgt gca gct gcc       979
Lys His Gly Thr Thr Phe Gly Gly Asn Pro Val Ala Cys Ala Ala Ala
        280                 285                 290 aag gca gtg ctg tct gtt gtc gat gac gct ttc tgc gca gaa gtt gcc      1027
Lys Ala Val Leu Ser Val Val Asp Asp Ala Phe Cys Ala Glu Val Ala
    295                 300                 305 cgc aag ggc gag ctg ttc aag gaa ctt ctt gcc aag gtt gac ggc gtt      1075
Arg Lys Gly Glu Leu Phe Lys Glu Leu Leu Ala Lys Val Asp Gly Val
310                 315                 320                 325 gta gac gtc cgt ggc agg ggc ttg atg ttg ggc gtg gtg ctg gag cgc      1123
Val Asp Val Arg Gly Arg Gly Leu Met Leu Gly Val Val Leu Glu Arg
                330                 335                 340 gac gtc gca aag caa gct gtt ctt gat ggt ttt aag cac ggc gtt att      1171
Asp Val Ala Lys Gln Ala Val Leu Asp Gly Phe Lys His Gly Val Ile
            345                 350                 355 ttg aat gca ccg gcg gac aac att atc cgt ttg acc ccg ccg ctg gtg      1219
Leu Asn Ala Pro Ala Asp Asn Ile Ile Arg Leu Thr Pro Pro Leu Val
        360                 365                 370 atc acc gac gaa gaa atc gca gac gca gtc aag gct att gcc gag aca      1267
Ile Thr Asp Glu Glu Ile Ala Asp Ala Val Lys Ala Ile Ala Glu Thr
    375                 380                 385 atc gca taaaggactc aaacttatga ctt                                    1296
Ile Ala
390
```

<210> SEQ ID NO 58

<211> LENGTH: 391
<212> TYPE: PRT
<213> ORGANISM: Corynebacterium glutamicum

<400> SEQUENCE: 58

```
Met Ser Thr Leu Glu Thr Trp Pro Gln Val Ile Ile Asn Thr Tyr Gly
  1               5                  10                  15

Thr Pro Pro Val Glu Leu Val Ser Gly Lys Gly Ala Thr Val Thr Asp
             20                  25                  30

Asp Gln Gly Asn Val Tyr Ile Asp Leu Leu Ala Gly Ile Ala Val Asn
         35                  40                  45

Ala Leu Gly His Ala His Pro Ala Ile Ile Glu Ala Val Thr Asn Gln
     50                  55                  60

Ile Gly Gln Leu Gly His Val Ser Asn Leu Phe Ala Ser Arg Pro Val
 65                  70                  75                  80

Val Glu Val Ala Glu Glu Leu Ile Lys Arg Phe Ser Leu Asp Asp Ala
                 85                  90                  95

Thr Leu Ala Ala Gln Thr Arg Val Phe Phe Cys Asn Ser Gly Ala Glu
            100                 105                 110

Ala Asn Glu Ala Ala Phe Lys Ile Ala Arg Leu Thr Gly Arg Ser Arg
        115                 120                 125

Ile Leu Ala Ala Val His Gly Phe His Gly Arg Thr Met Gly Ser Leu
130                 135                 140

Ala Leu Thr Gly Gln Pro Asp Lys Arg Glu Ala Phe Leu Pro Met Pro
145                 150                 155                 160

Ser Gly Val Glu Phe Tyr Pro Tyr Gly Asp Thr Asp Tyr Leu Arg Lys
                165                 170                 175

Met Val Glu Thr Asn Pro Thr Asp Val Ala Ala Ile Phe Leu Glu Pro
            180                 185                 190

Ile Gln Gly Glu Thr Gly Val Val Pro Ala Pro Glu Gly Phe Leu Lys
        195                 200                 205

Ala Val Arg Glu Leu Cys Asp Glu Tyr Gly Ile Leu Met Ile Thr Asp
    210                 215                 220

Glu Val Gln Thr Gly Val Gly Arg Thr Gly Asp Phe Phe Ala His Gln
225                 230                 235                 240

His Asp Gly Val Val Pro Asp Val Val Thr Met Ala Lys Gly Leu Gly
                245                 250                 255

Gly Gly Leu Pro Ile Gly Ala Cys Leu Ala Thr Gly Arg Ala Ala Glu
            260                 265                 270

Leu Met Thr Pro Gly Lys His Gly Thr Thr Phe Gly Gly Asn Pro Val
        275                 280                 285

Ala Cys Ala Ala Ala Lys Ala Val Leu Ser Val Asp Asp Ala Phe
    290                 295                 300

Cys Ala Glu Val Ala Arg Lys Gly Glu Leu Phe Lys Glu Leu Leu Ala
305                 310                 315                 320

Lys Val Asp Gly Val Val Asp Val Arg Gly Arg Gly Leu Met Leu Gly
                325                 330                 335

Val Val Leu Glu Arg Asp Val Ala Lys Gln Ala Val Leu Asp Gly Phe
            340                 345                 350

Lys His Gly Val Ile Leu Asn Ala Pro Ala Asp Asn Ile Ile Arg Leu
        355                 360                 365

Thr Pro Pro Leu Val Ile Thr Asp Glu Glu Ile Ala Asp Ala Val Lys
    370                 375                 380

Ala Ile Ala Glu Thr Ile Ala
```

<210> SEQ ID NO 59
<211> LENGTH: 1008
<212> TYPE: DNA
<213> ORGANISM: Corynebacterium glutamicum
<220> FEATURE:
<221> NAME/KEY: CDS
<222> LOCATION: (101)..(985)
<223> OTHER INFORMATION: RXC00733

<400> SEQUENCE: 59

| | |
|---|---:|
| acggcgaggt tgtcggtatt ggaacgcaca cgaatttgct gaacacgtgc ggtacctacc | 60 |
| gtgaaattgt tgaatcccaa gagactgcgc aggcgcaatc atg agt aat act gca<br>                                                                      Met Ser Asn Thr Ala<br>                                                                       1                5 | 115 |
| ggc ccc cgc ggg cgt tcc cat cag gca gac gcc gcg ccg aat caa aag<br>Gly Pro Arg Gly Arg Ser His Gln Ala Asp Ala Ala Pro Asn Gln Lys<br>                 10                      15                     20 | 163 |
| gca cag aat ttc gga cca tct gcc aaa agg ctt ttc gga att cta ggc<br>Ala Gln Asn Phe Gly Pro Ser Ala Lys Arg Leu Phe Gly Ile Leu Gly<br>                25                      30                     35 | 211 |
| cat gac cgt aac acc tta att ttt gtt atc ttc cta gcc gtc ctg agc<br>His Asp Arg Asn Thr Leu Ile Phe Val Ile Phe Leu Ala Val Leu Ser<br>        40                      45                     50 | 259 |
| gtt gga ctt acc gtc ttg ggc cca tgg ttg ctg ggt aaa gcc acc aac<br>Val Gly Leu Thr Val Leu Gly Pro Trp Leu Leu Gly Lys Ala Thr Asn<br>55                      60                     65 | 307 |
| gtg gtg ttt gaa gga ttc cta tct aag cgc atg ccg gct ggt gcg tca<br>Val Val Phe Glu Gly Phe Leu Ser Lys Arg Met Pro Ala Gly Ala Ser<br> 70                     75                     80                   85 | 355 |
| aag gaa gat atc atc gcg cag ttg cag gct gca ggt aaa cat aat cag<br>Lys Glu Asp Ile Ile Ala Gln Leu Gln Ala Ala Gly Lys His Asn Gln<br>                 90                      95                    100 | 403 |
| gct tcc atg atg gaa gac atg aac ctt gtt cca ggc tca ggc att gat<br>Ala Ser Met Met Glu Asp Met Asn Leu Val Pro Gly Ser Gly Ile Asp<br>              105                    110                    115 | 451 |
| ttt gaa aaa tta gcc atg atc ctc gga ctg gtg atc ggt gct tat ctc<br>Phe Glu Lys Leu Ala Met Ile Leu Gly Leu Val Ile Gly Ala Tyr Leu<br>          120                    125                    130 | 499 |
| atc ggt agc ctg ttg tcg ttg ttc cag gcg cgg atg ctc aac cgc atc<br>Ile Gly Ser Leu Leu Ser Leu Phe Gln Ala Arg Met Leu Asn Arg Ile<br>135                  140                    145 | 547 |
| gtg caa agt gcc atg cac cgg ctc cgc atg gag gtg gag gaa aaa atc<br>Val Gln Ser Ala Met His Arg Leu Arg Met Glu Val Glu Glu Lys Ile<br>150                  155                    160                    165 | 595 |
| cac cgc cta ccg ctg agc tat ttc gat tcc atc aaa cgt ggt gat ctg<br>His Arg Leu Pro Leu Ser Tyr Phe Asp Ser Ile Lys Arg Gly Asp Leu<br>                 170                    175                    180 | 643 |
| ctt agc cgt gtg acc aac gat gtg gat aat atc ggt caa tcc ctg caa<br>Leu Ser Arg Val Thr Asn Asp Val Asp Asn Ile Gly Gln Ser Leu Gln<br>             185                    190                    195 | 691 |
| caa acc ttg tca cag gcg atc act tcc cta ctg acc gtc atc ggt gtg<br>Gln Thr Leu Ser Gln Ala Ile Thr Ser Leu Leu Thr Val Ile Gly Val<br>        200                    205                    210 | 739 |
| ttg gtg atg atg ttt atc atc tcc cca ctg ctc gca ctc gtg gcg ctg<br>Leu Val Met Met Phe Ile Ile Ser Pro Leu Leu Ala Leu Val Ala Leu<br>215                  220                    225 | 787 |
| gta tcc att ccg gtc acc atc gtg gtc act gtg gtg gtt gcg agc cgt<br>Val Ser Ile Pro Val Thr Ile Val Val Thr Val Val Val Ala Ser Arg<br>230                  235                    240                    245 | 835 |

```
tcc cag aaa ctc ttt gcg gaa cag tgg aag cag acc ggt att ttg aat       883
Ser Gln Lys Leu Phe Ala Glu Gln Trp Lys Gln Thr Gly Ile Leu Asn
            250                 255                 260 gcg cgc ctg gag gaa acc tac tct ggc cac gcc gtg gtt aag gtt ttc       931
Ala Arg Leu Glu Glu Thr Tyr Ser Gly His Ala Val Val Lys Val Phe
        265                 270                 275 gga cac caa aag gat gtt caa gaa gca ttc gag gaa gaa aat caa gct       979
Gly His Gln Lys Asp Val Gln Glu Ala Phe Glu Glu Glu Asn Gln Ala
    280                 285                 290 tgt gta taaggccagc tttggtgccc agt                                    1008
Cys Val
    295

<210> SEQ ID NO 60
<211> LENGTH: 295
<212> TYPE: PRT
<213> ORGANISM: Corynebacterium glutamicum

<400> SEQUENCE: 60

Met Ser Asn Thr Ala Gly Pro Arg Gly Arg Ser His Gln Ala Asp Ala
 1               5                  10                  15

Ala Pro Asn Gln Lys Ala Gln Asn Phe Gly Pro Ser Ala Lys Arg Leu
            20                  25                  30

Phe Gly Ile Leu Gly His Asp Arg Asn Thr Leu Ile Phe Val Ile Phe
        35                  40                  45

Leu Ala Val Leu Ser Val Gly Leu Thr Val Leu Gly Pro Trp Leu Leu
    50                  55                  60

Gly Lys Ala Thr Asn Val Val Phe Glu Gly Phe Leu Ser Lys Arg Met
65                  70                  75                  80

Pro Ala Gly Ala Ser Lys Glu Asp Ile Ile Ala Gln Leu Gln Ala Ala
                85                  90                  95

Gly Lys His Asn Gln Ala Ser Met Met Glu Asp Met Asn Leu Val Pro
            100                 105                 110

Gly Ser Gly Ile Asp Phe Glu Lys Leu Ala Met Ile Leu Gly Leu Val
        115                 120                 125

Ile Gly Ala Tyr Leu Ile Gly Ser Leu Leu Ser Leu Phe Gln Ala Arg
    130                 135                 140

Met Leu Asn Arg Ile Val Gln Ser Ala Met His Arg Leu Arg Met Glu
145                 150                 155                 160

Val Glu Glu Lys Ile His Arg Leu Pro Leu Ser Tyr Phe Asp Ser Ile
                165                 170                 175

Lys Arg Gly Asp Leu Leu Ser Arg Val Thr Asn Asp Val Asp Asn Ile
            180                 185                 190

Gly Gln Ser Leu Gln Gln Thr Leu Ser Gln Ala Ile Thr Ser Leu Leu
        195                 200                 205

Thr Val Ile Gly Val Leu Val Met Met Phe Ile Ile Ser Pro Leu Leu
    210                 215                 220

Ala Leu Val Ala Leu Val Ser Ile Pro Val Thr Ile Val Thr Val
225                 230                 235                 240

Val Val Ala Ser Arg Ser Gln Lys Leu Phe Ala Glu Gln Trp Lys Gln
                245                 250                 255

Thr Gly Ile Leu Asn Ala Arg Leu Glu Glu Thr Tyr Ser Gly His Ala
            260                 265                 270

Val Val Lys Val Phe Gly His Gln Lys Asp Val Gln Glu Ala Phe Glu
        275                 280                 285
```

Glu Glu Asn Gln Ala Cys Val
    290              295

<210> SEQ ID NO 61
<211> LENGTH: 426
<212> TYPE: DNA
<213> ORGANISM: Corynebacterium glutamicum
<220> FEATURE:
<221> NAME/KEY: CDS
<222> LOCATION: (1)..(426)
<223> OTHER INFORMATION: RXC00861

<400> SEQUENCE: 61

```
atg gct cct cac aag gtc atg ctg att acc act ggt act cag ggt gag      48
Met Ala Pro His Lys Val Met Leu Ile Thr Thr Gly Thr Gln Gly Glu
 1               5                  10                  15 cct atg gct gcg ctg tct cgc atg gcg cgt cgt gag cac cga cag atc      96
Pro Met Ala Ala Leu Ser Arg Met Ala Arg Arg Glu His Arg Gln Ile
             20                  25                  30 act gtc cgt gat gga gac ttg att atc ctt tct tcc tcc ctg gtt cca     144
Thr Val Arg Asp Gly Asp Leu Ile Ile Leu Ser Ser Ser Leu Val Pro
         35                  40                  45 ggt aac gaa gaa gca gtg ttc ggt gtc atc aac atg ctg gct cag atc     192
Gly Asn Glu Glu Ala Val Phe Gly Val Ile Asn Met Leu Ala Gln Ile
     50                  55                  60 ggt gca act gtt gtt acc ggt cgc gac gcc aag gtg cac acc tcg ggc     240
Gly Ala Thr Val Val Thr Gly Arg Asp Ala Lys Val His Thr Ser Gly
 65                  70                  75                  80 cac ggc tac tcc gga gag ctg ttg ttc ttg tac aac gcc gct cgt ccg     288
His Gly Tyr Ser Gly Glu Leu Leu Phe Leu Tyr Asn Ala Ala Arg Pro
                 85                  90                  95 aag aac gct atg cct gtc cac ggc gag tgg cgc cac ctg cgc gcc aac     336
Lys Asn Ala Met Pro Val His Gly Glu Trp Arg His Leu Arg Ala Asn
            100                 105                 110 aag gaa ctg gct atc tcc act ggt gtt aac cgc gac aac gtt gtg ctt     384
Lys Glu Leu Ala Ile Ser Thr Gly Val Asn Arg Asp Asn Val Val Leu
        115                 120                 125 gca caa aac ggt gtt gtg gtt gat atg gtc aac ggt cgc gca             426
Ala Gln Asn Gly Val Val Val Asp Met Val Asn Gly Arg Ala
    130                 135                 140
```

<210> SEQ ID NO 62
<211> LENGTH: 142
<212> TYPE: PRT
<213> ORGANISM: Corynebacterium glutamicum

<400> SEQUENCE: 62

```
Met Ala Pro His Lys Val Met Leu Ile Thr Thr Gly Thr Gln Gly Glu
 1               5                  10                  15

Pro Met Ala Ala Leu Ser Arg Met Ala Arg Arg Glu His Arg Gln Ile
             20                  25                  30

Thr Val Arg Asp Gly Asp Leu Ile Ile Leu Ser Ser Ser Leu Val Pro
         35                  40                  45

Gly Asn Glu Glu Ala Val Phe Gly Val Ile Asn Met Leu Ala Gln Ile
     50                  55                  60

Gly Ala Thr Val Val Thr Gly Arg Asp Ala Lys Val His Thr Ser Gly
 65                  70                  75                  80

His Gly Tyr Ser Gly Glu Leu Leu Phe Leu Tyr Asn Ala Ala Arg Pro
                 85                  90                  95

Lys Asn Ala Met Pro Val His Gly Glu Trp Arg His Leu Arg Ala Asn
            100                 105                 110
```

```
Lys Glu Leu Ala Ile Ser Thr Gly Val Asn Arg Asp Asn Val Val Leu
        115                 120                 125

Ala Gln Asn Gly Val Val Val Asp Met Val Asn Gly Arg Ala
130                 135                 140

<210> SEQ ID NO 63
<211> LENGTH: 1066
<212> TYPE: DNA
<213> ORGANISM: Corynebacterium glutamicum
<220> FEATURE:
<221> NAME/KEY: CDS
<222> LOCATION: (101)..(1066)
<223> OTHER INFORMATION: RXC00866

<400> SEQUENCE: 63
gcatcaacgt aggagatcct cgacttccaa ttatggctcc aaatgagcag gaacttgagg        60
ctctccgaga agacatgaaa aaagctggag ttctataaat atg aat gat tcc cga        115
                                             Met Asn Asp Ser Arg
                                              1               5 aat cgc ggc cgg aag gtt acc cgc aag gcg ggc cca cca gaa gct ggt        163
Asn Arg Gly Arg Lys Val Thr Arg Lys Ala Gly Pro Pro Glu Ala Gly
             10                  15                  20 cag gaa aac cat ctg gat acc cct gtc ttt cag gca cca gat gct tcc        211
Gln Glu Asn His Leu Asp Thr Pro Val Phe Gln Ala Pro Asp Ala Ser
         25                  30                  35 tct aac cag agc gct gta aaa gct gag acc gcc gga aac gac aat cgg        259
Ser Asn Gln Ser Ala Val Lys Ala Glu Thr Ala Gly Asn Asp Asn Arg
     40                  45                  50 gat gct gcg caa ggt gct caa gga tcc caa gat tct cag ggt tcc cag        307
Asp Ala Ala Gln Gly Ala Gln Gly Ser Gln Asp Ser Gln Gly Ser Gln
 55                  60                  65 aac gct caa ggt tcc cag aac cgc gag tcc gga aac aac aac cgc aac        355
Asn Ala Gln Gly Ser Gln Asn Arg Glu Ser Gly Asn Asn Asn Arg Asn
 70                  75                  80                  85 cgt tcc aac aac aac cgt cgc ggt ggt cgt gga cgt cgt gga tcc gga        403
Arg Ser Asn Asn Asn Arg Arg Gly Gly Arg Gly Arg Arg Gly Ser Gly
                 90                  95                 100 aac gcc aat gag ggc gcg aac aac aac agc ggt aac cag aac cgt cag        451
Asn Ala Asn Glu Gly Ala Asn Asn Asn Ser Gly Asn Gln Asn Arg Gln
             105                 110                 115 ggc gga aac cgt ggc aac cgc ggt ggc gga cgc cga aac gtt gtt aag        499
Gly Gly Asn Arg Gly Asn Arg Gly Gly Gly Arg Arg Asn Val Val Lys
         120                 125                 130 tcg atg cag ggt gcg gat ctg acc cag cgc ctg cca gag cca cca aag        547
Ser Met Gln Gly Ala Asp Leu Thr Gln Arg Leu Pro Glu Pro Pro Lys
 135                 140                 145 gca ccg gca aac ggt ctg cgt att tac gca ctt ggt ggc att tcc gaa        595
Ala Pro Ala Asn Gly Leu Arg Ile Tyr Ala Leu Gly Gly Ile Ser Glu
150                 155                 160                 165 atc ggt cgc aac atg acc gtg ttt gag tac aac aac cgt ctg ctc atc        643
Ile Gly Arg Asn Met Thr Val Phe Glu Tyr Asn Asn Arg Leu Leu Ile
                 170                 175                 180 gtg gac tgt ggt gtg ctc ttc cca tct tca ggt gag cca ggc gtt gac        691
Val Asp Cys Gly Val Leu Phe Pro Ser Ser Gly Glu Pro Gly Val Asp
             185                 190                 195 ctg att ctt cct gac ttc ggc cca att gag gat cac ctg cac cgc gtc        739
Leu Ile Leu Pro Asp Phe Gly Pro Ile Glu Asp His Leu His Arg Val
         200                 205                 210 gat gca ttg gtg gtt act cac gga cac gaa gac cac att ggt gct att        787
Asp Ala Leu Val Val Thr His Gly His Glu Asp His Ile Gly Ala Ile
```

```
      215                 220                 225
ccc tgg ctg ctg aag ctg cgc aac gat atc cca atc ttg gca tcc cgt     835
Pro Trp Leu Leu Lys Leu Arg Asn Asp Ile Pro Ile Leu Ala Ser Arg
230                 235                 240                 245 ttc acc ttg gct ctg att gca gct aag tgt aag gaa cac cgt cag cgt     883
Phe Thr Leu Ala Leu Ile Ala Ala Lys Cys Lys Glu His Arg Gln Arg
                250                 255                 260 ccg aag ctg atc gag gtc aac gag cag tcc aat gag gac cgc gga ccg     931
Pro Lys Leu Ile Glu Val Asn Glu Gln Ser Asn Glu Asp Arg Gly Pro
            265                 270                 275 ttc aac att cgc ttc tgg gct gtt aac cac tcc atc cca gac tgc ctt     979
Phe Asn Ile Arg Phe Trp Ala Val Asn His Ser Ile Pro Asp Cys Leu
        280                 285                 290 ggt ctt gct atc aag act cct gct ggt ttg gtc atc cac acc ggt gac    1027
Gly Leu Ala Ile Lys Thr Pro Ala Gly Leu Val Ile His Thr Gly Asp
    295                 300                 305 atc aag ctg gat cag act cct cct gat gga cgc cca act                1066
Ile Lys Leu Asp Gln Thr Pro Pro Asp Gly Arg Pro Thr
310                 315                 320

<210> SEQ ID NO 64
<211> LENGTH: 322
<212> TYPE: PRT
<213> ORGANISM: Corynebacterium glutamicum

<400> SEQUENCE: 64

Met Asn Asp Ser Arg Asn Arg Gly Arg Lys Val Thr Arg Lys Ala Gly
1               5                   10                  15

Pro Pro Glu Ala Gly Gln Glu Asn His Leu Asp Thr Pro Val Phe Gln
                20                  25                  30

Ala Pro Asp Ala Ser Ser Asn Gln Ser Ala Val Lys Ala Glu Thr Ala
            35                  40                  45

Gly Asn Asp Asn Arg Asp Ala Ala Gln Gly Ala Gln Gly Ser Gln Asp
        50                  55                  60

Ser Gln Gly Ser Gln Asn Ala Gln Gly Ser Gln Asn Arg Glu Ser Gly
65                  70                  75                  80

Asn Asn Asn Arg Asn Arg Ser Asn Asn Asn Arg Arg Gly Gly Arg Gly
                85                  90                  95

Arg Arg Gly Ser Gly Asn Ala Asn Glu Gly Ala Asn Asn Asn Ser Gly
            100                 105                 110

Asn Gln Asn Arg Gln Gly Gly Asn Arg Gly Asn Arg Gly Gly Gly Arg
        115                 120                 125

Arg Asn Val Val Lys Ser Met Gln Gly Ala Asp Leu Thr Gln Arg Leu
    130                 135                 140

Pro Glu Pro Pro Lys Ala Pro Ala Asn Gly Leu Arg Ile Tyr Ala Leu
145                 150                 155                 160

Gly Gly Ile Ser Glu Ile Gly Arg Asn Met Thr Val Phe Glu Tyr Asn
                165                 170                 175

Asn Arg Leu Leu Ile Val Asp Cys Gly Val Leu Phe Pro Ser Ser Gly
            180                 185                 190

Glu Pro Gly Val Asp Leu Ile Leu Pro Asp Phe Gly Pro Ile Glu Asp
        195                 200                 205

His Leu His Arg Val Asp Ala Leu Val Val Thr His Gly His Glu Asp
    210                 215                 220

His Ile Gly Ala Ile Pro Trp Leu Leu Lys Leu Arg Asn Asp Ile Pro
225                 230                 235                 240
```

-continued

```
Ile Leu Ala Ser Arg Phe Thr Leu Ala Leu Ile Ala Ala Lys Cys Lys
            245                 250                 255

Glu His Arg Gln Arg Pro Lys Leu Ile Glu Val Asn Glu Gln Ser Asn
        260                 265                 270

Glu Asp Arg Gly Pro Phe Asn Ile Arg Phe Trp Ala Val Asn His Ser
    275                 280                 285

Ile Pro Asp Cys Leu Gly Leu Ala Ile Lys Thr Pro Ala Gly Leu Val
290                 295                 300

Ile His Thr Gly Asp Ile Lys Leu Asp Gln Thr Pro Pro Asp Gly Arg
305                 310                 315                 320

Pro Thr

<210> SEQ ID NO 65
<211> LENGTH: 1527
<212> TYPE: DNA
<213> ORGANISM: Corynebacterium glutamicum
<220> FEATURE:
<221> NAME/KEY: CDS
<222> LOCATION: (101)..(1504)
<223> OTHER INFORMATION: RXC02095

<400> SEQUENCE: 65
ctctcttggt cctctcccca cccattttta agtactcaag acccttccaa cagaaaggat        60
tactccccca acaggctcaa aaatactgaa aggctcacgc atg aaa act gag caa       115
                                            Met Lys Thr Glu Gln
                                              1               5 tcc caa aaa gca caa tta gcc cct aag aaa gca cct gaa aag cca caa       163
Ser Gln Lys Ala Gln Leu Ala Pro Lys Lys Ala Pro Glu Lys Pro Gln
             10                  15                  20 cgc atc cgc caa ctt att tcc gtg gcg tgg cag cga cct tgg ctc acc       211
Arg Ile Arg Gln Leu Ile Ser Val Ala Trp Gln Arg Pro Trp Leu Thr
         25                  30                  35 tca ttc acc gta atc agc gct tta gct gca acg ttg ttt gaa ctt aca       259
Ser Phe Thr Val Ile Ser Ala Leu Ala Ala Thr Leu Phe Glu Leu Thr
     40                  45                  50 ctt cct ctt ttg acc ggt ggc gcc atc gat atc gcg ctc gga aat acc       307
Leu Pro Leu Leu Thr Gly Gly Ala Ile Asp Ile Ala Leu Gly Asn Thr
 55                  60                  65 gga gat act tta acc act gac ctg ctg gac cgg ttc act ccg agt gga       355
Gly Asp Thr Leu Thr Thr Asp Leu Leu Asp Arg Phe Thr Pro Ser Gly
 70                  75                  80                  85 tta agc gtg ttg acc agc gtc att gcc ctt atc gtg ctt ctc gcg ttg       403
Leu Ser Val Leu Thr Ser Val Ile Ala Leu Ile Val Leu Leu Ala Leu
                 90                  95                 100 ctt cgc tat gcc agt caa ttt gga cgg cga tac acc gca ggc aag ctc       451
Leu Arg Tyr Ala Ser Gln Phe Gly Arg Arg Tyr Thr Ala Gly Lys Leu
            105                 110                 115 agc atg ggg gta cag cat gat gtc cgg ctt aaa acg atg cgc tca ttg       499
Ser Met Gly Val Gln His Asp Val Arg Leu Lys Thr Met Arg Ser Leu
        120                 125                 130 cag aac ctc gat ggg cca ggt cag gac tct att cgc aca ggc caa gta       547
Gln Asn Leu Asp Gly Pro Gly Gln Asp Ser Ile Arg Thr Gly Gln Val
    135                 140                 145 gtc agt cgg tcc att tcg gat atc aac atg gtg caa agc ctt gtg gcg       595
Val Ser Arg Ser Ile Ser Asp Ile Asn Met Val Gln Ser Leu Val Ala
150                 155                 160                 165 atg ttg ccg atg ttg atc gga aat gtg gtc aag ctt gtg ctc act ttg       643
Met Leu Pro Met Leu Ile Gly Asn Val Val Lys Leu Val Leu Thr Leu
                170                 175                 180
```

```
gtg atc atg ctg gct att tcc ccg ccg ctg acc atc atc gct gca gtg      691
Val Ile Met Leu Ala Ile Ser Pro Pro Leu Thr Ile Ile Ala Ala Val
            185                 190                 195 ttg gtg cct ttg ctg ttg tgg gcc gtg gcc tat tcg cga aaa gcg ctt      739
Leu Val Pro Leu Leu Leu Trp Ala Val Ala Tyr Ser Arg Lys Ala Leu
        200                 205                 210 ttt gcg tcc acg tgg tcg gcc cag caa aag gct gcg gat ctg acc act      787
Phe Ala Ser Thr Trp Ser Ala Gln Gln Lys Ala Ala Asp Leu Thr Thr
        215                 220                 225 cat gtg gaa gaa act gtc acg ggt atc cgc gtg gtc aag gca ttt gcg      835
His Val Glu Glu Thr Val Thr Gly Ile Arg Val Val Lys Ala Phe Ala
230                 235                 240                 245 cag gaa gac cgc gag acc gac aaa ttg gat ctc acc gca cgt gag tta      883
Gln Glu Asp Arg Glu Thr Asp Lys Leu Asp Leu Thr Ala Arg Glu Leu
                250                 255                 260 ttt gcc cag cgc atg cgc act gca cgt ctg acg gca aag ttc atc ccc      931
Phe Ala Gln Arg Met Arg Thr Ala Arg Leu Thr Ala Lys Phe Ile Pro
            265                 270                 275 atg gtt gag cag ctt ccg cag ctt gct ttg gtg gtc aac att gtt ggc      979
Met Val Glu Gln Leu Pro Gln Leu Ala Leu Val Val Asn Ile Val Gly
        280                 285                 290 ggt ggc tat ttg gcc atg act ggt cac atc acg gtg ggc acg ttt gtg     1027
Gly Gly Tyr Leu Ala Met Thr Gly His Ile Thr Val Gly Thr Phe Val
        295                 300                 305 gcg ttt tct tcc tat ctc act agc ttg tcg gcg gtg gct agg tcc ctg     1075
Ala Phe Ser Ser Tyr Leu Thr Ser Leu Ser Ala Val Ala Arg Ser Leu
310                 315                 320                 325 tcg ggc atg ctc atg cgc gtg cag ttg gcg ctg tct tct gtg gag cgc     1123
Ser Gly Met Leu Met Arg Val Gln Leu Ala Leu Ser Ser Val Glu Arg
                330                 335                 340 atc ttt gaa gtc att gat ctt cag cct gaa cgc acc gat cct gca cac     1171
Ile Phe Glu Val Ile Asp Leu Gln Pro Glu Arg Thr Asp Pro Ala His
            345                 350                 355 ccc ctg tca ctt ccc gac act ccc ctg ggt ctg tcg ttc aac aac gta     1219
Pro Leu Ser Leu Pro Asp Thr Pro Leu Gly Leu Ser Phe Asn Asn Val
        360                 365                 370 gat ttc cgt ggg att ctc aac ggt ttt gag ctg ggt gtt cag gcc ggt     1267
Asp Phe Arg Gly Ile Leu Asn Gly Phe Glu Leu Gly Val Gln Ala Gly
        375                 380                 385 gaa acc gtt gtg ttg gtg ggc cct cca ggt tca ggc aag acc atg gct     1315
Glu Thr Val Val Leu Val Gly Pro Pro Gly Ser Gly Lys Thr Met Ala
390                 395                 400                 405 gtg cag ctt gct gga aac ttt tat caa cca gac agc ggc cac atc gcc     1363
Val Gln Leu Ala Gly Asn Phe Tyr Gln Pro Asp Ser Gly His Ile Ala
                410                 415                 420 ttt gat agc aac ggc cat cgc act cgc ttc gac gac ctc acc cac agc     1411
Phe Asp Ser Asn Gly His Arg Thr Arg Phe Asp Asp Leu Thr His Ser
            425                 430                 435 gat atc cgc agg aat ctc atc gcg gtt ttt gat gag ccg ttc ttg tac     1459
Asp Ile Arg Arg Asn Leu Ile Ala Val Phe Asp Glu Pro Phe Leu Tyr
        440                 445                 450 tcc tcc tcc ata ccg cga gaa cat ctc gat ggg ttt gga tgt cag         1504
Ser Ser Ser Ile Pro Arg Glu His Leu Asp Gly Phe Gly Cys Gln
        455                 460                 465 tgatgagcag atcgaacacg cag                                            1527

<210> SEQ ID NO 66
<211> LENGTH: 468
<212> TYPE: PRT
<213> ORGANISM: Corynebacterium glutamicum
```

<400> SEQUENCE: 66

```
Met Lys Thr Glu Gln Ser Gln Lys Ala Gln Leu Ala Pro Lys Lys Ala
 1               5                  10                  15
Pro Glu Lys Pro Gln Arg Ile Arg Gln Leu Ile Ser Val Ala Trp Gln
                20                  25                  30
Arg Pro Trp Leu Thr Ser Phe Thr Val Ile Ser Ala Leu Ala Ala Thr
            35                  40                  45
Leu Phe Glu Leu Thr Leu Pro Leu Leu Thr Gly Gly Ala Ile Asp Ile
        50                  55                  60
Ala Leu Gly Asn Thr Gly Asp Thr Leu Thr Thr Asp Leu Leu Asp Arg
 65                  70                  75                  80
Phe Thr Pro Ser Gly Leu Ser Val Leu Thr Ser Val Ile Ala Leu Ile
                 85                  90                  95
Val Leu Leu Ala Leu Leu Arg Tyr Ala Ser Gln Phe Gly Arg Arg Tyr
            100                 105                 110
Thr Ala Gly Lys Leu Ser Met Gly Val Gln His Asp Val Arg Leu Lys
        115                 120                 125
Thr Met Arg Ser Leu Gln Asn Leu Asp Gly Pro Gly Gln Asp Ser Ile
    130                 135                 140
Arg Thr Gly Gln Val Val Ser Arg Ser Ile Ser Asp Ile Asn Met Val
145                 150                 155                 160
Gln Ser Leu Val Ala Met Leu Pro Met Leu Ile Gly Asn Val Val Lys
                165                 170                 175
Leu Val Leu Thr Leu Val Ile Met Leu Ala Ile Ser Pro Pro Leu Thr
            180                 185                 190
Ile Ile Ala Ala Val Leu Val Pro Leu Leu Leu Trp Ala Val Ala Tyr
        195                 200                 205
Ser Arg Lys Ala Leu Phe Ala Ser Thr Trp Ser Ala Gln Gln Lys Ala
    210                 215                 220
Ala Asp Leu Thr Thr His Val Glu Glu Thr Val Thr Gly Ile Arg Val
225                 230                 235                 240
Val Lys Ala Phe Ala Gln Glu Asp Arg Glu Thr Asp Lys Leu Asp Leu
                245                 250                 255
Thr Ala Arg Glu Leu Phe Ala Gln Arg Met Arg Thr Ala Arg Leu Thr
            260                 265                 270
Ala Lys Phe Ile Pro Met Val Glu Gln Leu Pro Gln Leu Ala Leu Val
        275                 280                 285
Val Asn Ile Val Gly Gly Tyr Leu Ala Met Thr Gly His Ile Thr
    290                 295                 300
Val Gly Thr Phe Val Ala Phe Ser Ser Tyr Leu Thr Ser Leu Ser Ala
305                 310                 315                 320
Val Ala Arg Ser Leu Ser Gly Met Leu Met Arg Val Gln Leu Ala Leu
                325                 330                 335
Ser Ser Val Glu Arg Ile Phe Glu Val Ile Asp Leu Gln Pro Glu Arg
            340                 345                 350
Thr Asp Pro Ala His Pro Leu Ser Leu Pro Asp Thr Pro Leu Gly Leu
        355                 360                 365
Ser Phe Asn Asn Val Asp Phe Arg Gly Ile Leu Asn Gly Phe Glu Leu
    370                 375                 380
Gly Val Gln Ala Gly Glu Thr Val Val Leu Val Gly Pro Pro Gly Ser
385                 390                 395                 400
Gly Lys Thr Met Ala Val Gln Leu Ala Gly Asn Phe Tyr Gln Pro Asp
```

```
                 405                 410                 415
Ser Gly His Ile Ala Phe Asp Ser Asn Gly His Arg Thr Arg Phe Asp
            420                 425                 430

Asp Leu Thr His Ser Asp Ile Arg Arg Asn Leu Ile Ala Val Phe Asp
            435                 440                 445

Glu Pro Phe Leu Tyr Ser Ser Ser Ile Pro Arg Glu His Leu Asp Gly
        450                 455                 460

Phe Gly Cys Gln
465

<210> SEQ ID NO 67
<211> LENGTH: 295
<212> TYPE: DNA
<213> ORGANISM: Corynebacterium glutamicum
<220> FEATURE:
<221> NAME/KEY: CDS
<222> LOCATION: (84)..(272)
<223> OTHER INFORMATION: RXC03185
<220> FEATURE:
<221> NAME/KEY: misc_feature
<222> LOCATION: 57
<223> OTHER INFORMATION: n = a, c, t, or g

<400> SEQUENCE: 67
agcgcccaac cgttcagacc agcggtttct ctgaggatgc aaagtccatg atgggtnagg      60
tcactgagct gtccgaaacc acc atg aat gat ctt gca gct gaa ggt gaa aac     113
                         Met Asn Asp Leu Ala Ala Glu Gly Glu Asn
                           1               5                  10 gat cct tac cgc atg gtt cag cag ctg cgc cgc aag ctc tct cgc ttc       161
Asp Pro Tyr Arg Met Val Gln Gln Leu Arg Arg Lys Leu Ser Arg Phe
                15                  20                  25 gtc gag cag aag tgg aag cgc cag ccg gtc atc atg cca acc gtc att       209
Val Glu Gln Lys Trp Lys Arg Gln Pro Val Ile Met Pro Thr Val Ile
            30                  35                  40 ccg atg act gcg gaa acc acg cac atc ggt gac gat gag gtt cgc gct       257
Pro Met Thr Ala Glu Thr Thr His Ile Gly Asp Asp Glu Val Arg Ala
        45                  50                  55 tca cgc gag tcc ctg taaaagcatt tcgcttttcg acg                         295
Ser Arg Glu Ser Leu
    60

<210> SEQ ID NO 68
<211> LENGTH: 63
<212> TYPE: PRT
<213> ORGANISM: Corynebacterium glutamicum

<400> SEQUENCE: 68

Met Asn Asp Leu Ala Ala Glu Gly Glu Asn Asp Pro Tyr Arg Met Val
  1               5                  10                  15

Gln Gln Leu Arg Arg Lys Leu Ser Arg Phe Val Glu Gln Lys Trp Lys
            20                  25                  30

Arg Gln Pro Val Ile Met Pro Thr Val Ile Pro Met Thr Ala Glu Thr
        35                  40                  45

Thr His Ile Gly Asp Asp Glu Val Arg Ala Ser Arg Glu Ser Leu
    50                  55                  60

<210> SEQ ID NO 69
<211> LENGTH: 1170
<212> TYPE: DNA
<213> ORGANISM: Corynebacterium glutamicum
<220> FEATURE:
<221> NAME/KEY: CDS
```

-continued

```
<222> LOCATION: (101)..(1147)
<223> OTHER INFORMATION: RXA00115

<400> SEQUENCE: 69
tggattctcg agtctgtaca cccttgatca aagcccgagt gttccgtaga ttaactttgt      60
cgtatattgt gacctacacc ccatactgtt aggagttttc atg ctc gac aat agt      115
                                             Met Leu Asp Asn Ser
                                               1               5 ttt tac acc gca gag gtt cag ggc cca tac gaa acc gct tcc att ggc      163
Phe Tyr Thr Ala Glu Val Gln Gly Pro Tyr Glu Thr Ala Ser Ile Gly
             10                  15                  20 cgg ctc gaa ctc gaa gaa ggg ggt gtg att gag gat tgc tgg ttg gct      211
Arg Leu Glu Leu Glu Glu Gly Gly Val Ile Glu Asp Cys Trp Leu Ala
         25                  30                  35 tac gct aca gct gga acg ctc aac gag gac aag tcc aac gcc atc ctc      259
Tyr Ala Thr Ala Gly Thr Leu Asn Glu Asp Lys Ser Asn Ala Ile Leu
     40                  45                  50 att ccg acg tgg tac tcc gga acc cat cag acc tgg ttc cag cag tac      307
Ile Pro Thr Trp Tyr Ser Gly Thr His Gln Thr Trp Phe Gln Gln Tyr
 55                  60                  65 atc ggc act gat cat gcg ctg gat cca tca aag tat ttc atc atc tcc      355
Ile Gly Thr Asp His Ala Leu Asp Pro Ser Lys Tyr Phe Ile Ile Ser
 70                  75                  80                  85 atc aac caa atc ggt aat ggt ttg tcg gtc tcc cct gcc aac acg gct      403
Ile Asn Gln Ile Gly Asn Gly Leu Ser Val Ser Pro Ala Asn Thr Ala
                 90                  95                 100 gat gac agc atc tcg atg tcc aag ttc ccg aat gtt cgc att ggt gat      451
Asp Asp Ser Ile Ser Met Ser Lys Phe Pro Asn Val Arg Ile Gly Asp
            105                 110                 115 gat gtc gtt gcc cag gac cgg ctc ttg cgc caa gag ttt ggt att acc      499
Asp Val Val Ala Gln Asp Arg Leu Leu Arg Gln Glu Phe Gly Ile Thr
        120                 125                 130 gag ctc ttt gcc gtc gtt ggt ggt tcg atg ggt gcg cag caa acc tat      547
Glu Leu Phe Ala Val Val Gly Gly Ser Met Gly Ala Gln Gln Thr Tyr
    135                 140                 145 gag tgg att gtt cgc ttc cct gac caa gtt cat cga gca gct ccg atc      595
Glu Trp Ile Val Arg Phe Pro Asp Gln Val His Arg Ala Ala Pro Ile
150                 155                 160                 165 gcg ggc act gcg aag aac act cct cat gat ttc atc ttc acc cag act      643
Ala Gly Thr Ala Lys Asn Thr Pro His Asp Phe Ile Phe Thr Gln Thr
                170                 175                 180 ctt aat gag acc gtt gag gcc gat cca ggg ttc aat ggc ggc gaa tac      691
Leu Asn Glu Thr Val Glu Ala Asp Pro Gly Phe Asn Gly Gly Glu Tyr
            185                 190                 195 tcc tcc cat gaa gag gta gct gat gga ctt cgc cgt caa tcg cat ctt      739
Ser Ser His Glu Glu Val Ala Asp Gly Leu Arg Arg Gln Ser His Leu
        200                 205                 210 tgg gct gcc atg gga ttt tcc aca gag ttc tgg aag cag gag gca tgg      787
Trp Ala Ala Met Gly Phe Ser Thr Glu Phe Trp Lys Gln Glu Ala Trp
    215                 220                 225 cgt cgc ctg gga ctt gaa agt aag gag tca gtg ctc gcg gac ttc ctg      835
Arg Arg Leu Gly Leu Glu Ser Lys Glu Ser Val Leu Ala Asp Phe Leu
230                 235                 240                 245 gat ccg ctg ttc atg tcc atg gat cct aat acc ttg ctc aac aac gct      883
Asp Pro Leu Phe Met Ser Met Asp Pro Asn Thr Leu Leu Asn Asn Ala
                250                 255                 260 tgg aag tgg cag cat ggc gat gtc tct cgc cac acc ggc ggc gac ttg      931
Trp Lys Trp Gln His Gly Asp Val Ser Arg His Thr Gly Gly Asp Leu
            265                 270                 275
```

```
gca gcg gct ctt ggc cga gtg aag gct aag acc ttc gtt atg ccc atc    979
Ala Ala Ala Leu Gly Arg Val Lys Ala Lys Thr Phe Val Met Pro Ile
        280                 285                 290 agc gag gac atg ttc ttt cct gtt cgt gac tgt gcc gca gaa caa gca   1027
Ser Glu Asp Met Phe Phe Pro Val Arg Asp Cys Ala Ala Glu Gln Ala
295                 300                 305 ctc atc cca ggc agc gag ctt cga gtg atc gaa gac atc gcc ggt cac   1075
Leu Ile Pro Gly Ser Glu Leu Arg Val Ile Glu Asp Ile Ala Gly His
310                 315                 320                 325 ctt ggg ctt ttt aac gtc tct gag aat tac atc cca cag atc gac aaa   1123
Leu Gly Leu Phe Asn Val Ser Glu Asn Tyr Ile Pro Gln Ile Asp Lys
                330                 335                 340 aat ctg aaa gag ctg ttc gag agc taaacactga tgtcaaagag cct         1170
Asn Leu Lys Glu Leu Phe Glu Ser
            345
```

<210> SEQ ID NO 70
<211> LENGTH: 349
<212> TYPE: PRT
<213> ORGANISM: Corynebacterium glutamicum

<400> SEQUENCE: 70

```
Met Leu Asp Asn Ser Phe Tyr Thr Ala Glu Val Gln Gly Pro Tyr Glu
 1               5                  10                  15

Thr Ala Ser Ile Gly Arg Leu Glu Leu Glu Gly Gly Val Ile Glu
            20                  25                  30

Asp Cys Trp Leu Ala Tyr Ala Thr Ala Gly Thr Leu Asn Glu Asp Lys
        35                  40                  45

Ser Asn Ala Ile Leu Ile Pro Thr Trp Tyr Ser Gly Thr His Gln Thr
    50                  55                  60

Trp Phe Gln Gln Tyr Ile Gly Thr Asp His Ala Leu Asp Pro Ser Lys
65                  70                  75                  80

Tyr Phe Ile Ile Ser Ile Asn Gln Ile Gly Asn Gly Leu Ser Val Ser
                85                  90                  95

Pro Ala Asn Thr Ala Asp Asp Ser Ile Ser Met Ser Lys Phe Pro Asn
            100                 105                 110

Val Arg Ile Gly Asp Asp Val Val Ala Gln Asp Arg Leu Leu Arg Gln
        115                 120                 125

Glu Phe Gly Ile Thr Glu Leu Phe Ala Val Val Gly Gly Ser Met Gly
    130                 135                 140

Ala Gln Gln Thr Tyr Glu Trp Ile Val Arg Phe Pro Asp Gln Val His
145                 150                 155                 160

Arg Ala Ala Pro Ile Ala Gly Thr Ala Lys Asn Thr Pro His Asp Phe
                165                 170                 175

Ile Phe Thr Gln Thr Leu Asn Glu Thr Val Glu Ala Asp Pro Gly Phe
            180                 185                 190

Asn Gly Gly Glu Tyr Ser Ser His Glu Glu Val Ala Asp Gly Leu Arg
        195                 200                 205

Arg Gln Ser His Leu Trp Ala Ala Met Gly Phe Ser Thr Glu Phe Trp
    210                 215                 220

Lys Gln Glu Ala Trp Arg Arg Leu Gly Leu Glu Ser Lys Glu Ser Val
225                 230                 235                 240

Leu Ala Asp Phe Leu Asp Pro Leu Phe Met Ser Met Asp Pro Asn Thr
                245                 250                 255

Leu Leu Asn Asn Ala Trp Lys Trp Gln His Gly Asp Val Ser Arg His
            260                 265                 270
```

```
Thr Gly Gly Asp Leu Ala Ala Ala Leu Gly Arg Val Lys Ala Lys Thr
            275                 280                 285

Phe Val Met Pro Ile Ser Glu Asp Met Phe Phe Pro Val Arg Asp Cys
            290                 295                 300

Ala Ala Glu Gln Ala Leu Ile Pro Gly Ser Glu Leu Arg Val Ile Glu
305                 310                 315                 320

Asp Ile Ala Gly His Leu Gly Leu Phe Asn Val Ser Glu Asn Tyr Ile
                325                 330                 335

Pro Gln Ile Asp Lys Asn Leu Lys Glu Leu Phe Glu Ser
            340                 345

<210> SEQ ID NO 71
<211> LENGTH: 1254
<212> TYPE: DNA
<213> ORGANISM: Corynebacterium glutamicum
<220> FEATURE:
<221> NAME/KEY: CDS
<222> LOCATION: (101)..(1231)
<223> OTHER INFORMATION: RXN00403

<400> SEQUENCE: 71
tttttcagac tcgtgagaat gcaaactaga ctagacagag ctgtccatat acactggacg      60 aagtttagt cttgtccacc cagaacaggc ggttattttc atg ccc acc ctc gcg       115
                                             Met Pro Thr Leu Ala
                                               1               5 cct tca ggt caa ctt gaa atc caa gcg atc ggt gat gtc tcc acc gaa      163
Pro Ser Gly Gln Leu Glu Ile Gln Ala Ile Gly Asp Val Ser Thr Glu
            10                  15                  20 gcc gga gca atc att aca aac gct gaa atc gcc tat cac cgc tgg ggt      211
Ala Gly Ala Ile Ile Thr Asn Ala Glu Ile Ala Tyr His Arg Trp Gly
        25                  30                  35 gaa tac cgc gta gat aaa gaa gga cgc agc aat gtc gtt ctc atc gaa      259
Glu Tyr Arg Val Asp Lys Glu Gly Arg Ser Asn Val Val Leu Ile Glu
    40                  45                  50 cac gcc ctc act gga gat tcc aac gca gcc gat tgg tgg gct gac ttg      307
His Ala Leu Thr Gly Asp Ser Asn Ala Ala Asp Trp Trp Ala Asp Leu
55                  60                  65 ctc ggt ccc ggc aaa gcc atc aac act gat att tac tgc gtg atc tgt      355
Leu Gly Pro Gly Lys Ala Ile Asn Thr Asp Ile Tyr Cys Val Ile Cys
70                  75                  80                  85 acc aac gtc atc ggt ggt tgc aac ggt tcc acc gga cct ggc tcc atg      403
Thr Asn Val Ile Gly Gly Cys Asn Gly Ser Thr Gly Pro Gly Ser Met
                90                  95                 100 cat cca gat gga aat ttc tgg ggt aat cgc ttc ccc gcc acg tcc att      451
His Pro Asp Gly Asn Phe Trp Gly Asn Arg Phe Pro Ala Thr Ser Ile
            105                 110                 115 cgt gat cag gta aac gcc gaa aaa caa ttc ctc gac gca ctc ggc atc      499
Arg Asp Gln Val Asn Ala Glu Lys Gln Phe Leu Asp Ala Leu Gly Ile
        120                 125                 130 acc acg gtc gcc gca gta ctt ggt ggt tcc atg ggt ggt gcc cgc acc      547
Thr Thr Val Ala Ala Val Leu Gly Gly Ser Met Gly Gly Ala Arg Thr
    135                 140                 145 cta gag tgg gcc gca atg tac cca gaa act gtt ggc gca gct gct gtt      595
Leu Glu Trp Ala Ala Met Tyr Pro Glu Thr Val Gly Ala Ala Ala Val
150                 155                 160                 165 ctt gca gtt tct gca cgc gcc agc gcc tgg caa atc ggc att caa tcc      643
Leu Ala Val Ser Ala Arg Ala Ser Ala Trp Gln Ile Gly Ile Gln Ser
                170                 175                 180 gcc caa att aag gcg att gaa aac gac cac cac tgg cac gaa ggc aac      691
Ala Gln Ile Lys Ala Ile Glu Asn Asp His His Trp His Glu Gly Asn
```

```
                185                 190                 195
tac tac gaa tcc ggc tgc aac cca gcc acc gga ctc ggc gcc gcc cga      739
Tyr Tyr Glu Ser Gly Cys Asn Pro Ala Thr Gly Leu Gly Ala Ala Arg
        200                 205                 210 cgc atc gcc cac ctc acc tac cgt ggc gaa cta gaa atc gac gaa cgc      787
Arg Ile Ala His Leu Thr Tyr Arg Gly Glu Leu Glu Ile Asp Glu Arg
    215                 220                 225 ttc ggc acc aaa gcc caa aag aac gaa aac cca ctc ggt ccc tac cgc      835
Phe Gly Thr Lys Ala Gln Lys Asn Glu Asn Pro Leu Gly Pro Tyr Arg
230                 235                 240                 245 aag ccc gac cag cgc ttc gcc gtg gaa tcc tac ttg gac tac caa gca      883
Lys Pro Asp Gln Arg Phe Ala Val Glu Ser Tyr Leu Asp Tyr Gln Ala
                250                 255                 260 gac aag cta gta cag cgt ttc gac gcc ggc tcc tac gtc ttg ctc acc      931
Asp Lys Leu Val Gln Arg Phe Asp Ala Gly Ser Tyr Val Leu Leu Thr
            265                 270                 275 gac gcc ctc aac cgc cac gac att ggt cgc gac cgc gga ggc ctc aac      979
Asp Ala Leu Asn Arg His Asp Ile Gly Arg Asp Arg Gly Gly Leu Asn
        280                 285                 290 aag gca ctc gaa tcc atc aaa gtt cca gtc ctt gtc gca ggc gta gat     1027
Lys Ala Leu Glu Ser Ile Lys Val Pro Val Leu Val Ala Gly Val Asp
    295                 300                 305 acc gat att ttg tac ccc tac cac cag caa gaa cac ctc tcc aga aac     1075
Thr Asp Ile Leu Tyr Pro Tyr His Gln Gln Glu His Leu Ser Arg Asn
310                 315                 320                 325 ctg gga aat cta ctg gca atg gca aaa atc gta tcc cct gtc ggc cac     1123
Leu Gly Asn Leu Leu Ala Met Ala Lys Ile Val Ser Pro Val Gly His
                330                 335                 340 gat gct ttc ctc acc gaa agc cgc caa atg gat cgc atc gtg agg aac     1171
Asp Ala Phe Leu Thr Glu Ser Arg Gln Met Asp Arg Ile Val Arg Asn
            345                 350                 355 ttc ttc agc ctc atc tcc cca gac gaa gac aac cct tcg acc tac atc     1219
Phe Phe Ser Leu Ile Ser Pro Asp Glu Asp Asn Pro Ser Thr Tyr Ile
        360                 365                 370 gag ttc tac atc taataggtat ttacgacaaa tag                           1254
Glu Phe Tyr Ile
    375

<210> SEQ ID NO 72
<211> LENGTH: 377
<212> TYPE: PRT
<213> ORGANISM: Corynebacterium glutamicum

<400> SEQUENCE: 72

Met Pro Thr Leu Ala Pro Ser Gly Gln Leu Glu Ile Gln Ala Ile Gly
1               5                   10                  15

Asp Val Ser Thr Glu Ala Gly Ala Ile Ile Thr Asn Ala Glu Ile Ala
                20                  25                  30

Tyr His Arg Trp Gly Tyr Arg Val Asp Lys Glu Gly Arg Ser Asn
            35                  40                  45

Val Val Leu Ile Glu His Ala Leu Thr Gly Asp Ser Asn Ala Ala Asp
        50                  55                  60

Trp Trp Ala Asp Leu Leu Gly Pro Gly Lys Ala Ile Asn Thr Asp Ile
65                  70                  75                  80

Tyr Cys Val Ile Cys Thr Asn Val Ile Gly Gly Cys Asn Gly Ser Thr
                85                  90                  95

Gly Pro Gly Ser Met His Pro Asp Gly Asn Phe Trp Gly Asn Arg Phe
            100                 105                 110
```

```
Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Leu Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Phe Ser Leu Ile Ser Pro Asp Glu Asp Asn
        355                 360                 365

Pro Ser Thr Tyr Ile Glu Phe Tyr Ile
    370                 375

<210> SEQ ID NO 73
<211> LENGTH: 1210
<212> TYPE: DNA
<213> ORGANISM: Corynebacterium glutamicum
<220> FEATURE:
<221> NAME/KEY: CDS
<222> LOCATION: (101)..(1210)
<223> OTHER INFORMATION: FRXA00403

<400> SEQUENCE: 73
tttttcagac tcgtgagaat gcaaactaga ctagacagag ctgtccatat acactggacg      60 aagtttagt cttgtccacc cagaacaggc ggttatttc atg ccc acc ctc gcg         115
                                            Met Pro Thr Leu Ala
                                              1               5 cct tca ggt caa ctt gaa atc caa gcg atc ggt gat gtc tcc acc gaa       163
Pro Ser Gly Gln Leu Glu Ile Gln Ala Ile Gly Asp Val Ser Thr Glu
             10                  15                  20 gcc gga gca atc att aca aac gct gaa atc gcc tat cac cgc tgg ggt       211
Ala Gly Ala Ile Ile Thr Asn Ala Glu Ile Ala Tyr His Arg Trp Gly
         25                  30                  35 gaa tac cgc gta gat aaa gaa gga cgc agc aat gtc gtt ctc atc gaa       259
Glu Tyr Arg Val Asp Lys Glu Gly Arg Ser Asn Val Val Leu Ile Glu
```

-continued

|  |  |  |  |  |  |  |  |  |  |  |  |  |  |  |  |
|---|---|---|---|---|---|---|---|---|---|---|---|---|---|---|---|
|  |  | 40 |  |  |  | 45 |  |  |  | 50 |  |  |  |  |  |

```
cac gcc ctc act gga gat tcc aac gca gcc gat tgg tgg gct gac ttg      307
His Ala Leu Thr Gly Asp Ser Asn Ala Ala Asp Trp Trp Ala Asp Leu
        55                  60                  65 ctc ggt ccc ggc aaa gcc atc aac act gat att tac tgc gtg atc tgt      355
Leu Gly Pro Gly Lys Ala Ile Asn Thr Asp Ile Tyr Cys Val Ile Cys
70                  75                  80                  85 acc aac gtc atc ggt ggt tgc aac ggt tcc acc gga cct ggc tcc atg      403
Thr Asn Val Ile Gly Gly Cys Asn Gly Ser Thr Gly Pro Gly Ser Met
                90                  95                 100 cat cca gat gga aat ttc tgg ggt aat cgc ttc ccc gcc acg tcc att      451
His Pro Asp Gly Asn Phe Trp Gly Asn Arg Phe Pro Ala Thr Ser Ile
            105                 110                 115 cgt gat cag gta aac gcc gaa aaa caa ttc ctc gac gca ctc ggc atc      499
Arg Asp Gln Val Asn Ala Glu Lys Gln Phe Leu Asp Ala Leu Gly Ile
        120                 125                 130 acc acg gtc gcc gca gta ctt ggt ggt tcc atg ggt ggt gcc cgc acc      547
Thr Thr Val Ala Ala Val Leu Gly Gly Ser Met Gly Gly Ala Arg Thr
    135                 140                 145 cta gag tgg gcc gca atg tac cca gaa act gtt ggc gca gct gct gtt      595
Leu Glu Trp Ala Ala Met Tyr Pro Glu Thr Val Gly Ala Ala Ala Val
150                 155                 160                 165 ctt gca gtt tct gca cgc gcc agc gcc tgg caa atc ggc att caa tcc      643
Leu Ala Val Ser Ala Arg Ala Ser Ala Trp Gln Ile Gly Ile Gln Ser
                170                 175                 180 gcc caa att aag gcg att gaa aac gac cac cac tgg cac gaa ggc aac      691
Ala Gln Ile Lys Ala Ile Glu Asn Asp His His Trp His Glu Gly Asn
            185                 190                 195 tac tac gaa tcc ggc tgc aac cca gcc acc gga ctc ggc gcc gcc cga      739
Tyr Tyr Glu Ser Gly Cys Asn Pro Ala Thr Gly Leu Gly Ala Ala Arg
        200                 205                 210 cgc atc gcc cac ctc acc tac cgt ggc gaa cta gaa atc gac gaa cgc      787
Arg Ile Ala His Leu Thr Tyr Arg Gly Glu Leu Glu Ile Asp Glu Arg
    215                 220                 225 ttc ggc acc aaa gcc caa aag aac gaa aac cca ctc ggt ccc tac cgc      835
Phe Gly Thr Lys Ala Gln Lys Asn Glu Asn Pro Leu Gly Pro Tyr Arg
230                 235                 240                 245 aag ccc gac cag cgc ttc gcc gtg gaa tcc tac ttg gac tac caa gca      883
Lys Pro Asp Gln Arg Phe Ala Val Glu Ser Tyr Leu Asp Tyr Gln Ala
                250                 255                 260 gac aag cta gta cag cgt ttc gac gcc ggc tcc tac gtc ttg ctc acc      931
Asp Lys Leu Val Gln Arg Phe Asp Ala Gly Ser Tyr Val Leu Leu Thr
            265                 270                 275 gac gcc ctc aac cgc cac gac att ggt cgc gac cgc gga ggc ctc aac      979
Asp Ala Leu Asn Arg His Asp Ile Gly Arg Asp Arg Gly Gly Leu Asn
        280                 285                 290 aag gca ctc gaa tcc atc aaa gtt cca gtc ctt gtc gca ggc gta gat     1027
Lys Ala Leu Glu Ser Ile Lys Val Pro Val Leu Val Ala Gly Val Asp
    295                 300                 305 acc gat att ttg tac ccc tac cac cag caa gaa cac ctc tcc aga aac     1075
Thr Asp Ile Leu Tyr Pro Tyr His Gln Gln Glu His Leu Ser Arg Asn
310                 315                 320                 325 ctg gga aat cta ctg gca atg gca aaa atc gta tcc cct gtc ggc cac     1123
Leu Gly Asn Leu Leu Ala Met Ala Lys Ile Val Ser Pro Val Gly His
                330                 335                 340 gat gct ttc ctc acc gaa agc cgc caa atg gat cgc atc gtg agg aac     1171
Asp Ala Phe Leu Thr Glu Ser Arg Gln Met Asp Arg Ile Val Arg Asn
            345                 350                 355 ttc ttc agc ctc atc tcc cca gac gaa gac aac cct tcg                 1210
```

Phe Phe Ser Leu Ile Ser Pro Asp Glu Asp Asn Pro Ser
        360                 365                 370

<210> SEQ ID NO 74
<211> LENGTH: 370
<212> TYPE: PRT
<213> ORGANISM: Corynebacterium glutamicum

<400> SEQUENCE: 74

Met Pro Thr Leu Ala Pro Ser Gly Gln Leu Glu Ile Gln Ala Ile Gly
  1               5                  10                  15

Asp Val Ser Thr Glu Ala Gly Ala Ile Ile Thr Asn Ala Glu Ile Ala
             20                  25                  30

Tyr His Arg Trp Gly Glu Tyr Arg Val Asp Lys Glu Gly Arg Ser Asn
         35                  40                  45

Val Val Leu Ile Glu His Ala Leu Thr Gly Asp Ser Asn Ala Ala Asp
     50                  55                  60

Trp Trp Ala Asp Leu Leu Gly Pro Gly Lys Ala Ile Asn Thr Asp Ile
 65                  70                  75                  80

Tyr Cys Val Ile Cys Thr Asn Val Ile Gly Gly Cys Asn Gly Ser Thr
                 85                  90                  95

Gly Pro Gly Ser Met His Pro Asp Gly Asn Phe Trp Gly Asn Arg Phe
            100                 105                 110

Pro Ala Thr Ser Ile Arg Asp Gln Val Asn Ala Glu Lys Gln Phe Leu
        115                 120                 125

Asp Ala Leu Gly Ile Thr Thr Val Ala Ala Val Leu Gly Gly Ser Met
    130                 135                 140

Gly Gly Ala Arg Thr Leu Glu Trp Ala Ala Met Tyr Pro Glu Thr Val
145                 150                 155                 160

Gly Ala Ala Ala Val Leu Ala Val Ser Ala Arg Ala Ser Ala Trp Gln
                165                 170                 175

Ile Gly Ile Gln Ser Ala Gln Ile Lys Ala Ile Glu Asn Asp His His
            180                 185                 190

Trp His Glu Gly Asn Tyr Tyr Glu Ser Gly Cys Asn Pro Ala Thr Gly
        195                 200                 205

Leu Gly Ala Ala Arg Arg Ile Ala His Leu Thr Tyr Arg Gly Glu Leu
    210                 215                 220

Glu Ile Asp Glu Arg Phe Gly Thr Lys Ala Gln Lys Asn Glu Asn Pro
225                 230                 235                 240

Leu Gly Pro Tyr Arg Lys Pro Asp Gln Arg Phe Ala Val Glu Ser Tyr
                245                 250                 255

Leu Asp Tyr Gln Ala Asp Lys Leu Val Gln Arg Phe Asp Ala Gly Ser
            260                 265                 270

Tyr Val Leu Leu Thr Asp Ala Leu Asn Arg His Asp Ile Gly Arg Asp
        275                 280                 285

Arg Gly Gly Leu Asn Lys Ala Leu Glu Ser Ile Lys Val Pro Val Leu
    290                 295                 300

Val Ala Gly Val Asp Thr Asp Ile Leu Tyr Pro Tyr His Gln Gln Glu
305                 310                 315                 320

His Leu Ser Arg Asn Leu Gly Asn Leu Leu Ala Met Ala Lys Ile Val
                325                 330                 335

Ser Pro Val Gly His Asp Ala Phe Leu Thr Glu Ser Arg Gln Met Asp
            340                 345                 350

Arg Ile Val Arg Asn Phe Ser Leu Ile Ser Pro Asp Glu Asp Asn
        355                 360                 365

```
Pro Ser
    370

<210> SEQ ID NO 75
<211> LENGTH: 687
<212> TYPE: DNA
<213> ORGANISM: Corynebacterium glutamicum
<220> FEATURE:
<221> NAME/KEY: CDS
<222> LOCATION: (101)..(664)
<223> OTHER INFORMATION: RXS03158

<400> SEQUENCE: 75
caaagctcac cgaaggcacc aacgccaagt tggttgttga caacaccttg gcatccccat      60
acctgcagca gccactaaaa ctcggcgcac acgcaagtcc ttg cac tcc acc acc      115
                                             Leu His Ser Thr Thr
                                               1               5 aag tac atc gaa gga cac tcc gac gtt gtt ggc ggc ctt gtg ggt acc      163
Lys Tyr Ile Glu Gly His Ser Asp Val Val Gly Gly Leu Val Gly Thr
             10                  15                  20 aac gac cag gaa atg gac gaa gaa ctg ctg ttc atg cag ggc ggc atc      211
Asn Asp Gln Glu Met Asp Glu Glu Leu Leu Phe Met Gln Gly Gly Ile
         25                  30                  35 gga ccg atc cca tca gtt ttt gat gca tac ctg acc gcc cgt ggc ctc      259
Gly Pro Ile Pro Ser Val Phe Asp Ala Tyr Leu Thr Ala Arg Gly Leu
     40                  45                  50 aag acc ctt gca gtg cgc atg gat cgc cac tgc gac aac gca gaa aag      307
Lys Thr Leu Ala Val Arg Met Asp Arg His Cys Asp Asn Ala Glu Lys
 55                  60                  65 atc gcg gaa ttc ctg gac tcc cgc cca gag gtc tcc acc gtg ctc tac      355
Ile Ala Glu Phe Leu Asp Ser Arg Pro Glu Val Ser Thr Val Leu Tyr
 70                  75                  80                  85 cca ggt ctg aag aac cac cca ggc cac gaa gtc gca gcg aag cag atg      403
Pro Gly Leu Lys Asn His Pro Gly His Glu Val Ala Ala Lys Gln Met
                 90                  95                 100 aag cgc ttc ggc ggc atg atc tcc gtc cgt ttc gca ggc ggc gaa gaa      451
Lys Arg Phe Gly Gly Met Ile Ser Val Arg Phe Ala Gly Gly Glu Glu
            105                 110                 115 gca gct aag aag ttc tgt acc tcc acc aaa ctg atc tgt ctg gcc gag      499
Ala Ala Lys Lys Phe Cys Thr Ser Thr Lys Leu Ile Cys Leu Ala Glu
        120                 125                 130 tcc ctc ggt ggc gtg gaa tcc ctc ctg gag cac cca gca acc atg acc      547
Ser Leu Gly Gly Val Glu Ser Leu Leu Glu His Pro Ala Thr Met Thr
    135                 140                 145 cac cag tca gct gcc ggc tct cag ctc gag gtt ccc cgc gac ctc gtg      595
His Gln Ser Ala Ala Gly Ser Gln Leu Glu Val Pro Arg Asp Leu Val
150                 155                 160                 165 cgc atc tcc att ggt att gaa gac att gaa gac ctg ctc gca gat gtc      643
Arg Ile Ser Ile Gly Ile Glu Asp Ile Glu Asp Leu Leu Ala Asp Val
                170                 175                 180 gag cag gcc ctc aat aac ctt tagaaactat ttggcggcaa gca                687
Glu Gln Ala Leu Asn Asn Leu
                185

<210> SEQ ID NO 76
<211> LENGTH: 188
<212> TYPE: PRT
<213> ORGANISM: Corynebacterium glutamicum

<400> SEQUENCE: 76

Leu His Ser Thr Thr Lys Tyr Ile Glu Gly His Ser Asp Val Val Gly
```

```
  1               5                  10                 15
Gly Leu Val Gly Thr Asn Asp Gln Glu Met Asp Glu Leu Leu Phe
             20                 25                 30

Met Gln Gly Gly Ile Gly Pro Ile Pro Ser Val Phe Asp Ala Tyr Leu
             35                 40                 45

Thr Ala Arg Gly Leu Lys Thr Leu Ala Val Arg Met Asp Arg His Cys
         50                 55                 60

Asp Asn Ala Glu Lys Ile Ala Glu Phe Leu Asp Ser Arg Pro Glu Val
 65                 70                 75                 80

Ser Thr Val Leu Tyr Pro Gly Leu Lys Asn His Pro Gly His Glu Val
             85                 90                 95

Ala Ala Lys Gln Met Lys Arg Phe Gly Gly Met Ile Ser Val Arg Phe
             100                105                110

Ala Gly Gly Glu Glu Ala Ala Lys Lys Phe Cys Thr Ser Thr Lys Leu
             115                120                125

Ile Cys Leu Ala Glu Ser Leu Gly Gly Val Glu Ser Leu Leu Glu His
             130                135                140

Pro Ala Thr Met Thr His Gln Ser Ala Ala Gly Ser Gln Leu Glu Val
145                 150                155                160

Pro Arg Asp Leu Val Arg Ile Ser Ile Gly Ile Glu Asp Ile Glu Asp
             165                170                175

Leu Leu Ala Asp Val Glu Gln Ala Leu Asn Asn Leu
             180                185

<210> SEQ ID NO 77
<211> LENGTH: 617
<212> TYPE: DNA
<213> ORGANISM: Corynebacterium glutamicum
<220> FEATURE:
<221> NAME/KEY: CDS
<222> LOCATION: (1)..(594)
<223> OTHER INFORMATION: FRXA00254

<400> SEQUENCE: 77 cag cca cta aaa ctc ggc gca cac gca gtc ttg cac tcc acc acc aag      48
Gln Pro Leu Lys Leu Gly Ala His Ala Val Leu His Ser Thr Thr Lys
  1               5                  10                 15 tac atc gga gga cac tcc gac gtt gtt ggc ggc ctt gtg gtt acc aac      96
Tyr Ile Gly Gly His Ser Asp Val Val Gly Gly Leu Val Val Thr Asn
             20                 25                 30 gac cag gaa atg gac gaa gaa ctg ctg ttc atg cag ggc ggc atc gga     144
Asp Gln Glu Met Asp Glu Glu Leu Leu Phe Met Gln Gly Gly Ile Gly
         35                 40                 45 ccg atc cca tca gtt ttc gat gca tac ctg acc gcc cgt ggc ctc aag     192
Pro Ile Pro Ser Val Phe Asp Ala Tyr Leu Thr Ala Arg Gly Leu Lys
 50                 55                 60 acc ctt gca gtg cgc atg gat cgc cac tgc gac aac gca gaa aag atc     240
Thr Leu Ala Val Arg Met Asp Arg His Cys Asp Asn Ala Glu Lys Ile
 65                 70                 75                 80 gcg gaa ttc ctg gac tcc cgc cca gag gtc tcc acc gtg ctc tac cca     288
Ala Glu Phe Leu Asp Ser Arg Pro Glu Val Ser Thr Val Leu Tyr Pro
             85                 90                 95 ggt ctg aag aac cac cca ggc cac gaa gtc gca gcg aag cag atg aag     336
Gly Leu Lys Asn His Pro Gly His Glu Val Ala Ala Lys Gln Met Lys
             100                105                110 cgc ttc ggc ggc atg atc tcc gtc cgt ttc gca ggc ggc gaa gaa gca     384
Arg Phe Gly Gly Met Ile Ser Val Arg Phe Ala Gly Gly Glu Glu Ala
             115                120                125
```

```
gct aag aag ttc tgt acc tcc acc aaa ctg atc tgt ctg gcc gag tcc        432
Ala Lys Lys Phe Cys Thr Ser Thr Lys Leu Ile Cys Leu Ala Glu Ser
130                 135                 140 ctc ggt ggc gtg gaa tcc ctc ctg gag cac cca gca acc atg acc cac        480
Leu Gly Gly Val Glu Ser Leu Leu Glu His Pro Ala Thr Met Thr His
145                 150                 155                 160 cag tca gct gcc ggc tct cag ctc gag gtt ccc cgc gac ctc gtg cgc        528
Gln Ser Ala Ala Gly Ser Gln Leu Glu Val Pro Arg Asp Leu Val Arg
            165                 170                 175 atc tcc att ggt att gaa gac att gaa gac ctg ctc gca gat gtc gag        576
Ile Ser Ile Gly Ile Glu Asp Ile Glu Asp Leu Leu Ala Asp Val Glu
        180                 185                 190 cag gcc ctc aat aac ctt tagaaactat ttggcggcaa gca                      617
Gln Ala Leu Asn Asn Leu
            195

<210> SEQ ID NO 78
<211> LENGTH: 198
<212> TYPE: PRT
<213> ORGANISM: Corynebacterium glutamicum

<400> SEQUENCE: 78

Gln Pro Leu Lys Leu Gly Ala His Ala Val Leu His Ser Thr Thr Lys
 1               5                  10                  15

Tyr Ile Gly Gly His Ser Asp Val Val Gly Leu Val Val Thr Asn
            20                  25                  30

Asp Gln Glu Met Asp Glu Glu Leu Leu Phe Met Gln Gly Gly Ile Gly
        35                  40                  45

Pro Ile Pro Ser Val Phe Asp Ala Tyr Leu Thr Ala Arg Gly Leu Lys
    50                  55                  60

Thr Leu Ala Val Arg Met Asp Arg His Cys Asp Asn Ala Glu Lys Ile
65                  70                  75                  80

Ala Glu Phe Leu Asp Ser Arg Pro Glu Val Ser Thr Val Leu Tyr Pro
                85                  90                  95

Gly Leu Lys Asn His Pro Gly His Glu Val Ala Ala Lys Gln Met Lys
            100                 105                 110

Arg Phe Gly Gly Met Ile Ser Val Arg Phe Ala Gly Gly Glu Glu Ala
        115                 120                 125

Ala Lys Lys Phe Cys Thr Ser Thr Lys Leu Ile Cys Leu Ala Glu Ser
    130                 135                 140

Leu Gly Gly Val Glu Ser Leu Leu Glu His Pro Ala Thr Met Thr His
145                 150                 155                 160

Gln Ser Ala Ala Gly Ser Gln Leu Glu Val Pro Arg Asp Leu Val Arg
                165                 170                 175

Ile Ser Ile Gly Ile Glu Asp Ile Glu Asp Leu Leu Ala Asp Val Glu
            180                 185                 190

Gln Ala Leu Asn Asn Leu
        195

<210> SEQ ID NO 79
<211> LENGTH: 1170
<212> TYPE: DNA
<213> ORGANISM: Corynebacterium glutamicum
<220> FEATURE:
<221> NAME/KEY: CDS
<222> LOCATION: (101)..(1147)
<223> OTHER INFORMATION: RXA02532

<400> SEQUENCE: 79
```

-continued

| | | |
|---|---|---|
| gatgaatttt tacccaccat ctgtacctat taaccctgcg tggcgtccac ccacagtaac | | 60 |
| tgtgcaagcg ggacggccag ccagaactcc tggtgcgccg atg aac cca cct atc<br>Met Asn Pro Pro Ile<br>1 5 | | 115 |
| acg ttg tcc agc act tat gtt cat gat tca gaa aaa gct tat ggg cgc<br>Thr Leu Ser Ser Thr Tyr Val His Asp Ser Glu Lys Ala Tyr Gly Arg<br>10 15 20 | | 163 |
| gat ggc aat gat gga tgg ggt gca ttt gag gct gcc atg gga act cta<br>Asp Gly Asn Asp Gly Trp Gly Ala Phe Glu Ala Ala Met Gly Thr Leu<br>25 30 35 | | 211 |
| gat ggt ggg ttc gcg gta tct tat tct tca ggt ttg gca gcg gca acg<br>Asp Gly Gly Phe Ala Val Ser Tyr Ser Ser Gly Leu Ala Ala Ala Thr<br>40 45 50 | | 259 |
| tcg att gct gat ttg gtt cct act ggt ggc aca gtt gtt tta cct aaa<br>Ser Ile Ala Asp Leu Val Pro Thr Gly Gly Thr Val Val Leu Pro Lys<br>55 60 65 | | 307 |
| gct gcc tat tat ggc gtg acc aat att ttc gcc agg atg gaa gcc cgc<br>Ala Ala Tyr Tyr Gly Val Thr Asn Ile Phe Ala Arg Met Glu Ala Arg<br>70 75 80 85 | | 355 |
| gga agg ctg aag gtt cga act gtt gat gca gac aat acc gaa gaa gtg<br>Gly Arg Leu Lys Val Arg Thr Val Asp Ala Asp Asn Thr Glu Glu Val<br>90 95 100 | | 403 |
| att gct gct gct caa ggt gca gat gtg gtg tgg gtg gaa tcg atc gct<br>Ile Ala Ala Ala Gln Gly Ala Asp Val Val Trp Val Glu Ser Ile Ala<br>105 110 115 | | 451 |
| aat ccg acg atg gtg gta gct gat atc cct gca ata gtc gac ggt gtg<br>Asn Pro Thr Met Val Val Ala Asp Ile Pro Ala Ile Val Asp Gly Val<br>120 125 130 | | 499 |
| cgt ggg ctt gga gtt ttg act gtc gtt gac gcg act ttc gca acg cca<br>Arg Gly Leu Gly Val Leu Thr Val Val Asp Ala Thr Phe Ala Thr Pro<br>135 140 145 | | 547 |
| ctt cgt caa cgt cca ttg gaa ctt ggt gct gat att gtg ctt tac tcg<br>Leu Arg Gln Arg Pro Leu Glu Leu Gly Ala Asp Ile Val Leu Tyr Ser<br>150 155 160 165 | | 595 |
| gca acc aaa ctt atc ggt gga cac tct gat ctt ctt ctt gga gtc gca<br>Ala Thr Lys Leu Ile Gly Gly His Ser Asp Leu Leu Leu Gly Val Ala<br>170 175 180 | | 643 |
| gtg tgc aag tct gag cac cat gcg cag ttt ctt gcc act cac cgt cat<br>Val Cys Lys Ser Glu His His Ala Gln Phe Leu Ala Thr His Arg His<br>185 190 195 | | 691 |
| gat cat ggt tca gtg ccg gga ggt ctt gaa gcg ttt ctt gct ctc cgt<br>Asp His Gly Ser Val Pro Gly Gly Leu Glu Ala Phe Leu Ala Leu Arg<br>200 205 210 | | 739 |
| gga ttg tat tcc ttg gcg gtg cgt ctt gat cga gca gaa tcc aac gca<br>Gly Leu Tyr Ser Leu Ala Val Arg Leu Asp Arg Ala Glu Ser Asn Ala<br>215 220 225 | | 787 |
| gca gaa ctt tcg cgg cga ctt aac gcg cat cct tcg gtt acc cgc gtc<br>Ala Glu Leu Ser Arg Arg Leu Asn Ala His Pro Ser Val Thr Arg Val<br>230 235 240 245 | | 835 |
| aat tat cca gga ctt cct gat gat ccc caa cat gaa aaa gcc gtg cga<br>Asn Tyr Pro Gly Leu Pro Asp Asp Pro Gln His Glu Lys Ala Val Arg<br>250 255 260 | | 883 |
| gtc cta ccc tct gga tgt gga aac atg ttg tca ttt gag ctt gat gca<br>Val Leu Pro Ser Gly Cys Gly Asn Met Leu Ser Phe Glu Leu Asp Ala<br>265 270 275 | | 931 |
| aca cct gaa cga act gat gag att ctc gaa agc ctg tca ctt tta acc<br>Thr Pro Glu Arg Thr Asp Glu Ile Leu Glu Ser Leu Ser Leu Leu Thr<br>280 285 290 | | 979 |
| cac gcg acc agt tgg gga ggt gtg gaa aca gcc att gaa cgt cgc acc | | 1027 |

```
His Ala Thr Ser Trp Gly Gly Val Glu Thr Ala Ile Glu Arg Arg Thr
    295                 300                 305 agg cgg gat gct gaa gtg gtg gca gaa gta ccg atg act ctt tgc cgc      1075
Arg Arg Asp Ala Glu Val Val Ala Glu Val Pro Met Thr Leu Cys Arg
310                 315                 320                 325 gtt tcc gta gga att gaa gac gtt gaa gat cta tgg gaa gac ctc aac      1123
Val Ser Val Gly Ile Glu Asp Val Glu Asp Leu Trp Glu Asp Leu Asn
                330                 335                 340 gcc tca atc gac aaa gtt ctg ggt tagaactcgt agccagtaac cag            1170
Ala Ser Ile Asp Lys Val Leu Gly
            345

<210> SEQ ID NO 80
<211> LENGTH: 349
<212> TYPE: PRT
<213> ORGANISM: Corynebacterium glutamicum

<400> SEQUENCE: 80

Met Asn Pro Pro Ile Thr Leu Ser Ser Thr Tyr Val His Asp Ser Glu
  1               5                  10                  15

Lys Ala Tyr Gly Arg Asp Gly Asn Asp Gly Trp Gly Ala Phe Glu Ala
             20                  25                  30

Ala Met Gly Thr Leu Asp Gly Gly Phe Ala Val Ser Tyr Ser Ser Gly
         35                  40                  45

Leu Ala Ala Ala Thr Ser Ile Ala Asp Leu Val Pro Thr Gly Gly Thr
     50                  55                  60

Val Val Leu Pro Lys Ala Ala Tyr Tyr Gly Val Thr Asn Ile Phe Ala
 65                  70                  75                  80

Arg Met Glu Ala Arg Gly Arg Leu Lys Val Arg Thr Val Asp Ala Asp
                 85                  90                  95

Asn Thr Glu Glu Val Ile Ala Ala Ala Gln Gly Ala Asp Val Val Trp
            100                 105                 110

Val Glu Ser Ile Ala Asn Pro Thr Met Val Val Ala Asp Ile Pro Ala
        115                 120                 125

Ile Val Asp Gly Val Arg Gly Leu Gly Val Leu Thr Val Val Asp Ala
    130                 135                 140

Thr Phe Ala Thr Pro Leu Arg Gln Arg Pro Leu Glu Leu Gly Ala Asp
145                 150                 155                 160

Ile Val Leu Tyr Ser Ala Thr Lys Leu Ile Gly Gly His Ser Asp Leu
                165                 170                 175

Leu Leu Gly Val Ala Val Cys Lys Ser Glu His His Ala Gln Phe Leu
            180                 185                 190

Ala Thr His Arg His Asp His Gly Ser Val Pro Gly Gly Leu Glu Ala
        195                 200                 205

Phe Leu Ala Leu Arg Gly Leu Tyr Ser Leu Ala Val Arg Leu Asp Arg
    210                 215                 220

Ala Glu Ser Asn Ala Ala Glu Leu Ser Arg Arg Leu Asn Ala His Pro
225                 230                 235                 240

Ser Val Thr Arg Val Asn Tyr Pro Gly Leu Pro Asp Asp Pro Gln His
                245                 250                 255

Glu Lys Ala Val Arg Val Leu Pro Ser Gly Cys Gly Asn Met Leu Ser
            260                 265                 270

Phe Glu Leu Asp Ala Thr Pro Glu Arg Thr Asp Glu Ile Leu Glu Ser
        275                 280                 285

Leu Ser Leu Leu Thr His Ala Thr Ser Trp Gly Gly Val Glu Thr Ala
    290                 295                 300
```

Ile Glu Arg Arg Thr Arg Arg Asp Ala Glu Val Val Ala Glu Val Pro
305                 310                 315                 320

Met Thr Leu Cys Arg Val Ser Val Gly Ile Glu Asp Val Glu Asp Leu
                325                 330                 335

Trp Glu Asp Leu Asn Ala Ser Ile Asp Lys Val Leu Gly
                340                 345

<210> SEQ ID NO 81
<211> LENGTH: 861
<212> TYPE: DNA
<213> ORGANISM: Corynebacterium glutamicum
<220> FEATURE:
<221> NAME/KEY: CDS
<222> LOCATION: (101)..(838)
<223> OTHER INFORMATION: RXS03159

<400> SEQUENCE: 81 agggctagt tttacacaaa agtggacagc ttggtctatc attgccagaa gaccggtcct     60
tttagggcca tagaattctg attacaggag ttgatctacc ttg tct ttt gac cca    115
                                             Leu Ser Phe Asp Pro
                                              1               5 aac acc cag ggt ttc tcc act gca tcg att cac gct ggg tat gag cca    163
Asn Thr Gln Gly Phe Ser Thr Ala Ser Ile His Ala Gly Tyr Glu Pro
         10                  15                  20 gac gac tac tac ggt tcg att aac acc cca atc tat gcc tcc acc acc    211
Asp Asp Tyr Tyr Gly Ser Ile Asn Thr Pro Ile Tyr Ala Ser Thr Thr
             25                  30                  35 ttc gcg cag aac gct cca aac gaa ctg cgc aaa ggc tac gag tac acc    259
Phe Ala Gln Asn Ala Pro Asn Glu Leu Arg Lys Gly Tyr Glu Tyr Thr
         40                  45                  50 cgt gtg ggc aac ccc acc atc gtg gca tta gag cag acc gtc gca gca    307
Arg Val Gly Asn Pro Thr Ile Val Ala Leu Glu Gln Thr Val Ala Ala
     55                  60                  65 ctc gaa ggc gca aag tat ggc cgc gca ttc tcc tcc ggc atg gct gca    355
Leu Glu Gly Ala Lys Tyr Gly Arg Ala Phe Ser Ser Gly Met Ala Ala
 70                  75                  80                  85 acc gac atc ctg ttc cgc atc atc ctc aag ccg ggc gat cac atc gtc    403
Thr Asp Ile Leu Phe Arg Ile Ile Leu Lys Pro Gly Asp His Ile Val
                 90                  95                 100 ctc ggc aac gat gct tac ggc gga acc tac cgc ctg atc gac acc gta    451
Leu Gly Asn Asp Ala Tyr Gly Gly Thr Tyr Arg Leu Ile Asp Thr Val
            105                 110                 115 ttc acc gca tgg ggc gtc gaa tac acc gtt gtt gat acc tcc gtc gtg    499
Phe Thr Ala Trp Gly Val Glu Tyr Thr Val Val Asp Thr Ser Val Val
        120                 125                 130 gaa gag gtc aag gca gcg atc aag gac aac acc aag ctg atc tgg gtg    547
Glu Glu Val Lys Ala Ala Ile Lys Asp Asn Thr Lys Leu Ile Trp Val
    135                 140                 145 gaa acc cca acc aac cca gca ctt ggc atc acc gac atc gaa gca gta    595
Glu Thr Pro Thr Asn Pro Ala Leu Gly Ile Thr Asp Ile Glu Ala Val
150                 155                 160                 165 gca aag ctc acc gaa ggc acc aac gcc aag ttg gtt gtt gac aac acc    643
Ala Lys Leu Thr Glu Gly Thr Asn Ala Lys Leu Val Val Asp Asn Thr
                170                 175                 180 ttg gca tcc cca tac ctg cag cag cca cta aaa ctc ggc gca cac gca    691
Leu Ala Ser Pro Tyr Leu Gln Gln Pro Leu Lys Leu Gly Ala His Ala
            185                 190                 195 agt cct tgc act cca cca cca agt aca tcg aag gac act ccg acg ttg    739
Ser Pro Cys Thr Pro Pro Pro Ser Thr Ser Lys Asp Thr Pro Thr Leu
        200                 205                 210

```
ttg gcg gcc ttg tgg gta cca acg acc agg aaa tgg acg aag aac tgc      787
Leu Ala Ala Leu Trp Val Pro Thr Thr Arg Lys Trp Thr Lys Asn Cys
    215                 220                 225 tgt tca tgc agg gcg gca tcg gac cga tcc cat cag ttt tcg atg cat      835
Cys Ser Cys Arg Ala Ala Ser Asp Arg Ser His Gln Phe Ser Met His
230                 235                 240                 245 acc tgaccgcccg tggcctcaag acc                                        861
Thr

<210> SEQ ID NO 82
<211> LENGTH: 246
<212> TYPE: PRT
<213> ORGANISM: Corynebacterium glutamicum

<400> SEQUENCE: 82

Leu Ser Phe Asp Pro Asn Thr Gln Gly Phe Ser Thr Ala Ser Ile His
  1               5                  10                  15

Ala Gly Tyr Glu Pro Asp Tyr Tyr Gly Ser Ile Asn Thr Pro Ile
             20                  25                  30

Tyr Ala Ser Thr Thr Phe Ala Gln Asn Ala Pro Asn Glu Leu Arg Lys
         35                  40                  45

Gly Tyr Glu Tyr Thr Arg Val Gly Asn Pro Thr Ile Val Ala Leu Glu
     50                  55                  60

Gln Thr Val Ala Ala Leu Glu Gly Ala Lys Tyr Gly Arg Ala Phe Ser
 65                  70                  75                  80

Ser Gly Met Ala Ala Thr Asp Ile Leu Phe Arg Ile Ile Leu Lys Pro
                 85                  90                  95

Gly Asp His Ile Val Leu Gly Asn Asp Ala Tyr Gly Gly Thr Tyr Arg
            100                 105                 110

Leu Ile Asp Thr Val Phe Thr Ala Trp Gly Val Glu Tyr Thr Val Val
        115                 120                 125

Asp Thr Ser Val Val Glu Glu Val Lys Ala Ala Ile Lys Asp Asn Thr
    130                 135                 140

Lys Leu Ile Trp Val Glu Thr Pro Thr Asn Pro Ala Leu Gly Ile Thr
145                 150                 155                 160

Asp Ile Glu Ala Val Ala Lys Leu Thr Glu Gly Thr Asn Ala Lys Leu
                165                 170                 175

Val Val Asp Asn Thr Leu Ala Ser Pro Tyr Leu Gln Gln Pro Leu Lys
            180                 185                 190

Leu Gly Ala His Ala Ser Pro Cys Thr Pro Pro Ser Thr Ser Lys
        195                 200                 205

Asp Thr Pro Thr Leu Leu Ala Ala Leu Trp Val Pro Thr Thr Arg Lys
    210                 215                 220

Trp Thr Lys Asn Cys Cys Ser Cys Arg Ala Ala Ser Asp Arg Ser His
225                 230                 235                 240

Gln Phe Ser Met His Thr
                245

<210> SEQ ID NO 83
<211> LENGTH: 703
<212> TYPE: DNA
<213> ORGANISM: Corynebacterium glutamicum
<220> FEATURE:
<221> NAME/KEY: CDS
<222> LOCATION: (101)..(703)
<223> OTHER INFORMATION: FRXA02768
<220> FEATURE:
<221> NAME/KEY: misc_feature
```

```
<222> LOCATION: 598,676,687,690,691,693
<223> OTHER INFORMATION: n = a, c, t, or g
<220> FEATURE:
<221> NAME/KEY: VARIANT
<222> LOCATION: 192
<223> OTHER INFORMATION: Xaa = His or Gln
<220> FEATURE:
<221> NAME/KEY: VARIANT
<222> LOCATION: 196
<223> OTHER INFORMATION: Xaa = Ile, Thr, Asn, or Ser
<220> FEATURE:
<221> NAME/KEY: VARIANT
<222> LOCATION: 197
<223> OTHER INFORMATION: Xaa = Phe, Leu, Ser, Tyr, STOP CODON, Cys, or
      Trp
<220> FEATURE:
<221> NAME/KEY: VARIANT
<222> LOCATION: 198
<223> OTHER INFORMATION: Xaa = Val, Ala, Glu, or Gly

<400> SEQUENCE: 83 agggctagt tttacacaaa agtggacagc ttggtctatc attgccagaa gaccggtcct      60
tttagggcca tagaattctg attacaggag ttgatctacc ttg tct ttt gac cca     115
                                             Leu Ser Phe Asp Pro
                                              1               5 aac acc cag ggt ttc tcc act gca tcg att cac gct ggg tat gag cca     163
Asn Thr Gln Gly Phe Ser Thr Ala Ser Ile His Ala Gly Tyr Glu Pro
             10                  15                  20 gac gac tac tac ggt tcg att aac acc cca atc tat gcc tcc acc acc     211
Asp Asp Tyr Tyr Gly Ser Ile Asn Thr Pro Ile Tyr Ala Ser Thr Thr
         25                  30                  35 ttc gcg cag aac gct cca aac gaa ctg cgc aaa ggc tac gag tac acc     259
Phe Ala Gln Asn Ala Pro Asn Glu Leu Arg Lys Gly Tyr Glu Tyr Thr
     40                  45                  50 cgt gtg ggc aac ccc acc atc gtg gca tta gag cag acc gtc gca gca     307
Arg Val Gly Asn Pro Thr Ile Val Ala Leu Glu Gln Thr Val Ala Ala
 55                  60                  65 ctc gaa ggc gca aag tat ggc cgc gca ttc tcc tcc ggc atg gct gca     355
Leu Glu Gly Ala Lys Tyr Gly Arg Ala Phe Ser Ser Gly Met Ala Ala
 70                  75                  80                  85 acc gac atc ctg ttc cgc atc atc ctc aag ccg ggc gat cac atc gtc     403
Thr Asp Ile Leu Phe Arg Ile Ile Leu Lys Pro Gly Asp His Ile Val
                 90                  95                 100 ctc ggc aac gat gct tac ggc gga acc tac cgc ctg atc gac acc gta     451
Leu Gly Asn Asp Ala Tyr Gly Gly Thr Tyr Arg Leu Ile Asp Thr Val
             105                 110                 115 ttc acc gca tgg ggc gtc gaa tac acc gtt gtt gat acc tcc gtc gtg     499
Phe Thr Ala Trp Gly Val Glu Tyr Thr Val Val Asp Thr Ser Val Val
         120                 125                 130 gaa gag gtc aag gca gcg atc aag gac aac acc aag gct gat ctt ggt     547
Glu Glu Val Lys Ala Ala Ile Lys Asp Asn Thr Lys Ala Asp Leu Gly
     135                 140                 145 gga aac ccc aac caa ccc agc act ttg gca tta ccc gac atc gaa gca     595
Gly Asn Pro Asn Gln Pro Ser Thr Leu Ala Leu Pro Asp Ile Glu Ala
 150                 155                 160                 165 gtn tgc aaa act tca ccc gaa agg cac caa ccc caa gct tgt tgt ttg     643
Val Cys Lys Thr Ser Pro Glu Arg His Gln Pro Gln Ala Cys Cys Leu
                 170                 175                 180 aca aca cct tcg cat tcc cca tac ctg cag can cca ctt aaa ant tnn     691
Thr Thr Pro Ser His Ser Pro Tyr Leu Gln Xaa Pro Leu Lys Xaa Xaa
             185                 190                 195 gng cac acg cag                                                      703
Xaa His Thr Gln
         200
```

<210> SEQ ID NO 84
<211> LENGTH: 201
<212> TYPE: PRT
<213> ORGANISM: Corynebacterium glutamicum
<220> FEATURE:
<221> NAME/KEY: VARIANT
<222> LOCATION: 192
<223> OTHER INFORMATION: Xaa = His or Gln
<220> FEATURE:
<221> NAME/KEY: VARIANT
<222> LOCATION: 196
<223> OTHER INFORMATION: Xaa = Ile, Thr, Asn, or Ser
<220> FEATURE:
<221> NAME/KEY: VARIANT
<222> LOCATION: 197
<223> OTHER INFORMATION: Xaa = Phe, Leu, Ser, Tyr, STOP CODON, Cys, or Trp
<220> FEATURE:
<221> NAME/KEY: VARIANT
<222> LOCATION: 198
<223> OTHER INFORMATION: Xaa = Val, Ala, Glu, or Gly

<400> SEQUENCE: 84

```
Leu Ser Phe Asp Pro Asn Thr Gln Gly Phe Ser Thr Ala Ser Ile His
  1               5                  10                  15

Ala Gly Tyr Glu Pro Asp Asp Tyr Tyr Gly Ser Ile Asn Thr Pro Ile
             20                  25                  30

Tyr Ala Ser Thr Thr Phe Ala Gln Asn Ala Pro Asn Glu Leu Arg Lys
         35                  40                  45

Gly Tyr Glu Tyr Thr Arg Val Gly Asn Pro Thr Ile Val Ala Leu Glu
     50                  55                  60

Gln Thr Val Ala Ala Leu Glu Gly Ala Lys Tyr Gly Arg Ala Phe Ser
 65                  70                  75                  80

Ser Gly Met Ala Ala Thr Asp Ile Leu Phe Arg Ile Leu Lys Pro
                 85                  90                  95

Gly Asp His Ile Val Leu Gly Asn Asp Ala Tyr Gly Gly Thr Tyr Arg
                100                 105                 110

Leu Ile Asp Thr Val Phe Thr Ala Trp Gly Val Glu Tyr Thr Val Val
            115                 120                 125

Asp Thr Ser Val Val Glu Glu Val Lys Ala Ala Ile Lys Asp Asn Thr
130                 135                 140

Lys Ala Asp Leu Gly Gly Asn Pro Asn Gln Pro Ser Thr Leu Ala Leu
145                 150                 155                 160

Pro Asp Ile Glu Ala Val Cys Lys Thr Ser Pro Glu Arg His Gln Pro
                165                 170                 175

Gln Ala Cys Cys Leu Thr Thr Pro Ser His Ser Pro Tyr Leu Gln Xaa
                180                 185                 190

Pro Leu Lys Xaa Xaa Xaa His Thr Gln
        195                 200
```

<210> SEQ ID NO 85
<211> LENGTH: 1113
<212> TYPE: DNA
<213> ORGANISM: Corynebacterium glutamicum
<220> FEATURE:
<221> NAME/KEY: CDS
<222> LOCATION: (101)..(1090)
<223> OTHER INFORMATION: RXA00216

<400> SEQUENCE: 85
gtgttgctcg cggccaggca gcagtgctgt acctgcctga cgcggatggt gacatcgttc    60

-continued

| | |
|---|---|
| ttggatcagg caccatctgc cacacggagt cttaagaaaa ttg ggc gct tat ggt<br>                                                                            Leu Gly Ala Tyr Gly<br>                                                                             1                5 | 115 |
| tta ggt gag ctt cct gga aaa tcc gcc gcg gaa gcc gcc gac att att<br>Leu Gly Glu Leu Pro Gly Lys Ser Ala Ala Glu Ala Ala Asp Ile Ile<br>                10                      15                        20 | 163 |
| cag ggt gaa acg ggc gat ctt ctc cat att cct cag ctt ccg gcg cga<br>Gln Gly Glu Thr Gly Asp Leu Leu His Ile Pro Gln Leu Pro Ala Arg<br>             25                      30                      35 | 211 |
| ggt ttg ggt gct gat ctg atc ggt cga acc gtc ggt ctg ctg gac atg<br>Gly Leu Gly Ala Asp Leu Ile Gly Arg Thr Val Gly Leu Leu Asp Met<br>        40                      45                      50 | 259 |
| atc aac gtt gat cgc ggg gcc cga tct tgg gtg atg agc aca cgc ccc<br>Ile Asn Val Asp Arg Gly Ala Arg Ser Trp Val Met Ser Thr Arg Pro<br>      55                      60                      65 | 307 |
| agc aga ttg acg cac ctg acc ggc gat ttc ctt gac atg gat ttg gat<br>Ser Arg Leu Thr His Leu Thr Gly Asp Phe Leu Asp Met Asp Leu Asp<br> 70                      75                      80                      85 | 355 |
| gcg tgc gag gaa acc tgg gga acg ggc gtc gac aag cta aaa atc caa<br>Ala Cys Glu Glu Thr Trp Gly Thr Gly Val Asp Lys Leu Lys Ile Gln<br>             90                      95                    100 | 403 |
| gtt gct ggt ccc tgg act tta ggt gcg cgc att gag ttg gcc aat ggc<br>Val Ala Gly Pro Trp Thr Leu Gly Ala Arg Ile Glu Leu Ala Asn Gly<br>                105                    110                    115 | 451 |
| cat cgc gtt ttg tct gat cgc ggt gcg atg cgt gat ctc acg cag gcg<br>His Arg Val Leu Ser Asp Arg Gly Ala Met Arg Asp Leu Thr Gln Ala<br>            120                    125                    130 | 499 |
| ctg atc gcc ggc atc gat gcg cat gca cgc aag gtt gct ggg cga ttt<br>Leu Ile Ala Gly Ile Asp Ala His Ala Arg Lys Val Ala Gly Arg Phe<br> 135                      140                    145 | 547 |
| cgc gcc gaa gtg cag gtg caa att gat gag ccg gag ctg aaa tcg ctt<br>Arg Ala Glu Val Gln Val Gln Ile Asp Glu Pro Glu Leu Lys Ser Leu<br>150                    155                    160                    165 | 595 |
| atc gac ggc tcc ctc cct ggc act tcc acc ttt gac att att cct gcg<br>Ile Asp Gly Ser Leu Pro Gly Thr Ser Thr Phe Asp Ile Ile Pro Ala<br>                170                    175                    180 | 643 |
| gtg aat gtc gct gat gcc agt gaa cgt ttg cag cag gtc ttt agc tcg<br>Val Asn Val Ala Asp Ala Ser Glu Arg Leu Gln Gln Val Phe Ser Ser<br>            185                    190                    195 | 691 |
| att gag ggg ccg aca tat ctc aac ctc acc ggc cag att cct act tgg<br>Ile Glu Gly Pro Thr Tyr Leu Asn Leu Thr Gly Gln Ile Pro Thr Trp<br>        200                      205                    210 | 739 |
| gat gtg gct cgg ggt gcg ggc gcc gat act gtg cag att tcc atg gat<br>Asp Val Ala Arg Gly Ala Gly Ala Asp Thr Val Gln Ile Ser Met Asp<br>215                    220                    225 | 787 |
| caa gtc cgt gga aat gaa cat ttg gat ggt ttt ggt gaa acc atc acc<br>Gln Val Arg Gly Asn Glu His Leu Asp Gly Phe Gly Glu Thr Ile Thr<br>230                    235                    240                    245 | 835 |
| agt gga att cgt ctt ggt ttg ggc att acg aca gga aaa gat gtc gta<br>Ser Gly Ile Arg Leu Gly Leu Gly Ile Thr Thr Gly Lys Asp Val Val<br>                250                    255                    260 | 883 |
| gat gaa ctg ctc gag cga ccg cgg caa aag gcc gtt gag gta gca cgc<br>Asp Glu Leu Leu Glu Arg Pro Arg Gln Lys Ala Val Glu Val Ala Arg<br>            265                    270                    275 | 931 |
| ttt ttt gat cgt tta ggt gtg ggc cga aac tat ctc gtg gat gct gtt<br>Phe Phe Asp Arg Leu Gly Val Gly Arg Asn Tyr Leu Val Asp Ala Val<br>        280                      285                    290 | 979 |
| gat att cat ccg ggt gag gat ttg gtg cag ggg acc atc acc gag gcc<br>Asp Ile His Pro Gly Glu Asp Leu Val Gln Gly Thr Ile Thr Glu Ala<br>295                    300                    305 | 1027 |

```
gcg cag gct tat cgc atg gcc cgg gtg atg tcg gag atg ttg tcg aag      1075
Ala Gln Ala Tyr Arg Met Ala Arg Val Met Ser Glu Met Leu Ser Lys
310             315                 320                 325 gat tca tgc gac ctt taaggcttta ccggcgctgg gtg                        1113
Asp Ser Cys Asp Leu
            330
```

<210> SEQ ID NO 86
<211> LENGTH: 330
<212> TYPE: PRT
<213> ORGANISM: Corynebacterium glutamicum

<400> SEQUENCE: 86

```
Leu Gly Ala Tyr Gly Leu Gly Glu Leu Pro Gly Lys Ser Ala Ala Glu
 1               5                  10                  15

Ala Ala Asp Ile Ile Gln Gly Glu Thr Gly Asp Leu Leu His Ile Pro
            20                  25                  30

Gln Leu Pro Ala Arg Gly Leu Gly Ala Asp Leu Ile Gly Arg Thr Val
        35                  40                  45

Gly Leu Leu Asp Met Ile Asn Val Asp Arg Gly Ala Arg Ser Trp Val
    50                  55                  60

Met Ser Thr Arg Pro Ser Arg Leu Thr His Leu Thr Gly Asp Phe Leu
65                  70                  75                  80

Asp Met Asp Leu Asp Ala Cys Glu Glu Thr Trp Gly Thr Gly Val Asp
                85                  90                  95

Lys Leu Lys Ile Gln Val Ala Gly Pro Trp Thr Leu Gly Ala Arg Ile
            100                 105                 110

Glu Leu Ala Asn Gly His Arg Val Leu Ser Asp Arg Gly Ala Met Arg
        115                 120                 125

Asp Leu Thr Gln Ala Leu Ile Ala Gly Ile Asp Ala His Ala Arg Lys
    130                 135                 140

Val Ala Gly Arg Phe Arg Ala Glu Val Gln Val Gln Ile Asp Glu Pro
145                 150                 155                 160

Glu Leu Lys Ser Leu Ile Asp Gly Ser Leu Pro Gly Thr Ser Thr Phe
                165                 170                 175

Asp Ile Ile Pro Ala Val Asn Val Ala Asp Ala Ser Glu Arg Leu Gln
            180                 185                 190

Gln Val Phe Ser Ser Ile Glu Gly Pro Thr Tyr Leu Asn Leu Thr Gly
        195                 200                 205

Gln Ile Pro Thr Trp Asp Val Arg Gly Ala Gly Ala Asp Thr Val
    210                 215                 220

Gln Ile Ser Met Asp Gln Val Arg Gly Asn Glu His Leu Asp Gly Phe
225                 230                 235                 240

Gly Glu Thr Ile Thr Ser Gly Ile Arg Leu Gly Leu Gly Ile Thr Thr
                245                 250                 255

Gly Lys Asp Val Val Asp Glu Leu Leu Glu Arg Pro Arg Gln Lys Ala
            260                 265                 270

Val Glu Val Ala Arg Phe Phe Asp Arg Leu Gly Val Gly Arg Asn Tyr
        275                 280                 285

Leu Val Asp Ala Val Asp Ile His Pro Gly Glu Asp Leu Val Gln Gly
    290                 295                 300

Thr Ile Thr Glu Ala Ala Gln Ala Tyr Arg Met Ala Arg Val Met Ser
305                 310                 315                 320

Glu Met Leu Ser Lys Asp Ser Cys Asp Leu
                325                 330
```

<210> SEQ ID NO 87
<211> LENGTH: 551
<212> TYPE: DNA
<213> ORGANISM: Corynebacterium glutamicum
<220> FEATURE:
<221> NAME/KEY: CDS
<222> LOCATION: (1)..(528)
<223> OTHER INFORMATION: RXA02197

<400> SEQUENCE: 87

```
gcc gaa cgc atg cgc ttt agc ttc cca cgc cag cag cgc ggc agg ttc      48
Ala Glu Arg Met Arg Phe Ser Phe Pro Arg Gln Gln Arg Gly Arg Phe
 1               5                  10                  15 ttg tgc atc gcg gat ttc att cgc cca cgc gag caa gct gtc aag gac      96
Leu Cys Ile Ala Asp Phe Ile Arg Pro Arg Glu Gln Ala Val Lys Asp
             20                  25                  30 ggc caa gtg gac gtc atg cca ttc cag ctg gtc acc atg ggt aat cct     144
Gly Gln Val Asp Val Met Pro Phe Gln Leu Val Thr Met Gly Asn Pro
         35                  40                  45 att gct gat ttc gcc aac gag ttg ttc gca gcc aat gaa tac cgc gag     192
Ile Ala Asp Phe Ala Asn Glu Leu Phe Ala Ala Asn Glu Tyr Arg Glu
     50                  55                  60 tac ttg gaa gtt cac ggc atc ggc gtg cag ctc acc gaa gca ttg gcc     240
Tyr Leu Glu Val His Gly Ile Gly Val Gln Leu Thr Glu Ala Leu Ala
 65                  70                  75                  80 gag tac tgg cac tcc cga gtg cgc agc gaa ctc aag ctg aac gac ggt     288
Glu Tyr Trp His Ser Arg Val Arg Ser Glu Leu Lys Leu Asn Asp Gly
                 85                  90                  95 gga tct gtc gct gat ttt gat cca gaa gac aag acc aag ttc ttc gac     336
Gly Ser Val Ala Asp Phe Asp Pro Glu Asp Lys Thr Lys Phe Phe Asp
            100                 105                 110 ctg gat tac cgc ggc gcc cgc ttc tcc ttt ggt tac ggt tct tgc cct     384
Leu Asp Tyr Arg Gly Ala Arg Phe Ser Phe Gly Tyr Gly Ser Cys Pro
        115                 120                 125 gat ctg gaa gac cgc gca aag ctg gtg gaa ttg ctc gag cca ggc cgt     432
Asp Leu Glu Asp Arg Ala Lys Leu Val Glu Leu Leu Glu Pro Gly Arg
    130                 135                 140 atc ggc gtg gag ttg tcc gag gaa ctc cag ctg cac cca gag cag tcc     480
Ile Gly Val Glu Leu Ser Glu Glu Leu Gln Leu His Pro Glu Gln Ser
145                 150                 155                 160 aca gac gcg ttt gtg ctc tac cac cca gag gca aag tac ttt aac gtc     528
Thr Asp Ala Phe Val Leu Tyr His Pro Glu Ala Lys Tyr Phe Asn Val
                165                 170                 175 taacaccttt gagagggaaa act                                            551
```

<210> SEQ ID NO 88
<211> LENGTH: 176
<212> TYPE: PRT
<213> ORGANISM: Corynebacterium glutamicum

<400> SEQUENCE: 88

```
Ala Glu Arg Met Arg Phe Ser Phe Pro Arg Gln Gln Arg Gly Arg Phe
 1               5                  10                  15

Leu Cys Ile Ala Asp Phe Ile Arg Pro Arg Glu Gln Ala Val Lys Asp
             20                  25                  30

Gly Gln Val Asp Val Met Pro Phe Gln Leu Val Thr Met Gly Asn Pro
         35                  40                  45

Ile Ala Asp Phe Ala Asn Glu Leu Phe Ala Ala Asn Glu Tyr Arg Glu
     50                  55                  60
```

```
Tyr Leu Glu Val His Gly Ile Gly Val Gln Leu Thr Glu Ala Leu Ala
 65                  70                  75                  80

Glu Tyr Trp His Ser Arg Val Arg Ser Glu Leu Lys Leu Asn Asp Gly
                 85                  90                  95

Gly Ser Val Ala Asp Phe Asp Pro Glu Asp Lys Thr Lys Phe Phe Asp
            100                 105                 110

Leu Asp Tyr Arg Gly Ala Arg Phe Ser Phe Gly Tyr Gly Ser Cys Pro
        115                 120                 125

Asp Leu Glu Asp Arg Ala Lys Leu Val Glu Leu Leu Glu Pro Gly Arg
130                 135                 140

Ile Gly Val Glu Leu Ser Glu Glu Leu Gln Leu His Pro Glu Gln Ser
145                 150                 155                 160

Thr Asp Ala Phe Val Leu Tyr His Pro Glu Ala Lys Tyr Phe Asn Val
                165                 170                 175

<210> SEQ ID NO 89
<211> LENGTH: 2599
<212> TYPE: DNA
<213> ORGANISM: Corynebacterium glutamicum
<220> FEATURE:
<221> NAME/KEY: CDS
<222> LOCATION: (101)..(2599)
<223> OTHER INFORMATION: RXN02198

<400> SEQUENCE: 89
agactagtgg cgctttgcct gtgttgctta ggcggcgttg aaaatgaact acgaatgaaa    60
agttcgggaa ttgtctaatc cgtactaagc tgtctacaca atg tct act tca gtt   115
                                             Met Ser Thr Ser Val
                                               1               5 act tca cca gcc cac aac aac gca cat tcc tcc gaa ttt ttg gat gcg   163
Thr Ser Pro Ala His Asn Asn Ala His Ser Ser Glu Phe Leu Asp Ala
                10                  15                  20 ttg gca aac cat gtg ttg atc ggc gac ggc gcc atg ggc acc cag ctc   211
Leu Ala Asn His Val Leu Ile Gly Asp Gly Ala Met Gly Thr Gln Leu
            25                  30                  35 caa ggc ttt gac ctg gac gtg gaa aag gat ttc ctt gat ctg gag ggg   259
Gln Gly Phe Asp Leu Asp Val Glu Lys Asp Phe Leu Asp Leu Glu Gly
        40                  45                  50 tgt aat gag att ctc aac gac acc cgc cct gat gtg ttg agg cag att   307
Cys Asn Glu Ile Leu Asn Asp Thr Arg Pro Asp Val Leu Arg Gln Ile
 55                  60                  65 cac cgc gcc tac ttt gag gcg gga gct gac ttg gtt gag acc aat act   355
His Arg Ala Tyr Phe Glu Ala Gly Ala Asp Leu Val Glu Thr Asn Thr
 70                  75                  80                  85 ttt ggt tgc aac ctg ccg aac ttg gcg gat tat gac atc gct gat cgt   403
Phe Gly Cys Asn Leu Pro Asn Leu Ala Asp Tyr Asp Ile Ala Asp Arg
                 90                  95                 100 tgc cgt gag ctt gcc tac aag ggc act gca gtg gct agg gaa gtg gct   451
Cys Arg Glu Leu Ala Tyr Lys Gly Thr Ala Val Ala Arg Glu Val Ala
            105                 110                 115 gat gag atg ggg ccg ggc cga aac ggc atg cgg cgt ttc gtg gtt ggt   499
Asp Glu Met Gly Pro Gly Arg Asn Gly Met Arg Arg Phe Val Val Gly
        120                 125                 130 tcc ctg gga cct gga acg aag ctt cca tcg ctg ggc cat gca ccg tat   547
Ser Leu Gly Pro Gly Thr Lys Leu Pro Ser Leu Gly His Ala Pro Tyr
135                 140                 145 gca gat ttg cgt ggg cac tac aag gaa gca gcg ctt ggc atc atc gac   595
Ala Asp Leu Arg Gly His Tyr Lys Glu Ala Ala Leu Gly Ile Ile Asp
150                 155                 160                 165
```

| | |
|---|---|
| ggt ggt ggc gat gcc ttt ttg att gag act gct cag gac ttg ctt cag<br>Gly Gly Gly Asp Ala Phe Leu Ile Glu Thr Ala Gln Asp Leu Leu Gln<br>170 175 180 | 643 |
| gtc aag gct gcg gtt cac ggc gtt caa gat gcc atg gct gaa ctt gat<br>Val Lys Ala Ala Val His Gly Val Gln Asp Ala Met Ala Glu Leu Asp<br>185 190 195 | 691 |
| aca ttc ttg ccc att att tgc cac gtc acc gta gag acc acc ggc acc<br>Thr Phe Leu Pro Ile Ile Cys His Val Thr Val Glu Thr Thr Gly Thr<br>200 205 210 | 739 |
| atg ctc atg ggt tct gag atc ggt gcc gcg ttg aca gcg ctg cag cca<br>Met Leu Met Gly Ser Glu Ile Gly Ala Ala Leu Thr Ala Leu Gln Pro<br>215 220 225 | 787 |
| ctg ggt atc gac atg att ggt ctg aac tgc gcc acc ggc cca gat gag<br>Leu Gly Ile Asp Met Ile Gly Leu Asn Cys Ala Thr Gly Pro Asp Glu<br>230 235 240 245 | 835 |
| atg agc gag cac ctg cgt tac ctg tcc aag cac gcc gat att cct gtg<br>Met Ser Glu His Leu Arg Tyr Leu Ser Lys His Ala Asp Ile Pro Val<br>250 255 260 | 883 |
| tcg gtg atg cct aac gca ggt ctt cct gtc ctg ggt aaa aac ggt gca<br>Ser Val Met Pro Asn Ala Gly Leu Pro Val Leu Gly Lys Asn Gly Ala<br>265 270 275 | 931 |
| gaa tac cca ctt gag gct gag gat ttg gcg cag gcg ctg gct gga ttc<br>Glu Tyr Pro Leu Glu Ala Glu Asp Leu Ala Gln Ala Leu Ala Gly Phe<br>280 285 290 | 979 |
| gtc tcc gaa tat ggc ctg tcc atg gtg ggt ggt tgt tgt ggc acc aca<br>Val Ser Glu Tyr Gly Leu Ser Met Val Gly Gly Cys Cys Gly Thr Thr<br>295 300 305 | 1027 |
| cct gag cac atc cgt gcg gtc cgc gat gcg gtg gtt ggt gtt cca gag<br>Pro Glu His Ile Arg Ala Val Arg Asp Ala Val Val Gly Val Pro Glu<br>310 315 320 325 | 1075 |
| cag gaa acc tcc aca ctg acc aag atc cct gca ggc cct gtt gag cag<br>Gln Glu Thr Ser Thr Leu Thr Lys Ile Pro Ala Gly Pro Val Glu Gln<br>330 335 340 | 1123 |
| gcc tcc cgc gag gtg gag aaa gag gac tcc gtc gcg tcg ctg tac acc<br>Ala Ser Arg Glu Val Glu Lys Glu Asp Ser Val Ala Ser Leu Tyr Thr<br>345 350 355 | 1171 |
| tcg gtg cca ttg tcc cag gaa acc ggc att tcc atg atc ggt gag cgc<br>Ser Val Pro Leu Ser Gln Glu Thr Gly Ile Ser Met Ile Gly Glu Arg<br>360 365 370 | 1219 |
| acc aac tcc aac ggt tcc aag gca ttc cgt gag gca atg ctg tct ggc<br>Thr Asn Ser Asn Gly Ser Lys Ala Phe Arg Glu Ala Met Leu Ser Gly<br>375 380 385 | 1267 |
| gat tgg gaa aag tgt gtg gat att gcc aag cag caa acc cgc gat ggt<br>Asp Trp Glu Lys Cys Val Asp Ile Ala Lys Gln Gln Thr Arg Asp Gly<br>390 395 400 405 | 1315 |
| gca cac atg ctg gat ctt tgt gtg gat tac gtg gga cga gac ggc acc<br>Ala His Met Leu Asp Leu Cys Val Asp Tyr Val Gly Arg Asp Gly Thr<br>410 415 420 | 1363 |
| gcc gat atg gcg acc ttg gca gca ctt ctt gct acc agc tcc act ttg<br>Ala Asp Met Ala Thr Leu Ala Ala Leu Leu Ala Thr Ser Ser Thr Leu<br>425 430 435 | 1411 |
| cca atc atg att gac tcc acc gag cca gag gtt att cgc aca ggc ctt<br>Pro Ile Met Ile Asp Ser Thr Glu Pro Glu Val Ile Arg Thr Gly Leu<br>440 445 450 | 1459 |
| gag cac ttg ggt gga cga agc atc gtt aac tcc gtc aac ttt gaa gac<br>Glu His Leu Gly Gly Arg Ser Ile Val Asn Ser Val Asn Phe Glu Asp<br>455 460 465 | 1507 |
| ggc gat ggc cct gag tcc cgc tac cag cgc atc atg aaa ctg gta aag<br>Gly Asp Gly Pro Glu Ser Arg Tyr Gln Arg Ile Met Lys Leu Val Lys<br>470 475 480 485 | 1555 |

-continued

| | |
|---|---|
| cag cac ggt gcg gcc gtg gtt gcg ctg acc att gat gag gaa ggc cag<br>Gln His Gly Ala Ala Val Val Ala Leu Thr Ile Asp Glu Glu Gly Gln<br>              490                    495                 500 | 1603 |
| gca cgt acc gct gag cac aag gtg cgc att gct aaa cga ctg att gac<br>Ala Arg Thr Ala Glu His Lys Val Arg Ile Ala Lys Arg Leu Ile Asp<br>     505                   510                  515 | 1651 |
| gat atc acc ggc agc tac ggc ctg gat atc aaa gac atc gtt gtg gac<br>Asp Ile Thr Gly Ser Tyr Gly Leu Asp Ile Lys Asp Ile Val Val Asp<br>         520                   525               530 | 1699 |
| tgc ctg acc ttc ccg atc tct act ggc cag gaa gaa acc agg cga gat<br>Cys Leu Thr Phe Pro Ile Ser Thr Gly Gln Glu Glu Thr Arg Arg Asp<br>535                  540                   545 | 1747 |
| ggc att gaa acc atc gaa gcc atc cgc gag ctg aag aag ctc tac cca<br>Gly Ile Glu Thr Ile Glu Ala Ile Arg Glu Leu Lys Lys Leu Tyr Pro<br>550                  555                560              565 | 1795 |
| gaa atc cac acc acc ctg ggt ctg tcc aat att tcc ttc ggc ctg aac<br>Glu Ile His Thr Thr Leu Gly Leu Ser Asn Ile Ser Phe Gly Leu Asn<br>              570                   575              580 | 1843 |
| cct gct gca cgc cag gtt ctt aac tct gtg ttc ctc aat gag tgc att<br>Pro Ala Ala Arg Gln Val Leu Asn Ser Val Phe Leu Asn Glu Cys Ile<br>         585                   590               595 | 1891 |
| gag gct ggt ctg gac tct gcg att gcg cac agc tcc aag att ttg ccg<br>Glu Ala Gly Leu Asp Ser Ala Ile Ala His Ser Ser Lys Ile Leu Pro<br>600                  605                610 | 1939 |
| atg aac cgc att gat gat cgc cag cgc gaa gtg gcg ttg gat atg gtc<br>Met Asn Arg Ile Asp Asp Arg Gln Arg Glu Val Ala Leu Asp Met Val<br>         615                   620               625 | 1987 |
| tat gat cgc cgc acc gag gat tac gat ccg ctg cag gaa ttc atg cag<br>Tyr Asp Arg Arg Thr Glu Asp Tyr Asp Pro Leu Gln Glu Phe Met Gln<br>630                  635                640              645 | 2035 |
| ctg ttt gag ggc gtt tct gct gcc gat gcc aag gat gct cgc gct gaa<br>Leu Phe Glu Gly Val Ser Ala Ala Asp Ala Lys Asp Ala Arg Ala Glu<br>              650                   655               660 | 2083 |
| cag ctg gcc gct atg cct ttg ttt gag cgt ttg gca cag cgc atc atc<br>Gln Leu Ala Ala Met Pro Leu Phe Glu Arg Leu Ala Gln Arg Ile Ile<br>         665                   670               675 | 2131 |
| gac ggc gat aag aat ggc ctt gag gat gat ctg gaa gca ggc atg aag<br>Asp Gly Asp Lys Asn Gly Leu Glu Asp Asp Leu Glu Ala Gly Met Lys<br>680                  685                690 | 2179 |
| gag aag tct cct att gcg atc atc aac gag gac ctt ctc aac ggc atg<br>Glu Lys Ser Pro Ile Ala Ile Ile Asn Glu Asp Leu Leu Asn Gly Met<br>     695                   700                  705 | 2227 |
| aag acc gtg ggt gag ctg ttt ggt tcc gga cag atg cag ctg cca ttc<br>Lys Thr Val Gly Glu Leu Phe Gly Ser Gly Gln Met Gln Leu Pro Phe<br>710                  715                720              725 | 2275 |
| gtg ctg caa tcg gca gaa acc atg aaa act gcg gtg gcc tat ttg gaa<br>Val Leu Gln Ser Ala Glu Thr Met Lys Thr Ala Val Ala Tyr Leu Glu<br>              730                   735               740 | 2323 |
| ccg ttc atg gaa gag gaa gca gaa gct acc gga tct gcg cag gca gag<br>Pro Phe Met Glu Glu Glu Ala Glu Ala Thr Gly Ser Ala Gln Ala Glu<br>         745                   750               755 | 2371 |
| ggc aag ggc aaa atc gtc gtg gcc acc gtc aag ggt gac gtg cac gat<br>Gly Lys Gly Lys Ile Val Val Ala Thr Val Lys Gly Asp Val His Asp<br>              760                   765               770 | 2419 |
| atc ggc aag aac ttg gtg gac atc att ttg tcc aac aac ggt tac gac<br>Ile Gly Lys Asn Leu Val Asp Ile Ile Leu Ser Asn Asn Gly Tyr Asp<br>         775                   780               785 | 2467 |
| gtg gtg aac ttg ggc atc aag cag cca ctg tcc gcc atg ttg gaa gca<br>Val Val Asn Leu Gly Ile Lys Gln Pro Leu Ser Ala Met Leu Glu Ala | 2515 |

```
                790             795             800             805
gcg gaa gaa cac aaa gca gac gtc atc ggc atg tcg gga ctt ctt gtg    2563
Ala Glu Glu His Lys Ala Asp Val Ile Gly Met Ser Gly Leu Leu Val
                810                 815                 820 aag tcc acc gtg gtg atg aag caa acc atc agc gac                    2599
Lys Ser Thr Val Val Met Lys Gln Thr Ile Ser Asp
                825                 830

<210> SEQ ID NO 90
<211> LENGTH: 833
<212> TYPE: PRT
<213> ORGANISM: Corynebacterium glutamicum

<400> SEQUENCE: 90

Met Ser Thr Ser Val Thr Ser Pro Ala His Asn Asn Ala His Ser Ser
 1               5                   10                  15

Glu Phe Leu Asp Ala Leu Ala Asn His Val Leu Ile Gly Asp Gly Ala
             20                  25                  30

Met Gly Thr Gln Leu Gln Gly Phe Asp Leu Asp Val Glu Lys Asp Phe
         35                  40                  45

Leu Asp Leu Glu Gly Cys Asn Glu Ile Leu Asn Asp Thr Arg Pro Asp
     50                  55                  60

Val Leu Arg Gln Ile His Arg Ala Tyr Phe Glu Ala Gly Ala Asp Leu
 65                  70                  75                  80

Val Glu Thr Asn Thr Phe Gly Cys Asn Leu Pro Asn Leu Ala Asp Tyr
                 85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
            260                 265                 270

Gly Lys Asn Gly Ala Glu Tyr Pro Leu Glu Ala Glu Asp Leu Ala Gln
        275                 280                 285

Ala Leu Ala Gly Phe Val Ser Glu Tyr Gly Leu Ser Met Val Gly Gly
    290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
```

-continued

```
                325                 330                 335
Gly Pro Val Glu Gln Ala Ser Arg Glu Val Lys Glu Asp Ser Val
                340                 345                 350
Ala Ser Leu Tyr Thr Ser Val Pro Leu Ser Gln Glu Thr Gly Ile Ser
                355                 360                 365
Met Ile Gly Glu Arg Thr Asn Ser Asn Gly Ser Lys Ala Phe Arg Glu
                370                 375                 380
Ala Met Leu Ser Gly Asp Trp Glu Lys Cys Val Asp Ile Ala Lys Gln
385                 390                 395                 400
Gln Thr Arg Asp Gly Ala His Met Leu Asp Leu Cys Val Asp Tyr Val
                405                 410                 415
Gly Arg Asp Gly Thr Ala Asp Met Ala Thr Leu Ala Ala Leu Leu Ala
                420                 425                 430
Thr Ser Ser Thr Leu Pro Ile Met Ile Asp Ser Thr Glu Pro Glu Val
                435                 440                 445
Ile Arg Thr Gly Leu Glu His Leu Gly Gly Arg Ser Ile Val Asn Ser
                450                 455                 460
Val Asn Phe Glu Asp Gly Asp Gly Pro Glu Ser Arg Tyr Gln Arg Ile
465                 470                 475                 480
Met Lys Leu Val Lys Gln His Gly Ala Ala Val Val Ala Leu Thr Ile
                485                 490                 495
Asp Glu Glu Gly Gln Ala Arg Thr Ala Glu His Lys Val Arg Ile Ala
                500                 505                 510
Lys Arg Leu Ile Asp Asp Ile Thr Gly Ser Tyr Gly Leu Asp Ile Lys
                515                 520                 525
Asp Ile Val Val Asp Cys Leu Thr Phe Pro Ile Ser Thr Gly Gln Glu
                530                 535                 540
Glu Thr Arg Arg Asp Gly Ile Glu Thr Ile Glu Ala Ile Arg Glu Leu
545                 550                 555                 560
Lys Lys Leu Tyr Pro Glu Ile His Thr Thr Leu Gly Leu Ser Asn Ile
                565                 570                 575
Ser Phe Gly Leu Asn Pro Ala Ala Arg Gln Val Leu Asn Ser Val Phe
                580                 585                 590
Leu Asn Glu Cys Ile Glu Ala Gly Leu Asp Ser Ala Ile Ala His Ser
                595                 600                 605
Ser Lys Ile Leu Pro Met Asn Arg Ile Asp Asp Arg Gln Arg Glu Val
                610                 615                 620
Ala Leu Asp Met Val Tyr Asp Arg Arg Thr Glu Asp Tyr Asp Pro Leu
625                 630                 635                 640
Gln Glu Phe Met Gln Leu Phe Glu Gly Val Ser Ala Ala Asp Ala Lys
                645                 650                 655
Asp Ala Arg Ala Glu Gln Leu Ala Ala Met Pro Leu Phe Glu Arg Leu
                660                 665                 670
Ala Gln Arg Ile Ile Asp Gly Asp Lys Asn Gly Leu Glu Asp Asp Leu
                675                 680                 685
Glu Ala Gly Met Lys Glu Lys Ser Pro Ile Ala Ile Asn Glu Asp
                690                 695                 700
Leu Leu Asn Gly Met Lys Thr Val Gly Glu Leu Phe Gly Ser Gly Gln
705                 710                 715                 720
Met Gln Leu Pro Phe Val Leu Gln Ser Ala Glu Thr Met Lys Thr Ala
                725                 730                 735
Val Ala Tyr Leu Glu Pro Phe Met Glu Glu Ala Glu Ala Thr Gly
                740                 745                 750
```

```
Ser Ala Gln Ala Glu Gly Lys Gly Lys Ile Val Val Ala Thr Val Lys
            755                 760                 765

Gly Asp Val His Asp Ile Gly Lys Asn Leu Val Asp Ile Ile Leu Ser
            770                 775                 780

Asn Asn Gly Tyr Asp Val Val Asn Leu Gly Ile Lys Gln Pro Leu Ser
785                 790                 795                 800

Ala Met Leu Glu Ala Ala Glu His Lys Ala Asp Val Ile Gly Met
                805                 810                 815

Ser Gly Leu Leu Val Lys Ser Thr Val Val Met Lys Gln Thr Ile Ser
            820                 825                 830

Asp

<210> SEQ ID NO 91
<211> LENGTH: 2578
<212> TYPE: DNA
<213> ORGANISM: Corynebacterium glutamicum
<220> FEATURE:
<221> NAME/KEY: CDS
<222> LOCATION: (101)..(2578)
<223> OTHER INFORMATION: FRXA02198

<400> SEQUENCE: 91
agactagtgg cgctttgcct gtgttgctta ggcggcgttg aaaatgaact acgaatgaaa        60
agttcgggaa ttgtctaatc cgtactaagc tgtctacaca atg tct act tca gtt      115
                                              Met Ser Thr Ser Val
                                                1               5 act tca cca gcc cac aac aac gca cat tcc tcc gaa ttt ttg gat gcg      163
Thr Ser Pro Ala His Asn Asn Ala His Ser Ser Glu Phe Leu Asp Ala
                10                  15                  20 ttg gca aac cat gtg ttg atc ggc gac ggc gcc atg ggc acc cag ctc      211
Leu Ala Asn His Val Leu Ile Gly Asp Gly Ala Met Gly Thr Gln Leu
            25                  30                  35 caa ggc ttt gac ctg gac gtg gaa aag gat ttc ctt gat ctg gag ggg      259
Gln Gly Phe Asp Leu Asp Val Glu Lys Asp Phe Leu Asp Leu Glu Gly
        40                  45                  50 tgt aat gag att ctc aac gac acc cgc cct gat gtg ttg agg cag att      307
Cys Asn Glu Ile Leu Asn Asp Thr Arg Pro Asp Val Leu Arg Gln Ile
    55                  60                  65 cac cgc gcc tac ttt gag gcg gga gct gac ttg gtt gag acc aat act      355
His Arg Ala Tyr Phe Glu Ala Gly Ala Asp Leu Val Glu Thr Asn Thr
70                  75                  80                  85 ttt ggt tgc aac ctg ccg aac ttg gca gat tat gac atc gct gat cgt      403
Phe Gly Cys Asn Leu Pro Asn Leu Ala Asp Tyr Asp Ile Ala Asp Arg
                90                  95                 100 tgc cgt gag ctt gcc tac aag ggc act gca gtg gct agg gaa gtg gct      451
Cys Arg Glu Leu Ala Tyr Lys Gly Thr Ala Val Ala Arg Glu Val Ala
            105                 110                 115 gat gag atg ggg ccg ggc cga aac ggc atg cgg cgt ttc gtg gtt ggt      499
Asp Glu Met Gly Pro Gly Arg Asn Gly Met Arg Arg Phe Val Val Gly
        120                 125                 130 tcc ctg gga cct gga acg aag ctt cca tcg ctg ggc cat gca ccg tat      547
Ser Leu Gly Pro Gly Thr Lys Leu Pro Ser Leu Gly His Ala Pro Tyr
    135                 140                 145 gca gat ttg cgt ggg cac tac aag gaa gca gcg ctt ggc atc atc gac      595
Ala Asp Leu Arg Gly His Tyr Lys Glu Ala Ala Leu Gly Ile Ile Asp
150                 155                 160                 165 ggt ggt ggc gat gcc ttt ttg att gag act gct cag gac ttg ctt cag      643
Gly Gly Gly Asp Ala Phe Leu Ile Glu Thr Ala Gln Asp Leu Leu Gln
                170                 175                 180
```

```
gtc aag gct gcg gtt cac ggc gtt caa gat gcc atg gct gaa ctt gat    691
Val Lys Ala Ala Val His Gly Val Gln Asp Ala Met Ala Glu Leu Asp
        185                 190                 195 aca ttc ttg ccc att att tgc cac gtc acc gta gag acc acc ggc acc    739
Thr Phe Leu Pro Ile Ile Cys His Val Thr Val Glu Thr Thr Gly Thr
    200                 205                 210 atg ctc atg ggt tct gag atc ggt gcc gcg ttg aca gcg ctg cag cca    787
Met Leu Met Gly Ser Glu Ile Gly Ala Ala Leu Thr Ala Leu Gln Pro
215                 220                 225 ctg ggt atc gac atg att ggt ctg aac tgc gcc acc ggc cca gat gag    835
Leu Gly Ile Asp Met Ile Gly Leu Asn Cys Ala Thr Gly Pro Asp Glu
230                 235                 240                 245 atg agc gag cac ctg cgt tac ctg tcc aag cac gcc gat att cct gtg    883
Met Ser Glu His Leu Arg Tyr Leu Ser Lys His Ala Asp Ile Pro Val
        250                 255                 260 tcg gtg atg cct aac gca ggt ctt cct gtc ctg ggt aaa aac ggt gca    931
Ser Val Met Pro Asn Ala Gly Leu Pro Val Leu Gly Lys Asn Gly Ala
    265                 270                 275 gaa tac cca ctt gag gct gag gat ttg gcg cag gcg ctg gct gga ttc    979
Glu Tyr Pro Leu Glu Ala Glu Asp Leu Ala Gln Ala Leu Ala Gly Phe
280                 285                 290 gtc tcc gaa tat ggc ctg tcc atg gtg ggt ggt tgt tgt ggc acc aca   1027
Val Ser Glu Tyr Gly Leu Ser Met Val Gly Gly Cys Cys Gly Thr Thr
295                 300                 305 cct gag cac atc cgt gcg gtc cgc gat gcg gtg gtt ggt gtt cca gag   1075
Pro Glu His Ile Arg Ala Val Arg Asp Ala Val Val Gly Val Pro Glu
310                 315                 320                 325 cag gaa acc tcc aca ctg acc aag atc cct gca ggc cct gtt gag cag   1123
Gln Glu Thr Ser Thr Leu Thr Lys Ile Pro Ala Gly Pro Val Glu Gln
        330                 335                 340 gcc tcc cgc gag gtg gag aaa gag gac tcc gtc gcg tcg ctg tac acc   1171
Ala Ser Arg Glu Val Glu Lys Glu Asp Ser Val Ala Ser Leu Tyr Thr
    345                 350                 355 tcg gtg cca ttg tcc cag gaa acc ggc att tcc atg atc ggt gag cgc   1219
Ser Val Pro Leu Ser Gln Glu Thr Gly Ile Ser Met Ile Gly Glu Arg
360                 365                 370 acc aac tcc aac ggt tcc aag gca ttc cgt gag gca atg ctg tct ggc   1267
Thr Asn Ser Asn Gly Ser Lys Ala Phe Arg Glu Ala Met Leu Ser Gly
375                 380                 385 gat tgg gaa aag tgt gtg gat att gcc aag cag caa acc cgc gat ggt   1315
Asp Trp Glu Lys Cys Val Asp Ile Ala Lys Gln Gln Thr Arg Asp Gly
390                 395                 400                 405 gca cac atg ctg gat ctt tgt gtg gat tac gtg gga cga gac ggc acc   1363
Ala His Met Leu Asp Leu Cys Val Asp Tyr Val Gly Arg Asp Gly Thr
        410                 415                 420 gcc gat atg gcg acc ttg gca gca ctt ctt gct acc agc tcc act ttg   1411
Ala Asp Met Ala Thr Leu Ala Ala Leu Leu Ala Thr Ser Ser Thr Leu
    425                 430                 435 cca atc atg att gac tcc acc gag cca gag gtt att cgc aca ggc ctt   1459
Pro Ile Met Ile Asp Ser Thr Glu Pro Glu Val Ile Arg Thr Gly Leu
440                 445                 450 gag cac ttg ggt gga cga agc atc gtt aac tcc gtc aac ttt gaa gac   1507
Glu His Leu Gly Gly Arg Ser Ile Val Asn Ser Val Asn Phe Glu Asp
455                 460                 465 ggc gat ggc cct gag tcc cgc tac cag cgc atc atg aaa ctg gta aag   1555
Gly Asp Gly Pro Glu Ser Arg Tyr Gln Arg Ile Met Lys Leu Val Lys
470                 475                 480                 485 cag cac ggt gcg gcc gtg gtt gcg ctg acc att gat gag gaa ggc cag   1603
Gln His Gly Ala Ala Val Val Ala Leu Thr Ile Asp Glu Glu Gly Gln
```

-continued

```
                 490                 495                 500
gca cgt acc gct gag cac aag gtg cgc att gct aaa cga ctg att gac      1651
Ala Arg Thr Ala Glu His Lys Val Arg Ile Ala Lys Arg Leu Ile Asp
            505                 510                 515 gat atc acc ggc agc tac ggc ctg gat atc aaa gac atc gtt gtg gac      1699
Asp Ile Thr Gly Ser Tyr Gly Leu Asp Ile Lys Asp Ile Val Val Asp
        520                 525                 530 tgc ctg acc ttc ccg atc tct act ggc cag gaa gaa acc agg cga gat      1747
Cys Leu Thr Phe Pro Ile Ser Thr Gly Gln Glu Glu Thr Arg Arg Asp
    535                 540                 545 ggc att gaa acc atc gaa gcc atc cgc gag ctg aag aag ctc tac cca      1795
Gly Ile Glu Thr Ile Glu Ala Ile Arg Glu Leu Lys Lys Leu Tyr Pro
550                 555                 560                 565 gaa atc cac acc acc ctg ggt ctg tcc aat att tcc ttc ggc ctg aac      1843
Glu Ile His Thr Thr Leu Gly Leu Ser Asn Ile Ser Phe Gly Leu Asn
                570                 575                 580 cct gct gca cgc cag gtt ctt aac tct gtg ttc ctc aat gag tgc att      1891
Pro Ala Ala Arg Gln Val Leu Asn Ser Val Phe Leu Asn Glu Cys Ile
            585                 590                 595 gag gct ggt ctg gac tct gcg att gcg cac agc tcc aag att ttg ccg      1939
Glu Ala Gly Leu Asp Ser Ala Ile Ala His Ser Ser Lys Ile Leu Pro
        600                 605                 610 atg aac cgc att gat gat cgc cag cgc gaa gtg gcg ttg gat atg gtc      1987
Met Asn Arg Ile Asp Asp Arg Gln Arg Glu Val Ala Leu Asp Met Val
    615                 620                 625 tat gat cgc cgc acc gag gat tac gat ccg ctg cag gaa ttc atg cag      2035
Tyr Asp Arg Arg Thr Glu Asp Tyr Asp Pro Leu Gln Glu Phe Met Gln
630                 635                 640                 645 ctg ttt gag ggc gtt tct gct gcc gat gcc aag gat gct cgc gct gaa      2083
Leu Phe Glu Gly Val Ser Ala Ala Asp Ala Lys Asp Ala Arg Ala Glu
                650                 655                 660 cag ctg gcc gct atg cct ttg ttt gag cgt ttg gca cag cgc atc atc      2131
Gln Leu Ala Ala Met Pro Leu Phe Glu Arg Leu Ala Gln Arg Ile Ile
            665                 670                 675 gac ggc gat aag aat ggc ctt gag gat gat ctg gaa gca ggc atg aag      2179
Asp Gly Asp Lys Asn Gly Leu Glu Asp Asp Leu Glu Ala Gly Met Lys
        680                 685                 690 gag aag tct cct att gcg atc atc aac gag gac ctt ctc aac ggc atg      2227
Glu Lys Ser Pro Ile Ala Ile Ile Asn Glu Asp Leu Leu Asn Gly Met
    695                 700                 705 aag acc gtg ggt gag ctg ttt ggt tcc gga cag atg cag ctg cca ttc      2275
Lys Thr Val Gly Glu Leu Phe Gly Ser Gly Gln Met Gln Leu Pro Phe
710                 715                 720                 725 gtg ctg caa tcg gca gaa acc atg aaa act gcg gtg gcc tat ttg gaa      2323
Val Leu Gln Ser Ala Glu Thr Met Lys Thr Ala Val Ala Tyr Leu Glu
                730                 735                 740 ccg ttc atg gaa gag gaa gca gaa gct acc gga tct gcg cag gca gag      2371
Pro Phe Met Glu Glu Glu Ala Glu Ala Thr Gly Ser Ala Gln Ala Glu
            745                 750                 755 ggc aag ggc aaa atc gtc gtg gcc acc gtc aag ggt gac gtg cac gat      2419
Gly Lys Gly Lys Ile Val Val Ala Thr Val Lys Gly Asp Val His Asp
        760                 765                 770 atc ggc aag aac ttg gtg gac atc att ttg tcc aac aac ggt tac gac      2467
Ile Gly Lys Asn Leu Val Asp Ile Ile Leu Ser Asn Asn Gly Tyr Asp
    775                 780                 785 gtg gtg aac ttg ggc atc aag cag cca ctg tcc gcc atg ttg gaa gca      2515
Val Val Asn Leu Gly Ile Lys Gln Pro Leu Ser Ala Met Leu Glu Ala
790                 795                 800                 805 gcg gaa gaa cac aaa gca gac gtc atc ggc atg tcg gga ctt ctt gtg      2563
```

```
Ala Glu Glu His Lys Ala Asp Val Ile Gly Met Ser Gly Leu Leu Val
            810                 815                 820 aag tcc acc gtg gtg                                                      2578
Lys Ser Thr Val Val
            825

<210> SEQ ID NO 92
<211> LENGTH: 826
<212> TYPE: PRT
<213> ORGANISM: Corynebacterium glutamicum

<400> SEQUENCE: 92

Met Ser Thr Ser Val Thr Ser Pro Ala His Asn Asn Ala His Ser Ser
  1               5                  10                  15

Glu Phe Leu Asp Ala Leu Ala Asn His Val Leu Ile Gly Asp Gly Ala
             20                  25                  30

Met Gly Thr Gln Leu Gln Gly Phe Asp Leu Asp Val Glu Lys Asp Phe
         35                  40                  45

Leu Asp Leu Glu Gly Cys Asn Glu Ile Leu Asn Asp Thr Arg Pro Asp
 50                  55                  60

Val Leu Arg Gln Ile His Arg Ala Tyr Phe Glu Ala Gly Ala Asp Leu
 65                  70                  75                  80

Val Glu Thr Asn Thr Phe Gly Cys Asn Leu Pro Asn Leu Ala Asp Tyr
             85                  90                  95

Asp Ile Ala Asp Arg Cys Arg Glu Leu Ala Tyr Lys Gly Thr Ala Val
            100                 105                 110

Ala Arg Glu Val Ala Asp Glu Met Gly Pro Gly Arg Asn Gly Met Arg
        115                 120                 125

Arg Phe Val Val Gly Ser Leu Gly Pro Gly Thr Lys Leu Pro Ser Leu
    130                 135                 140

Gly His Ala Pro Tyr Ala Asp Leu Arg Gly His Tyr Lys Glu Ala Ala
145                 150                 155                 160

Leu Gly Ile Ile Asp Gly Gly Asp Ala Phe Leu Ile Glu Thr Ala
                165                 170                 175

Gln Asp Leu Leu Gln Val Lys Ala Ala Val His Gly Val Gln Asp Ala
            180                 185                 190

Met Ala Glu Leu Asp Thr Phe Leu Pro Ile Ile Cys His Val Thr Val
        195                 200                 205

Glu Thr Thr Gly Thr Met Leu Met Gly Ser Glu Ile Gly Ala Ala Leu
    210                 215                 220

Thr Ala Leu Gln Pro Leu Gly Ile Asp Met Ile Gly Leu Asn Cys Ala
225                 230                 235                 240

Thr Gly Pro Asp Glu Met Ser Glu His Leu Arg Tyr Leu Ser Lys His
                245                 250                 255

Ala Asp Ile Pro Val Ser Val Met Pro Asn Ala Gly Leu Pro Val Leu
            260                 265                 270

Gly Lys Asn Gly Ala Glu Tyr Pro Leu Glu Ala Glu Asp Leu Ala Gln
        275                 280                 285

Ala Leu Ala Gly Phe Val Ser Glu Tyr Gly Leu Ser Met Val Gly Gly
    290                 295                 300

Cys Cys Gly Thr Thr Pro Glu His Ile Arg Ala Val Arg Asp Ala Val
305                 310                 315                 320

Val Gly Val Pro Glu Gln Glu Thr Ser Thr Leu Thr Lys Ile Pro Ala
                325                 330                 335

Gly Pro Val Glu Gln Ala Ser Arg Glu Val Glu Lys Glu Asp Ser Val
```

-continued

```
               340                 345                 350
Ala Ser Leu Tyr Thr Ser Val Pro Leu Ser Gln Glu Thr Gly Ile Ser
            355                 360                 365

Met Ile Gly Glu Arg Thr Asn Ser Asn Gly Ser Lys Ala Phe Arg Glu
        370                 375                 380

Ala Met Leu Ser Gly Asp Trp Glu Lys Cys Val Asp Ile Ala Lys Gln
385                 390                 395                 400

Gln Thr Arg Asp Gly Ala His Met Leu Asp Leu Cys Val Asp Tyr Val
                405                 410                 415

Gly Arg Asp Gly Thr Ala Asp Met Ala Thr Leu Ala Ala Leu Leu Ala
            420                 425                 430

Thr Ser Ser Thr Leu Pro Ile Met Ile Asp Ser Thr Glu Pro Glu Val
        435                 440                 445

Ile Arg Thr Gly Leu Glu His Leu Gly Gly Arg Ser Ile Val Asn Ser
    450                 455                 460

Val Asn Phe Glu Asp Gly Asp Gly Pro Glu Ser Arg Tyr Gln Arg Ile
465                 470                 475                 480

Met Lys Leu Val Lys Gln His Gly Ala Ala Val Val Ala Leu Thr Ile
                485                 490                 495

Asp Glu Glu Gly Gln Ala Arg Thr Ala Glu His Lys Val Arg Ile Ala
            500                 505                 510

Lys Arg Leu Ile Asp Asp Ile Thr Gly Ser Tyr Gly Leu Asp Ile Lys
        515                 520                 525

Asp Ile Val Val Asp Cys Leu Thr Phe Pro Ile Ser Thr Gly Gln Glu
    530                 535                 540

Glu Thr Arg Arg Asp Gly Ile Glu Thr Ile Glu Ala Ile Arg Glu Leu
545                 550                 555                 560

Lys Lys Leu Tyr Pro Glu Ile His Thr Thr Leu Gly Leu Ser Asn Ile
                565                 570                 575

Ser Phe Gly Leu Asn Pro Ala Ala Arg Gln Val Leu Asn Ser Val Phe
            580                 585                 590

Leu Asn Glu Cys Ile Glu Ala Gly Leu Asp Ser Ala Ile Ala His Ser
        595                 600                 605

Ser Lys Ile Leu Pro Met Asn Arg Ile Asp Asp Arg Gln Arg Glu Val
    610                 615                 620

Ala Leu Asp Met Val Tyr Asp Arg Arg Thr Glu Asp Tyr Asp Pro Leu
625                 630                 635                 640

Gln Glu Phe Met Gln Leu Phe Glu Gly Val Ser Ala Ala Asp Ala Lys
                645                 650                 655

Asp Ala Arg Ala Glu Gln Leu Ala Ala Met Pro Leu Phe Glu Arg Leu
            660                 665                 670

Ala Gln Arg Ile Ile Asp Gly Asp Lys Asn Gly Leu Glu Asp Asp Leu
        675                 680                 685

Glu Ala Gly Met Lys Glu Lys Ser Pro Ile Ala Ile Asn Glu Asp
    690                 695                 700

Leu Leu Asn Gly Met Lys Thr Val Gly Glu Leu Phe Gly Ser Gly Gln
705                 710                 715                 720

Met Gln Leu Pro Phe Val Leu Gln Ser Ala Glu Thr Met Lys Thr Ala
                725                 730                 735

Val Ala Tyr Leu Glu Pro Phe Met Glu Glu Ala Glu Ala Thr Gly
            740                 745                 750

Ser Ala Gln Ala Glu Gly Lys Gly Lys Ile Val Val Ala Thr Val Lys
        755                 760                 765
```

```
Gly Asp Val His Asp Ile Gly Lys Asn Leu Val Asp Ile Ile Leu Ser
        770                 775                 780

Asn Asn Gly Tyr Asp Val Val Asn Leu Gly Ile Lys Gln Pro Leu Ser
785                 790                 795                 800

Ala Met Leu Glu Ala Ala Glu His Lys Ala Asp Val Ile Gly Met
            805                 810                 815

Ser Gly Leu Leu Val Lys Ser Thr Val Val
        820                 825

<210> SEQ ID NO 93
<211> LENGTH: 621
<212> TYPE: DNA
<213> ORGANISM: Corynebacterium glutamicum
<220> FEATURE:
<221> NAME/KEY: CDS
<222> LOCATION: (101)..(598)
<223> OTHER INFORMATION: RXN03074

<400> SEQUENCE: 93
```

| | |
|---|---|
| tttgtgggca atctggtttt ttcgtaattg tgtgggatga atctcttaaa aattcacatt | 60 |
| tagcaggaca agcatactgt tttagttcta tgctgtgggc atg act caa agt gct<br>                                                                                      Met Thr Gln Ser Ala<br>                                                                                       1              5 | 115 |

```
cca gaa ttc att gcc acc gca gac ctc gta gac atc atc ggc gac aac     163
Pro Glu Phe Ile Ala Thr Ala Asp Leu Val Asp Ile Ile Gly Asp Asn
            10                  15                  20 gcg caa tca tgc gac act cag ttt caa aac ctt gga ggt gcc aca gaa     211
Ala Gln Ser Cys Asp Thr Gln Phe Gln Asn Leu Gly Gly Ala Thr Glu
        25                  30                  35 ttc cac gga ata ata acc acc gtg aaa tgc ttc caa gac aac gcc ctc     259
Phe His Gly Ile Ile Thr Thr Val Lys Cys Phe Gln Asp Asn Ala Leu
 40                  45                  50 ctg aaa tcc atc ctg agc gag gat aat cct ggg gga gtg ctg gtt atc     307
Leu Lys Ser Ile Leu Ser Glu Asp Asn Pro Gly Gly Val Leu Val Ile
     55                  60                  65 gat ggc gac gca tcc gtg cac acc gcg cta gtt ggc gac atc att gca     355
Asp Gly Asp Ala Ser Val His Thr Ala Leu Val Gly Asp Ile Ile Ala
 70                  75                  80                  85 gga ctt gga aaa gat cat ggt tgg tcc gga gta att gtc aac gga gca     403
Gly Leu Gly Lys Asp His Gly Trp Ser Gly Val Ile Val Asn Gly Ala
             90                  95                 100 att cga gac tcc gca gtc atc ggc acc atg acc ttt ggt tgt aaa gcc     451
Ile Arg Asp Ser Ala Val Ile Gly Thr Met Thr Phe Gly Cys Lys Ala
        105                 110                 115 ctt gga acc aac ccg cgg aaa tcc act aaa act ggt tcc ggc gaa cga     499
Leu Gly Thr Asn Pro Arg Lys Ser Thr Lys Thr Gly Ser Gly Glu Arg
    120                 125                 130 gac gta gtg gta tcg att ggt ggc att gac ttc att cct ggt cat tac     547
Asp Val Val Val Ser Ile Gly Gly Ile Asp Phe Ile Pro Gly His Tyr
135                 140                 145 gtc tac gcg gac tct gac gga att atc gtc acc gag gcg cca att aag     595
Val Tyr Ala Asp Ser Asp Gly Ile Ile Val Thr Glu Ala Pro Ile Lys
150                 155                 160                 165 cag taatttgttt tgacgacgca gta                                       621
Gln

<210> SEQ ID NO 94
<211> LENGTH: 166
<212> TYPE: PRT
<213> ORGANISM: Corynebacterium glutamicum
```

<400> SEQUENCE: 94

```
Met Thr Gln Ser Ala Pro Glu Phe Ile Ala Thr Ala Asp Leu Val Asp
 1               5                  10                  15

Ile Ile Gly Asp Asn Ala Gln Ser Cys Asp Thr Gln Phe Gln Asn Leu
             20                  25                  30

Gly Gly Ala Thr Glu Phe His Gly Ile Ile Thr Val Lys Cys Phe
         35                  40                  45

Gln Asp Asn Ala Leu Leu Lys Ser Ile Leu Ser Glu Asp Asn Pro Gly
 50                  55                  60

Gly Val Leu Val Ile Asp Gly Asp Ala Ser Val His Thr Ala Leu Val
 65                  70                  75                  80

Gly Asp Ile Ile Ala Gly Leu Gly Lys Asp His Gly Trp Ser Gly Val
             85                  90                  95

Ile Val Asn Gly Ala Ile Arg Asp Ser Ala Val Ile Gly Thr Met Thr
            100                 105                 110

Phe Gly Cys Lys Ala Leu Gly Thr Asn Pro Arg Lys Ser Thr Lys Thr
        115                 120                 125

Gly Ser Gly Glu Arg Asp Val Val Ser Ile Gly Ile Asp Phe
    130                 135                 140

Ile Pro Gly His Tyr Val Tyr Ala Asp Ser Asp Gly Ile Ile Val Thr
145                 150                 155                 160

Glu Ala Pro Ile Lys Gln
                165
```

<210> SEQ ID NO 95
<211> LENGTH: 621
<212> TYPE: DNA
<213> ORGANISM: Corynebacterium glutamicum
<220> FEATURE:
<221> NAME/KEY: CDS
<222> LOCATION: (101)..(598)
<223> OTHER INFORMATION: FRXA02906

<400> SEQUENCE: 95

```
tttgtgggca atctggtttt tcgtaattg tgtgggatga atctcttaaa aattcacatt      60
tagcaggaca agcatactgt tttagttcta tgctgtgggc atg act caa agt gct     115
                                            Met Thr Gln Ser Ala
                                             1               5 cca gaa ttc att gcc acc gca gac ctc gta gac atc atc ggc gac aac     163
Pro Glu Phe Ile Ala Thr Ala Asp Leu Val Asp Ile Ile Gly Asp Asn
             10                  15                  20 gcg caa tca tgc gac act cag ttt caa aac ctt gga ggt gcc aca gaa     211
Ala Gln Ser Cys Asp Thr Gln Phe Gln Asn Leu Gly Gly Ala Thr Glu
         25                  30                  35 ttc cac gga ata ata acc acc gtg aaa tgc ttc caa gac aac gcc ctc     259
Phe His Gly Ile Ile Thr Thr Val Lys Cys Phe Gln Asp Asn Ala Leu
     40                  45                  50 ctg aaa tcc atc ctg agc gag gat aat cct ggg gga gtg ctg gtt atc     307
Leu Lys Ser Ile Leu Ser Glu Asp Asn Pro Gly Gly Val Leu Val Ile
 55                  60                  65 gat ggc gac gca tcc gtg cac acc gcg cta gtt ggc gac atc att gca     355
Asp Gly Asp Ala Ser Val His Thr Ala Leu Val Gly Asp Ile Ile Ala
 70                  75                  80                  85 gga ctt gga aaa gat cat ggt tgg tcc gga gta att gtc aac gga gca     403
Gly Leu Gly Lys Asp His Gly Trp Ser Gly Val Ile Val Asn Gly Ala
             90                  95                 100 att cga gac tcc gca gtc atc ggc acc atg acc ttt ggt tgt aaa gcc     451
Ile Arg Asp Ser Ala Val Ile Gly Thr Met Thr Phe Gly Cys Lys Ala
```

-continued

```
Ile Arg Asp Ser Ala Val Ile Gly Thr Met Thr Phe Gly Cys Lys Ala
            105                 110                 115 ctt gga acc aac ccg cgg aaa tcc act aaa act ggt tcc ggc gaa cga        499
Leu Gly Thr Asn Pro Arg Lys Ser Thr Lys Thr Gly Ser Gly Glu Arg
        120                 125                 130 gac gta gtg gta tcg att ggt ggc att gac ttc att cct ggt cat tac        547
Asp Val Val Val Ser Ile Gly Gly Ile Asp Phe Ile Pro Gly His Tyr
        135                 140                 145 gtc tac gcg gac tct gac gga att atc gtc acc gag gcg cca att aag        595
Val Tyr Ala Asp Ser Asp Gly Ile Ile Val Thr Glu Ala Pro Ile Lys
150                 155                 160                 165 cag taatttgttt tgacgacgca gta                                          621
Gln
```

```
<210> SEQ ID NO 96
<211> LENGTH: 166
<212> TYPE: PRT
<213> ORGANISM: Corynebacterium glutamicum

<400> SEQUENCE: 96

Met Thr Gln Ser Ala Pro Glu Phe Ile Ala Thr Ala Asp Leu Val Asp
1               5                   10                  15

Ile Ile Gly Asp Asn Ala Gln Ser Cys Asp Thr Gln Phe Gln Asn Leu
            20                  25                  30

Gly Gly Ala Thr Glu Phe His Gly Ile Ile Thr Thr Val Lys Cys Phe
        35                  40                  45

Gln Asp Asn Ala Leu Leu Lys Ser Ile Leu Ser Glu Asp Asn Pro Gly
    50                  55                  60

Gly Val Leu Val Ile Asp Gly Asp Ala Ser Val His Thr Ala Leu Val
65                  70                  75                  80

Gly Asp Ile Ile Ala Gly Leu Gly Lys Asp His Gly Trp Ser Gly Val
                85                  90                  95

Ile Val Asn Gly Ala Ile Arg Asp Ser Ala Val Ile Gly Thr Met Thr
            100                 105                 110

Phe Gly Cys Lys Ala Leu Gly Thr Asn Pro Arg Lys Ser Thr Lys Thr
        115                 120                 125

Gly Ser Gly Glu Arg Asp Val Val Val Ser Ile Gly Gly Ile Asp Phe
    130                 135                 140

Ile Pro Gly His Tyr Val Tyr Ala Asp Ser Asp Gly Ile Ile Val Thr
145                 150                 155                 160

Glu Ala Pro Ile Lys Gln
                165
```

```
<210> SEQ ID NO 97
<211> LENGTH: 1557
<212> TYPE: DNA
<213> ORGANISM: Corynebacterium glutamicum
<220> FEATURE:
<221> NAME/KEY: CDS
<222> LOCATION: (101)..(1534)
<223> OTHER INFORMATION: RXN00132

<400> SEQUENCE: 97
aacagcttca atcaattcgg tgtccactcc aacatgtaga gtggtgcgcg ttaaaaagt          60 tttcctaatt ttcattttct taaaggagc tcgccaggac atg gca cag gtt atg         115
                                            Met Ala Gln Val Met
                                            1               5 gac ttc aag gtt gcc gat ctt tca cta gca gag gca gga cgt cac cag        163
Asp Phe Lys Val Ala Asp Leu Ser Leu Ala Glu Ala Gly Arg His Gln
```

-continued

|  | 10 | 15 | 20 |  |
|---|---|---|---|---|
| att cgt ctt gca gag tat gag atg cca ggt ctc atg cag ttg cgc aag<br>Ile Arg Leu Ala Glu Tyr Glu Met Pro Gly Leu Met Gln Leu Arg Lys<br>25 30 35 | | | | 211 |
| gaa ttc gca gac gag cag cct ttg aag ggc gcc cga att gct ggt tct<br>Glu Phe Ala Asp Glu Gln Pro Leu Lys Gly Ala Arg Ile Ala Gly Ser<br>40 45 50 | | | | 259 |
| atc cac atg acg gtc cag acc gcc gtg ctt att gag acc ctc act gct<br>Ile His Met Thr Val Gln Thr Ala Val Leu Ile Glu Thr Leu Thr Ala<br>55 60 65 | | | | 307 |
| ttg ggc gct gag gtt cgt tgg gct tcc tgc aac att ttc tcc acc cag<br>Leu Gly Ala Glu Val Arg Trp Ala Ser Cys Asn Ile Phe Ser Thr Gln<br>70 75 80 85 | | | | 355 |
| gat gag gct gca gcg gct atc gtt gtc ggc tcc ggc acc gtc gaa gag<br>Asp Glu Ala Ala Ala Ala Ile Val Val Gly Ser Gly Thr Val Glu Glu<br>90 95 100 | | | | 403 |
| cca gct ggt gtt cca gta ttc gcg tgg aag ggt gag tca ctg gag gag<br>Pro Ala Gly Val Pro Val Phe Ala Trp Lys Gly Glu Ser Leu Glu Glu<br>105 110 115 | | | | 451 |
| tac tgg tgg tgc atc aac cag atc ttc agc tgg ggc gat gag ctg cca<br>Tyr Trp Trp Cys Ile Asn Gln Ile Phe Ser Trp Gly Asp Glu Leu Pro<br>120 125 130 | | | | 499 |
| aac atg atc ctc gac gac ggc ggt gac gcc acc atg gct gtt att cgc<br>Asn Met Ile Leu Asp Asp Gly Gly Asp Ala Thr Met Ala Val Ile Arg<br>135 140 145 | | | | 547 |
| ggt cgc gaa tac gag cag gct ggt ctg gtt cca cca gca gag gcc aac<br>Gly Arg Glu Tyr Glu Gln Ala Gly Leu Val Pro Pro Ala Glu Ala Asn<br>150 155 160 165 | | | | 595 |
| gat tcc gat gag tac atc gca ttc ttg ggc atg ctg cgt gag gtt ctt<br>Asp Ser Asp Glu Tyr Ile Ala Phe Leu Gly Met Leu Arg Glu Val Leu<br>170 175 180 | | | | 643 |
| gct gca gag cct ggc aag tgg ggc aag atc gct gag gcc gtt aag ggt<br>Ala Ala Glu Pro Gly Lys Trp Gly Lys Ile Ala Glu Ala Val Lys Gly<br>185 190 195 | | | | 691 |
| gtc acc gag gaa acc acc acc ggt gtg cac cgc ctg tac cac ttc gct<br>Val Thr Glu Glu Thr Thr Thr Gly Val His Arg Leu Tyr His Phe Ala<br>200 205 210 | | | | 739 |
| gaa gaa ggc gtg ctg cct ttc cca gcg atg aac gtc aac gac gct gtc<br>Glu Glu Gly Val Leu Pro Phe Pro Ala Met Asn Val Asn Asp Ala Val<br>215 220 225 | | | | 787 |
| acc aag tcc aag ttt gat aac aag tac ggc acc cgc cac tcc ctg atc<br>Thr Lys Ser Lys Phe Asp Asn Lys Tyr Gly Thr Arg His Ser Leu Ile<br>230 235 240 245 | | | | 835 |
| gac ggc atc aac cgc gcc act gac atg ctc atg ggc ggc aag aac gtg<br>Asp Gly Ile Asn Arg Ala Thr Asp Met Leu Met Gly Gly Lys Asn Val<br>250 255 260 | | | | 883 |
| ctt gtc tgc ggt tac ggc gat gtc ggc aag ggc tgc gct gag gct ttc<br>Leu Val Cys Gly Tyr Gly Asp Val Gly Lys Gly Cys Ala Glu Ala Phe<br>265 270 275 | | | | 931 |
| gac ggc cag ggc gct cgc gtc aag gtc acc gaa gct gac cca atc aac<br>Asp Gly Gln Gly Ala Arg Val Lys Val Thr Glu Ala Asp Pro Ile Asn<br>280 285 290 | | | | 979 |
| gct ctt cag gct ctg atg gat ggc tac tct gtg gtc acc gtt gat gag<br>Ala Leu Gln Ala Leu Met Asp Gly Tyr Ser Val Val Thr Val Asp Glu<br>295 300 305 | | | | 1027 |
| gcc atc gag gac gcc gac atc gtg atc acc gcg acc ggc aac aag gac<br>Ala Ile Glu Asp Ala Asp Ile Val Ile Thr Ala Thr Gly Asn Lys Asp<br>310 315 320 325 | | | | 1075 |
| atc att tcc ttc gag cag atg ctc aag atg aag gat cac gct ctg ctg | | | | 1123 |

-continued

```
Ile Ile Ser Phe Glu Gln Met Leu Lys Met Lys Asp His Ala Leu Leu
                330                 335                 340 ggc aac atc ggt cac ttt gat aat gag atc gat atg cat tcc ctg ttg      1171
Gly Asn Ile Gly His Phe Asp Asn Glu Ile Asp Met His Ser Leu Leu
            345                 350                 355 cac cgc gac gac gtc acc cgc acc acg atc aag cca cag gtc gac gag      1219
His Arg Asp Asp Val Thr Arg Thr Thr Ile Lys Pro Gln Val Asp Glu
        360                 365                 370 ttc acc ttc tcc acc ggt cgc tcc atc atc gtc ctg tcc gaa ggt cgc      1267
Phe Thr Phe Ser Thr Gly Arg Ser Ile Ile Val Leu Ser Glu Gly Arg
    375                 380                 385 ctg ttg aac ctt ggc aac gcc acc gga cac cca tca ttt gtc atg tcc      1315
Leu Leu Asn Leu Gly Asn Ala Thr Gly His Pro Ser Phe Val Met Ser
390                 395                 400                 405 aac tct ttc gcc gat cag acc att gcg cag atc gaa ctg ttc caa aac      1363
Asn Ser Phe Ala Asp Gln Thr Ile Ala Gln Ile Glu Leu Phe Gln Asn
                410                 415                 420 gaa gga cag tac gag aac gag gtc tac cgt ctg cct aag gtt ctc gac      1411
Glu Gly Gln Tyr Glu Asn Glu Val Tyr Arg Leu Pro Lys Val Leu Asp
            425                 430                 435 gaa aag gtg gca cgc atc cac gtt gag gct ctc ggc ggt cag ctc acc      1459
Glu Lys Val Ala Arg Ile His Val Glu Ala Leu Gly Gly Gln Leu Thr
        440                 445                 450 gaa ctg acc aag gag cag gct gag tac atc ggc gtt gac gtt gca ggc      1507
Glu Leu Thr Lys Glu Gln Ala Glu Tyr Ile Gly Val Asp Val Ala Gly
    455                 460                 465 cca ttc aag ccg gag cac tac cgc tac taatgattgt cagcattgag gga        1557
Pro Phe Lys Pro Glu His Tyr Arg Tyr
470                 475
```

<210> SEQ ID NO 98
<211> LENGTH: 478
<212> TYPE: PRT
<213> ORGANISM: Corynebacterium glutamicum

<400> SEQUENCE: 98

```
Met Ala Gln Val Met Asp Phe Lys Val Ala Asp Leu Ser Leu Ala Glu
  1               5                  10                  15

Ala Gly Arg His Gln Ile Arg Leu Ala Glu Tyr Glu Met Pro Gly Leu
                 20                  25                  30

Met Gln Leu Arg Lys Glu Phe Ala Asp Glu Gln Pro Leu Lys Gly Ala
             35                  40                  45

Arg Ile Ala Gly Ser Ile His Met Thr Val Gln Thr Ala Val Leu Ile
         50                  55                  60

Glu Thr Leu Thr Ala Leu Gly Ala Glu Val Arg Trp Ala Ser Cys Asn
 65                  70                  75                  80

Ile Phe Ser Thr Gln Asp Glu Ala Ala Ala Ile Val Val Gly Ser
                 85                  90                  95

Gly Thr Val Glu Glu Pro Ala Gly Val Pro Val Phe Ala Trp Lys Gly
                100                 105                 110

Glu Ser Leu Glu Glu Tyr Trp Trp Cys Ile Asn Gln Ile Phe Ser Trp
            115                 120                 125

Gly Asp Glu Leu Pro Asn Met Ile Leu Asp Asp Gly Asp Ala Thr
        130                 135                 140

Met Ala Val Ile Arg Gly Arg Glu Tyr Glu Gln Ala Gly Leu Val Pro
145                 150                 155                 160

Pro Ala Glu Ala Asn Asp Ser Asp Glu Tyr Ile Ala Phe Leu Gly Met
                165                 170                 175
```

Leu Arg Glu Val Leu Ala Ala Glu Pro Gly Lys Trp Gly Lys Ile Ala
            180                 185                 190
Glu Ala Val Lys Gly Val Thr Glu Thr Thr Thr Gly Val His Arg
        195                 200                 205
Leu Tyr His Phe Ala Glu Glu Gly Val Leu Pro Phe Pro Ala Met Asn
    210                 215                 220
Val Asn Asp Ala Val Thr Lys Ser Lys Phe Asp Asn Lys Tyr Gly Thr
225                 230                 235                 240
Arg His Ser Leu Ile Asp Gly Ile Asn Arg Ala Thr Asp Met Leu Met
                245                 250                 255
Gly Gly Lys Asn Val Leu Val Cys Gly Tyr Gly Asp Val Gly Lys Gly
            260                 265                 270
Cys Ala Glu Ala Phe Asp Gly Gln Gly Ala Arg Val Lys Val Thr Glu
        275                 280                 285
Ala Asp Pro Ile Asn Ala Leu Gln Ala Leu Met Asp Gly Tyr Ser Val
    290                 295                 300
Val Thr Val Asp Glu Ala Ile Glu Asp Ala Asp Ile Val Ile Thr Ala
305                 310                 315                 320
Thr Gly Asn Lys Asp Ile Ile Ser Phe Glu Gln Met Leu Lys Met Lys
                325                 330                 335
Asp His Ala Leu Leu Gly Asn Ile Gly His Phe Asp Asn Glu Ile Asp
            340                 345                 350
Met His Ser Leu Leu His Arg Asp Asp Val Thr Arg Thr Thr Ile Lys
        355                 360                 365
Pro Gln Val Asp Glu Phe Thr Phe Ser Thr Gly Arg Ser Ile Ile Val
    370                 375                 380
Leu Ser Glu Gly Arg Leu Leu Asn Leu Gly Asn Ala Thr Gly His Pro
385                 390                 395                 400
Ser Phe Val Met Ser Asn Ser Phe Ala Asp Gln Thr Ile Ala Gln Ile
                405                 410                 415
Glu Leu Phe Gln Asn Glu Gly Gln Tyr Glu Asn Glu Val Tyr Arg Leu
            420                 425                 430
Pro Lys Val Leu Asp Glu Lys Val Ala Arg Ile His Val Glu Ala Leu
        435                 440                 445
Gly Gly Gln Leu Thr Glu Leu Thr Lys Glu Gln Ala Glu Tyr Ile Gly
    450                 455                 460
Val Asp Val Ala Gly Pro Phe Lys Pro Glu His Tyr Arg Tyr
465                 470                 475

<210> SEQ ID NO 99
<211> LENGTH: 128
<212> TYPE: DNA
<213> ORGANISM: Corynebacterium glutamicum
<220> FEATURE:
<221> NAME/KEY: CDS
<222> LOCATION: (1)..(105)
<223> OTHER INFORMATION: FRXA00132

<400> SEQUENCE: 99 cac gtt gag gct ctc ggc ggt cag ctc acc gaa ctg acc aag gag cag        48
His Val Glu Ala Leu Gly Gly Gln Leu Thr Glu Leu Thr Lys Glu Gln
  1               5                  10                  15 gct gag tac atc ggc gtt gac gtt gca ggc cca ttc aag ccg gag cac        96
Ala Glu Tyr Ile Gly Val Asp Val Ala Gly Pro Phe Lys Pro Glu His
                 20                  25                  30 tac cgc tac taatgattgt cagcattgag gga                                 128
Tyr Arg Tyr

```
<210> SEQ ID NO 100
<211> LENGTH: 35
<212> TYPE: PRT
<213> ORGANISM: Corynebacterium glutamicum

<400> SEQUENCE: 100

His Val Glu Ala Leu Gly Gly Gln Leu Thr Glu Leu Thr Lys Glu Gln
 1               5                  10                  15

Ala Glu Tyr Ile Gly Val Asp Val Ala Gly Pro Phe Lys Pro Glu His
            20                  25                  30

Tyr Arg Tyr
        35

<210> SEQ ID NO 101
<211> LENGTH: 1396
<212> TYPE: DNA
<213> ORGANISM: Corynebacterium glutamicum
<220> FEATURE:
<221> NAME/KEY: CDS
<222> LOCATION: (101)..(1396)
<223> OTHER INFORMATION: FRXA01371

<400> SEQUENCE: 101
aacagcttca atcaattcgg tgtccactcc aacatgtaga gtggtgcgcg ttaaaaagt      60 tttcctaatt ttcattttct taaaggagc tcgccaggac atg gca cag gtt atg     115
                                            Met Ala Gln Val Met
                                             1               5 gac ttc aag gtt gcc gat ctt tca cta gca gag gca gga cgt cac cag    163
Asp Phe Lys Val Ala Asp Leu Ser Leu Ala Glu Ala Gly Arg His Gln
             10                  15                  20 att cgt ctt gca gag tat gag atg cca ggt ctc atg cag ttg cgc aag    211
Ile Arg Leu Ala Glu Tyr Glu Met Pro Gly Leu Met Gln Leu Arg Lys
         25                  30                  35 gaa ttc gca gac gag cag cct ttg aag ggc gcc cga att gct ggt tct    259
Glu Phe Ala Asp Glu Gln Pro Leu Lys Gly Ala Arg Ile Ala Gly Ser
     40                  45                  50 atc cac atg acg gtc cag acc gcc gtg ctt att gag acc ctc act gct    307
Ile His Met Thr Val Gln Thr Ala Val Leu Ile Glu Thr Leu Thr Ala
 55                  60                  65 ttg ggc gct gag gtt cgt tgg gct tcc tgc aac att ttc tcc acc cag    355
Leu Gly Ala Glu Val Arg Trp Ala Ser Cys Asn Ile Phe Ser Thr Gln
 70                  75                  80                  85 gat gag gct gca gcg gct atc gtt gtc ggc tcc ggc acc gtc gaa gag    403
Asp Glu Ala Ala Ala Ala Ile Val Val Gly Ser Gly Thr Val Glu Glu
                 90                  95                 100 cca gct ggt gtt cca gta ttc gcg tgg aag ggt gag tca ctg gag gag    451
Pro Ala Gly Val Pro Val Phe Ala Trp Lys Gly Glu Ser Leu Glu Glu
             105                 110                 115 tac tgg tgg tgc atc aac cag atc ttc agc tgg ggc gat gag ctg cca    499
Tyr Trp Trp Cys Ile Asn Gln Ile Phe Ser Trp Gly Asp Glu Leu Pro
         120                 125                 130 aac atg atc ctc gac gac ggc ggt gac gcc acc atg gct gtt att cgc    547
Asn Met Ile Leu Asp Asp Gly Gly Asp Ala Thr Met Ala Val Ile Arg
     135                 140                 145 ggt cgc gaa tac gag cag gct ggt ctg gtt cca cca gca gag gcc aac    595
Gly Arg Glu Tyr Glu Gln Ala Gly Leu Val Pro Pro Ala Glu Ala Asn
150                 155                 160                 165 gat tcc gat gag tac atc gca ttc ttg ggc atg ctg cgt gag gtt ctt    643
Asp Ser Asp Glu Tyr Ile Ala Phe Leu Gly Met Leu Arg Glu Val Leu
```

```
                                                  -continued

Asp Ser Asp Glu Tyr Ile Ala Phe Leu Gly Met Leu Arg Glu Val Leu
                170                 175                 180 gct gca gag cct ggc aag tgg ggc aag atc gct gag gcc gtt aag ggt       691
Ala Ala Glu Pro Gly Lys Trp Gly Lys Ile Ala Glu Ala Val Lys Gly
            185                 190                 195 gtc acc gag gaa acc acc acc ggt gtg cac cgc ctg tac cac ttc gct       739
Val Thr Glu Glu Thr Thr Thr Gly Val His Arg Leu Tyr His Phe Ala
        200                 205                 210 gaa gaa ggc gtg ctg cct ttc cca gcg atg aac gtc aac gac gct gtc       787
Glu Glu Gly Val Leu Pro Phe Pro Ala Met Asn Val Asn Asp Ala Val
    215                 220                 225 acc aag tcc aag ttt gat aac aag tac ggc acc cgc cac tcc ctg atc       835
Thr Lys Ser Lys Phe Asp Asn Lys Tyr Gly Thr Arg His Ser Leu Ile
230                 235                 240                 245 gac ggc atc aac cgc gcc act gac atg ctc atg ggc ggc aag aac gtg       883
Asp Gly Ile Asn Arg Ala Thr Asp Met Leu Met Gly Gly Lys Asn Val
                250                 255                 260 ctt gtc tgc ggt tac ggc gat gtc ggc aag ggc tgc gct gag gct ttc       931
Leu Val Cys Gly Tyr Gly Asp Val Gly Lys Gly Cys Ala Glu Ala Phe
            265                 270                 275 gac ggc cag ggc gct cgc gtc aag gtc acc gaa gct gac cca atc aac       979
Asp Gly Gln Gly Ala Arg Val Lys Val Thr Glu Ala Asp Pro Ile Asn
        280                 285                 290 gct ctt cag gct ctg atg gat ggc tac tct gtg gtc acc gtt gat gag      1027
Ala Leu Gln Ala Leu Met Asp Gly Tyr Ser Val Val Thr Val Asp Glu
    295                 300                 305 gcc atc gag gac gcc gac atc gtg atc acc gcg acc ggc aac aag gac      1075
Ala Ile Glu Asp Ala Asp Ile Val Ile Thr Ala Thr Gly Asn Lys Asp
310                 315                 320                 325 atc att tcc ttc gag cag atg ctc aag atg aag gat cac gct ctg ctg      1123
Ile Ile Ser Phe Glu Gln Met Leu Lys Met Lys Asp His Ala Leu Leu
                330                 335                 340 ggc aac atc ggt cac ttt gat aat gag atc gat atg cat tcc ctg ttg      1171
Gly Asn Ile Gly His Phe Asp Asn Glu Ile Asp Met His Ser Leu Leu
            345                 350                 355 cac cgc gac gac gtc acc cgc acc acg atc aag cca cag gtc gac gag      1219
His Arg Asp Asp Val Thr Arg Thr Thr Ile Lys Pro Gln Val Asp Glu
        360                 365                 370 ttc acc ttc tcc acc ggt cgc tcc atc atc gtc ctg tcc gaa ggt cgc      1267
Phe Thr Phe Ser Thr Gly Arg Ser Ile Ile Val Leu Ser Glu Gly Arg
    375                 380                 385 ctg ttg aac ctt ggc aac gcc acc gga cac cca tca ttt gtc atg tcc      1315
Leu Leu Asn Leu Gly Asn Ala Thr Gly His Pro Ser Phe Val Met Ser
390                 395                 400                 405 aac tct ttc gcc gat cag acc att gcg cag atc gaa ctg ttc caa aac      1363
Asn Ser Phe Ala Asp Gln Thr Ile Ala Gln Ile Glu Leu Phe Gln Asn
                410                 415                 420 gaa gga cag tac gag aac gag gtc tac cgt ctg                          1396
Glu Gly Gln Tyr Glu Asn Glu Val Tyr Arg Leu
            425                 430

<210> SEQ ID NO 102
<211> LENGTH: 432
<212> TYPE: PRT
<213> ORGANISM: Corynebacterium glutamicum

<400> SEQUENCE: 102

Met Ala Gln Val Met Asp Phe Lys Val Ala Asp Leu Ser Leu Ala Glu
 1               5                  10                  15

Ala Gly Arg His Gln Ile Arg Leu Ala Glu Tyr Glu Met Pro Gly Leu
```

-continued

```
                    20                  25                  30
Met Gln Leu Arg Lys Glu Phe Ala Asp Glu Gln Pro Leu Lys Gly Ala
            35                  40                  45
Arg Ile Ala Gly Ser Ile His Met Thr Val Gln Thr Ala Val Leu Ile
        50                  55                  60
Glu Thr Leu Thr Ala Leu Gly Ala Glu Val Arg Trp Ala Ser Cys Asn
 65                  70                  75                  80
Ile Phe Ser Thr Gln Asp Ala Ala Ala Ile Val Val Gly Ser
                85                  90                  95
Gly Thr Val Glu Glu Pro Ala Gly Val Pro Val Phe Ala Trp Lys Gly
                100                 105                 110
Glu Ser Leu Glu Glu Tyr Trp Trp Cys Ile Asn Gln Ile Phe Ser Trp
            115                 120                 125
Gly Asp Glu Leu Pro Asn Met Ile Leu Asp Asp Gly Asp Ala Thr
        130                 135                 140
Met Ala Val Ile Arg Gly Arg Glu Tyr Glu Gln Ala Gly Leu Val Pro
145                 150                 155                 160
Pro Ala Glu Ala Asn Asp Ser Asp Glu Tyr Ile Ala Phe Leu Gly Met
                165                 170                 175
Leu Arg Glu Val Leu Ala Ala Glu Pro Gly Lys Trp Gly Lys Ile Ala
            180                 185                 190
Glu Ala Val Lys Gly Val Thr Glu Glu Thr Thr Thr Gly Val His Arg
        195                 200                 205
Leu Tyr His Phe Ala Glu Glu Gly Val Leu Pro Phe Pro Ala Met Asn
    210                 215                 220
Val Asn Asp Ala Val Thr Lys Ser Lys Phe Asp Asn Lys Tyr Gly Thr
225                 230                 235                 240
Arg His Ser Leu Ile Asp Gly Ile Asn Arg Ala Thr Asp Met Leu Met
                245                 250                 255
Gly Gly Lys Asn Val Leu Val Cys Gly Tyr Gly Asp Val Gly Lys Gly
            260                 265                 270
Cys Ala Glu Ala Phe Asp Gly Gln Gly Ala Arg Val Lys Val Thr Glu
        275                 280                 285
Ala Asp Pro Ile Asn Ala Leu Gln Ala Leu Met Asp Gly Tyr Ser Val
    290                 295                 300
Val Thr Val Asp Glu Ala Ile Glu Asp Ala Asp Ile Val Ile Thr Ala
305                 310                 315                 320
Thr Gly Asn Lys Asp Ile Ile Ser Phe Glu Gln Met Leu Lys Met Lys
                325                 330                 335
Asp His Ala Leu Leu Gly Asn Ile Gly His Phe Asp Asn Glu Ile Asp
            340                 345                 350
Met His Ser Leu Leu His Arg Asp Asp Val Thr Arg Thr Thr Ile Lys
        355                 360                 365
Pro Gln Val Asp Glu Phe Thr Phe Ser Thr Gly Arg Ser Ile Ile Val
    370                 375                 380
Leu Ser Glu Gly Arg Leu Leu Asn Leu Gly Asn Ala Thr Gly His Pro
385                 390                 395                 400
Ser Phe Val Met Ser Asn Ser Phe Ala Asp Gln Thr Ile Ala Gln Ile
                405                 410                 415
Glu Leu Phe Gln Asn Glu Gly Gln Tyr Glu Asn Glu Val Tyr Arg Leu
            420                 425                 430
```

<210> SEQ ID NO 103

```
<211> LENGTH: 2358
<212> TYPE: DNA
<213> ORGANISM: Corynebacterium glutamicum
<220> FEATURE:
<221> NAME/KEY: CDS
<222> LOCATION: (101)..(2335)
<223> OTHER INFORMATION: RXN02085

<400> SEQUENCE: 103
cacccggtga tttcgcgaac cttgaaacat cgtcagaaga ttgccgtgcg tcctagccgg      60
gatccgcacg ttcggctcaa gcagaaagtc tttaactcac atg act tcc aac ttt     115
                                             Met Thr Ser Asn Phe
                                               1               5 tct tcc act gtc gct ggt ctt cct cgc atc gga gcg aag cgt gaa ctg     163
Ser Ser Thr Val Ala Gly Leu Pro Arg Ile Gly Ala Lys Arg Glu Leu
             10                  15                  20 aag ttc gcg ctc gaa ggc tac tgg aat gga tca att gaa ggt cgc gaa     211
Lys Phe Ala Leu Glu Gly Tyr Trp Asn Gly Ser Ile Glu Gly Arg Glu
         25                  30                  35 ctt gcg cag acc gcc cgc caa ttg gtc aac act gca tcg gat tct ttg     259
Leu Ala Gln Thr Ala Arg Gln Leu Val Asn Thr Ala Ser Asp Ser Leu
     40                  45                  50 tct gga ttg gat tcc gtt ccg ttt gca gga cgt tcc tac tac gac gca     307
Ser Gly Leu Asp Ser Val Pro Phe Ala Gly Arg Ser Tyr Tyr Asp Ala
 55                  60                  65 atg ctc gat acc gcc gct att ttg ggt gtg ctg ccg gag cgt ttt gat     355
Met Leu Asp Thr Ala Ala Ile Leu Gly Val Leu Pro Glu Arg Phe Asp
 70                  75                  80                  85 gac atc gct gat cat gaa aac gat ggt ctc cca ctg tgg att gac cgc     403
Asp Ile Ala Asp His Glu Asn Asp Gly Leu Pro Leu Trp Ile Asp Arg
                 90                  95                 100 tac ttt ggc gct gct cgc ggt act gag acc ctg cct gca cag gca atg     451
Tyr Phe Gly Ala Ala Arg Gly Thr Glu Thr Leu Pro Ala Gln Ala Met
            105                 110                 115 acc aag tgg ttt gat acc aac tac cac tac ctc gtg ccg gag ttg tct     499
Thr Lys Trp Phe Asp Thr Asn Tyr His Tyr Leu Val Pro Glu Leu Ser
        120                 125                 130 gcg gat aca cgt ttc gtt ttg gat gcg tcc gcg ctg att gag gat ctc     547
Ala Asp Thr Arg Phe Val Leu Asp Ala Ser Ala Leu Ile Glu Asp Leu
    135                 140                 145 cgt tgc cag cag gtt cgt ggc gtt aat gcc cgc cct gtt ctg gtt ggt     595
Arg Cys Gln Gln Val Arg Gly Val Asn Ala Arg Pro Val Leu Val Gly
150                 155                 160                 165 cca ctg act ttc ctt tcc ctt gct cgc acc act gat ggt tcc aat cct     643
Pro Leu Thr Phe Leu Ser Leu Ala Arg Thr Thr Asp Gly Ser Asn Pro
                170                 175                 180 ttg gat cac ctg cct gca ctg ttt gag gtc tac gag cgc ctc atc aag     691
Leu Asp His Leu Pro Ala Leu Phe Glu Val Tyr Glu Arg Leu Ile Lys
            185                 190                 195 tct ttc gat act gag tgg gtt cag atc gat gag cct gcg ttg gtc acc     739
Ser Phe Asp Thr Glu Trp Val Gln Ile Asp Glu Pro Ala Leu Val Thr
        200                 205                 210 gat gtt gct cct gag gtt ttg gag cag gtc cgc gct ggt tac acc act     787
Asp Val Ala Pro Glu Val Leu Glu Gln Val Arg Ala Gly Tyr Thr Thr
    215                 220                 225 ttg gct aag cgc gat ggc gtg ttt gtc aat act tac ttc ggc tct ggc     835
Leu Ala Lys Arg Asp Gly Val Phe Val Asn Thr Tyr Phe Gly Ser Gly
230                 235                 240                 245 gat cag gcg ctg aac act ctt gcg ggc atc ggc ctt ggc gcg att ggc     883
Asp Gln Ala Leu Asn Thr Leu Ala Gly Ile Gly Leu Gly Ala Ile Gly
                250                 255                 260
```

| | |
|---|---|
| gtt gac ttg gtc acc cat ggc gtc act gag ctt gct gcg tgg aag ggt<br>Val Asp Leu Val Thr His Gly Val Thr Glu Leu Ala Ala Trp Lys Gly<br>265                            270                       275 | 931 |
| gag gag ctg ctg gtt gcg ggc atc gtt gat ggt cgt aac att tgg cgc<br>Glu Glu Leu Leu Val Ala Gly Ile Val Asp Gly Arg Asn Ile Trp Arg<br>        280                       285                       290 | 979 |
| acc gac ctg tgt gct gct ctt gct tcc ctg aag cgc ctg gca gct cgc<br>Thr Asp Leu Cys Ala Ala Leu Ala Ser Leu Lys Arg Leu Ala Ala Arg<br>295                            300                       305 | 1027 |
| ggc cca atc gca gtg tct acc tct tgt tca ctg ctg cac gtt cct tac<br>Gly Pro Ile Ala Val Ser Thr Ser Cys Ser Leu Leu His Val Pro Tyr<br>310                            315                       320                       325 | 1075 |
| acc ctc gag gct gag aac att gag cct gag gtc cgc gac tgg ctt gcc<br>Thr Leu Glu Ala Glu Asn Ile Glu Pro Glu Val Arg Asp Trp Leu Ala<br>                   330                       335                       340 | 1123 |
| ttc ggc tcg gag aag atc acc gag gtc aag ctg ctt gcc gac gcc cta<br>Phe Gly Ser Glu Lys Ile Thr Glu Val Lys Leu Leu Ala Asp Ala Leu<br>                   345                       350                       355 | 1171 |
| gcc ggc aac atc gac gcg gct gcg ttc gat gcg gcg tcc gca gca att<br>Ala Gly Asn Ile Asp Ala Ala Ala Phe Asp Ala Ala Ser Ala Ala Ile<br>                   360                       365                       370 | 1219 |
| gct tct cga cgc acc tcc cca cgc acc gca cca atc acg cag gaa ctc<br>Ala Ser Arg Arg Thr Ser Pro Arg Thr Ala Pro Ile Thr Gln Glu Leu<br>375                            380                       385 | 1267 |
| cct ggc cgt agc cgt gga tcc ttc gac act cgt gtt acg ctg cag gag<br>Pro Gly Arg Ser Arg Gly Ser Phe Asp Thr Arg Val Thr Leu Gln Glu<br>390                            395                       400                       405 | 1315 |
| aag tca ctg gag ctt cca gct ctg cca acc acc acc att ggt tct ttc<br>Lys Ser Leu Glu Leu Pro Ala Leu Pro Thr Thr Thr Ile Gly Ser Phe<br>                   410                       415                       420 | 1363 |
| cca cag acc cca tcc att cgt tct gct cgc gct cgt ctg cgc aag gaa<br>Pro Gln Thr Pro Ser Ile Arg Ser Ala Arg Ala Arg Leu Arg Lys Glu<br>                   425                       430                       435 | 1411 |
| tcc atc act ttg gag cag tac gaa gag gca atg cgc gaa gaa atc gat<br>Ser Ile Thr Leu Glu Gln Tyr Glu Glu Ala Met Arg Glu Glu Ile Asp<br>440                            445                       450 | 1459 |
| ctg gtc atc gcc aag cag gaa gaa ctt ggt ctt gat gtg ttg gtt cac<br>Leu Val Ile Ala Lys Gln Glu Glu Leu Gly Leu Asp Val Leu Val His<br>                   455                       460                       465 | 1507 |
| ggt gag cca gag cgc aac gac atg gtt cag tac ttc tct gaa ctt ctc<br>Gly Glu Pro Glu Arg Asn Asp Met Val Gln Tyr Phe Ser Glu Leu Leu<br>470                            475                       480                       485 | 1555 |
| gac ggt ttc ctc tca acc gcc aac ggc tgg gtc caa agc tac ggc tcc<br>Asp Gly Phe Leu Ser Thr Ala Asn Gly Trp Val Gln Ser Tyr Gly Ser<br>                   490                       495                       500 | 1603 |
| cgc tgt gtt cgt cct cca gtg ttg ttc gga aac gtt tcc cgc cca gcg<br>Arg Cys Val Arg Pro Pro Val Leu Phe Gly Asn Val Ser Arg Pro Ala<br>                   505                       510                       515 | 1651 |
| cca atg act gtc aag tgg ttc cag tac gca cag agc ctg acc cag aag<br>Pro Met Thr Val Lys Trp Phe Gln Tyr Ala Gln Ser Leu Thr Gln Lys<br>520                            525                       530 | 1699 |
| cat gtc aag gga atg ctc acc ggt cca gtc acc atc ctt gca tgg tcc<br>His Val Lys Gly Met Leu Thr Gly Pro Val Thr Ile Leu Ala Trp Ser<br>535                            540                       545 | 1747 |
| ttc gtt cgc gat gat cag ccg ctg gct acc act gct gac cag gtt gca<br>Phe Val Arg Asp Asp Gln Pro Leu Ala Thr Thr Ala Asp Gln Val Ala<br>550                            555                       560                       565 | 1795 |
| ctg gca ctg cgc gat gaa att aac gat ctc atc gag gct ggc gcg aag<br>Leu Ala Leu Arg Asp Glu Ile Asn Asp Leu Ile Glu Ala Gly Ala Lys | 1843 |

```
                      570                 575                 580
atc atc cag gtg gat gag cct gcg att cgt gaa ctg ttg ccg cta cga     1891
Ile Ile Gln Val Asp Glu Pro Ala Ile Arg Glu Leu Leu Pro Leu Arg
            585                 590                 595 gac gtc gat aag cct gcc tac ctg cag tgg tcc gtg gac tcc ttc cgc     1939
Asp Val Asp Lys Pro Ala Tyr Leu Gln Trp Ser Val Asp Ser Phe Arg
        600                 605                 610 ctg gcg act gcc ggc gca ccc gac gac gtc caa atc cac acc cac atg     1987
Leu Ala Thr Ala Gly Ala Pro Asp Asp Val Gln Ile His Thr His Met
    615                 620                 625 tgc tac tcc gag ttc aac gaa gtg atc tcc tcg gtc atc gcg ttg gat     2035
Cys Tyr Ser Glu Phe Asn Glu Val Ile Ser Ser Val Ile Ala Leu Asp
630                 635                 640                 645 gcc gat gtc acc acc atc gaa gca gca cgt tcc gac atg cag gtc ctc     2083
Ala Asp Val Thr Thr Ile Glu Ala Ala Arg Ser Asp Met Gln Val Leu
                650                 655                 660 gct gct ctg aaa tct tcc ggc ttc gag ctc ggc gtc gga cct ggt gtg     2131
Ala Ala Leu Lys Ser Ser Gly Phe Glu Leu Gly Val Gly Pro Gly Val
            665                 670                 675 tgg gat atc cac tcc ccg cgc gtt cct tcc gcg cag aaa gtg gac ggt     2179
Trp Asp Ile His Ser Pro Arg Val Pro Ser Ala Gln Lys Val Asp Gly
        680                 685                 690 ctc ctc gag gct gca ctg cag tcc gtg gat cct cgc cag ctg tgg gtc     2227
Leu Leu Glu Ala Ala Leu Gln Ser Val Asp Pro Arg Gln Leu Trp Val
    695                 700                 705 aac cca gac tgt ggt ctg aag acc cgt gga tgg cca gaa gtg gaa gct     2275
Asn Pro Asp Cys Gly Leu Lys Thr Arg Gly Trp Pro Glu Val Glu Ala
710                 715                 720                 725 tcc cta aag gtt ctc gtt gag tcc gct aag cag gct cgt gag aaa atc     2323
Ser Leu Lys Val Leu Val Glu Ser Ala Lys Gln Ala Arg Glu Lys Ile
                730                 735                 740 gga gca act atc taaattgggt taccgctagg aac                           2358
Gly Ala Thr Ile
            745

<210> SEQ ID NO 104
<211> LENGTH: 745
<212> TYPE: PRT
<213> ORGANISM: Corynebacterium glutamicum

<400> SEQUENCE: 104

Met Thr Ser Asn Phe Ser Ser Thr Val Ala Gly Leu Pro Arg Ile Gly
 1               5                  10                  15

Ala Lys Arg Glu Leu Lys Phe Ala Leu Glu Gly Tyr Trp Asn Gly Ser
            20                  25                  30

Ile Glu Gly Arg Glu Leu Ala Gln Thr Ala Arg Gln Leu Val Asn Thr
        35                  40                  45

Ala Ser Asp Ser Leu Ser Gly Leu Asp Ser Val Pro Phe Ala Gly Arg
    50                  55                  60

Ser Tyr Tyr Asp Ala Met Leu Asp Thr Ala Ala Ile Leu Gly Val Leu
65                  70                  75                  80

Pro Glu Arg Phe Asp Asp Ile Ala Asp His Glu Asn Asp Gly Leu Pro
                85                  90                  95

Leu Trp Ile Asp Arg Tyr Phe Gly Ala Ala Arg Gly Thr Glu Thr Leu
            100                 105                 110

Pro Ala Gln Ala Met Thr Lys Trp Phe Asp Thr Asn Tyr His Tyr Leu
        115                 120                 125

Val Pro Glu Leu Ser Ala Asp Thr Arg Phe Val Leu Asp Ala Ser Ala
```

-continued

```
        130                 135                 140
Leu Ile Glu Asp Leu Arg Cys Gln Gln Val Arg Gly Val Asn Ala Arg
145                 150                 155                 160
Pro Val Leu Val Gly Pro Leu Thr Phe Leu Ser Leu Ala Arg Thr Thr
                165                 170                 175
Asp Gly Ser Asn Pro Leu Asp His Leu Pro Ala Leu Phe Glu Val Tyr
            180                 185                 190
Glu Arg Leu Ile Lys Ser Phe Asp Thr Glu Trp Val Gln Ile Asp Glu
        195                 200                 205
Pro Ala Leu Val Thr Asp Val Ala Pro Glu Val Leu Glu Gln Val Arg
210                 215                 220
Ala Gly Tyr Thr Thr Leu Ala Lys Arg Asp Gly Val Phe Val Asn Thr
225                 230                 235                 240
Tyr Phe Gly Ser Gly Asp Gln Ala Leu Asn Thr Leu Ala Gly Ile Gly
                245                 250                 255
Leu Gly Ala Ile Gly Val Asp Leu Val Thr His Gly Val Thr Glu Leu
            260                 265                 270
Ala Ala Trp Lys Gly Glu Glu Leu Leu Val Ala Gly Ile Val Asp Gly
        275                 280                 285
Arg Asn Ile Trp Arg Thr Asp Leu Cys Ala Ala Leu Ala Ser Leu Lys
290                 295                 300
Arg Leu Ala Ala Arg Gly Pro Ile Ala Val Ser Thr Ser Cys Ser Leu
305                 310                 315                 320
Leu His Val Pro Tyr Thr Leu Glu Ala Glu Asn Ile Glu Pro Glu Val
                325                 330                 335
Arg Asp Trp Leu Ala Phe Gly Ser Glu Lys Ile Thr Glu Val Lys Leu
            340                 345                 350
Leu Ala Asp Ala Leu Ala Gly Asn Ile Asp Ala Ala Ala Phe Asp Ala
        355                 360                 365
Ala Ser Ala Ala Ile Ala Ser Arg Arg Thr Ser Pro Arg Thr Ala Pro
370                 375                 380
Ile Thr Gln Glu Leu Pro Gly Arg Ser Arg Gly Ser Phe Asp Thr Arg
385                 390                 395                 400
Val Thr Leu Gln Glu Lys Ser Leu Glu Leu Pro Ala Leu Pro Thr Thr
                405                 410                 415
Thr Ile Gly Ser Phe Pro Gln Thr Pro Ser Ile Arg Ser Ala Arg Ala
            420                 425                 430
Arg Leu Arg Lys Glu Ser Ile Thr Leu Glu Gln Tyr Glu Glu Ala Met
        435                 440                 445
Arg Glu Glu Ile Asp Leu Val Ile Ala Lys Gln Glu Glu Leu Gly Leu
450                 455                 460
Asp Val Leu Val His Gly Glu Pro Glu Arg Asn Asp Met Val Gln Tyr
465                 470                 475                 480
Phe Ser Glu Leu Leu Asp Gly Phe Leu Ser Thr Ala Asn Gly Trp Val
                485                 490                 495
Gln Ser Tyr Gly Ser Arg Cys Val Arg Pro Val Leu Phe Gly Asn
            500                 505                 510
Val Ser Arg Pro Ala Pro Met Thr Val Lys Trp Phe Gln Tyr Ala Gln
        515                 520                 525
Ser Leu Thr Gln Lys His Val Lys Gly Met Leu Thr Gly Pro Val Thr
530                 535                 540
Ile Leu Ala Trp Ser Phe Val Arg Asp Asp Gln Pro Leu Ala Thr Thr
545                 550                 555                 560
```

```
Ala Asp Gln Val Ala Leu Ala Leu Arg Asp Glu Ile Asn Asp Leu Ile
                565                 570                 575

Glu Ala Gly Ala Lys Ile Ile Gln Val Asp Glu Pro Ala Ile Arg Glu
            580                 585                 590

Leu Leu Pro Leu Arg Asp Val Asp Lys Pro Ala Tyr Leu Gln Trp Ser
        595                 600                 605

Val Asp Ser Phe Arg Leu Ala Thr Ala Gly Ala Pro Asp Asp Val Gln
    610                 615                 620

Ile His Thr His Met Cys Tyr Ser Glu Phe Asn Glu Val Ile Ser Ser
625                 630                 635                 640

Val Ile Ala Leu Asp Ala Asp Val Thr Thr Ile Glu Ala Ala Arg Ser
                645                 650                 655

Asp Met Gln Val Leu Ala Ala Leu Lys Ser Ser Gly Phe Glu Leu Gly
            660                 665                 670

Val Gly Pro Gly Val Trp Asp Ile His Ser Pro Arg Val Pro Ser Ala
        675                 680                 685

Gln Lys Val Asp Gly Leu Leu Glu Ala Ala Leu Gln Ser Val Asp Pro
    690                 695                 700

Arg Gln Leu Trp Val Asn Pro Asp Cys Gly Leu Lys Thr Arg Gly Trp
705                 710                 715                 720

Pro Glu Val Glu Ala Ser Leu Lys Val Leu Val Glu Ser Ala Lys Gln
                725                 730                 735

Ala Arg Glu Lys Ile Gly Ala Thr Ile
            740                 745
```

<210> SEQ ID NO 105
<211> LENGTH: 1923
<212> TYPE: DNA
<213> ORGANISM: Corynebacterium glutamicum
<220> FEATURE:
<221> NAME/KEY: CDS
<222> LOCATION: (101)..(1900)
<223> OTHER INFORMATION: FRXA02085

<400> SEQUENCE: 105

```
cacccggtga tttcgcgaac cttgaaacat cgtcagaaga ttgccgtgcg tcctagccgg      60
gatccgcacg ttcggctcaa gcagaaagtc tttaactcac atg act tcc aac ttt      115
                                              Met Thr Ser Asn Phe
                                                1               5 tct tcc act gtc gct ggt ctt cct cgc atc gga gcg aag cgt gaa ctg      163
Ser Ser Thr Val Ala Gly Leu Pro Arg Ile Gly Ala Lys Arg Glu Leu
             10                  15                  20 aag ttc gcg ctc gaa ggc tac tgg aat gga tca att gaa ggt cgc gaa      211
Lys Phe Ala Leu Glu Gly Tyr Trp Asn Gly Ser Ile Glu Gly Arg Glu
         25                  30                  35 ctt gcg cag acc gcc cgc caa ttg gtc aac act gca tcg gat tct ttg      259
Leu Ala Gln Thr Ala Arg Gln Leu Val Asn Thr Ala Ser Asp Ser Leu
     40                  45                  50 tct gga ttg gat tcc gtt ccg ttt gca gga cgt tcc tac tac gac gca      307
Ser Gly Leu Asp Ser Val Pro Phe Ala Gly Arg Ser Tyr Tyr Asp Ala
 55                  60                  65 atg ctc gat acc gcc gct att ttg ggt gtg ctg ccg gag cgt ttt gat      355
Met Leu Asp Thr Ala Ala Ile Leu Gly Val Leu Pro Glu Arg Phe Asp
 70                  75                  80                  85 gac atc gct gat cat gaa aac gat ggt ctc cca ctg tgg att gac cgc      403
Asp Ile Ala Asp His Glu Asn Asp Gly Leu Pro Leu Trp Ile Asp Arg
             90                  95                 100
```

-continued

| | |
|---|---|
| tac ttt ggc gct gct cgc ggt act gag acc ctg cct gca cag gca atg<br>Tyr Phe Gly Ala Ala Arg Gly Thr Glu Thr Leu Pro Ala Gln Ala Met<br>105                110                115 | 451 |
| acc aag tgg ttt gat acc aac tac cac tac ctc gtg ccg gag ttg tct<br>Thr Lys Trp Phe Asp Thr Asn Tyr His Tyr Leu Val Pro Glu Leu Ser<br>       120                125                130 | 499 |
| gcg gat aca cgt ttc gtt ttg gat gcg tcc gcg ctg att gag gat ctc<br>Ala Asp Thr Arg Phe Val Leu Asp Ala Ser Ala Leu Ile Glu Asp Leu<br>135                140                145 | 547 |
| cgt tgc cag cag gtt cgt ggc gtt aat gcc cgc cct gtt ctg gtt ggt<br>Arg Cys Gln Gln Val Arg Gly Val Asn Ala Arg Pro Val Leu Val Gly<br>150                155                160                165 | 595 |
| cca ctg act ttc ctt tcc ctt gct cgc acc act gat ggt tcc aat cct<br>Pro Leu Thr Phe Leu Ser Leu Ala Arg Thr Thr Asp Gly Ser Asn Pro<br>       170                175                180 | 643 |
| ttg gat cac ctg cct gca ctg ttt gag gtc tac gag cgc ctc atc aag<br>Leu Asp His Leu Pro Ala Leu Phe Glu Val Tyr Glu Arg Leu Ile Lys<br>185                190                195 | 691 |
| tct ttc gat act gag tgg gtt cag atc gat gag cct gcg ttg gtc acc<br>Ser Phe Asp Thr Glu Trp Val Gln Ile Asp Glu Pro Ala Leu Val Thr<br>       200                205                210 | 739 |
| gat gtt gct cct gag gtt ttg gag cag gtc cgc gct ggt tac acc act<br>Asp Val Ala Pro Glu Val Leu Glu Gln Val Arg Ala Gly Tyr Thr Thr<br>215                220                225 | 787 |
| ttg gct aag cgc gat ggc gtg ttt gtc aat act tac ttc ggc tct ggc<br>Leu Ala Lys Arg Asp Gly Val Phe Val Asn Thr Tyr Phe Gly Ser Gly<br>230                235                240                245 | 835 |
| gat cag gcg ctg aac act ctt gcg ggc atc ggc ctt ggc gcg att ggc<br>Asp Gln Ala Leu Asn Thr Leu Ala Gly Ile Gly Leu Gly Ala Ile Gly<br>       250                255                260 | 883 |
| gtt gac ttg gtc acc cat ggc gtc act gag ctt gct gcg tgg aag ggt<br>Val Asp Leu Val Thr His Gly Val Thr Glu Leu Ala Ala Trp Lys Gly<br>265                270                275 | 931 |
| gag gag ctg ctg gtt gcg ggc atc gtt gat ggt cgt aac att tgg cgc<br>Glu Glu Leu Leu Val Ala Gly Ile Val Asp Gly Arg Asn Ile Trp Arg<br>       280                285                290 | 979 |
| acc gac ctg tgt gct gct ctt gct tcc ctg aag cgc ctg gca gct cgc<br>Thr Asp Leu Cys Ala Ala Leu Ala Ser Leu Lys Arg Leu Ala Ala Arg<br>295                300                305 | 1027 |
| ggc cca atc gca gtg tct acc tct tgt tca ctg ctg cac gtt cct tac<br>Gly Pro Ile Ala Val Ser Thr Ser Cys Ser Leu Leu His Val Pro Tyr<br>310                315                320                325 | 1075 |
| acc ctc gag gct gag aac att gag cct gag gtc cgc gac tgg ctt gcc<br>Thr Leu Glu Ala Glu Asn Ile Glu Pro Glu Val Arg Asp Trp Leu Ala<br>       330                335                340 | 1123 |
| ttc ggc tcg gag aag atc acc gag gtc aag ctg ctt gcc gac gcc cta<br>Phe Gly Ser Glu Lys Ile Thr Glu Val Lys Leu Leu Ala Asp Ala Leu<br>       345                350                355 | 1171 |
| gcc ggc aac atc gac gcg gct gcg ttc gat gcg gcg tcc gca gca att<br>Ala Gly Asn Ile Asp Ala Ala Ala Phe Asp Ala Ala Ser Ala Ala Ile<br>       360                365                370 | 1219 |
| gct tct cga cgc acc tcc cca cgc acc gca cca atc acg cag gaa ctc<br>Ala Ser Arg Arg Thr Ser Pro Arg Thr Ala Pro Ile Thr Gln Glu Leu<br>375                380                385 | 1267 |
| cct ggc cgt agc cgt gga tcc ttc gac act cgt gtt acg ctg cag gag<br>Pro Gly Arg Ser Arg Gly Ser Phe Asp Thr Arg Val Thr Leu Gln Glu<br>390                395                400                405 | 1315 |
| aag tca ctg gag ctt cca gct ctg cca acc acc acc att ggt tct ttc<br>Lys Ser Leu Glu Leu Pro Ala Leu Pro Thr Thr Thr Ile Gly Ser Phe<br>       410                415                420 | 1363 |

```
cca cag acc cca tcc att cgt tct gct cgc gct cgt ctg cgc aag gaa    1411
Pro Gln Thr Pro Ser Ile Arg Ser Ala Arg Ala Arg Leu Arg Lys Glu
            425                 430                 435 tcc atc act ttg gag cag tac gaa gag gca atg cgc gaa gaa atc gat    1459
Ser Ile Thr Leu Glu Gln Tyr Glu Glu Ala Met Arg Glu Glu Ile Asp
    440                 445                 450 ctg gtc atc gcc aag cag gaa gaa ctt ggt ctt gat gtg ttg gtt cac    1507
Leu Val Ile Ala Lys Gln Glu Glu Leu Gly Leu Asp Val Leu Val His
455                 460                 465 ggt gag cca gag cgc aac gac atg gtt cag tac ttc tct gaa ctt ctc    1555
Gly Glu Pro Glu Arg Asn Asp Met Val Gln Tyr Phe Ser Glu Leu Leu
470                 475                 480                 485 gac ggt ttc ctc tca acc gcc aac ggc tgg gtc caa agc tac ggc tcc    1603
Asp Gly Phe Leu Ser Thr Ala Asn Gly Trp Val Gln Ser Tyr Gly Ser
                490                 495                 500 cgc tgt gtt cgt cct cca gtg ttg ttc gga aac gtt tcc cgc cca gcg    1651
Arg Cys Val Arg Pro Pro Val Leu Phe Gly Asn Val Ser Arg Pro Ala
            505                 510                 515 cca atg act gtc aag tgg ttc cag tac gca cag agc ctg acc cag aag    1699
Pro Met Thr Val Lys Trp Phe Gln Tyr Ala Gln Ser Leu Thr Gln Lys
        520                 525                 530 cat gtc aag gga atg ctc acc ggt cca gtc acc atc ctt gca tgg tcc    1747
His Val Lys Gly Met Leu Thr Gly Pro Val Thr Ile Leu Ala Trp Ser
535                 540                 545 ttc gtt cgc gat gat cag ccg ctg gct acc act gct gac cag gtt gca    1795
Phe Val Arg Asp Asp Gln Pro Leu Ala Thr Thr Ala Asp Gln Val Ala
550                 555                 560                 565 ctg gca ctg cgc gat gaa att aac gat ctc atc gag gct ggc gcg aag    1843
Leu Ala Leu Arg Asp Glu Ile Asn Asp Leu Ile Glu Ala Gly Ala Lys
                570                 575                 580 atc atc cag gtg gat gag cct gcg att cgt gaa ctg ttg ccc gct acg    1891
Ile Ile Gln Val Asp Glu Pro Ala Ile Arg Glu Leu Leu Pro Ala Thr
            585                 590                 595 aga cgt cga taagcctgcc tacctgcagt ggt                              1923
Arg Arg Arg
        600

<210> SEQ ID NO 106
<211> LENGTH: 600
<212> TYPE: PRT
<213> ORGANISM: Corynebacterium glutamicum

<400> SEQUENCE: 106

Met Thr Ser Asn Phe Ser Ser Thr Val Ala Gly Leu Pro Arg Ile Gly
  1               5                  10                  15

Ala Lys Arg Glu Leu Lys Phe Ala Leu Glu Gly Tyr Trp Asn Gly Ser
                 20                  25                  30

Ile Glu Gly Arg Glu Leu Ala Gln Thr Ala Arg Gln Leu Val Asn Thr
             35                  40                  45

Ala Ser Asp Ser Leu Ser Gly Leu Asp Ser Val Pro Phe Ala Gly Arg
         50                  55                  60

Ser Tyr Tyr Asp Ala Met Leu Asp Thr Ala Ala Ile Leu Gly Val Leu
 65                  70                  75                  80

Pro Glu Arg Phe Asp Asp Ile Ala Asp His Glu Asn Asp Gly Leu Pro
                 85                  90                  95

Leu Trp Ile Asp Arg Tyr Phe Gly Ala Ala Arg Gly Thr Glu Thr Leu
            100                 105                 110

Pro Ala Gln Ala Met Thr Lys Trp Phe Asp Thr Asn Tyr His Tyr Leu
```

-continued

```
            115                 120                 125
Val Pro Glu Leu Ser Ala Asp Thr Arg Phe Val Leu Asp Ala Ser Ala
130                 135                 140

Leu Ile Glu Asp Leu Arg Cys Gln Gln Val Arg Gly Val Asn Ala Arg
145                 150                 155                 160

Pro Val Leu Val Gly Pro Leu Thr Phe Leu Ser Leu Ala Arg Thr Thr
                165                 170                 175

Asp Gly Ser Asn Pro Leu Asp His Leu Pro Ala Leu Phe Glu Val Tyr
                180                 185                 190

Glu Arg Leu Ile Lys Ser Phe Asp Thr Glu Trp Val Gln Ile Asp Glu
                195                 200                 205

Pro Ala Leu Val Thr Asp Val Ala Pro Glu Val Leu Glu Gln Val Arg
210                 215                 220

Ala Gly Tyr Thr Thr Leu Ala Lys Arg Asp Gly Val Phe Val Asn Thr
225                 230                 235                 240

Tyr Phe Gly Ser Gly Asp Gln Ala Leu Asn Thr Leu Ala Gly Ile Gly
                245                 250                 255

Leu Gly Ala Ile Gly Val Asp Leu Val Thr His Gly Val Thr Glu Leu
                260                 265                 270

Ala Ala Trp Lys Gly Glu Glu Leu Leu Val Ala Gly Ile Val Asp Gly
                275                 280                 285

Arg Asn Ile Trp Arg Thr Asp Leu Cys Ala Ala Leu Ala Ser Leu Lys
                290                 295                 300

Arg Leu Ala Ala Arg Gly Pro Ile Ala Val Ser Thr Ser Cys Ser Leu
305                 310                 315                 320

Leu His Val Pro Tyr Thr Leu Glu Ala Glu Asn Ile Glu Pro Glu Val
                325                 330                 335

Arg Asp Trp Leu Ala Phe Gly Ser Glu Lys Ile Thr Glu Val Lys Leu
                340                 345                 350

Leu Ala Asp Ala Leu Ala Gly Asn Ile Asp Ala Ala Ala Phe Asp Ala
                355                 360                 365

Ala Ser Ala Ala Ile Ala Ser Arg Arg Thr Ser Pro Arg Thr Ala Pro
370                 375                 380

Ile Thr Gln Glu Leu Pro Gly Arg Ser Arg Gly Ser Phe Asp Thr Arg
385                 390                 395                 400

Val Thr Leu Gln Glu Lys Ser Leu Glu Leu Pro Ala Leu Pro Thr Thr
                405                 410                 415

Thr Ile Gly Ser Phe Pro Gln Thr Pro Ser Ile Arg Ser Ala Arg Ala
                420                 425                 430

Arg Leu Arg Lys Glu Ser Ile Thr Leu Glu Gln Tyr Glu Glu Ala Met
                435                 440                 445

Arg Glu Glu Ile Asp Leu Val Ile Ala Lys Gln Glu Glu Leu Gly Leu
                450                 455                 460

Asp Val Leu Val His Gly Glu Pro Glu Arg Asn Asp Met Val Gln Tyr
465                 470                 475                 480

Phe Ser Glu Leu Leu Asp Gly Phe Leu Ser Thr Ala Asn Gly Trp Val
                485                 490                 495

Gln Ser Tyr Gly Ser Arg Cys Val Arg Pro Val Leu Phe Gly Asn
                500                 505                 510

Val Ser Arg Pro Ala Pro Met Thr Val Lys Trp Phe Gln Tyr Ala Gln
                515                 520                 525

Ser Leu Thr Gln Lys His Val Lys Gly Met Leu Thr Gly Pro Val Thr
                530                 535                 540
```

| | | | | | | | | | | | |
|---|---|---|---|---|---|---|---|---|---|---|---|
| Ile | Leu | Ala | Trp | Ser | Phe | Val | Arg | Asp | Asp | Gln | Pro | Leu | Ala | Thr | Thr |
| 545 | | | | | 550 | | | | | 555 | | | | | 560 |

| | | | | | | | | | | | |
|---|---|---|---|---|---|---|---|---|---|---|---|
| Ala | Asp | Gln | Val | Ala | Leu | Ala | Leu | Arg | Asp | Glu | Ile | Asn | Asp | Leu | Ile |
| | | | | 565 | | | | | 570 | | | | | 575 | |

| | | | | | | | | | | | |
|---|---|---|---|---|---|---|---|---|---|---|---|
| Glu | Ala | Gly | Ala | Lys | Ile | Ile | Gln | Val | Asp | Glu | Pro | Ala | Ile | Arg | Glu |
| | | | | 580 | | | | | 585 | | | | | 590 | |

| | | | |
|---|---|---|---|
| Leu | Leu | Pro | Ala | Thr | Arg | Arg | Arg |
| | | | 595 | | | | 600 |

```
<210> SEQ ID NO 107
<211> LENGTH: 603
<212> TYPE: DNA
<213> ORGANISM: Corynebacterium glutamicum
<220> FEATURE:
<221> NAME/KEY: CDS
<222> LOCATION: (101)..(580)
<223> OTHER INFORMATION: FRXA02086

<400> SEQUENCE: 107
```

| | |
|---|---|
| gatgatcagc cgctggctac cactgctgac caggttgcac tggcactgcg cgatgaaatt | 60 |
| aacgatctca tcgaggctgg cgcgaagatc atccaggtgg atg agc ctg cga ttc<br>                                                    Met Ser Leu Arg Phe<br>                                                    1                5 | 115 |
| gtg aac tgt tgc ccg cta cga gac gtc gat aag cct gcc tac ctg cag<br>Val Asn Cys Cys Pro Leu Arg Asp Val Asp Lys Pro Ala Tyr Leu Gln<br>            10                    15                    20 | 163 |
| tgg tcc gtg gac tcc ttc cgc ctg gcg act gcc ggc gca ccc gac gac<br>Trp Ser Val Asp Ser Phe Arg Leu Ala Thr Ala Gly Ala Pro Asp Asp<br>         25                    30                    35 | 211 |
| gtc caa atc cac acc cac atg tgc tac tcc gag ttc aac gaa gtg atc<br>Val Gln Ile His Thr His Met Cys Tyr Ser Glu Phe Asn Glu Val Ile<br>  40                    45                    50 | 259 |
| tcc tcg gtc atc gcg ttg gat gcc gat gtc acc acc atc gaa gca gca<br>Ser Ser Val Ile Ala Leu Asp Ala Asp Val Thr Thr Ile Glu Ala Ala<br>55                    60                    65 | 307 |
| cgt tcc gac atg cag gtc ctc gct gct ctg aaa tct tcc ggc ttc gag<br>Arg Ser Asp Met Gln Val Leu Ala Ala Leu Lys Ser Ser Gly Phe Glu<br>70                  75                  80                  85 | 355 |
| ctc ggc gtc gga cct ggt gtg tgg gat atc cac tcc ccg cgc gtt cct<br>Leu Gly Val Gly Pro Gly Val Trp Asp Ile His Ser Pro Arg Val Pro<br>            90                    95                   100 | 403 |
| tcc gcg cag aaa gtg gac ggt ctc ctc gag gct gca ctg cag tcc gtg<br>Ser Ala Gln Lys Val Asp Gly Leu Leu Glu Ala Ala Leu Gln Ser Val<br>         105                   110                 115 | 451 |
| gat cct cgc cag ctg tgg gtc aac cca gac tgt ggt ctg aag acc cgt<br>Asp Pro Arg Gln Leu Trp Val Asn Pro Asp Cys Gly Leu Lys Thr Arg<br>120                  125                  130 | 499 |
| gga tgg cca gaa gtg gaa gct tcc cta aag gtt ctc gtt gag tcc gct<br>Gly Trp Pro Glu Val Glu Ala Ser Leu Lys Val Leu Val Glu Ser Ala<br>135                  140                  145 | 547 |
| aag cag gct cgt gag aaa atc gga gca act atc taaattgggt taccgctagg<br>Lys Gln Ala Arg Glu Lys Ile Gly Ala Thr Ile<br>150                  155                  160 | 600 |
| aac | 603 |

```
<210> SEQ ID NO 108
<211> LENGTH: 160
<212> TYPE: PRT
<213> ORGANISM: Corynebacterium glutamicum
```

```
<400> SEQUENCE: 108

Met Ser Leu Arg Phe Val Asn Cys Cys Pro Leu Arg Asp Val Asp Lys
  1               5                  10                  15

Pro Ala Tyr Leu Gln Trp Ser Val Asp Ser Phe Arg Leu Ala Thr Ala
             20                  25                  30

Gly Ala Pro Asp Val Gln Ile His Thr His Met Cys Tyr Ser Glu
         35                  40                  45

Phe Asn Glu Val Ile Ser Ser Val Ile Ala Leu Asp Ala Asp Val Thr
     50                  55                  60

Thr Ile Glu Ala Ala Arg Ser Asp Met Gln Val Leu Ala Ala Leu Lys
 65                  70                  75                  80

Ser Ser Gly Phe Glu Leu Gly Val Gly Pro Gly Val Trp Asp Ile His
                 85                  90                  95

Ser Pro Arg Val Pro Ser Ala Gln Lys Val Asp Gly Leu Leu Glu Ala
             100                 105                 110

Ala Leu Gln Ser Val Asp Pro Arg Gln Leu Trp Val Asn Pro Asp Cys
         115                 120                 125

Gly Leu Lys Thr Arg Gly Trp Pro Glu Val Glu Ala Ser Leu Lys Val
     130                 135                 140

Leu Val Glu Ser Ala Lys Gln Ala Arg Glu Lys Ile Gly Ala Thr Ile
145                 150                 155                 160

<210> SEQ ID NO 109
<211> LENGTH: 1326
<212> TYPE: DNA
<213> ORGANISM: Corynebacterium glutamicum
<220> FEATURE:
<221> NAME/KEY: CDS
<222> LOCATION: (101)..(1303)
<223> OTHER INFORMATION: RXN02648

<400> SEQUENCE: 109
atgaataaaa ttccgggtgc agtgaccgta ggtgaggtaa acgcggttag agtcgaatga      60
gagtttgata ctttctttcg acttttagat tggattttca atg agc cag aac cgc     115
                                              Met Ser Gln Asn Arg
                                                1               5 atc agg acc act cac gtt ggt tcc ttg ccc cgt acc cca gag cta ctt     163
Ile Arg Thr Thr His Val Gly Ser Leu Pro Arg Thr Pro Glu Leu Leu
             10                  15                  20 gat gca aac atc aag cgt tct aac ggt gag att ggg gag gag gaa ttc     211
Asp Ala Asn Ile Lys Arg Ser Asn Gly Glu Ile Gly Glu Glu Glu Phe
         25                  30                  35 ttc cag att ctg cag tct tct gta gat gac gtg atc aag cgc cag gtt     259
Phe Gln Ile Leu Gln Ser Ser Val Asp Asp Val Ile Lys Arg Gln Val
     40                  45                  50 gac ctg ggt atc gac atc ctt aac gag ggc gaa tac ggc cac gtc acc     307
Asp Leu Gly Ile Asp Ile Leu Asn Glu Gly Glu Tyr Gly His Val Thr
 55                  60                  65 tcc ggt gca gtt gac ttc ggt gca tgg tgg aac tac tcc ttc acc cgc     355
Ser Gly Ala Val Asp Phe Gly Ala Trp Trp Asn Tyr Ser Phe Thr Arg
                 75                  80                  85 ctg ggc gga ctg acc atg acc gat acc gac cgt tgg gca agc cag gaa     403
Leu Gly Gly Leu Thr Met Thr Asp Thr Asp Arg Trp Ala Ser Gln Glu
             90                  95                 100 gca gtg cgt tcc acc cct ggc aac atc gag ctg acc agc ttc tct gat     451
Ala Val Arg Ser Thr Pro Gly Asn Ile Glu Leu Thr Ser Phe Ser Asp
         105                 110                 115 cgt cgc gac cgc gca ttg ttc agc gaa gca tac gag gat cca gta tct     499
```

```
Arg Arg Asp Arg Ala Leu Phe Ser Glu Ala Tyr Glu Asp Pro Val Ser
        120                 125                 130 ggc atc ttc acc ggt cgc gct tct gtg ggc aac cca gag ttc acc gga        547
Gly Ile Phe Thr Gly Arg Ala Ser Val Gly Asn Pro Glu Phe Thr Gly
135                 140                 145 cct att acc tac att ggc cag gaa gaa act cag acg gat gtt gat ctg        595
Pro Ile Thr Tyr Ile Gly Gln Glu Glu Thr Gln Thr Asp Val Asp Leu
150                 155                 160                 165 ctg aag aag ggc atg aac gca gcg gga gct acc gac ggc ttc gtt gca        643
Leu Lys Lys Gly Met Asn Ala Ala Gly Ala Thr Asp Gly Phe Val Ala
                170                 175                 180 gca cta tcc cca gga tct gca gct cga ttg acc aac aag ttc tac gac        691
Ala Leu Ser Pro Gly Ser Ala Ala Arg Leu Thr Asn Lys Phe Tyr Asp
            185                 190                 195 act gat gaa gaa gtc gtc gca gca tgt gct gat gcg ctt tcc cag gaa        739
Thr Asp Glu Glu Val Val Ala Ala Cys Ala Asp Ala Leu Ser Gln Glu
        200                 205                 210 tac aag atc atc acc gat gca ggt ctg acc gtt cag ctc gac gca ccg        787
Tyr Lys Ile Ile Thr Asp Ala Gly Leu Thr Val Gln Leu Asp Ala Pro
    215                 220                 225 gac ttg gca gaa gca tgg gat cag atc aac cca gag cca agc gtg aag        835
Asp Leu Ala Glu Ala Trp Asp Gln Ile Asn Pro Glu Pro Ser Val Lys
230                 235                 240                 245 gat tac ttg gac tgg atc ggt aca cgc atc gat gcc atc aac agt gca        883
Asp Tyr Leu Asp Trp Ile Gly Thr Arg Ile Asp Ala Ile Asn Ser Ala
                250                 255                 260 gtg aag ggc ctt cca aag gaa cag acc cgc ctg cac atc tgc tgg ggc        931
Val Lys Gly Leu Pro Lys Glu Gln Thr Arg Leu His Ile Cys Trp Gly
            265                 270                 275 tct tgg cac gga cca cac gtc act gac atc cca ttc ggt gac atc att        979
Ser Trp His Gly Pro His Val Thr Asp Ile Pro Phe Gly Asp Ile Ile
        280                 285                 290 ggt gag atc ctg cgc gca gag gtc ggc ggc ttc tcc ttc gaa ggc gca       1027
Gly Glu Ile Leu Arg Ala Glu Val Gly Gly Phe Ser Phe Glu Gly Ala
    295                 300                 305 tct cct cgt cac gca cac gag tgg cgt gta tgg gaa gaa aac aag ctt       1075
Ser Pro Arg His Ala His Glu Trp Arg Val Trp Glu Glu Asn Lys Leu
310                 315                 320                 325 cct gaa ggc tct gtt atc tac cct ggt gtt gtg tct cac tcc atc aac       1123
Pro Glu Gly Ser Val Ile Tyr Pro Gly Val Val Ser His Ser Ile Asn
                330                 335                 340 gct gtg gag cac cca cgc ctg gtt gct gat cgt atc gtt cag ttc gcc       1171
Ala Val Glu His Pro Arg Leu Val Ala Asp Arg Ile Val Gln Phe Ala
            345                 350                 355 aag ctt gtt ggc cct gag aac gtc att gcg tcc act gac tgt ggt ctg       1219
Lys Leu Val Gly Pro Glu Asn Val Ile Ala Ser Thr Asp Cys Gly Leu
        360                 365                 370 ggc gga cgt ctg cat tcc cag atc gca tgg gca aag ctg gag tcc cta       1267
Gly Gly Arg Leu His Ser Gln Ile Ala Trp Ala Lys Leu Glu Ser Leu
    375                 380                 385 gta gag ggc gct cgc att gca tca aag gaa ctg ttc taagctagac            1313
Val Glu Gly Ala Arg Ile Ala Ser Lys Glu Leu Phe
390                 395                 400 aacgagggtt gct                                                         1326

<210> SEQ ID NO 110
<211> LENGTH: 401
<212> TYPE: PRT
<213> ORGANISM: Corynebacterium glutamicum
```

-continued

```
<400> SEQUENCE: 110

Met Ser Gln Asn Arg Ile Arg Thr Thr His Val Gly Ser Leu Pro Arg
 1               5                  10                  15

Thr Pro Glu Leu Leu Asp Ala Asn Ile Lys Arg Ser Asn Gly Glu Ile
            20                  25                  30

Gly Glu Glu Glu Phe Phe Gln Ile Leu Gln Ser Ser Val Asp Asp Val
        35                  40                  45

Ile Lys Arg Gln Val Asp Leu Gly Ile Asp Ile Leu Asn Glu Gly Glu
 50                  55                  60

Tyr Gly His Val Thr Ser Gly Ala Val Asp Phe Gly Ala Trp Trp Asn
 65                  70                  75                  80

Tyr Ser Phe Thr Arg Leu Gly Gly Leu Thr Met Thr Asp Thr Asp Arg
                85                  90                  95

Trp Ala Ser Gln Glu Ala Val Arg Ser Thr Pro Gly Asn Ile Glu Leu
            100                 105                 110

Thr Ser Phe Ser Asp Arg Arg Asp Arg Ala Leu Phe Ser Glu Ala Tyr
        115                 120                 125

Glu Asp Pro Val Ser Gly Ile Phe Thr Gly Arg Ala Ser Val Gly Asn
    130                 135                 140

Pro Glu Phe Thr Gly Pro Ile Thr Tyr Ile Gly Gln Glu Thr Gln
145                 150                 155                 160

Thr Asp Val Asp Leu Leu Lys Lys Gly Met Asn Ala Ala Gly Ala Thr
                165                 170                 175

Asp Gly Phe Val Ala Ala Leu Ser Pro Gly Ser Ala Ala Arg Leu Thr
            180                 185                 190

Asn Lys Phe Tyr Asp Thr Asp Glu Glu Val Val Ala Ala Cys Ala Asp
        195                 200                 205

Ala Leu Ser Gln Glu Tyr Lys Ile Ile Thr Asp Ala Gly Leu Thr Val
    210                 215                 220

Gln Leu Asp Ala Pro Asp Leu Ala Glu Ala Trp Asp Gln Ile Asn Pro
225                 230                 235                 240

Glu Pro Ser Val Lys Asp Tyr Leu Asp Trp Ile Gly Thr Arg Ile Asp
                245                 250                 255

Ala Ile Asn Ser Ala Val Lys Gly Leu Pro Lys Glu Gln Thr Arg Leu
            260                 265                 270

His Ile Cys Trp Gly Ser Trp His Gly Pro His Val Thr Asp Ile Pro
        275                 280                 285

Phe Gly Asp Ile Ile Gly Glu Ile Leu Arg Ala Glu Val Gly Gly Phe
    290                 295                 300

Ser Phe Glu Gly Ala Ser Pro Arg His Ala His Glu Trp Arg Val Trp
305                 310                 315                 320

Glu Glu Asn Lys Leu Pro Glu Gly Ser Val Ile Tyr Pro Gly Val Val
                325                 330                 335

Ser His Ser Ile Asn Ala Val Glu His Pro Arg Leu Val Ala Asp Arg
            340                 345                 350

Ile Val Gln Phe Ala Lys Leu Val Gly Pro Glu Asn Val Ile Ala Ser
        355                 360                 365

Thr Asp Cys Gly Leu Gly Gly Arg Leu His Ser Gln Ile Ala Trp Ala
    370                 375                 380

Lys Leu Glu Ser Leu Val Glu Gly Ala Arg Ile Ala Ser Lys Glu Leu
385                 390                 395                 400

Phe
```

```
<210> SEQ ID NO 111
<211> LENGTH: 548
<212> TYPE: DNA
<213> ORGANISM: Corynebacterium glutamicum
<220> FEATURE:
<221> NAME/KEY: CDS
<222> LOCATION: (1)..(525)
<223> OTHER INFORMATION: FRXA02648

<400> SEQUENCE: 111 gac gca ccg gac ttg gca gaa gca tgg gat cag atc aac cca gag cca       48
Asp Ala Pro Asp Leu Ala Glu Ala Trp Asp Gln Ile Asn Pro Glu Pro
 1               5                  10                  15 agc gtg aag gat tac ttg gac tgg atc ggt aca cgc atc gat gcc atc       96
Ser Val Lys Asp Tyr Leu Asp Trp Ile Gly Thr Arg Ile Asp Ala Ile
            20                  25                  30 aac agt gca gtg aag ggc ctt cca aag gaa cag acc cgc ctg cac atc      144
Asn Ser Ala Val Lys Gly Leu Pro Lys Glu Gln Thr Arg Leu His Ile
        35                  40                  45 tgc tgg ggc tct tgg cac gga cca cac gtc act gac atc cca ttc ggt      192
Cys Trp Gly Ser Trp His Gly Pro His Val Thr Asp Ile Pro Phe Gly
    50                  55                  60 gac atc att ggt gag atc ctg cgc gca gag gtc ggt ggc ttc tcc ttc      240
Asp Ile Ile Gly Glu Ile Leu Arg Ala Glu Val Gly Gly Phe Ser Phe
65                  70                  75                  80 gaa ggc gca tct cct cgt cac gca cac gag tgg cgt gta tgg gaa gaa      288
Glu Gly Ala Ser Pro Arg His Ala His Glu Trp Arg Val Trp Glu Glu
                85                  90                  95 aac aag ctt cct gaa ggc tct gtt atc tac cct ggt gtt gtg tct cac      336
Asn Lys Leu Pro Glu Gly Ser Val Ile Tyr Pro Gly Val Val Ser His
            100                 105                 110 tcc atc aac gct gtg gag cac cca cgc ctg gtt gct gat cgt atc gtt      384
Ser Ile Asn Ala Val Glu His Pro Arg Leu Val Ala Asp Arg Ile Val
        115                 120                 125 cag ttc gcc aag ctt gtt ggc cct gag aac gtc att gcg tcc act gac      432
Gln Phe Ala Lys Leu Val Gly Pro Glu Asn Val Ile Ala Ser Thr Asp
    130                 135                 140 tgt ggt ctg ggc gga cgt ctg cat tcc cag atc gca tgg gca aag ctg      480
Cys Gly Leu Gly Gly Arg Leu His Ser Gln Ile Ala Trp Ala Lys Leu
145                 150                 155                 160 gag tcc cta gta gag ggc gct cgc att gca tca aag gaa ctg ttc          525
Glu Ser Leu Val Glu Gly Ala Arg Ile Ala Ser Lys Glu Leu Phe
                165                 170                 175 taagctagac aacgagggtt gct                                             548

<210> SEQ ID NO 112
<211> LENGTH: 175
<212> TYPE: PRT
<213> ORGANISM: Corynebacterium glutamicum

<400> SEQUENCE: 112

Asp Ala Pro Asp Leu Ala Glu Ala Trp Asp Gln Ile Asn Pro Glu Pro
 1               5                  10                  15

Ser Val Lys Asp Tyr Leu Asp Trp Ile Gly Thr Arg Ile Asp Ala Ile
            20                  25                  30

Asn Ser Ala Val Lys Gly Leu Pro Lys Glu Gln Thr Arg Leu His Ile
        35                  40                  45

Cys Trp Gly Ser Trp His Gly Pro His Val Thr Asp Ile Pro Phe Gly
    50                  55                  60

Asp Ile Ile Gly Glu Ile Leu Arg Ala Glu Val Gly Gly Phe Ser Phe
```

-continued

```
             65                  70                  75                  80
Glu Gly Ala Ser Pro Arg His Ala His Glu Trp Arg Val Trp Glu Glu
                 85                  90                  95
Asn Lys Leu Pro Glu Gly Ser Val Ile Tyr Pro Gly Val Val Ser His
            100                 105                 110
Ser Ile Asn Ala Val Glu His Pro Arg Leu Val Ala Asp Arg Ile Val
        115                 120                 125
Gln Phe Ala Lys Leu Val Gly Pro Glu Asn Val Ile Ala Ser Thr Asp
    130                 135                 140
Cys Gly Leu Gly Gly Arg Leu His Ser Gln Ile Ala Trp Ala Lys Leu
145                 150                 155                 160
Glu Ser Leu Val Glu Gly Ala Arg Ile Ala Ser Lys Glu Leu Phe
                165                 170                 175

<210> SEQ ID NO 113
<211> LENGTH: 784
<212> TYPE: DNA
<213> ORGANISM: Corynebacterium glutamicum
<220> FEATURE:
<221> NAME/KEY: CDS
<222> LOCATION: (101)..(784)
<223> OTHER INFORMATION: FRXA02658

<400> SEQUENCE: 113
atgaataaaa ttccgggtgc agtgaccgta ggtgaggtaa acgcggttag agtcgaatga     60
gagtttgata ctttctttcg acttttagat tggattttca atg agc cag aac cgc    115
                                             Met Ser Gln Asn Arg
                                               1               5 atc agg acc act cac gtt ggt tcc ttg ccc cgt acc cca gag cta ctt    163
Ile Arg Thr Thr His Val Gly Ser Leu Pro Arg Thr Pro Glu Leu Leu
             10                  15                  20 gat gca aac atc aag cgt tct aac ggt gag att ggg gag gag gaa ttc    211
Asp Ala Asn Ile Lys Arg Ser Asn Gly Glu Ile Gly Glu Glu Glu Phe
         25                  30                  35 ttc cag att ctg cag tct tct gta gat gac gtg atc aag cgc cag gtt    259
Phe Gln Ile Leu Gln Ser Ser Val Asp Asp Val Ile Lys Arg Gln Val
     40                  45                  50 gac ctg ggt atc gac atc ctt aac gag ggc gaa tac ggc cac gtc acc    307
Asp Leu Gly Ile Asp Ile Leu Asn Glu Gly Glu Tyr Gly His Val Thr
 55                  60                  65 tcc ggt gca gtt gac ttc ggt gca tgg tgg aac tac tcc ttc acc cgc    355
Ser Gly Ala Val Asp Phe Gly Ala Trp Trp Asn Tyr Ser Phe Thr Arg
 70                  75                  80                  85 ctg ggc gga ctg acc atg acc gat acc gac cgt tgg gca agc cag gaa    403
Leu Gly Gly Leu Thr Met Thr Asp Thr Asp Arg Trp Ala Ser Gln Glu
                 90                  95                 100 gca gtg cgt tcc acc cct ggc aac atc gag ctg acc agc ttc tct gat    451
Ala Val Arg Ser Thr Pro Gly Asn Ile Glu Leu Thr Ser Phe Ser Asp
            105                 110                 115 cgt cgc gac cgc gca ttg ttc agc gaa gca tac gag gat cca gta tct    499
Arg Arg Asp Arg Ala Leu Phe Ser Glu Ala Tyr Glu Asp Pro Val Ser
        120                 125                 130 ggc atc ttc acc ggt cgc gct tct gtg ggc aac cca gag ttc acc gga    547
Gly Ile Phe Thr Gly Arg Ala Ser Val Gly Asn Pro Glu Phe Thr Gly
    135                 140                 145 cct att acc tac att ggc cag gaa gaa act cag acg gat gtt gat ctg    595
Pro Ile Thr Tyr Ile Gly Gln Glu Glu Thr Gln Thr Asp Val Asp Leu
150                 155                 160                 165 ctg aag aag ggc atg aac gca gcg gga gct acc gac ggc ttc gtt gca    643
```

```
Leu Lys Lys Gly Met Asn Ala Ala Gly Ala Thr Asp Gly Phe Val Ala
                170                 175                 180 gca cta tcc cca gga tct gca gct cga ttg acc aac aag ttc tac gac    691
Ala Leu Ser Pro Gly Ser Ala Ala Arg Leu Thr Asn Lys Phe Tyr Asp
            185                 190                 195 act gat gaa gaa gtc gtc gca gca tgt gct gat gcg ctt tcc cag gaa    739
Thr Asp Glu Glu Val Val Ala Ala Cys Ala Asp Ala Leu Ser Gln Glu
        200                 205                 210 tac aag atc atc acc gat gca ggt ctg acc gtt cag ctc gac gca        784
Tyr Lys Ile Ile Thr Asp Ala Gly Leu Thr Val Gln Leu Asp Ala
    215                 220                 225
```

<210> SEQ ID NO 114
<211> LENGTH: 228
<212> TYPE: PRT
<213> ORGANISM: Corynebacterium glutamicum

<400> SEQUENCE: 114

```
Met Ser Gln Asn Arg Ile Arg Thr Thr His Val Gly Ser Leu Pro Arg
 1               5                  10                  15

Thr Pro Glu Leu Leu Asp Ala Asn Ile Lys Arg Ser Asn Gly Glu Ile
            20                  25                  30

Gly Glu Glu Glu Phe Phe Gln Ile Leu Gln Ser Ser Val Asp Asp Val
        35                  40                  45

Ile Lys Arg Gln Val Asp Leu Gly Ile Asp Ile Leu Asn Glu Gly Glu
    50                  55                  60

Tyr Gly His Val Thr Ser Gly Ala Val Asp Phe Gly Ala Trp Trp Asn
65                  70                  75                  80

Tyr Ser Phe Thr Arg Leu Gly Gly Leu Thr Met Thr Asp Thr Asp Arg
                85                  90                  95

Trp Ala Ser Gln Glu Ala Val Arg Ser Thr Pro Gly Asn Ile Glu Leu
            100                 105                 110

Thr Ser Phe Ser Asp Arg Arg Asp Arg Ala Leu Phe Ser Glu Ala Tyr
        115                 120                 125

Glu Asp Pro Val Ser Gly Ile Phe Thr Gly Arg Ala Ser Val Gly Asn
    130                 135                 140

Pro Glu Phe Thr Gly Pro Ile Thr Tyr Ile Gly Gln Glu Glu Thr Gln
145                 150                 155                 160

Thr Asp Val Asp Leu Leu Lys Lys Gly Met Asn Ala Ala Gly Ala Thr
                165                 170                 175

Asp Gly Phe Val Ala Ala Leu Ser Pro Gly Ser Ala Ala Arg Leu Thr
            180                 185                 190

Asn Lys Phe Tyr Asp Thr Asp Glu Glu Val Val Ala Ala Cys Ala Asp
        195                 200                 205

Ala Leu Ser Gln Glu Tyr Lys Ile Ile Thr Asp Ala Gly Leu Thr Val
    210                 215                 220

Gln Leu Asp Ala
225
```

<210> SEQ ID NO 115
<211> LENGTH: 408
<212> TYPE: DNA
<213> ORGANISM: Corynebacterium glutamicum
<220> FEATURE:
<221> NAME/KEY: CDS
<222> LOCATION: (101)..(385)
<223> OTHER INFORMATION: RXC02238

<400> SEQUENCE: 115

```
ggcgcttagc caaaacatag agcggtaggg tatgcttatc cgattgagca acctttcccg      60
ctcttaacac tactgtccat atactttga aaaggtgtca gtg acc aac gtg agc         115
                                            Val Thr Asn Val Ser
                                             1               5 aac gag acc aac gcc acc aag gcc gtc ttc gat ccg cca gtg ggc att        163
Asn Glu Thr Asn Ala Thr Lys Ala Val Phe Asp Pro Pro Val Gly Ile
             10                  15                  20 acc gct cct ccg atc gat gaa ctg ctg gat aag gtc act tcc aag tac        211
Thr Ala Pro Pro Ile Asp Glu Leu Leu Asp Lys Val Thr Ser Lys Tyr
         25                  30                  35 gcc ctc gtg atc ttc gca gcc aag cgt gcg cgc cag atc aac agc ttc        259
Ala Leu Val Ile Phe Ala Ala Lys Arg Ala Arg Gln Ile Asn Ser Phe
     40                  45                  50 tac cat cag gca gat gag gga gta ttc gag ttc atc gga cca ttg gtt        307
Tyr His Gln Ala Asp Glu Gly Val Phe Glu Phe Ile Gly Pro Leu Val
 55                  60                  65 act ccg cag cca ggc gaa aag cca ctt tct att gct ctg cgt gag atc        355
Thr Pro Gln Pro Gly Glu Lys Pro Leu Ser Ile Ala Leu Arg Glu Ile
 70                  75                  80                  85 aat gca ggt ctg ttg gac cac gag gaa ggt taaaagacct taaacttca           405
Asn Ala Gly Leu Leu Asp His Glu Glu Gly
                 90                  95 cac                                                                    408

<210> SEQ ID NO 116
<211> LENGTH: 95
<212> TYPE: PRT
<213> ORGANISM: Corynebacterium glutamicum

<400> SEQUENCE: 116

Val Thr Asn Val Ser Asn Glu Thr Asn Ala Thr Lys Ala Val Phe Asp
 1               5                  10                  15

Pro Pro Val Gly Ile Thr Ala Pro Pro Ile Asp Glu Leu Leu Asp Lys
             20                  25                  30

Val Thr Ser Lys Tyr Ala Leu Val Ile Phe Ala Ala Lys Arg Ala Arg
         35                  40                  45

Gln Ile Asn Ser Phe Tyr His Gln Ala Asp Glu Gly Val Phe Glu Phe
     50                  55                  60

Ile Gly Pro Leu Val Thr Pro Gln Pro Gly Glu Lys Pro Leu Ser Ile
 65                  70                  75                  80

Ala Leu Arg Glu Ile Asn Ala Gly Leu Leu Asp His Glu Glu Gly
                 85                  90                  95

<210> SEQ ID NO 117
<211> LENGTH: 1827
<212> TYPE: DNA
<213> ORGANISM: Corynebacterium glutamicum
<220> FEATURE:
<221> NAME/KEY: CDS
<222> LOCATION: (101)..(1804)
<223> OTHER INFORMATION: RXC00128

<400> SEQUENCE: 117
ccattttccg tttggtcttg cctaaagaac cgcatggaaa ttatcgtgaa gcaccgatcc      60
cgttgatcgc tccagagaca ccgtgggaag gggagcagca gtg agt aaa att tcg       115
                                               Val Ser Lys Ile Ser
                                                1               5 acg aaa ctg aag gcc ctc acc gcg gtg ctg tct gtg acc act ctg gtg        163
Thr Lys Leu Lys Ala Leu Thr Ala Val Leu Ser Val Thr Thr Leu Val
             10                  15                  20
```

-continued

```
                 10                  15                  20
gct ggg tgt tcc acg ctt ccg cag aac acg gat ccg caa gtg ctg cgc      211
Ala Gly Cys Ser Thr Leu Pro Gln Asn Thr Asp Pro Gln Val Leu Arg
             25                  30                  35 tca ttt tcc ggg tcc caa agc aca caa gag ata gca ggg ccg acc ccg      259
Ser Phe Ser Gly Ser Gln Ser Thr Gln Glu Ile Ala Gly Pro Thr Pro
         40                  45                  50 aat caa gat ccg gat ttg ttg atc cgc ggc ttc ttc agc gca ggt gcg      307
Asn Gln Asp Pro Asp Leu Leu Ile Arg Gly Phe Phe Ser Ala Gly Ala
 55                  60                  65 tat ccg act cag cag tat gaa gcg gcg aag gcg tat ctg acg gaa ggg      355
Tyr Pro Thr Gln Gln Tyr Glu Ala Ala Lys Ala Tyr Leu Thr Glu Gly
 70                  75                  80                  85 acg cgc agc acg tgg aat ccg gct gcg tcg act cgt att ttg gat cgc      403
Thr Arg Ser Thr Trp Asn Pro Ala Ala Ser Thr Arg Ile Leu Asp Arg
             90                  95                 100 att gat ctg aac act ctg cca ggt tcg acg aat gcg gaa cga acg att      451
Ile Asp Leu Asn Thr Leu Pro Gly Ser Thr Asn Ala Glu Arg Thr Ile
                105                 110                 115 gcg atc cgt gga acg cag gtc gga acg ttg ctc agc ggt ggc gtg tat      499
Ala Ile Arg Gly Thr Gln Val Gly Thr Leu Leu Ser Gly Gly Val Tyr
            120                 125                 130 cag ccg gag aat gcg gag ttt gaa gct gag atc acg atg cgt cgg gaa      547
Gln Pro Glu Asn Ala Glu Phe Glu Ala Glu Ile Thr Met Arg Arg Glu
        135                 140                 145 gat ggg gag tgg cgt atc gat gct ttg ccg gac ggg att tta tta gag      595
Asp Gly Glu Trp Arg Ile Asp Ala Leu Pro Asp Gly Ile Leu Leu Glu
150                 155                 160                 165 aga aac gat ctg cgg aac cat tac act ccg cac gat gtg tat ttc ttt      643
Arg Asn Asp Leu Arg Asn His Tyr Thr Pro His Asp Val Tyr Phe Phe
                170                 175                 180 gat cct tct ggc cag gtg ttg gtg ggg gat cgg cgt tgg ttg ttc aat      691
Asp Pro Ser Gly Gln Val Leu Val Gly Asp Arg Arg Trp Leu Phe Asn
            185                 190                 195 gag tcg cag tcg atg tcc acg gtg ctg atg gcc ctt ctg gtt aat ggt      739
Glu Ser Gln Ser Met Ser Thr Val Leu Met Ala Leu Leu Val Asn Gly
        200                 205                 210 cct tcg ccg gca att tct cct ggt gtg gtc aat cag ctg tcc acg gat      787
Pro Ser Pro Ala Ile Ser Pro Gly Val Val Asn Gln Leu Ser Thr Asp
        215                 220                 225 gcg tcg ttc gtg ggg ttc aat gat ggg gag tat cag ttc act ggt ttg      835
Ala Ser Phe Val Gly Phe Asn Asp Gly Glu Tyr Gln Phe Thr Gly Leu
230                 235                 240                 245 gga aat ttg gat gat gat gcg cgt ttg cgt ttc gcc gcc cag gcc gtg      883
Gly Asn Leu Asp Asp Asp Ala Arg Leu Arg Phe Ala Ala Gln Ala Val
                250                 255                 260 tgg acg ttg gcg cat gct gat gtc gca ggc ccc tac act ttg gtc gct      931
Trp Thr Leu Ala His Ala Asp Val Ala Gly Pro Tyr Thr Leu Val Ala
            265                 270                 275 gac ggc gcg ccg ttg ctg tcg gag ttc cca acg ctc acc acc gat gac      979
Asp Gly Ala Pro Leu Leu Ser Glu Phe Pro Thr Leu Thr Thr Asp Asp
        280                 285                 290 ctc gcc gaa tac aac cca gag gct tac acc aac acg gtg tcc acg ttg     1027
Leu Ala Glu Tyr Asn Pro Glu Ala Tyr Thr Asn Thr Val Ser Thr Leu
        295                 300                 305 ttt gcg ttg cag gat gga tcg ttg tcg agg gtc agt tcc ggc aat gtg     1075
Phe Ala Leu Gln Asp Gly Ser Leu Ser Arg Val Ser Ser Gly Asn Val
310                 315                 320                 325 agt cca cta cag ggc att tgg agc ggt gga gat atc gat tct gca gcg     1123
```

```
Ser Pro Leu Gln Gly Ile Trp Ser Gly Gly Asp Ile Asp Ser Ala Ala
            330                 335                 340
att tcc tcc tcc gcc aat gtg gtg gca gcg gta cgc cac gaa aac aac      1171
Ile Ser Ser Ser Ala Asn Val Val Ala Ala Val Arg His Glu Asn Asn
        345                 350                 355 gag gca gtg ctt act gtt ggc tcc atg gaa ggc gtg act tca gat gcg      1219
Glu Ala Val Leu Thr Val Gly Ser Met Glu Gly Val Thr Ser Asp Ala
    360                 365                 370 ttg agg agt gaa acg atc act cgt ccc acc ttt gaa tac gcg tcg agt      1267
Leu Arg Ser Glu Thr Ile Thr Arg Pro Thr Phe Glu Tyr Ala Ser Ser
375                 380                 385 ggg ttg tgg gct gtg gtg gat ggg gag acg cct gtc cga gtc gca cga      1315
Gly Leu Trp Ala Val Val Asp Gly Glu Thr Pro Val Arg Val Ala Arg
390                 395                 400                 405 tcg gca aca acc ggt gag ctc gtc cag acg gag gcg gag att gtg ctg      1363
Ser Ala Thr Thr Gly Glu Leu Val Gln Thr Glu Ala Glu Ile Val Leu
            410                 415                 420 cca agg gat gtg acg ggt ccg atc tct gaa ttc caa ctg tca cga act      1411
Pro Arg Asp Val Thr Gly Pro Ile Ser Glu Phe Gln Leu Ser Arg Thr
                425                 430                 435 ggg gtc cgg gcc gcc atg atc att gaa ggc aag gtg tac gtg ggc gtc      1459
Gly Val Arg Ala Ala Met Ile Ile Glu Gly Lys Val Tyr Val Gly Val
                440                 445                 450 gta acg cgt cct ggt ccg ggc gag cgg cgc gtg aca aat atc acg gag      1507
Val Thr Arg Pro Gly Pro Gly Glu Arg Arg Val Thr Asn Ile Thr Glu
        455                 460                 465 gtg gcg ccg agc ttg ggc gag gcg gcg ctg tcg atc aac tgg cgc cca      1555
Val Ala Pro Ser Leu Gly Glu Ala Ala Leu Ser Ile Asn Trp Arg Pro
470                 475                 480                 485 gac ggc att ttg ctt gtg ggc acg tca att cca gag acg ccg ctg tgg      1603
Asp Gly Ile Leu Leu Val Gly Thr Ser Ile Pro Glu Thr Pro Leu Trp
            490                 495                 500 cgc gtc gag cag gac gga tcg gcg att tcg tcg atg ccg agc ggg aat      1651
Arg Val Glu Gln Asp Gly Ser Ala Ile Ser Ser Met Pro Ser Gly Asn
                505                 510                 515 ctc agc gcg ccg gtg gtg gcg gtg gca agt tcc gcg acg acg gtc tac      1699
Leu Ser Ala Pro Val Val Ala Val Ala Ser Ser Ala Thr Thr Val Tyr
                520                 525                 530 gtc act gat tcg cat gcg atg ctt cag ctg ccg act gcc gat aat gat      1747
Val Thr Asp Ser His Ala Met Leu Gln Leu Pro Thr Ala Asp Asn Asp
        535                 540                 545 att tgg cgc gag gtg ccc ggt ttg ctg ggc acg cgt gcg gcg ccg gtg      1795
Ile Trp Arg Glu Val Pro Gly Leu Leu Gly Thr Arg Ala Ala Pro Val
550                 555                 560                 565 gtt gcg tac tgatggagct gttcttcccg cgc                                1827
Val Ala Tyr <210> SEQ ID NO 118
<211> LENGTH: 568
<212> TYPE: PRT
<213> ORGANISM: Corynebacterium glutamicum

<400> SEQUENCE: 118

Val Ser Lys Ile Ser Thr Lys Leu Lys Ala Leu Thr Ala Val Leu Ser
  1               5                  10                  15

Val Thr Thr Leu Val Ala Gly Cys Ser Thr Leu Pro Gln Asn Thr Asp
                20                  25                  30

Pro Gln Val Leu Arg Ser Phe Ser Gly Ser Gln Ser Thr Gln Glu Ile
            35                  40                  45
```

-continued

```
Ala Gly Pro Thr Pro Asn Gln Asp Pro Asp Leu Leu Ile Arg Gly Phe
     50                  55                  60

Phe Ser Ala Gly Ala Tyr Pro Thr Gln Gln Tyr Glu Ala Ala Lys Ala
 65                  70                  75                  80

Tyr Leu Thr Glu Gly Thr Arg Ser Thr Trp Asn Pro Ala Ala Ser Thr
                 85                  90                  95

Arg Ile Leu Asp Arg Ile Asp Leu Asn Thr Leu Pro Gly Ser Thr Asn
            100                 105                 110

Ala Glu Arg Thr Ile Ala Ile Arg Gly Thr Gln Val Gly Thr Leu Leu
            115                 120                 125

Ser Gly Gly Val Tyr Gln Pro Glu Asn Ala Glu Phe Glu Ala Glu Ile
        130                 135                 140

Thr Met Arg Arg Glu Asp Gly Glu Trp Arg Ile Asp Ala Leu Pro Asp
145                 150                 155                 160

Gly Ile Leu Leu Glu Arg Asn Asp Leu Arg Asn His Tyr Thr Pro His
                165                 170                 175

Asp Val Tyr Phe Phe Asp Pro Ser Gly Gln Val Leu Val Gly Asp Arg
            180                 185                 190

Arg Trp Leu Phe Asn Glu Ser Gln Ser Met Ser Thr Val Leu Met Ala
        195                 200                 205

Leu Leu Val Asn Gly Pro Ser Pro Ala Ile Ser Pro Gly Val Val Asn
210                 215                 220

Gln Leu Ser Thr Asp Ala Ser Phe Val Gly Phe Asn Asp Gly Glu Tyr
225                 230                 235                 240

Gln Phe Thr Gly Leu Gly Asn Leu Asp Asp Ala Arg Leu Arg Phe
                245                 250                 255

Ala Ala Gln Ala Val Trp Thr Leu Ala His Ala Asp Val Ala Gly Pro
            260                 265                 270

Tyr Thr Leu Val Ala Asp Gly Ala Pro Leu Leu Ser Glu Phe Pro Thr
        275                 280                 285

Leu Thr Thr Asp Asp Leu Ala Glu Tyr Asn Pro Glu Ala Tyr Thr Asn
290                 295                 300

Thr Val Ser Thr Leu Phe Ala Leu Gln Asp Gly Ser Leu Ser Arg Val
305                 310                 315                 320

Ser Ser Gly Asn Val Ser Pro Leu Gln Gly Ile Trp Ser Gly Gly Asp
                325                 330                 335

Ile Asp Ser Ala Ala Ile Ser Ser Ala Asn Val Ala Ala Val
            340                 345                 350

Arg His Glu Asn Asn Glu Ala Val Leu Thr Val Gly Ser Met Glu Gly
        355                 360                 365

Val Thr Ser Asp Ala Leu Arg Ser Glu Thr Ile Thr Arg Pro Thr Phe
370                 375                 380

Glu Tyr Ala Ser Ser Gly Leu Trp Ala Val Val Asp Gly Glu Thr Pro
385                 390                 395                 400

Val Arg Val Ala Arg Ser Ala Thr Thr Gly Glu Leu Val Gln Thr Glu
                405                 410                 415

Ala Glu Ile Val Leu Pro Arg Asp Val Thr Gly Pro Ile Ser Glu Phe
            420                 425                 430

Gln Leu Ser Arg Thr Gly Val Arg Ala Ala Met Ile Ile Glu Gly Lys
        435                 440                 445

Val Tyr Val Gly Val Val Thr Arg Pro Gly Pro Gly Glu Arg Arg Val
450                 455                 460

Thr Asn Ile Thr Glu Val Ala Pro Ser Leu Gly Glu Ala Ala Leu Ser
```

```
                465                 470                 475                 480
Ile Asn Trp Arg Pro Asp Gly Ile Leu Leu Val Gly Thr Ser Ile Pro
                    485                 490                 495

Glu Thr Pro Leu Trp Arg Val Glu Gln Asp Gly Ser Ala Ile Ser Ser
                500                 505                 510

Met Pro Ser Gly Asn Leu Ser Ala Pro Val Val Ala Val Ala Ser Ser
            515                 520                 525

Ala Thr Thr Val Tyr Val Thr Asp Ser His Ala Met Leu Gln Leu Pro
        530                 535                 540

Thr Ala Asp Asn Asp Ile Trp Arg Glu Val Pro Gly Leu Leu Gly Thr
545                 550                 555                 560

Arg Ala Ala Pro Val Val Ala Tyr
                565

<210> SEQ ID NO 119
<211> LENGTH: 1344
<212> TYPE: DNA
<213> ORGANISM: Corynebacterium glutamicum
<220> FEATURE:
<221> NAME/KEY: CDS
<222> LOCATION: (101)..(1321)
<223> OTHER INFORMATION: RXA02240

<400> SEQUENCE: 119
cagctagacc actgacattg cagttttaga cagcttggtc tatattggtt ttttgtattt       60
aagactattt attctcaact tcttcgaaag aagggtattt gtg gct cag cca acc       115
                                                Val Ala Gln Pro Thr
                                                  1               5 gcc gtc cgt ttg ttc acc agt gaa tct gta act gag gga cat cca gac       163
Ala Val Arg Leu Phe Thr Ser Glu Ser Val Thr Glu Gly His Pro Asp
             10                  15                  20 aaa ata tgt gat gct att tcc gat acc att ttg gac gcg ctc ctc gaa       211
Lys Ile Cys Asp Ala Ile Ser Asp Thr Ile Leu Asp Ala Leu Leu Glu
         25                  30                  35 aaa gat ccg cag tcg cgc gtc gca gtg gaa act gtg gtc acc acc gga       259
Lys Asp Pro Gln Ser Arg Val Ala Val Glu Thr Val Val Thr Thr Gly
     40                  45                  50 atc gtc cat gtt gtt ggc gag gtc cgt acc agc gct tac gta gag atc       307
Ile Val His Val Val Gly Glu Val Arg Thr Ser Ala Tyr Val Glu Ile
 55                  60                  65 cct caa tta gtc cgc aac aag ctc atc gaa atc gga ttc aac tcc tct       355
Pro Gln Leu Val Arg Asn Lys Leu Ile Glu Ile Gly Phe Asn Ser Ser
 70                  75                  80                  85 gag gtt gga ttc gac gga cgc acc tgt ggc gtc tca gta tcc atc ggt       403
Glu Val Gly Phe Asp Gly Arg Thr Cys Gly Val Ser Val Ser Ile Gly
             90                  95                 100 gag cag tcc cag gaa atc gct gac ggc gtg gat aac tcc gac gaa gcc       451
Glu Gln Ser Gln Glu Ile Ala Asp Gly Val Asp Asn Ser Asp Glu Ala
        105                 110                 115 cgc acc aac ggc gac gtt gaa gaa gac gac cgc gca ggt gct ggc gac       499
Arg Thr Asn Gly Asp Val Glu Glu Asp Asp Arg Ala Gly Ala Gly Asp
    120                 125                 130 cag ggc ctg atg ttc ggc tac gcc acc aac gaa acc gaa gag tac atg       547
Gln Gly Leu Met Phe Gly Tyr Ala Thr Asn Glu Thr Glu Glu Tyr Met
135                 140                 145 cct ctt cct atc gcg ttg gcg cac cga ctg tca cgt cgt ctg acc cag       595
Pro Leu Pro Ile Ala Leu Ala His Arg Leu Ser Arg Arg Leu Thr Gln
150                 155                 160                 165 gtt cgt aaa gag ggc atc gtt cct cac ctg cgt cca gac gga aaa acc       643
```

```
                                                         -continued

Val Arg Lys Glu Gly Ile Val Pro His Leu Arg Pro Asp Gly Lys Thr
                170                 175                 180 cag gtc acc ttc gca tac gat gcg caa gac cgc cct agc cac ctg gat    691
Gln Val Thr Phe Ala Tyr Asp Ala Gln Asp Arg Pro Ser His Leu Asp
            185                 190                 195 acc gtt gtc atc tcc acc cag cac gac cca gaa gtt gac cgt gca tgg    739
Thr Val Val Ile Ser Thr Gln His Asp Pro Glu Val Asp Arg Ala Trp
        200                 205                 210 ttg gaa acc caa ctg cgc gaa cac gtc att gat tgg gta atc aaa gac    787
Leu Glu Thr Gln Leu Arg Glu His Val Ile Asp Trp Val Ile Lys Asp
    215                 220                 225 gca ggc att gag gat ctg gca acc ggt gag atc acc gtg ttg atc aac    835
Ala Gly Ile Glu Asp Leu Ala Thr Gly Glu Ile Thr Val Leu Ile Asn
230                 235                 240                 245 cct tca ggt tcc ttc att ctg ggt ggc ccc atg ggt gat gcg ggt ctg    883
Pro Ser Gly Ser Phe Ile Leu Gly Gly Pro Met Gly Asp Ala Gly Leu
                250                 255                 260 acc ggc cgc aag atc atc gtg gat acc tac ggt ggc atg gct cgc cat    931
Thr Gly Arg Lys Ile Ile Val Asp Thr Tyr Gly Gly Met Ala Arg His
            265                 270                 275 ggt ggt gga gca ttc tcc ggt aag gat cca agc aag gtg gac cgc tct    979
Gly Gly Gly Ala Phe Ser Gly Lys Asp Pro Ser Lys Val Asp Arg Ser
        280                 285                 290 gct gca tac gcc atg cgt tgg gta gca aag aac atc gtg gca gca ggc   1027
Ala Ala Tyr Ala Met Arg Trp Val Ala Lys Asn Ile Val Ala Ala Gly
    295                 300                 305 ctt gct gat cgc gct gaa gtt cag gtt gca tac gcc att gga cgc gca   1075
Leu Ala Asp Arg Ala Glu Val Gln Val Ala Tyr Ala Ile Gly Arg Ala
310                 315                 320                 325 aag cca gtc gga ctt tac gtt gaa acc ttt gac acc aac aag gaa ggc   1123
Lys Pro Val Gly Leu Tyr Val Glu Thr Phe Asp Thr Asn Lys Glu Gly
                330                 335                 340 ctg agc gac gag cag att cag gct gcc gtg ttg gag gtc ttt gac ctg   1171
Leu Ser Asp Glu Gln Ile Gln Ala Ala Val Leu Glu Val Phe Asp Leu
            345                 350                 355 cgt cca gca gca att atc cgt gag ctt gat ctg ctt cgt ccg atc tac   1219
Arg Pro Ala Ala Ile Ile Arg Glu Leu Asp Leu Leu Arg Pro Ile Tyr
        360                 365                 370 gct gac act gct gcc tac ggc cac ttt ggt cgc act gat ttg gac ctt   1267
Ala Asp Thr Ala Ala Tyr Gly His Phe Gly Arg Thr Asp Leu Asp Leu
    375                 380                 385 cct tgg gag gct atc gac cgc gtt gat gaa ctt cgc gca gcc ctc aag   1315
Pro Trp Glu Ala Ile Asp Arg Val Asp Glu Leu Arg Ala Ala Leu Lys
390                 395                 400                 405 ttg gcc taaaaatctg atgtagtatc ttc                                 1344
Leu Ala

<210> SEQ ID NO 120
<211> LENGTH: 407
<212> TYPE: PRT
<213> ORGANISM: Corynebacterium glutamicum

<400> SEQUENCE: 120

Val Ala Gln Pro Thr Ala Val Arg Leu Phe Thr Ser Glu Ser Val Thr
  1               5                  10                  15

Glu Gly His Pro Asp Lys Ile Cys Asp Ala Ile Ser Asp Thr Ile Leu
             20                  25                  30

Asp Ala Leu Leu Glu Lys Asp Pro Gln Ser Arg Val Ala Val Glu Thr
         35                  40                  45
```

-continued

```
Val Val Thr Thr Gly Ile Val His Val Val Gly Glu Val Arg Thr Ser
     50                  55                  60

Ala Tyr Val Glu Ile Pro Gln Leu Val Arg Asn Lys Leu Ile Glu Ile
 65                  70                  75                  80

Gly Phe Asn Ser Ser Glu Val Gly Phe Asp Gly Arg Thr Cys Gly Val
                 85                  90                  95

Ser Val Ser Ile Gly Glu Gln Ser Gln Glu Ile Ala Asp Gly Val Asp
            100                 105                 110

Asn Ser Asp Glu Ala Arg Thr Asn Gly Asp Val Glu Asp Asp Arg
            115                 120                 125

Ala Gly Ala Gly Asp Gln Gly Leu Met Phe Gly Tyr Ala Thr Asn Glu
        130                 135                 140

Thr Glu Glu Tyr Met Pro Leu Pro Ile Ala Leu Ala His Arg Leu Ser
145                 150                 155                 160

Arg Arg Leu Thr Gln Val Arg Lys Glu Gly Ile Val Pro His Leu Arg
                165                 170                 175

Pro Asp Gly Lys Thr Gln Val Thr Phe Ala Tyr Asp Ala Gln Asp Arg
            180                 185                 190

Pro Ser His Leu Asp Thr Val Val Ile Ser Thr Gln His Asp Pro Glu
        195                 200                 205

Val Asp Arg Ala Trp Leu Glu Thr Gln Leu Arg Glu His Val Ile Asp
    210                 215                 220

Trp Val Ile Lys Asp Ala Gly Ile Glu Asp Leu Ala Thr Gly Glu Ile
225                 230                 235                 240

Thr Val Leu Ile Asn Pro Ser Gly Ser Phe Ile Leu Gly Gly Pro Met
                245                 250                 255

Gly Asp Ala Gly Leu Thr Gly Arg Lys Ile Ile Val Asp Thr Tyr Gly
            260                 265                 270

Gly Met Ala Arg His Gly Gly Gly Ala Phe Ser Gly Lys Asp Pro Ser
        275                 280                 285

Lys Val Asp Arg Ser Ala Ala Tyr Ala Met Arg Trp Val Ala Lys Asn
    290                 295                 300

Ile Val Ala Ala Gly Leu Ala Asp Arg Ala Glu Val Gln Val Ala Tyr
305                 310                 315                 320

Ala Ile Gly Arg Ala Lys Pro Val Gly Leu Tyr Val Glu Thr Phe Asp
                325                 330                 335

Thr Asn Lys Glu Gly Leu Ser Asp Glu Gln Ile Gln Ala Ala Val Leu
            340                 345                 350

Glu Val Phe Asp Leu Arg Pro Ala Ala Ile Ile Arg Glu Leu Asp Leu
        355                 360                 365

Leu Arg Pro Ile Tyr Ala Asp Thr Ala Ala Tyr Gly His Phe Gly Arg
    370                 375                 380

Thr Asp Leu Asp Leu Pro Trp Glu Ala Ile Asp Arg Val Asp Glu Leu
385                 390                 395                 400

Arg Ala Ala Leu Lys Leu Ala
                405
```

<210> SEQ ID NO 121
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 121
tcgggtatcc gcgctacact taga                                          24

<210> SEQ ID NO 122
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 122
ggaaaccggg gcatcgaaac tta                                           23

<210> SEQ ID NO 123
<211> LENGTH: 18
<212> TYPE: DNA
<213> ORGANISM: Artificial Sequence
<220> FEATURE:
<223> OTHER INFORMATION: Description of Artificial Sequence: primer

<400> SEQUENCE: 123
ggaaacagta tgaccatg                                                 18

<210> SEQ ID NO 124
<211> LENGTH: 17
<212> TYPE: DNA
<213> ORGANISM: Artificial Sequence
<220> FEATURE:
<223> OTHER INFORMATION: Description of Artificial Sequence: primer

<400> SEQUENCE: 124
gtaaaacgac ggccagt                                                  17

<210> SEQ ID NO 125
<211> LENGTH: 4334
<212> TYPE: DNA
<213> ORGANISM: Corynebacterium glutamicum

<400> SEQUENCE: 125
aaatcgcttg accattgcag gttggtttat gactgttgag ggagagactg gctcgtggcc     60
gacaatcaat gaagctatgt ctgaatttag cgtgtcacgt cagaccgtga atagagcact    120
taagtctgcg ggcattgaac ttccacgagg acgccgtaaa gcttcccagt aaatgtgcca    180
tctcgtaggc agaaaacggt tccccccgta ggggtctctc tcttggcctc ctttctaggt    240
cgggctgatt gctcttgaag ctctctaggg gggctcacac cataggcaga taacggttcc    300
ccaccggctc acctcgtaag cgcacaagga ctgctcccaa agatcttcaa agccactgcc    360
gcgactccgc ttcgcgaagc cttgccccgc ggaaatttcc tccaccgagt tcgtgcacac    420
ccctatgcca agcttctttc accctaaatt cgagagattg gattcttacc gtggaaattc    480
ttcgcaaaaa tcgtcccctg atcgcccttg cgacgttgct cgcggcggtg ccgctggttg    540
cgcttggctt gaccgacttg atcagcttgc atgcctgcag gtcgacggat ccccgggtgg    600
gaaagccacg ttgtgtctca aaatctctga tgttacattg cacaagataa aaatatatca    660
tcatgaacaa taaaactgtc tgcttacata aacagtaata caagggtgtg tatgagccat    720
attcaacggg aaacgtcttg ctcgaggccg cgattaaatt ccaacatgga tgctgattta    780
tatgggtata aatgggctcg cgataatgtc gggcaatcag gtgcgacaat ctatcgattg    840
tatgggaagc ccgatgcgcc agagttgttt ctgaaacatg gcaaaggtag cgttgccaat    900
gatgttacag atgagatggt cagactaaac tggctgacgg aatttatgcc tcttccgacc    960
atcaagcatt ttatccgtac tcctgatgat gcatggttac tcaccactgc gatccccggg   1020

```
aaaacagcat tccaggtatt agaagaatat cctgattcag gtgaaaatat tgttgatgcg    1080
ctggcagtgt tcctgcgccg gttgcattcg attcctgttt gtaattgtcc ttttaacagc    1140
gatcgcgtat ttcgtctcgc tcaggcgcaa tcacgaatga ataacggttt ggttgatgcg    1200
agtgattttg atgacgagcg taatggctgg cctgttgaac aagtctggaa agaaatgcat    1260
aagcttttgc cattctcacc ggattcagtc gtcactcatg gtgatttctc acttgataac    1320 cttattttg  acgaggggaa attaataggt tgtattgatg ttggacgagt cggaatcgca    1380
gaccgatacc aggatcttgc catcctatgg aactgcctcg gtgagttttc tccttcatta    1440
cagaaacggc ttttcaaaa atatggtatt gataatcctg atatgaataa attgcagttt    1500
catttgatgc tcgatgagtt tttctaatca gaattggtta attggttgta acactggcag    1560
agcattacgc tgacttgacg ggacggcggc tttgttgaat aaatcgaact tttgctgagt    1620
tgaaggatca gatcacgcat cttcccgaca acgcagaccg ttccgtggca aagcaaaagt    1680
tcaaaatcac caactggtcc acctacaaca aagctctcat caaccgtggc tccctcactt    1740
tctggctgga tgatggggcg attcaggcct ggtatgagtc agcaacaccct tcttcacgag    1800 gcagacctca gcgcccccga attgatcagt actgcggcgt cgctgatcgc cctcgcgacg    1860
ttgtgcgggt ggcttgtccc tgagggcgct gcgacagata gctaaaaatc tgcgtcagga    1920
tcgccgtaga gcgcgcgtcg cgtcgattgg aggcttcccc tttggttgac ggtcttcaat    1980
cgctctacgg cgatcctgac gcttttttgt tgcgtaccgt cgatcgtttt atttctgtcg    2040
atcccgaaaa agtttttgcc ttttgtaaaa aacttctcgg tcgccccgca aattttcgat    2100
tccagatttt ttaaaaacca agccagaaat acgacacacc gtttgcagat aatctgtctt    2160
tcggaaaaat caagtgcgat acaaaatttt tagcacccct gagctgcgca aagtcccgct    2220
tcgtgaaaat tttcgtgccg cgtgattttc cgccaaaaac tttaacgaac gttcgttata    2280
atggtgtcat gaccttcacg acgaagtacc aaaattggcc cgaatcatca gctatggatc    2340
tctctgatgt cgcgctggag tccgacgcgc tcgatgctgc cgtcgattta aaaacggtga    2400 tcggatttttt ccgagctctc gatacgacgg acgcgccagc atcacgagac tgggccagtg    2460
ccgcgagcga cctagaaact ctcgtggcgg atcttgagga gctggctgac gagctgcgtg    2520
ctcggcagcg ccaggaggac gcacagtagt ggaggatcga atcagttgcg cctactgcgg    2580
tggcctgatt cctccccggc ctgacccgcg aggacggcgc gcaaaatatt gctcagatgc    2640
gtgtcgtgcc gcagccagcc gcgagcgcgc caacaaacgc cacgccgagg agctggaggc    2700
ggctaggtcg caaatggcgc tggaagtgcg tcccccgagc gaaattttgg ccatggtcgt    2760
cacagagctg gaagcggcag cgagaattat ccgcgatcgt ggcgcggtgc ccgcaggcat    2820
gacaaacatc gtaaatgccg cgtttcgtgt ggccgtggcc gcccaggacg tgtcagcgcc    2880
gccaccacct gcaccgaatc ggcagcagcg tcgcgcgtcg aaaaagcgca caggcggcaa    2940
gaagcgataa gctgcacgaa tacctgaaaa atgttgaacg ccccgtgagc ggtaactcac    3000
agggcgtcgg ctaaccccca gtccaaacca gggagaaagc gctcaaaaat gactctagcg    3060
gattcacgag acattgacac accggcctgg aaatttttccg ctgatctgtt cgacacccat    3120
cccgagctcg cgctgcgatc acgtggctgg acgagcgaag accgccgcga attcctcgct    3180
cacctgggca gagaaaattt ccagggcagc aagacccgcg acttcgccag cgcttggatc    3240
aaagacccgg acacgggaga aacacagccg aagttatacc gagttggttc aaaatcgctt    3300
gcccggtgcc agtatgttgc tctgacgcac gcgcagcacg cagccgtgct tgtcctggac    3360
```

-continued

```
attgatgtgc cgagccacca ggccggcggg aaaatcgagc acgtaaaccc cgaggtctac    3420
gcgattttgg agcgctgggc acgcctggaa aaagcgccag cttggatcgg cgtgaatcca    3480
ctgagcggga aatgccagct catctggctc attgatccgg tgtatgccgc agcaggcatg    3540
agcagcccga atatgcgcct gctggctgca acgaccgagg aaatgacccg cgttttcggc    3600
gctgaccagg cttttcaca taggctgagc cggtggccac tgcacgtctc cgacgatccc     3660
accgcgtacc gctggcatgc ccagcacaat cgcgtggatc gcctagctga tcttatggag    3720
gttgctcgca tgatctcagg cacagaaaaa cctaaaaaac gctatgagca ggagttttct    3780
agcggacggg cacgtatcga agcggcaaga aaagccactg cggaagcaaa agcacttgcc    3840
acgcttgaag caagcctgcc gagcgccgct gaagcgtctg gagagctgat cgacggcgtc    3900
cgtgtcctct ggactgctcc agggcgtgcc gcccgtgatg agacggcttt tcgccacgct    3960
ttgactgtgg gataccagtt aaaagcggct ggtgagcgcc taaaagacac caagatcatc    4020
gacgcctacg agcgtgccta caccgtcgct caggcggtcg gagcagacgg ccgtgagcct    4080
gatctgccgc cgatgcgtga ccgccagacg atggcgcgac gtgtgcgcgg ctacgtcgct    4140
aaaggccagc cagtcgtccc tgctcgtcag acagagacgc agagcagccg agggcgaaaa    4200
gctctggcca ctatgggaag acgtggcggt aaaaaggccg cagaacgctg gaaagaccca    4260
aacagtgagt acgcccgagc acagcgagaa aaactagcta agtccagtca acgacaagct    4320
aggaaagcta aagg                                                      4334
```